United States Patent
Gharat et al.

(10) Patent No.: US 10,821,100 B2
(45) Date of Patent: *Nov. 3, 2020

(54) TRIAZOLONE COMPOUNDS AS MPGES-1 INHIBITORS

(71) Applicant: Glenmark Pharmaceuticals S.A., La Chaux-de-Fonds (CH)

(72) Inventors: Laxmikant A. Gharat, Thane (IN); Nagarajan Muthukaman, Erode (IN); Neelima Khairatkar-Joshi, Thane (IN); Vidya G. Kattige, Thane (IN)

(73) Assignee: Ichnos Sciences SA, La Chaux-de-Fonds (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/423,992

(22) Filed: May 28, 2019

(65) Prior Publication Data

US 2019/0282548 A1 Sep. 19, 2019

Related U.S. Application Data

(63) Continuation of application No. 15/919,460, filed on Mar. 13, 2018, now Pat. No. 10,391,083, which is a continuation of application No. 15/228,681, filed on Aug. 4, 2016, now Pat. No. 9,949,955, which is a continuation of application No. 14/745,204, filed on Jun. 19, 2015, now Pat. No. 9,439,890, which is a continuation of application No. 14/123,409, filed as
(Continued)

(30) Foreign Application Priority Data

Jun. 15, 2012 (IN) .......................... 1733/MUM/2012
Nov. 19, 2012 (IN) .......................... 3319/MUM/2012
Feb. 8, 2013 (IN) ............................ 387/MUM/2013

(51) Int. Cl.
| | |
|---|---|
| *A61K 31/4196* | (2006.01) |
| *C07D 401/04* | (2006.01) |
| *C07D 401/10* | (2006.01) |
| *C07D 403/04* | (2006.01) |
| *C07D 403/10* | (2006.01) |
| *C07D 403/12* | (2006.01) |
| *C07D 405/12* | (2006.01) |
| *C07D 409/14* | (2006.01) |
| *C07D 413/10* | (2006.01) |
| *C07D 417/10* | (2006.01) |
| *C07D 417/12* | (2006.01) |
| *A61K 31/4245* | (2006.01) |
| *A61K 31/428* | (2006.01) |
| *A61K 31/433* | (2006.01) |
| *A61K 31/4439* | (2006.01) |
| *A61K 31/5377* | (2006.01) |
| *C07D 249/12* | (2006.01) |
| *C07D 413/12* | (2006.01) |
| *A61K 31/422* | (2006.01) |

(52) U.S. Cl.
CPC ........ *A61K 31/4196* (2013.01); *A61K 31/422* (2013.01); *A61K 31/428* (2013.01); *A61K 31/4245* (2013.01); *A61K 31/433* (2013.01); *A61K 31/4439* (2013.01); *A61K 31/5377* (2013.01); *C07D 249/12* (2013.01); *C07D 401/04* (2013.01); *C07D 401/10* (2013.01); *C07D 403/04* (2013.01); *C07D 403/10* (2013.01); *C07D 403/12* (2013.01); *C07D 405/12* (2013.01); *C07D 409/14* (2013.01); *C07D 413/10* (2013.01); *C07D 413/12* (2013.01); *C07D 417/10* (2013.01); *C07D 417/12* (2013.01)

(58) Field of Classification Search
CPC .................................................. A61K 31/4196
See application file for complete search history.

(56) References Cited

U.S. PATENT DOCUMENTS

| | | |
|---|---|---|
| 2002/0045651 A1 | 4/2002 | Brenner et al. |
| 2012/0108583 A1 | 5/2012 | Gharat et al. |

(Continued)

FOREIGN PATENT DOCUMENTS

| | | |
|---|---|---|
| GB | 1068083 A | 5/1967 |
| WO | WO-2004058731 A1 | 7/2004 |

(Continued)

OTHER PUBLICATIONS

International Search Report issued in PCT/IB2013/054752 dated Sep. 2, 2013.

(Continued)

*Primary Examiner* — Karen Cheng
(74) *Attorney, Agent, or Firm* — Blank Rome LLP

(57) ABSTRACT

The present disclosure is directed to compounds of formula (I), and pharmaceutically acceptable salts thereof, as mPGES-1 inhibitors. These compounds are inhibitors of the microsomal prostaglandin E synthase-1 (mPGES-1) enzyme and are therefore useful in the treatment of pain and/or inflammation from a variety of diseases or conditions, such as asthma, osteoarthritis, rheumatoid arthritis, acute or chronic pain and neurodegenerative diseases.

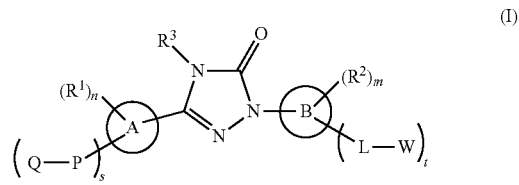

8 Claims, No Drawings

Related U.S. Application Data application No. PCT/IB2013/054752 on Jun. 10, 2013, now Pat. No. 9,096,545.

(60) Provisional application No. 61/792,225, filed on Mar. 15, 2013, provisional application No. 61/735,679, filed on Dec. 11, 2012, provisional application No. 61/668,146, filed on Jul. 5, 2012.

(56) References Cited

U.S. PATENT DOCUMENTS

| | | |
|---|---|---|
| 2013/0289058 A1 | 10/2013 | Patel et al. |
| 2014/0018319 A1 | 1/2014 | Purandare et al. |
| 2014/0113855 A1 | 4/2014 | Jumaa et al. |
| 2014/0171404 A1 | 6/2014 | Furminger et al. |
| 2014/0200227 A1 | 7/2014 | Xue et al. |
| 2015/0315194 A1 | 11/2015 | Murray et al. |
| 2015/0315209 A1 | 11/2015 | Koike et al. |

FOREIGN PATENT DOCUMENTS

| | | |
|---|---|---|
| WO | WO-2004083189 A1 | 9/2004 |
| WO | WO-2004083190 A1 | 9/2004 |
| WO | WO-2006063466 A1 | 6/2006 |
| WO | WO-2006117657 A1 | 11/2006 |
| WO | WO-2007059610 A1 | 5/2007 |
| WO | WO-2010034796 A1 | 4/2010 |
| WO | WO-2010100249 A1 | 9/2010 |
| WO | WO-2011104322 A1 | 9/2011 |
| WO | WO-2012055995 A1 | 5/2012 |
| WO | WO-2012110860 A1 | 8/2012 |
| WO | WO-2013038308 A1 | 3/2013 |
| WO | WO-2013156559 A1 | 10/2013 |
| WO | WO-2013163279 A1 | 10/2013 |
| WO | WO-2013170068 A2 | 11/2013 |
| WO | WO-2013171639 A1 | 11/2013 |
| WO | WO-2014008285 A1 | 1/2014 |
| WO | WO-2014009447 A1 | 1/2014 |
| WO | WO-2014026997 A1 | 2/2014 |
| WO | WO-2014035860 A1 | 3/2014 |
| WO | WO-2014041131 A1 | 3/2014 |
| WO | WO-2014060411 A1 | 4/2014 |
| WO | WO-2014090709 A1 | 6/2014 |
| WO | WO-2014100323 A1 | 6/2014 |
| WO | WO-2014100719 A2 | 6/2014 |

OTHER PUBLICATIONS

Goedken, et al., HTRF-Based Assay for Microsomal Prostaglandin E2 Synthase-1 Activity, Journal of Biomolecular Screening, 2008, 13:7:619-625.

Gomez-Hernandez, et al., Overexpression of COX-2, Prostaglandin E Synthase-1 and Prostaglandin E Receptors in Blood Mononuclear Cells and Plaque of Patients with Carotid Athereosclerosis: Regulation by Nuclear Factor-kB, Atherosclerosis, 2006, 187:139-149.

Kojima, et al., Defective Generation of Humoral Immune Response is Associated with a Reduced Incidence and Severity of Collagen-Induced Arthritis in Microsomal Prostaglandin E Synthase-1 Null Mice, The Journal of Immunology, 2013, 8361-8368.

Korotkova, et al., Effects of Immunosuppressive Treatment on Microsomal Prostaglandin E Synthase 1 and Cyclooxygenases Expression in Muscle Tissue of Patients with polymyositis or Dermatomyositis, Ann Rheum Dis, 2008, 67:1596-1602.

Masse, et al., An Automated Multistep High-Throughput Screening Assay for the Identification of Lead Inhibitors of the Inducible Enzyme mPGES-1, Journal of Biomolecular Screening, 2005, 10:6:599-605.

Nakanishi, et al., Genetic Deletion of mPGES-1 Suppresses Intestinal Tumorgenesis, Cancer Res, 2008, 68:9:3251-3259.

Ouellet, et al., Purification and Characterization of Recombinant Microsomal Prostaglandin E Synthase-1, Protein Expression and Purification, 2002, 26:489-495.

Schoder, et al., 15-deoxy-$\Delta$ 12, 14-prostaglandin J2 Inhibits the Expression of Microsomal Prostaglandin E Synthase Type 2 in Colon Cancer Cells, Journal of Lipid Research, 2006, 47:1071-1080.

Wang, et al., Deletion of Microsomal Prostaglandin E Synthase-1 Augments Prostacyclin and Retards Atherogeneis, PNAS, 2006, 103:39:14507-14512.

Wang, et al., Microsomal Prostaglandin E Synthase-1 Deletion Suppresses Oxidative Stress and Angiotensin II-Induced Abdominal Aortic Aneurysm Formation, Circulation, 2008, 117:1302-1309.

Xu, et al., MF63 [2-(6-Chloro-1H-phenanthro[9, 10-d]imidazol-2yl)-isophthalonitrile], a Selective Microsomal Prostaglandin E Synthase-1 Inhibitor, Relieves Pyresis and Pain in Preclinical Models of Inflammation, The Journal of Pharmacology and Experimental Therapeutics, 2008, 326:1:754-763.

European Search Report issued in EP 13745477.3, dated May 5, 2014.

Park, et al., Bull. Korean Chem. Soc., 2010, 31:8:2143-2143.

Deng, et al., A Novel and Efficient Synthesis of 2,5-substituted 1,2,4-triazol-3-ones, Tetrahedron Letters, 2005, 46:7993-7996.

Chang, 2011, Future Med Chem. vol. 3, p. 1909-1934.

TRIAZOLONE COMPOUNDS AS MPGES-1 INHIBITORS

RELATED APPLICATIONS

This application is a continuation of U.S. patent application Ser. No. 15/919,460, filed Mar. 13, 2018, which is a continuation of U.S. patent application Ser. No. 15/228,681, filed Aug. 4, 2016, now U.S. Pat. No. 9,949,955, which is a continuation of U.S. patent application Ser. No. 14/745,204, filed Jun. 19, 2015, now U.S. Pat. No. 9,439,890, which is a continuation of U.S. patent application Ser. No. 14/123,409, filed Dec. 2, 2013, now U.S. Pat. No. 9,096,545, which is the U.S. national phase of International Application No. PCT/IB2013/054752, filed Jun. 10, 2013, which claims the benefit of Indian Provisional Application Nos. 1733/MUM/2012 filed on 15 Jun. 2012; 3319/MUM/2012 filed on 19 Nov. 2012; and 387/MUM/2013 filed on 8 Feb. 2013; and U.S. Provisional Application Nos. 61/668,146 filed on 5 Jul. 2012; 61/735,679 filed on 11 Dec. 2012; and 61/792,225 filed on 15 Mar. 2013, each of which is hereby incorporated by reference in its entirety.

TECHNICAL FIELD

The present application relates to triazolone compounds as mPGES-1 inhibitors.

BACKGROUND OF THE INVENTION

There are many diseases or disorders that are inflammatory in their nature. One of the major problems associated with existing treatments of inflammatory conditions is inadequate efficacy and/or the prevalence of side effects. Inflammatory diseases that affect the population include asthma, inflammatory bowel disease, rheumatoid arthritis, osteoarthritis, rhinitis, conjunctivitis and dermatitis. Inflammation is also a common cause of pain.

The enzyme cyclooxygenase (COX) converts arachidonic acid to an unstable intermediate, prostaglandin $H_2$ ($PGH_2$), which is further converted to other prostaglandins, including $PGE_2$, $PGF_{2\alpha}$, $PGD_2$, prostacyclin and thromboxane $A_2$. These arachidonic acid metabolites are known to have pronounced physiological and pathophysiological activity, including pro-inflammatory effects. The COX enzyme exists in two forms, one that is constitutively expressed in many cells and tissues (COX-1), and another that in most cells and tissues is induced by pro-inflammatory stimuli, such as cytokines, during an inflammatory response (COX-2).

Among all prostaglandin metabolites, $PGE_2$ is particularly known to be a strong pro-inflammatory mediator, and is also known to induce fever and pain. Consequently, numerous drugs have been developed with a view to inhibiting the formation of $PGE_2$, including "NSAIDs" (non-steroidal anti-inflammatory drugs) and "coxibs" (selective COX-2 inhibitors). These drugs act predominantly by inhibition of COX-1 and/or COX-2, thereby reducing the formation of $PGE_2$. However, the inhibition of COXs has the disadvantage of reducing the formation of all metabolites of $PGH_2$, thereby decreasing the beneficial properties of some of the metabolites. In view of this, drugs which act by inhibition of COXs are suspected to cause adverse biological effects. For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

A combination of pharmacological, genetic and neutralizing antibody approaches demonstrates the importance of $PGE_2$ in inflammation. The conversion of $PGH_2$ to $PGE_2$ by prostaglandin E synthases (PGES) may, therefore, represent a pivotal step in the propagation of inflammatory stimuli. There are two microsomal prostaglandin E synthases (mPGES-1 and mPGES-2), and one cytosolic prostaglandin E synthase (cPGES). mPGES-1 is an inducible PGES after exposure to pro-inflammatory stimuli. mPGES-1 is induced in the periphery and CNS by inflammation, and represents therefore a target for acute and chronic inflammatory disorders. $PGE_2$ is a major prostanoid, produced from arachidonic acid liberated by phospholipases (PLAs), which drives the inflammatory processes. Arachidonic acid is transformed by the action of prostaglandin H synthase (PGH synthase, cycloxygenase) into $PGH_2$ which is a substrate for mPGES-1, the terminal enzyme transforming $PGH_2$ to the pro-inflammatory $PGE_2$.

Agents that are capable of inhibiting the action of mPGES-1, and thus reducing the formation of the specific arachidonic acid metabolite $PGE_2$, are beneficial in the treatment of inflammation. Further, agents that are capable of inhibiting the action of the proteins involved in the synthesis of the leukotrienes are also beneficial in the treatment of asthma and COPD.

Blocking the formation of $PGE_2$ in animal models of inflammatory pain results in reduced inflammation, pain and fever response (Kojima et. al, *The Journal of Immunology* 2008, 180, 8361-6; Xu et. al., *The Journal of Pharmacology and Experimental Therapeutics* 2008, 326, 754-63). In abdominal aortic aneurism, inflammation leads to connective tissue degradation and smooth muscle apoptosis ultimately leading to aortic dilation and rupture. In animals lacking mPGES-1 a slower disease progression and disease severity has been demonstrated (Wang et. al., *Circulation*, 2008, 117, 1302-1309).

Several lines of evidence indicate that $PGE_2$ is involved in malignant growth. $PGE_2$ facilitates tumor progression by stimulation of cellular proliferation and angiogenesis and by modulation of immunosuppression. In support of a role for $PGE_2$ in cancers, genetic deletion of mPGES-1 in mice suppresses intestinal tumourogenesis (Nakanishi et. al., *Cancer Research* 2008, 68(9), 3251-9). In human beings, mPGES-1 is also upregulated in cancers such as colorectal cancer (Schroder, *Journal of Lipid Research* 2006, 47, 1071-80).

Myositis is a chronic muscle disorder characterized by muscle weakness and fatigue. Proinflammatory cytokines and prostanoids have been implicated in the development of myositis. In skeletal muscle tissue from patients suffering from myositis an increase in cyclooxygenases and mPGES-1 has been demonstrated, implicating mPGES-1 as a target for treating this condition. (Korotkova, *Annals of the Rheumatic Diseases* 2008, 67, 1596-1602).

In atherosclerosis, inflammation of the vasculature leads to atheroma formation that eventually may progress into infarction. In patients with carotid atherosclerosis an increase in mPGES-1 in plaque regions has been reported (Gomez-Hernandez *Atherosclerosis* 2006, 187, 139-49). In an animal model of atherosclerosis, mice lacking the mPGES-1 receptor were found to show a retarded atherogenesis and a concomitant reduction in macrophage-derived foam cells together with an increase in vascular smooth muscle cells (Wang, *Proceedings of National Academy Of Sciences* 2006, 103(39), 14507-12).

International Publication Nos. WO 2006/063466, WO 2007/059610, WO 2010/034796, WO 2010/100249, WO 2012/055995, WO 2012/110860 and WO 2013/038308 disclose numerous heterocyclic compounds which are stated to be inhibitors of the microsomal prostaglandin E synthase-1 (mPGES-1) enzyme.

The present application is directed to compounds that act as inhibitors of the mPGES-1 enzyme and, therefore, are useful for the treatment of pain and inflammation in a variety of diseases or conditions.

SUMMARY OF THE INVENTION

In one aspect, the present invention relates to a compound of formula (I)

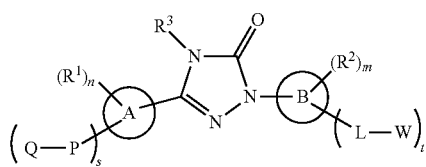

or a pharmaceutically acceptable salt thereof,
wherein, ring A is selected from $C_{6-14}$aryl, 5-14 membered heteroaryl, $C_{3-12}$cycloalkyl and 3-15 membered heterocyclyl;

ring B is selected from $C_{6-14}$aryl, 5-14 membered heteroaryl, $C_{3-12}$cycloalkyl and 3-15 membered heterocyclyl;

each occurrence of L is independently selected from —$(CR^xR^y)_q NR^xC(O)$—, and —$(CR^xR^y)_q NR^xS(O)_2$—;

each occurrence of P is independently selected from —$(CR^xR^y)_q NR^xC(O)$—, and $(CR^xR^y)_q NR^xS(O)_2$—;

each occurrence of Q is independently selected from $C_{1-8}$alkyl, $C_{2-10}$alkenyl, $C_{2-10}$alkynyl; $C_{1-8}$alkoxy, $C_{1-8}$alkoxyC$_{1-8}$alkyl, haloC$_{1-8}$alkyl, hydroxyC$_{1-8}$alkyl, carboxylC$_{1-8}$alkyl, $C_{3-12}$cycloalkyl, $C_{6-14}$aryl, $C_{6-14}$arylC$_{1-8}$alkyl, 3-15 membered heterocyclyl, and 5-14 membered heteroaryl;

each occurrence of W is independently selected from $C_{1-8}$alkyl, $C_{2-10}$alkenyl, $C_{2-10}$alkynyl, $C_{1-8}$alkoxy, $C_{1-8}$alkoxyC$_{1-8}$alkyl, haloC$_{1-8}$alkyl, hydroxyC$_{1-8}$alkyl, carboxylC$_{1-8}$alkyl, $C_{3-12}$cycloalkyl, $C_{6-14}$aryl, $C_{6-14}$arylC$_{1-8}$alkyl, 3-15 membered heterocyclyl, and 5-14 membered heteroaryl;

each occurrence of $R^1$ is independently selected from halogen, cyano, $C_{1-8}$alkyl, $C_{1-8}$alkoxy, $C_{1-8}$alkoxyC$_{1-8}$alkyl, haloC$_{1-8}$alkoxyC$_{1-8}$alkyl, haloC$_{1-8}$alkyl, haloC$_{1-8}$alkoxy, hydroxyC$_{1-8}$alkyl, $C_{3-12}$cycloalkyl, $C_{3-8}$cycloalkylC$_{1-8}$alkyl, $C_{6-14}$aryl, $C_{6-14}$arylC$_{1-8}$alkyl, $C_{6-14}$aryloxy, 3-15 membered heterocyclyl, 3-15 membered heterocyclylC$_{1-8}$alkyl, 5-14 membered heteroaryl, 5-14 membered heteroarylC$_{1-8}$alkyl, —C(O)NHR, —S(O)$_2$NHR, —NHC(O)R, —CH$_2$S(O)NHR and —C≡CR;

each occurrence of $R^2$ is independently selected from halogen, cyano, $C_{1-8}$alkyl, $C_{1-8}$alkoxy, $C_{1-8}$alkoxyC$_{1-8}$alkyl, haloC$_{1-8}$alkyl, haloC$_{1-8}$alkoxy, hydroxyC$_{1-8}$alkyl, $C_{3-12}$cycloalkyl, $C_{3-8}$ cycloalkylC$_{1-8}$alkyl, $C_{6-14}$aryl, $C_{6-14}$arylC$_{1-8}$alkyl, $C_{6-14}$aryloxy, 3-15 membered heterocyclyl, 3-15 membered heterocyclylC$_{1-8}$alkyl, 5-14 membered heteroaryl, 5-14 membered heteroarylC$_{1-8}$alkyl, —NHR, —C(O)NHR, —S(O)$_2$NHR, —NHC(O)R, —CH$_2$S(O)NHR and —C≡CR;

each occurrence of R is independently selected from $C_{1-8}$alkyl, $C_{3-12}$cycloalkyl, $C_{3-8}$cycloalkylC$_{1-8}$alkyl, $C_{6-14}$aryl, $C_{6-14}$arylC$_{1-8}$alkyl, 3-15 membered heterocyclyl and 5-14 membered heteroaryl;

$R^3$ is independently selected from hydrogen, $C_{1-8}$alkyl, $C_{3-12}$cycloalkyl and $C_{6-14}$aryl;

at each occurrence, $R^x$ and $R^y$, which may be the same or different, are independently selected from hydrogen, $C_{1-8}$alkyl, $C_{3-12}$cycloalkyl and $C_{6-14}$aryl; or $R^x$ and $R^y$ together with the common atom to which they are attached, form a cyclic ring which is substituted or unsubstituted and wherein the cyclic ring optionally contains one or more hetero atoms selected from O, N or S;

'm' is an integer ranging from 0 to 3, both inclusive;
'n' is an integer ranging from 0 to 3, both inclusive;
'q' is an integer ranging from 1 to 4, both inclusive;
's' is an integer ranging from 0 to 1, both inclusive; and
't' is an integer ranging from 0 to 1, both inclusive;
with the proviso that 'm' and 'n' are not '0' simultaneously.

The compounds of formula (I) may involve one or more embodiments. Embodiments of formula (I) include compounds of formula (II), compounds of formula (III) and compounds of formula (IV) as described hereinafter. It is to be understood that the embodiments below are illustrative of the present invention and are not intended to limit the claims to the specific embodiments exemplified. It is also to be understood that the embodiments defined herein may be used independently or in conjunction with any definition of any other embodiment defined herein. Thus, the invention contemplates all possible combinations and permutations of the various independently described embodiments. For example, the invention provides compounds of formula (I) as defined above, wherein $R^3$ is hydrogen (according to an embodiment defined below), 'n' is 0, 1 or 2 (according to another embodiment defined below), and 's' is 1 and 't' is 0 (according to another embodiment defined below).

According to one embodiment, specifically provided are compounds of formula (I), in which ring A is $C_{6-14}$ aryl (e.g. phenyl) or 5-14 membered heteroaryl (e.g. pyridinyl).

According to another embodiment, specifically provided are compounds of formula (I), in which ring A is phenyl or pyridinyl.

According to yet another embodiment, specifically provided are compounds of formula (I), in which ring B is $C_{6-14}$aryl (e.g. phenyl), 5-14 membered heteroaryl (e.g. pyridinyl) or $C_{3-12}$cycloalkyl (e.g. cyclopentyl or cyclohexyl).

According to yet another embodiment, specifically provided are compounds of formula (I), in which ring B is phenyl, pyridinyl, cyclopentyl or cyclohexyl.

According to yet another embodiment, specifically provided are compounds of formula (I), in which $R^3$ is hydrogen.

According to yet another embodiment, specifically provided are compounds of formula (I), in which $R^3$ is $C_{1-8}$alkyl (e.g. methyl or ethyl).

According to yet another embodiment, specifically provided are compounds of formula (I), in which $R^3$ is hydrogen, methyl or ethyl.

According to yet another embodiment, specifically provided are compounds of formula (I), in which P is —$(CR^xR^y)_q NR^xC(O)$— or —$(CR^xR^y)_q NR^xS(O)_2$—. In this embodiment, $R^x$ and $R^y$ are independently selected from hydrogen and $C_{1-4}$ alkyl (e.g. methyl or ethyl), and 'q' is 1.

According to yet another embodiment, specifically provided are compounds of formula (I), in which P is —CH$_2$NHC(O)— or —CH$_2$NHS(O)$_2$—.

According to yet another embodiment, specifically provided are compounds of formula (I), in which L is —(CR$^x$R$^y$)$_q$NR$^x$C(O)— or —(CR$^x$R$^y$)$_q$NR$^x$S(O)$_2$—. In this embodiment, R$^x$ and R$^y$ are independently selected from hydrogen and C$_{1-4}$alkyl (e.g. methyl or ethyl), and 'q' is 1.

According to yet another embodiment, specifically provided are compounds of formula (I), in which L is —CH$_2$NHC(O)— or —CH$_2$NHS(O)$_2$—.

According to yet another embodiment, specifically provided are compounds of formula (I), in which each occurrence of R$^1$ is independently selected from cyano, halogen (e.g. F, Cl or Br), C$_{1-8}$alkyl (e.g. methyl), haloC$_{1-8}$alkyl (e.g. trifluoromethyl or difluoromethyl), C$_{1-8}$alkoxy (e.g. methoxy), haloC$_{1-8}$alkoxyC$_{1-8}$alkyl (e.g. (2,2,2-trifluoroethoxy)methyl), C$_{3-12}$cycloalkyl (e.g. cyclopropyl), 3-15 membered heterocyclylC$_{1-8}$alkyl (e.g. (pyrrolidin-1-yl)methyl), 5-14 membered heteroaryl (e.g. 4-methylthiophenyl or 5-isopropyl-1,3,4-oxadiazol-2-yl), 5-14 membered heteroarylC$_{1-8}$alkyl (e.g. (3,5-dimethyl-1H-pyrazol-1-yl)methyl), —S(O)$_2$NHR, —NHCOR, —CONHR and —C≡CR.

According to yet another embodiment, specifically provided are compounds of formula (I), in which each occurrence of R$^1$ is independently selected from —S(O)$_2$NHR, —NHCOR, —CONHR and —C≡CR. In this embodiment R is independently selected from C$_{1-8}$alkyl (e.g. isopropyl or tert-butyl), C$_{3-12}$ cycloalkyl (e.g. cyclopropyl) and C$_{6-14}$aryl (e.g. 3,5-difluorophenyl, 4-(trifluoromethyl)phenyl, 3-(trifluoromethyl)phenyl, 4-fluoro-3-(trifluoromethyl)phenyl, 2-fluoro-5-(trifluoromethyl)phenyl, 2-chloro-4-methylphenyl, 2,5-dichlorophenyl, 4-chloro-2-fluorophenyl, 3-chloro-2-fluorophenyl, 2-chloro-4-(trifluoromethyl)phenyl, 3-(difluoromethyl)-4-fluorophenyl or 3-(difluoromethyl)phenyl).

According to yet another embodiment, specifically provided are compounds of formula (I), in which each occurrence of R$^1$ is independently cyano, F, Cl, Br, methyl, trifluoromethyl, difluoromethyl, methoxy, (2,2,2-trifluoroethoxy)methyl, cyclopropyl, (pyrrolidin-1-yl)methyl, 4-methylthiophenyl, 5-isopropyl-1,3,4-oxadiazol-2-yl, (3,5-dimethyl-1H-pyrazol-1-yl)methyl, —S(O)$_2$NHR, —NHCOR, —CONHR and —C≡CR. In this embodiment R is independently selected from isopropyl, tert-butyl, cyclopropyl, 3,5-difluorophenyl, 4-(trifluoromethyl)phenyl, 3-(trifluoromethyl)phenyl, 4-fluoro-3-(trifluoromethyl)phenyl, 2-fluoro-5-(trifluoromethyl)phenyl, 2-chloro-4-methylphenyl, 2,5-dichlorophenyl, 4-chloro-2-fluorophenyl, 3-chloro-2-fluorophenyl, 2-chloro-4-(trifluoromethyl)phenyl, 3-(difluoromethyl)-4-fluorophenyl and 3-(difluoromethyl)phenyl.

According to yet another embodiment, specifically provided are compounds of formula (I), in which each occurrence of R$^1$ is independently cyano, F, Cl, Br, methyl, trifluoromethyl, difluoromethyl, methoxy, (2,2,2-trifluoroethoxy)methyl, cyclopropyl, (pyrrolidin-1-yl)methyl, 4-methylthiophenyl, 5-isopropyl-1,3,4-oxadiazol-2-yl, (3,5-dimethyl-1H-pyrazol-1-yl)methyl, N-cyclopropylsulfamoyl, 4-(trifluoromethyl)benzamide, 3,5-difluorobenzamide, 3,3-dimethylbut-1-ynyl, 2-cyclopropylethynyl, (2,5-dichlorophenyl)ethynyl, (4-chloro-2-fluorophenyl)ethynyl, (3-chloro-2-fluorophenyl)ethynyl, [2-chloro-4-(trifluoromethyl)phenyl]ethynyl, —CONH-[4-(trifluoromethyl)phenyl], —CONH-[3-(trifluoromethyl)phenyl], —CONH-[3-(difluoromethyl)phenyl], —CONH-[4-fluoro-3-(trifluoromethyl)phenyl], —CONH-[2-fluoro-5-(trifluoromethyl)phenyl] or —CONH-[2-chloro-4-methylphenyl].

According to yet another embodiment, specifically provided are compounds of formula (I), in which 'n' is 0, 1 or 2.

According to yet another embodiment, specifically provided are compounds of formula (I), in which 'n' is 1 or 2.

According to yet another embodiment, specifically provided are compounds of formula (I), in which each occurrence of R$^2$ is independently cyano, halogen (e.g. F, Cl or Br), C$_{1-8}$alkyl (e.g. methyl), haloC$_{1-8}$alkyl (e.g. trifluoromethyl), haloC$_{1-8}$alkoxy (e.g. trifluoromethoxy), C$_{3-12}$cycloalkyl (e.g. cyclopropyl), C$_{1-8}$alkoxy (e.g. methoxy), C$_{6-14}$aryl (e.g. 3-(trifluoromethoxy)phenyl), 5-14 membered heteroaryl (e.g. 3-isopropyl-1,2,4-oxadiazol-5-yl, 3-(4-chlorophenyl)-1,2,4-oxadiazol-5-yl, 3-(4-fluorophenyl)-1,2,4-oxadiazol-5-yl, 3-(3,5-dimethoxyphenyl)-1,2,4-oxadiazol-5-yl, 3-(3-fluoro-5-(trifluoromethyl)phenyl)-1,2,4-oxadiazol-5-yl, 4-methylthiophen-2-yl, 6-(trifluoromethyl)pyridin-3-yl, 1,5,6-dimethyl-1H-benzo[d]imidazol-2-yl or 5-(trifluoromethyl)-1H-benzo[d]imidazol-2-yl), —NHR, —C(O)NHR, —NHC(O)R or —C≡CR.

According to yet another embodiment, specifically provided are compounds of formula (I), in which each occurrence of R$^2$ is independently —NHR, —C(O)NHR or —NHC(O)R. In this embodiment R is independently selected from C$_{1-8}$alkyl (e.g. isopropyl or tert-butyl), C$_{3-12}$cycloalkyl (e.g. cyclopropyl, 1-[2-(trifluoromethyl)phenyl]cyclopropyl, or 1-[4-(trifluoromethyl)phenyl]cyclopropyl), C$_{3-8}$cycloalkylC$_{1-8}$alkyl (e.g. (cyclopropyl)methyl), C$_{6-14}$ aryl (e.g. 2,5-dichlorophenyl, 4-chloro-2-fluorophenyl, 3-chloro-2-fluorophenyl, 4-(trifluoromethyl)phenyl, 3-(trifluoromethyl)phenyl, 2-(trifluoromethyl)phenyl, 3-(difluoromethyl)phenyl, 2-chloro-4-(trifluoromethyl)phenyl, 4-fluoro-3-(trifluoromethyl)phenyl, 2-fluoro-5-(trifluoromethyl)phenyl, 2-chloro-4-methylphenyl, 2-fluoro-4-methylphenyl, 5-chloro-2-methylphenyl, 3-(difluoromethyl)-4-fluorophenyl, 3-(difluoromethyl)phenyl, 4-(methylsulfonyl)phenyl or 2-chloro-5-(cyclopropanecarboxamidomethyl)phenyl), C$_{6-14}$arylC$_{1-8}$alkyl (e.g. 2-(trifluoromethyl)benzyl or 4-fluoro-2-(trifluoromethyl)benzyl), and 5-14 membered heteroaryl (e.g. 6-fluorobenzo[d]thiazol-2-yl, 1H-benzo[d]imidazol-2-yl, 5-(trifluoromethyl)-1,3,4-thiadiazol-2-yl, 6-fluoropyridin-3-yl, 5-(trifluoromethyl)pyridin-2-yl, 3-chloropyridin-4-yl, 2-morpholinopyrimidin-5-yl; or 6-(morpholin-4-yl)pyridin-3-yl).

According to yet another embodiment, specifically provided are compounds of formula (I), in which each occurrence of R$^2$ is —C≡CR. In this embodiment R is independently selected from C$_{1-8}$alkyl (e.g. isopropyl or tert-butyl), C$_{3-12}$cycloalkyl (e.g. cyclopropyl), C$_{6-14}$aryl (2,5-dichlorophenyl, 4-chloro-2-fluorophenyl, 3-chloro-2-fluorophenyl, 2-chloro-4-(trifluoromethyl)phenyl, or 2-(trifluoromethyl)phenyl) and 5-14 membered heteroaryl (e.g. 6-fluoropyridin-3-yl, 5-(trifluoromethyl)pyridin-2-yl, 3-chloropyridin-4-yl, 2-morpholinopyrimidin-5-yl, or 6-(morpholin-4-yl)pyridin-3-yl).

According to yet another embodiment, specifically provided are compounds of formula (I), in which each occurrence of R$^2$ is —C≡CR. In this embodiment R is independently selected from isopropyl, tert-butyl, cyclopropyl, 2,5-dichlorophenyl, 4-chloro-2-fluorophenyl, 3-chloro-2-fluorophenyl, 2-chloro-4-(trifluoromethyl)phenyl, 2-(trifluoromethyl)phenyl, 6-fluoropyridin-3-yl, 5-(trifluoromethyl)pyridin-2-yl, 3-chloropyridin-4-yl, 2-morpholinopyrimidin-5-yl, and 6-(morpholin-4-yl)pyridin-3-yl.

According to yet another embodiment, specifically provided are compounds of formula (I), in which each occurrence of $R^2$ is —NHR. In this embodiment R is 3-(trifluoromethyl)phenyl.

According to yet another embodiment, specifically provided are compounds of formula (I), in which each occurrence of $R^2$ is —NHC(O)R. In this embodiment R is cyclopropyl.

According to yet another embodiment, specifically provided are compounds of formula (I), in which each occurrence of $R^2$ is —C(O)NHR. In this embodiment R is (cyclopropyl)methyl, 4-(trifluoromethyl)phenyl, 3-(trifluoromethyl)phenyl, 3-(difluoromethyl)phenyl, 4-fluoro-3-(trifluoromethyl)phenyl, 2-fluoro-5-(trifluoromethyl)phenyl, 2-chloro-4-methylphenyl, 2-fluoro-4-methylphenyl, 5-chloro-2-methylphenyl, 3-(difluoromethyl)-4-fluorophenyl, 3-(difluoromethyl)phenyl, 2-chloro-5-(cyclopropanecarboxamidomethyl)phenyl, 2-(trifluoromethyl)benzyl, 4-fluoro-2-(trifluoromethyl)benzyl, 1-[2-(trifluoromethyl)phenyl]cyclopropyl, 1-[4-(trifluoromethyl)phenyl]cyclopropyl, 6-fluorobenzo[d]thiazol-2-yl, 1H-benzo[d]imidazol-2-yl, 5-(trifluoromethyl)-1,3,4-thiadiazol-2-yl or 4-(methylsulfonyl)phenyl.

According to yet another embodiment, specifically provided are compounds of formula (I), in which each occurrence of $R^2$ is independently cyano, F, Cl, Br, methyl, trifluoromethyl, trifluoromethoxy, methoxy, cyclopropyl, 3-(trifluoromethoxy)phenyl, 3-isopropyl-1,2,4-oxadiazol-5-yl, 3-(4-chlorophenyl)-1,2,4-oxadiazol-5-yl, 3-(4-fluorophenyl)-1,2,4-oxadiazol-5-yl, 3-(3,5-dimethoxyphenyl)-1,2,4-oxadiazol-5-yl, 3-(3-fluoro-5-(trifluoromethyl)phenyl)-1,2,4-oxadiazol-5-yl, 4-methylthiophen-2-yl, 6-(trifluoromethyl)pyridin-3-yl, 1,5,6-trimethyl-1H-benzo[d]imidazol-2-yl, 5-(trifluoromethyl)-1H-benzo[d]imidazol-2-yl, [3-(trifluoromethyl)phenyl]amine, cyclopropanecarboxamido, 3,3-dimethylbut-1-ynyl, 2-cyclopropylethynyl, (2,5-dichlorophenyl)ethynyl, (4-chloro-2-fluorophenyl)ethynyl, (3-chloro-2-fluorophenyl)ethynyl, [2-chloro-4-(trifluoromethyl)phenyl]ethynyl, [2-(trifluoromethyl)phenyl]ethynyl, (6-fluoropyridin-3-yl)ethynyl, [5-(trifluoromethyl)pyridin-2-yl]ethynyl, (3-chloropyridin-4-yl)ethynyl, (2-morpholinopyrimidin-5-yl)ethynyl, [6-(morpholin-4-yl)pyridin-3-yl]ethynyl, C(O)NH-[(cyclopropyl)methyl], —CONH-[4-(trifluoromethyl)phenyl]-CONH-[3-(trifluoromethyl)phenyl], —CONH-[3-(difluoromethyl)phenyl], —CONH-[4-fluoro-3-(trifluoromethyl)phenyl], —CONH-[2-fluoro-5-(trifluoromethyl)phenyl], —CONH-[2-chloro-4-methylphenyl], —CONH-[2-fluoro-4-methylphenyl], —CONH-[5-chloro-2-methylphenyl], —CONH-[3-(difluoromethyl)-4-fluorophenyl], —CONH-[3-(difluoromethyl)phenyl], —CONH-{2-chloro-5-(cyclopropanecarboxamidomethyl)phenyl}, —CONH-[2-(trifluoromethyl)benzyl], —CONH-[4-fluoro-2-(trifluoromethyl)benzyl], —CONH-{1-[2-(trifluoromethyl)phenyl]cyclopropyl}, —CONH-{1-[4-(trifluoromethyl)phenyl]cyclopropyl}, —CONH-6-fluorobenzo[d]thiazol-2-yl), —CONH-{1H-benzo[d]imidazol-2-yl}, —CONH-{5-(trifluoromethyl)-1,3,4-thiadiazol-2-yl}, or —CONH-[4-(methylsulfonyl)phenyl].

According to yet another embodiment, specifically provided are compounds of formula (I), in which each occurrence of $R^2$ is —C(O)NHR or —C≡CR. In this embodiment R is cyclopropyl or cyclopropylmethyl, each of which may be optionally substituted with one or more substituents selected from halogen (e.g. F, Cl or Br), $C_{1-8}$alkyl (e.g. methyl or ethyl), halo$C_{1-8}$alkyl (e.g. trifluoromethyl) and substituted phenyl (e.g. 2-(trifluoromethyl)phenyl and 4-(trifluoromethyl)phenyl).

According to yet another embodiment, specifically provided are compounds of formula (I), in which each occurrence of $R^2$ is —C(O)NHR or In this embodiment R is phenyl optionally substituted with one or more substituents selected from halogen (e.g. F, Cl or Br), $C_{1-8}$ alkyl (e.g. methyl or ethyl), halo$C_{1-8}$alkyl (e.g. trifluoromethyl or difluoromethyl), $C_{1-8}$ alkoxy (e.g. methoxy or ethoxy), halo$C_{1-8}$ alkoxy (e.g. trifluoromethoxy) and —$SO_2R^{x'}$ (e.g. methylsulfonyl).

According to yet another embodiment, specifically provided are compounds of formula (I), in which each occurrence of $R^2$ is —C(O)NHR or —C≡CR. In this embodiment R is benzyl optionally substituted with one or more substituents selected from halogen (e.g. F, Cl or Br), $C_{1-8}$alkyl (e.g. methyl or ethyl) and halo$C_{1-8}$alkyl (e.g. trifluoromethyl).

According to yet another embodiment, specifically provided are compounds of formula (I), in which each occurrence of $R^2$ is —C≡CR. In this embodiment R is pyridine or pyrimidine, each of which may be optionally substituted with one or more substituents selected from halogen (e.g. F, Cl or Br), $C_{1-8}$alkyl (e.g. methyl or ethyl), halo$C_{1-8}$alkyl (e.g. trifluoromethyl) and 5 membered heterocyclyl (e.g. morpholinyl).

According to yet another embodiment, specifically provided are compounds of formula (I), in which 'm' is 0, 1 or 2.

According to yet another embodiment, specifically provided are compounds of formula (I), in which 'm' is 1 or 2.

According to yet another embodiment, specifically provided are compounds of formula (I), in which each occurrence of W is $C_{1-8}$alkyl (e.g. isopropyl or tert-butyl), halo$C_{1-8}$ alkyl (e.g. trifluoromethyl or 1-fluoro-2-methylpropan-2-yl), hydroxy$C_{1-8}$alkyl (e.g. 1-hydroxy-2-methylpropan-2-yl) or $C_{3-12}$cycloalkyl (e.g. cyclopropyl).

According to yet another embodiment, specifically provided are compounds of formula (I), in which each occurrence of W is $C_{1-4}$alkyl (e.g. isopropyl or tert-butyl), halo$C_{1-8}$ alkyl (e.g. trifluoromethyl or 1-fluoro-2-methylpropan-2-yl), hydroxy$C_{1-8}$alkyl (e.g. 1-hydroxy-2-methylpropan-2-yl) or $C_{3-6}$cycloalkyl (e.g. cyclopropyl).

According to yet another embodiment, specifically provided are compounds of formula (I), in which each occurrence of W is isopropyl, tert-butyl, trifluoromethyl, 1-fluoro-2-methylpropan-2-yl, 1-hydroxy-2-methylpropan-2-yl or cyclopropyl.

According to yet another embodiment, specifically provided are compounds of formula (I), in which each occurrence of Q is $C_{1-8}$alkyl (e.g. isopropyl or tert-butyl), halo$C_{1-8}$ alkyl (e.g. trifluoromethyl or 1-fluoro-2-methylpropan-2-yl), $C_{1-8}$alkoxy$C_{1-8}$alkyl (e.g. 1-methoxy-2-methylpropan-2-yl), hydroxy$C_{1-8}$alkyl (e.g. 1-hydroxy-2-methylpropan-2-yl), $C_{3-12}$cycloalkyl (e.g. cyclopropyl, cyclobutyl or cyclopentyl), $C_{6-14}$aryl (e.g. 2-fluorophenyl), 3-15 membered heterocyclyl (e.g. tetrahydrofuranyl, tetrahydrofuran-2-yl, (S)-tetrahydrofuran-2-yl or (R)-tetrahydrofuran-2-yl) or 5-14 membered heteroaryl (e.g. isoxazolyl or 1-methyl-1H-imidazole-2-yl).

According to yet another embodiment, specifically provided are compounds of formula (I), in which each occurrence of Q is isopropyl, tert-butyl, trifluoromethyl, 1-fluoro-2-methylpropan-2-yl, 1-methoxy-2-methylpropan-2-yl, 1-hydroxy-2-methylpropan-2-yl, cyclopropyl, cyclobutyl, cyclopentyl, 2-fluorophenyl, tetrahydrofuranyl, tetrahydrofuranyl, tetrahydrofuran-2-yl, (S)-tetrahydrofuran-2-yl, (R)-tetrahydrofuran-2-yl, isoxazolyl or 1-methyl-1H-imidazole-2-yl.

According to yet another embodiment, specifically provided are compounds of formula (I), in which 's' is 0 and 't' is 1.

According to yet another embodiment, specifically provided are compounds of formula (I), in which 's' is 1 and 't' is 0.

According to yet another embodiment, specifically provided are compounds of formula (I), in which 's' is 1 and 't' is 1.

According to yet another embodiment, specifically provided are compounds of formula (I), in which 's' is 0 and 't' is 0.

According to yet another embodiment, specifically provided are compounds of formula (I), in which each occurrence of R is independently selected from $C_{1-8}$alkyl (e.g. isopropyl or tert-butyl), $C_{3-12}$ cycloalkyl (e.g. cyclopropyl, 1-[2-(trifluoromethyl)phenyl]cyclopropyl, or 1-[4-(trifluoromethyl)phenyl]cyclopropyl), $C_{3-8}$cycloalkyl$C_{1-8}$alkyl (e.g. (cyclopropyl)methyl), $C_{6-14}$aryl (e.g. 2,5-dichlorophenyl, 4-chloro-2-fluorophenyl, 3-chloro-2-fluorophenyl, 4-(trifluoromethyl)phenyl, 3-(trifluoromethyl)phenyl, 2-(trifluoromethyl)phenyl, 3-(difluoromethyl)phenyl, 2-chloro-4-(trifluoromethyl)phenyl, 4-fluoro-3-(trifluoromethyl)phenyl, 2-fluoro-5-(trifluoromethyl)phenyl, 2-chloro-4-methylphenyl, 2-fluoro-4-methylphenyl, 5-chloro-2-methylphenyl, 3-(difluoromethyl)-4-fluorophenyl, 3-(difluoromethyl)phenyl, 4-(methylsulfonyl)phenyl or 2-chloro-5-(cyclopropanecarboxamidomethyl)phenyl), $C_{6-14}$aryl$C_{1-8}$alkyl (e.g. 2-(trifluoromethyl)benzyl or 4-fluoro-2-(trifluoromethyl) benzyl), and 5-14 membered heteroaryl (e.g. 6-fluorobenzo[d]thiazol-2-yl, 1H-benzo[d]imidazol-2-yl, or 5-(trifluoromethyl)-1,3,4-thiadiazol-2-yl).

According to yet another embodiment, specifically provided are compounds of formula (I), in which each occurrence of R is independently selected from isopropyl, tert-butyl, cyclopropyl, 1-[2-(trifluoromethyl)phenyl]cyclopropyl, 1-[4-(trifluoromethyl)phenyl]cyclopropyl), (cyclopropyl)methyl, 2,5-dichlorophenyl, 4-chloro-2-fluorophenyl, 3-chloro-2-fluorophenyl, 4-(trifluoromethyl)phenyl, 3-(trifluoromethyl)phenyl, 2-(trifluoro methyl)phenyl, 3-(difluoromethyl)phenyl, 2-chloro-4-(trifluoromethyl)phenyl, 4-fluoro-3-(trifluoromethyl)phenyl, 2-fluoro-5-(trifluoromethyl)phenyl, 2-chloro-4-methylphenyl, 2-fluoro-4-methylphenyl, 5-chloro-2-methylphenyl, 3-(difluoromethyl)-4-fluorophenyl, 3-(difluoromethyl)phenyl, 4-(methylsulfonyl)phenyl, 2-chloro-5-(cyclopropanecarboxamidomethyl)phenyl, 2-(trifluoromethyl)benzyl, 4-fluoro-2-(trifluoromethyl)benzyl), 6-fluorobenzo[d]thiazol-2-yl, 1H-benzo[d]imidazol-2-yl, or 5-(trifluoromethyl)-1,3,4-thiadiazol-2-yl.

According to an embodiment, specifically provided are compounds of formula (I) that exhibit an $IC_{50}$ value of less than 500 nM, preferably less than 100 nM, more preferably less than 50 nM, with respect to mPGES-1 inhibition.

Further embodiments relating to groups $R^1$, $R^2$, m, n, s, t, P, L, Q and W (and groups defined therein) are described hereinafter in relation to the compounds of formula (II), formula (III) and formula (IV). It is to be understood that these embodiments are not limited to use in conjunction with formula (II), formula (III) or formula (IV), but apply independently and individually to the compounds of formula (I). For example, in an embodiment described hereinafter; the invention specifically provides compounds of formula (II), formula (III) or formula (IV) in which 'n' is 0, 1 or 2, and consequently, there is also provided a compound of formula (I) in which 'n' is 0, 1 or 2.

The invention also provides a compound of formula (II), which is an embodiment of a compound of formula (I).

Accordingly the invention provides a compound of formula (II)

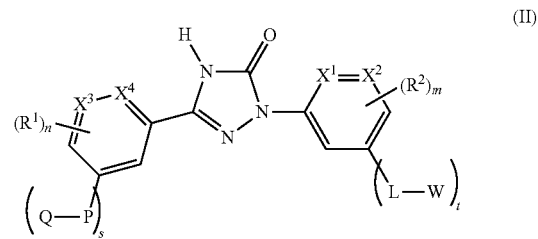

(II)

or a pharmaceutically acceptable salt thereof,
wherein,
$X^1$, $X^2$, $X^3$ and $X^4$ are each independently selected from CH and N;
each occurrence of L is independently selected from —$CH_2NHC(O)$— and —$CH_2NHS(O)_2$—;
each occurrence of P is independently selected from —$CH_2NHC(O)$— and —$CH_2NHS(O)_2$—;
each occurrence of Q is independently selected from $C_{1-8}$alkyl, halo$C_{1-8}$alkyl, $C_{1-8}$alkoxy$C_{1-8}$alkyl, hydroxy$C_{1-8}$alkyl, carboxyl$C_{1-8}$alkyl, $C_{3-12}$cycloalkyl, $C_{6-14}$ aryl, 3-15 membered heterocyclyl, and 5-14 membered heteroaryl;
each occurrence of W is independently selected from $C_{1-8}$alkyl, halo$C_{1-8}$alkyl, $C_{1-8}$alkoxy$C_{1-8}$alkyl, hydroxy$C_{1-8}$alkyl, carboxyl$C_{1-8}$alkyl, $C_{3-12}$cycloalkyl, $C_{6-14}$aryl, 3-15 membered heterocyclyl, and 5-14 membered heteroaryl;
each occurrence of $R^1$ is independently selected from halogen, cyano, $C_{1-8}$alkyl, $C_{1-8}$alkoxy, halo$C_{1-8}$alkoxy$C_{1-8}$alkyl, halo$C_{1-8}$alkyl, $C_{3-6}$ cycloalkyl, 5 membered heterocyclyl$C_{1-8}$alkyl, 5 membered heteroaryl, 5 membered heteroaryl$C_{1-8}$alkyl, and —C≡CR;
each occurrence of $R^2$ is independently selected from halogen, cyano, $C_{1-8}$alkyl, $C_{1-8}$alkoxy, halo$C_{1-8}$alkyl, $C_{3-6}$cycloalkyl, 5 membered heteroaryl, —C(O)NHR, —NHC(O)R, —S(O)$_2$NHR and —C≡CR;
each occurrence of R is independently selected from $C_{1-8}$alkyl, $C_{3-12}$cycloalkyl, and $C_{6-14}$aryl;
'm' is an integer ranging from 0 to 3, both inclusive;
'n' is an integer ranging from 0 to 3, both inclusive;
's' is an integer ranging from 0 to 1, both inclusive; and
't' is an integer ranging from 0 to 1, both inclusive;
with the provisos that (i) 's' and 't' are not '0' simultaneously, and (ii) 'm' and 'n' are not '0' simultaneously.

The compounds of formula (II) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition of any other embodiment defined herein. Thus the invention contemplates all possible combinations and permutations of the various independently described embodiments. For example, the invention provides compounds of formula (II) as defined above wherein $X^1$, $X^2$, $X^3$ and $X^4$ are CH (according to an embodiment defined below), 'm' is 0, 1 or 2 (according to another embodiment defined below), and 's' is 0 and 't' is 1 (according to another embodiment defined below).

According to one embodiment, specifically provided are compounds of formula (II), in which $X^1$, $X^2$, $X^3$ and $X^4$ are CH.

According to another embodiment, specifically provided are compounds of formula (II), in which $X^1$ is N and $X^2$, $X^3$ and $X^4$ are CH.

According to yet another embodiment, specifically provided are compounds of formula (II), in which $X^2$ is N and $X^1$, $X^3$ and $X^4$ are CH.

According to yet another embodiment, specifically provided are compounds of formula (II), in which $X^3$ is N and $X^1$, $X^2$ and $X^4$ are CH.

According to yet another embodiment, specifically provided are compounds of formula (II), in which each occurrence of L is —CH$_2$NHC(O)—.

According to yet another embodiment, specifically provided are compounds of formula (II), in which each occurrence of P is —CH$_2$NHC(O)—.

According to yet another embodiment, specifically provided are compounds of formula (II), in which each occurrence of $R^1$ is independently selected from cyano, halogen (e.g. F, Cl or Br), $C_{1-8}$alkyl (e.g. methyl), halo$C_{1-8}$alkyl (e.g. trifluoromethyl or difluoromethyl), $C_{1-8}$alkoxy (e.g. methoxy), halo$C_{1-8}$alkoxy$C_{1-8}$alkyl (e.g. (2,2,2-trifluoroethoxy)methyl), $C_{3-6}$cycloalkyl (e.g. cyclopropyl), 5 membered heterocyclyl$C_{1-8}$alkyl (e.g. (pyrrolidin-1-yl)methyl), 5 membered heteroaryl (e.g. 4-methylthiophenyl, 5-isopropyl-1,3,4-oxadiazol-2-yl), 5 membered heteroaryl$C_{1-8}$alkyl (e.g. (3,5-dimethyl-1H-pyrazol-1-yl)methyl) and —C≡CR.

According to yet another embodiment, specifically provided are compounds of formula (II), in which each occurrence of $R^1$ is independently selected from cyano, Cl, F, CHF$_2$, CF$_3$, OCH$_3$, CH$_3$, (2,2,2-trifluoroethoxy)methyl, cyclopropyl, (pyrrolidin-1-yl)methyl, 4-methylthiophenyl, 5-isopropyl-1,3,4-oxadiazol-2-yl, (3,5-dimethyl-1H-pyrazol-1-yl)methyl and —C≡CR. In this embodiment R is isopropyl, tert-butyl, cyclopropyl, 4-chloro-2-fluorophenyl, 3-chloro-2-fluorophenyl, 3-(trifluoromethyl)phenyl or 2-chloro-4-(trifluoromethyl)phenyl.

According to yet another embodiment, specifically provided are compounds of formula (II), in which each occurrence of $R^1$ is independently selected from cyano, Cl, F, CHF$_2$, CF$_3$, OCH$_3$, CH$_3$, (2,2,2-trifluoroethoxy)methyl, cyclopropyl, (pyrrolidin-1-yl)methyl, 4-methylthiophenyl, 5-isopropyl-1,3,4-oxadiazol-2-yl, (3,5-dimethyl-1H-pyrazol-1-yl)methyl, 3,3-dimethylbut-1-ynyl, 2-cyclopropylethynyl, (2,5-dichlorophenyl)ethynyl, (4-chloro-2-fluorophenyl)ethynyl, (3-chloro-2-fluorophenyl)ethynyl, (3-(trifluoro methyl)phenyl)ethynyl and (2-chloro-4-(trifluoromethyl)phenyl)ethynyl.

According to yet another embodiment, specifically provided are compounds of formula (II), in which each occurrence of $R^1$ is independently cyano, Cl, F, CHF$_2$, CF$_3$, OCH$_3$, CH$_3$, (2,2,2-trifluoroethoxy)methyl, cyclopropyl, (pyrrolidin-1-yl)methyl, 4-methylthiophenyl, 5-isopropyl-1,3,4-oxadiazol-2-yl, (3,5-dimethyl-1H-pyrazol-I-yl)methyl, 3,3-dimethylbut-1-ynyl, 2-cyclopropylethynyl, (2,5-dichlorophenyl)ethynyl, (4-chloro-2-fluorophenyl)ethynyl, (3-chloro-2-fluorophenyl)ethynyl, (3-(trifluoromethyl)phenyl)ethynyl or (2-chloro-4-(trifluoromethyl)phenyl)ethynyl; and 'n' is 1 or 2.

According to yet another embodiment, specifically provided are compounds of formula (II), in which 'n' is 0, 1 or 2.

According to yet another embodiment, specifically provided are compounds of formula (II), in which each occurrence of $R^2$ is independently selected from cyano, halogen (e.g. F, Cl or Br), $C_{1-8}$alkyl (e.g. methyl), halo$C_{1-8}$alkyl (e.g. trifluoromethyl), $C_{1-8}$alkoxy (e.g. methoxy), 5 membered heteroaryl (e.g. 3-(4-chlorophenyl)-1,2,4-oxadiazol-5-yl), —C(O)NHR, —NHC(O)R and —C≡CR.

According to yet another embodiment, specifically provided are compounds of formula (II), in which each occurrence of $R^2$ is independently —C(O)NHR, —NHC(O)R or —C≡CR. In this embodiment R is isopropyl, tert-butyl, cyclopropyl, 4-chloro-2-fluorophenyl, 3-chloro-2-fluorophenyl, 3-(trifluoromethyl)phenyl, 2-chloro-4-(trifluoromethyl)phenyl, 3-(difluoromethyl)-4-fluorophenyl or 3-(difluoromethyl)phenyl).

According to yet another embodiment, specifically provided are compounds of formula (II), in which each occurrence of $R^2$ is independently cyano, Cl, F, CH$_3$, CF$_3$, OCH$_3$, 3-(4-chlorophenyl)-1,2,4-oxadiazol-5-yl, cyclopropanecarboxamido, 3,3-dimethylbut-1-ynyl, 2-cyclopropylethynyl, —CONH-[3-(trifluoromethyl)phenyl], CONH[3-(difluoromethyl)-4-fluorophenyl] or —CONH-[3-(difluoromethyl)phenyl].

According to yet another embodiment, specifically provided are compounds of formula (II), in which each occurrence of $R^2$ is independently cyano, Cl, F, CH$_3$, CF$_3$, OCH$_3$, 3-(4-chlorophenyl)-1,2,4-oxadiazol-5-yl, cyclopropanecarboxamido, 3,3-dimethylbut-1-ynyl, 2-cyclopropylethynyl, —CONH-[3-(trifluoromethyl)phenyl], —CONH-[3-(difluoromethyl)-4-fluorophenyl] or —CONH[3-(difluoromethyl) phenyl]; and 'm' is 1 or 2.

According to yet another embodiment, specifically provided are compounds of formula (II), in which 'm' is 0, 1 or 2.

According to yet another embodiment, specifically provided are compounds of formula (II), in which each occurrence of W is $C_{1-8}$alkyl (e.g. isopropyl or tert-butyl), halo$C_{1-8}$ alkyl (e.g. trifluoromethyl or 1-fluoro-2-methylpropan-2-yl), hydroxy$C_{1-8}$alkyl (e.g. 1-hydroxy-2-methylpropan-2-yl) or $C_{3-12}$ cycloalkyl (e.g. cyclopropyl).

According to yet another embodiment, specifically provided are compounds of formula (II), in which each occurrence of W is $C_{1-4}$alkyl (e.g. isopropyl or tert-butyl), halo$C_{1-8}$ alkyl (e.g. trifluoromethyl or 1-fluoro-2-methylpropan-2-yl), hydroxy$C_{1-8}$alkyl (e.g. 1-hydroxy-2-methylpropan-2-yl) or $C_{3-6}$cycloalkyl (e.g. cyclopropyl).

According to yet another embodiment, specifically provided are compounds of formula (II), in which each occurrence of W is isopropyl, tert-butyl, trifluoromethyl, 1-fluoro-2-methylpropan-2-yl, 1-hydroxy-2-methylpropan-2-yl or cyclopropyl.

According to yet another embodiment, specifically provided are compounds of formula (II), in which W is isopropyl, tert-butyl, trifluoromethyl, 1-fluoro-2-methylpropan-2-yl, 1-hydroxy-2-methylpropan-2-yl or cyclopropyl; 't' is 1; and 's' is 0.

According to yet another embodiment, specifically provided are compounds of formula (II), in which each occurrence of Q is $C_{1-8}$alkyl (e.g. isopropyl or tert-butyl), halo$C_{1-8}$ alkyl (e.g. trifluoromethyl or 1-fluoro-2-methylpropan-2-yl), $C_{1-8}$ alkoxy$C_{1-8}$alkyl (e.g. 1-methoxy-2-methylpropan-2-yl), hydroxy$C_{1-8}$alkyl (e.g. 1-hydroxy-2-methylpropan-2-yl), $C_{3-12}$cycloalkyl (e.g. cyclopropyl, cyclobutyl or cyclopentyl), $C_{6-14}$aryl (e.g. 2-fluorophenyl), 3-15 membered heterocyclyl (e.g. tetrahydrofuranyl, tetrahydrofuran-2-yl, (S)-tetrahydrofuran-2-yl or (R)-tetrahydrofuran-2-yl) or 5-14 membered heteroaryl (e.g. isoxazolyl or 1-methyl-1H-imidazole-2-yl).

According to yet another embodiment, specifically provided are compounds of formula (II), in which each occurrence of Q is isopropyl, tert-butyl, trifluoromethyl, 1-fluoro-2-methylpropan-2-yl, 1-methoxy-2-methylpropan-2-yl, 1-hydroxy-2-methylpropan-2-yl, cyclopropyl, cyclobutyl, cyclopentyl, 2-fluorophenyl, tetrahydrofuranyl, tetrahydrofuranyl, tetrahydrofuran-2-yl, (S)-tetrahydrofuran-2-yl, (R)-tetrahydrofuran-2-yl, isoxazolyl or 1-methyl-1H-imidazole-2-yl.

According to yet another embodiment, specifically provided are compounds of formula (II), in which Q is isopropyl, tert-butyl, trifluoromethyl, 1-fluoro-2-methylpropan-2-yl, 1-methoxy-2-methylpropan-2-yl, 1-hydroxy-2-methylpropan-2-yl, cyclopropyl, cyclobutyl, cyclopentyl, 2-fluorophenyl, tetrahydrofuranyl, tetrahydrofuranyl, tetrahydrofuran-2-yl, (S)-tetrahydrofuran-2-yl, (R)-tetrahydrofuran-2-yl, isoxazolyl or 1-methyl-1H-imidazole-2-yl; 's' is 1; and 't' is 0.

According to yet another embodiment, specifically provided are compounds of formula (II), in which 's' is 0 and 't' is 1.

According to yet another embodiment, specifically provided are compounds of formula (II), in which 's' is 1 and T is 0.

According to yet another embodiment, specifically provided are compounds of formula (II), in which 's' is 1 and 't' is 1.

According to yet another embodiment, specifically provided are compounds of formula (II), in which each occurrence of R is independently selected from $C_{1-8}$alkyl (e.g. isopropyl or tert-butyl), $C_{3-12}$Cycloalkyl (e.g. cyclopropyl) and $C_{6-14}$aryl (e.g. 4-chloro-2-fluorophenyl, 3-chloro-2-fluorophenyl, 3-(trifluoromethyl)phenyl, 2-chloro-4-(trifluoromethyl)phenyl, 3-(difluoromethyl)-4-fluorophenyl or 3-(difluoromethyl)phenyl).

According to yet another embodiment, specifically provided are compounds of formula (II), in which each occurrence of R is phenyl optionally substituted with one or more substituents selected from Cl, F, $CH_3$, trifluoromethyl and difluoromethyl.

According to yet another embodiment, specifically provided are compounds of formula (II), in which each occurrence of R is independently isopropyl, tert-butyl, cyclopropyl, 4-chloro-2-fluorophenyl, 3-chloro-2-fluorophenyl, 3-(trifluoromethyl)phenyl, 2-chloro-4-(trifluoromethyl)phenyl, 3-(difluoromethyl)-4-fluorophenyl or 3-(difluoromethyl)phenyl.

According to an embodiment, specifically provided are compounds of formula (II) that exhibit an $IC_{50}$ value of less than 500 nM, preferably less than 100 nM, more preferably less than 50 nM with respect to mPGES-1 inhibition.

Further embodiments relating to groups $R^1$, $R^2$; m, n, s, t, P, L, Q and W (and groups defined therein) are described herein in relation to the compounds of formula (I), formula (III) or formula (IV). It is to be understood that these embodiments are not limited to use in conjunction with formula (I), formula (III) or formula (IV), but apply independently and individually to the compounds of formula (II). For example, in an embodiment described hereinafter, the invention specifically provides compounds of formula (I), formula (III) or formula (IV) in which 'n' is 0, 1 or 2, and consequently there is also provided a compound of formula (II) in which 'n' is 0, 1 or 2.

The invention also provides a compound of formula (III), which is an embodiment of a compound of formula (I).

Accordingly the invention provides the compound of formula (III)

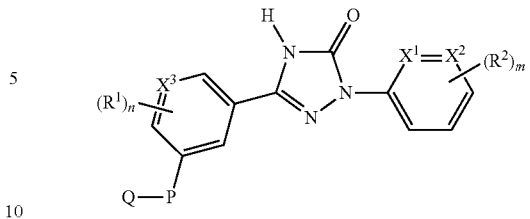

(III)

or a pharmaceutically acceptable salt thereof,
wherein,
$X^1$, $X^2$ and $X^3$ are each independently selected from CH and N;
P is selected from —$CH_2$NHC(O)— and —$CH_2$NHS$(O)_2$—;
Q is selected from $C_{1-8}$alkyl, halo$C_{1-8}$alkyl, $C_{1-8}$alkoxy$C_{1-8}$alkyl, hydroxy$C_{1-8}$alkyl, carboxyl$C_{1-8}$alkyl, $C_{3-12}$cycloalkyl, $C_{6-14}$ aryl, 3-15 membered heterocyclyl, and 5-14 membered heteroaryl;
each occurrence of $R^1$ is independently selected from halogen, cyano, $C_{1-8}$alkyl, $C_{1-8}$alkoxy, halo$C_{1-8}$alkyl and $C_{3-6}$ cycloalkyl;
each occurrence of $R^2$ is independently selected from halogen, cyano, $C_{1-8}$alkyl, $C_{1-8}$alkoxy, halo$C_{1-8}$alkyl, $C_{3-6}$cycloalkyl, 5 membered heteroaryl, —C(O)NHR, —NHC(O)R, —S(O)$_2$NHR and —C≡CR;
each occurrence of R is independently selected from $C_{1-8}$alkyl, $C_{3-12}$cycloalkyl, and $C_{6-14}$aryl;
'm' is an integer ranging from 0 to 3, both inclusive; and
'n' is an integer ranging from 0 to 3, both inclusive;
with the proviso that 'm' and 'n' are not '0' simultaneously.

The compounds of formula (III) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition of any other embodiment defined herein. Thus the invention contemplates all possible combinations and permutations of the various independently described embodiments. For example, the invention provides compounds of formula (III) as defined above wherein $X^1$, $X^2$ and $X^3$ are CH (according to an embodiment defined below), 'm' is 0, 1 or 2 (according to another embodiment defined below) and 'n' is 0, 1 or 2 (according to another embodiment defined below).

According to one embodiment, specifically provided are compounds of formula (III), in which $X^1$, $X^2$ and $X^3$ are CH.

According to another embodiment, specifically provided are compounds of formula (III), in which $X^1$ is N and $X^2$ and $X^3$ are CH.

According to yet another embodiment, specifically provided are compounds of formula (III), in which $X^2$ is N and $X^1$ and $X^3$ are CH.

According to yet another embodiment, specifically provided are compounds of formula (III), in which $X^3$ is N and $X^1$ and $X^2$ are CH.

According to yet another embodiment, specifically provided are compounds of formula (III), in which P is —$CH_2$NHC(O)—.

According to yet another embodiment, specifically provided are compounds of formula (III), in which each occurrence of $R^1$ is independently selected from cyano, halogen (e.g. F, Cl or Br), $C_{1-8}$alkyl (e.g. methyl), halo$C_{1-8}$alkyl (e.g.

trifluoromethyl or difluoromethyl), $C_{1-8}$alkoxy (e.g. methoxy) and $C_{3-6}$cycloalkyl (e.g. cyclopropyl).

According to yet another embodiment, specifically provided are compounds of formula (III), in which each occurrence of $R^1$ is independently selected from cyano, Cl, F, $CHF_2$, $CF_3$, $OCH_3$, $CH_3$ and cyclopropyl.

According to yet another embodiment, specifically provided are compounds of formula (III), in which each occurrence of $R^1$ is independently cyano, Cl, F, $CHF_2$, $CF_3$, $OCH_3$, $CH_3$ or cyclopropyl; and 'n' is 1 or 2.

According to yet another embodiment, specifically provided are compounds of formula (III), in which 'n' is 0, 1 or 2.

According to yet another embodiment, specifically provided are compounds of formula (III), in which each occurrence of $R^2$ is independently selected from cyano, halogen (e.g. F, Cl or Br), $C_{1-8}$alkyl (e.g. methyl), halo$C_{1-8}$alkyl (e.g. trifluoromethyl), $C_{1-8}$alkoxy (e.g. methoxy), 5 membered heteroaryl (e.g. 3-(4-chlorophenyl)-1,2,4-oxadiazol-5-yl), —C(O)NHR, —NHC(O)R and —C≡CR.

According to yet another embodiment, specifically provided are compounds of formula (III), in which each occurrence of $R^2$ is independently —C(O)NHR, —NHC(O)R and —C≡CR. R is isopropyl, tert-butyl, cyclopropyl, 4-chloro-2-fluorophenyl, 3-chloro-2-fluorophenyl, 3-(trifluoromethyl)phenyl, 2-chloro-4-(trifluoromethyl)phenyl, 3-(difluoromethyl)-4-fluorophenyl or 3-(difluoromethyl)phenyl.

According to yet another embodiment, specifically provided are compounds of formula (III), in which each occurrence of $R^2$ is independently cyano, Cl, F, $CH_3$, $CF_3$, $OCH_3$, 3-(4-chlorophenyl)-1,2,4-oxadiazol-5-yl, cyclopropanecarboxamido, 3,3-dimethylbut-1-ynyl, 2-cyclopropylethynyl, —CONH[3-(trifluoromethyl)phenyl], —CONH-[3-(difluoromethyl)-4-fluorophenyl] or —CONH[3-(difluoromethyl) phenyl].

According to yet another embodiment, specifically provided are compounds of formula (III), in which $R^2$ is independently cyano, Cl, F, $CH_3$, $CF_3$, $OCH_3$, 3-(4-chlorophenyl)-1,2,4-oxadiazol-5-yl, cyclopropanecarboxamido, 3,3-dimethyl but-1-ynyl, 2-cyclopropylethynyl, —CONH-[3-(trifluoromethyl)phenyl], —CONH-[3-(difluoromethyl)-4-fluorophenyl] or —CONH-[3-(difluoromethyl)phenyl]; and 'm' is 1 or 2.

According to yet another embodiment, specifically provided are compounds of formula (III), in which 'm' is 0, 1 or 2.

According to yet another embodiment, specifically provided are compounds of formula (III), in which Q is $C_{1-8}$alkyl (e.g. isopropyl or tert-butyl), halo$C_{1-8}$alkyl (e.g. trifluoromethyl or 1-fluoro-2-methylpropan-2-yl), $C_{1-8}$ alkoxy$C_{1-8}$alkyl (e.g. 1-methoxy-2-methylpropan-2-yl), hydroxy$C_{1-8}$alkyl (e.g. 1-hydroxy-2-methylpropan-2-yl), $C_{3-12}$cycloalkyl (e.g. cyclopropyl, cyclobutyl or cyclopentyl), $C_{6-14}$ aryl (e.g. 2-fluorophenyl), 3-15 membered heterocyclyl (e.g. tetrahydrofuranyl, tetrahydrofuran-2-yl, (S)-tetrahydrofuran-2-yl or (R)-tetrahydrofuran-2-yl) or 5-14 membered heteroaryl (e.g. isoxazolyl or 1-methyl-1H-imidazole-2-yl).

According to yet another embodiment, specifically provided are compounds of formula (III), in which Q is isopropyl, tert-butyl, trifluoromethyl, 1-fluoro-2-methylpropan-2-yl, 1-methoxy-2-methylpropan-2-yl, 1-hydroxy-2-methylpropan-2-yl, cyclopropyl, cyclobutyl, cyclopentyl, 2-fluorophenyl, tetrahydrofuranyl, tetrahydrofuran-2-yl, (S)-tetrahydrofuran-2-yl, (R)-tetrahydrofuran-2-yl, isoxazolyl or 1-methyl-1H-imidazole-2-yl.

According to yet another embodiment, specifically provided are compounds of formula (III), in which each occurrence of R is independently selected from $C_{1-8}$alkyl (e.g. isopropyl or tert-butyl), $C_{3-12}$cycloalkyl (e.g. cyclopropyl) and $C_{6-14}$aryl (e.g. 4-chloro-2-fluorophenyl, 3-chloro-2-fluorophenyl, 3-(trifluoromethyl)phenyl, 2-chloro-4-(trifluoromethyl)phenyl, 3-(difluoromethyl)-4-fluorophenyl or 3-(difluoromethyl)phenyl).

According to yet another embodiment, specifically provided are compounds of formula (III), in which each occurrence of R is phenyl, optionally substituted with one or more substituents selected from Cl, F, $CH_3$, trifluoromethyl and difluoromethyl.

According to yet another embodiment, specifically provided are compounds of formula (III), in which each occurrence of R is independently isopropyl, tert-butyl, cyclopropyl, 4-chloro-2-fluorophenyl, 3-chloro-2-fluorophenyl, 3-(trifluoromethyl)phenyl, 2-chloro-4-(trifluoromethyl)phenyl, 3-(difluoromethyl)-4-fluorophenyl or 3-(difluoromethyl)phenyl.

According to yet another embodiment, specifically provided are compounds of formula (III), in which:
each $R^1$ is, independently, cyano, Cl, F, $CHF_2$, $CF_3$, $OCH_3$, $CH_3$ or cyclopropyl;
each $R^2$ is, independently, cyano, Cl, F, $CH_3$, $CF_3$ or $OCH_3$;
P is —$CH_2$NHC(O)—;
'm' is 1 or 2;
'n' is 0, 1 or 2; and
Q is isopropyl, tert-butyl, trifluoromethyl, 1-fluoro-2-methylpropan-2-yl, 1-methoxy-2-methylpropan-2-yl, 1-hydroxy-2-methylpropan-2-yl, cyclopropyl, cyclobutyl, cyclopentyl, 2-fluorophenyl, tetrahydrofuranyl, tetrahydrofuran-2-yl, (S)-tetrahydrofuran-2-yl, (R)-tetrahydrofuran-2-yl, isoxazolyl or 1-methyl-1H-imidazole-2-yl.

According to an embodiment, specifically provided are compounds of formula (III) which exhibit an $IC_{50}$ value of less than 500 nM, preferably less than 100 nM, more preferably less than 50 nM with respect to mPGES-1 inhibition.

Further embodiments relating to groups $R^1$; $R^2$, m, n, s, t, P, L, Q and W (and groups defined therein) are described herein in relation to the compounds of formula (I), formula (II) or formula (IV). It is to be understood that these embodiments are not limited to use in conjunction with formula (I), formula (II) or formula (IV), but apply independently and individually to the compounds of formula (III). For example, in an embodiment described hereinafter, the invention specifically provides compounds of formula (I), formula (II) or formula (IV) in which 'n' is 0, 1 or 2, and consequently there is also provided a compound of formula (III) in which 'n' is 0, 1 or 2.

The invention also provides a compound of formula (IV), which is an embodiment of a compound of formula (I).

Accordingly the invention provides the compound of formula (IV)

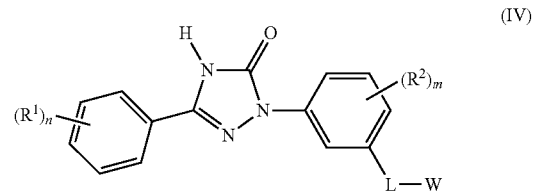

(IV)

or a pharmaceutically acceptable salt thereof, wherein,

L is selected from —CH₂NHC(O)— and —CH₂NHS(O)₂—;

W is selected from C$_{1-8}$alkyl, haloC$_{1-8}$alkyl, C$_{1-8}$alkoxyC$_{1-8}$alkyl, hydroxyC$_{1-8}$alkyl, carboxylC$_{1-8}$alkyl, C$_{3-12}$cycloalkyl, C$_{6-14}$aryl, 3-15 membered heterocyclyl, and 5-14 membered heteroaryl;

each occurrence of R$^1$ is independently selected from halogen, cyano, C$_{1-8}$alkyl, C$_{1-8}$ alkoxy, haloC$_{1-8}$alkoxyC$_{1-8}$alkyl, haloC$_{1-8}$alkyl, C$_{3-6}$cycloalkyl, 5 membered heterocyclylC$_{1-8}$alkyl, 5 membered heteroaryl, 5 membered heteroarylC$_{1-8}$alkyl, and —C≡CR;

each occurrence of R$^2$ is independently selected from halogen, cyano, C$_{1-8}$alkyl, C$_{1-8}$alkoxy and haloC$_{1-8}$alkyl;

each occurrence of R is independently selected from C$_{1-8}$alkyl, C$_{3-12}$cycloalkyl, and C$_{6-14}$ aryl;

'm' is an integer ranging from 0 to 3, both inclusive; and

'n' is an integer ranging from 0 to 3, both inclusive;

with the proviso that 'm' and 'n' are not '0' simultaneously.

The compounds of formula (IV) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition of any other embodiment defined herein. Thus the invention contemplates all possible combinations and permutations of the various independently described embodiments. For example, the invention provides compounds of formula (IV) as defined above wherein L is —CH₂NHC(O)— (according to an embodiment defined below), 'm' is 0, 1 or 2 (according to another embodiment defined below), and 'n' is 0, 1 or 2 (according to another embodiment defined below).

According to one embodiment, specifically provided are compounds of formula (IV), in which L is —CH₂NHC(O)—.

According to another embodiment, specifically provided are compounds of formula (IV), in which each occurrence of R$^1$ is independently selected from cyano, halogen (e.g. F, Cl or Br), C$_{1-8}$alkyl (e.g. methyl), haloC$_{1-8}$alkyl (e.g. trifluoromethyl or difluoromethyl), C$_{1-8}$alkoxy (e.g. methoxy), haloC$_{1-8}$alkoxyC$_{1-8}$alkyl (e.g. (2,2,2-trifluoroethoxy)methyl), 5 membered heterocyclylC$_{1-8}$alkyl (e.g. (pyrrolidin-1-yl)methyl), 5 membered heteroaryl (e.g. 4-methylthiophenyl, 5-isopropyl-1,3,4-oxadiazol-2-yl), 5 membered heteroarylC$_{1-8}$alkyl (e.g. (3,5-dimethyl-1H-pyrazol-1-yl)methyl) and —C≡CR.

According to yet another embodiment, specifically provided are compounds of formula (IV), in which each occurrence of R$^1$ is independently selected from cyano, Cl, F, CHF₂, CF₃, OCH₃, CH₃, (2,2,2-trifluoroethoxy)methyl, (pyrrolidin-1-yl)methyl, 4-methylthiophenyl, 5-isopropyl-1,3,4-oxadiazol-2-yl, (3,5-dimethyl-1H-pyrazol-1-yl)methyl and —C≡CR. In this embodiment R is isopropyl, tert-butyl, cyclopropyl, 4-chloro-2-fluorophenyl, 3-chloro-2-fluorophenyl, 3-(trifluoromethyl)phenyl or 2-chloro-4-(trifluoromethyl)phenyl.

According to yet another embodiment, specifically provided are compounds of formula (IV), in which each occurrence of R$^1$ is independently selected from cyano, Cl, F, CHF₂, CF₃, OCH₃, CH₃, (2,2,2-trifluoroethoxy)methyl, (pyrrolidin-1-yl)methyl, 4-methylthiophenyl, 5-isopropyl-1,3,4-oxadiazol-2-yl, (3,5-dimethyl-1H-pyrazol-1-yl)methyl, 3,3-dimethylbut-1-ynyl, 2-cyclopropylethynyl, (2,5-dichlorophenyl)ethynyl, (4-chloro-2-fluorophenyl)ethynyl, (3-chloro-2-fluorophenyl)ethynyl, (3-(trifluoromethyl)phenyl)ethynyl and (2-chloro-4-(trifluoromethyl)phenyl)ethynyl.

According to yet another embodiment, specifically provided are compounds of formula (IV), in which each occurrence of R$^1$ is independently cyano, Cl, F, CHF₂, CF₃, OCH₃, CH₃, (2,2,2-trifluoroethoxy)methyl, (pyrrolidin-1-yl)methyl, 4-methylthiophenyl, 5-isopropyl-1,3,4-oxadiazol-2-yl, (3,5-dimethyl-1H-pyrazol-1-yl)methyl, 3,3-dimethylbut-1-ynyl, 2-cyclopropylethynyl, (2,5-dichlorophenyl)ethynyl, (4-chloro-2-fluorophenyl)ethynyl, (3-chloro-2-fluorophenyl)ethynyl, (3-(trifluoromethyl)phenyl)ethynyl or (2-chloro-4-(trifluoromethyl)phenyl)ethynyl; and 'n' is 1 or 2.

According to yet another embodiment, specifically provided are compounds of formula (IV), in which 'n' is 0, 1 or 2.

According to yet another embodiment, specifically provided are compounds of formula (IV), in which each occurrence of R$^2$ is independently selected from cyano, halogen (e.g. F, Cl or Br), C$_{1-8}$alkyl (e.g. methyl), haloC$_{1-8}$alkyl (e.g. trifluoromethyl) and C$_{1-8}$alkoxy (e.g. methoxy).

According to yet another embodiment, specifically provided are compounds of formula (N), in which each occurrence of R$^2$ is independently cyano, Cl, F, CH₃, CF₃ or OCH₃.

According to yet another embodiment, specifically provided are compounds of formula (N), in which each occurrence of R$^2$ is independently cyano, Cl, F, CH₃, CF₃ or OCH₃; and 'm' is 1 or 2.

According to yet another embodiment, specifically provided are compounds of formula (IV), in which 'm' is 0, 1 or 2.

According to yet another embodiment, specifically provided are compounds of formula (IV), in which W is C$_{1-8}$alkyl (e.g. isopropyl or ten-butyl), haloC$_{1-8}$alkyl (e.g. trifluoromethyl or 1-fluoro-2-methylpropan-2-yl), hydroxyC$_{1-8}$alkyl (e.g. 1-hydroxy-2-methylpropan-2-yl) or C$_{3-12}$Cycloalkyl (e.g. cyclopropyl).

According to yet another embodiment, specifically provided are compounds of formula (IV), in which W is C$_{1-4}$alkyl (e.g. isopropyl or tert-butyl), haloC$_{1-8}$alkyl (e.g. trifluoromethyl or 1-fluoro-2-methylpropan-2-yl), hydroxyC$_{1-8}$alkyl (e.g. 1-hydroxy-2-methylpropan-2-yl) or C$_{3-6}$cycloalkyl (e.g. cyclopropyl).

According to yet another embodiment, specifically provided are compounds of formula (IV), in which W is isopropyl, tert-butyl, trifluoromethyl, 1-fluoro-2-methylpropan-2-yl, 1-hydroxy-2-methylpropan-2-yl or cyclopropyl.

According to yet another embodiment, specifically provided are compounds of formula (IV), in which each occurrence of R is independently selected from C$_{1-8}$alkyl (e.g. isopropyl or tert-butyl), C$_{3-12}$cycloalkyl (e.g. cyclopropyl) and C$_{6-14}$aryl (e.g. 4-chloro-2-fluorophenyl, 3-chloro-2-fluorophenyl, 3-(trifluoromethyl)phenyl, 2-chloro-4-(trifluoromethyl)phenyl, 3-(difluoromethyl)-4-fluorophenyl or 3-(difluoromethyl)phenyl).

According to yet another embodiment, specifically provided are compounds of formula (IV), in which each occurrence of R is phenyl optionally substituted with one or more substituents selected from Cl, F, trifluoromethyl and difluoromethyl.

According to yet another embodiment, specifically provided are compounds of formula (IV), in which each occurrence of R is independently isopropyl, tert-butyl, cyclopropyl, 4-chloro-2-fluorophenyl, 3-chloro-2-fluorophenyl, 3-(trifluoromethyl)phenyl, 2-chloro-4-(trifluoromethyl)phenyl, 3-(difluoromethyl)-4-fluorophenyl or 3-(difluoromethyl)phenyl).

According to yet another embodiment, specifically provided are compounds of formula (IV), in which:

each occurrence of $R^1$ is independently Cl, F, $CHF_2$, $CF_3$, $OCH_3$, $CH_3$, 3,3-dimethylbut-1-ynyl, 2-cyclopropylethynyl, (2,5-dichlorophenyl)ethynyl, (4-chloro-2-fluorophenyl)ethynyl, 3-chloro-2-fluorophenyl)ethynyl, 3-(trifluoromethyl)phenyl)ethynyl or 2-chloro-4-(trifluoromethyl)phenyl)ethynyl;

each occurrence of $R^2$ is independently Cl, F, $CH_3$, $CF_3$ or $OCH_3$;

L is —$CH_2NHC(O)$—;

'm' is 1 or 2;

'n' is 0, 1 or 2; and

W is isopropyl, tert-butyl, trifluoromethyl, 1-fluoro-2-methylpropan-2-yl, 1-hydroxy-2-methylpropan-2-yl or cyclopropyl.

According to an embodiment, specifically provided are compounds of formula (IV) that exhibit an $IC_{50}$ value of less than 500 nM, preferably less than 100 nM, more preferably less than 50 nM with respect to mPGES-1 inhibition.

It should be understood that the formulas (I), (II), (III) and (IV), structurally encompass all geometrical isomers, stereoisomers, enantiomers and diastereomers, N-oxides, and pharmaceutically acceptable salts that may be contemplated from the chemical structure of the genera described herein.

Compounds of the present invention include the compounds in Examples 1-192.

According to an embodiment, the compounds of formula (I) (wherein $R^3$ is H), formula (II), formula (III) or formula (IV) structurally encompass all tautomeric forms whether such tautomer exists in equilibrium or predominantly in one form. Such tautomeric form may be different or the same when the compound is bound to the mPGES-1 enzyme.

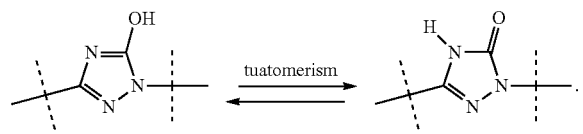

The present application also provides a pharmaceutical composition that includes at least one compound described herein and at least one pharmaceutically acceptable excipient (such as a pharmaceutically acceptable carrier or diluent). Preferably, the pharmaceutical composition comprises a therapeutically effective amount of at least one compound described herein. The compounds described herein may be associated with a pharmaceutically acceptable excipient (such as a carrier or a diluent) or be diluted by a carrier, or enclosed within a carrier which can be in the form of a capsule, sachet, paper or other container.

The compounds and pharmaceutical compositions of the present invention are useful for inhibiting the activity of mPGES-1, which is related to a variety of disease states.

The present invention further provides a method of inhibiting mPGES-1 in a subject in need thereof by administering to the subject one or more compounds described herein in an amount effective to cause inhibition of such receptor.

DETAILED DESCRIPTION OF THE INVENTION

Definitions

The terms "halogen" or "halo" means fluorine (fluoro), chlorine (chloro), bromine (bromo), or iodine (iodo).

The term "alkyl" refers to a hydrocarbon chain radical that includes solely carbon and hydrogen atoms in the backbone, containing no unsaturation, having from one to eight carbon atoms (i.e. $C_{1-8}$alkyl), and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl chain having 1 to 6 carbon atoms. The term "$C_{1-4}$alkyl" refers to an alkyl chain having 1 to 4 carbon atoms. Unless set forth or recited to the contrary, all alkyl groups described or claimed herein may be straight chain or branched, substituted or unsubstituted.

The term "alkenyl" refers to a hydrocarbon chain containing from 2 to 10 carbon atoms (i.e. $C_{2-10}$alkenyl) and including at least one carbon-carbon double bond. Non-limiting examples of alkenyl groups include ethenyl, 1-propenyl, 2-propenyl (allyl), iso-propenyl, 2-methyl-1-propenyl, 1-butenyl, and 2-butenyl. Unless set forth or recited to the contrary, all alkenyl groups described or claimed herein may be straight chain or branched, substituted or unsubstituted.

The term "alkynyl" refers to a hydrocarbyl radical having at least one carbon-carbon triple bond, and having 2 to about 12 carbon atoms (with radicals having 2 to about 10 carbon atoms being preferred i.e. $C_{2-10}$alkynyl). Non-limiting examples of alkynyl groups include ethynyl, propynyl, and butynyl. Unless set forth or recited to the contrary, all alkynyl groups described or claimed herein may be straight chain or branched, substituted or unsubstituted.

The term "alkoxy" denotes an alkyl group attached via an oxygen linkage to the rest of the molecule (i.e. $C_{1-8}$ alkoxy). Representative examples of such groups are —$OCH_3$ and —$OC_2H_5$. Unless set forth or recited to the contrary, all alkoxy groups described or claimed herein may be straight chain or branched, substituted or unsubstituted.

The term "alkoxyalkyl" or "alkyloxyalkyl" refers to an alkoxy or alkyloxy group as defined above directly bonded to an alkyl group as defined above (i.e. $C_{1-8}$alkoxy$C_{1-8}$alkyl or $C_{1-8}$alkyloxy$C_{1-8}$alkyl). Example of such alkoxyalkyl moiety includes, but are not limited to, —$CH_2OCH_3$ and —$CH_2OC_2H_5$. Unless set forth or recited to the contrary, all alkoxyalkyl groups described herein may be straight chain or branched, substituted or unsubstituted.

The term "haloalkyl" refers to at least one halo group (selected from F, Cl, Br or I), linked to an alkyl group as defined above (i.e. halo$C_{1-8}$alkyl). Examples of such haloalkyl moiety include, but are not limited to, trifluoromethyl, difluoromethyl and fluoromethyl groups. Unless set forth or recited to the contrary, all haloalkyl groups described herein may be straight chain or branched, substituted or unsubstituted.

The term "haloalkoxy" refers to an alkoxy group substituted with one or more halogen atoms (i.e. halo$C_{1-8}$alkoxy). Examples of "haloalkoxy" include but are not limited to fluoromethoxy, difluoromethoxy, trifluoromethoxy, 2,2,2-trifluoroethoxy, pentafluoroethoxy, pentachloroethoxy, chloromethoxy, dichlorormethoxy, trichloromethoxy and 1-bromoethoxy. Unless set forth or recited to the contrary, all haloalkoxy groups described herein may be straight chain or branched, substituted or unsubstituted.

The term "haloalkoxyalkyl" refers to haloalkoxy group as defined above directly bonded to an alkyl group as defined above (i.e. halo$C_{1-8}$alkoxy$C_{1-8}$alkyl). Examples of "halo$C_{1-8}$alkoxy$C_{1-8}$alkyl" include but are not limited to (2,2,2-trifluoroethoxy)methyl or (2,2-difluoroethoxy)methyl. Unless set forth or recited to the contrary, all haloalkoxyalkyl groups described herein may be straight chain or branched, substituted or unsubstituted.

The term "hydroxyalkyl" refers to an alkyl group as defined above wherein one to three hydrogen atoms on different carbon atoms is/are replaced by hydroxyl groups (i.e. hydroxy$C_{1-8}$alkyl). Examples of hydroxyalkyl moieties include, but are not limited to —$CH_2OH$, —$C_2H_4OH$ and —$CH(OH)C_2H_4OH$. Unless set forth or recited to the contrary, all hydroxyalkyl groups described herein may be straight chain or branched, substituted or unsubstituted.

The term "carboxyl" means the group —COOH.

The term "carboxylalkyl" refers to $C_{1-8}$alkyl group as defined above wherein at least one of the hydrogen atoms of the $C_{1-8}$alkyl group is replaced by a carboxyl group (i.e. "carboxyl$C_{1-8}$alkyl"). Examples of carboxylalkyl moieties include, but are not limited to carboxylmethyl (—$CH_2$—COOH), carboxylethyl (—$CH_2$—$CH_2$—COOH), carboxylisopropyl (—$C(CH_3)_2$—COOH) and carboxyltertbutyl (—$C(CH_3)_2CH_2$—COOH). Unless set forth or recited to the contrary, all carboxylalkyl groups described herein may be straight chain or branched, substituted or unsubstituted.

The term "cycloalkyl" denotes a non-aromatic mono or multicyclic ring system of 3 to about 12 carbon atoms, (i.e. $C_{3-12}$cycloalkyl). Examples of monocyclic cycloalkyl include but are not limited to cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups or spirobicyclic groups, e.g., spiro(4,4)non-2-yl. The term "$C_{3-6}$cycloalkyl" refers to the cyclic ring having 3 to 6 carbon atoms. Unless set forth or recited to the contrary, all cycloalkyl groups described or claimed herein may be substituted or unsubstituted.

The term "cycloalkylalkyl" refers to a non-aromatic cyclic ring-containing radical having 3 to about 8 carbon atoms directly attached to an alkyl group (i.e. $C_{3-8}$cycloalkyl$C_{1-8}$alkyl). The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl. Unless set forth or recited to the contrary, all cycloalkylalkyl groups described or claimed herein may be substituted or unsubstituted.

The term "cycloalkenyl" refers to a cyclic ring-containing radical having 3 to about 8 carbon atoms with at least one carbon-carbon double bond, (i.e. $C_{3-8}$cycloalkenye. Examples of "cycloalkenyl" include but are not limited to cyclopropenyl, cyclobutenyl, and cyclopentenyl. Unless set forth or recited to the contrary, all cycloalkenyl groups described or claimed herein may be substituted or unsubstituted.

The term "cycloalkenylalkyl" refers to a non-aromatic cyclic ring-containing radical having 3 to about 8 carbon atoms with at least one carbon-carbon double bond, directly attached to an alkyl group, (i.e. $C_{3-8}$ cycloalkenyl$C_{1-8}$alkyl). Unless set forth or recited to the contrary, all cycloalkenylalkyl groups described or claimed herein may be substituted or unsubstituted.

The term "aryl" refers to an aromatic radical having 6 to 14 carbon atoms (i.e. $C_{6-14}$aryl), including monocyclic, bicyclic and tricyclic aromatic systems, such as phenyl, naphthyl, tetrahydronapthyl, indanyl, and biphenyl. Unless set forth or recited to the contrary, all aryl groups described or claimed herein may be substituted or unsubstituted.

The term "aryloxy" refers to an aryl group as defined above attached via an oxygen linkage to the rest of the molecule (i.e. $C_{6-14}$aryloxy). Examples of aryloxy moieties include, but are not limited to phenoxy and naphthoxy. Unless set forth or recited to the contrary, all aryloxy groups described herein may be substituted or unsubstituted.

The term "arylalkyl" refers to an aryl group as defined above directly bonded to an alkyl group as defined above, i.e. $C_{6-14}$aryl$C_{1-8}$alkyl, such as —$CH_2C_6H_5$ and —$C_2H_4C_6H_5$. Unless set forth or recited to the contrary, all arylalkyl groups described or claimed herein may be substituted or unsubstituted.

The term "heterocyclic ring" or "heterocyclyl" unless otherwise specified refers to substituted or unsubstituted non-aromatic 3 to 15 membered ring radical (i.e. 3 to 15 membered heterocyclyl) which consists of carbon atoms and from one to five hetero atoms selected from nitrogen, phosphorus, oxygen and sulfur. The heterocyclic ring radical may be a mono-, bi- or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; also, unless otherwise constrained by the definition the heterocyclic ring or heterocyclyl may optionally contain one or more olefinic bond(s). Examples of such heterocyclic ring radicals include, but are not limited to azepinyl, azetidinyl, benzodioxolyl, benzodioxanyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, oxadiazolyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl or tetrahydrofuranyl, tetrahydropyranyl, thiazolinyl, thiazolidinyl, thiamorpholinyl, thiamorpholinyl sulfoxide and thiamorpholinyl sulfone. Unless set forth or recited to the contrary, all heterocyclyl groups described or claimed herein may be substituted or unsubstituted.

The term "heterocyclylalkyl" refers to a heterocyclic ring radical directly bonded to an alkyl group (i.e. 3 to 15 membered heterocyclyl$C_{1-8}$alkyl). Unless set forth or recited to the contrary, all heterocyclylalkyl groups described or claimed herein may be substituted or unsubstituted.

The term "heteroaryl" unless otherwise specified refers to substituted or unsubstituted 5 to 14 membered aromatic heterocyclic ring radical with one or more heteroatom(s) independently selected from N, O or S (i.e. 5 to 14 membered heteroaryl). The heteroaryl may be a mono-, bi- or tricyclic ring system. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, thiazolyl, isothiazolyl, pyridyl, pyrimidinyl, pyrazinyl, pyridazinyl, pyrazolyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl and phthalazinyl. Unless set forth or recited to the contrary, all heteroaryl groups described or claimed herein may be substituted or unsubstituted.

The term "heteroarylalkyl" refers to a heteroaryl ring radical directly bonded to an alkyl group (i.e. 5 to 14 membered hetearyl$C_{1-8}$alkyl). Unless set forth or recited to the contrary, all heteroarylalkyl groups described or claimed herein may be substituted or unsubstituted.

Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, substituted or unsubstituted haloalkyl, substituted or unsubstituted hydroxyl alkyl, substituted or unsubstituted alkoxy, substituted or unsubstituted haloalkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted amino, substituted or unsubstituted aryl, substituted or unsubstituted arylalkyl, substituted or unsubstituted heteroaryl, substituted or unsubstituted heteroarylalkyl, substituted or unsubstituted heterocyclylalkyl, substituted or unsubstituted heterocyclic ring, substituted or unsubstituted guanidine, —COOR$^{x'}$, —C(O)R$^{x'}$, —C(S)R$^{x'}$, —C(O)NR$^{x'}$R$^{y'}$, —C(O)ONR$^{x'}$R$^{y'}$, —NR$^{x'}$CONR$^{y'}$R$^{z'}$, —N(R$^{x'}$)SOR$^{y'}$, —N(R$^{x'}$)SO$_2$R$^{y'}$, —(=N—N(R$^{x'}$)R$^{y'}$), —NR$^{x'}$C(O)OR$^{y'}$, —NR$^{x'}$R$^{y'}$, —NR$^{x'}$C(O)R$^{y'}$, —NR$^{x'}$C(S)R$^{y'}$, —NR$^{x'}$C(S)NR$^{y'}$R$^{z'}$, —SONR$^{x'}$R$^{y'}$, —SO$_2$NR$^{x'}$R$^{y'}$, —OR$^{x'}$, —OC(O)NR$^{y'}$R$^{z'}$, —OC(O)OR$^{y'}$, —OC(O)R$^{x'}$, —OC(O)NR$^{x'}$R$^{y'}$, —SR$^{x'}$, —SOR$^{x'}$, —SO$_2$R$^{x'}$, and —ONO$_2$, wherein each occurrence of R$^{x'}$, R$^{y'}$ and R$^{z'}$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted amino, substituted or unsubstituted aryl, substituted or unsubstituted heteroaryl, substituted heterocyclylalkyl, substituted or unsubstituted heteroarylalkyl, and substituted or unsubstituted heterocyclic ring. The substituents in the aforementioned "substituted" groups cannot be further substituted. For example, when the substituent on "substituted alkyl" is "substituted aryl", the substituent on "substituted aryl" can be unsubstituted alkenyl but cannot be "substituted alkenyl".

The term "pharmaceutically acceptable salt" includes salts prepared from pharmaceutically acceptable bases or acids including inorganic or organic bases and inorganic or organic acids. Examples of such salts include, but are not limited to, acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate, diphosphate, polygalacturonate, salicylate, stearate, sulfate, subacetate, succinate, tannate, tartrate, teoclate, tosylate, triethiodide and valerate. Examples of salts derived from inorganic bases include, but are not limited to, aluminum, ammonium, calcium, copper, ferric, ferrous, lithium, magnesium, manganic, mangamous, potassium, sodium, and zinc.

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or, condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" may vary depending on the compound, the disease and its severity and the age, weight, physical condition and responsiveness of the subject to be treated.

The sensation of pain can be triggered by any number of physical or chemical stimuli and the sensory neurons which mediate the response to this harmful stimulus are termed as "nociceptors". Nociceptors are primary sensory afferent (C and Aδ fibers) neurons that are activated by a wide variety of noxious stimuli including chemical, mechanical, thermal, and proton (pH <6) modalities. Nociceptors are the nerves which sense and respond to parts of the body which suffer from damage. They signal tissue irritation, impending injury, or actual injury. When activated, they transmit pain signals (via the peripheral nerves as well as the spinal cord) to the brain.

The term "chronic pain" usually refers to pain which persists for 3 months or longer and can lead to significant changes in a patient's personality, lifestyle, functional ability and overall quality of life. Chronic pain can be classified as either nociceptive or neuropathic. Nociceptive pain includes tissue injury-induced pain and inflammatory pain such as that associated with arthritis. Neuropathic pain is caused by damage to the sensory nerves of the peripheral or central nervous system and is maintained by aberrant somatosensory processing. The pain is typically well localized, constant, and often with an aching or throbbing quality. Visceral pain is the subtype of nociceptive pain that involves the internal organs. It tends to be episodic and poorly localized. Nociceptive pain is usually time limited, meaning when the tissue damage heals, the pain typically resolves (arthritis is a notable exception in that it is not time limited).

Pharmaceutical Compositions

The compounds of the invention are typically administered in the form of a pharmaceutical composition. Such compositions can be prepared using procedures known in the pharmaceutical art and comprise at least one compound of the invention. The pharmaceutical composition of the present patent application comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents, and solvents.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters, and polyoxyethylene.

The pharmaceutical composition may also include one or more pharmaceutically acceptable auxiliary agents, wetting agents, suspending agents, preserving agents, buffers, sweetening agents, flavoring agents, colorants or any combination of the foregoing.

The pharmaceutical compositions may be in conventional forms, for example, capsules, tablets, solutions, suspensions, injectables or products for topical application. Further, the pharmaceutical composition of the present invention may be formulated so as to provide a desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the patent application to the appropriate or desired site of action. Suitable routes of administration include, but are not limited to, oral, nasal, buccal, dermal, intradermal, transdermal, parenteral, rectal, subcutaneous, intravenous, intraurethral, intramuscular, or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions, and sterile injectable liquids, such as suspensions or solutions.

Topical dosage forms of the compounds include ointments, pastes, creams, lotions, powders, solutions, eye or ear drops, and impregnated dressings, and may contain appropriate conventional additives such as preservatives, solvents to assist drug penetration.

The pharmaceutical compositions of the present patent application may be prepared by conventional techniques, e.g., as described in *Remington: The Science and Practice of Pharmacy*, 20$^{th}$ Ed., 2003 (Lippincott Williams & Wilkins).

Suitable doses of the compounds for use in treating the diseases and disorders described herein can be determined by those skilled in the relevant art. Therapeutic doses are generally identified through a dose ranging study in humans based on preliminary evidence derived from animal studies. Doses are generally sufficient to result in a desired therapeutic benefit without causing unwanted side effects. Mode of administration, dosage forms, and suitable pharmaceutical excipients can also be well used and adjusted by those skilled in the art. All changes and modifications are envisioned within the scope of the present patent application.

In another embodiment, the present invention relates to a pharmaceutical composition comprising a compound as described herein, a second therapeutic agent, and optionally a pharmaceutically-acceptable excipient. In one embodiment, the pharmaceutical composition includes a compound as described herein and a second therapeutic agent, wherein each of the compound described herein and the second therapeutic agent is formulated in admixture with a pharmaceutically-acceptable excipient.

Methods of Treatment

Compounds of the present invention are particularly useful because they may inhibit the activity of prostaglandin E synthases (and particularly microsomal prostaglandin E synthase-1 (mPGES-1)), i.e., they prevent, inhibit, or suppress the action of mPGES-1 or a complex of which the mPGES-1 enzyme forms a part, and/or may elicit mPGES-1 modulating effect. Compounds of the invention are thus useful in the treatment of those conditions treatable by inhibition of a PGES, and particularly mPGES-1.

Compounds of the invention are thus expected to be useful in the treatment of inflammation. The term "inflammation" will be understood by those skilled in the art to include any condition characterized by a localized or a systemic protective response, which may be elicited by physical trauma, infection, chronic diseases, such as those mentioned hereinbefore, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow.

The term "inflammation" is also understood to include any inflammatory disease, disorder or condition per se, any condition that has an inflammatory component associated with it, and/or any condition characterized by inflammation as a symptom, including, inter alia, acute, chronic, ulcerative, specific, allergic, infection by pathogens, immune reactions due to hypersensitivity, entering foreign bodies, physical injury, and necrotic inflammation, and other forms of inflammation known to those skilled in the art. The term thus also includes, for the purposes of this invention, inflammatory pain, pain generally and/or fever.

The compounds of the present invention may also be useful in the treatment of asthma, chronic obstructive pulmonary disease, pulmonary fibrosis, inflammatory bowel disease, irritable bowel syndrome, inflammatory pain, chronic pain, acute pain, fever, migraine, headache, low back pain, fibromyalgia, myofascial disorders, viral infections (e.g. influenza, common cold, herpes zoster, hepatitis C and AIDS), bacterial infections, fungal infections, dysmenorrhea, burns, surgical or dental procedures, malignancies (e.g. breast cancer, colon cancer, and prostate cancer), hyperprostaglandin E syndrome, classic Bartter syndrome, atherosclerosis, gout, arthritis, osteoarthritis, juvenile arthritis, rheumatoid arthritis, juvenile onset rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, psoriasis, stroke, diabetes mellitus, neurodegenerative disorders such as Alzheimer's disease and multiple sclerosis, autoimmune diseases, allergic disorders, rhinitis, ulcers, mild to moderately active ulcerative colitis, familial adenomatous polyposis, coronary heart disease, sarcoidosis and any other disease with an inflammatory component.

Compounds of the invention may also have effects that are not linked to inflammatory mechanisms, such as in the reduction of bone loss in a subject. Conditions that may be mentioned in this regard include osteoporosis, osteoarthritis, Paget's disease and/or periodontal diseases.

By virtue of the mPGES-1 inhibitory activity of compounds of the present invention, the compounds are useful for the relief of pain, fever and inflammation of a variety of conditions including rheumatic fever, symptoms associated with influenza or other viral infections, common cold, low back and neck pain, dysmenorrhea, headache, migraine (acute and prophylactic treatment), toothache, sprains and strains, myositis, neuralgia, synovitis, arthritis, including rheumatoid arthritis, juvenile rheumatoid arthritis, degenerative joint diseases (osteoarthritis), acute gout and ankylosing spondylitis, acute, subacute and chronic musculoskeletal pain syndromes such as bursitis, burns, injuries, and pain following surgical (post-operative pain) and dental procedures as well as the preemptive treatment of surgical pain. The pain may be mild pain, moderate pain, severe pain, musculoskeletal pain, complex regional pain syndrome, neuropathic pain, back pain such as acute visceral pain, neuropathies, acute trauma, chemotherapy-induced mononeuropathy pain states, polyneuropathy pain states (such as diabetic peripheral neuropathy & chemotherapy induced neuropathy), autonomic neuropathy pain states, pheriphaeral nervous system (PNS) lesion or central nervous system (CNS) lesion or disease related pain states, polyradiculopathies of cervical, lumbar or sciatica type, cauda equina syndrome, piriformis syndrome, paraplegia, quadriplegia, pain states related to various Polyneuritis conditions underlying various infections, chemical injuries, radiation exposure, underlying disease or deficiency conditions (such as beriberi, vitamin deficiencies, hypothyroidism, porphyria, cancer, HIV, autoimmune disease such as multiple sclerosis and spinal-cord injury, fibromyalgia, nerve injury, ischaemia, neurodegeneration, stroke, post stroke pain, inflammatory disorders, oesophagitis, gastroeosophagal reflux disorder (GERD), irritable bowel syndrome, inflammatory bowel disease, pelvic hypersensitivity, urinary incontinence, cystitis, stomach duodenal ulcer, muscle pain, pain due to colicky and referred pain. Compounds of the present invention may also be useful for the treatment or prevention of endometriosis, hemophilic arthropathy and Parkinson's disease.

Compounds of the present invention will also inhibit prostanoid-induced smooth muscle contraction by preventing the synthesis of contractile prostanoids and hence may be of use in the treatment of dysmenorrhea, premature labor and asthma.

In addition, the compounds of the present invention may inhibit cellular neoplastic transformations and metastic tumor growth and hence can be used in the treatment of cancer, and pain associated with cancer. Furthermore, the present invention provides preferred embodiments of the methods and uses as described herein, in which cancer includes Acute Lymphoblastic Leukemia, Acute Myeloid Leukemia, Adolescents Cancer, Adrenocortical Carcinoma, Anal Cancer, Appendix Cancer, Astrocytomas, Atypical Teratoid, Basal Cell Carcinoma, Bile Duct Cancer, Extrahepatic, Bladder Cancer, Bone Cancer, Brain Stem Glioma, Brain Tumor, Breast Cancer; Bronchial Tumors, Burkitt Lymphoma, Carcinoid Tumor, Carcinoma of Unknown Primary, Cardiac (Heart) Tumors, Central Nervous System tumors, Cervical Cancer, Childhood Cancers, Chordoma, Chronic Lymphocytic Leukemia, Chronic Myelogenous Leukemia, Chronic Myeloproliferative Disorders, Colon Cancer, Colorectal Cancer, Craniopharyngioma, Cutaneous T-Cell Lymphoma, Duct Bile Extrahepatic cancer, Ductal Carcinoma In Situ, Embryonal Tumors, Central Nervous System cancer, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Malignant, and Osteosarcoma, Gall bladder Cancer, Gastric (Stomach) Cancer, Gastrointestinal Carcinoid Tumor, Gastrointestinal Stromal Tumors, Germ Cell Tumor, Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors, Pancreatic Neuroendocrine Tumors, Kaposi Sarcoma, Kidney cancer, Langerhans Cell Histiocytosis, Laryngeal Cancer, Acute Lymphoblastic Leukemia, Acute Myeloid Leukemia, Chronic Lymphocytic Leukemia, Chronic Myelogenous Leukemia, Hairy Cell Leukemia, Lip and Oral Cavity Cancer, Liver Cancer, Lobular Carcinoma In Situ, Lung Cancer, AIDS-Related Lymphoma, Cutaneous T-Cell Lymphoma, Hodgkin Lymphoma, Non-Hodgkin Lymphoma, Primary Central Nervous System (CNS) Lymphoma, Macroglobulinemia, Waldenström, Male Breast Cancer, Malignant Fibrous Histiocytoma of Bone and Osteosarcoma, Melanoma, Merkel Cell Carcinoma, Mesothelioma, Malignant, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic, Myeloid Leukemia Acute, Multiple Myeloma, Chronic Myeloproliferative Disorders, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer, Pancreatic Cancer, Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Ewing Sarcoma, Kaposi Sarcoma, Osteosarcoma, Rhadomyosarcoma, Soft Tissue Sarcoma, Uterine Sarcoma, Sézary Syndrome, Skin Cancer, Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, T-Cell Lymphoma, Cutaneous, Testicular Cancer, Throat Cancer, Thymoma and Thymic Carcinoma, Thyroid Cancer, Transitional Cell Cancer of the Renal Pelvis and Ureter, Trophoblastic Tumor, Gestational, Unknown Primary, Carcinoma of, Ureter and Renal Pelvis, Transitional Cell Cancer, Urethral Cancer, Uterine Cancer, Endometrial, Uterine Sarcoma, Vaginal Cancer, Vulvar Cancer, Waldenström, Macroglobulinemia, Wilms Tumor and Women's Cancers.

The compounds of the present invention may be useful in the treatment of disease, disorder, syndrome or condition selected from the group consisting of inflammation, asthma, chronic obstructive pulmonary disease, pulmonary fibrosis, inflammatory bowel disease, irritable bowel syndrome, pain, inflammatory pain, chronic pain, acute pain, fever, migraine, headache, low back pain, fibromyalgia, myofascial disorders, viral infections, influenza, common cold, herpes zoster, hepatitis C, AIDS, bacterial infections, fungal infections, dysmenorrhea, burns, surgical or dental procedures, malignancies hyperprostaglandin E syndrome, classic Bartter syndrome, synovitis, atherosclerosis, gout, arthritis, osteoarthritis, juvenile arthritis, rheumatoid arthritis, juvenile onset rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, psoriasis, stroke, diabetes mellitus, cancer, neurodegenerative disorders such as Alzheimer's disease, Parkinson's disease, Amyotrophic lateral sclerosis and multiple sclerosis, autoimmune diseases, allergic disorders, rhinitis, ulcers, mild to moderately active ulcerative colitis, familial adenomatous polyposis, coronary heart disease, and sarcoidosis.

The compounds of the present invention may be useful in the treatment of pain, chronic pain, acute pain, rheumatoid arthritic pain or osteoarthritic pain.

The compounds of the present invention may be useful in the treatment of inflammation, neurodegenerative disorders such as Parkinson's disease, Alzheimer's disease and amyotrophic lateral sclerosis.

The compounds of the present invention may be useful in the treatment prevention or management of the cancer.

the general reaction sequences may be of insufficient purity. These compounds can be purified by using any of the methods for purification of organic compounds known to persons skilled in the art, for example, crystallization or silica gel or alumina column chromatography using different solvents in suitable ratios. All possible geometrical isomers and stereo isomers are envisioned within the scope of this invention.

A general approach for the preparation of a compound of formula (I) or (Ia) is depicted in the Synthetic Scheme-I (wherein ring A, ring B, $R^1$, $R^2$, $R^3$, L, P, Q, W, m, n, s and t are as defined with respect to a compound of formula (I)).

Synthetic Scheme-I

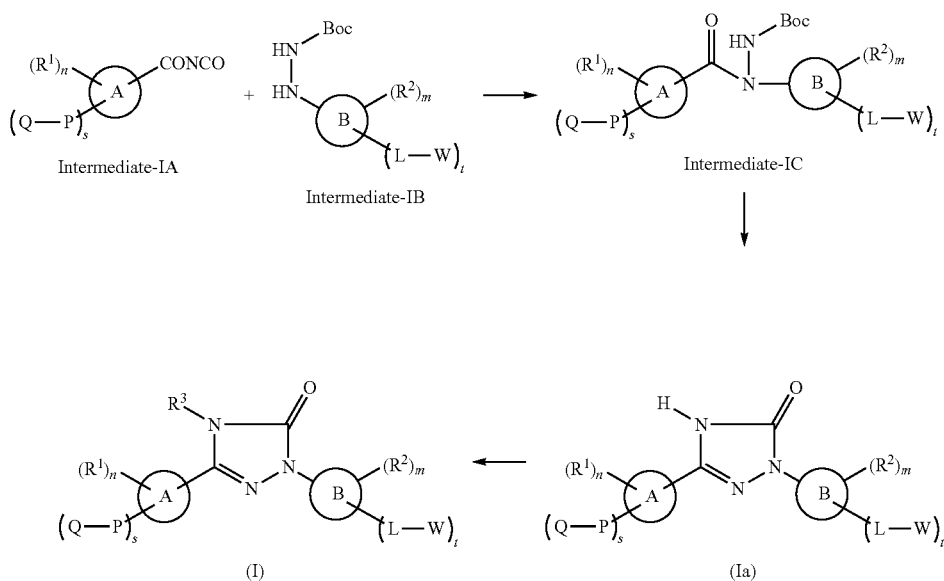

Compounds of the present invention are indicated both in the therapeutic and/or prophylactic treatment of the above-mentioned conditions. For the above-mentioned therapeutic uses the dosage administered will, of course, vary with the compound employed, the mode of administration, the treatment desired and the disorder indicated. The daily dosage of the compound of the invention may be in the range from 0.05 mg/kg to 100 mg/kg.

General Methods of Preparation

The compounds described herein, including compounds of general formula (I), (II), (III), and (IV) and specific examples can be prepared using techniques known to one skilled in the art through the reaction sequences depicted in Synthetic Scheme-I, Synthetic Scheme-II, Synthetic Scheme-III, Synthetic Scheme-IV, Synthetic Scheme-V, Synthetic Scheme-VI, Synthetic Scheme-VII, Synthetic Scheme-VIM Synthetic Scheme-IX, Synthetic Scheme-X and Synthetic Scheme-XI as well as by other methods. Furthermore, in the following schemes, where specific acids, bases, reagents, coupling agents, solvents, etc. are mentioned, it is understood that other suitable acids, bases, reagents, coupling agents etc. may be used and are included within the scope of the present invention. Modifications to reaction conditions, for example, temperature, duration of the reaction or combinations thereof, are envisioned as part of the present invention. The compounds obtained by using An Isocynate compound of formula (Intermediate-IA) may be obtained from a corresponding acid, amide or acid halide derivative.

A compound of formula (Intermediate-IA) can be treated (or coupled) with a compound of formula (Intermediate-IB) to form a compound of formula (Intermediate-IC). The compound of formula (Intermediate-IA) can be reacted with the compound of formula (intermediate-IB) in solvent such as DCM, toluene or EDC. According to the process, the compound of formula Intermediate-IC may be isolated or not isolated.

A compound of formula (Intermediate-IC) can be deprotected (e.g., treated with an acid) to obtain a compound of formula (Ia). The acid used in the conversion of the compound of formula (Intermediate-IC) may be organic acid such as TFA, CSA or methane sulphonic acid.

A compound of formula (I) (wherein $R^3$ is not hydrogen) can be prepared from a compound of formula (Ia) by general alkylation methods by using $C_{1-8}$alkyl halide/$C_{3-12}$cycloalkyl halide/$C_{6-14}$aryl halide in the presence of one or more inorganic bases such as NaH, $K_2CO_3$ or $CsCO_3$.

In another approach, the compound of formula (II) can be prepared following the synthetic steps depicted in Synthetic Scheme-II (wherein $R^1$, $R^2$, L, Q, W, $X^1$, $X^2$, $X^3$, $X^4$, m, n, s and t are as defined with respect to a compound of formula (II)).

Synthetic Scheme-II

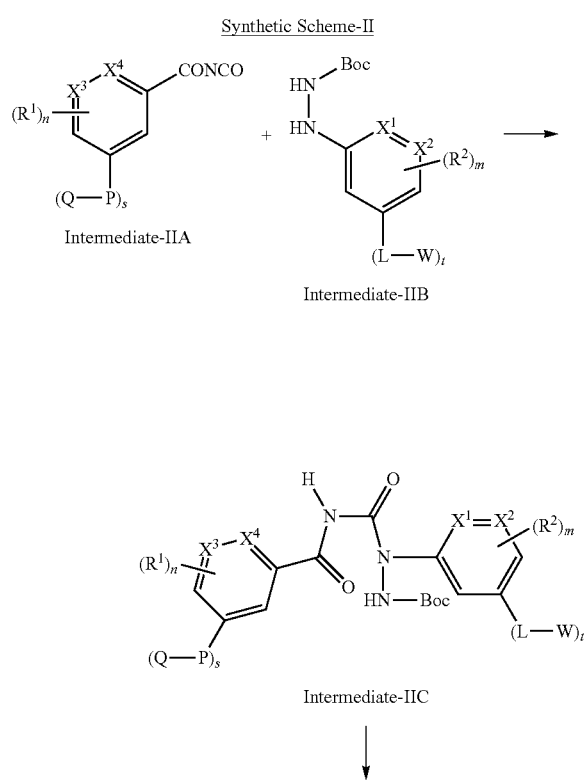

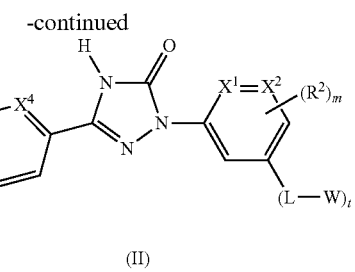

An Isocyanate compound of formula (Intermediate-IIA) may be obtained from a corresponding acid, amide or acid halide derivative. A compound of formula (Intermediate-IIA) can be treated with (or coupled to) a compound of formula (Intermediate-IIB) to form a compound of formula (Intermediate-IIC). A compound of formula (Intermediate-IIC) can be treated with an acid such as an organic acid (e.g. TFA, CSA or methane sulphonic acid) at room temperature to obtain a compound of formula (II). According to the process, the compound of formula (Intermediate-IIA) can be reacted with the compound of formula (Intermediate-BB) in a solvent such as DCM, toluene or EDC. According to the process, the compound of formula Intermediate-IIC may be isolated or not isolated.

An approach for the preparation of compound of formula (IVa) is schematically represented in Synthetic Scheme-III (wherein $R^1$, $R^2$, W, m, and n are as defined with respect to a compound of formula (IV)).

Synthetic Scheme-III

SCHEME-IIIA

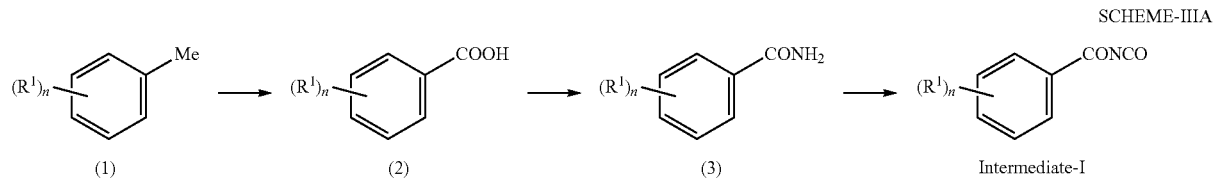

SCHEME-IIIB

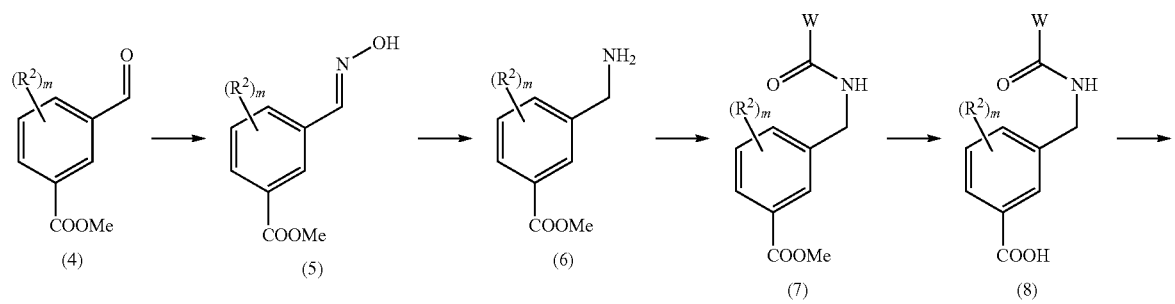

-continued

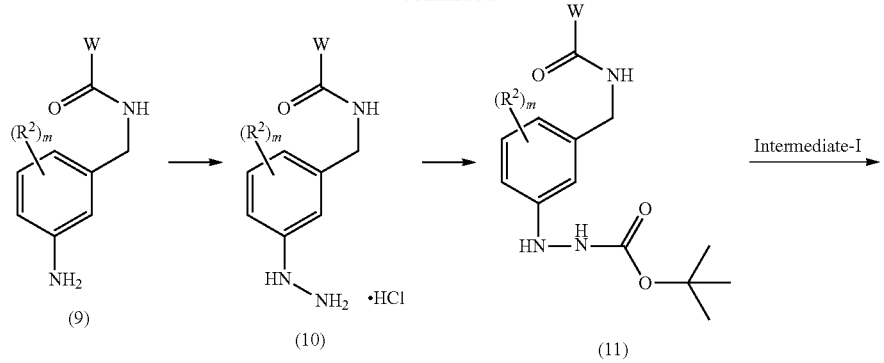

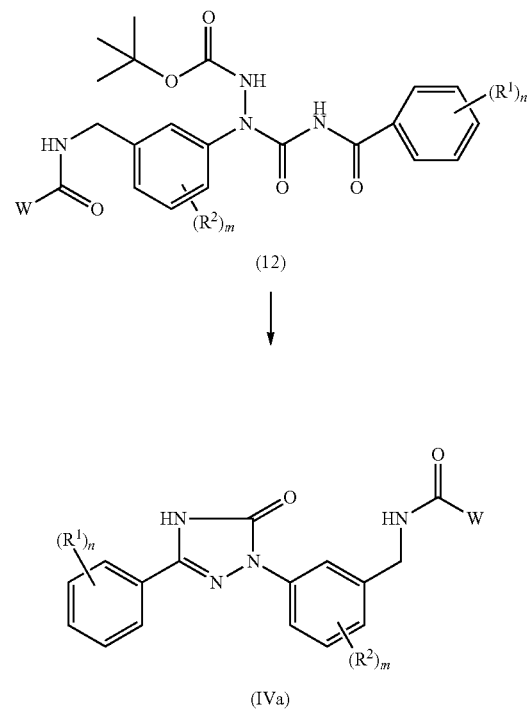

A compound of formula (I) (Scheme-IIIA) can be Converted to a compound of formula (2) by using general oxidation methods known in the art using oxidizing agents such as $KMnO_4$, $CrO_3$, $K_2Cr_2O_7$ etc. A compound of formula (2) can be converted to a compound of formula (3) by using reaction conditions such as oxalyl chloride/$NH_3$, thionyl chloride/$NH_3$ or EDCI/$NH_4Cl$. A compound of formula (3) can be treated with oxalyl chloride in solvents such as EDC or toluene to obtain Intermediate-1 (Scheme-IIIA).

A compound of formula (5) (Scheme-IIIB) can be prepared from a compound of formula (4) according to known procedures in the literature and can be further converted to a compound of formula (6) by known reducing agents such as Fe/HCl or Zn/HCl. A compound of formula (6) can be converted to a compound of formula (7) by reacting it with aromatic or aliphatic carbonyl chloride using solvent such as dry THF. A compound of formula (7) can be converted to a compound of formula (8) by hydrolysis, for example with NaOH, KOH or LiOH. A compound of formula (8) can be treated with $NaN_3$ and conc. $H_2SO_4$ (e.g., at about 50° C.) to give a compound of formula (9). A compound of formula (9) can be converted to a compound of formula (10) by reaction with an aqueous solution of sodium nitrite and a solution of stannous chloride in conc. HO. A compound of formula (10) can be converted to a compound of formula (11) by using an aqueous solution of inorganic bases such as $Na_2CO_3$ or $K_2CO_3$ and BOC anhydride in a solvent such as THF or DMF. A compound of formula (11) can be treated with Intermediate-I to obtain a compound of formula (12). The compound of formula (11) can be reacted with the Intermediate-I in an aprotic solvent such as DCM, toluene or EDC to obtain the compound of formula (12). A compound of formula (12) can be treated with organic acid to obtain compound of formula (IVa) (Scheme-IIIB). The organic acid used in the conversion of the compound of formula (12) may be TFA, CSA or methane sulphonic acid.

An approach for the preparation of compound of formula (IIIa) is schematically represented in Synthetic Scheme-IV (wherein $R^1$, $R^2$, Q, m, and n are as defined with respect to a compound of formula (III)).

Synthetic Scheme-IV
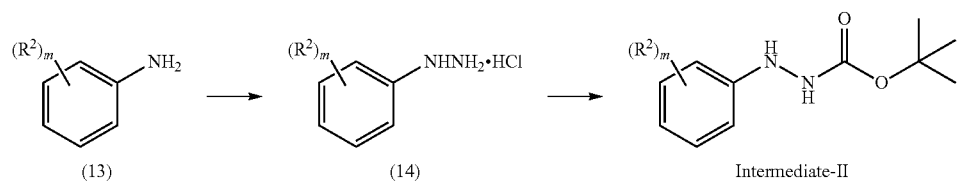
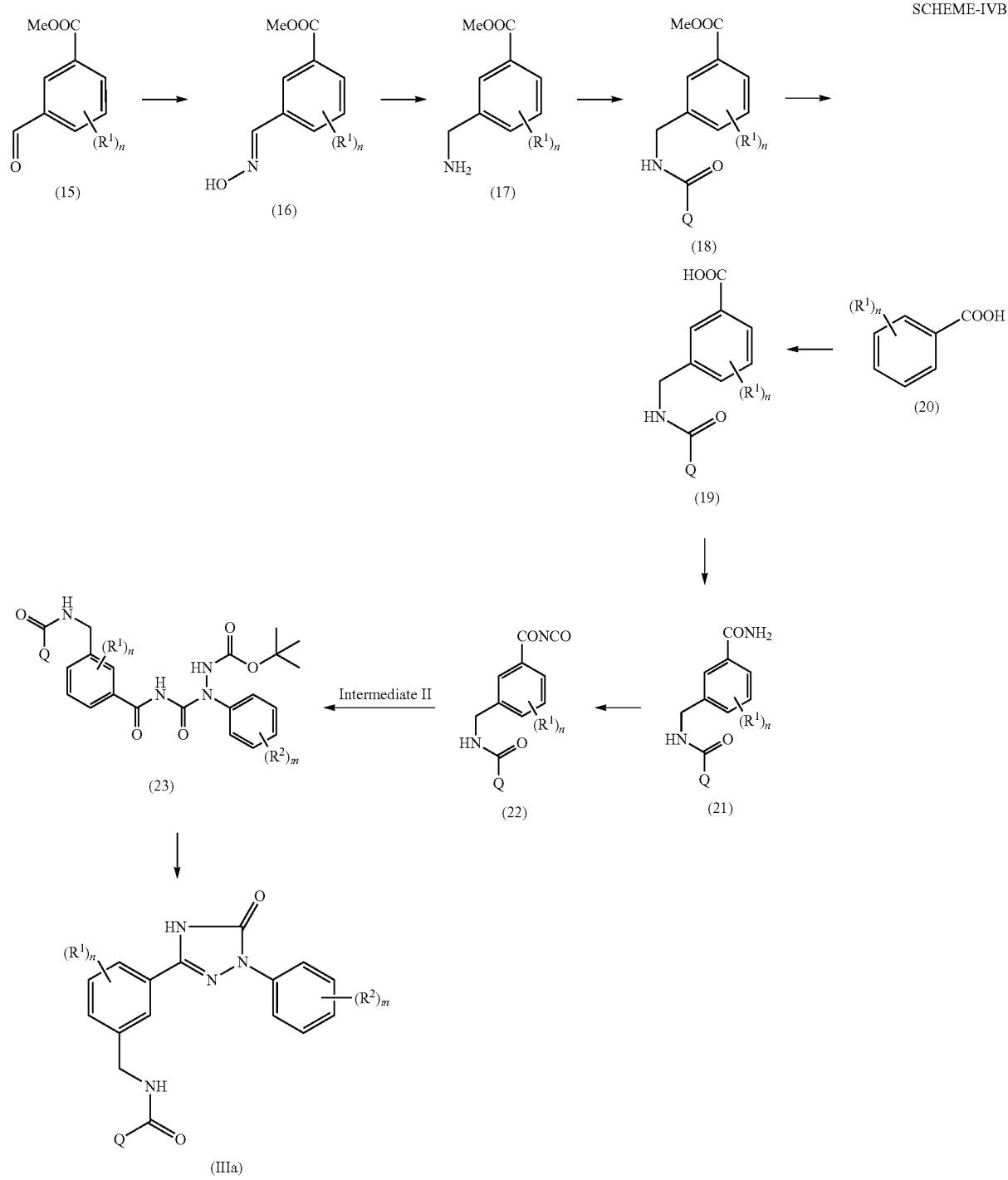

A compound of formula (13) can be converted to a compound of formula (14) by reaction with an aqueous solution of sodium nitrite and a solution of stannous chloride in conc. HCl, which can be further converted to Intermediate-H by using BOC protection methods known in the art of synthesis in the presence of inorganic bases such as $Na_2CO_3$, $K_2CO_3$ by using aprotic solvents such as THF, DMF at 0-100° C. A compound of formula (19) can be prepared from a compound of formula (15) by following the reaction steps as given in scheme IIB for a compound of formula (8). Also, a compound of formula (19) can be directly prepared from a compound of formula (20) by using 2,2,2-trifluoro-N-(hydroxymethyl)acetamide and sulphuric acid. A compound of formula (19) can be converted to a compound of formula (21) by using reaction conditions such as oxalyl chloride/ $NH_3$, thionyl chloride/$NH_3$ or EDCI/$NH_4Cl$, which can be further treated with oxalyl chloride in a solvent such as EDC or toluene to give a compound of formula (22).

A compound of formula (22) can be treated with Intermediate-II to obtain a compound of formula (23). The compound of formula (22) can be treated with the Intermediate-II in an aprotic solvent, such as DCM, toluene or EDC to obtain a compound of formula (23). A compound of formula (23) can be treated with organic acid to obtain compound of formula (Ma). The organic acid used in the conversion of a compound of formula (23) may be TFA, CSA or methane sulphonic acid. The compound of formula (Ma) can be converted to a free amine for further amide derivatization by procedures known in the art of synthesis.

An approach for the preparation of compound of formula (IIb) is schematically represented in Synthetic Scheme-V (wherein L, W, $R^1$, $R^2$, R, t, m, and n are as defined with respect to a compound of formula (II)).

Synthetic Scheme-V

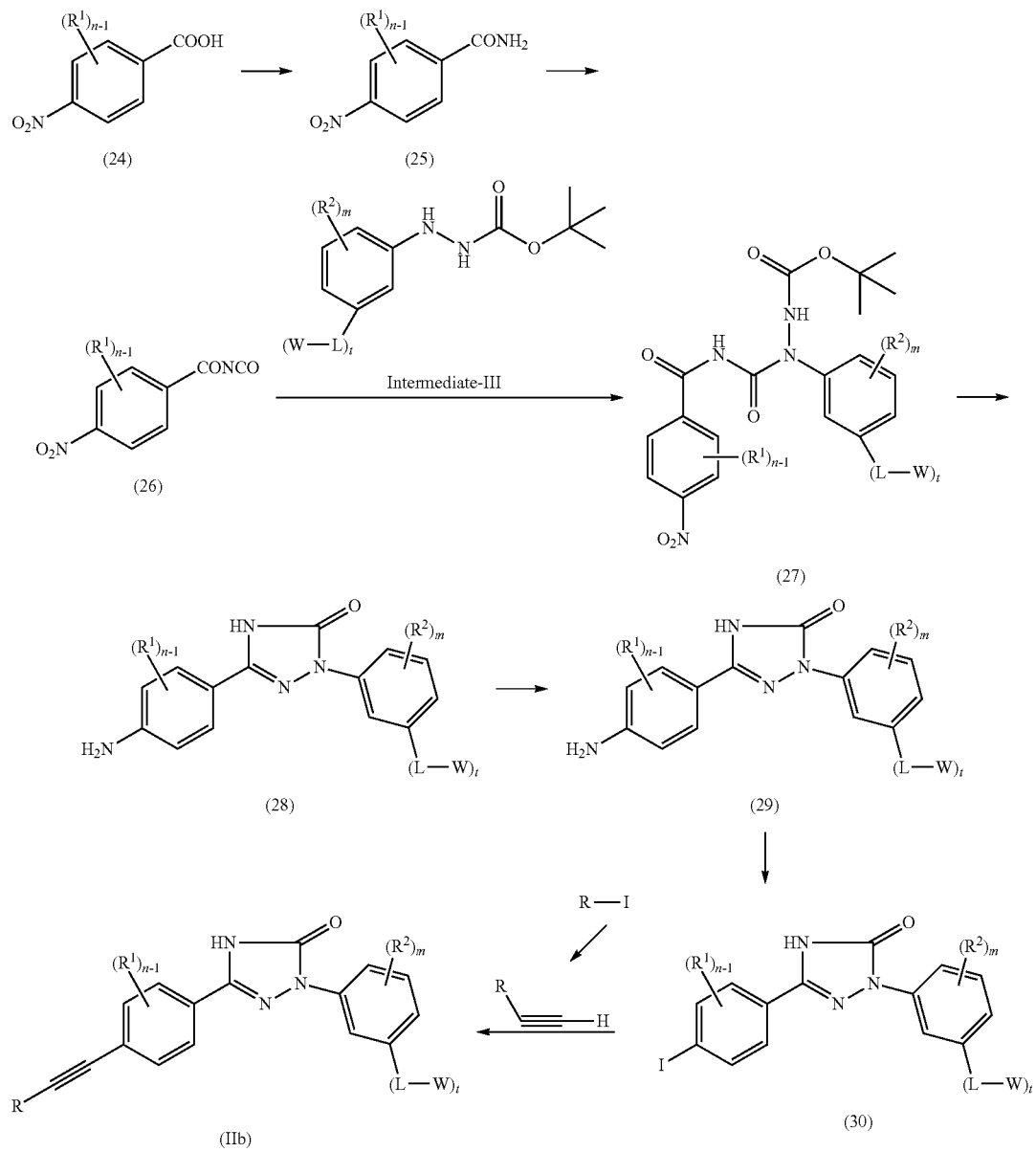

A compound of formula (24) can be converted to a compound of formula (25) by using reaction conditions such as oxalyl chloride/NH$_3$, thionyl chloride/NH$_3$ or EDCI/NH$_4$Cl, which can be further treated with oxalyl chloride in a solvent such as EDC or toluene to give a compound of formula (26). A compound of formula (26) can be treated with Intermediate-III in an aprotic solvent, such as DCM, toluene or EDC to obtain a compound of formula (27), which then further treated with an organic acid, such as TFA, CSA or methane sulphonic acid at room temperature give a compound of formula (28). A compound of formula (28) can be converted to a compound of formula (29) by reduction methods known in the art of synthesis such as Pd/C, Fe—HCl or Raney Nickel in a solvent such as MeOH or EtOH, which can be further converted to a compound of formula (30) by iodination using KI followed by diazotization using PTSA and NaNO$_2$. A compound of formula (30) can be converted to a compound of formula (IIb) by a sequence of transformations such as transition metal catalyzed reactions for example Sonogashira coupling.

An approach for the preparation of compound of formula (IIc) is schematically represented in Synthetic Scheme-VI (wherein L, W, R$^1$, R$^2$, R, m, and n are as defined with respect to a compound of formula (II)).

Synthetic Scheme-VI

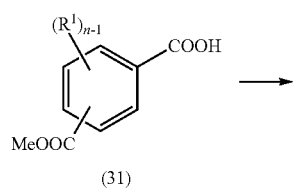

(31)

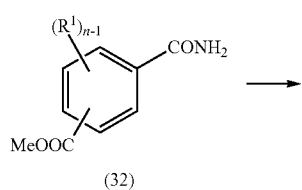

(32)

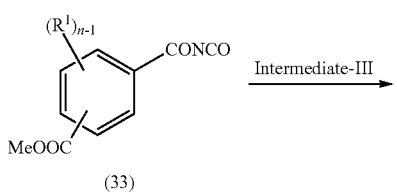

(33)

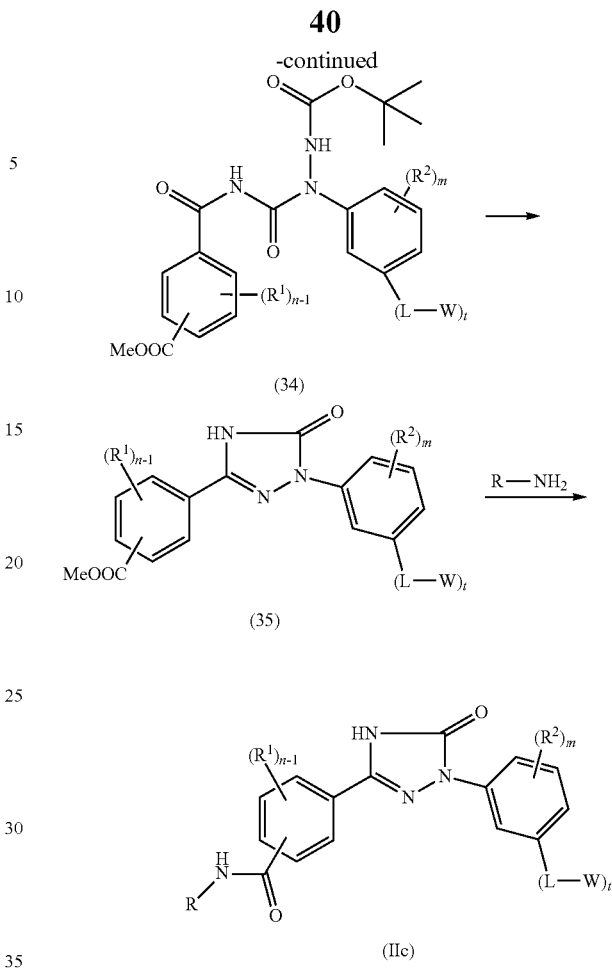

A compound of formula (31) can be converted to a compound of formula (32) by using standard conditions such as oxalyl chloride/NH$_3$, thionyl chloride/NH$_3$ or EDCI/NH$_4$Cl, which can be further treated with oxalyl chloride in a solvent, such as EDC or toluene to give a compound of formula (33). A compound of formula (33) can be treated with (or coupled to) Intermediate-III in an aprotic solvent, such as DCM, toluene or EDC to obtain a compound of formula (34), which when further treated with organic acid, such as TFA, CSA or methane sulphonic acid at room temperature give a compound of formula (35). A compound of formula (IIc) can be prepared from a compound of formula (35) by using trimethyl aluminum and solvents such as toluene, xylene or EDC at a temperature of 0-100° C.

Alternatively, the methyl ester of a compound of formula (35) can be converted to its acid derivative under hydrolysis condition, which can be further treated with the amines of the formula R—NH$_2$ to give compound of formula (IIc) using standard coupling conditions such as EDCI, HBTU, TBTU, DCC etc.

An approach for the preparation of a compound of formula (IVd) is schematically represented in Synthetic Scheme-VII (wherein R$^1$, R$^2$, R, W, m, and n are as defined with respect to a compound of formula (IV)).

Synthetic Scheme-VII

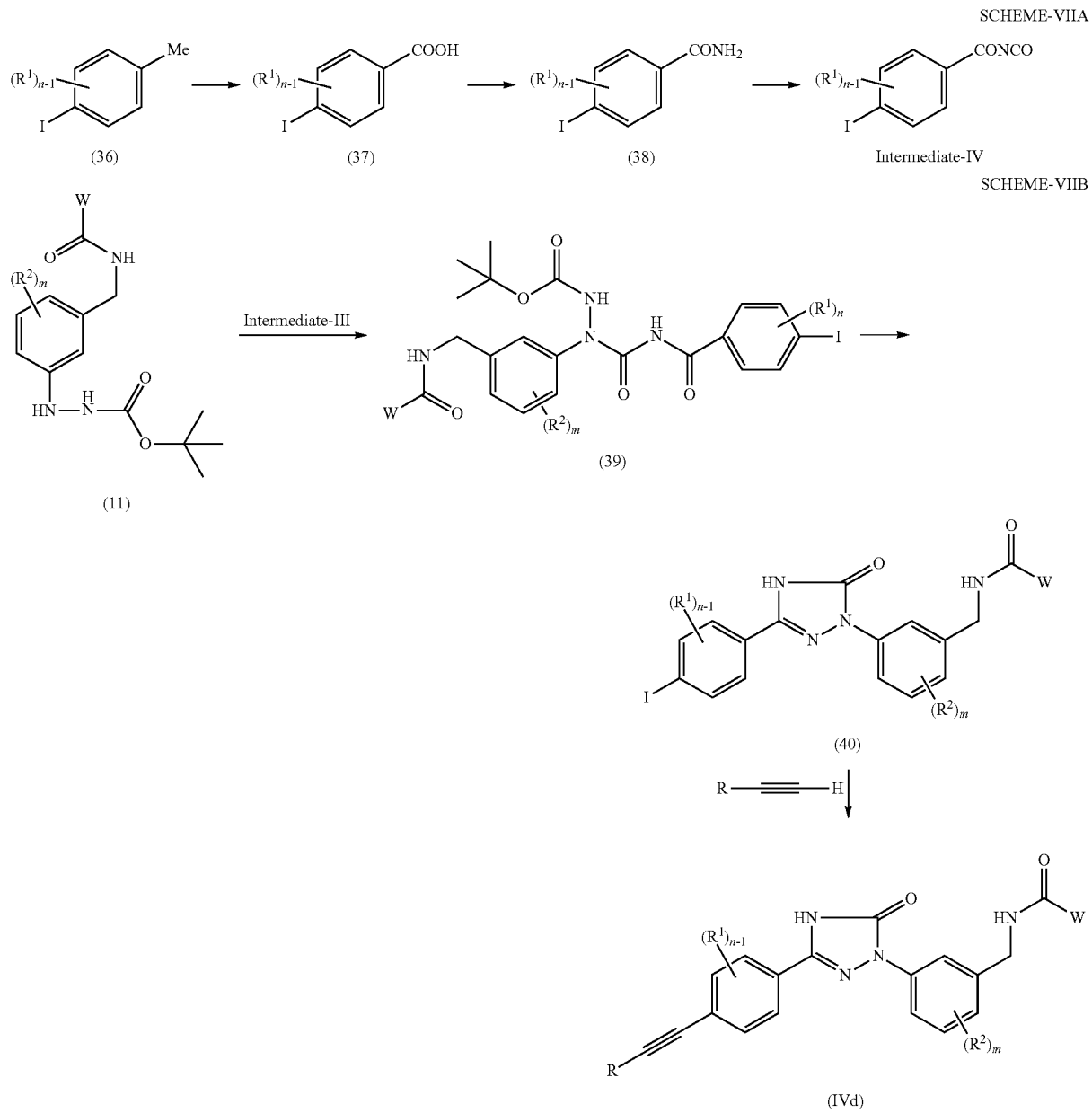

A compound of formula (36) can be converted to Intermediate-IV by following the same reaction steps as for Intermediate-I described in scheme IIIA. A compound of formula (11) can be treated with Intermediate-IV in an aprotic solvent, such as DCM, toluene or EDC to Obtain a compound of formula (39), which when further treated with organic acid, such as TFA, CSA or methane sulphonic acid at room temperature give a compound of formula (40). A compound of formula (40) can be converted to a compound of formula (IVd) by a sequence of transformations such as transition metal catalyzed reactions for example Sonogashira coupling.

In another approach, the compound of formula (Mb) can be prepared following the synthetic steps depicted in Synthetic Scheme-VIII (wherein $X^1$, $X^2$, $X^3$, $R^1$, $R^2$, Q, m and n are as defined with respect to a compound of formula (III)).

Synthetic Scheme-VIII

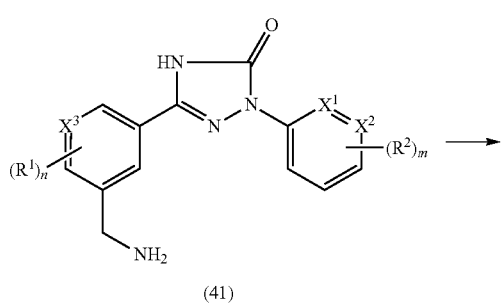

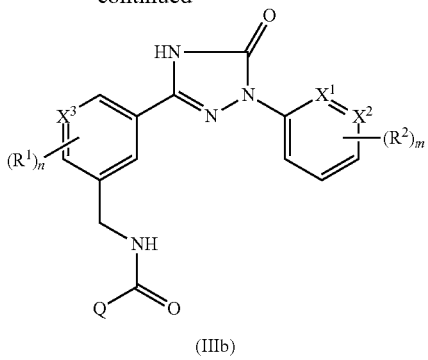

(IIIb)

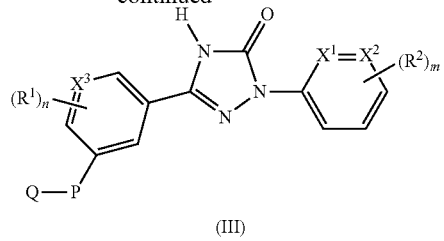

(III)

A compound of formula (41) can be reacted with Q-C(O)LG (wherein LG represents a suitable leaving group (e.g., OH or Cl or Br or O-alkyl)) under suitable reaction conditions to obtain a compound of formula (IIIb). When LG represents Cl the reaction can be performed in a suitable solvent such as DMF, DCM or THF in the temperature range of 0-120° C., optionally in the presence of a suitable base such as DIPEA or Et$_3$N. Furthermore, when LG represents O-alkyl the reaction can be performed with a suitable reagent such as trimethylaluminium or a strong base such as sodium hydride (NaH) in a suitable solvent such as toluene or DMF. When LG represents OH, the reaction can be performed with a suitable coupling reagent known in the art, for example, 1-ethyl-3-(3-dimethylaminopropyl)carbodiimide (EDCI) in a suitable solvent such as DMF or tetrahydrofuran (THF) in the temperature range of 0-120° C., optionally in the presence of a suitable base such as DIPEA (diisopropylethyl amine) or Et$_3$N. Alternatively, the reaction can be performed using a suitable reagent such as isobutyl chloroformate, oxalyl chloride or thionyl chloride in a suitable solvent such as DMF, DCM or THF, in the presence of a suitable base such as DIPEA or Et$_3$N.

In another approach, the compound of formula (III) can be prepared following the synthetic steps depicted in Synthetic Scheme-IX (wherein R$^1$, R$^2$, P, Q, X$^1$, X$^2$, X$^3$, m and n are as defined with respect to a compound of formula (III)).

Synthetic Scheme-IX

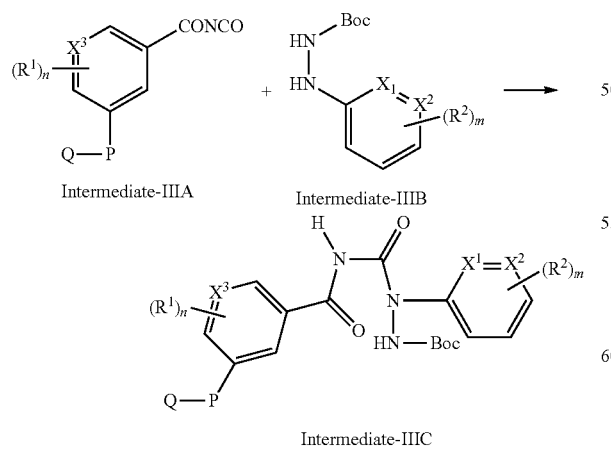

An Isocyanate compound of formula (Intermediate-IIIA) may be obtained from a corresponding acid, amide or acid halide derivative. A compound of formula (Intermediate-IIIA) can be reacted with a compound of formula (Intermediate-IIIB) to form a compound of formula (Intermediate-IIIC) and the compound of formula (Intermediate-IIIC) can be converted to a compound of formula (III). According to the process, the compound of formula (Intermediate-IIIA) can be reacted with the compound of formula (Intermediate-IIIB) in a solvent such as DCM, toluene or EDC. According to the process, the compound of formula (Intermediate-IIIC) may be isolated or not isolated. According to the process, the compound of formula (Intermediate-IIIC) is converted to compound of formula (III) using an acid. The acid used in the process can be an organic acid such as TFA, CSA or methane sulphonic acid.

In another approach, the compound of formula (IV) can be prepared following the synthetic steps depicted in Synthetic Scheme-X (wherein R$^1$, R$^2$, L, W, m and n are as, defined with respect to a compound of formula (IV)).

Synthetic Scheme-X

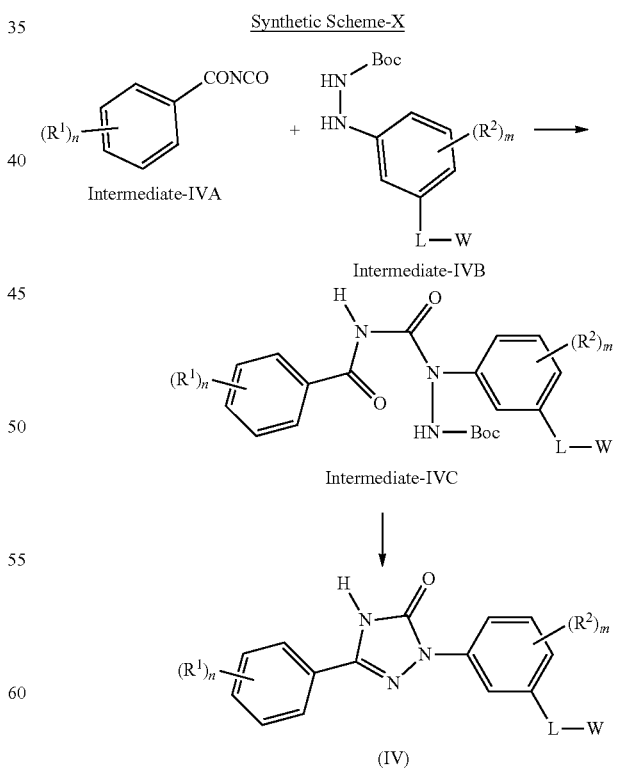

An Isocyanate compound of formula (Intermediate-IVA) may be obtained from a corresponding acid, amide or acid halide derivative. A compound of formula (Intermediate- IVA) can be reacted with a compound of formula (Intermediate-IVB) to form a compound of formula (Intermediate-IVC) and the compound of formula (Intermediate-IVC) can be converted to a compound of formula (IV). According to the process, the compound of formula (Intermediate-IVA) can be reacted with the compound of formula (Intermediate-IVB) in solvent such as DCM, toluene or EDC. According to the process, the compound of formula (Intermediate-IVC) may be isolated or not isolated. According to the process, the compound of formula (Intermediate-IVC) is converted to a compound of formula (IV) using an acid. The acid used in the process can be an organic acid such as TFA, CSA or methane sulphonic acid.

In another approach, the compound of formula (II) can be prepared following the synthetic steps depicted in Synthetic Scheme-XI (wherein $R^1$, $R^2$, L, P, Q, $X^2$, $X^3$, $X^4$, m, n, s and t are as defined with respect to a compound of formula (II) and $PG^1$ represents an amine protecting group such as, but not limited to, tert-Butoxycarbonyl (Boc) or carboxybenzyl (Cbz) or benzyl.

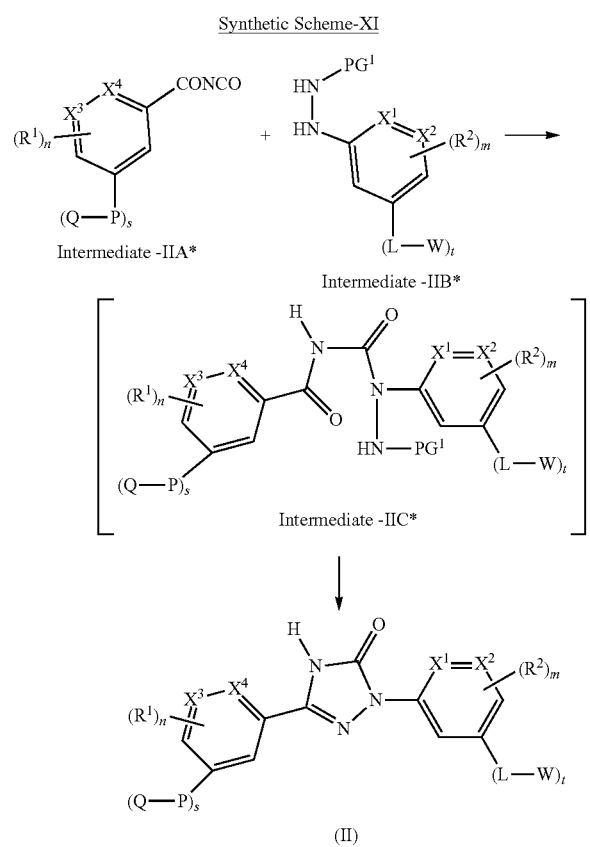

An Isocyanate compound of formula (Intermediate-IIA*) may be obtained from a corresponding acid, amide or acid halide derivative. A compound of formula (Intermediate-IIA*) can be reacted with a compound of formula (Intermediate-IIB*) to form a compound of formula (Intermediate-IIC*) and the compound of formula (Intermediate-IIC*) can be converted to the compound of formula (II). According to the process, the compound of formula (Intermediate-IIA*) can be reacted with the compound of formula (Intermediate-IIB*) in a solvent such as DCM, toluene or EDC. According to the process, the compound of formula Intermediate-IIC* may be isolated or not isolated. According to the process, the compound of formula (Intermediate-IIC*) is converted to compound of formula (II) using an acid. The acid used in the process can be an organic acid such as TFA, CSA or methane sulphonic acid.

Q, W or other substituents (e.g. $R^1$ or $R^2$) if present in the formula (I), (II), (III) or (IV) may be transformed into another chemical group at a chemically compatible stage of the synthetic sequence, in the presence of a suitable reagent by following the procedures known in the art of organic synthesis to obtain the final compound of formula (I), (II), (III) or (IV).

Experimental

Unless otherwise stated, work-up includes distribution of the reaction mixture between the organic and aqueous phase indicated within parentheses, separation of layers and drying the organic layer over sodium sulphate ($Na_2SO_4$), filtration and evaporation of the solvent under reduced pressure. Purification, unless otherwise mentioned, includes purification by silica gel chromatographic techniques, in suitable solvents of a suitable polarity as the mobile phase. Abbreviations used in the description of the chemistry and in the examples that follow are: AIBN: Azobisisobutyronitrile; NBS: N-Bromosuccinimide; $CCl_4$: Carbon tetrachloride; CSA: Camphor sulphonic acid; TEA: Trifluoro acetic acid; $NaHCO_3$: Sodium bicarbonate; $PCl_5$: Phosphorous pentachloride; $POCl_3$: Phosphorous oxychloride; NaO$^t$Bu:Sodium O-tert butyl; $K_2CO_3$:Potassium carbonate; DIPEA: N,N-Diisopropylethylamine; LDA: Lithium diisopropylamide; TEA: Triethylamine; TBAF: Tetra-n-butylammonium fluoride; DCC: N,N'-Dicyclohexylcarbodiimide; HOBT: 1-Hydroxybenzotriazole; TBTU: O-(Benzotriazol-1-yl)-N,N,N',N'-tetramethyluronium tetrafluoroborate; HBTU: O-(Benzo triazol-1-yl)-N,N,N',N'-tetramethyluronium hexafluorophosphate; EDCI: 1-ethyl-3-(3-dimethylaminopropyl)carbodiimide; BOP: (Benzotriazol-1-yloxy)tris(dimethylamino)phosphonium hexafluorophosphate; Boc/BOC: tert-Butoxycarbonyl; BOC anhydride: Di-tert-butyl dicarbonate; Cbz: Benzyloxycarbonyl; DAST: Diethylaminosulfur trifluoride; PTSA: p-Toluenesulfonic acid; DBU: 1,8-Diazabicyclo[5.4.0]undec-7-ene; DCM or MDC: Dichloromethane; DEE: Diethylether; DMSO: Di-methyl sulfoxide; THF: Tetrahydrofuran; EDC: Ethylene dichloride; EtOAc or EA: Ethyl acetate; $CHCl_3$: Chloroform; MeOH: Methanol; RT: Room temperature; h: hours.

Intermediate-1

2-(4-Bromophenyl)-5-(2-chloro-6-fluorophenyl)-2,4-dihydro-3H-1,2,4-triazol-3-one

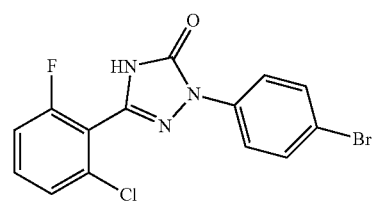

Step-1:—Preparation of (2E)-1-(4-bromophenyl)-2-(2-chloro-6-fluorobenzylidene) hydrazine

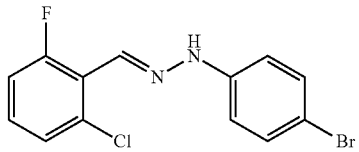 [SMILES: Fc1cccc(Cl)c1/C=N/Nc1ccc(Br)cc1]

To a solution of 2-chloro-6-fluorobenzaldehyde (1.0 g, 6.32 mmol) in ethanol was added (4-bromophenyl)hydrazine (1.7 g, 7.59 mmol) and aq. solution of NaHCO$_3$ (0.637 g, 4.59 mmol). The reaction mixture was stirred at RT for 5-6 h. The reaction mass was quenched in water and extracted with ethyl acetate. The organic layer was dried over anhydrous sodium sulphate and concentrated. The obtained crude product was purified by column chromatography on silica gel, eluting with 4.6% EA: pet. ether to afford 0.650 g of the desired product. $^1$H NMR (300 MHz, DMSO d$_6$): δ 6.98 (d, J=7.8 Hz, 2H), 7.23-7.40 (m, 5H), 8.07 (s, 1H), 10.87 (br s, 1H). MS (m/z): 329.17 (M+H)$^+$.

Step-2:—Preparation of N-(4-bromophenyl)-2-chloro-6-fluorobenzenecarbohydrazonoyl chloride

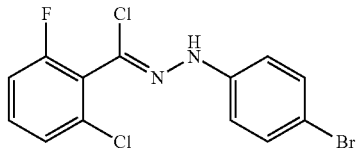 [SMILES: Fc1cccc(Cl)c1/C(Cl)=N/Nc1ccc(Br)cc1]

To a solution of (2E)-1-(4-bromophenyl)-2-(2-chloro-6-fluorobenzylidene) hydrazine (0.300 g, 1.32 mmol) in benzene (10 mL) was added PCl$_5$ (0.330 g, 1.58 mmol). The reaction mixture was stirred at RT for 18 h. The reaction mass was quenched in water, neutralized with NaHCO$_3$ and extracted with ethyl acetate. The organic layer was dried over anhydrous sodium sulphate and concentrated to afford 0.110 g of the desired product. $^1$H NMR (300 MHz, DMSO d$_6$): δ 7.17 (d, J=8.7 Hz, 2H), 7.41 (d, J=8.7 Hz, 3H), 7.45-7.61 (m, 2H), 10.26 (s, 1H). MS (m/z): 361.34 (M–H)$^-$.

Step-3:—Preparation of N'-(4-bromophenyl)-2-chloro-6-fluorobenzenecarbohydrazonamide

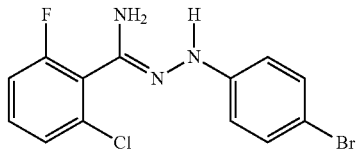 [SMILES: N/C(=N\Nc1ccc(Br)cc1)c1c(F)cccc1Cl]

To a cold solution of N-(4-bromophenyl)-2-chloro-6-fluorobenzenecarbohydrazonoyl chloride (0.070 g, 0.267 mmol) in dry THF was added aq. ammonia. The reaction mass was stirred at 0-5° C. for 2-3 h. The reaction mass was quenched in water, neutralized with dilute acetic acid and extracted with DCM. The organic layer was dried over anhydrous sodium sulphate and concentrated to afford 0.040 g of the desired product. $^1$H NMR (300 MHz, DMSO d$_6$): δ 6.29 (br s, 2H), 6.80 (d, J=8.4 Hz, 2H), 7.24 (d, J=9.3 Hz, 2H), 7.28-7.50 (m, 3H), 8.33 (s, 1H).

Step-4:—Preparation of 2-(4-bromophenyl)-5-(2-chloro-6-fluorophenyl)-2,4-dihydro-3H-1,2,4-triazol-3-one To a cold solution of N'-(4-bromophenyl)-2-chloro-6-fluorobenzenecarbohydrazonamide (0.050 g, 0.146 mmol) in CHCl$_3$ was added pyridine (0.5 mL) and phosgene (1.0 mL) at 0-5° C. The reaction mass was stirred at 0-5° C. for 2-3 h. The reaction mass was quenched in water, neutralized with dilute acetic acid and extracted with DCM. The organic layer was dried over anhydrous sodium sulphate and concentrated. The obtained crude product was purified with column chromatography on silica gel eluting with 1.0% MeOH: DCM to afford 0.020 g of the desired product. $^1$H NMR (300 MHz, DMSO d$_6$): δ 7.50 (t, J=8.7 Hz, 1H), 7.56-7.71 (m, 4H), 7.89 (d, J=9.3 Hz, 2H), 12.69 (s, 1H). MS (m/z): 368.15 (M)$^+$.

Intermediate-2

5-(2-Chloro-6-fluorophenyl)-2-(4-ethynylphenyl)-2,4-dihydro-3H-1,2,4-triazol-3-one

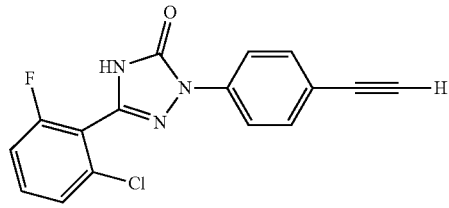 [SMILES: C#Cc1ccc(-n2nc(-c3c(F)cccc3Cl)[nH]c2=O)cc1]

Step-1:—Preparation of (1E)-1-(2-chloro-6-fluorobenzylidene)-2-(4-iodophenyl)hydrazine

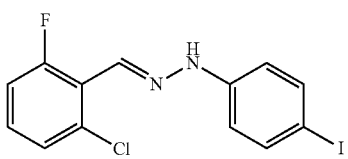 [SMILES: Fc1cccc(Cl)c1/C=N/Nc1ccc(I)cc1]

To a solution of (4-iodophenyl)hydrazine (1.0 g, 4.27 mmol) in ethanol (10 mL) was slowly added solution of 2-chloro-6-fluorobenzaldehyde (0.675 g, 4.27 mmol) in ethanol (10 mL). The reaction mass was stirred at RT for 5-6 h. The reaction mass was quenched in water and extracted with ethyl acetate. The organic layer was concentrated to afford 1.2 g of desired product. $^1$H NMR (300 MHz, DMSO d$_6$): δ 6.87 (d, J=8.4 Hz, 2H), 7.26-7.36 (m, 3H), 7.53 (d, J=9.0 Hz, 2H), 8.06 (s, 1H), 10.84 (s, 1H). MS (m/z): 374.87 (M)$^+$.

Step-2:—Preparation of 2-chloro-6-fluoro-N-(4-iodophenyl)benzenecarbohydrazonoyl chloride

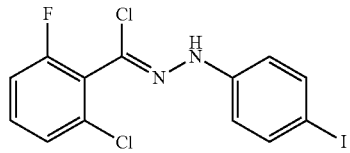

The title compound was prepared according to the procedure described in step-2 of Intermediate-1 using (1E)-1-(2-chloro-6-fluorobenzylidene)-2-(4-iodophenyl)hydrazine (1.2 g, 3.20 mmol), PCl$_5$ (0.990 g, 4.8 mmol) and benzene (20 mL) to afford 1.0 g of desired product. $^1$H NMR. (300 MHz, DMSO d$_6$): δ 7.00 (d, J=8.7 Hz, 2H), 7.41 (d, J=8.7 Hz, 1H), 7.48-7.60 (m, 4H), 10.22 (s, 1H).

Step-3:—Preparation of 2-chloro-6-fluoro-N-(4-iodophenyl)benzenecarbohydrazonamide

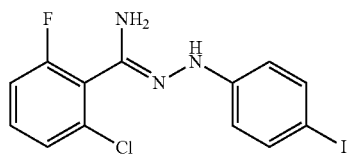 [SMILES: N/C(=N\Nc1ccc(I)cc1)c1c(F)cccc1Cl]

The title compound was prepared according to the procedure described in step-3 of Intermediate-1 by using 2-chloro-6-fluoro-N-(4-iodophenyl)benzenecarbohydrazonoyl chloride (1.00 g, 2.44 mmol), aq. ammonia (2.0 mL) and dry THF (10 mL) to afford 0.900 g of the desired product. $^1$H NMR (300 MHz, DMSO d$_6$): δ 6.28 (br s, 2H), 6.70 (d, J=8.4 Hz, 2H), 7.27 (t, J=8.7 Hz, 1H), 7.36-7.42 (m, 3H), 7.45-7.51 (m, 1H), 8.33 (s, 1H).

Step-4:—Preparation of 5-(2-chloro-6-fluorophenyl)-2-(4-iodophenyl)-2,4-dihydro-3H-1,2,4-triazol-3-one

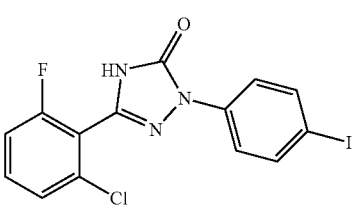 [SMILES: O=c1[nH]c(-c2c(F)cccc2Cl)nn1-c1ccc(I)cc1]

The title a compound was prepared according to the procedure described in step-4 of Intermediate-1 using 2-chloro-6-fluoro-N'-(4-iodophenyl)benzene carbohydrazonamide (0.900 g, 2.31 mmol), pyridine (0.65 mL, 5.79 mmol), phosgene (2.50 mL, 4.63 mmol) and CHCl$_3$ (20 mL). The obtained crude product was purified with column chromatography on silica gel eluting with 1.0% MeOH: DCM to afford 0.400 g of the desired product. $^1$H NMR (300 MHz, DMSO d$_6$): δ 7.47 (t, J=9.0 Hz, 2H), 7.54-7.82 (m, 5H), 12.62 (s, 1H). MS (m/z): 414.25 (M–H)$^-$.

Step-5:—Preparation of 5-(2-chloro-6-fluorophenyl)-2-{4-[(trimethylsilyl)ethynyl]phenyl}-2,4-dihydro-3H-1,2,4-triazol-3-one

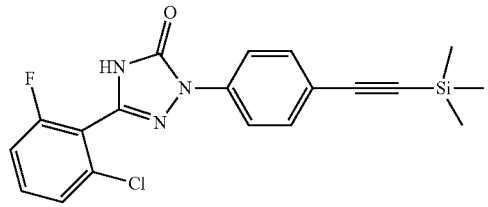 [SMILES: C[Si](C)(C)C#Cc1ccc(-n2nc(-c3c(F)cccc3Cl)[nH]c2=O)cc1]

To a solution of 5-(2-chloro-6-fluorophenyl)-2-(4-iodophenyl)-2,4-dihydro-3H-1,2,4-triazol-3-one (0.200 g, 0.483 mmol) in DMSO (2 mL) was added ethynyl(trimethyl)silane (0.071 g, 0.724 mmol), copper iodide (0.005 g, 0.007 mmol), bis(triphenylphosphine) palladium(II) chloride (0.200 g, mmol) and TEA (2.0 mL). The reaction mass was stirred at RT for 24 h. The reaction mass was quenched in water and neutralized with dilute acetic acid and extracted with DCM. The organic layer was dried over anhydrous sodium sulphate and concentrated to afford 0.200 g of the desired product. $^1$H NMR (300 MHz, DMSO d$_6$): δ 2.31 (s, 9H), 7.44-7.47 (m, 3H), 7.54-7.71 (m, 3H), 7.94-8.01 (m, 1H), 77.95 (br s, 1H). MS (m/z): 384.29 (M–H)$^-$.

Step-6:—Preparation of 5-(2-chloro-6-fluorophenyl)-2-(4-ethynylphenyl)-2,4-dihydro-3H-1,2,4-triazol-3-one To a solution of 5-(2-chloro-6-fluorophenyl)-2-(4-[(trimethylsilyl)ethynyl]phenyl)-2,4-dihydro-3H-1,2,4-triazol-3-one (0.200 g, 0.570 mmol) in DCM was added TBAF (0.362 g, 1.11 mmol). The reaction mass was stirred at RT for 2-3 h. The reaction mass was quenched in water and filtered through celite bed and concentrated. The obtained crude product was purified with column chromatography on silica gel eluting with 2.0% MeOH: DCM to afford 0.400 g of the desired product. $^1$H NMR (300 MHz, DMSO d$_6$): δ 4.21 (s, 1H), 7.50 (t, J=9.3 Hz, 1H), 7.58 (d, J=8.4 Hz, 3H), 7.67-7.71 (m, 1H), 7.96 (d, J=8.1 Hz, 2H), 12.69 (br s, 1H).

Intermediate-3

1-(4-bromophenyl)-5-chloro-3-(2-chloro-6-fluorophenyl)-1H-1,2,4-triazole

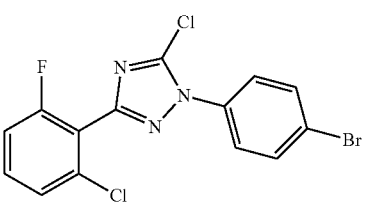 [SMILES: Fc1cccc(Cl)c1-c1nc(Cl)n(-c2ccc(Br)cc2)n1]

To 2-(4-bromophenyl)-5-(2-chloro-6-fluorophenyl)-2,4-dihydro-3H-1,2,4-triazol-3-one (Intermediate-1, 0.100 g, 0.271 mmol) was added POCl$_3$. The reaction mass was refluxed for 48 h. The reaction mass was quenched in water, basified with NaHCO$_3$ and extracted with ethyl acetate and concentrated. The obtained crude product was purified with column chromatography on silica gel eluting with 0.5% EA:DCM to afford 0.110 g of the desired product. $^1$H NMR (300 MHz, DMSO $d_6$): δ 7.44 (t, J=9.3 Hz, 1H), 7.53 (d, J=7.8 Hz, 1H), 7.60-7.68 (m, 1H), 7.72 (d, J=9.0 Hz, 2H), 7.85 (d, J=8.7 Hz, 2H). MS (m/z): 388.22 (M+H)$^+$.

Intermediate-4

3-Chloro-4-iodopyridine

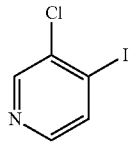

To a cold solution of 3-chloro pyridine (1.0 g, 8.88 mmol) in THF (30.0 mL) was added LDA (5.9 mL, 8.88 mmol) at −75° C. The reaction mixture was stirred at −75° C. for 4 h. Iodine (2.2 g, 8.88 mmol) was added and continued stirring at −75° C. for 1 h. The reaction mixture was quenched in water at −70° C., extracted with ethyl acetate and concentrated to afford 0.500 g of desired product. $^1$H NMR (300 MHz, DMSO $d_6$): δ 8.01 (d, J=5.1 Hz, 1H), 8.14 (d, J=4.8 Hz, 1H), 8.63 (s, 1H).

Intermediate-5

4-(5-Iodopyrimidin-2-yl)morpholine

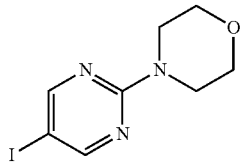 [SMILES: Ic1cnc(N2CCOCC2)nc1]

Step-1:—Preparation of 5-iodopyrimidin-2-amine

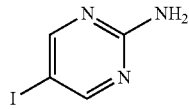

To a solution of pyrimidin-2-amine (1.0 g, 0.010 mol) in DMSO (10 mL) was added iodine (3.2 g, 0.012 mol). The reaction mixture was stirred at 120° C. for 1 h. The reaction mass was quenched in water and excess of iodine was neutralised with sodium metabisulphate. The reaction mass was extracted with ethyl acetate and concentrated to afford 0.400 g of the desired product.

Step-2:—Preparation of 2-chloro-5-iodopyrimidine

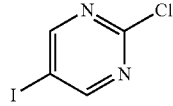

To a solution of 5-iodopyrimidin-2-amine (10.0 g, 0.045 mol) in acetonitrile (150 mL) was added CuCl$_2$ (11.57 g, 0.067 mol) and tert-butyl nitrite (6.99 g, 0.067 mol). The reaction mass was heated at 70° C. for 5-6 h. The reaction mass was diluted with ether and the solid obtained was filtered off. The obtained product was purified with column chromatography on silica gel eluting with DCM to afford 1.700 g of the desired product.

Step-3:—Preparation of 4-(5-iodopyrimidin-2-yl)morpholine

The mixture of 2-chloro-5-iodopyrimidine (0.200 g, 0.836 mmol) in morpholine (3.0 mL) was refluxed for 2-3 h. The reaction mass was quenched in water and the solid obtained was filtered off. The obtained solid was dried to afford 0.180 g of the desired product. $^1$H NMR (300 MHz, DMSO $d_6$): δ 3.63 (s, 8H), 8.52 (s, 2H); MS (m/z): 292.25 (M+H)$^+$.

Intermediate-6

4-(5-Iodopyridin-2-yl)morpholine

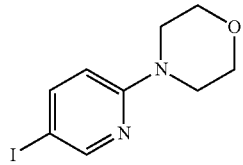 [SMILES: Ic1ccc(N2CCOCC2)nc1]

A solution of 2-chloro-5-iodo pyridine (0.200 g, 0.836 mmol) in morpholine (3.0 mL) was refluxed for 12-15 h. The reaction mass was quenched in ice and the solid obtained was filtered off to afford 0.170 g of the desired product. $^1$H NMR (300 MHz, DMSO $d_6$): δ 3.40 (t, J=4.8 Hz, 4H), 3.67 (t, J=4.5 Hz, 4H), 6.74 (d, J=8.7 Hz, 1H), 7.77-7.81 (m, 1H), 8.28 (s, 1H).

Intermediate-7 tert-Butyl 2-[4-(methoxycarbonyl)phenyl]hydrazinecarboxylate

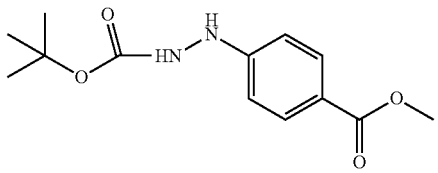 [SMILES: COC(=O)c1ccc(NNC(=O)OC(C)(C)C)cc1]

Step-1:—Preparation of methyl 4-aminobenzoate

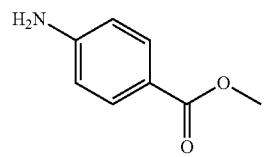

To a solution of 4-amino benzoic acid (20.0 g, 0.14 mol) in methanol (400 mL) was added conc. sulphuric acid (40 mL). The reaction mass was stirred at RT for 6-7 h. The reaction mass was quenched with water and basified with NaHCO$_3$ and extracted with DCM. The organic layer was dried over anhydrous sodium sulphate and concentrated to afford 15.0 g of the desired product. $^1$H NMR (300 MHz, DMSO d$_6$): δ 3.72 (s, 3H), 5.96 (br s, 2H), 6.55 (d, J=8.1 Hz, 2H), 7.64 (d, J=8.4 Hz, 2H) MS (m/z): 152.21 (M+H)$^+$.

Step-2:—Preparation of methyl 4-hydrazinylbenzoate

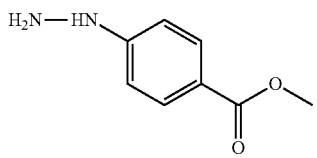

To a cold solution of methyl 4-aminobenzoate (15.0 g, 0.099 mol) in conc. HCl was added aq. solution of sodium nitrite (7.5 g, 0.109 mmol) at 0-5° C. The reaction mass was stirred at RT for 1-2 h. The reaction mass was cooled to 0° C. and stannous chloride (0.049 g, 0.210 mmol) was added and further stirred at RT for 2-3 h. The reaction mass was filtered to afford 17.0 g of desired product. $^1$H NMR (300 MHz, DMSO d$_6$): δ 3.77 (s, 3H), 7.03 (d, J=8.4 Hz, 2H), 7.82 (d, J=8.4 Hz, 2H), 10.69 (br s, 2H); MS (m/z): 167.28 (M+H)$^+$.

Step-3:—Preparation of tert-butyl 2-[4-(methoxycarbonyl)phenyl]hydrazinecarboxylate To a solution of methyl 4-hydrazinylbenzoate (10.0 g, 0.049 mol) in DCM (150 mL) was added TEA (10 mL) and BOC anhydride (10.7 g, 0.049 mmol). The reaction mass was stirred at RT for 12 h. The reaction mass was quenched in water and extracted with DCM. The organic layer was dried over anhydrous sodium sulphate and concentrated. The obtained solid was washed with pentane to afford 6.5 g of desired product. $^1$H NMR (300 MHz, DMSO d$_6$): δ 1.40 (s, 9H), 3.74 (s, 3H), 6.65 (d, J=8.4 Hz, 2H), 7.74 (d, J=8.7 Hz, 2H), 8.31 (s, 1H), 8.93 (br s, 1H).

Intermediate-8

2-Chloro-6-fluorobenzoyl isocyanate

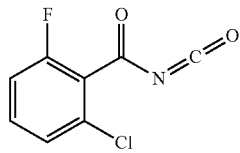 [SMILES: O=C=NC(=O)c1c(F)cccc1Cl]

Step-1:—Preparation 2-chloro-6-fluorobenzamide

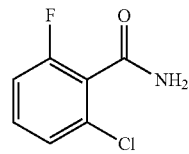 [SMILES: NC(=O)c1c(F)cccc1Cl]

A solution of 2-chloro-6-fluorobenzonitrile (8.0 g, 51.61 mmol) in conc. sulphuric acid (50 mL) was heated at 60-70° C. for 6-7 h. The reaction mass was quenched in water and extracted with DCM. The organic layer was dried over anhydrous sodium sulphate and concentrated to afford 5.5 g of desired product.

Step-2:—Preparation of 2-chloro-6-fluorobenzoyl isocyanate

To a solution of 2-chloro-6-fluorobenzamide (2.0 g, 0.011 mmol) in EDC (10 mL) was added oxalyl chloride (2.18 g, 0.017 mmol). The reaction mass was refluxed for 24 h. Excess of solvent was removed under vacuum to afford 2.0 g of desired product.

Intermediate-9

4-[3-(2-Chloro-6-fluorophenyl)-5-oxo-4,5-dihydro-1H-1,2,4-triazol-1-yl]benzoic acid

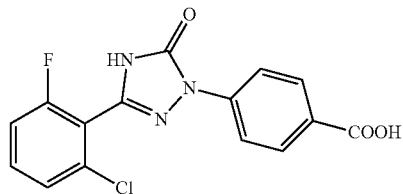 [SMILES: O=C(O)c1ccc(-n2nc(-c3c(F)cccc3Cl)[nH]c2=O)cc1]

Step-1:—Preparation of tert-butyl 2-[(2-chloro-6-fluorobenzoyl)carbamoyl]-2-[4-(methoxycarbonyl)phenyl]hydrazinecarboxylate

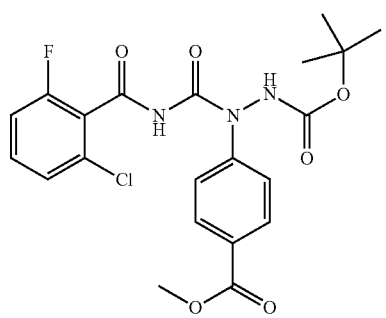 [SMILES: COC(=O)c1ccc(N(NC(=O)OC(C)(C)C)C(=O)NC(=O)c2c(F)cccc2Cl)cc1]

To a solution of tert-butyl 2-[4-(methoxycarbonyl)phenyl] hydrazinecarboxylate (Intermediate-7, 2.0 g, 7.54 mmol) in DCM (15 mL) was added 2-chloro-6-fluorobenzoyl isocyanate (Intermediate-8, 1.50 g, 7.54 mmol). The reaction mass was stirred at RT for 2 h. Excess of solvent was removed under vacuum to afford 3.0 g of desired product. $^1$H NMR (300 MHz, DMSO d$_6$): δ 1.42 (s, 9H), 3.83 (s, 3H), 7.24-7.46 (m, 5H), 7.94 (d, J=7.2 Hz, 2H), 9.91 (br s, 1H), 11.34-11.39 (br m, 1H); MS (m/z): 464.06 (M–H)$^-$.

Step-2:—Preparation of methyl 4-[3-(2-chloro-6-fluorophenyl)-5-oxo-4,5-dihydro-1H-1,2,4-triazol-1-yl]benzoate

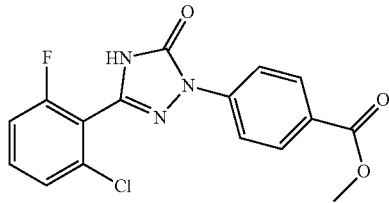 [SMILES: COC(=O)c1ccc(-n2nc(-c3c(F)cccc3Cl)[nH]c2=O)cc1]

To a solution of tert-butyl 2-[(2-chloro-6-fluorobenzoyl)carbamoyl]-2-[4-(methoxycarbonyl)phenyl]hydrazinecarboxylate (3.0 g, 6.45 mmol) in DCM (30 mL) was added trifluoro acetic acid (2.0 mL). The reaction mass was stirred at RT for 2-3 h. Excess of solvent was removed at low temperature. The reaction mass was quenched in ice and filtered off to afford 2.0 g of desired product. $^1$H NMR (300 MHz, DMSO d$_6$): δ 3.86 (s, 3H), 7.51-7.60 (m, 2H), 7.70 (br s, 1H), 8.09 (br s, 4H), 12.79 (br s, 1H); MS (m/z): 348.55 (M+H)$^+$.

Step-3:—Preparation of 4-[3-(2-chloro-6-fluorophenyl)-5-oxo-4,5-dihydro-1H-1,2,4-triazol-1-yl]benzoic acid To a solution of methyl 4-[3-(2-chloro-6-fluorophenyl)-5-oxo-4,5-dihydro-1H-1,2,4-triazol-1-yl]benzoate (2.0 g, 5.76 mmol) in THF:water (5 mL:10 mL) was added sodium hydroxide (0.691 g, 17.27 mmol). The reaction mass was stirred at RT for 3 h. The reaction mass was diluted with water and washed the aqueous layer with diethyl ether and toluene. The aqueous layer was cooled to 15° C. and acidified with dilute HCl. The reaction mass was filtered off to afford 1.0 g of desired product. $^1$H NMR (300 MHz, DMSO d$_6$): δ 7.50 (t, J=9.0 Hz, 1H), 7.58 (d, J=7.8 Hz, 1H), 7.67-7.74 (m, 1H), 8.06 s, 4H), 12.77 (br s, 1H).

Intermediate-10 tert-Butyl 2-[4-methoxy-3-(methoxycarbonyl)phenyl]hydrazinecarboxylate

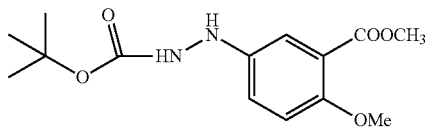 [SMILES: COC(=O)c1cc(NNC(=O)OC(C)(C)C)ccc1OC]

Step-1:—Preparation of 2-methoxy-5-nitrobenzoic acid

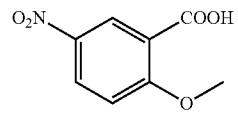

To a solution of 2-chloro-5-nitrobenzoic acid (3.0 g, 0.14 mol) in methanol (500 mL) was added sodium methoxide (28.1 g, 0.520 mol). The reaction mass was refluxed for 15 h. Excess of solvent was removed under vacuum and the reaction mass was diluted with water and acidified with dilute HCl to obtain solid which was filtered off to afford 25.0 g of desired product. $^1$H NMR (300 MHz, DMSO d$_6$): δ 3.96 (s, 3H), 7.36 (d, J=9.3 Hz, 1H), 8.37 (d, J=9.0 Hz, 1H), 8.45 (s, 1H), 13.32 (br s, 1H)); MS (m/z): 198.25 (M+H)$^+$.

Step-2:—Preparation of methyl 2-methoxy-5-nitrobenzoate

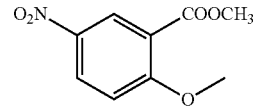

To a solution of 2-methoxy-5-nitrobenzoic acid (25.0 g, 0.12 mol) in DMF (100 mL) was added K$_2$CO$_3$ (26.3 g, 0.19 mol). The reaction mass was stirred at 80° C. for 1 h followed by addition of methyl iodide (12.3 mL, 0.19 mol). The reaction mass was further stirred at 80° C. for 5-6 h. The reaction mass was filtered and the obtained filtrate was concentrated. The residue was further diluted with water and obtained solid was filtered off to afford 20.0 g of desired product. $^1$H NMR (300 MHz, DMSO d$_6$): δ 3.83 (s, 3H), 3.97 (s, 3H), 7.38 (d, 0.1=9.3 Hz, 1H), 8.41 (dd, J=2.4 Hz & 2.4 Hz, 1H), 8.47 (s, 1H); MS (m/z): 212.44 (M+H)$^+$.

Step-3:—Preparation of methyl 5-amino-2-methoxybenzoate

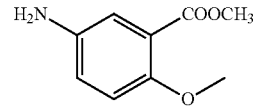

A solution of methyl 2-methoxy-5-nitrobenzoate (20.0 g, 0.097 mol) in methanol (300 mL) and 10% Pd/C (5.0 g) was stirred under hydrogen atmosphere under 70-80 psi pressure in Parr apparatus for 4-5 h. The reaction mass was filtered and the obtained filtrate was concentrated to afford 15.0 g of desired product. $^1$H NMR (300 MHz, DMSO d$_6$): δ 3.67 (s, 3H), 3.74 (s, 3H), 4.96 (br s, 2H), 6.75 (dd, J=2.4 Hz, 1H), 6.85 (d, J=8.7 Hz, 1H), 6.92 (s, 1H); MS (m/z): 182.25 (M+H)$^+$.

Step-4:—Preparation of methyl
5-hydrazinyl-2-methoxybenzoate

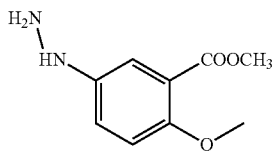

The title compound was prepared according to the procedure described in step-2 of Intermediate-7 by using methyl 5-amino-2-methoxybenzoate (15.0 g, 0.082 mol), stannous chloride (37.25 g, 0.16 mmol), sodium nitrite (6.28 g, 0.091 mmol), conc. HCl (400 mL) and water (100 mL) to afford 14.0 g of desired product. $^1$H NMR (300 MHz, DMSO d$_6$): δ 3.75 (s, 6H), 7.09 (m, 1H), 7.20-7.23 (m, 1H), 7.34 (s, 1H), 10.20 (br s, 2H); MS (m/z): 197.27 (M+H)$^+$.

Step-5:—Preparation of tert-butyl 2-[4-(methoxycarbonyl)phenyl]hydrazinecarboxylate The title compound was prepared according to the procedure described in step-3 of Intermediate-7 by using methyl 5-hydrazinyl-2-methoxybenzoate (10.0 g, 0.051 mol), DCM (150 mL), TEA (10 mL) and BOC anhydride (11.2 g, 0.051 mmol) to afford 2.0 g of desired product. $^1$H NMR (300 MHz, DMSO d$_6$): δ 1.43 (s, 9H), 3.71 (s, 3H), 3.79 (s, 3H), 6.81-6.85 (m, 1H), 6.97-6.99 (m, 2H), 7.45 (s, 1H), 8.78 (s, 1H); MS (m/z): 295.19 (M–H)$^-$.

Intermediate-11

5-[3-(2-Chloro-6-fluorophenyl)-5-oxo-4,5-dihydro-1H-1,2,4-triazol-1-yl]-2-methoxy benzoic acid

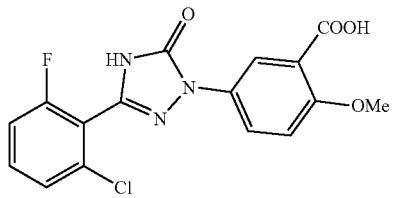 [SMILES: COc1ccc(-n2nc(-c3c(F)cccc3Cl)[nH]c2=O)cc1C(=O)O]

Step-1:—Preparation tert-butyl 2-[(2-chloro-6-fluorobenzoyl)carbamoyl]-2-[4-methoxy-3-(methoxycarbonyl)phenyl]hydrazinecarboxylate

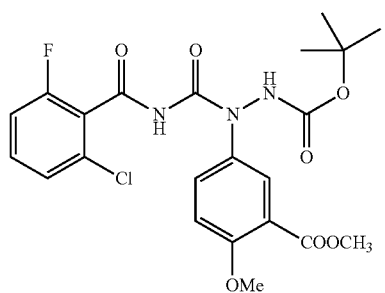 [SMILES: COC(=O)c1cc(N(NC(=O)OC(C)(C)C)C(=O)NC(=O)c2c(F)cccc2Cl)ccc1OC]

The title compound was prepared according to the procedure described in step-1 of Intermediate-9 by using 2-chloro-6-fluorobenzoyl isocyanate (Intermediate-8, 2.0 g, 6.75 mmol), tert-butyl 2-[4-methoxy-3-(methoxycarbonyl)phenyl]hydrazinecarboxylate (Intermediate-10, 1.61 g, 8.18 mmol) and DCM (30 mL) to afford 3.0 g of desired product. $^1$H NMR (300 MHz, DMSO d$_6$): δ 1.40 (s, 9H), 3.81 (s, 6H), 7.13-7.83 (m, 6H), 9.6 (br s, 114), 11.13 (br s, 1H); MS (m/z): 494.05 (M–H)$^-$.

Step-2:—Preparation of methyl 5-[3-(2-chloro-6-fluorophenyl)-5-oxo-4,5-dihydro-1H-1,2,4-triazol-1-yl]-2-methoxybenzoate

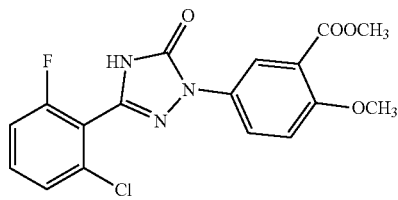 [SMILES: COC(=O)c1cc(-n2nc(-c3c(F)cccc3Cl)[nH]c2=O)ccc1OC]

The title compound was prepared according to the procedure described in step-2 of Intermediate-9 by using tert-butyl 2-[(2-chloro-6-fluorobenzoyl)carbamoyl]-2-[4-methoxy-3-(methoxycarbonyl)phenyl]hydrazinecarboxylate (3.0 g, 6.06 mmol), DCM (30 mL) and trifluoro acetic acid (3.0 mL) to afford 2.0 g of desired product. $^1$H NMR (300 MHz, DMSO d$_6$): δ 3.80 (s, 3H), 3.84 (s, 3H), 7.28 (d, J=9.3 Hz, 1H), 7.49 (t, J=8.7 Hz, 1H), 7.57 (d, J=8.4 Hz, 1H), 7.65-7.73 (m, 1H), 8.06 (d, J=9.0 Hz, 1H), 8.18 (s, 1H), 12.62 (s, 1H); MS (m/z): 376.27 (M–H)$^-$.

Step-3:—Preparation of 5-[3-(2-chloro-6-fluorophenyl)-5-oxo-4,5-dihydro-1H-1,2,4-triazol-1-yl]-2-methoxybenzoic acid The title compound was prepared according to the procedure described in step-3 of Intermediate-9 by using of methyl 5-[3-(2-chloro-6-fluorophenyl)-5-oxo-4,5-dihydro-1H-1,2,4-triazol-1-yl]-2-methoxybenzoate (1.5 g, 3.97 mol) and sodium hydroxide (0.320 g, 7.95 mmol) to afford 0.700 g of desired product. $^1$H NMR (300 MHz, DMSO d$_6$): δ 3.84 (s, 3H), 7.24 (t, J=9.3 Hz, 1H), 7.48 (t, J=8.7 Hz, 1H), 7.57 (d, J=8.7 Hz, 1H), 7.65-7.72 (m, 1H), 8.00 (d, J=8.7 Hz, 1H), 8.17 (s, 1H), 12.60 (s, 1H), 12.85 (br s, 1H).

Intermediate-12

1-[2-(Trifluoromethyl)phenyl]cyclopropanamine

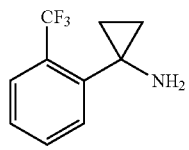

To a cold solution of 2-(trifluoromethyl)benzonitrile (1.0 g, 0.58 mmol) in diethyl ether (20 mL) was added titanium isopropoxide (2.0 g, 0.70 mmol) at –70° C. and ethyl magnesium bromide (4.30 mL, 12.86 mmol). The reaction mass was stirred at RT for 2-3 h. Followed by addition of boron trifluoride solution (1.5 mL) and continued stirring for 2 h at RT. The reaction mass was quenched in 1N HCl and basified with NaOH solution. The obtained crude product was further purified by column chromatography on silica gel eluting with 1% EtOAC: DCM eluent to afford 0.250 g of desired product. ¹H NMR (300 MHz, DMSO d₆): δ 0.82-0.84 (s, 2H), 0.91-0.93 (br s, 2H), 2.24 (br s, 2H), 7.41 (t, J=6.6 Hz, 1H), 7.58-7.67 (m, 3H).

Intermediate-13

1-[4-(Trifluoromethyl)phenyl]cyclopropanamine

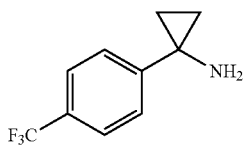

The title compound was prepared according to the procedure described in Intermediate-12 by using of 4-(trifluoromethyl)benzonitrile (1.0 g, 0.58 mmol), diethyl ether (20 mL), titanium isopropoxide (2.0 g, 0.70 mmol), ethyl magnesium bromide (4.30 mL, 12.86 mmol) and boron trifluoride solution (1.5 mL) to afford 0.210 g of desired product. ¹HNMR (CDCl₃): δ 1.05 (s, 2H), 1.60 (s, 2H), 1.78 (s, 2H), 7.36 (d, J=7.8 Hz, 2H), 7.55 (d, J=8.1 Hz, 2H).

Intermediate-14 tert-Butyl 2-(3-methoxy-4-(methoxycarbonyl)phenyl)hydrazinecarboxylate

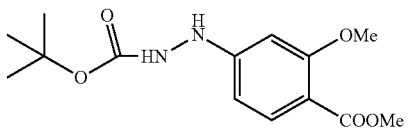 [SMILES: COC(=O)c1ccc(NNC(=O)OC(C)(C)C)cc1OC]

Step-1:—Preparation of methyl 4-hydrazinyl-2-methoxybenzoate

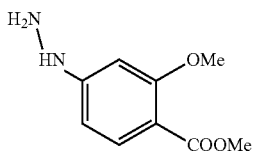 [SMILES: COC(=O)c1ccc(NN)cc1OC]

The title compound was prepared according to the procedure described in step-2 of Intermediate-7 by using methyl 4-amino-2-methoxybenzoate (10.0 g, 0.055 mol), stannous chloride (31.00 g, 0.138 mmol), sodium nitrite (4.57 g, 0.066 mmol), 6 N HCl (200 mL) and water (100 mL) to afford 14.0 g of desired product. ¹H NMR (300 MHz, DMSO d₆): δ 3.73 (s, 3H), 3.80 (s, 3H), 6.51 (d, J=8.4 Hz, 1H), 6.69 (s, 1H), 7.68 (d, J=8.4 Hz, 1H), 8.75 (br s, 1H), 10.28 (br hump, 2H); MS (m/z): 197.01 (M+H)⁺.

Step-2:—Preparation of tert-butyl 2-(3-methoxy-4-(methoxycarbonyl)phenyl)hydrazine carboxylate The title compound was prepared according to the procedure described in step-3 of Intermediate-7 by using methyl 4-hydrazinyl-2-methoxybenzoate (5.0 g, 0.025 mol), DCM (70 mL), TEA (5.0 mL) and BOC anhydride (6.11 g, 0.028 mmol) to afford 3.50 g of desired product. ¹H NMR (300 MHz, DMSO d₆): δ 1.40 (s, 9H), 3.68 (s, 3H), 3.72 (s, 3H), 6.26 (s, 2H), 7.59 (d, J=8.7 Hz, 1H), 8.26 (s, 1H), 8.94 (s, 1H); MS (m/z): 297.02 (M+H)⁺.

Intermediate-15

4-(3-(2-Chloro-6-fluorophenyl)-5-oxo-4,5-dihydro-1H-1,2,4-triazol-1-yl)-2-methoxybenzoic acid

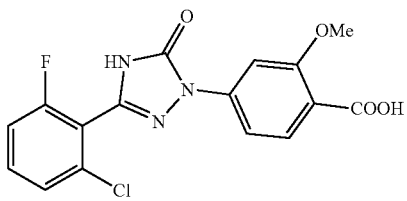 [SMILES: COc1cc(-n2nc(-c3c(F)cccc3Cl)[nH]c2=O)ccc1C(=O)O]

Step-1:—Preparation of tert-butyl 2-((2-chloro-6-fluorobenzoyl)carbamoyl)-2-(3-methoxy-4-(methoxycarbonyl)phenyl)hydrazinecarboxylate

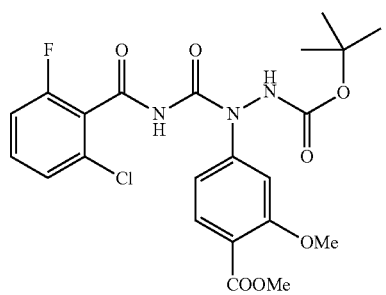 [SMILES: COC(=O)c1ccc(N(NC(=O)OC(C)(C)C)C(=O)NC(=O)c2c(F)cccc2Cl)cc1OC]

The title compound was prepared according to the procedure described in step-1 of Intermediate-9 by using 2-chloro-6-fluorobenzoyl isocyanate (Intermediate-8, 2.0 g, 6.75 mmol), tert-butyl 2-(3-methoxy-4-(methoxycarbonyl)phenyl)hydrazinecarboxylate (Intermediate-14, 2.0 g, 10.10 mmol) and DCM (30 mL) to afford 3.0 g of desired product. ¹H NMR (300 MHz, DMSO d₆): δ 1.42 (s, 9H), 3.76 (s, 6H), 6.99 (d, J=8.1 Hz, 1H), 7.11 (s, 1H), 7.2-7.50 (at, 4H), 9.88 (s, 1H), 11.32 (s, 1H); MS (m/z): 493.92 (M−H)⁻.

Step-2:—Preparation of methyl 4-(3-(2-chloro-6-fluorophenyl)-5-oxo-4,5-dihydro-1H-1,2,4-triazol-1-yl)-2-methoxybenzoate

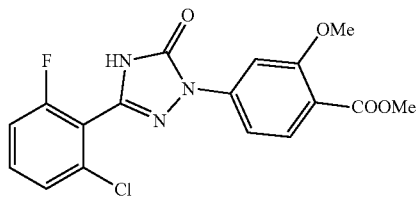 [SMILES: COC(=O)c1ccc(-n2nc(-c3c(F)cccc3Cl)[nH]c2=O)cc1OC]

The title compound was prepared according to the procedure described in step-2 of Intermediate-9 by using tert-butyl 2-((2-chloro-6-fluorobenzoyl)carbamoyl)-2-(3-methoxy-4-(methoxycarbonyl)phenyl)hydrazinecarboxylate (3.0 g, 6.06 mmol), DCM (30 mL) and trifluoro acetic acid (2.0 mL) to afford 2.0 g of desired product. $^1$H NMR (300 MHz, DMSO d$_6$): δ 3.81 (s, 3H), 3.85 (s, 3H), 7.34-7.73 (m, 6H), 12.80 (s, 1H); MS (m/z): 376.16 (M−H)$^−$.

Step-3:—Preparation of 4-(3-(2-chloro-6-fluorophenyl)-5-oxo-4,5-dihydro-1H-1,2,4-triazol-1-yl)-2-methoxybenzoic acid The title compound was prepared according to the procedure described in step-3 of Intermediate-9 by using of methyl 4-(3-(2-chloro-6-fluorophenyl)-5-oxo-4,5-dihydro-1H-1,2,4-triazol-1-yl)-2-methoxybenzoate (1.0 g, 2.65 mol) and sodium hydroxide (0.210 g, 5.30 mmol) to afford 0.600 g of desired product. $^1$H NMR (300 MHz, DMSO d$_6$): δ 3.84 (s, 3H), 7.59 (t, J=7.8 Hz, 2H), 7.67-7.75 (m, 3H), 7.81 (d, J=8.4 Hz, 1H), 12.58 (br, 1H), 12.80 (s, 1H); MS (m/z): 362.21 (M−H)$^−$.

Intermediate-16

(4-Fluoro-2-(trifluoromethyl)phenyl)methanamine

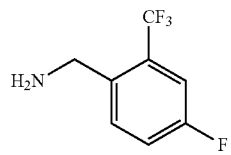 [SMILES: NCc1ccc(F)cc1C(F)(F)F]

To a solution of 4-fluoro-2-(trifluoromethyl)benzonitrile (2.0 g) in ethanol (10.0 mL) was added Raney Ni (catalytic amount). The reaction mixture was subjected for hydrogenation in Parr apparatus under 50 psi for 2-3 h. The reaction mass, was filtered through celite and the filtrate was concentrated to afford 0.400 g of desired product. $^1$HNMR (CDCl$_3$): δ 3.98 (s, 2H), 7.24 (t, J=9.0 Hz, 1H), 7.34 (d, J=8.7 Hz, 1H), 7.54 (t, J=7.8 Hz, 11-1); MS [M+H]$^+$:194.03.

Intermediate-17

4-(3-(2-Chloro-6-fluorophenyl)-5-oxo-4,5-dihydro-1H-1,2,4-triazol-1-yl)benzamide

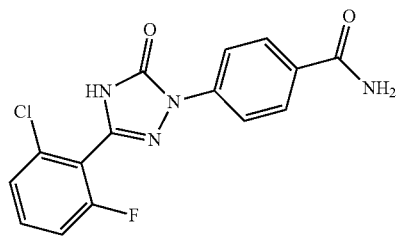 [SMILES: NC(=O)c1ccc(-n2nc(-c3c(F)cccc3Cl)[nH]c2=O)cc1]

Step-1:—Preparation of 4-hydrazinylbenzonitrile

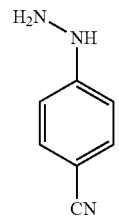

To a cold solution of 4-cyanoaniline (6.0 g, 0.050 mol) in conc. HCl was added aq. solution of sodium nitrite (3.85 g, 0.055 mmol) at −15° C. The reaction mass was stirred at 0-10° C. for 15 minutes and filtered off to remove insolubles. The filtrate was added to stannous chloride in conc. HCl (24.0 g, 0.166 mmol). The reaction mass was stirred at −15° C. for 30 minutes. The reaction mass was filtered to afford 5.2 g of desired product. $^1$H NMR (300 MHz, DMSO d$_6$): δ 7.04 (d, 2H), 7.70 (d, 2H), 9.17 (br s, 1H), 10.66 (br s, 2H).

Step-2:—Preparation of tert-butyl 2-(4-cyanophenyl)hydrazinecarboxylate

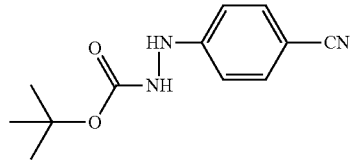 [SMILES: CC(C)(C)OC(=O)NNc1ccc(C#N)cc1]

The title compound was prepared according to the procedure described in step-3 of Intermediate-7 by using 4-hydrazinylbenzonitrile (10.0 g, 0.059 mmol), BOC anhydride (14.5 g, 0.065 mmol), TEA and DCM to afford 12.0 g of desired product. $^1$H NMR (300 MHz, DMSO d$_6$): δ 1.41 (s, 9H), 6.70 (d, J=8.4 Hz, 2H), 7.53 (d, J=8.4 Hz, 2H), 8.48 (br s, 1H), 9.00 (br s, 1H); (M+H)$^+$. 233.94.

Step-3:—Preparation of tert-butyl 2-((2-chloro-6-fluorobenzoyl)carbamoyl)-2-(4-cyanophenyl)hydrazinecarboxylate

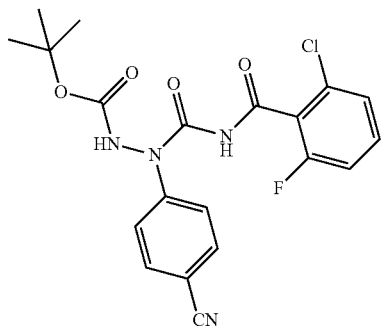 [SMILES: CC(C)(C)OC(=O)NN(C(=O)NC(=O)c1c(F)cccc1Cl)c1ccc(C#N)cc1]

To a solution of tert-butyl 2-(4-cyanophenyl)hydrazinecarboxylate (2.5 g, 0.01 mmol) in DCM (15 mL) was added 2-chloro-6-fluorobenzoyl isocyanate (Intermediate-8, 2.56 g, 0.012 mmol). The reaction mass was stirred at RT for 2 h. Excess of solvent was removed under vacuum to afford 4.0 g of desired product. $^1$H NMR (300 MHz, DMSO d$_6$): δ 1.42 (s, 9H), 7.25-7.38 (m, 2H), 7.47-7.60 (m, 3H), 7.82-7.85 (m, 2H), 9.96 (br s, 1H), 11.43 (br s, 1H); MS (m/z): 431.02 (M+H)$^+$.

Step-4:—Preparation of 4-(3-(2-chloro-6-fluorophenyl)-5-oxo-4,5-dihydro-1H-1,2,4-triazol-1-yl)benzonitrile

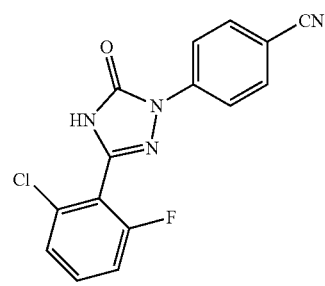 [SMILES: N#Cc1ccc(-n2nc(-c3c(F)cccc3Cl)[nH]c2=O)cc1]

The title compound was prepared according to the procedure described in step-2 of Intermediate-9 by using tert-butyl 2-((2-chloro-6-fluorobenzoyl)carbamoyl)-2-cyanophenyl)hydrazinecarboxylate (4.0 g, 00.009 mol), DCM (30 mL), trifluoro acetic acid (5.0 mL) to afford 2.2 g of desired product. $^1$H NMR (300 MHz, DMSO d$_6$): δ 7.50 (t, 1H), 7.58 (d, 1H), 7.70 (q, 1H), 7.95 (d, J=8.7 Hz, 2H), 7.53 (d, J=8.4 Hz, 2H), 12.80 (br s, 1H); MS (m/z): 331.80 (M+H)$^+$.

Step-5:—Preparation of 4-(3-(2-chloro-6-fluorophenyl)-5-oxo-4,5-dihydro-1H-1,2,4-triazol-1-yl)benzamide A solution of 4-(3-(2-chloro-6-fluorophenyl)-5-oxo-4,5-dihydro-1H-1,2,4-triazol-1-yl)benzonitrile (1.0 g, 0.003 mol) in conc. sulphuric acid (10 mL) was heated to 70° C. for 15 h. The reaction mixture was quenched in ice water. The reaction mass was basified till pH ~6-6.5 with dilute NaOH. The obtained solid was filtered off, washed with water and suck dried to afford 0.300 g of desired product. $^1$H NMR (300 MHz, DMSO d$_6$): δ 7.36 (br s, 1H), 7.84 (t, 1H), 7.57 (d, 1H), 7.67 (d, 1H), 7.98 (m, 5H), 12.70 (br s, 1H); MS (m/z): 333.11 (M+H)$^+$.

Intermediate-18

4-Fluoro-N-hydroxybenzimidamide

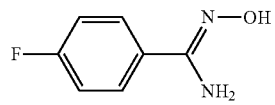

To a solution of 4-fluorobenzonitrile (0.500 g, 4.13 mmol) in ethanol (3 mL) was added hydroxyl amine HCl (0.427 g, 6.19 mmol) and potassium carbonate (1.14 g, 8.26 mmol). The reaction mass was stirred at RT for 15-17 h. Excess of solvent was removed under vacuum. The obtained residue was diluted with water, acidified with dilute HCl and extracted with DCM. The organic layer was separated, dried over anhydrous sodium sulphate and concentrated to afford 0.450 g of desired product. $^1$H NMR (300 MHz, DMSO d$_6$): δ 5.84 (br s, 2H), 7.17-7.27 (m, 2H), 7.68-7.73 (m, 2H), 9.64 (br s, 1H); MS (m/z): 155.13 (M+H)$^+$.

Intermediate-19

4-Chloro-N'-hydroxybenzimidamide

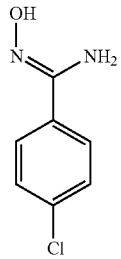

To a solution of 4-chloro benzonitrile (1.000 g, 7.26 mmol) in ethanol (20 mL) was added hydroxyl amine HCl (0.752 g, 10.90 mmol) and potassium carbonate (3.00 g, 21.80 mmol). The reaction mass was refluxed for 10-12 h. Excess of solvent was removed under vacuum and the residue was diluted with water, acidified with dilute HCl. Precipitate obtained was filtered off and sucked dried to afford 0.500 g of desired product. $^1$H NMR (300 MHz, DMSO d$_6$): δ 5.88 (br s, 2H), 7.42 (d, J=8.1 Hz, 2H), 7.68 (d, J=8.4 Hz, 2H), 9.70 (br s, 1H); MS (m/z): 171.13 (M+H)$^+$.

Intermediate-20

N'-Hydroxy-3,5-dimethoxybenzimidamide

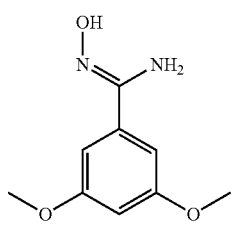

The title compound was prepared according to the procedure described in intermediate-19 by using 3,5-dimethoxy benzonitrile (1.00 g, 6.13 mmol), hydroxyl amine HCl (0.634 g, 9.23 mmol) and potassium carbonate (2.53 g, 18.40 mmol), ethanol (20 mL) to afford 0.400 g of desired product. $^1$H NMR (300 MHz, DMSO d$_6$): δ 3.75 (s, 6H), 5.79 (s, 2H), 6.49 (s, 1H), 6.84 (s, 2H), 9.62 (br s, 1H); MS (m/z): 197.11 (M-t-H)$^+$.

Intermediate-21

Methyl 4-(3-(2,6-dichlorophenyl)-5-oxo-4,5-dihydro-1H-1,2,4-triazol-1-yl)-2-methoxybenzoate

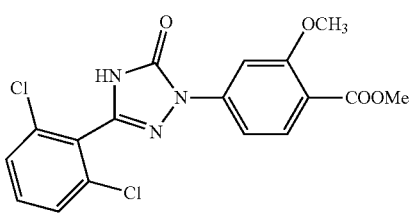 [SMILES: COC(=O)c1ccc(-n2nc(-c3c(Cl)cccc3Cl)[nH]c2=O)cc1OC]

Step-1:—Preparation of 2,6-dichlorobenzoyl isocyanate

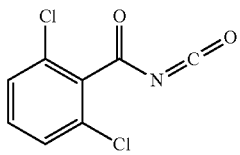 [SMILES: O=C=NC(=O)c1c(Cl)cccc1Cl]

The title compound was prepared according to the procedure described in step-2 of Intermediate-8 by using 2,6-dichlorobenzamide (1.00 g, 5.26 mmol), oxalyl chloride (0.795 g, 6.31 mmol) and toluene (10 mL) to afford 1.00 g of desired product.

Step-2:—Preparation of tert-butyl 2-((2,6-dichlorobenzoyl)carbamoyl)-2-(3-methoxy-4-(methoxycarbonyl)phenyl)hydrazinecarboxylate

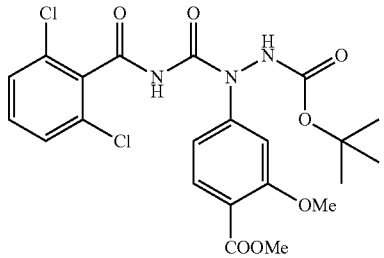 [SMILES: COC(=O)c1ccc(N(NC(=O)OC(C)(C)C)C(=O)NC(=O)c2c(Cl)cccc2Cl)cc1OC]

The title compound was prepared according to the procedure described in step-1 of Intermediate-9 by using 2,6-dichlorobenzoyl isocyanate (1.0 g, 3.38 mmol), tert-butyl 2-(3-methoxy-4-(methoxycarbonyl)phenyl)hydrazinecarboxylate (Intermediate-14, 0.805 g, 3.72 mmol) and DCM (20 mL) to afford 1.5 g of desired product. $^1$H NMR (300 MHz, DMSO d$_6$): δ 1.42 (s, 9H), 3.76 (s, 6H), 6.99 (d, J=6.0 Hz, 1H), 7.10 (s, 1H), 7.60-7.37 (m, 3H), 7.67 (d, J=7.8 Hz, 1H), 9.86 (br s, 1H), 11.30 (br s, 1H).

Step-3:—Preparation of methyl 4-(3-(2,6-dichlorophenyl)-5-oxo-4,5-dihydro-1H-1,2,4-triazol-1-yl)-2-methoxybenzoate The title compound was prepared according to the procedure described in step-2 of Intermediate-9 by using tert-butyl 2-((2,6-dichlorobenzoyl)carbamoyl)-2-(3-methoxy-4-(methoxycarbonyl)phenyl)hydrazinecarboxylate (1.5 g, 2.2 mmol), DCM (50 mL) and trifluoro acetic acid (5.0 mL) to afford 0.900 g of desired product. $^1$H NMR (300 MHz, DMSO d$_6$): δ 3.78 (s, 3H), 3.84 (s, 3H), 7.62-7.30 (m, 5H), 7.82 (d, J=8.7 Hz, 1H), 12.76 (br s, 1H); MS (m/z): 393.85 (M+H)$^+$.

Intermediate-22

3-Fluoro-N'-hydroxy-5-(trifluoromethyl)benzimidamide

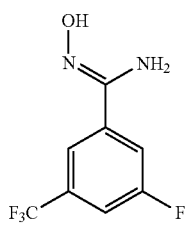

The title compound was prepared according to the procedure described in Intermediate-19 by using 3-fluoro-5-(trifluoromethyl)benzonitrile (2.00 g, 10.0 mmol), hydroxyl amine HCl (1.09 g, 15 mmol) and potassium carbonate (2.2 g, 15 mmol), ethanol (20 mL) to afford 0.900 g of the desired product. $^1$H NMR (300 MHz, DMSO d$_6$): δ 6.10 (s, 2H), 7.69 (d, J=7.8 Hz, 1H), 7.79 (d, J=10.2 Hz, 1H), 10.03 (s, 1H); MS (m/z): 223.17 (M+H)$^+$.

Intermediate-23

1,4-Dichloro-2-ethynylbenzene

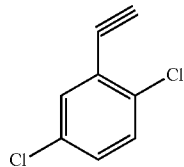

The title compound was prepared according to the procedure described in step-5 and step-6 of Intermediate-2 by using 1,4-dichloro-2-iodobenzene (1.0 g, 3.6 mmol), ethynyl (trimethyl)silane (0.541 g, 5.5 mmol), copper iodide (0.027 g, 0.14 mmol), bis(triphenylphosphine) palladium(II) chloride (0.050 g, 0.072 mmol), TBAF (catalytic) and DCM to afford 0.550 g of desired product. $^1$H NMR (300 MHz, DMSO d$_6$): δ 4.73 (s, 1H), 7.50 (d, J=8.7 Hz, 1H), 7.58 (d, J=8.7 Hz, 1H), 7.71 (s, 1H).

Intermediate-24

1-Chloro-3-ethynyl-2-fluorobenzene

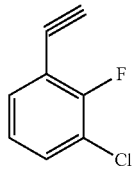

The title compound was prepared according to the procedure described in step-5 and step-6 of Intermediate-2 by using 1-chloro-2-fluoro-3-iodobenzene (1.0 g, 3.9 mmol), ethynyl(trimethyl)silane (0.541 g, 5.5 mmol), copper iodide (0.027 g, 0.14 mmol), bis(triphenylphosphine) palladium(II) chloride (0.050 g, 0:072 mmol), TBAF (catalytic) and DCM to afford 0.500 g of desired product. $^1$H NMR (300 MHz, DMSO d$_6$): δ 4.66 (s, 1H), 7.25 (t, J=8.4 Hz, 1H), 7.54 (t, J=7.2 Hz, 1H), 7.65 (t, J. 7.8 Hz, 1H).

Intermediate-25

2-Chloro-1-ethynyl-4-(trifluoromethyl)benzene

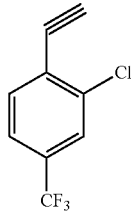

The title compound was prepared according to the procedure described in step-5 and step-6 of Intermediate-2 by using 2-chloro-1-iodo-4-(trifluoromethyl)benzene (1.0 g, 3.2 mmol), ethynyl(trimethyl)silane (0.541 g, 5.5 mmol), copper iodide (0.027 g, 0.14 mmol), bis(triphenylphosphine) palladium(II) chloride (0.050 g, 0.072 mmol), TBAF (catalytic) and DCM to afford 0.525 g of desired product. $^1$H NMR (300 MHz, DMSO d$_6$): δ 4.88 (s, 1H), 7.73 (d, J=8.4 Hz, 1H), 7.83 (d, J=7.8 Hz, 1H), 8.01 (s, 1H).

Intermediate-26

4-(3-(5-(Aminomethyl)-2-chlorophenyl)-5-oxo-4,5-dihydro-1H-1,2,4-triazol-1-yl)-2-methoxy-N-(3-(trifluoromethyl)phenyl)benzamide

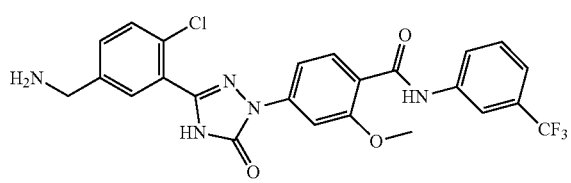 [SMILES: COc1cc(-n2nc(-c3cc(CN)ccc3Cl)[nH]c2=O)ccc1C(=O)Nc1cccc(C(F)(F)F)c1]

Step 1: Preparation of 2-chloro-5-{[(trifluoroacetyl)amino]methyl}benzoic acid

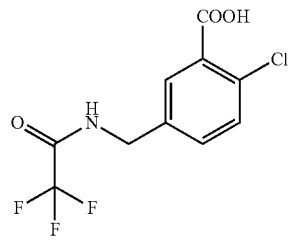 [SMILES: O=C(O)c1cc(CNC(=O)C(F)(F)F)ccc1Cl]

To a solution of 2-chlorobenzoic acid (0.500 g, 3.49 mmol) in conc. H$_2$SO$_4$ was added 2,2,2-trifluoro-N-(hydroxymethyl)acetamide (0.547 g, 3.49 mmol). The mixture was stirred at RT for 16 h. The reaction mixture was poured into ice-water and stirred for 2 h. The precipitate obtained was collected by filtration, dried and re-crystallized from toluene/butan-2-one (7:1) to afford 0.800 g of the title product. $^1$H NMR (300 MHz, DMSO d$_6$): δ 4.42 (d, J=6.0 Hz, 2H), 7.43 (d, J=9.9 Hz, 1H), 7.54 (d, J=8.4 Hz, 1H), 7.71 (s, 1H), 10.06 (br s, 1H), 13.47 (br s, 1H); MS (m/z): 280.18 (M–H)$^-$.

Step 2: Preparation of 2-chloro-5-((2,2,2-trifluoroacetamido)methyl)benzamide

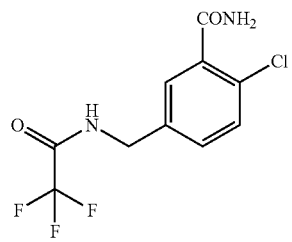 [SMILES: NC(=O)c1cc(CNC(=O)C(F)(F)F)ccc1Cl]

To a cold solution of 2-chloro-5-{[(trifluoroacetyl)amino] methyl}benzoic acid (1.50 g, 5.33 mmol) in THF:DCM (20:10 mL) was added oxalyl chloride (0.6 mL, 6.40 mmol) and DMF (2-3 drop) at 0° C. The reaction mixture was stirred at RT for 2 h and concentrated. A solution of the concentrated mass in THF (15 mL) was treated with ammonia gas (purged through reaction mass) at 0° C. and the reaction mixture was stirred at RT for 1 h. The reaction mixture was diluted with ethyl acetate. The reaction mixture was washed with water, dilute HCl and brine. The organic layer was separated, dried, filtered and concentrated to afford 0.800 g of the desired product. ¹H NMR (300 MHz, DMSO d₆): δ 4.39 (s, 2H), 7.30-7.34 (m, 2H), 7.46 (d, J=7.8 Hz, 1H), 7.63 (s, 1H), 7.90 (s, 1H), 10.06 (s, 1H).

Step 3: Preparation of 2-chloro-5-((2,2,2-trifluoroacetamido)methyl)benzoyl isocyanate

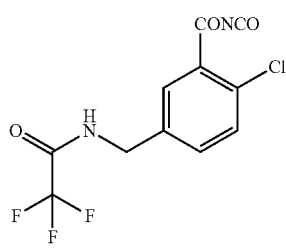

The title compound was prepared according to the procedure described in step-2 of Intermediate-8 by using 2-chloro-5-((2,2,2-trifluoroacetamido)methyl)benzamide (0.700 g, 2.5 mmol), oxalyl chloride (0.3 mL, 3.0 mmol) and EDC (30 mL) to afford 0.700 g of the desired product.

Step 4: Preparation of tert-butyl 2-((2-chloro-5-((2,2,2-trifluoroacetamido)methyl) benzoyl)carbamoyl)-2-(3-methoxy-4-(methoxycarbonyl)phenyl)hydrazinecarboxylate

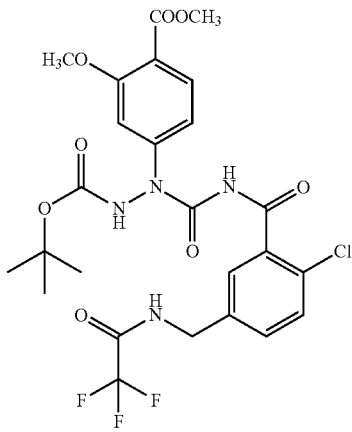 [SMILES: COC(=O)c1ccc(N(NC(=O)OC(C)(C)C)C(=O)NC(=O)c2cc(CNC(=O)C(F)(F)F)ccc2Cl)cc1OC]

The title compound was prepared according to the procedure described in step-1 of Intermediate-9 by using 2-chloro-5-((2,2,2-trifluoroacetamido)methyl)benzoyl isocyanate (0.700 g, 2.2 mmol), tert-butyl 2-(3-methoxy-4-(methoxycarbonyl)phenyl) hydrazinecarboxylate (Intermediate-14, 0.675 mL, 2.20 mmol) and DCM (30 mL) to afford 1.2 g of the desired product. ¹H NMR (300 MHz, DMSO d₆): δ 1.39 (s, 9H), 3.09 (m, 6H), 4.48 (s, 2H), 6.22-6.26 (m, 2H), 7.13-7.76 (m, 4H), 8.94 (s, 1H), 10.08 (s, 1H), 11.02 (s, 1H); MS (m/z): (M)⁺. 602.72.

Step 5: Preparation of methyl 4-(3-(2-chloro-5-((2,2,2-trifluoroacetamido)methyl) phenyl)-5-oxo-4,5-dihydro-1H-1,2,4-triazol-1-yl)-2-methoxybenzoate

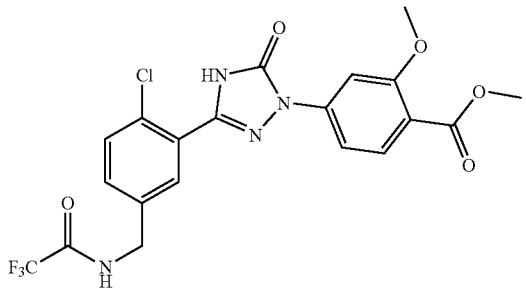 [SMILES: COC(=O)c1ccc(-n2nc(-c3cc(CNC(=O)C(F)(F)F)ccc3Cl)[nH]c2=O)cc1OC]

The title compound was prepared according to the procedure described in step-2 of Intermediate-9 by using tert-butyl 2-((2-chloro-5-((2,2,2-trifluoroacetamido)methyl) benzoyl)carbamoyl)-2-(3-methoxy-4-(methoxycarbonyl)phenyl)hydrazinecarboxylate (1.20 g, 1.99 mmol), TFA (2 mL) and DCM (20 mL) to afford 0.280 g of desired product. ¹H NMR (300 MHz, DMSO d₆): δ 3.78 (s, 3H), 3.85 (s, 3H), 4.46 (d, J=6.0 Hz, 2H), 7.51 (t, J=8.1 Hz, 1H), 7.65-7.68 (m, 3H), 7.78-7.84 (m, 2H), 10.09 (m, 1H), 12.70 (br s, 1H); MS (m/z): (M)⁺. 484.95.

Step 6: Preparation of 4-(3-(2-chloro-5-((2,2,2-trifluoroacetamido)methyl)phenyl)-5-oxo-4,5-dihydro-1H-1,2,4-triazol-1-yl)-2-methoxy-N-(3-(trifluoromethyl)phenyl)benzamide

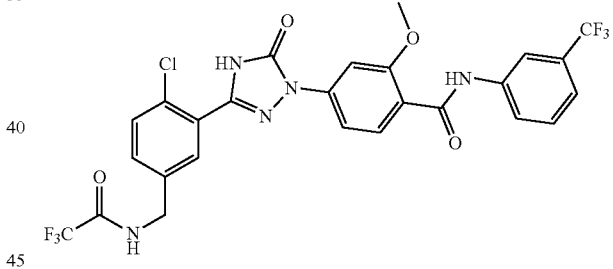

To a solution of methyl 4-(3-(2-chloro-5-((2,2,2-trifluoroacetamido)methyl)phenyl)-5-oxo-4,5-dihydro-1H-1,2,4-triazol-1-yl)-2-methoxybenzoate (0.200 g, 0.413 mmol) in dry toluene (3 mL) was added 3-(trifluoromethyl)aniline (0.100 g, 0.619 mmol) followed by addition of trimethyl aluminium (2M solution in toluene) (2 mL). The reaction mass was refluxed for 3-4 h. The reaction mass was quenched in water and extracted with ethyl acetate. The organic layer was dried over anhydrous sodium sulphate and concentrated to afford 0.170 g of desired product. ¹H NMR (300 MHz, DMSO d₆): δ 3.95 (s, 3H), 4.46 (d, J=6.0 Hz, 2H), 7.56 (t, J=6.0 Hz, 2H), 7.59-7.85 (m, 6H), 7.96 (d, J=7.8 Hz, 1H), 8.26 (s, 1H), 10.09 (s, 1H), 10.37 (s, 1H), 12.65 (s, 1H); MS (m/z): (M)⁺. 614.08.

Step 7: Preparation of 4-(3-(5-(aminomethyl)-2-chlorophenyl)-5-oxo-4,5-dihydro-1H-1,2,4-triazol-1-yl)-2-methoxy-N-(3-(trifluoromethyl)phenyl)benzamide To a solution of 4-(3-(2-chloro-6-((2,2,2-trifluoroacetamido)methyl)phenyl)-5-oxo-4,5-dihydro-1H-1,2,4-triazol- 1-yl)-2-methoxy-N-(3-(trifluoromethyl)phenyl)benzamide (0.150 g, 0.24 mmol) in THF was added aq. KOH (0.028 g, 0.48 mmol). The mixture was stirred at RT for 3-4 h. The reaction mixture was poured into water and extracted in DCM. Organic layer was dried and concentrated to afford 0.080 g of the title product. $^1$H NMR (300 MHz, DMSO d$_6$): δ 3.92-3.96 (m, 5H), 7.43-7.61 (m, 5H), 7.70-7.85 (m, 3H), 7.97 (m, 2H), 8.26 (s, 1H), 10.35 (m, 1H).

Intermediate-27

Methyl 4-(3-(2-chloro-6-methylphenyl)-5-oxo-4,5-dihydro-1H-1,2,4-triazol-1-yl)-2-methoxybenzoate

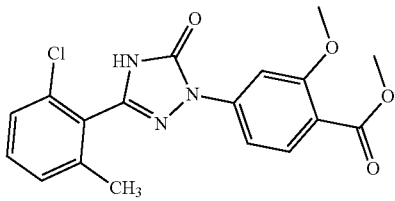 [SMILES: COC(=O)c1ccc(-n2nc(-c3c(C)cccc3Cl)[nH]c2=O)cc1OC]

Step 1: Preparation of 2-chloro-6-methylbenzamide

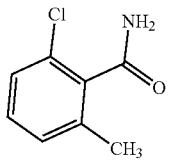

A solution of 2-chloro-6-methylbenzonitrile (2.0 g) in conc. sulphuric acid (10 mL) was heated at 100° C. for 3-4 h. The reaction mass was quenched in ice-water and the solid obtained was filtered. The precipitate was suck dried to afford 1.5 g of desired product. $^1$H NMR (300 MHz, DMSO d$_6$): δ 2.28 (s, 31-1), 7.21-7.27 (m, 3H), 7.65 (s, 1H), 7.91 (s, 1H).

Step 2: Preparation of 2-chloro-6-methylbenzoyl isocyanate

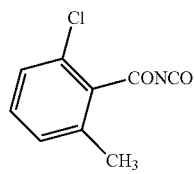

The title compound was prepared according to the procedure described in step-2 of Intermediate-8 by using 2-chloro-6-methylbenzamide (1.0 g, 5.9 mmol), oxalyl chloride (0.894 g, 7.1 mmol) and EDC (20 mL) to afford 1.00 g of the desired product.

Step 3: Preparation of tert-butyl 2-((2-chloro-6-methylbenzoyl)carbamoyl)-2-(3-methoxy-4-(methoxycarbonyl)phenyl)hydrazinecarboxylate

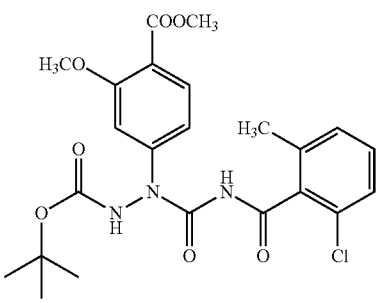 [SMILES: COC(=O)c1ccc(N(NC(=O)OC(C)(C)C)C(=O)NC(=O)c2c(C)cccc2Cl)cc1OC]

The title compound was prepared according to the procedure described in step-1 of Intermediate-9 by using 2-chloro-6-methylbenzoyl isocyanate (0.793 g, 4.06 mmol), tert-butyl 2-(3-methoxy-4-(methoxycarbonyl)phenyl)hydrazinecarboxylate (Intermediate 14, 1.2 g, 4.06 mmol) and DCM (30 mL) to afford 1.5 g of the desired product.

Step 4: Preparation of methyl 4-(3-(2-chloro-6-methylphenyl)-5-oxo-4,5-dihydro-1H-1,2,4-triazol-1-yl)-2-methoxybenzoate The title compound was prepared according to the procedure described in step-2 of Intermediate-9 by using tert-butyl 2-((2-chloro-6-methylbenzoyl)carbamoyl)-2-(3-methoxy-4-(methoxycarbonyl)phenyl)hydrazinecarboxylate (2.0 g), TFA (5 mL) and DCM (30 mL) to afford 0.700 g of the desired product. $^1$H NMR (300 MHz, DMSO d$_6$): δ 2.31 (s, 3H), 3.78 (s, 3H), 3.84 (s, 3H), 7.40 (s, 1H), 7.49 (s, 2H), 7.64 (d, J=8.4 Hz, 1H), 7.75 (s, 1H), 7.81 (d, J=8.7 Hz, 1H), 12.54 (s, 1H); MS (m/z): 373.95 (M+H)$^+$.

Intermediate-28

3-(Difluoromethyl)-4-fluoroaniline

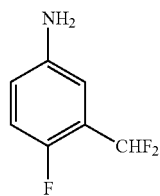

Step 1: Preparation of 2-(difluoromethyl)-1-fluoro-4-nitrobenzene

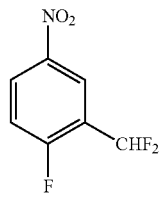 [SMILES: O=[N+]([O-])c1ccc(F)c(C(F)F)c1]

A solution of 2-fluoro-5-nitrobenzaldehyde (3.0 g, 17 mmol) in DCM (50 mL) was added DAST (3.42 g, 21 mmol) and stirred at RT for 18 h under nitrogen atmosphere. The reaction mass was quenched in ice-water and extracted with DCM. The organic layer was dried and concentrated to afford 2.5 g of desired product. $^1$H NMR (300 MHz, DMSO d$_6$): δ 7.31 (s, 1H), 7.69 (t, J=8.7 Hz, 1H), 8.46-8.50 (m, 2H).

Step 2: Preparation of 3-(difluoromethyl)-4-fluoroaniline

A solution of 2-(difluoromethyl)-1-fluoro-4-nitrobenzene (1.2 g, 6.2 mmol) in methanol (20 mL) was added iron powder (4.8 g, 24.8 mmol) followed by conc. HCl (5 mL) dropwise. The reaction mass was stirred at RT for 1-2 h. The reaction mass was quenched in ice-water, basified with NaHCO$_3$ and extracted with DCM. The organic layer was dried and concentrated to afford 0.800 g of desired product. $^1$H NMR (300 MHz, DMSO d$_6$): δ 5.25 (s, 2H), 6.66-6.73 (m, 2H), 6.86-7.04 (m, 2H).

Intermediate-29

3-(Difluoromethyl)aniline

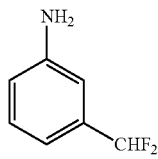

Step 1: Preparation of 1-(difluoromethyl)-3-nitrobenzene

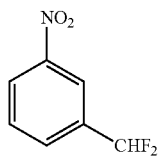

The title compound was prepared according to the procedure described in step-1 of Intermediate-28 by using 3-nitrobenzaldehyde (2.0 g, 13 mmol), DAST (2.55 g, 15 mmol) and DCM (30 mL) to afford 1.5 g of desired product. $^1$H NMR (300 MHz, DMSO d$_6$): δ 7.21 (s, 1H), 7.83 (t, J=8.1 Hz, 1H), 8.05 (m, 1H), 8.40 (br s, 2H).

Step 2: Preparation of 3-(difluoromethyl)aniline

The title compound was prepared according to the procedure described in step-2 of Intermediate-28 by using 1-(difluoromethyl)-3-nitrobenzene (1.0 g, 5.0 mmol), Iron powder (3.0 g, 15.0 mmol), conc. HCl (5 mL) and methanol (20 mL) to afford 0.700 g of desired product. $^1$H NMR (300 MHz, DMSO d$_6$): δ 5.36 (br s, 2H), 6.62-6.82 (m, 4H), 7.11 (t, J=7.8 Hz, 1H); MS (m/z): 144.05 (M+H)$^+$.

Intermediate-30

Methyl 4-(3-(2-chloro-5-(cyclopropanecarboxamidomethyl)phenyl)-5-oxo-4,5-dihydro-1H-1,2,4-triazol-1-yl)-2-methoxybenzoate

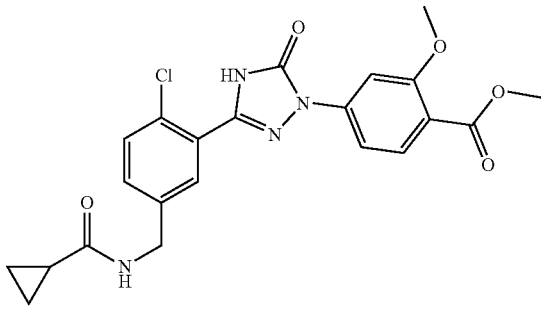 [SMILES: COC(=O)c1ccc(-n2nc(-c3cc(CNC(=O)C4CC4)ccc3Cl)[nH]c2=O)cc1OC]

Step 1: Preparation of methyl 4-(3-(5-(aminomethyl)-2-chlorophenyl)-5-oxo-4,5-dihydro-1H-1,2,4-triazol-1-yl)-2-methoxybenzoate hydrochloride

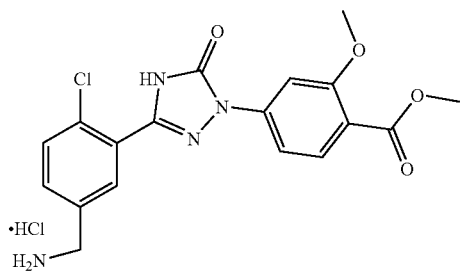 [SMILES: Cl ; COC(=O)c1ccc(-n2nc(-c3cc(CN)ccc3Cl)[nH]c2=O)cc1OC]

A solution of methyl 4-(3-(2-chloro-5-((2,2,2-trifluoroacetamido)methyl) phenyl)-5-oxo-4,5-dihydro-1H-1,2,4-triazol-1-yl)-2-methoxybenzoate (step-5 of Intermediate-26, 0.500 g) in methanol (20 mL) was added conc. HCl (5 mL) dropwise. The reaction mass was refluxed for 24 h. The reaction mass was concentrated to afford 0.450 g of desired product. $^1$H NMR (300 MHz, DMSO d$_6$): δ 3.78 (s, 3H), 3.85 (s, 3H), 4.10 (d, J=5.4 Hz, 2H), 7.63 (d, J=9.0 Hz, 1H), 7.74-7.84 (m, 4H), 7.94 (s, 1H), 8.57 (s, 2H), 12.81 (s, 2H); MS (m/z): 388.96 (M+H)$^+$.

Step 2: Preparation of methyl 4-(3-(2-chloro-5-(cyclopropanecarboxamidomethyl) phenyl)-5-oxo-4,5-dihydro-1H-1,2,4-triazol-1-yl)-2-methoxybenzoate A solution of methyl 4-(3-(5-(aminomethyl)-2-chlorophenyl)-5-oxo-4,5-dihydro-1H-1,2,4-triazol-1-yl)-2-methoxybenzoate hydrochloride (0.500 g, 1.29 mmol) in THF (20 mL) was added DIPEA (2 mL) and cyclopropyl carbonyl chloride (0.201 g, 1.9 mmol) under nitrogen atmosphere. The reaction mass was stirred at RT for 2-4 h. The reaction mass was quenched in water, extracted with DCM and concentrated to afford 0.400 g of desired product. $^1$H NMR (300 MHz, DMSO d$_6$): δ 0.69 (m, 4H), 1.60 (s, 1H), 3.79 (s, 3H), 3.86 (s, 3H), 4.33 (d, J=5.4 Hz, 2H), 7.41-7.54 (m, 3H), 7.61 (d, J=8.4 Hz, 1H), 7.73 (s, 1H), 7.79 (d, 1H), 8.71 (m, H); MS (m/z): 456.97 (M+H)$^+$.

Intermediate-31

$N^1$,4,5-Trimethylbenzene-1,2-diamine

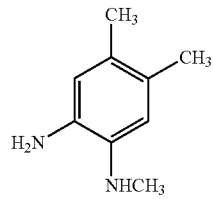

Step 1: Preparation of $N^1$,4,5-trimethyl-2-nitroaniline

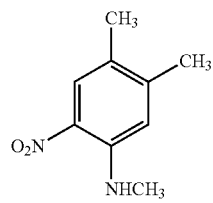

A solution of 4,5-dimethyl-2-nitroaniline (2.00 g, 12 mmol) in toluene (25 mL) was added NaOH (1.93 g, 48 mmol). The reaction mass was stirred at 100° C. for 1 h, followed by addition of dimethyl sulphate (4.6 g, 36 mmol) and reaction mass was stirred at RT for 24 h. The reaction mass was quenched in water, extracted with DCM and concentrated to afford 1.5 g of desired product. $^1$H NMR (300 MHz, DMSO $d_6$): δ 2.11 (s, 3H), 2.24 (d, J=7.8 Hz, 3H), 2.92 (s, 3H), 6.77 (m, 1H), 7.79 (m, 1H), 8.06 (s, 1H); MS (m/z): 180.92 (M–H)$^+$.

Step 2: Preparation of N',4,5-trimethylbenzene-1,2-diamine

The title compound was prepared according to the procedure described in step-2 of Intermediate-28 by using N',4,5-trimethyl-2-nitroaniline (0.350 g, 1.9 mmol), methanol (20 mL), Iron powder (1.75 g, 9.75 mmol), conc. HCl (5 mL) to afford 0.120 g of desired product.

Intermediate-32

3-(2-Chloro-6-fluorophenyl)-1-(4-iodo-3-methoxyphenyl)-1H-1,2,4-triazol-5(4H)-one

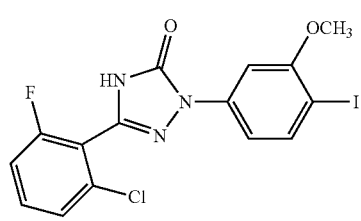 [SMILES: COc1cc(-n2nc(-c3c(F)cccc3Cl)[nH]c2=O)ccc1I]

Step-1:—Preparation of 4-fluoro-2-methoxy-1-nitrobenzene

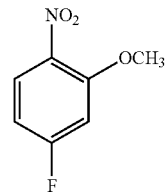

To a solution of 4-fluoro-2-hydroxy-1-nitrobenzene (5.0 g, 31.8 mmol) in DMF (10 mL) was added $K_2CO_3$ (13.1 g, 95.4 mmol). The reaction mixture was stirred at RT for 1 h followed by addition of methyl iodide (9.93 g, 69.9 mmol) and the reaction mixture was stirred at 60° C. for 2 h. The reaction mass was concentrated and quenched in water. The reaction mass was basified with saturated sodium bicarbonate solution and extracted with ethyl acetate. The organic layer was dried over anhydrous sodium sulphate and concentrated to afford 4.5 g of desired product. $^1$HNMR (300 MHz, DMSO $d_6$): δ 3.93 (s, 3H), 6.97 (t, J=7.8 Hz, 1H), 7.31 (d, J=8.7 Hz, 1H), 8.02 (s, 1H).

Step-2:—Preparation of (3-methoxy-4-nitrophenyl)hydrazine

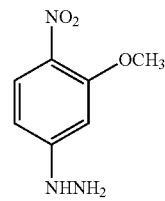

To a solution of 4-fluoro-2-methoxy-1-nitrobenzene (2.5 g, 14.60 mmol) in ethanol (25 mL) was added hydrazine hydrate (2.1 g, 43.8 mmol). The reaction mixture was refluxed for 3-4 h. The reaction mixture was concentrated to afford 2.0 g of desired product. $^1$H NMR (300 MHz, DMSO $d_6$): δ 3.84 (s, 3H), 4.46 (s, 2H), 6.31 (d, J=9.3 Hz, 1H), 6.50 (s, 1H), 7.83 (d, J=9.3 Hz, 1H), 8.25 (s, 1H); MS (m/z): (184.01 M)$^+$.

Step-3:—Preparation of tert-butyl 2-(3-methoxy-4-nitrophenyl)hydrazinecarboxylate

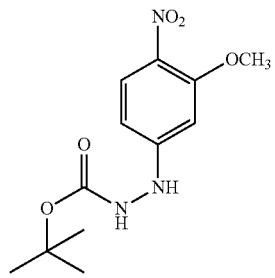 [SMILES: COc1cc(NNC(=O)OC(C)(C)C)ccc1[N+](=O)[O-]]

The title compound was prepared according to the procedure described in step-3 of Intermediate-7 by using (3-methoxy-4-nitrophenyl)hydrazine (0.500 g, 2.68 mmol), BOC anhydride (0.703 g, 3.22 mmol), sodium carbonate (0.426 g, 4.02 mmol) and DCM to afford 0.200 g of desired product. $^1$H NMR (300 MHz, DMSO $d_6$): δ 1.36 (s, 9H), 3.81 (s, 3H), 6.25-6.29 (m, 2H), 7.87 (d, J=8.7 Hz, 1H), 7.78 (s, 1H), 9.12 (s, 1H); MS (m/z): 283.88 (M)$^+$.

Step-4:—Preparation of 3-(2-chloro-6-fluorophenyl)-1-(3-methoxy-4-nitrophenyl)-1H-1,2,4-triazol-5(4H)-one

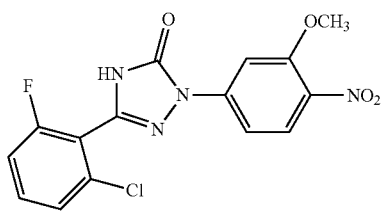

The title compound was prepared according to the procedure described in step-1 and step-2 of Intermediate-9 by using tert-butyl 2-(3-methoxy-4-nitrophenyl) hydrazinecarboxylate (1.0 g) and 2-chloro-6-fluorobenzoyl isocyanate (Intermediate-8, 1.0 g), TFA (5 mL) and DCM (40 mL) to afford 0.900 g of desired product. $^1$H NMR (300 MHz, DMSO $d_6$): δ 3.96 (s, 3H), 7.51 (t, J=8.7 Hz, 1H), 7.59 (d, J=7.8 Hz, 1H), 7.68-7.73 (m, 2H), 7.88 (s, 1H), 8.09 (d, J=8.7 Hz, 1H), 12.93 (s, 1H); MS (m/z): 363 (M)$^-$.

Step-5:—Preparation of 1-(4-amino-3-methoxyphenyl)-3-(2-chloro-6-fluorophenyl)-1H-1,2,4-triazol-5(4H)-one

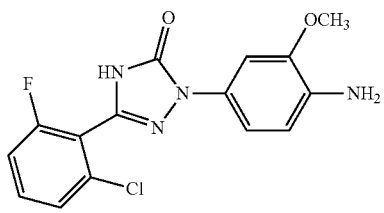 [SMILES: COc1cc(-n2nc(-c3c(F)cccc3Cl)[nH]c2=O)ccc1[N+](=O)[O-]]

The title compound was prepared according to the procedure described in step-2 of Intermediate-28 by using 3-(2-chloro-6-fluorophenyl)-1-(3-methoxy-4-nitrophenyl)-1H-1,2,4-triazol-5(4H)-one (0.100 g), iron powder (catalytic), conc. HCl (5-6 drops) and methanol (5 mL) to afford 0.070 g of desired product. $^1$H NMR (300 MHz, DMSO $d_6$): δ 3.77 (s, 3H), 4.81 (s, 2H), 6.66 (d, J=8.7 Hz, 1H), 7.17 (d, =8.1 Hz, 1H), 7.26 (s, 1H), 7.50-7.57 (m, 2H), 7.68 (m, 1H), 12.39 (s, 1H).

Step-6:—Preparation of 3-(2-chloro-6-fluorophenyl)-1-(4-iodo-3-methoxyphenyl)-1H-1,2,4-triazol-5(4H)-one

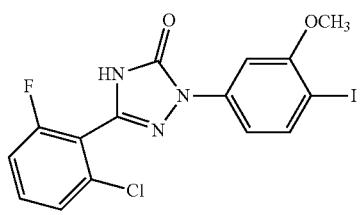 [SMILES: COc1cc(-n2nc(-c3c(F)cccc3Cl)[nH]c2=O)ccc1I]

To a solution of 1-(4-amino-3-methoxyphenyl)-3-(2-chloro-6-fluorophenyl)-1H-1,2,4-triazol-5(4H)-one (0.280 g, 0.83 mmol) in acetonitrile (5.0 ml) was added PTSA (0.477 g, 2.51 mmol). The reaction mass was stirred at RT for 1 h followed by addition of potassium iodide (0.347 g, 2.0 mmol) and sodium nitrite (0.115 g, 1.67 mmol) at 0-5° C. and further stirred for 2 h. Excess solvent was removed under vacuum and the residue reaction mass was quenched in water and extracted with ethyl acetate. The organic layer was washed with sodium metabisulphate and concentrated to obtain a crude product, which was further purified by column chromatography on silica gel eluting with 10% EtOAc: pet. ether to afford 0.200 g of desired product. $^1$H NMR (300 MHz, DMSO $d_6$): δ 3.85 (s, 3H), 7.40 (d, J=8.7 Hz, 1H), 7.46-7.74 (m, 4H), 7.83 (d, J=8.1 Hz, 1H), 12.71 (br s, 1H); MS (m/z): 445.84 (M–H)$^+$.

Intermediate-33

2-Chloro-6-iodobenzoyl isocyanate

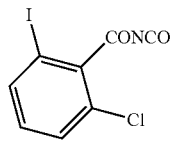

Step-1:—Preparation of 2-chloro-6-iodobenzoic acid

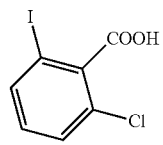 [SMILES: O=C(O)c1c(Cl)cccc1I]

To the cold solution of 2-amino-6-chlorobenzoic acid (2.0 g, 11.6 mmol) in conc. HCl (10 mL) was added aq. solution of sodium nitrite (0.8 g, 11.6 mmol) at 0° C. followed by addition of solution of potassium iodide (2.88 g, 17.4 mmol) in water and conc. sulphuric acid (1 mL). The reaction mixture was refluxed for 2 h. The reaction mass was washed with sodium metabisulphate solution and extracted with ethyl acetate. The organic layer was dried over anhydrous sodium sulphate and concentrated to afford 2.0 g of desired product. ¹H NMR (300 MHz, DMSO d₆): δ 7.08 (t, J=7.8 Hz, 1H), 7.42 (d, J=8.4 Hz, 1H), 7.76 (d, J=7.8 Hz, 1H), 8.37 (br s, 1H); MS (m/z): 280.59 (my.

Step-2:—Preparation of 2-chloro-6-iodobenzamide

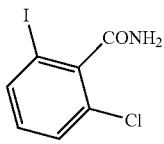 [SMILES: NC(=O)c1c(Cl)cccc1I]

The title compound was prepared according to the procedure described in step-2 of Intermediate-26 by using 2-chloro-6-iodobenzoic acid (2.7 g, 9.6 mmol), oxalyl chloride (1.4 g, 11.5 mmol), ammonia gas, THF (20 mL) and DCM (10 mL) to afford 2.3 g of the desired product. ¹H NMR (300 MHz, DMSO d₆): δ 7.11 (t, J=7.8 Hz, 1H), 7.49 (d, J=8.4 Hz, 1H), 7.73 (s, 1H), 7.80 (d, J=7.8 Hz, 1H), 8.00 (s, 1H); MS (m/z): 281.98 (M+H)⁺.

Step-3:—Preparation of 2-chloro-6-iodobenzoyl isocyanate

The title compound was prepared according to the procedure described in step-2 of Intermediate-8 by using 2-chloro-6-iodobenzamide (1.0 g, 3.5 mmol), oxalyl chloride (0.538 g, 4.2 mmol) and EDC (20 mL) to afford 1.00 g of the desired product.

Intermediate-34

4-(3-(2-Chloro-6-iodophenyl)-5-oxo-4,5-dihydro-1H-1,2,4-triazol-1-yl)-2-methoxy-N-(3-(trifluoromethyl)phenyl)benzamide

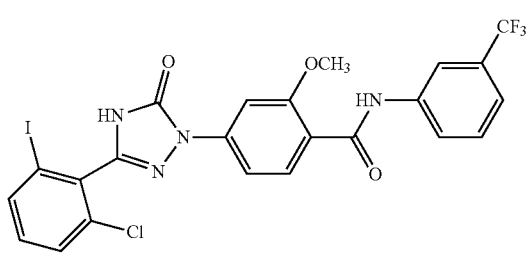 [SMILES: COc1cc(-n2nc(-c3c(Cl)cccc3I)[nH]c2=O)ccc1C(=O)Nc1cccc(C(F)(F)F)c1]

Step-1:—Preparation of methyl 4-(3-(2-chloro-6-iodophenyl)-5-oxo-4,5-dihydro-1H-1,2,4-triazol-1-yl)-2-methoxybenzoate

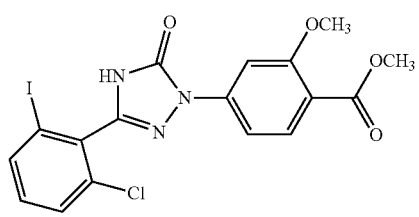 [SMILES: COC(=O)c1ccc(-n2nc(-c3c(Cl)cccc3I)[nH]c2=O)cc1OC]

The title compound was prepared according to the procedure described in step-1 and step-2 of Intermediate-9 by using tert-butyl 2-(3-methoxy-4-(methoxycarbonyl)phenyl)hydrazinecarboxylate (Intermediate-14, 1.0 g) and 2-chloro-6-iodobenzoyl isocyanate (Intermediate-33, 1.0 g), TFA (5 mL) and DCM (40 mL) to afford 0.900 g of desired product. ¹H NMR (300 MHz, DMSO d₆): δ 3.78 (s, 3H), 3.85 (s, 3H), 3.37 (t, J=7.8 Hz, 1H), 7.63 (d, J=9.0 Hz, 1H), 7.70-7.81 (m, 3H), 8.00 (d, J=7.8 Hz, 1H), 12.65 (br s, 1H); MS (m/z): 285.75 (M+H)⁺.

Step-2:—Preparation of 4-(3-(2-chloro-6-iodophenyl)-5-oxo-4,5-dihydro-1H-1,2,4-triazol-1-yl)-2-methoxy-N-(3-(trifluoromethyl)phenyl)benzamide The title compound was prepared by following the procedure as described for step-6 of Intermediate-26 by using methyl 4-(3-(2-chloro-6-iodophenyl)-5-oxo-4,5-dihydro-1H-1,2,4-triazol-1-yl)-2-methoxybenzoate (0.100 g, 0.206 mmol), 3-(trifluoromethyl)aniline (0.041 g, 0.247 mmol), trimethyl aluminium (2M solution in toluene) (0.5 mL), dry toluene (10.0 mL) to afford 0.075 g of desired product. ¹H NMR (300 MHz, DMSO d₆): δ 3.95 (s, 3H), 7.19-8.03 (m, 9H), 8.25 (s, 1H), 10.36 (s, 1H), 12.65 (s, 1H); MS (m/z): 614.98 (M+H)⁺.

Intermediate-35

4-(3-(5-(Aminomethyl)-2-chlorophenyl)-5-oxo-4,5-dihydro-1H-1,2,4-triazol-1-yl)-N-(3-(difluoromethyl)-4-fluorophenyl)-2-methoxybenzamide

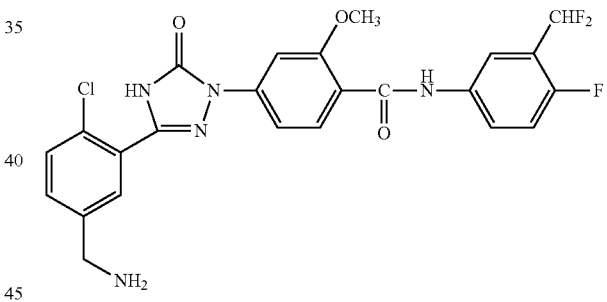

Step-1:—Preparation of 4-(3-(2-chloro-5-((2,2,2-trifluoroacetamido)methyl)phenyl)-5-oxo-4,5-dihydro-1H-1,2,4-triazol-1-yl)-N-(3-(difluoromethyl)-4-fluorophenyl)-2-methoxybenzamide

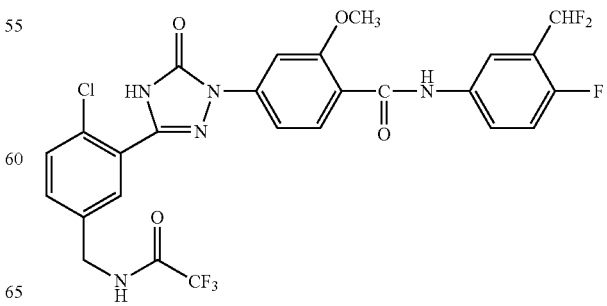

The title compound was prepared by following the procedure as described for step-6 of Intermediate-26 by using methyl 4-(3-(2-chloro-6-((2,2,2-trifluoroacetamido) methyl)phenyl)-5-oxo-4,5-dihydro-1H-1,2,4-triazol-1-yl)-2-methoxybenzoate (Step-5 of Intermediate-26, 0.100 g, 0.20 mmol), 3-(difluoromethyl)-4-fluoroaniline (0.050 g, 0.30 mmol), trimethyl aluminium (2M solution in toluene) (1 mL) to afford 0.070 g of desired product. $^1$H NMR (300 MHz, DMSO d$_6$): δ 3.95 (s, 3H), 4.47 (s, 2H), 6.71 (m, 1H), 7.04 (m, 1H), 7.34-7.40 (m, 1H), 7.50-7.54 (m, 1H), 7.65-7.70 (m, 3H), 7.79-7.87 (m, 3H), 8.12 (s, 1H), 10.09 (m, 1H), 10.28 (s, 1H), 12.67 (brs, 1H); MS (m/z): 614.04 (M+H)$^+$.

Step-2:—Preparation of 4-(3-(5-(aminomethyl)-2-chlorophenyl)-5-oxo-4,5-dihydro-1H-1,2,4-triazol-1-yl)-N-(3-(difluoromethyl)-4-fluorophenyl)-2-methoxybenzamide The solution of 4-(3-(2-chloro-5-((2,2,2-trifluoroacetamido)methyl)phenyl)-5-oxo-4,5-dihydro-1H-1,2,4-triazol-1-yl)-N-(3-(difluoromethyl)-4-fluorophenyl)-2-methoxybenzamide (0.070 g, 0.11 mmol) in 20% aq. KOH (10 mL) and aq. NH$_3$ (2 mL) was stirred for 24 h at RT. Excess of solvent was removed under vacuum and filtered off to afford 0.015 g of desired product.

Intermediate-36

N-(3-Amino-4-chlorobenzyl)cyclopropanecarboxamide

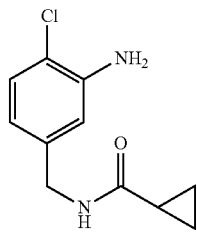

Step-1:—Preparation of N-(4-chloro-3-nitrobenzyl)-2,2,2-trifluoroacetamide

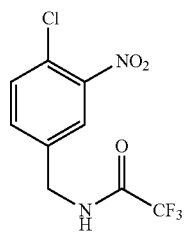 [SMILES: O=C(NCc1ccc(Cl)c([N+](=O)[O-])c1)C(F)(F)F]

To a solution of 1-chloro-2-nitrobenzene (10.0 g, 0.063 mmol) in conc. sulphuric acid (150 mL) was added N-hydroxy methyl trifluoro acetamide (9.98 g, 0.069 mmol). The reaction mixture was heated at 70-80° C. for 24 h. The reaction mass was quenched in ice cold water, neutralised with sodium hydroxide and extracted with DCM. The organic layer was concentrated and the obtained crude product was purified by column chromatography on silica gel eluting with 4% EtOAc: pet. ether to afford 5.5 g of desired product. $^1$H NMR (300 MHz, DMSO d$_6$): 4.48 (d, J=3.9 Hz, 2H), 7.62-7.64 (m, 1H), 7.72-7.78 (m, 1H), 7.97-8.01 (m, 1H), 10.09 (brs, 1H).

Step-2:—Preparation of (4-chloro-3-nitrophenyl)methanamine hydrochloride

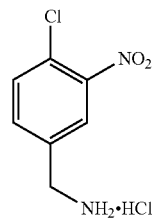

To a solution of N-(4-chloro-3-nitrobenzyl)-2,2,2-trifluoroacetamide (0.800 g) in methanol (20 mL) was added conc. HCl (2.0 ml). The reaction mass was refluxed for 18 h. Excess solvent was removed under vacuum to afford 0.700 g of desired product. $^1$H NMR (300 MHz, DMSO d$_6$): δ 7.18 (s, 1H), 7.35 (s, 1H), 7.52 (s, 1H), 7.86 (s, 2H); 8.28 (s, 1H), 8.72 (br s, 2H).

Step-3:—Preparation of N-(4-chloro-3-nitrobenzyl)cyclopropanecarboxamide

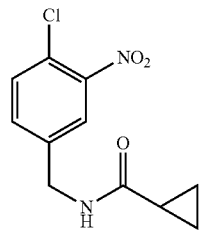 [SMILES: O=C(NCc1ccc(Cl)c([N+](=O)[O-])c1)C1CC1]

The title compound was prepared by following the procedure as described in step-2 of Intermediate-30 by using (4-chloro-3-nitrophenyl)methanamine hydrochloride (0.700 g, 3.14 mmol), cyclopropylcarbonyl chloride (0.490 g, 4.71 mmol), DIPEA (3.0 mL) and THF (15 mL) to afford 0.400 g of desired product. $^1$H NMR (300 MHz, DMSO d$_6$): δ 0.69 (d, J=6.0 Hz, 2H), 1.55-1.61 (m, 1H), 4.33 (d, J=6.0 Hz), 7.55 (d, J=7.8 Hz, 1H), 7.70 (d, J=8.4 Hz, 1H), 7.87 (s, 1H), 8.68 (br s, 1H); MS (m/z): 255.09 (M+H)$^+$.

Step-4:—Preparation of N-(3-amino-4-chlorobenzyl)cyclopropanecarboxamide

The title compound was prepared by following the procedure as described in step-2 of Intermediate-28 by using N-(4-chloro-3-nitrobenzyl)cyclopropanecarboxamide (0.400 g), methanol (10 mL), iron powder (catalytic) and conc. HCl (5 mL). The reaction mass was refluxed for 2 h. The reaction mass was quenched in water and basified with NaHCO$_3$ and extracted with DCM. The organic layer was dried over anhydrous sodium sulphate and concentrated to afford 0.200 g of desired product. $^1$H NMR (300 MHz, DMSO d$_6$): δ 0.65 (d, J=8.4 Hz, 4H), 1.57 (m, 1H), 4.11 (d, J=5.4 Hz, 2H), 5.34 (s, 2H), 6.41 (d, J=7.2 Hz, 1H), 7.10 (d, J=7.8 Hz, 1H), 8.50 (br s, 1H); MS (m/z): 225.07 (M+H)+.

Intermediate-37

N-(3-(1-(4-Amino-3-methoxyphenyl)-5-oxo-4,5-dihydro-1H-1,2,4-triazol-3-yl)-4-chlorobenzyl)cyclopropanecarboxamide

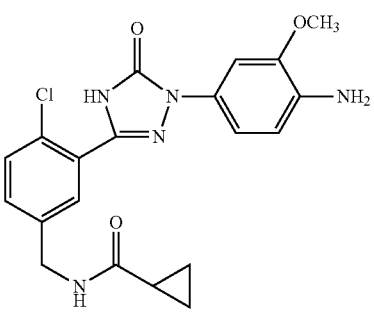 [SMILES: COc1cc(-n2nc(-c3cc(CNC(=O)C4CC4)ccc3Cl)[nH]c2=O)ccc1N]

Step-1:—Preparation of tert-butyl 2-((2-chloro-5-((2,2,2-trifluoroacetamido) methyl)benzoyl)carbamoyl)-2-(3-methoxy-4-nitrophenyl)hydrazinecarboxylate

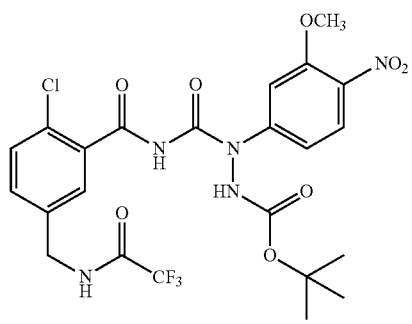 [SMILES: COc1cc(N(NC(=O)OC(C)(C)C)C(=O)NC(=O)c2cc(CNC(=O)C(F)(F)F)ccc2Cl)ccc1[N+](=O)[O-]]

The title compound was prepared according to the procedure described in step-1 of Intermediate-9 by using 2-chloro-5-((2,2,2-trifluoroacetamido)methyl)benzoyl isocyanate (step-3 of Intermediate-26, 1.400 g, 4.57 mmol), tert-butyl 2-(3-methoxy-4-nitrophenyl)hydrazinecarboxylate (step-3 of Intermediate-32, 1.30 g, 4.57 mmol) and DCM 30 mL) to afford 2.0 g of the desired product. $^1$H NMR (300 MHz, DMSO d$_6$): δ 1.33-1.46 (m, 9H), 3.87 (s, 3H), 4.40 (s, 2H), 7.06 (d, J=8.4 Hz, 1H), 7.32-7.36 (m, 3H), 7.45-7.52 (m, 1H), 7.96 (d, J=8.7 Hz, 1H), 9.92 (s, 1H), 10.07 (br s, 1H), 11.13 (br s, 1H); MS (m/z): 589.69 (M)+.

Step-2:—Preparation of N-(4-chloro-3-(1-(3-methoxy-4-nitrophenyl)-5-oxo-4,5-dihydro-1H-1,2,4-triazol-3-yl)benzyl)-2,2,2-trifluoroacetamide

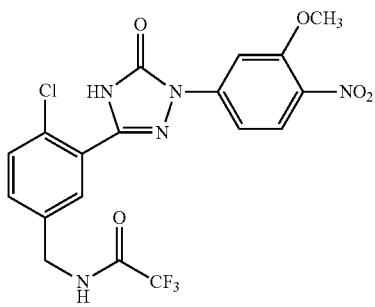 [SMILES: COc1cc(-n2nc(-c3cc(CNC(=O)C(F)(F)F)ccc3Cl)[nH]c2=O)ccc1[N+](=O)[O-]]

The title compound was prepared according to the procedure described in step-2 of Intermediate-9 by using tert-butyl 2-((2-chloro-5-((2,2,2-trifluoroacetamido) methyl)benzoyl)carbamoyl)-2-(3-methoxy-4-nitrophenyl) hydrazinecarboxylate (2.0 g, 4.23 mmol), TFA (30 mL) and DCM (5 mL) to afford 1.300 g of the desired product. $^1$H NMR (300 MHz, DMSO d$_6$): δ 3.96 (s, 3H), 4.47 (d, J=5.4 Hz, 2H), 7.54 (d, J=8.7 Hz, 1H), 7.67-7.74 (m, 3H), 7.93 (s, 1H), 8.10 (d, J=9.0 Hz, 1H), 10.11 (m, 1H), 12.86 (br s, 1H); MS (m/z): 471.88 (M+H)+.

Step-3:—Preparation of 3-(5-(aminomethyl)-2-chlorophenyl)-1-(3-methoxy-4-nitrophenyl)-1H-1,2,4-triazol-5(4H)-one

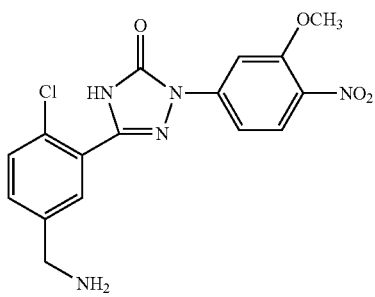 [SMILES: COc1cc(-n2nc(-c3cc(CN)ccc3Cl)[nH]c2=O)ccc1[N+](=O)[O-]]

The solution of N-(4-chloro-3-(1-(3-methoxy-4-nitrophenyl)-5-oxo-4,5-dihydro-1H-1,2,4-triazol-3-yl)benzyl)-2,2,2-trifluoroacetamide (0.500 g, 1.06 mmol) in 20% aq. KOH (20 mL) was stirred for 2-3 h at RT. Excess of solvent was removed under vacuum and filtered off remaining reaction mass to afford 0.400 g of desired product. $^1$H NMR (300 MHz, DMSO d$_6$): δ1.80 (br s, 2H), 3.72 (s, 2H), 3.91 (s, 3H), 7.27-7.39 (m, 2H), 7.78 (d, J=9.9 Hz, 2H), 8.98 (d, J=8.7 Hz, 1H), 8.25 (s, 1H); MS (m/z): 375.91 (M)+.

Step-4:—Preparation of N-(4-chloro-3-(1-(3-methoxy-4-nitrophenyl)-5-oxo-4,5-dihydro-1H-1,2,4-triazol-3-yl)benzyl)cyclopropanecarboxamide

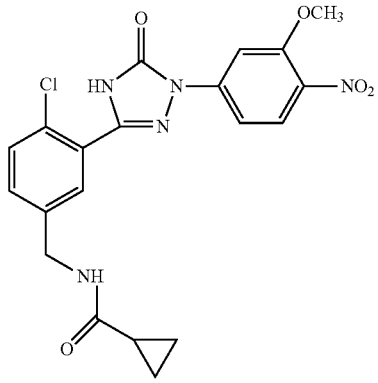 [SMILES: COc1cc(-n2nc(-c3cc(CNC(=O)C4CC4)ccc3Cl)[nH]c2=O)ccc1[N+](=O)[O-]]

The title compound was prepared according to the procedure as described in step-2 Intermediate-30 by using 3-(5-(aminomethyl)-2-chlorophenyl)-1-(3-methoxy-4-nitrophenyl)-1H-1,2,4-triazol-5(4H)-one (0.500 g, 1.33 mmol), cyclopropylcarbonyl chloride (0.207 g, 1.99 mmol), DIPEA (2.0 mL) and THF (30 mL) to afford 0.300 g of crude product which was triturated with methanol: DEE to afford 0.300 g of pure product. $^1$H NMR (300 MHz, DMSO d$_6$): δ 0.69 (s, 4H), 1.60 (m, 1H), 3.97 (s, 3H), 4.33 (d, J=5.4 Hz, 2H), 7.42-7.55 (m 3H), 7.70 (d, J=8.4 Hz, 1H), 7.87 (s, 1H), 8.12 (d, J=8.7 Hz, 1H), 8.69-8.71 (m, 1H), 12.83 (s, 1H); MS (m/z): 442.14 (M−H)$^-$.

Step-5:—Preparation of N-(3-(1-(4-amino-3-methoxyphenyl)-5-oxo-4,5-dihydro-1H-1,2,4-triazol-3-yl)-4-chlorobenzyl)cyclopropanecarboxamide The title compound was prepared according to the procedure as described in step-2 Intermediate-28 by using N-(4-chloro-3-(1-(3-methoxy-4-nitrophenyl)-5-oxo-4,5-dihydro-1H-1,2,4-triazol-3-yl)benz yl)cyclopropanecarboxamide (0.500 g, 1.12 mmol), iron powder (catalytic amount), methanol (20 mL), conc. HCl (5.0 mL) to afford 0.350 g of desired product. $^1$H NMR (300 MHz, DMSO d$_6$): δ 0.69 (s, 4H), 1.22 (br s, 2H), 1.60 (m, 1H), 3.97 (s, 3H), 4.33 (d, J=5.4 Hz, 2H), 7.45-7.58 (m, 3H), 7.70 (d, J=9.3 Hz, 1H), 7.87 (s, 1H), 8.13 (d, J=9.0 Hz, 1H), 8.71 (m, 1H), 12.30 (br s, 1H); MS (m/z): 414.09 (M+H)$^+$.

Intermediate-38

4-(3-(2,6-Dichlorophenyl)-5-oxo-4,5-dihydro-1H-1,2,4-triazol-1-yl)-2-methoxy-N-(4-(methylthio)phenyl)benzamide

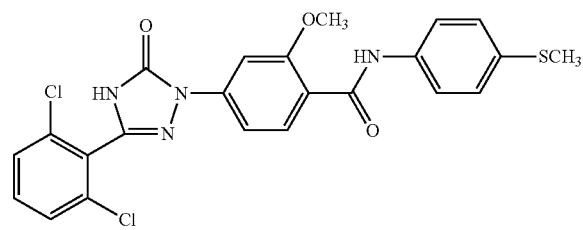 [SMILES: COc1cc(-n2nc(-c3c(Cl)cccc3Cl)[nH]c2=O)ccc1C(=O)Nc1ccc(SC)cc1]

The title compound was prepared according to the procedure as described for step-6 of Intermediate-26 by using methyl 4-(3-(2,6-dichlorophenyl)-5-oxo-4,5-dihydro-1H-1,2,4-triazol-1-yl)-2-methoxybenzoate (Intermediate-21, 0.150 g, 0.380 mmol), 4-(methylthio)aniline (0.079 g, 0.570 mmol), trimethyl aluminium (2M solution in toluene) (1 mL) and dry toluene (5.0 mL) to afford 0.080 g of desired product. $^1$H NMR (300 MHz, DMSO d$_6$): δ 2.46 (s, 3H), 3.94 (s, 3H), 7.26 (d, J=8.4 Hz, 2H), 7.69-7.72 (m, 6H), 7.78 (d, J=6.9 Hz, 1H), 7.82 (s, 1H), 10.06 (s, 1H), 12.76 (br s, 1H); MS (m/z): 501.0 (M)$^+$.

Intermediate-39

4-(3-(5-(Aminomethyl)-2-chlorophenyl)-5-oxo-4,5-dihydro-1H-1,2,4-triazol-1-yl)-N-(3-(difluoromethyl)phenyl)-2-methoxybenzamide

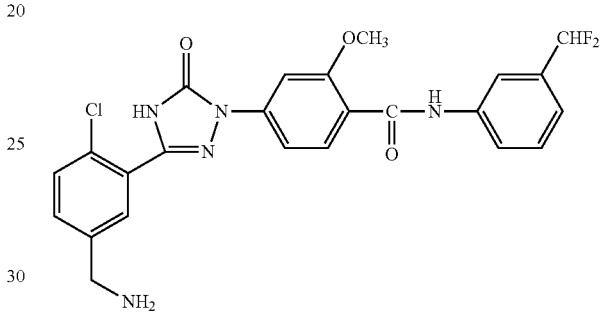

Step-1:—Preparation of 4-(3-(2-chloro-5-((2,2,2-trifluoroacetamido)methyl)phenyl)-5-oxo-4,5-dihydro-1H-1,2,4-triazol-1-yl)-N-(3-(difluoromethyl)phenyl)-2-methoxybenzamide

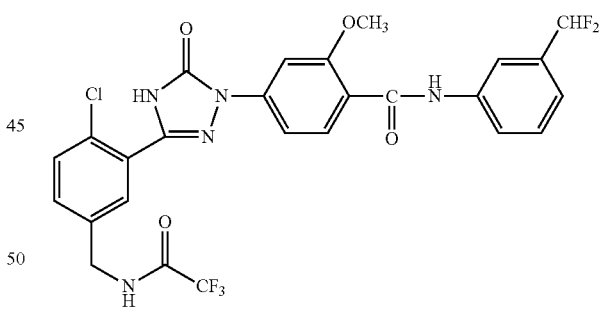

The title compound was prepared according to the procedure described in step-6 of Intermediate-26 by using methyl 4-(3-(2-chloro-5-((2,2,2-trifluoroacetamido)methyl)phenyl)-5-oxo-4,5-dihydro-1H-1,2,4-triazol-1-yl)-2-methoxybenzoate (step-5 of Intermediate-26, 0.100 g, 0.20 mmol), 3-(difluoromethyl)aniline (Intermediate-29, 0.045 g, 0.30 mmol), trimethyl aluminium (2M solution in toluene) (1.0 mL) and dry toluene (5.0 mL) to afford 0.080 g of crude product which was triturated with methanol:DCM:ether to afford 0.080 g of pure product. $^1$H NMR (300 MHz, DMSO d$_6$): δ 3.95 (s, 3H), 4.47 (d, J=5.7 Hz, 2H), 7.05 (m, 1H), 7.30 (m, 1H), 7.50 (d, J=7.8 Hz, 2H), 7.70 (m, 3H), 7.80 (d, J=6.3 Hz, 3H), 8.08 (s, 1H), 10.11 (br s, 1H), 10.28 (s, 1H), 12.72 (br s, 1H); MS (m/z): 596.12 (M+H)$^+$.

Step-2:—Preparation of 4-(3-(5-(aminomethyl)-2-chlorophenyl)-5-oxo-4,5-dihydro-1H-1,2,4-triazol-1-yl)-N-(3-(difluoromethyl)phenyl)-2-methoxybenzamide The solution of 4-(3-(2-chloro-5-((2,2,2-trifluoroacetamido)methyl)phenyl)-5-oxo-4,5-dihydro-1H-1,2,4-triazol-1-yl)-N-(3-(difluoromethyl)phenyl)-2-methoxybenzamide (0.070 g, 0.11 mmol) in 20% aq. KOH (10 mL) and aq. NH$_3$ (2 mL) was stirred for 24 h at RT. Excess of solvent was removed under vacuum and filtered off to afford 0.015 g of desired product.

Intermediate-40

Methyl 4-(3-(2-chloro-5-(N-cyclopropylsulfamoyl)phenyl)-5-oxo-4,5-dihydro-1H-1,2,4-triazol-1-yl)-2-methoxybenzoate

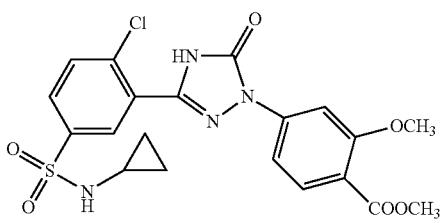 [SMILES: COC(=O)c1ccc(-n2nc(-c3cc(S(=O)(=O)NC4CC4)ccc3Cl)[nH]c2=O)cc1OC]

Step-1:—Preparation of 2-chloro-5-(chlorosulfonyl)benzoic acid

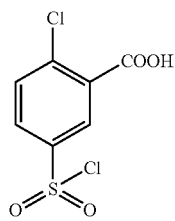 [SMILES: O=C(O)c1cc(S(=O)(=O)Cl)ccc1Cl]

To a solution of 2-chlorobenzoic acid (5.0 g, 31.93 mmol) was slowly added chlorosulphonic acid (25 mL). The reaction mixture was heated at 100° C. for 5-6 h, followed by stirring at RT for 24 h. The reaction mass was quenched in ice cold water slowly and the solid obtained was filtered off, washed with water and dried to afford 4.0 g of pure product. $^1$H NMR (300 MHz, DMSO d$_6$): δ 7.50 (d, J=7.8 Hz, 1H), 7.68 (d, J=8.1 Hz, 1H), 7.96 (d, J=1.5 Hz, 1H), 12.69-12.94 (br s, 1H).

Step-2:—Preparation of 2-chloro-5-(N-cyclopropylsulfamoyl)benzoic acid

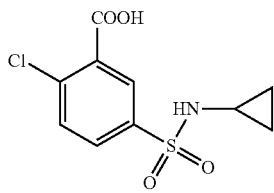 [SMILES: O=C(O)c1cc(S(=O)(=O)NC2CC2)ccc1Cl]

To a solution of 2-chloro-5-(chlorosulfonyl)benzoic acid (4.0 g, 15.68 mmol) in DCM (60 mL) was added cyclopropyl amine (1.8 g, 31.57 mmol) and the reaction mixture was stirred at RT for 16 h. The reaction mass was concentrated and the residue was diluted with ice cold water and acidified with dilute HCl. The crude solid was filtered off, washed with water and dried to afford 3.0 g of pure product. $^1$H NMR (300 MHz, DMSO d$_6$): δ 0.37 (s, 2H), 0.49 (d, J=5.4 Hz, 2H), 2.12-2.13 (m, 1H), 7.82 (d, J=8.4 Hz, 1H), 7.91 (d, J=8.4 Hz, 1H), 8.13 (s, 1H), 8.18 (s, 1H), 13.92 (br s, 1H).

Step-3:—Preparation of 2-chloro-5-(N-cyclopropylsulfamoyl)benzamide

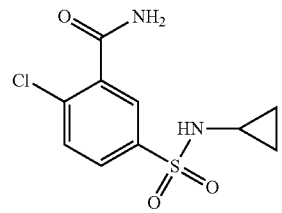 [SMILES: NC(=O)c1cc(S(=O)(=O)NC2CC2)ccc1Cl]

The title compound was prepared by following procedure as described for step-2 of Intermediate-26 by using 2-chloro-5-(N-cyclopropylsulfamoyl)benzoic acid (3.0 g, 10.0 mmol), DCM (30 mL), oxalyl chloride, ammonia gas (1.2 mL, 13.0 mmol), DMF (2-3 drop) and THF (40 mL) to afford 2.500 g of the desired product. $^1$H NMR (300 MHz, DMSO d$_6$): δ 0.41 (m, 2H), 0.47-0.51 (m, 2H), 2.12 (m, 2H), 7.74-7.82 (m, 4H), 8.11 (br s, 2H); MS (m/z): 273.00 (M−H)$^−$.

Step-4:—Preparation of 2-chloro-5-(N-cyclopropylsulfamoyl)benzoyl isocyanate

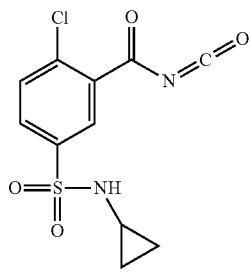 [SMILES: O=C=NC(=O)c1cc(S(=O)(=O)NC2CC2)ccc1Cl]

To a solution of 2-chloro-5-(N-cyclopropylsulfamoyl)benzamide (1.50 g, 5.46 mmol) in EDC (20 mL) was added oxalyl chloride (0.59 mL, 6.55 mmol). The reaction mass was refluxed for 1-2 h. Excess of solvent was removed under vacuum to afford 1.5 g of desired product.

Step-5:—Preparation of tert-butyl 2-((2-chloro-5-(N-cyclopropylsulfamoyl) benzoyl)carbamoyl)-2-(3-methoxy-4-(methoxycarbonyl)phenyl) hydrazinecarboxylate

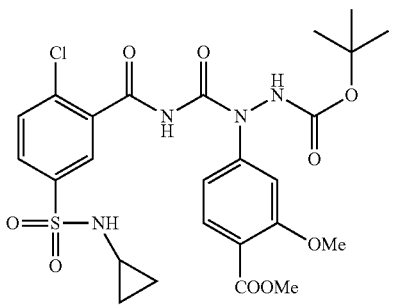 [SMILES: COC(=O)c1ccc(N(NC(=O)OC(C)(C)C)C(=O)NC(=O)c2cc(S(=O)(=O)NC3CC3)ccc2Cl)cc1OC]

To a solution of tert-butyl 2-(3-methoxy-4-(methoxycarbonyl)phenyl) hydrazinecarboxylate (Intermediate 14, 1.5 g, 5.08 mmol) in DCM (20 mL) was added 2-chloro-5-(N-cyclopropylsulfamoyl)benzoyl isocyanate (1.6 g, 5.32 mmol). The reaction mass was stirred at RT for 2 h. Excess of solvent was removed under vacuum to afford 0.500 g of desired product. $^1$H NMR (300 MHz, DMSO $d_6$): δ 0.50 (m, 4H), 1.41 (s, 9H), 2.11 (m, 1H), 3.68-3.75 (m, 6H), 7.59 (d, J=8.7 Hz, 1H), 7.78-7.87 (m, 4H), 8.10 (m, 2H), 8.27 (s, 1H), 8.95 (s, 1H).

Step-6:—Preparation of methyl 4-(3-(2-chloro-5-(N-cyclopropylsulfamoyl)phenyl)-5-oxo-4,5-dihydro-1H-1,2,4-triazol-1-yl)-2-methoxybenzoate The title compound was prepared according to the procedure described in step-2 of Intermediate-9 by using tert-butyl 2-((2-chloro-5-(N-cyclopropylsulfamoyl) benzoyl) carbamoyl)-2-(3-methoxy-4-(methoxycarbonyl)phenyl) hydrazinecarboxylate (0.500 g, 0.83 mmol), TFA (2 mL) and DCM (10 mL) to afford 0.100 g of the desired product. $^1$H NMR (300 MHz, DMSO $d_6$): δ 0.40 (m, 2H), 0.52 (d, J=5.4 Hz, 2H), 2.18 (m, 1H), 3.77 (s, 3H), 3.85 (s, 3H), 7.65 (d, J=9.0 Hz, 1H), 7.82 (d, J=8.1 Hz, 2H), 7.93 (s, 2H), 8.18 (s, 2H), 12.8 (br s, 1H); MS (m/z): 478.97 (M+H)$^+$.

Intermediate-41

Methyl 4-(3-(2,6-dichlorophenyl)-4-ethyl-5-oxo-4,5-dihydro-1H-1,2,4-triazol-1-yl)-2-methoxybenzoate

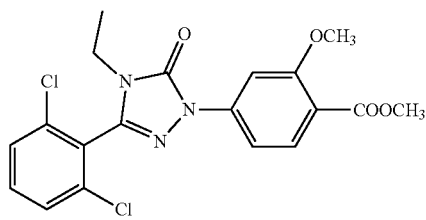 [SMILES: CCn1c(-c2c(Cl)cccc2Cl)nn(-c2ccc(C(=O)OC)c(OC)c2)c1=O]

To a solution of methyl 4-(3-(2,6-dichlorophenyl)-5-oxo-4,5-dihydro-1H-1,2,4-triazol-1-yl)-2-methoxybenzoate (Intermediate-21, 0.100 g, 0.25 mmol) in dry DMF (3 mL) was added NaH (0.012 g, 0.30 mmol) at 0° C. and the reaction mixture was stirred for 20-30 minutes. Ethyl bromide (0.028 g, 0.25 mmol) was added and the reaction mixture was further stirred at 60° C. for 5-6 h. The reaction mass was quenched with water and extracted in ethyl acetate. The organic layer was dried and concentrated to afford 0.040 g of the crude product which was further purified by column chromatography in basic alumina eluting with 0.5-1.0% methanol: DCM to afford 0.040 g of pure product. $^1$H NMR (300 MHz, DMSO $d_6$): δ 1.13 (t, 3H), 3.54-3.56 (m, 2H), 3.78 (s, 3H), 186 (s, 3H), 7.65 (d, J=8.4 Hz, 1H), 7.77 (m, 4H), 7.84 (d, J=8.4 Hz, 1H); MS (m/z): 421.95 (M+H)$^+$.

Intermediate-42

Methyl 4-(3-(2-chloro-5-(cyclopropanecarboxamidomethyl)phenyl)-5-oxo-4,5-dihydro-1H-1,2,4-triazol-1-yl)benzoate

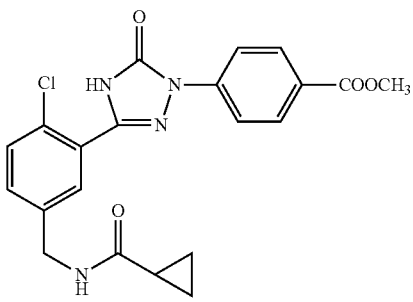 [SMILES: COC(=O)c1ccc(-n2nc(-c3cc(CNC(=O)C4CC4)ccc3Cl)[nH]c2=O)cc1]

Step-1:—Preparation of methyl 4-(3-(2-chloro-5-((2,2,2-trifluoroacetamido) methyl)phenyl)-5-oxo-4,5-dihydro-1H-1,2,4-triazol-1-yl)benzoate

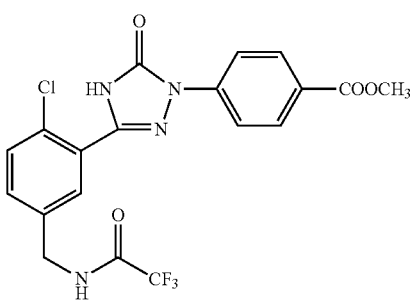 [SMILES: COC(=O)c1ccc(-n2nc(-c3cc(CNC(=O)C(F)(F)F)ccc3Cl)[nH]c2=O)cc1]

The title compound was prepared according to the procedure described in step-1 and step-2 of Intermediate-9 by using 2-chloro-5-((2,2,2-trifluoroacetamido)methyl)benzoyl isocyanate (step-3 of Intermediate-26, 1.300 g, 4.2 mmol) and tert-butyl 2-[4-(methoxycarbonyl)phenyl]hydrazinecarboxylate (Intermediate-7, 1.150 g, 3.8 mmol) in TFA (5-7 mL) and DCM (40 mL). The reaction mass was quenched with water and extracted with DCM. The organic layer was dried over anhydrous sodium sulphate and concentrated to afford 1.300 g of the desired product. $^1$H NMR (300 MHz, DMSO $d_6$): δ 3.84 (s, 3H), 4.44 (d, J=5.7 Hz, 2H), 7.49 (t, 1H), 7.66 (d, J=8.7 Hz, 2H), 8.04-8.13 (m, 4H), 10.07 (m, 114), 12.69 (s, 1H); MS (m/z): 453.14 (M-H)$^-$.

Step-2:—Preparation of methyl 4-(3-(5-(aminomethyl)-2-chlorophenyl)-5-oxo-4,5-dihydro-1H-1,2,4-triazol-1-yl)benzoate hydrochloride

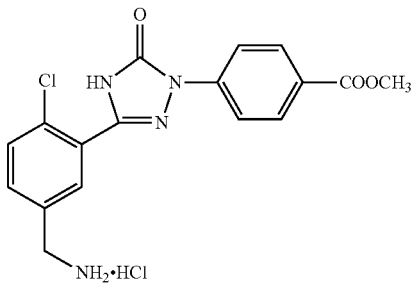

The title compound was prepared according to the procedure described in step-1 of Intermediate-30 by using methyl 4-(3-(2-chloro-5-((2,2,2-trifluoroacetamido) methyl) phenyl)-5-oxo-4,5-dihydro-1H-1,2,4-triazol-1-yl)benzoate (1.00 g, 2.19 mmol), methanol (20 mL) and HCl (10 mL) to afford 1.00 g of desired product.

Step-3:—Preparation of methyl 4-(3-(2-chloro-5-(cyclopropanecarboxamidomethyl) phenyl)-5-oxo-4, 5-dihydro-1H-1,2,4-triazol-1-yl)benzoate The title compound was prepared by following the procedure as described for step-2 of Intermediate-30 by using methyl 4-(3-(5-(aminomethyl)-2-chlorophenyl)-5-oxo-4,5-dihydro-1H-1,2,4-triazol-1-yl)benzoate hydrochloride (0.250 g, 0.5 mmol), cyclopropane carbonyl chloride (0.108 g, 1.0 mmol), DIPEA (2.0 mL), THF (10 mL) to afford 0.200 g of desired product. $^1$H NMR (300 MHz, DMSO d$_6$): δ 1.05 (s, 2H), 1.60 (m, 2H), 3.14 (m, 1H), 3.87 (s, 3H), 4.33 (d, J=5.7 Hz, 2H), 7.41-7.61 (m, 4H), 8.11-8.17 (m, 3H), 8.69 (m, 1H), 12.65 (br s, 1H); MS (m/z): 427.14 (M+H)$^+$.

Intermediate-43

4-(3-(2-Chloro-6-iodophenyl)-5-oxo-4,5-dihydro-1H-1,2,4-triazol-1-yl)-N-(4-fluoro-3-(trifluoromethyl)phenyl)-2-methoxybenzamide

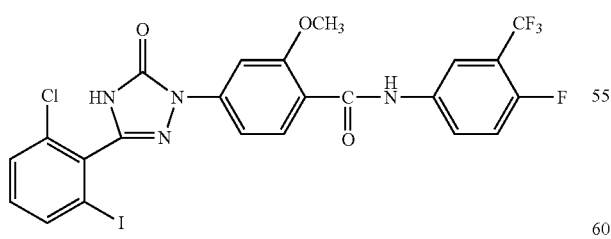

The title compound was prepared by following the procedure as described for step-6 of Intermediate-26 by using methyl 4-(3-(2-chloro-6-iodophenyl)-5-oxo-4,5-dihydro-1H-1,2,4-triazol-1-yl)-2-methoxybenzoate (step-1 of Intermediate-34, 0.100 g, 0.20 mmol), 4-fluoro-3-(trifluoromethyl)aniline (0.044 g, 0.34 mmol), trimethyl aluminium (2M solution in toluene) (1.0 mL) and dry toluene (8.0 mL) to afford 0.020 g of desired product. $^1$H NMR (300 MHz, DMSO d$_6$): δ 3.94 (s, 3H), 3.78 (t, 1H), 7.52 (t, 2H), 7.71-7.82 (m, 3H), 8.03 (d, J=6.6 Hz, 2H), 10.38 (s, 1H), 12.69 (br s, 1H).

Intermediate-44 tert-Butyl 2-(2,6-dichlorophenyl)hydrazinecarboxylate

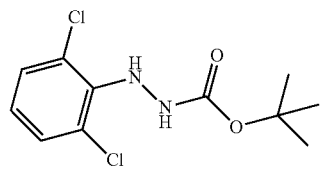 [SMILES: CC(C)(C)OC(=O)NNc1c(Cl)cccc1Cl]

Step-1:—Preparation of (2,6-dichlorophenyl)hydrazine hydrochloride

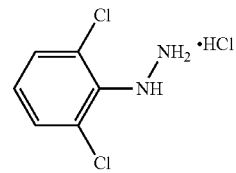

To a cold solution of 2,6-dichloroaniline (10.0 g, 61.72 mmol) in conc. HCl was added aqueous solution of sodium nitrite (5.11 g, 74.00 mmol) at −15° C. The reaction mass was stirred at 0-10° C. for 15 minutes. The reaction mass was filtered off to remove insolubles and stannous chloride in conc. HCl (34.7 g, 150 mmol) was added to the filtrate. The reaction mass was further stirred at −15° C. for 30 min and filtered to afford 15.00 g of the desired product. $^1$H NMR (300 MHz, DMSO d$_6$): δ 7.18-7.28 (m, 1H), 7.39-7.52 (m, 2H), 10.30 (br s, 3H); MS (m/z): 176.90 (M)$^+$.

Step-2:—Preparation of tert-butyl 2-(2,6-dichlorophenyl)hydrazinecarboxylate To the cold solution of (2,6-dichlorophenyl)hydrazine hydrochloride (15.0 g, 84.0 mmol) in THF (50 mL) was added aqueous solution of K$_2$CO$_3$ (23.3 g, 169 mmol) and BOC anhydride solution in THF (20.3 g, 93.00 mmol) at 0° C. The reaction mass was stirred at RT for 12 h. The reaction mass was quenched in water and extracted with DCM. The organic layer was dried over anhydrous sodium sulphate and concentrated. The obtained solid was washed with pentane to afford 6.5 g of desired product. $^1$H NMR (300 MHz, DMSO d$_6$): δ 1.34 (s, 9H), 6.85 (m, 1H), 7.06 (s, 1H), 7.27 (d, J=7.8 Hz, 2H), 9.01 (s, 1H); MS (m/z): 276.88 (M−H)$^-$.

Intermediate-45

1-(2,6-Dichlorophenyl)-3-(4-iodo-3-methoxyphenyl)-1H-1,2,4-triazol-5(4H)-one

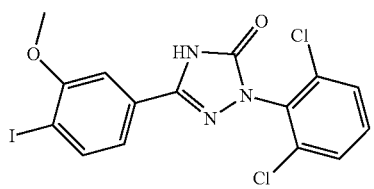 [SMILES: COc1cc(-c2nn(-c3c(Cl)cccc3Cl)c(=O)[nH]2)ccc1I]

Step-1:—Preparation of 3-methoxy-4-nitrobenzamide

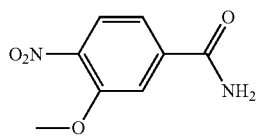

To a cold solution of 3-methoxy-4-nitrobenzoic acid (2.0 g, 10.10 mmol) in THF (25 mL) was added oxalyl chloride (1.1 mL, 12.1 mmol) and DMF (2-3 drop) at 0° C. The reaction mixture was stirred at RT for 2 h and concentrated. The solution of the concentrated mass in THF (15 mL) was treated with ammonia gas (purged through reaction mass) at 0° C. and the reaction mixture was stirred at RT for 1 h. The reaction mass was diluted with ethyl acetate, washed with water, dilute HCl and brine. The organic layer was separated, dried, filtered and concentrated. The concentrate was used for the next step without further purification. $^1$H NMR (300 MHz, DMSO d$_6$): δ 3.97 (s, 3H), 7.56 (d, J=8.1 Hz, 1H), 7.72-7.75 (m, 2H), 7.94 (d, J=8.4 Hz, 1H), 8.25 (s, 1H); MS (m/z): 195.98 (M)$^-$.

Step-2:—Preparation of 3-methoxy-4-nitrobenzoyl isocyanate

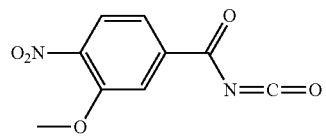 [SMILES: COc1cc(C(=O)N=C=O)ccc1[N+](=O)[O-]]

To a solution of 3-methoxy-4-nitrobenzamide (1.00 g, 5.10 mmol) in EDC (10 mL) was added oxalyl chloride (0.64 g, 6.12 mmol). The reaction mass was refluxed for 24 h. Excess of solvent was removed under vacuum to afford 1.0 g of desired product.

Step-3:—Preparation of tert-butyl 2-(2,6-dichlorophenyl)-2-((3-methoxy-4-nitrobenzoyl) carbamoyl) hydrazinecarboxylate

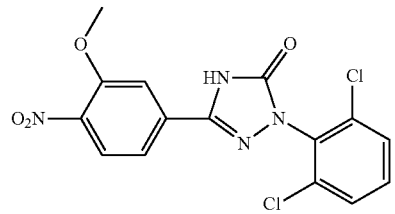 [SMILES: COc1cc(-c2nn(-c3c(Cl)cccc3Cl)c(=O)[nH]2)ccc1[N+](=O)[O-]]

To a solution of tert-butyl 2-(2,6-dichlorophenyl) hydrazinecarboxylate (Intermediate-44, 1.2 g, 4.5 mmol) in DCM (20 mL) was added 3-methoxy-4-nitrobenzoyl isocyanate (1.0 g, 4.5 mmol). The reaction mass was stirred at RT for 2 h. Excess of solvent was removed under vacuum to afford 1.5 g of desired product. $^1$H NMR (300 MHz, DMSO d$_6$): δ 1.35 (s, 9H), 3.97 (s, 3H), 7.89 (m, 1H), 7.27-7.35 (m, 2H), 7.55 (d, 1H), 7.62-7.75 (m, 1H), 7.94 (d, 1H), 8.26 (s, 1H), 9.03 (s, 1H); MS (m/z): 496.78 (M−H)$^-$.

Step-4:—Preparation of 1-(2,6-dichlorophenyl)-3-(3-methoxy-4-nitrophenyl)-1H-1,2,4-triazol-5(4H)-one To a solution of tert-butyl 2-(2,6-dichlorophenyl)-2-((3-methoxy-4-nitrobenzoyl) carbamoyl)hydrazinecarboxylate (1.0 g, 2.002 mmol) in DCM (20 mL) was added trifluoro acetic acid (2.0 mL). The reaction mass was stirred at RT for 2-3 h. Excess of solvent was removed at low temperature. The reaction mass was quenched in ice and filter off to afford 0.200 g of desired product. $^1$H NMR (300 MHz, DMSO d$_6$): δ 3.98 (s, 3H), 7.56-7.62 (m, 2H), 7.69-7.75 (m, 3H), 8.02 (d, J=8.4 Hz, 1H), 11-12 (br s, 1H); MS (m/z): 382.07 (M+H)$^+$.

Step-5:—Preparation of 3-(4-amino-3-methoxyphenyl)-1-(2,6-dichlorophenyl)-1H-1,2,4-triazol-5(4H)-one

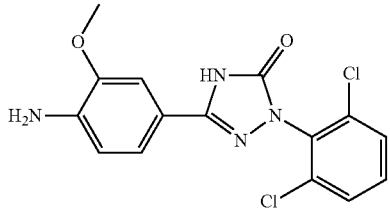 [SMILES: COc1cc(-c2nn(-c3c(Cl)cccc3Cl)c(=O)[nH]2)ccc1N]

To a solution of 1-(2,6-dichlorophenyl)-3-(3-methoxy-4-nitrophenyl)-1H-1,2,4-triazol-5(4H)-one (0.200 g, 0.52 mmol) in methanol (10 mL) was added iron powder (0.060 g, 1.84 mmol) and conc. HCl (2 mL). The reaction mixture was stirred at RT for 2 h. The reaction mass was quenched in water, basified with saturated sodium bicarbonate solution and extracted with DCM. The organic layer was dried over anhydrous sodium sulphate and concentrated to afford 0.150 g of desired product. $^1$H NMR (300 MHz, DMSO $d_6$): δ 3.80 (s, 3H), 5.34 (s, 2H), 6.66 (d, J=7.8 Hz, 1H), 7.18-7.21 (m, 2H), 7.58 (m, 1H), 7.69 (d, J=7.8 Hz, 2H), 12.27 (s, 1H); MS (m/z): 351.05 (M)$^+$.

Step-6:—Preparation of 1-(2,6-dichlorophenyl)-3-(4-iodo-3-methoxyphenyl)-1H-1,2,4-triazol-5(4H)-one To a solution of 3-(4-amino-3-methoxyphenyl)-1-(2,6-dichlorophenyl)-1H-1,2,4-triazol-5(4H)-one (0.300 g, 0.85 mmol) in acetonitrile (20 mL) was added PTSA (0.488 g, 2.56 mmol). The reaction mixture was stirred at RT for 2 h, followed by addition of aqueous solution of NaNO$_2$ (0.118 g, 1.170 mmol) and KI (0.284 g, 1.70 mmol). The reaction mixture was stirred at RT for 2 h. The reaction mass was concentrated and quenched in water. The reaction mass was washed with sodium metabisulphite solution and extracted with ethyl acetate. The organic layer was dried over anhydrous sodium sulphate and concentrated to afford 0.220 g of desired product. $^1$H NMR (300 MHz, DMSO $d_6$): δ 3.89 (s, 3H), 7.23 (d, J=7.8 Hz, 1H), 7.40 (s, 1H), 7.61 (m, 1H), 7.71-7.73 (m, 2H), 7.92 (d, J=8.4 Hz, 1H), 12.74 (s, 1H); MS (m/z): 461.93 (M)$^+$.

Intermediate-46

Methyl 4-(1-(2,6-dichlorophenyl)-5-oxo-4,5-dihydro-1H-1,2,4-triazol-3-yl)-2-methoxybenzoate

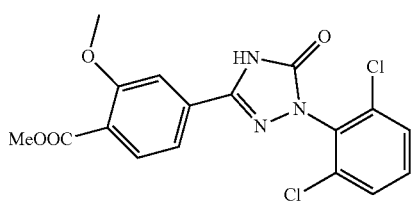 [SMILES: COC(=O)c1ccc(-c2nn(-c3c(Cl)cccc3Cl)c(=O)[nH]2)cc1OC]

Step-1:—Preparation of methyl 2-methoxy-4-methylbenzoate

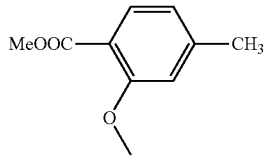

To a solution of 2-hydroxy-4-methylbenzoic acid (10.00 g, 65 mmol) in DMF (10 mL) was added K$_2$CO$_3$ (13.6 g, 98 mmol). The reaction mixture was stirred at 60° C. for 1 h. Methyl iodide (14.0 g, 98 mmol) was added to the reaction mixture and was stirred at 60° C. for 18 h. The reaction mass was quenched in water and concentrated. The reaction mass was extracted with ethyl acetate. The organic layer was dried over anhydrous sodium sulphate and concentrated to afford 10.00 g of desired product. $^1$H NMR (300 MHz, DMSO $d_6$): δ 2.34 (s, 3H), 3.74 (s, 3H), 3.79 (s, 3H), 6.81 (d, J=7.2 Hz, 1H), 6.97 (s, 1H), 7.56 (d, J=7.8 Hz, 1H); MS (m/z): 180.95 (M+H)$^+$.

Step-2:—Preparation of methyl 4-(bromomethyl)-2-methoxybenzoate

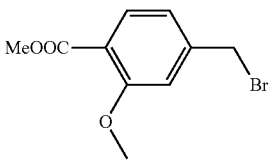

To a solution of methyl 2-methoxy-4-methylbenzoate (10.00 g, 55 mmol) in CCl$_4$ (150 mL) were added NBS (11.8 g, 66 mmol) and AIBN (0.100 g). The reaction mixture was refluxed for 18 h. The reaction mass was diluted with diethyl ether and washed with 25% NaOH solution. The organic layer was dried over anhydrous sodium sulphate and concentrated to afford 10.00 g of desired product. $^1$H NMR (300 MHz, DMSO $d_6$): δ 3.77 (m, 6H), 4.68 (s, 2H), 7.06 (d, J=7.8 Hz, 1H), 7.23 (s, 1H), 7.61 (d, J=7.8 Hz, 1H); MS (m/z): 259.13 (M)$^4$.

Step-3:—Preparation of methyl 4-formyl-2-methoxybenzoate

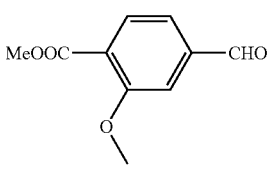

To a solution of sodium methoxide (0.260 g, 4.82 mmol) in methanol (200 mL) was added nitromethane (4.03 g, 11.58 mmol) under nitrogen atmosphere and the reaction mixture was stirred and reflux for 30 minutes. Methyl 4-(bromomethyl)-2-methoxybenzoate (10.00 g, 9.65 mmol) in methanol was added and the reaction mixture was refluxed for 7-8 h. The reaction mass was concentrated and diluted with CHCl₃. The diluted reaction mass was washed with 2N NaOH solution. The organic layer was dried over anhydrous sodium sulphate and concentrated to afford 6.00 g of desired product. ¹H NMR (300 MHz, DMSO d₆): δ 3.83 (m, 6H), 7.36 (d, J=6.6 Hz, 2H), 7.79 (d, J=7.8 Hz, 1H), 10.04 (s, 1H).

Step-4:—Preparation of 3-methoxy-4-(methoxycarbonyl)benzoic acid

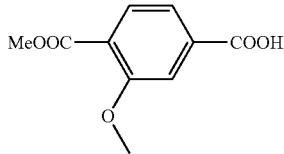

To a cold solution of methyl 4-formyl-2-methoxybenzoate (6.0 g, 7.73 mmol) in acetone (50 mL) was added aqueous sulphamic acid solution (4.5 g, 11.59 mmol) and aqueous sodium chlorite solution (4.04 g, 11.59 mmol) at 0-5° C. The reaction mixture was stirred at RT for 3-4 h. Excess of solvent was removed under vacuum. The obtained residue was diluted with water and basified with saturated sodium bicarbonate solution. The aqueous layer was washed with diethyl ether to remove organic impurities and the obtained aqueous layer was again acidified with conc. HCl. The solid obtained was filtered and suck dried to afford 2.00 g of desired product. ¹H NMR (300 MHz, DMSO d₆): δ 3.80 (s, 3H), 3.87 (s, 3H), 7.55-7.59 (m, 2H), 7.70 (d, J=7.8 Hz, 1H), 13.37 (s, 1H); MS (m/z): 210.97 (M+H)⁺.

Step-5:—Preparation of methyl 4-carbamoyl-2-methoxybenzoate

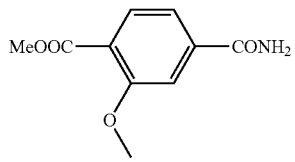

The title compound was prepared according to the procedure described in step-2 of Intermediate-26 by using 3-methoxy-4-(methoxycarbonyl)benzoic acid (2.00 g, 9.52 mmol), oxalyl chloride (1.02 g, 11.42 mmol), ammonia gas and THF (25 mL) to afford 1.40 g of the desired product. ¹H NMR (300 MHz, DMSO d₆): δ 3.79 (s, 3H), 3.87 (s, 3H), 7.49 (d, J=8.4 Hz, 1H), 7.57 (s, 2H), 7.68 (d, J=7.8 Hz, 1H), 8.14 (s, 1H); MS (m/z): 209.99 (M)⁺.

Step-6:—Preparation of methyl 4-(isocyanatocarbonyl)-2-methoxybenzoate

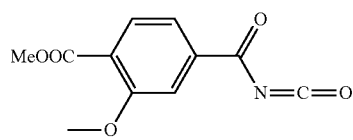

The title compound was prepared according to the procedure described in step-2 of Intermediate-8 by using methyl 4-carbamoyl-2-methoxybenzoate (1.4 g, 6.69 mmol), oxalyl chloride (0.72 mL, 8.03 mmol) and EDC (10 mL) to afford 1.00 g of the desired product.

Step-7:—Preparation of tert-butyl 2-(2,6-dichlorophenyl)-2-((3-methoxy-4-(methoxycarbonyl)benzoyl)carbamoyl)hydrazinecarboxylate

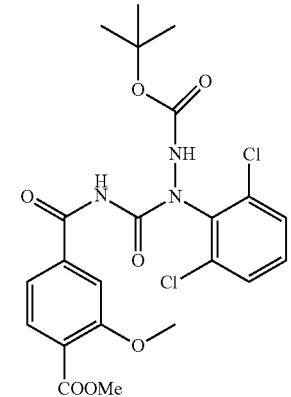 [SMILES: COC(=O)c1ccc(C(=O)NC(=O)N(NC(=O)OC(C)(C)C)c2c(Cl)cccc2Cl)cc1OC]

The title compound was prepared according to the procedure described in step-1 of Intermediate-9 by using methyl 4-(isocyanatocarbonyl)-2-methoxybenzoate (0.84 g, 3.61 mmol), tert-butyl 2-(2,6-dichlorophenyl)hydrazinecarboxylate (Intermediate-44, 1.0 g, 3.61 mmol) and DCM (20 mL) to afford 1.50 g of the desired product. ¹H NMR (300 MHz, DMSO d₆): δ 1.35 (s, 9H), 3.80 (s, 3H), 3.87 (s, 3H), 7.28-7.42 (m, 6H), 9.57 (s, 1H), 10.85 (s, 1H); MS (m/z): 511.73 (M)⁺.

Step-8:—Preparation of methyl 4-(1-(2,6-dichlorophenyl)-5-oxo-4,5-dihydro-1H-1,2,4-triazol-3-yl)-2-methoxybenzoate The title compound was prepared according to the procedure described in step-2 of Intermediate-9 by using tert-butyl 2-(2,6-dichlorophenyl)-2-((3-methoxy-4-(methoxycarbonyl) benzoyl)carbamoyl)hydrazinecarboxylate (1.5 g, 2.9 mmol), DCM (20 mL) and trifluoro acetic acid (2.0 mL) to afford 0.600 g of desired product. ¹H NMR (300 MHz, DMSO d₆): δ 3.80 (s, 3H), 3.80 (s, 3H), 7.49-7.71 (m, 3H), 7.74-7.79 (m, 3H), 12.85 (s, 1H); MS (m/z): 393.95 (M)⁺.

Intermediate-47

2-Fluoro-4-iodobenzoyl isocyanate

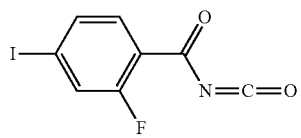

Step-1:—Preparation of 2-fluoro-4-iodobenzoic acid

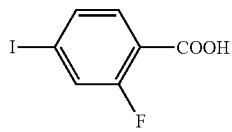

A solution of sodium dichromate (25.2 g, 84.0 mmol) in acetic acid (100 mL) was stirred for 10 min, followed by addition of 2-fluoro-4-iodo-1-methylbenzene (10.0 g, 42 mmol). The reaction mixture was stirred for 5 min followed by slow addition of conc. $H_2SO_4$ (60 mL) for 1-2 h. The reaction mixture stirred at 90-100° C. for 7-8 h. The reaction mixture was cooled and quenched with ice water. The reaction mass was extracted with ethyl acetate. The organic layer was dried over anhydrous sodium sulphate and concentrated to afford 5.0 g of the desired product. $^1$H NMR (300 MHz, DMSO $d_6$): δ 7.58 (t, J=8.4 Hz, 1H), 7.67 (d, J=7.5 Hz, 1H), 7.75 (d, J=8.4 Hz, 1H), 13 (br s, 1H); MS (m/z): 264.99 (M−H)$^-$.

Step-2:—Preparation of 2-fluoro-4-iodobenzamide

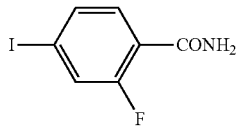 [SMILES: NC(=O)c1ccc(I)cc1F]

The title compound was prepared according to the procedure described in step-2 of Intermediate-26 by using 2-fluoro-4-iodobenzoic acid (5.00 g, 18.0 mmol), oxalyl chloride (2.0 mL, 22.0 mmol), ammonia gas, DCM (100 mL) and THF (100 mL) to afford 2.00 g of the desired product. $^1$H NMR (300 MHz, DMSO $d_6$): δ 7.40 (t, J=7.8 Hz, 1H), 7.63-7.76 (m, 1H); MS (m/z): 266.19 (M+H)$^+$.

Step-3:—Preparation of 2-fluoro-4-iodobenzoyl isocyanate

The title compound was prepared according to the procedure described in step-2 of Intermediate-8 by using 2-fluoro-4-iodobenzamide (0.500 g, 1.8 mmol), oxalyl chloride (0.285 g, 2.2 mmol) and EDC (10 mL) to afford 0.350 g of the desired product.

Intermediate-48

N-(4-Chloro-3-(3-(2-fluoro-4-iodophenyl)-5-oxo-4,5-dihydro-1H-1,2,4-triazol-1-yl)benzyl)cyclopropanecarboxamide

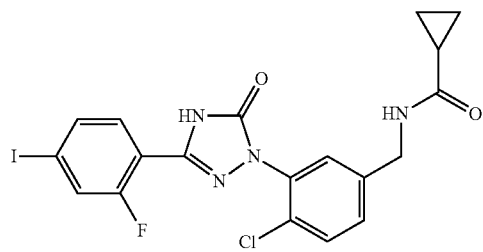 [SMILES: O=C(NCc1ccc(Cl)c(-n2nc(-c3ccc(I)cc3F)[nH]c2=O)c1)C1CC1]

Step-1:—Preparation of 5-(aminomethyl)-2-chlorobenzoic acid hydrochloride

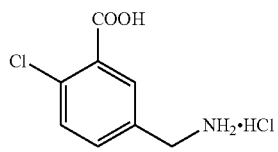

To a solution of 2-chloro-5-((2,2,2-trifluoroacetamido)methyl)benzoic acid (step-1 of Intermediate-26, 10.0 g, 35.50 mmol) in methanol (100 mL) was added conc. HCl (10 mL). The reaction mixture was refluxed for 18 h. The reaction mixture was concentrated and crude reaction mixture was used for next step.

Step-2:—Preparation of methyl 5-(aminomethyl)-2-chlorobenzoate

To a solution of 5-(aminomethyl)-2-chlorobenzoic acid hydrochloride (17.0 g, 76.5 mmol) in methanol (200 mL) was added conc. $H_2SO_4$ (15 mL). The reaction mixture was refluxed for 15 h. The reaction mixture was concentrated and water was added. The aq. solution was basified with sodium bicarbonate. The reaction mixture was extracted with 10% MeOH: DCM and concentrated to afford 15.0 g of desired product. $^1$H NMR (300 MHz, DMSO $d_6$): δ 2.1 (br s, 2H), 3.73 (s, 2H), 3.85 (s, 3H), 7.50 (s, 2H), 7.77 (s, 1H); MS (m/z): 200.05 (M+H)$^+$.

Step-3:—Preparation of methyl 2-chloro-5-(cyclopropanecarboxamidomethyl)benzoate

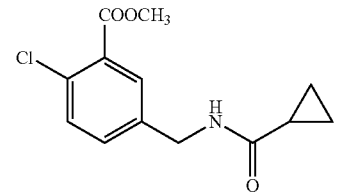 [SMILES: COC(=O)c1cc(CNC(=O)C2CC2)ccc1Cl]

To a solution of methyl 5-(aminomethyl)-2-chlorobenzoate (15.0 g, 75 mmol) in dry THF (150 mL) was added DIPEA (15 mL) under nitrogen atmosphere. Cyclopropanecarbonyl chloride was added to the reaction mixture at 10*C and (11.81 g, 113 mmol). The reaction mixture was stirred at RT for 5-6 h. The reaction mixture was quenched with ice water and extracted with ethyl acetate. The organic layer was washed with dilute HCl, followed with sodium bicarbonate solution and concentrated to afford 10.0 g of desired product. $^1$H NMR (300 MHz, DMSO $d_6$): δ 0.69 (m, 4H), 1.59 (m, 1H), 186 (s, 3H), 4.29 (d, J=6.0 Hz, 2H), 7.43

(d, J=6.6 Hz, 1H), 7.53 (d, J=8.4 Hz, 1H), 7.67 (s, 1H), 8.64 (br s, 1H); MS (m/z): 268.16 (M+H)⁺.

Step-4:—Preparation of 2-chloro-5-(cyclopropanecarboxamidomethyl)benzoic acid

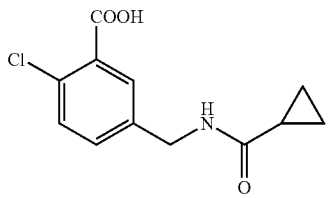 [SMILES: O=C(O)c1cc(CNC(=O)C2CC2)ccc1Cl]

To a solution of methyl 2-chloro-5-(cyclopropanecarboxamidomethyl)benzoate (10.0 g, 30 mmol) in THF:methanol (10:20 mL) was added aqueous solution of NaOH (6.0 g, 140 mmol). The reaction mixture was refluxed for 3-5 h. The reaction mixture was concentrated, diluted with water and acidified with dilute HCl. The reaction mixture was extracted with 10% MeOH: DCM and concentrated to afford 4.0 g of desired product. ¹H NMR (300 MHz, DMSO d₆): δ 0.67 (m, 4H), 1.59 (m, 1H), 4.28 (d, J=6.0 Hz, 2H), 7.37-7.50 (m, 2H), 7.65 (s, 1H), 8.64 (m, 1H), 13.40 (br s, 1H).

Step-5:—Preparation of N-(3-amino-4-chlorobenzyl)cyclopropanecarboxamide

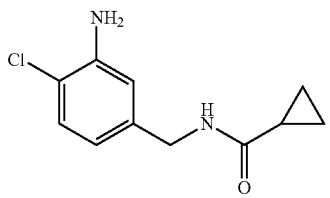 [SMILES: Nc1cc(CNC(=O)C2CC2)ccc1Cl]

To a solution of 2-chloro-5-(cyclopropanecarboxamidomethyl)benzoic acid (5.0 g, 19 mmol) in conc. H₂SO₄ (30 mL) was added NaN₃ (1.4 g, 21 mmol) lotwise at 50° C. The reaction mixture was stirred at 50° C. for 18 h. The reaction mass was quenched with ammonia and ice water. The solid obtained was filtered and suck dried to afford 3.0 g of desired product. ¹H NMR (300 MHz, DMSO d₆): δ 0.66 (m, 4H), 1.56 (m, 1H), 4.12 (d, J=6.0 Hz, 2H), 5.27 (s, 2H), 6.41 (d, J=6.9 Hz, 1H), 6.61 (s, 1H), 7.10 (d, J=8.4 Hz, 1H), 8.48 (m, 1H); MS (m/z): 225.22 (M+H)⁺.

Step-6:—Preparation of N-(4-chloro-3-hydrazinyl-benzyl)cyclopropanecarboxamide

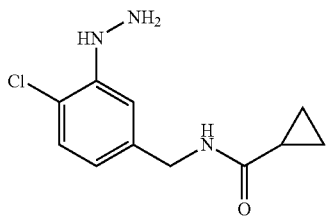 [SMILES: NNc1cc(CNC(=O)C2CC2)ccc1Cl]

To a cold solution of N-(3-amino-4-chlorobenzyl)cyclopropanecarboxamide (2.00 g, 8.90 mmol) in conc. HCl (25 mL) was added aqueous solution of sodium nitrite (0.676 g, 9.7 mmol) at −20° C. to −25° C. The reaction mass was stirred at −20° C. to −25° C. for 30 min, followed by addition of stannous chloride solution (5.0 g, 22.2 mmol) in conc. HCl slowly. The reaction mass was stirred at −20° C. to −25° C. for 1 h. The reaction mass was basified with aqueous NaOH at below 0° C. The reaction mass was diluted with water, extracted with 10% MeOH: DCM and concentrated to afford 1.6 g of desired product. ¹H NMR (300 MHz, DMSO d₆): δ 0.66 (m, 4H), 1.58 (m, 1H), 4.10 (s, 2H), 4.18 (d, J=5.4 Hz, 2H), 6.47 (m, 2H), 7.11 (m, 2H), 8.51 (br s, 1H); MS (m/z): 240.05 (M+H)⁺.

Step-7:—Preparation of tert-butyl 2-(2-chloro-5-(cyclopropanecarboxamidomethyl) phenyl)hydrazinecarboxylate

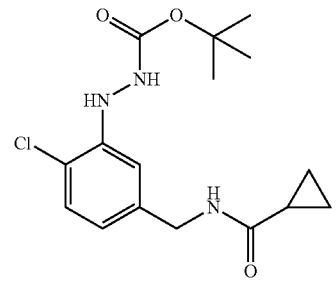 [SMILES: CC(C)(C)OC(=O)NNc1cc(CNC(=O)C2CC2)ccc1Cl]

To a cold solution of N-(4-chloro-3-hydrazinylbenzyl) cyclopropanecarboxamide (1.60 g, 6.69 mmol) in acetonitrile (20 mL) was added aqueous solution of Na₂CO₃ (1.06 g, 10.04 mmol) and BOC anhydride (1.06 g, 7.36 mmol). The reaction mass was stirred at RT for 12 h. The reaction mass was quenched in water and extracted with ethyl acetate and concentrated to afford 1.00 g of the crude product which was further purified by column chromatography using basic alumina eluting with 0.3% MeOH: DCM to afford 0.900 g of pure product. ¹H NMR (300 MHz, DMSO d₆): δ 0.63 (m, 4H), 1.40 (s, 9H), 1.54 (m, 4.15 (d, J=6.0 Hz, 2H), 6.59 (m, 2H), 7.17 (d, J=7.8 Hz, 1H), 7.31 (s, 1H), 8.51 (m, 1H), 8.87 (s, 1H); MS (m/z): 338.41 (M−H)⁻.

Step-8:—Preparation of tert-butyl 2-(2-chloro-5-(cyclopropanecarboxamidomethyl) phenyl)-2-((2-fluoro-4-iodobenzoyl)carbamoyl)hydrazinecarboxylate

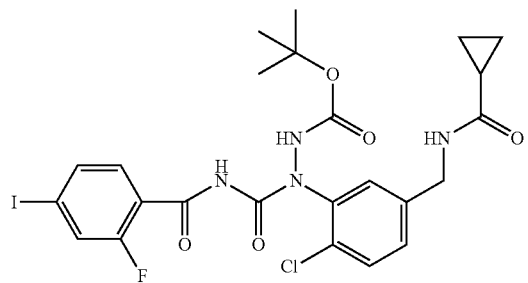 [SMILES: CC(C)(C)OC(=O)NN(C(=O)NC(=O)c1ccc(I)cc1F)c1cc(CNC(=O)C2CC2)ccc1Cl]

The title compound was prepared according to the procedure described in step-1 of Intermediate-9 by using 2-fluoro-4-iodobenzoyl isocyanate (intermediate-47, 0.500 g, 1.71 mmol), tert-butyl 2-(2-chloro-5-(cyclopropanecarboxamidomethyl)phenyl)hydrazine carboxylate (0.582 g, 1.71 mmol) and DCM (20 mL) to afford 0.200 g of the desired product. $^1$H NMR (300 MHz, DMSO d$_6$): δ 0.69 (m, 4H), 1.42 (s, 9H), 1.56 (m, 1H), 4.17 (d, J=5.7 Hz, 2H), 6.58-6.63 (m, 2H), 7.18 (d, J=8.1 Hz, 1H), 7.30 (m, 3H), 7.63-7.79 (m, 2H), 8.53 (m, 1H), 8.90 (s, 1H); MS (m/z): 630.85 (M+H)$^+$.

Step-9:—Preparation of N-(4-chloro-3-(3-(2-fluoro-4-iodophenyl)-5-oxo-4,5-dihydro-1H-1,2,4-triazol-1-yl)benzyl)cyclopropanecarboxamide To a solution of tert-butyl 2-(2-chloro-5-(cyclopropanecarboxamidomethyl)phenyl)-2-((2-fluoro-4-iodobenzoyl)carbamoyl)hydrazinecarboxylate (0.200 g, 0.31 mmol) in DCM (10 mL) was added trifluoro acetic acid (1.0 mL). The reaction mass was stirred at RT for 12 h and refluxed for 15 h. The reaction mass was cooled to RT, basified with NaHCO$_3$ (pH=8), extracted with DCM and concentrated to afford 0.110 g of desired product. $^1$H NMR (300 MHz, DMSO d$_6$): δ 0.68 (m, 4H), 1.59 (m, 1H), 4.32 (d, J=5.7 Hz, 2H), 7.38 (d, J=8.4 Hz, 1H), 7.45 (s, 1H), 7.51-7.63 (m, 2H), 7.75 (d, J=8.1 Hz, 1H), 7.88 (d, J=10.2 Hz, 1H), 8.68 (m, 1H), 12.43 (br s, 1H); MS (m/z): 513.01 (M+H)$^+$.

Intermediate-49

4-Chloro-1-ethynyl-2-fluorobenzene

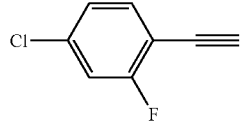

Step-1:—Preparation of ((4-chloro-2-fluorophenyl)ethynyl)trimethylsilane

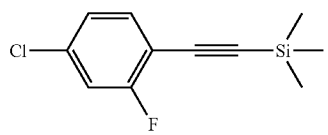

To a solution of 4-chloro-2-fluoro-1-iodobenzene (2.0 g, 7.8 mmol) in DMSO (10 mL) was added ethynyl(trimethyl)silane (1.14 g, 11.0 mmol), copper iodide (0.029 g, 0.15 mmol), bis(triphenylphosphine) palladium(II) chloride (0.218 g, 0.3 mmol) and TEA (1 mL). The reaction mass was stirred at RT for 4-5 h. The reaction mass quenched in water, passed through celite bed and extracted with ethyl acetate and concentrated to afford 1.0 g of desired product.

Step-2:—Preparation of 4-chloro-1-ethynyl-2-fluorobenzene

To a solution of ((4-chloro-2-fluorophenyl)ethynyl)trimethylsilane (1.0 g, 4.42 mmol) in DCM (20 mL) was added TBAF (catalytic) and reaction mixture was stirred for 1-2 h at RT. The reaction mass was quenched in water, extracted with DCM and concentrated to afford 0.900 g of the crude product which was further purified by column chromatography eluting with pet. ether to afford to afford 0.500 g of pure product. $^1$H NMR (300 MHz, DMSO d$_6$): δ 4.60 (s, 1H), 7.32 (d, J=8.1 Hz, 1H), 7.56-7.61 (m, 2H).

Intermediate-50

1-Ethynyl-3-(trifluoromethyl) benzene

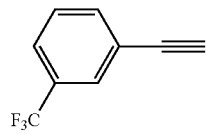

Step-1:—Preparation of trimethyl((3-(trifluoromethyl)phenyl)ethynyl)silane

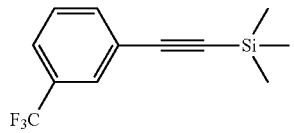

To a solution of 1-iodo-3-(trifluoromethyl)benzene (1.0 g, 3.6 mmol) in ethyl acetate (20 mL) was added ethynyl (trimethyl)silane (0.540 g, 5.5 mmol), copper iodide (0.042 g, 0.22 mmol), bis(triphenylphosphine) palladium(II) chloride (0.129 g, 0.18 mmol) and TEA (2.2 mL, 14.7 mmol). The reaction mass stirred at 50-60° C. for 24 h. The reaction mass was quenched in water, extracted with ethyl acetate and concentrated to afford 0.500 g of desired product. $^1$H NMR (300 MHz, DMSO d$_6$): δ 0.26 (s, 9H), 7.44 (t, J=7.8 Hz, 1H), 7.55 (d, J=7.8 Hz, 1H), 7.62 (d, J=7.2 Hz, 1H), 7.72 (s, 1H).

Step-2:—Preparation of 1-ethynyl-3-(trifluoromethyl)benzene

To a solution of trimethyl((3-(trifluoromethyl)phenyl)ethynyl)silane (0.500 g, 2.06 mmol) in ethanol (10 mL) was added potassium carbonate (0.253 g, 1.8 mmol) and the reaction mixture was stirred at RT for 18 h. The reaction mass was quenched in water, neutralized with dil. HCl and extracted with hexane and concentrated to afford 0.200 g of the crude product which was further purified by column chromatography using silica (60-120 mesh) eluting with pet. ether to afford 0.500 g of pure product. $^1$H NMR (300 MHz, DMSO d$_6$): δ 4.41 (s, 1H), 7.64 (d, J=7.5 Hz, 1H), 7.77-7.81 (m, 3H).

Intermediate-51

6-Chloro-2-fluoro-3-(pivalamidomethyl)benzoyl isocyanate

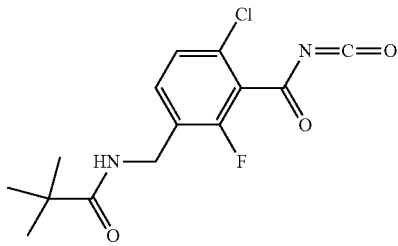 [SMILES: CC(C)(C)C(=O)NCc1ccc(Cl)c(C(=O)N=C=O)c1F]

Step-1:—Preparation of ethyl 6-chloro-2-fluoro-3-formylbenzoate

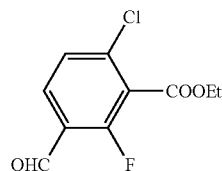 [SMILES: CCOC(=O)c1c(Cl)ccc(C=O)c1F]

To a cold solution of ethyl 2-chloro-6-fluorobenzoate (0.500 g, 24.7 mmol) in THF (35 mL) was added LDA (6.6 g, 61.8 mmol) at −78° C. The reaction mixture was stirred for 2 h at same temperature, followed by addition of DMF (2.7 g, 37 mmol). The reaction mixture was further stirred for 2 h at same temperature. The reaction mass was quenched in dilute HCl, extracted with ethyl acetate and concentrated to afford crude product which was further purified by column chromatography eluting with EtOAC: pet.ether to afford 2.00 g of pure product. $^1$H NMR (300 MHz, DMSO $d_6$): δ 1.31 (t, 3H), 4.42 (q, 2H), 7.94-7.99 (m, 2H), 10.14 (s, 1H).

Step-2:—Preparation of ethyl 6-chloro-2-fluoro-3-((hydroxyimino)methyl)benzoate

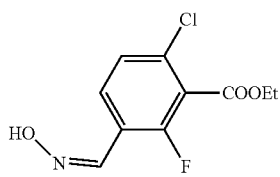 [SMILES: CCOC(=O)c1c(Cl)ccc(/C=N\O)c1F]

To a solution of ethyl 6-chloro-2-fluoro-3-formylbenzoate (1.1 g, 4.0 mmol) in MeOH (5 mL) was added (aq. solution) hydroxyl amine (4 mL) and the reaction mixture was heated at 60° C. for 2-3 h. The reaction mass was concentrated and extracted with EtOAC. The organic layer was washed with brine and concentrated to afford 0.900 g of the product. $^1$H NMR (300 MHz, DMSO $d_6$): δ 1.31 (t, J=6.9 Hz, 3H), 4.40 (q, J=6.6 Hz, 2H), 7.47 (d, J=9.0 Hz, 1H), 7.86 (t, J=8.1 Hz, 1H), 8.20 (s, 1H), 11.89 (br s, 1H).

Step-3:—Preparation of ethyl 3-(aminomethyl)-6-chloro-2-fluorobenzoate

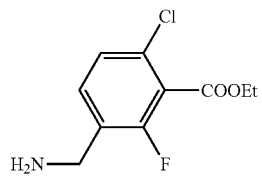

To a solution of ethyl 6-chloro-2-fluoro-3-((hydroxyimino)methyl)benzoate (0.800 g, 3.26 mmol) in MeOH (5 mL) was added Zn (0.850 g, 13.06 mmol), followed by dropwise addition of conc. HCl (catalytic) and the reaction mixture was heated at 60° C. for 2-3 h. Excess of solvent was removed under vacuum and the residue was diluted with water and basified with NaHCO$_3$, extracted with EtOAc and concentrated to afford 0.600 g of the product. $^1$H NMR (300 MHz, DMSO $d_6$): δ 1.31 (t, J=7.2 Hz, 3H), 3.76 (s, 2H), 4.38 (q, J=6.9 Hz, 2H), 7.41 (d, J=8.1 Hz, 1H), 7.65 (t, J=8.1 Hz, 1H).

Step-4:—Preparation of ethyl 6-chloro-2-fluoro-3-(pivalamidomethyl)benzoate

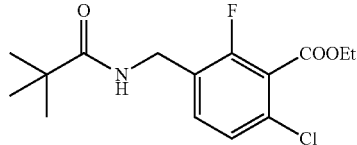 [SMILES: CCOC(=O)c1c(Cl)ccc(CNC(=O)C(C)(C)C)c1F]

To a solution of ethyl 3-(aminomethyl)-6-chloro-2-fluorobenzoate (0.540 g, 2.5 mmol) in THF (5 mL) was added pivaloyl chloride (0.335 g, 2.79 mmol) and TEA (0.1 mL) and the reaction mixture was stirred for 2-3 h at RT. Excess of solvent was removed under vacuum and the residue was diluted with water, extracted with EtOAC and concentrated to afford 0.500 g of the product. $^1$H NMR (300 MHz, DMSO $d_6$): δ 1.11 (s, 9H), 1.31 (t, J=7.5 Hz, 3H), 4.26 (d, J=5.1 Hz, 2H), 4.39 (q, J=6.6 Hz, 2H), 7.33-7.43 (m, 2H), 8.13 (m, 1H).

Step-5:—Preparation of 6-chloro-2-fluoro-3-(pivalamidomethyl)benzoic acid

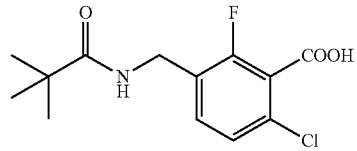 [SMILES: CC(C)(C)C(=O)NCc1ccc(Cl)c(C(=O)O)c1F]

The title compound was prepared according to the procedure described in step-4 of Intermediate-48 by using ethyl 6-chloro-2-fluoro-3-(pivalamidomethyl)benzoate (0.800 g) THF:methanol (2:2 mL) and aqueous solution of NaOH (1.0 g) to afford 0.500 g of the product. $^1$H NMR (300 MHz, DMSO $d_6$): δ 1.11 (s, 9H), 4.26 (d, J=5.4 Hz, 2H), 7.26-7.38 (m, 2H), 8.14 (m, 1H), 14.07 (br s, 1H).

Step-6:—Preparation of
6-chloro-2-fluoro-3-(pivalamidomethyl)benzamide

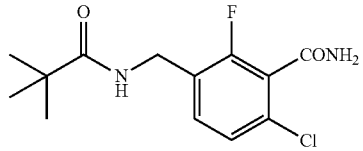 [SMILES: CC(C)(C)C(=O)NCc1ccc(Cl)c(C(N)=O)c1F]

The title compound was prepared according to the procedure described in step-2 of Intermediate-26 by using 6-chloro-2-fluoro-3-(pivalamidomethyl)benzoic acid (0.400 g, 1.39 mmol), THF (25 mL), oxalyl chloride (0.14 mL, 1.67 mmol) and ammonia gas to afford 0.220 g of the product. $^1$H NMR (300 MHz, DMSO d$_6$): δ 1.12 (s, 9H), 4.25 (d, J=5.4 Hz, 2H), 7.20 (d, J=8.4 Hz, 1H), 7.30 (d, J=8.4 Hz, 1H), 7.82 (s, 1H), 8.12 (br s, 2H); MS (m/z): 287.01 (M+H$^+$).

Step-7:—Preparation of
6-chloro-2-fluoro-3-(pivalamidomethyl)benzoyl isocyanate

To a solution of 6-chloro-2-fluoro-3-(pivalamidomethyl) benzamide (0.300 g, 1.04 mmol) in EDC (10 mL) was added oxalyl chloride (0.11 mL, 1.25 mmol). The reaction mass was heated at 60-70° C. for 4-5 h. Excess of solvent was removed under vacuum to afford 1.0 g of desired product.

Intermediate-52 tert-Butyl
2-(3,4-dichlorophenyl)hydrazinecarboxylate

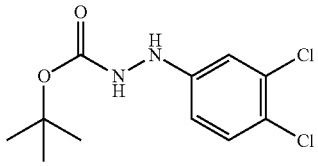 [SMILES: CC(C)(C)OC(=O)NNc1ccc(Cl)c(Cl)c1]

The title compound was prepared according to the procedure described in step-3 of Intermediate-7 by using (3,4-dichlorophenyl)hydrazine hydrochloride (1.00 g, 4.6 mmol), BOC anhydride (1.22 g, 5.6 mmol), Na$_2$CO$_3$ (1.24 g, 11.7 mmol), acetonitrile (20 mL) and water (10 mL) to afford 0.700 g of desired product. $^1$H NMR (300 MHz, DMSO d$_6$): δ 1.40 (s, 9H), 6.62 (d, J=8.7 Hz, 1H), 6.77 (s, 1H), 7.34 (d, J=8.7 Hz, 1H), 8.02 (s, 1H), 8.91 (s, 9H).

Intermediate-53 tert-Butyl
2-(4-(trifluoromethyl)phenyl)hydrazinecarboxylate

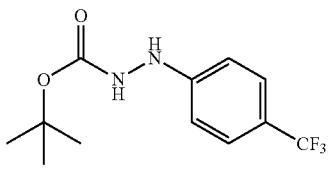 [SMILES: CC(C)(C)OC(=O)NNc1ccc(C(F)(F)F)cc1]

The title compound was prepared according to the procedure described in step-3 of Intermediate-7 by using 4-(trifluoromethyl)phenylhydrazine hydrochloride (1.00 g, 5.6 mmol), BOC anhydride (1.46 g, 6.8 mmol), Na$_2$CO$_3$ (0.900 g, 8.5 mmol), acetonitrile (20 mL) and water (10 mL) to afford 0.600 g of desired product. $^1$H NMR (300 MHz, DMSO d$_6$): δ 1.41 (s, 9H), 6.74 (d, J=8.7 Hz, 2H), 7.45 (d, J=9.0 Hz, 2H), 8.23 (s, 1H), 8.94 (br s, 1H).

Intermediate-54 tert-Butyl
2-(2,4-difluorophenyl)hydrazinecarboxylate

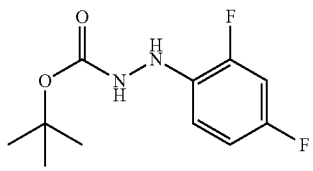 [SMILES: CC(C)(C)OC(=O)NNc1ccc(F)cc1F]

The title compound was prepared according to the procedure described in step-3 of Intermediate-7 by using (2,4-difluorophenyl)hydrazine hydrochloride (1.00 g, 5.54 mmol), BOC anhydride (1.81 g, 8.31 mmol), Na$_2$CO$_3$ (1.46 g, 13.85 mmol), acetonitrile (20 mL) and water (10 mL) to afford 0.500 g of desired product. $^1$H NMR (300 MHz, DMSO d$_6$): δ 1.40 (s, 9H), 6.70-6.72 (m, 1H), 6.90 (t, J=8.1 Hz, 1H), 7.07-7.14 (m, 1H), 7.47 (s, 1H), 8.83 (br s, 1H).

Intermediate-55 tert-Butyl
2-(4-methoxyphenyl)hydrazinecarboxylate

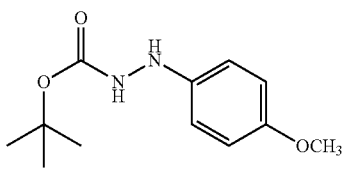 [SMILES: COc1ccc(NNC(=O)OC(C)(C)C)cc1]

The title compound was prepared according to the procedure described in step-3 of Intermediate-7 by using (4-methoxyphenyl)hydrazine hydrochloride (1.00 g, 5.72 mmol), BOC anhydride (1.8 g, 8.59 mmol), Na$_2$CO$_3$ (1.51 g, 14.31 mmol), acetonitrile (20 mL) and water (10 mL) to afford 0.400 g of desired product. $^1$H NMR (300 MHz, DMSO d$_6$): δ 1.39 (s, 9H), 3.64 (s, 3H), 6.60 (d, J=7.8 Hz, 2H), 7.74 (d, J=8.4 Hz, 2H), 7.18 (br s, 1H), 8.68 (br s, 1H).

Intermediate-56

2-Fluoro-4-(trifluoromethyl)benzoyl isocyanate

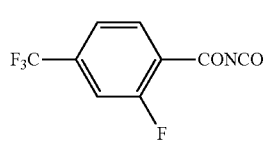

Step-1:—Preparation of 2-fluoro-4-(trifluoromethyl)benzamide

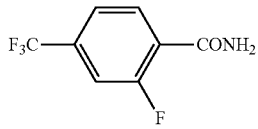

The title compound was prepared according to the procedure described in step-2 of Intermediate-26 by using 2-fluoro-4-(trifluoromethyl)benzoic acid (1.5 g), THF (25 mL), oxalyl chloride (0.5 mL) and ammonia gas to afford 1.35 g of the product. $^1$H NMR (300 MHz, DMSO d$_6$): δ 7.65 (d, J=8.4 Hz, 1H), 7.77-7.84 (m, 3H), 7.96 (br s, 1H); MS (m/z): 208.06 (M$^+$).

Step-2:—Preparation of 2-fluoro-4-(trifluoromethyl)benzoyl isocyanate

The title compound was prepared according to the procedure described in step-2 of Intermediate-8 by using 2-fluoro-4-(trifluoromethyl)benzamide (0.200 g, 0.96 mmol), EDC (10 mL) and oxalyl chloride (0.1 mL, 1.15 mmol) to afford 0.200 g of the product.

Intermediate-57 tert-Butyl 2-(6-chloro-2-fluoro-3-(pivalamidomethyl)phenyl)hydrazinecarboxylate

Step-1:—Preparation of N-(3-amino-4-chloro-2-fluorobenzyl)pivalamide

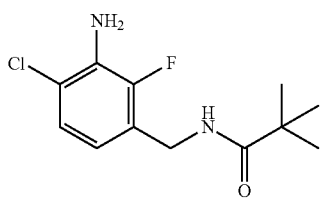 [SMILES: CC(C)(C)C(=O)NCc1ccc(Cl)c(N)c1F]

To a solution of 6-chloro-2-fluoro-3-(pivalamidomethyl) benzoic acid (step-5 of Intermediate-51, 1.0 g, 3.48 mmol) in conc. sulphuric acid (10.0 mL) was added sodium azide (0.271 g, 4.18 mmol). The reaction mass was stirred at 50-60° C. for 18 h. The reaction mass was quenched in ammonia solution (cold) and solid obtained was filtered and suck dried to afford 0.570 g of the product. $^1$H NMR (300 MHz, DMSO d$_6$): δ 1.11 (s, 9H), 4.21 (d, J=5.7 Hz, 2H), 5.30 (s, 2H), 6.39 (t, J=7.8 Hz, 1H), 7.00 (d, J=8.4 Hz, 1H), 7.98 (m, 1H); MS (m/z): 259.12 (M+H$^+$).

Step-2:—Preparation of N-(4-chloro-2-fluoro-3-hydrazinylbenzyl)pivalamide

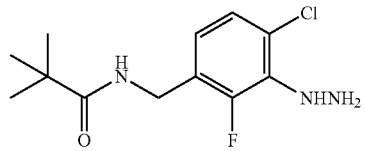 [SMILES: CC(C)(C)C(=O)NCc1ccc(Cl)c(NN)c1F]

The title compound was prepared according to the procedure described in step-2 of Intermediate-7 by using N-(3-amino-4-chloro-2-fluorobenzyl)pivalamide (0.500 g, 1.93 mmol), sodium nitrite (0.200 g, 2.90 mmol), stannous chloride.H$_2$O (4.84 g, 1.09 mmol), conc. HCl (20.0 g) and water (3 mL) to afford 0.300 g of the desired product. $^1$H NMR (300 MHz, DMSO d$_6$): δ 1.12 (s, 9H), 4.23 (d, J=5.4 Hz, 2H), 4.34 (br s, 2H), 5.91 (s, 1H), 6.65 (t, J=7.8 Hz, 1H), 8.02 (m, 1H); MS (m/z): 274.08 (M+H$^+$).

Step-3:—Preparation of tert-butyl 2-(6-chloro-2-fluoro-3-(pivalamidomethyl)phenyl) hydrazinecarboxylate The title compound was prepared according to the procedure described in step-3 of Intermediate-7 by using N-(4-chloro-2-fluoro-3-hydrazinylbenzyl)pivalamide (0.300 g, 1.09 mmol), BOC anhydride (0.360 g, 1.64 mmol), Na$_2$CO$_3$ (0.231 g, 2.18 mmol), acetonitrile (10 mL) and water (5 mL) to afford 0.150 g of desired product. $^1$H NMR (300 MHz, DMSO d$_6$): δ 1.11 (s, 9H), 1.37 (s, 9H), 4.20 (d, J=5.7 Hz, 2H), 6.64 (m, 1H), 7.06 (br s, 2H), 8.00 (br s, 1H), 8.98 (s, 1H).

Intermediate-58

4-Chloro-2-fluorobenzoyl isocyanate

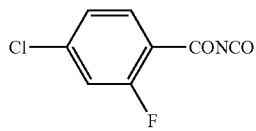

Step-1:—Preparation of 4-chloro-2-fluorobenzamide

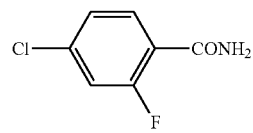

The title compound was prepared according to the procedure described in step-2 of Intermediate-26 by using 4-chloro-2-fluoro benzoic acid (1.5 g), THF (25 mL), oxalyl chloride (0.5 mL) and ammonia gas to afford 1.45 g of the product. $^1$H NMR (300 MHz, DMSO d$_6$): δ 7.36 (d, J=6.3 Hz, H), 7.53 (dd, J=8.7 Hz, 1H), 7.64-7.76 (m, 3H).

Step-2:—Preparation of 4-chloro-2-fluorobenzoyl isocyanate

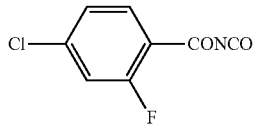

The title compound was prepared according to the procedure described in step-2 of Intermediate-8 by using 4-chloro-2-fluorobenzamide (0.200 g, 1.26 mmol), EDC (10 mL) and oxalyl chloride (0.14 mL, 1.15 mmol) to afford 0.200 g of the product.

Intermediate-59

4-(Trifluoromethyl)benzoyl isocyanate

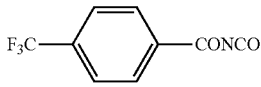

Step-1:—Preparation of 4-(trifluoromethyl)benzamide

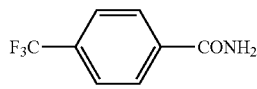 [SMILES: NC(=O)c1ccc(C(F)(F)F)cc1]

To a cold solution of 4-(trifluoromethyl)benzonitrile (0.500 g, 2.92 mmol) in DMSO (6.0 mL) was added $H_2O_2$ (50%) (5 mL) at 0° C., followed by portion-wise addition of $K_2CO_3$ (0.121 g, 0.87 mmol). The reaction mass was allowed to attain RT and stirred for 1 h. The reaction mass was quenched in ice water and extracted with DCM and concentrated to afford 0.300 g of product. $^1H$ NMR (400 MHz, DMSO $d_6$): δ 7.60 (br s, 1H), 7.82 (d, J=7.5 Hz, 2H), 8.05 (d, J=6.6 Hz, 2H), 8.17 (br s, 1H); MS (m/z): 190.11 (M+H$^+$).

Step-2:—Preparation of 4-(trifluoromethyl)benzoyl isocyanate

The title compound was prepared according to the procedure described in step-2 of Intermediate-8 by using 4-(trifluoromethyl)benzamide (0.200 g, 1.05 mmol), EDC (10 mL) and oxalyl chloride (0.15 LPL, 1.58 mmol) to afford 0.200 g of the product.

Intermediate-60 tert-Butyl 2-(5-(trifluoromethyl)pyridin-2-yl)hydrazinecarboxylate

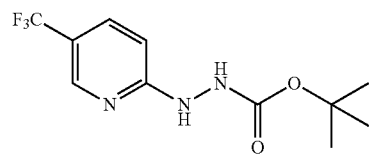 [SMILES: CC(C)(C)OC(=O)NNc1ccc(C(F)(F)F)cn1]

Step-1:—Preparation of 2-hydrazinyl-5-(trifluoromethyl)pyridine

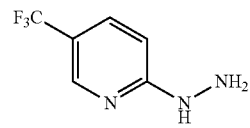

To a solution of 2-chloro-5-(trifluoromethyl)pyridine (1.5 g, 8.26 mmol) in ethanol (20.0 mL) was added hydrazine-hydrate (1.21 g, 24.79 mmol). The reaction mass was refluxed for 5-6 h. The reaction mass was concentrated and quenched in ice water and solid obtained was filtered and suck dried to afford 0.700 g of the product. $^1H$ NMR (300 MHz, DMSO $d_6$): δ 4.32 (br s, 2H), 6.78 (d, J=8.8 Hz, 1H), 7.67 (d, J=8.4 Hz, 1H), 8.25 (br s, 2H); MS (m/z): 178.15 (M+H$^+$).

Step-2:—Preparation of tert-butyl 2-(5-(trifluoromethyl)pyridin-2-yl)hydrazinecarboxylate The title compound was prepared according to the procedure described in step-3 of Intermediate-7 by using 2-hydrazinyl-5-(trifluoromethyl)pyridine (0.700 g, 3.95 mmol), BOC anhydride (1.3 g, 5.9 mmol), $Na_2CO_3$ (0.838 g, 7.90 mmol), acetonitrile (15 mL) and water (7 mL) to afford 0.500 g of desired product. $^1H$ NMR (400 MHz, DMSO $d_6$): δ 1.40 (s, 9H), 6.62 (d, J=8.8 Hz, 1H), 7.83 (dd, J=8.0 Hz, 1H), 8.37 (s, 1H), 8.95 (s, 1H), 9.01 (br s, 1H); MS (m/z): 278.00 (M+Fr).

Intermediate-61 tert-Butyl 2-(6-(trifluoromethyl)pyridin-3-yl)hydrazinecarboxylate

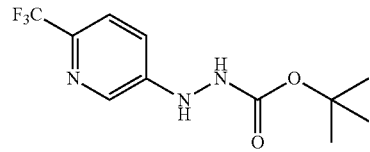 [SMILES: CC(C)(C)OC(=O)NNc1ccc(C(F)(F)F)nc1]

Step-1:—Preparation of 5-hydrazinyl-2-(trifluoromethyl)pyridine

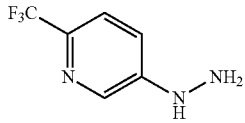 [SMILES: NNc1ccc(C(F)(F)F)nc1]

To a cold solution of 6-(trifluoromethyl)pyridin-3-amine (1.5 g, 9.25 mmol) in 4N Ha (60.0 mL) was added aqueous solution of $NaNO_2$ (0.766 g, 11.11 mmol) at 0° C. The reaction mass was stirred at same temperature for 30 minutes. The reaction mass was added to a solution of $SnCl_2.H_2O$ in 4N HCl at 80° C. and further continued stirring for 5-6 h at same temperature. The reaction mass was cooled, basified and extracted with DCM. The organic layer was dried and concentrated to afford 0.700 g of the product. $^1$H NMR (300 MHz, DMSO $d_6$): δ 4.29 (br s, 2H), 7.18 (dd, J=8.6 Hz, 1H), 7.51 (d, 0.1=8.8 Hz, 1H), 7.68 (s, 1H), 8.13 (d, J=2.4 Hz, 1H); MS (m/z): 178.15 (M+H$^+$).

Step-2:—Preparation of tert-butyl 2-(6-(trifluoromethyl)pyridin-3-yl)hydrazinecarboxylate The title compound was prepared according to the procedure described in step-3 of Intermediate-7 by using 5-hydrazinyl-2-(trifluoromethyl)pyridine (0.700 g, 3.95 mmol), BOC anhydride (1.3 g, 5.9 mmol), $Na_2CO_3$ (0.838 g, 7.90 mmol), acetonitrile (15 mL) and water (7 mL) to afford 0.400 g of desired product. $^1$H NMR (400 MHz, DMSO $d_6$): δ 1.31 (s, 9H), 7.10 (dd, J=8.0 Hz, 1H), 7.64 (d, J=8.6 Hz, 1H), 8.09 (d, 0.1=2.3 Hz, 1H), 8.55 (br s, 1H), 9.08 (br s, 1H); MS (m/z): 278.05 (M+H$^+$).

Intermediate-62 tert-Butyl 2-(4-chlorophenyl)hydrazinecarboxylate

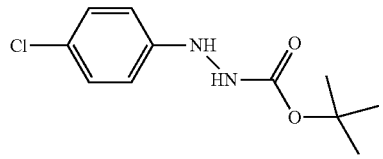 [SMILES: CC(C)(C)OC(=O)NNc1ccc(Cl)cc1]

The title compound was prepared according to the procedure described in step-3 of Intermediate-7 by using (4-chlorophenyl)hydrazine hydrochloride (1.5 g, 10.5 mmol), BOC anhydride (2.7 g, 12.6 mmol), $Na_2CO_3$ (2.23 g, 21.03 mmol), acetonitrile (20 mL) and water (10 mL) to afford 0.900 g of desired product.

Intermediate-63

3-(5-(Aminomethyl)-2-chlorophenyl)-1-(4-(trifluoromethyl)phenyl)-1H-1,2,4-triazol-5(4H)-one

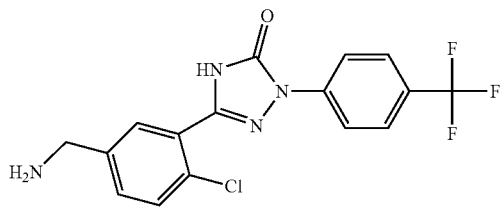 [SMILES: NCc1ccc(Cl)c(-c2nn(-c3ccc(C(F)(F)F)cc3)c(=O)[nH]2)c1]

Step-1:—Preparation of N-(4-chloro-3-(5-oxo-1-(4-(trifluoromethyl)phenyl)-4,5-dihydro-1H-1,2,4-triazol-3-yl)benzyl)-2,2,2-trifluoroacetamide

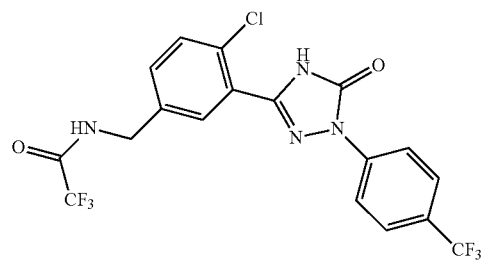 [SMILES: O=C(NCc1ccc(Cl)c(-c2nn(-c3ccc(C(F)(F)F)cc3)c(=O)[nH]2)c1)C(F)(F)F]

To a solution of tert-butyl 2-(4-(trifluoromethyl)phenyl) hydrazinecarboxylate (Intermediate-53, 1.00 g, 3.63 mmol) in DCM (20 mL), 2-chloro-5-((2,2,2-trifluoroacetamido) methyl)benzoyl isocyanate (step-3 of Intermediate-26, 1.30 g, 4.03 mmol) was added and the reaction mass was stirred at RT for 2 h. After completion of reaction, excess of solvent was removed under reduced pressure to obtain 0.700 g of the crude product. To a solution of obtained crude product in DCM (5.0 mL), TFA (5.0 mL) was added and the reaction mass was stirred at RT for 2-3 h. Excess of the solvent was removed from the reaction mass under reduced pressure and the reaction mass was quenched in ice and filtered to obtain 0.700 g of the desired title product. $^1$H NMR (300 MHz, DMSO $d_6$): δ 4.45 (d, 1H), 7.50 (d, J=4.8 Hz, 1H), 7.65-7.68 (m, 2H), 8.85 (d, J=6.6 Hz, 2H), 8.18 (d, J=6.3 Hz, 2H), 10.05 (s, 1H), 12.69 (s, 1H); MS (m/z): 463.17 (M−H)$^−$.

Step-2:—Preparation of 3-(5-(aminomethyl)-2-chlorophenyl)-1-(4-(trifluoromethyl) phenyl)-1H-1,2,4-triazol-5(4H)-one To a solution of N-(4-chloro-3-(5-oxo-1-(4-(trifluoromethyl)phenyl)-4,5-dihydro-1H-1,2,4-triazol-3-yl)benzyl)-2,2,2-trifluoroacetamide (0.400 g, 0.861 mmol) in THF (5.0 mL) was added KOH aqueous solution (0.096 g, 1.72 mmol) and the reaction mass was stirred at RT for 3-4 h. The reaction mass was quenched in water and extracted with ethyl acetate and concentrated to afford 0.200 g of the desired product.

Intermediate-64 tert-Butyl 2-Cyclohexyl hydrazinecarboxylate

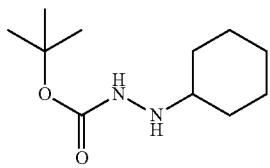

The title compound was prepared according to the procedure described in step-3 of Intermediate-7 by using cyclohexyl hydrazine hydrochloride (1.00 g, 6.6 mmol), BOC anhydride (1.73 g, 7.9 mmol), Na$_2$CO$_3$ (1.75 g, 16.6 mmol), acetonitrile (20 mL) and water (10 mL) to afford 0.500 g of desired product. $^1$H NMR (300 MHz, DMSO d$_6$): δ 0.95-1.02 (m, 2H), 1.07-1.14 (m, 2H), 1.16 (s, 9H), 1.39-1.51 (m, 2H), 1.67-1.98 (m, 2H), 2.61 (m, 1H), 8.16 (br s, 1H), 8.75 (br s, 1H). MS (m/z): 214.79 (M$^+$).

Intermediate-65

3-((2,2,2-Trifluoroacetamido)methyl)-2,6-dimethylbenzoyl isocyanate

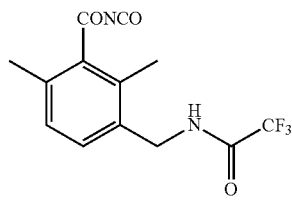

Step-1:—Preparation of 3-((2,2,2-trifluoroacetamido)methyl)-2,6-dimethylbenzoic acid

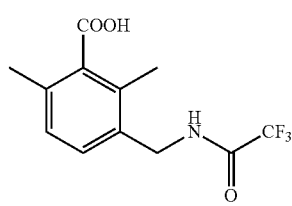 [SMILES: Cc1ccc(CNC(=O)C(F)(F)F)c(C)c1C(=O)O]

To a solution of 2,6-dimethyl benzoic acid (6.8 g, 0.045 mmol) in conc. H$_2$SO$_4$ (100 mL), 2,2,2-trifluoro-N-(hydroxymethyl)acetamide (7.1 g, 0.049 mmol) was added and the reaction mixture was stirred at RT for 24 h. After completion of the reaction, the reaction mass was quenched in ice water and stirred for 15 minutes. The obtained solid product was filtered and dried to afford 7.0 g of the desired title product. $^1$H NMR (300 MHz, DMSO d$_6$): δ 2.26 (s, 6H), 4.36 (t, J=12.3 Hz, 2H), 7.09 (m, 1H), 7.15 (m, 1H), 9.89-9.94 (m, 1H).

Step-2:—Preparation of 3-((2,2,2-trifluoroacetamido)methyl)-2,6-dimethylbenzamide

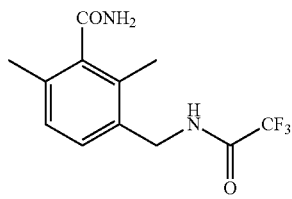 [SMILES: Cc1ccc(CNC(=O)C(F)(F)F)c(C)c1C(N)=O]

The title compound was prepared according to the procedure described in step-2 of Intermediate-26 by using 3-((2,2,2-trifluoroacetamido)methyl)-2,6-dimethylbenzoic acid (1.0 g), oxalyl chloride (1.0 mL), THF (50 mL) and ammonia gas to afford 0.800 g of the desired product.

Step-3:—Preparation of 3-((2,2,2-trifluoroacetamido)methyl)-2,6-dimethylbenzoyl isocyanate The title compound was prepared according to the procedure described in step-2 of Intermediate-8 by using 3-((2,2,2-trifluoroacetamido)methyl)-2,6-dimethylbenzamide (1.0 g, 3.6 mmol), oxalyl chloride and EDC (10 mL) to afford 0.900 g of the desired product.

Intermediate-66

5-(3-(Aminomethyl)-2,6-dimethylphenyl)-2-(4-(trifluoromethyl)phenyl)-2H-1,2,4-triazol-3(4H)-one

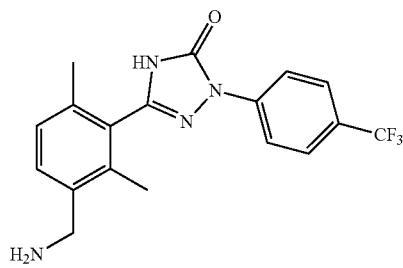 [SMILES: Cc1ccc(CN)c(C)c1-c1nn(-c2ccc(C(F)(F)F)cc2)c(=O)[nH]1]

To a solution of N-(3-(1-(4-(trifluoromethyl)phenyl)-4,5-dihydro-5-oxo-1H-1,2,4-triazol-3-yl)-2,4-dimethylbenzyl)-2,2,2-trifluoroacetamide (Example-106, 0.800 g, 1.74 mmol) in THF (10 mL), aqueous solution of KOH was added and the reaction mass was stirred at RT for 3-4 h. After completion of the reaction, the reaction mass was quenched with water and extracted with ethyl acetate. The organic layer was separated, dried over anhydrous sodium sulphate and concentrated to afford 0.200 g of the desired product. MS (m/z): 362.86 (M+H)$^+$.

Intermediate-67

4-Iodobenzoyl isocyanate

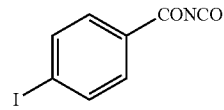

The title compound was prepared according to the procedures described in step-2 and step-3 of Intermediate-26 by using 4-iodo benzoic acid (2.0 g), oxalyl chloride (1.0 ml), ammonia gas, DCM (20 mL), THF (20 mL) to afford 1.5 g of the desired product. $^1$H NMR (400 MHz, DMSO d$_6$): δ 7.17 (br s, 1H), 7.64 (d, 2H), 8.01 (s, 2H); MS (m/z): 461.14 (M+H)$^+$.

Intermediate-68

N-(4-Chloro-2-fluoro-3-(4,5-dihydro-3-(4-iodophenyl)-5-oxo-1,2,4-triazol-1-yl)benzyl)pivalamide

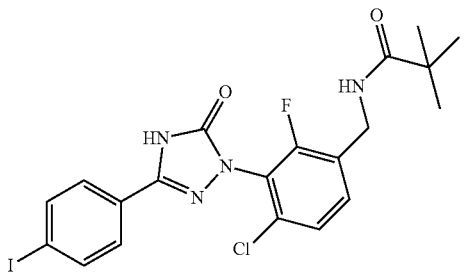 [SMILES: CC(C)(C)C(=O)NCc1ccc(Cl)c(-n2nc(-c3ccc(I)cc3)[nH]c2=O)c1F]

The title compound was prepared according to the procedure described in Example-83 by using tert-butyl 2-(6-chloro-2-fluoro-3-(pivalamidomethyl)phenyl)hydrazinecarboxylate (Intermediate-57, 0.250 g), 4-iodobenzoyl isocyanate (Intermediate-67, 0.250 g), DCM (10 mL) and trifluoro acetic acid (0.5 mL) to afford 0.150 g of the desired product. $^1$H NMR (400 MHz, DMSO d$_6$): δ 1.19 (s, 9H), 4.30 (d, J=3.3 Hz, 2H), 7.39 (m, 1H), 7.45 (d, 1H), 7.62 (d, 2H), 7.90 (d, J=3.6 Hz, 2H), 8.19 (t, 1H), 13.0 (br s, 1H); MS (m/z): 528.98 (M+H)$^+$.

Intermediate-69

5-((2,2,2-Trifluoroacetamido)methyl)-2-chloro-4-fluorobenzoyl isocyanate

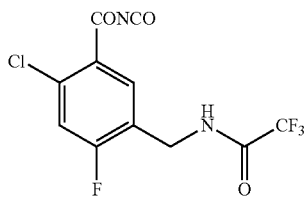

Step-1:—Preparation of 5-((2,2,2-trifluoroacetamido)methyl)-2-chloro-4-fluorobenzoic acid

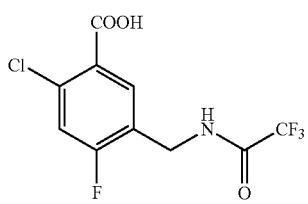 [SMILES: O=C(O)c1cc(CNC(=O)C(F)(F)F)c(F)cc1Cl]

The title compound was prepared according to the procedure described in step-1 of Intermediate-26 by using 2-chloro-4-fluorobenzoic acid (5.0 g, 0.002 mmol), 2,2,2-trifluoro-N-(hydroxymethyl)acetamide (4.0 g, 0.002 mmol) and conc. H$_2$SO$_4$ (50 mL) to afford 4.0 g of the desired product. $^1$H NMR (400 MHz, DMSO d$_6$): δ 4.44 (d, J=12.0 Hz, 2H), 7.59 (m, 1H), 7.92 (m, 1H), 10.0 (br s, 1H), 13.5 (br s, 1H).

Step-2:—Preparation of 5-((2,2,2-trifluoroacetamido)methyl)-2-chloro-4-fluorobenzamide

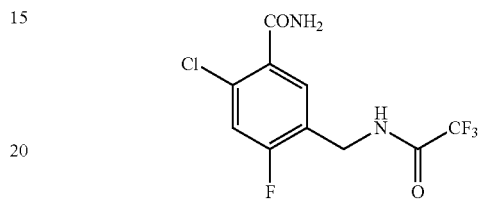

The title compound was prepared according to the procedure described in step-2 of Intermediate-26 by using 5-((2,2,2-trifluoroacetamido)methyl)-2-chloro-4-fluorobenzoic acid (1.0 g), oxalyl chloride (1.0 mL), THF (50 mL) and ammonia gas to afford 0.800 g of the desired product. $^1$H NMR (400 MHz, DMSO d$_6$): δ 4.53 (m, 2H), 7.43 (m, 1H) 7.44 (m, 2H), 7.48 (m, 1H), 10.0 (br s, 1H)); MS (m/z): 297.10 (M−H)$^-$.

Step-3:—Preparation of 5-((2,2,2-trifluoroacetamido)methyl)-2-chloro-4-fluorobenzoyl isocyanate The title compound was prepared according to the procedure described in step-2 of Intermediate-8 by using 5-((2,2,2-trifluoroacetamido)methyl)-2-chloro-4-fluorobenzamide (1.0 g, 3.6 mmol), oxalyl chloride (1.0 mL) and EDC (10 mL) to afford 0.750 g of the desired product.

Intermediate-70

5-(5-(Aminomethyl)-2-chloro-4-fluorophenyl)-2-(4-(trifluoromethyl)phenyl)-2H-1,2,4-triazol-3(4H)-one

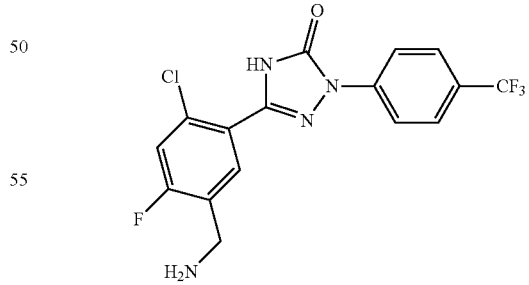

The title compound was prepared according to the procedure described in Intermediate-66 by using N-(4-chloro-2-fluoro-5-(1-(4-(trifluoromethyl)phenyl)-4,5-dihydro-5-oxo-1H-1,2,4-triazol-3-yl)benzyl)-2,2,2-trifluoroacetamide (Example-113; 0.100 g, 0.207 mmol), KOH (0.034 g, 0.622 mol), water (5 mL) and THF (5.0 mL) to afford 0.080 g of the desired product.

Intermediate-71 tert-Butyl 2-(4-chloro-3-fluorophenyl)hydrazinecarboxylate

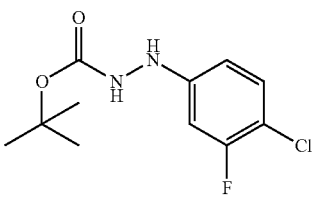 [SMILES: CC(C)(C)OC(=O)NNc1ccc(Cl)c(F)c1]

The title compound was prepared according to the procedure described in step-3 of Intermediate-7 by using 4-chloro3-fluoro phenylhydrazine hydrochloride (1.00 g), BOC anhydride (1.5 g), Na$_2$CO$_3$ (0.900 g, 8.5 mmol), acetonitrile (20 mL) and water (10 mL) to afford 0.600 g of the desired product.

Intermediate-72

4,4-Dimethyl tert-butyl 2-cyclohexyl hydrazinecarboxylate

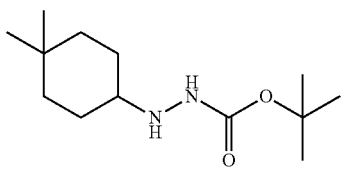 [SMILES: CC1(C)CCC(NNC(=O)OC(C)(C)C)CC1]

The title compound was prepared according to the procedure described in step-3 of Intermediate-7 by using 4,4-dimethylcyclohexylhydrazine hydrochloride (1.00 g), BOC anhydride (1.5 g), Na$_2$CO$_3$ (0.900 g, 8.5 mmol), acetonitrile (20 mL) and water (10 mL) to afford 0.600 g of the desired product.

Intermediate-73

5-(5-(Aminomethyl)-2-chlorophenyl)-2-(4,4-dimethylcyclohexyl)-2H-1,2,4-triazol-3(4H)-one

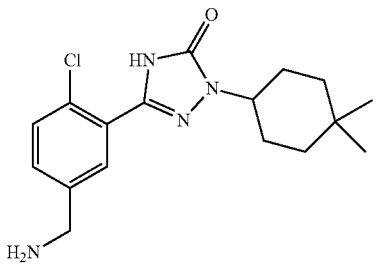 [SMILES: CC1(C)CCC(n2nc(-c3cc(CN)ccc3Cl)[nH]c2=O)CC1]

The title compound was prepared according to the procedure described in Intermediate-66 by using N-(4-chloro-3-(4,5-dihydro-1-(4,4-dimethylcyclohexyl)-5-oxo-1H-1,2,4-triazol-3-yl)benzyl)-2,2,2-trifluoroacetamide (Example-117, 0.150 g, 0.348 mmol), KOH (0.039 g, 0.696 mol), water (2 mL) and THF (5.0 mL) to afford 0.100 g of the desired product.

Intermediate-74 tert-Butyl 2-tert-butylhydrazinecarboxylate

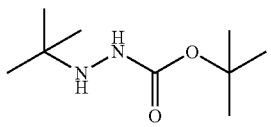

The title compound was prepared according to the procedure described in step-3 of Intermediate-7 by using tert-butylhydrazine (1.00 g), BOC anhydride (1.5 g), Na$_2$CO$_3$ (0.900 g, 8.5 mmol), acetonitrile (20 mL) and water (10 mL) to afford 0.600 g of the desired product.

Intermediate-75

2-tert-Butyl-5-(5-(aminomethyl)-2-chlorophenyl)-2H-1,2,4-triazol-3(4H)-one

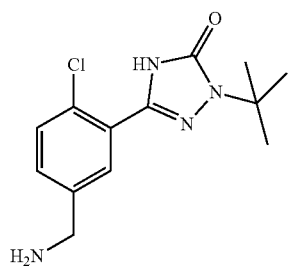 [SMILES: CC(C)(C)n1nc(-c2cc(CN)ccc2Cl)[nH]c1=O]

The title compound was prepared according to the procedure described in Intermediate-66 by using N-(3-(1-tert-butyl-4,5-dihydro-5-oxo-1H-1,2,4-triazol-3-yl)-4-chlorobenzyl)-2,2,2-trifluoroacetamide (Example-120, 0.400 g, 1.062 mmol), KOH (0.119 g, 2.12 mmol), water (5 mL) and THF (5.0 mL) to afford 0.300 g of the desired product.

Intermediate-76

5-(5-(Aminomethyl)-2-chlorophenyl)-2-(4-chloro-3-fluorophenyl)-2H-1,2,4-triazol-3(4H)-one

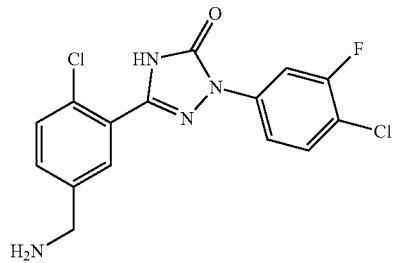 [SMILES: NCc1ccc(Cl)c(-c2nn(-c3ccc(Cl)c(F)c3)c(=O)[nH]2)c1]

The title compound was prepared according to the procedure described in Intermediate-66 by using N-(4-chloro-3-(1-(4-chloro-3-fluorophenyl)-4,5-dihydro-5-oxo-1H-1,2,4-triazol-3-yl)benzyl)-2,2,2-trifluoroacetamide (Example-116, 0.400 g, 0.890 mmol), KOH (0.099 g, 1.78 mmol), water (2 mL) and THF (4.0 mL) to afford 0.300 g of the desired product.

Intermediate-77

5-(5-(Aminomethyl)-2-chloro-4-fluorophenyl)-2-(4,4-dimethylcyclohexyl)-2H-1,2,4-triazol-3(4H)-one

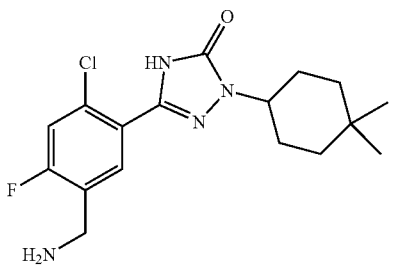 [SMILES: CC1(C)CCC(n2nc(-c3cc(CN)c(F)cc3Cl)[nH]c2=O)CC1]

The title compound was prepared according to the procedure described in Intermediate-66 by using N-(4-chloro-2-fluoro-5-(4,5-dihydro-1-(4,4-dimethylcyclohexyl)-5-oxo-1H-1,2,4-triazol-3-yl)benzyl)-2,2,2-trifluoroacetamide (Example-124, 1.0 g), KOH (1.0 g), water (5 mL) and THF (40.0 mL) to afford 0.700 g of the desired product.

Intermediate-78

5-(5-(Aminomethyl)-2-chloro-4-fluorophenyl)-2-(4-chlorophenyl)-2H-1,2,4-triazol-3(4H)-one

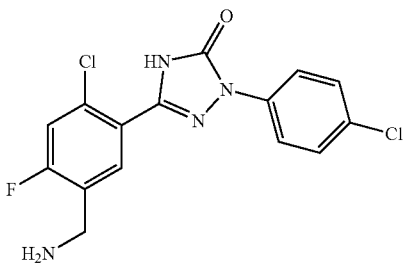 [SMILES: NCc1cc(-c2nn(-c3ccc(Cl)cc3)c(=O)[nH]2)c(Cl)cc1F]

Step-1:—Preparation of N-(4-chloro-5-(1-(4-chlorophenyl)-4,5-dihydro-5-oxo-1H-1,2,4-triazol-3-yl)-2-fluorobenzyl)-2,2,2-trifluoroacetamide

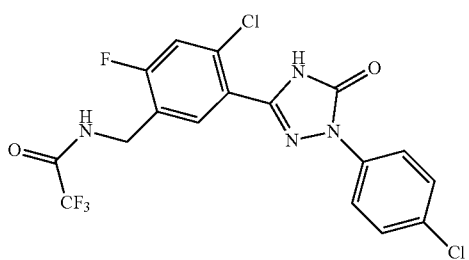 [SMILES: O=C(NCc1cc(-c2nn(-c3ccc(Cl)cc3)c(=O)[nH]2)c(Cl)cc1F)C(F)(F)F]

The title compound was prepared according to the procedure described in Example-83 by using 5-((2,2,2-trifluoroacetamido)methyl)-2-chloro-4-fluorobenzoyl isocyanate (Intermediate-69, 0.400 g), tert-butyl 2-(4-chlorophenyl)hydrazinecarboxylate (Intermediate-62, 0.400 g), DCM (20 mL) and trifluoro acetic acid (5.0 mL) to afford 0.250 g of the desired product.

Step-2:—Preparation of 5-(5-(aminomethyl)-2-chloro-4-fluorophenyl)-2-(4-chlorophenyl)-2H-1,2,4-triazol-3(4H)-one The title compound was prepared according to the procedure described in Intermediate-66 by using N-(4-chloro-5-(1-(4-chlorophenyl)-4,5-dihydro-5-oxo-1H-1,2,4-triazol-3-yl)-2-fluorobenzyl)-2,2,2-trifluoroacetamide (0.160 g), KOH (0.050 g), water (2 mL) and THF (10.0 mL) to afford 0.070 g of the desired product.

Intermediate-79

5-(5-(Aminomethyl)-2-chloro-4-methoxyphenyl)-2-(4-(trifluoromethyl)phenyl)-2H-1,2,4-triazol-3(4H)-one

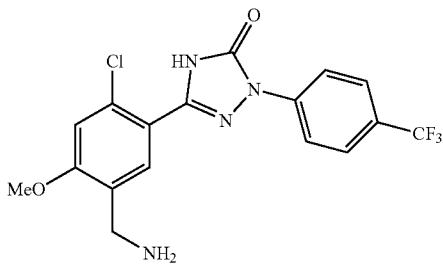 [SMILES: COc1cc(Cl)c(-c2nn(-c3ccc(C(F)(F)F)cc3)c(=O)[nH]2)cc1CN]

Step-1:—Preparation of 5-((2,2,2-trifluoroacetamido)methyl)-2-chloro-4-methoxybenzoic acid

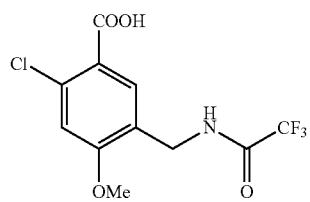 [SMILES: COc1cc(Cl)c(C(=O)O)cc1CNC(=O)C(F)(F)F]

The title compound was prepared according to the procedure described in step-1 of Intermediate-26 by using 2-chloro-4-methoxybenzoic acid (0.060 g), 2,2,2-trifluoro-N-(hydroxymethyl)acetamide (0.050 g) and $H_2SO_4$ (2 mL) to afford 0.040 g of the desired product.

Step-2:—Preparation of 5-((2,2,2-trifluoroacet-amido)methyl)-2-chloro-4-methoxybenzamide

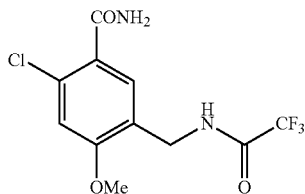 [SMILES: COc1cc(Cl)c(C(N)=O)cc1CNC(=O)C(F)(F)F]

The title compound was prepared according to the procedure described in step-2 of Intermediate-26 by using 5-((2,2,2-trifluoroacetamido)methyl)-2-chloro-4-methoxybenzoic acid (1.0 g), oxalyl chloride (1.0 mL), THF (50 mL) and ammonia gas to afford 0.800 g of the desired product.

Step-3:—Preparation of 5-((2,2,2-trifluoroacet-amido)methyl)-2-chloro-4-methoxybenzoyl isocyanate

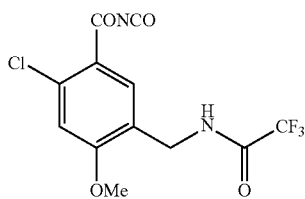

The title compound was prepared according to the procedure described in step-2 of Intermediate-8 by using 5-((2,2,2-trifluoroacetamido)methyl)-2-chloro-4-methoxybenzamide (1.0 g, 3.6 mmol), oxalyl chloride (1.0 mL) and EDC (10 mL) to afford 0.750 g of the desired product.

Step-4:—Preparation of N-(4-chloro-5-(1-(4-(trifluoromethyl)phenyl)-4,5-dihydro-5-oxo-1H-1,2,4-triazol-3-yl)-2-methoxybenzyl)-2,2,2-trifluoroacetamide

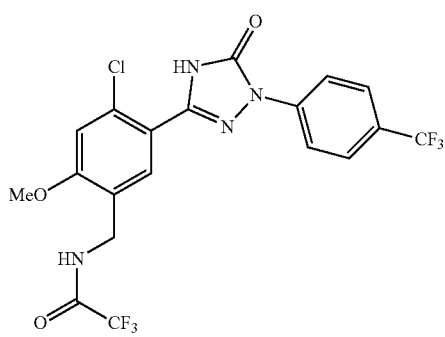 [SMILES: COc1cc(Cl)c(-c2nn(-c3ccc(C(F)(F)F)cc3)c(=O)[nH]2)cc1CNC(=O)C(F)(F)F]

The title compound was prepared according to the procedure described in Example-83 by using 5-((2,2,2-trifluoroacetamido)methyl)-2-chloro-4-methoxybenzoyl isocyanate (0.500 g), tert-butyl 2-(4-(trifluoromethyl)phenyl) hydrazinecarboxylate (Intermediate-53, 0.450 g), DCM (20 mL), and trifluoro acetic acid (5.0 mL) to afford 0.180 g of the desired product.

Step-5:—Preparation of 5-(5-(aminomethyl)-2-chloro-4-methoxyphenyl)-2-(4-(trifluoromethyl)phenyl)-2H-1,2,4-triazol-3(4H)-one The title compound was prepared according to the procedure described in Intermediate-66 by using N-(4-chloro-5-(1-(4-(trifluoromethyl)phenyl)-4,5-dihydro-5-oxo-1H-1,2,4-triazol-3-yl)-2-methoxybenzyl)-2,2,2-trifluoroacetamide (0.200 g), water (5 mL), KOH (0.200 g) and THF (10.0 mL) to afford 0.150 g of the desired product.

Intermediate-80 tert-Butyl 2-[4-fluoro-3-(trifluoromethyl)phenyl] hydrazinecarboxylate

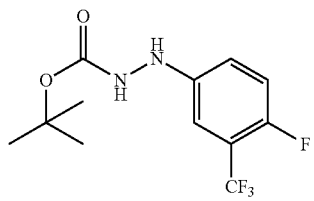 [SMILES: CC(C)(C)OC(=O)NNc1ccc(F)c(C(F)(F)F)c1]

Step 1:—Preparation of 1-(4-fluoro-3-(trifluoromethyl)phenyl)hydrazine

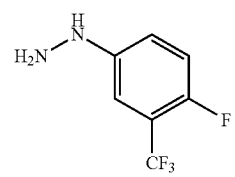 [SMILES: NNc1ccc(F)c(C(F)(F)F)c1]

The title compound was prepared according to the procedure described in step-1 of Intermediate-61 by using 4-fluoro-3-(trifluoromethyl)aniline (3.0 g, 0.016 mmol), NaNO$_2$ (1.73 g, 0.025 mmol), SnCl$_2$.2H$_2$O (9.39 g, 0.041 mmol) and conc. HCl (100 mL) to afford 2.0 g of the desired product.

Step-2:—Preparation of tert-butyl 2-[4-fluoro-3-(trifluoromethyl)phenyl]hydrazinecarboxylate The title compound was prepared according to the procedure described in step-3 of Intermediate-7 by using 1-(4-fluoro-3-(trifluoromethyl)phenyl)hydrazine (1.00 g), BOC anhydride (1.5 g), Na$_2$CO$_3$ (0.900 g, 8.5 mmol), acetonitrile (20 mL) and water (10 mL) to afford 0.600 g of the desired product. $^1$H NMR (300 MHz, CDCl$_3$): δ 1.40 (s, 9H), 6.86-6.94 (m, 2H), 7.26-7.32 (m, 1H), 7.98 (s, 1H), 8.95 (s, 1H); MS (m/z): 436.55 (M$^+$H)$^+$.

125

Intermediate-81

5-(5-(Aminomethyl)-2-chloro-4-fluorophenyl)-2-(4-fluoro-3-(trifluoromethyl)phenyl)-2H-1,2,4-triazol-3(4H)-one

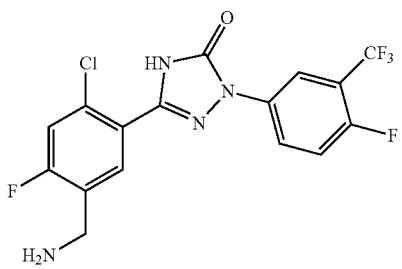 [SMILES: NCc1cc(-c2nn(-c3ccc(F)c(C(F)(F)F)c3)c(=O)[nH]2)c(Cl)cc1F]

Step-1:—Preparation of N-(4-chloro-2-fluoro-5-(1-(4-fluoro-3-(trifluoromethyl)phenyl)-4,5-dihydro-5-oxo-1H-1,2,4-triazol-3-yl)benzyl)-2,2,2-trifluoroacetamide

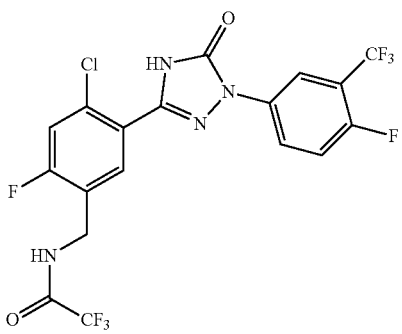 [SMILES: O=C(NCc1cc(-c2nn(-c3ccc(F)c(C(F)(F)F)c3)c(=O)[nH]2)c(Cl)cc1F)C(F)(F)F]

The title compound was prepared according to the procedure described in Example-83 by using 5-((2,2,2-trifluoroacetamido)methyl)-2-chloro-4-fluorobenzoyl isocyanate (Intermediate-69, 0.400 g), tert-butyl 2-[4-fluoro-3-(trifluoromethyl)phenyl]hydrazinecarboxylate (Intermediate-80, 0.400 g), DCM (20 mL) and TFA (5.0 mL) to afford 0.200 g of the desired product.

Step-2:—Preparation of 5-(5-(aminomethyl)-2-chloro-4-fluorophenyl)-2-(4-fluoro-3-(trifluoromethyl)phenyl)-2H-1,2,4-triazol-3(4H)-one The title compound was prepared according to the procedure described in Intermediate-66 by using N-(4-chloro-3-(1-(4-fluoro-3-(trifluoromethylphenyl)-4,5-dihydro-5-oxo-1H-1,2,4-triazol-3-yl)benzyl)-2,2,2-trifluoroacetamide (0.400 g), KOH (0.100 g) and THF (10.0 mL) to afford 0.150 g of desired product.

126

Intermediate-82

5-(5-(Aminomethyl)-2-chloro-4-fluorophenyl)-2-(6-(trifluoromethyl)pyridin-3-yl)-2H-1,2,4-triazol-3(4H)-one

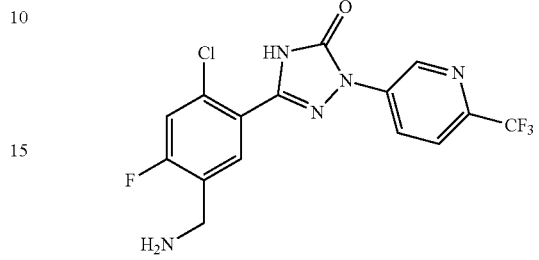

Step-1:—Preparation of N-(4-chloro-2-fluoro-5-(1-(6-(trifluoromethyl)pyridin-3-yl)-4,5-dihydro-5-oxo-1H-1,2,4-triazol-3-yl)benzyl)-2,2,2-trifluoroacetamide

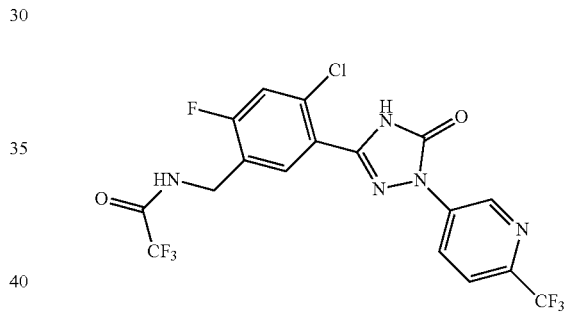

The title compound was prepared according to the procedure described in Example-83 by using 5-((2,2,2-trifluoroacetamido)methyl)-2-chloro-4-fluorobenzoyl isocyanate (Intermediate-69, 0.350 g), tert-butyl 2-[6-(trifluoromethyl)pyridin-3-yl]hydrazinecarboxylate (Intermediate-61, 0.350 g), DCM (20 mL) and TFA (5.0 mL) to afford 0.250 g of the desired product.

Step-2:—Preparation of 5-(5-(aminomethyl)-2-chloro-4-fluorophenyl)-2-(6-(trifluoromethyl)pyridin-3-yl)-2H-1,2,4-triazol-3(4H)-one The title compound was prepared according to the procedure described in Intermediate-66 by using N-(4-chloro-2-fluoro-5-(1-(6-(trifluoromethyl)pyridin-3-yl)-4,5-dihydro-5-oxo-1H-1,2,4-triazol-3-yl)benzyl)-2,2,2-trifluoroacetamide (0.500 g), KOH (0.200 g), water (5 mL) and THF (10.0 mL) to afford 0.150 g of desired product.

Intermediate-83 tert-Butyl 2-(2,4-dichloro-5-{[(2,2-dimethylpropanoyl)amino]methyl}phenyl) hydrazinecarboxylate

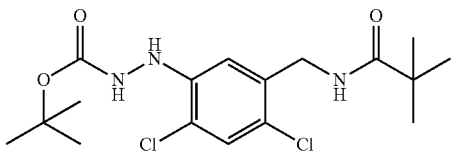 [SMILES: CC(C)(C)OC(=O)NNc1cc(CNC(=O)C(C)(C)C)c(Cl)cc1Cl]

Step-1:—Preparation of 2-(aminomethyl)-5-chloro-4-nitrobenzenamine

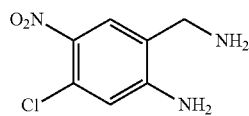 [SMILES: NCc1cc([N+](=O)[O-])c(Cl)cc1N]

To a solution of 2-amino-4-chloro-5-nitrobenzamide (3.0 g, 13.7 mmol) in dry THF (50 mL), borane dimethyl sulphide complex (1.56 g, 20.6 mmol) was added at RT and the reaction mass was refluxed for 24 h. The reaction mass was cooled to RT and dilute HCl was added till it became acidic. Further, the reaction mixture was stirred for 1 h and then the reaction mixture was basified with dilute NaOH and extracted with ethyl acetate. The organic layer was separated, dried over anhydrous sodium sulphate and concentrated to afford 2.0 g of the desired product. $^1$H NMR (300 MHz, DMSO d$_6$): δ 3.58 (s, 2H), 6.72 (br s, 3H), 8.04 (br s, 1H); MS (adz): 200.28 (M–H).

Step-2:—Preparation of N-(2-amino-4-chloro-5-nitrobenzyl)pivalamide

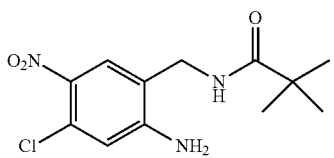 [SMILES: CC(C)(C)C(=O)NCc1cc([N+](=O)[O-])c(Cl)cc1N]

To a solution of 2-(aminomethyl)-5-chloro-4-nitrobenzenamine (2.5 g, 12.25 mmol) in THF (35 mL), TEA (3.0 mL) and pivaloyl chloride (1.96 mL, 14.7 mmol) were added and the reaction mass was stirred at RT for 5 h. The reaction mass was quenched with water and extracted with ethyl acetate. The organic layer was washed with dilute HCl and dilute sodium bicarbonate solution, separated, dried over anhydrous sodium sulphate and concentrated to afford 2.0 of the desired product. $^1$H NMR (300 MHz, DMSO d$_6$): δ 1.12 (s, 9H), 4.30 (d, J=5.4 Hz, 2H), 7.81 (d, J=9.9 Hz, 1H), 7.96 (d, J=6.3 Hz, 1H), 8.21 (m, 1H).

Step 3:—Preparation of N-(2,5-diamino-4-chlorobenzyl)pivalamide

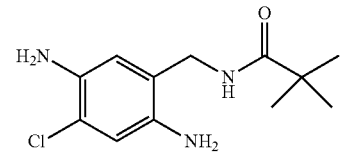

To a solution of N-(2-amino-4-chloro-5-nitrobenzyl)pivalamide (2.0 g, 6.9 mmol) in methanol (20 mL), Raney Ni (2.0 g) and hydrazine hydrate (5.0 mL) were added and the reaction mass was stirred at RT for 3 h. After the completion of the reaction, the reaction mass was filtered through celite pad and obtained filtrated was concentrated to afford 1.5 g of the desired product. $^1$H NMR (300 MHz, DMSO d$_6$): δ 1.11 (s, 9H), 3.97 (br d, 2H), 4.52 (br d, 2H), 5.44 (br s, 2H), 6.50 (d, J=11.4 Hz, 2H), 7.88 (m, 1H).

Step-4:—Preparation of N-(2,4-dichloro-5-hydrazinylbenzyl)-2,2-dimethylpropanamide

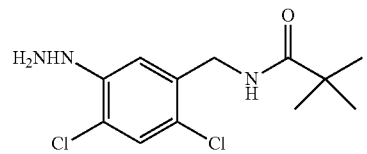

The title compound was prepared according to the procedure described in step-1 of Intermediate-61 by using N-(2,5-diamino-4-chlorobenzyl)pivalamide (1.5 g, 5.8 mmol), NaNO$_2$ (0.481 g, 6.9 mmol), SnCl$_2$.2H$_2$O (3.20 g, 14.5 mmol), conc. HCl (50 mL) to afford 1.0 g of the desired product. $^1$H NMR (300 MHz, DMSO d$_6$): δ 1.11 (s, 9H), 4.44 (m, 2H), 6.53 (m, 1H), 7.18 (m, 114), 7.99 (m, 114), 10.23 (s, 1H).

Step-5:—Preparation of tert-butyl 2-(2,4-dichloro-5-{[(2,2-dimethylpropanoyl) amino]methyl}phenyl) hydrazinecarboxylate The title compound was prepared according to the procedure described in step-3 of Intermediate-7 by using N-(2,4-dichloro-5-hydrazinylbenzyl)-2,2-dimethylpropanamide (1.0 g, 3.6 mmol), BOC anhydride (0.958 g, 4.39 mmol), Na$_2$CO$_3$ (0.776 g, 7.32 mmol), acetonitrile (10 mL) and water (5 mL) to afford 0.500 g of the desired product.

129

Intermediate-84

N-(2,4-Dichloro-5-(4,5-dihydro-3-(4-iodophenyl)-5-oxo-1,2,4-triazol-1-yl)benzyl)pivalamide

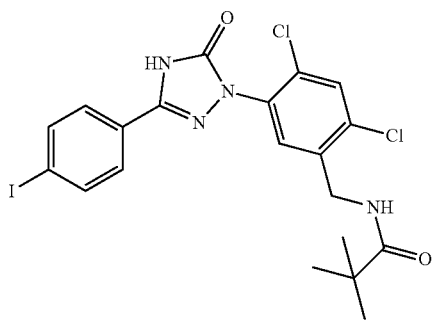 [SMILES: CC(C)(C)C(=O)NCc1cc(-n2nc(-c3ccc(I)cc3)[nH]c2=O)c(Cl)cc1Cl]

The title compound was prepared according to the procedure described in Example-83 by using 4-iodobenzoyl isocyanate (Intermediate-67, 0.300 g, 0.800 mmol), tert-butyl 2-(2,4-dichloro-5-{[(2,2-dimethylpropanoyl)amino]methyl}phenyl)hydrazine carboxylate (Intermediate-83, 0.397 g, 1.6 mmol), DCM (20 mL), trifluoro acetic acid (5.0 mL) to afford 0.150 g of the desired product. $^1$H NMR (300 MHz, DMSO d$_6$): δ 1.09 (s, 9H), 4.31 (d, J=4.2 Hz, 2H), 7.40-7.58 (m, 2H), 7.61-7.78 (m, 2H), 7.93-8.02 (br d, 2H), 8.17 (m, 1H).

Intermediate-85 tert-Butyl 2-(3-chloro-4-fluorophenyl)hydrazinecarboxylate

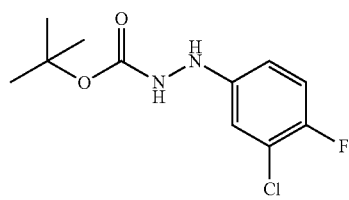 [SMILES: CC(C)(C)OC(=O)NNc1ccc(F)c(Cl)c1]

The title compound was prepared according to the procedure described in step-3 of Intermediate-7 by using 1-(3-chloro-4-fluorophenyl)hydrazine (3.0 g, 0.015 mmol), BOC anhydride (3.6 g, 0.16 mmol), Na$_2$CO$_3$ (2.40 g, 0.022 mmol), acetonitrile (30 mL) and water (5 mL) to afford 1.3 g of the desired product. $^1$H NMR (300 MHz, CDCl$_3$): δ 1.38 (s, 9H), 6.60 (m, 1H), 6.67 (m, 1H), 7.13-7.20 (m, 1H), 7.77 (s, 1H), 8.85 (s, 1H).

130

Intermediate-86

5-(5-(Aminomethyl)-2-chloro-4-fluorophenyl)-2-(3-Chloro-4-fluorophenyl)-2H-1,2,4-triazol-3(4H)-one

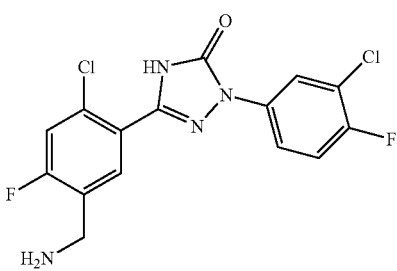

Step-1:—Preparation of N-(4-chloro-5-(1-(3-chloro-4-fluorophenyl)-4,5-dihydro-5-oxo-1H-1,2,4-triazol-3-yl)-2-fluorobenzyl)-2,2,2-trifluoroacetamide

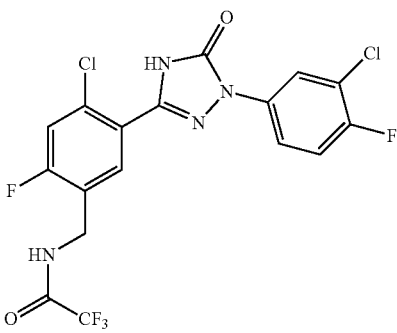 [SMILES: O=C(NCc1cc(-c2nn(-c3ccc(F)c(Cl)c3)c(=O)[nH]2)c(Cl)cc1F)C(F)(F)F]

The title compound was prepared according to the procedure described in Example-83 by using 5-((2,2,2-trifluoroacetamido)methyl)-2-chloro-4-fluorobenzoyl isocyanate (Intermediate-69, 0.300 g), tert-butyl 2-(3-chloro-4-fluorophenyl)hydrazinecarboxylate (Intermediate-85, 0.300 g), DCM (20 mL) and trifluoro acetic acid (5.0 mL) to afford 0.200 g of the desired product.

Step-2:—Preparation of 5-(5-(aminomethyl)-2-chloro-4-fluorophenyl)-2-(3-chloro-4-fluorophenyl)-2H-1,2,4-triazol-3(4H)-one The title compound was prepared according to the procedure described in Intermediate-66 by using N-(4-chloro-5-(1-(3-chloro-4-fluorophenyl)-4,5-dihydro-5-oxo-1H-1,2,4-triazol-3-yl)-2-fluorobenzyl)-2,2,2-trifluoroacetamide (0.300 g), KOH (0.100 g), water (2 ml) and THF (10.0 mL) to afford 0.100 g of the desired product.

Intermediate-87 tert-Butyl 2-(3-chloro-4-methylphenyl)hydrazinecarboxylate

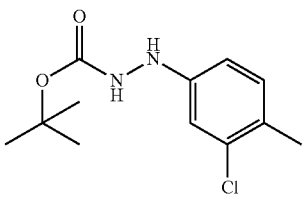 [SMILES: Cc1ccc(NNC(=O)OC(C)(C)C)cc1Cl]

Step-1:—Preparation of 1-(3-chloro-4-methylphenyl)hydrazine

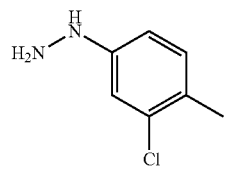

The title compound was prepared according to the procedure described in step-1 of Intermediate-61 by using 3-chloro-4-methylaniline (6.0 g, 0.0420 mmol), NaNO$_2$ (8.56 g, 0.050 mmol), SnCl$_2$.2H$_2$O (23.7 g, 0.105 mmol) and conc. HCl (100 mL) to afford 4.5 g of the desired product.

Step-2:—Preparation of tert-butyl 2-(3-chloro-4-methylphenyl)hydrazine carboxylate The title compound was prepared according to the procedure described in step-3 of Intermediate-7 by using 1-(3-chloro-4-methylphenyl)hydrazine (4.5 g, 0.028 mmol), BOC anhydride (6.8 g, 0.032 mmol), Na$_2$CO$_3$ (4.50 g, 0.041 mmol), acetonitrile (30 mL) and water (5 mL) to afford 1.300 g of the desired product. $^1$H NMR (300 MHz, DMSO d$_6$): δ 1.40 (s, 9H), 2.17 (s, 3H), 6.53 (d, J=10.4 Hz, 1H), 6.63 (s, 1H), 7.08 (d, J=10.82 Hz, 1H), 7.67 (s, 1H), 8.80 (s, 1H).

Intermediate-88

5-(5-(Aminomethyl)-2-chloro-4-fluorophenyl)-2-(3-chloro-4-methylphenyl)-2H-1,2,4-triazol-3(4H)-one

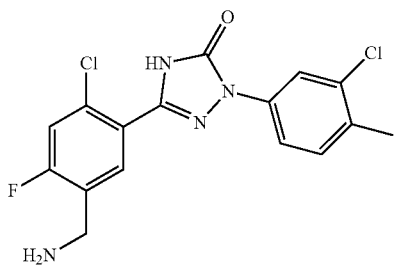 [SMILES: Cc1ccc(-n2nc(-c3cc(CN)c(F)cc3Cl)[nH]c2=O)cc1Cl]

Step-1:—Preparation of N-(4-chloro-5-(1-(3-chloro-4-methylphenyl)-4,5-dihydro-5-oxo-1H-1,2,4-triazol-3-yl)-2-fluorobenzyl)-2,2,2-trifluoroacetamide

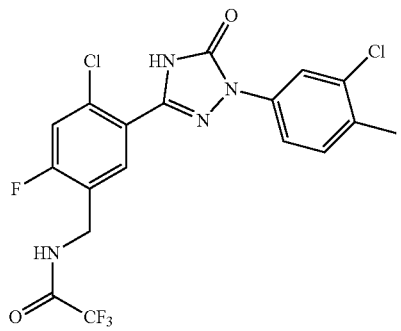 [SMILES: Cc1ccc(-n2nc(-c3cc(CNC(=O)C(F)(F)F)c(F)cc3Cl)[nH]c2=O)cc1Cl]

The title compound was prepared according to the procedure described in Example-83 by using 5-((2,2,2-trifluoroacetamido)methyl)-2-chloro-4-fluorobenzoyl isocyanate (Intermediate-69, 0.300 g), tert-butyl 2-(3-chloro-4-methylphenyl)hydrazinecarboxylate (Intermediate-87, 0.300 g), DCM (20 mL) and trifluoro acetic acid (5.0 mL) to afford 0.200 g of the desired product.

Step-2:—Preparation of 5-(5-(aminomethyl)-2-chloro-4-fluorophenyl)-2-(3-chloro-4-fluorophenyl)-2H-1,2,4-triazol-3(4H)-one The title compound was prepared according to the procedure described in Intermediate-66 by using N-(4-chloro-5-(1-(3-chloro-4-methylphenyl)-4,5-dihydro-5-oxo-1H-1,2,4-triazol-3-yl)-2-fluorobenzyl)-2,2,2-trifluoroacetamide (0.300 g), KOH (0.100 g), water (2 mL) and THF (10.0 mL) to afford 0.200 g of the desired product.

Intermediate-89 tert-Butyl 2-(2-chloro-4-fluoro-5-{[(trifluoroacetyl)amino]methyl}phenyl)hydrazinecarboxylate

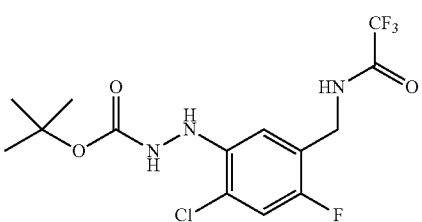 [SMILES: CC(C)(C)OC(=O)NNc1cc(CNC(=O)C(F)(F)F)c(F)cc1Cl]

Step-1:—Preparation of N-(5-amino-4-chloro-2-fluorobenzyl)-2,2,2-trifluoroacetamide

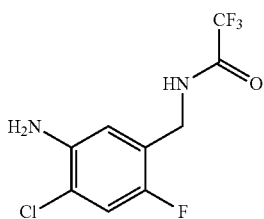 [SMILES: Nc1cc(CNC(=O)C(F)(F)F)c(F)cc1Cl]

The title compound was prepared according to the procedure described in step-1 of Intermediate-57 by using 5-((2,2,2-trifluoroacetamido)methyl)-2-chloro-4-fluorobenzoic acid (3.0 g), conc. H$_2$SO$_4$ and sodium azide (0.793 g, 0.012 mmol) to afford 2.1 g of the desired product.

Step-2:—Preparation of N-(4-chloro-2-fluoro-5-hydrazinylbenzyl)-2,2,2-trifluoroacetamide

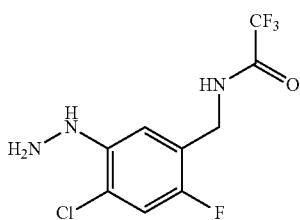 [SMILES: NNc1cc(CNC(=O)C(F)(F)F)c(F)cc1Cl]

The title compound was prepared according to the procedure described in step-1 of Intermediate-61 by using N-(5-amino-4-chloro-2-fluorobenzyl)-2,2,2-trifluoroacetamide (2.0 g, 0.007 mmol), NaNO$_2$ (0.612 g, 0.008 mmol), SnCl$_2$.2H$_2$O (4.10 g, 0.018 mmol), and conc. HCl (100 mL) to afford 1.0 g of the desired product.

Step-3:—Preparation of tert-butyl 2-(2-chloro-4-fluoro-5-{[(trifluoroacetyl)amino]methyl}phenyl) hydrazinecarboxylate The title compound was prepared according to the procedure described in step-3 of Intermediate-7 by using N-(4-chloro-2-fluoro-5-hydrazinylbenzyl)-2,2,2-trifluoroacetamide (1.00 g, 15 mmol), BOC anhydride (1.14 g, 5.26 mmol), Na$_2$CO$_3$ (0.743 g, 7.01 mmol), acetonitrile (20 mL) and water (10 mL) to afford 0.600 g of the desired product.

Intermediate-90

N-(4-Chloro-2-fluoro-5-(4,5-dihydro-3-(4-iodophenyl)-5-oxo-1,2,4-triazol-1-yl)benzyl)pivalamide

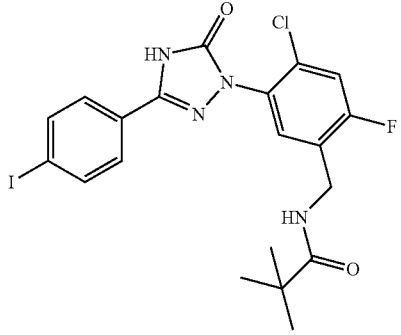 [SMILES: CC(C)(C)C(=O)NCc1cc(-n2nc(-c3ccc(I)cc3)[nH]c2=O)c(Cl)cc1F]

Step-1:—Preparation of N-(4-chloro-2-fluoro-5-(4,5-dihydro-3-(4-iodophenyl)-5-oxo-1,2,4-triazol-1-yl)benzyl)-2,2,2-trifluoroacetamide

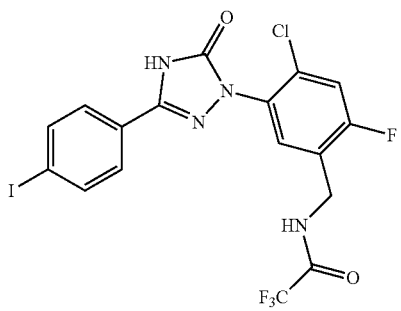 [SMILES: O=C(NCc1cc(-n2nc(-c3ccc(I)cc3)[nH]c2=O)c(Cl)cc1F)C(F)(F)F]

The title compound was prepared according to the procedure described in Example-83 by using 4-iodobenzoyl isocyanate (Intermediate-67, 0.700 g, 1.8 mmol), tert-butyl 2-(2-chloro-4-fluoro-5-{[(trifluoroacetyl)amino]methyl}phenyl)hydrazine carboxylate (Intermediate-89, 0.992 g, 3.63 mmol), DCM (50 mL), trifluoro acetic acid (5.0 mL) to afford 0.600 g of the desired product. $^1$H NMR (300 MHz, DMSO d$_6$): δ 4.47 (s, 2H), 7.61 (d, J=2.1 Hz, 3H), 7.86-7.90 (br d, 3H), 10.05 (br s, 1H).

Step-2:—Preparation of 2-(5-(aminomethyl)-2-chloro-4-fluorophenyl)-5-(4-iodophenyl)-2H-1,2,4-triazol-3(4H)-one

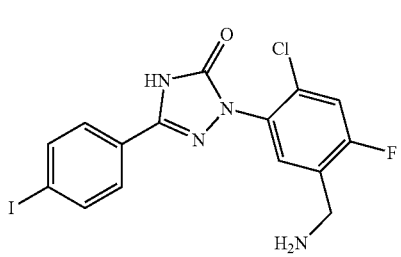 [SMILES: NCc1cc(-n2nc(-c3ccc(I)cc3)[nH]c2=O)c(Cl)cc1F]

The title compound was prepared according to the procedure described in Intermediate-66 by using N-(4-chloro-2-fluoro-5-(4,5-dihydro-3-(4-iodophenyl)-5-oxo-1,2,4-triazol-1-yl)benzyl)-2,2,2-trifluoroacetamide (0.550 g, 1.01 mmol), KOH (0.285 g, 5.09 mmol), water (5 mL) and THF (15.0 mL) to afford 0.400 g of the desired product. $^1$H NMR (300 MHz, DMSO d$_6$): δ 3.59 (m, 2H), 3.71 (s, 1H), 7.38 (d, J=9.6 Hz, 1H), 7.54 (d, J=7.8 Hz, 1H), 7.60-7.69 (m, 4H).

Step-3:—Preparation of N-(4-chloro-2-fluoro-5-(4,5-dihydro-3-(4-iodophenyl)-5-oxo-1,2,4-triazol-1-yl)benzyl)pivalamide The title compound was prepared according to the procedure described in step-2 of Intermediate-83 by using 2-(5-(aminomethyl)-2-chloro-4-fluorophenyl)-5-(4-iodophenyl)-2H-1,2,4-triazol-3(4H)-one (0.400 g, 0.900 mmol), pivaloyl chloride (0.2 mL, 1.35 mmol), DIPEA (2 mL), and THF (10 mL) to afford 0.300 g of the desired product. $^1$H NMR (300 MHz, DMSO d$_6$): δ 1.10 (s, 9H), 4.30 (d, J=5.4 Hz, 2H), 7.42-7.44 (m, 1H), 7.62-7.66 (m, 3H), 7.88-7.91 (br d, 1H), 8.14 (m, 1H); MS (m/z): 529.42 (M$^+$H)$^+$.

Intermediate-91

5-(5-(Aminomethyl)-2-chlorophenyl)-2-(6-(trifluoromethyl)pyridin-3-yl)-2H-1,2,4-triazol-3(4H)-one

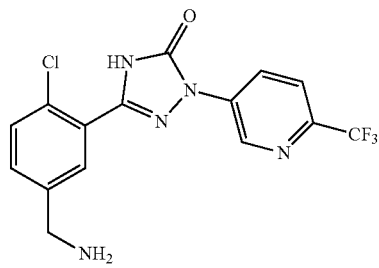 [SMILES: NCc1ccc(Cl)c(-c2nn(-c3ccc(C(F)(F)F)nc3)c(=O)[nH]2)c1]

Step-1:—Preparation N-(4-chloro-3-(1-(6-(trifluoromethyl)pyridin-3-yl)-4,5-dihydro-5-oxo-1H-1,2,4-triazol-3-yl)benzyl)-2,2,2-trifluoroacetamide

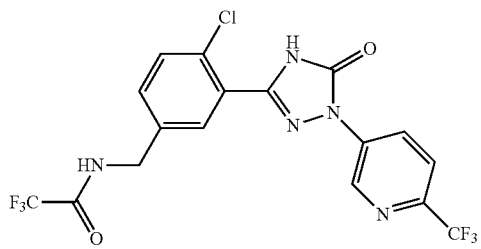 [SMILES: O=C(NCc1ccc(Cl)c(-c2nn(-c3ccc(C(F)(F)F)nc3)c(=O)[nH]2)c1)C(F)(F)F]

The title compound was prepared according to the procedure described in Example-83 by using 2-chloro-5-((2,2,2-trifluoroacetamido)methyl)benzoyl isocyanate (step-3 of Intermediate-26, 0.500 g, 1.55 mmol), tert-butyl 2-[6-(trifluoromethyl)pyridin-3-yl]hydrazinecarboxylate (Intermediate-61, 0.431 g, 1.55 mmol), DCM (50 mL) and trifluoro acetic acid (5.0 mL) to afford 0.500 g of the desired product.

Step-2:—Preparation of 5-(5-(aminomethyl)-2-chlorophenyl)-2-(6-(trifluoromethyl) pyridin-3-yl)-2H-1,2,4-triazol-3(4H)-one The title compound was prepared according to the procedure described in Intermediate-66 by using N-(4-chloro-3-(1-(6-(trifluoromethyl)pyridin-3-yl)-4,5-dihydro-5-oxo-1H-1,2,4-triazol-3-yl)benzyl)-2,2,2-trifluoroacetamide (0.400 g), KOH (0.400 g), THF (5.0 mL), and water (5 mL) to afford 0.350 g of the desired product.

Intermediate-92

5-(5-(Aminomethyl)-2-chlorophenyl)-2-(3-chloro-4-fluorophenyl)-2H-1,2,4-triazol-3(4H)-one

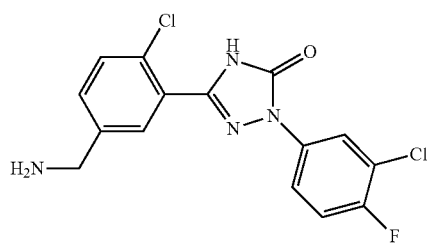 [SMILES: NCc1ccc(Cl)c(-c2nn(-c3ccc(F)c(Cl)c3)c(=O)[nH]2)c1]

Step-1:—Preparation of N-(4-chloro-3-(1-(3-chloro-4-fluorophenyl)-4,5-dihydro-5-oxo-1H-1,2,4-triazol-3-yl)benzyl)-2,2,2-trifluoroacetamide

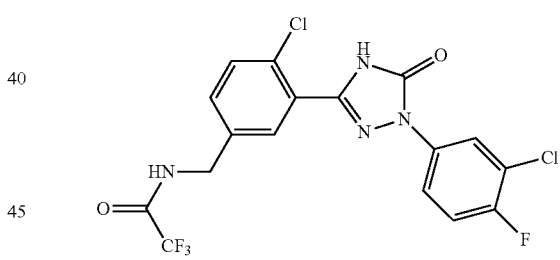

The title compound was prepared according to the procedure described in Example-83 by using 2-chloro-5-((2,2,2-trifluoroacetamido)methyl)benzoyl isocyanate (step-3 of Intermediate-26, 0.500 g, 1.55 mmol), tert-butyl 2-(3-chloro-4-fluorophenyl)hydrazinecarboxylate (Intermediate-85, 0.455 g, 1.55 mmol), DCM (20 mL) and trifluoro acetic acid (5.0 mL) to afford 0.200 g of the desired product.

Step-2:—Preparation of 5-(5-(aminomethyl)-2-chlorophenyl)-2-(3-chloro-4-fluorophenyl)-2H-1,2,4-triazol-3(4H)-one The title compound was prepared according to the procedure described in Intermediate-66 by using N-(4-chloro-3-(1-(3-chloro-4-fluorophenyl)-4,5-dihydro-5-oxo-1H-1,2,4-triazol-3-yl)benzyl)-2,2,2-trifluoroacetamide (0.300 g), KOH (0.300 g), water (5 mL) and THF (10.0 mL) to afford 0.150 g of the desired product.

Intermediate-93

5-(5-(Aminomethyl)-2-chlorophenyl)-2-(3-chloro-4-methylphenyl)-2H-1,2,4-triazol-3(4H)-one

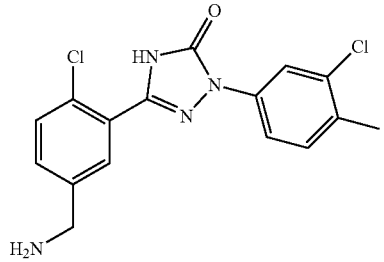 [SMILES: Cc1ccc(-n2nc(-c3cc(CN)ccc3Cl)[nH]c2=O)cc1Cl]

Step-1:—Preparation of N-(4-chloro-3-(1-(3-chloro-4-methylphenyl)-4,5-dihydro-5-oxo-1H-1,2,4-triazol-3-yl)benzyl)-2,2,2-trifluoroacetamide

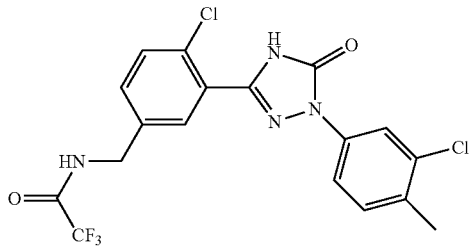 [SMILES: Cc1ccc(-n2nc(-c3cc(CNC(=O)C(F)(F)F)ccc3Cl)[nH]c2=O)cc1Cl]

The title compound was prepared according to the procedure described in Example-83 by using 2-chloro-5-((2,2,2-trifluoroacetamido)methyl)benzoyl isocyanate (step-3 of Intermediate-26, 0.500 g, 1.55 mmol), tert-butyl 2-(3-chloro-4-methylphenyl)hydrazinecarboxylate (Intermediate-87, 0.450 g, 1.55 mmol), DCM (20 mL) and trifluoro acetic acid (5.0 mL) to afford 0.180 g of the desired product.

Step-2:—Preparation of 5-(5-(aminomethyl)-2-chlorophenyl)-2-(3-chloro-4-methylphenyl)-2H-1,2,4-triazol-3(4H)-one The title compound was prepared according to the procedure described in Intermediate-66 by using N-(4-chloro-3-(1-(3-chloro-4-methylphenyl)-4,5-dihydro-5-oxo-1H-1,2,4-triazol-3-yl)benzyl)-2,2,2-trifluoroacetamide (0.400 g), KOH (0.400 g), water (5 mL) and THF (10.0 mL) to afford 0.350 g of the desired product.

Intermediate-94 tert-Butyl 2-(2-chloro-5-{[(2,2-dimethylpropanoyl)amino]methyl}phenyl) hydrazinecarboxylate

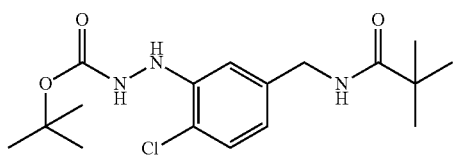 [SMILES: CC(C)(C)OC(=O)NNc1cc(CNC(=O)C(C)(C)C)ccc1Cl]

Step-1:—Preparation of N-(3-amino-4-chlorobenzyl)pivalamide

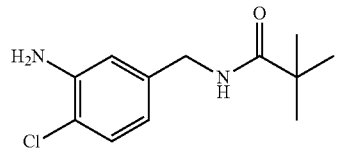 [SMILES: CC(C)(C)C(=O)NCc1ccc(Cl)c(N)c1]

The title compound was prepared according to the procedure described in step-2 of Intermediate-83 by using 5-(aminomethyl)-2-chlorobenzenamine (2.0 g), pivaloyl chloride (0.2 mL), TEA (2 mL) and THF (10 mL) to afford 2.0 g of the desired product.

Step-2:—Preparation of N-(4-chloro-3-hydrazinyl-benzyl)-2,2-dimethylpropanamide

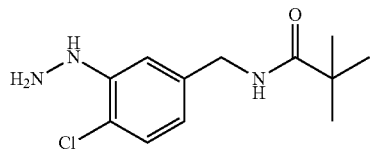 [SMILES: CC(C)(C)C(=O)NCc1ccc(Cl)c(NN)c1]

The title compound was prepared according to the procedure described in step-1 of Intermediate-61 by using N-(3-amino-4-chlorobenzyl)pivalamide (1.80 g), NaNO$_2$ (0.62 g, 0.009 mmol), SnCl$_2$.2H$_2$O (4.2 g, 0.018 mmol) and conc. HCl (30 mL) to afford 1.5 g of the desired product.

Step-3:—Preparation of tert-butyl 2-(2-chloro-5-{[(2,2-dimethylpropanoyl)amino]methyl}phenyl) hydrazinecarboxylate The title compound was prepared according to the procedure described in step-3 of Intermediate-7 by using N-(4-chloro-3-hydrazinylbenzyl)-2,2-dimethylpropanamide (1.5 g, 0.005 mmol), BOC anhydride (1.4 g, 0.006 mmol), Na$_2$CO$_3$ (0.922 g, 0.008 mmol), acetonitrile (30 mL) and water (5 mL) to afford 1.0 g of the desired product.

Intermediate-95

N-(4-Chloro-3-(4,5-dihydro-3-(4-iodophenyl)-5-oxo-1,2,4-triazol-1-yl)benzyl)pivalamide

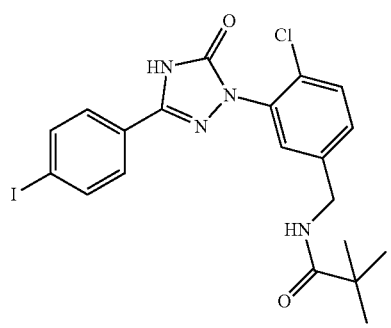 [SMILES: CC(C)(C)C(=O)NCc1ccc(Cl)c(-n2nc(-c3ccc(I)cc3)[nH]c2=O)c1]

To a solution of tert-butyl 2-(2-chloro-5-{[(2,2-dimethylpropanoyl)amino]methyl}phenyl hydrazine carboxylate (Intermediate-94, 0.450 g, 1.55 mmol) in DCM (20 mL) was added solution of 4-iodobenzoyl isocyanate (Intermediate-67, 0.500 g, 1.55 mmol) in DCM (10 mL) and the reaction mixture was stirred for 20 h at room temperature, followed by addition of trifluoro acetic acid (TFA, 3 mL) and further stirred for 20 h at same temperature. The reaction mass was quenched in water, extracted with DCM and concentrated to afford crude product which was purified by column chromatography eluting with MeOH: DCM to afford 0.180 g of the desired product.

Intermediate-96

5-(5-(Aminomethyl)-2-chlorophenyl)-2-(3-(trifluoromethyl)phenyl)-2H-1,2,4-triazol-3(4H)-one

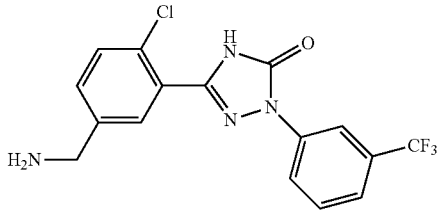 [SMILES: NCc1ccc(Cl)c(-c2nn(-c3cccc(C(F)(F)F)c3)c(=O)[nH]2)c1]

Step 1:—Preparation of tert-butyl 2-[3-(trifluoromethyl)phenyl]hydrazinecarboxylate

The title compound was prepared according to the procedure described in step-3 of Intermediate-7 by using [3-(trifluoromethyl)phenyl]hydrazine hydrochloride (1.00 g, 0.0056 mol), BOC anhydride (1.4 g, 0.0067 mol), Na$_2$CO$_3$ (0.800 g, 0.008 mol), acetonitrile (10 mL) and water (2 mL) to afford 0.500 g of the desired product.

Step 2:—Preparation of N-(4-chloro-3-(1-(3-(trifluoromethyl)phenyl)-4,5-dihydro-5-oxo-1H-1,2,4-triazol-3-yl)benzyl)-2,2,2-trifluoroacetamide

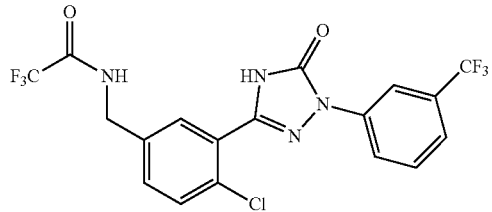 [SMILES: O=C(NCc1ccc(Cl)c(-c2nn(-c3cccc(C(F)(F)F)c3)c(=O)[nH]2)c1)C(F)(F)F]

The title compound was prepared according to the procedure described in Example-83 by using 2-chloro-5-((2,2,2-trifluoroacetamido)methyl)benzoyl isocyanate (step-3 of Intermediate-26, 0.500 g, 1.55 mmol), tert-butyl 2-[3-(trifluoromethyl)phenyl]hydrazinecarboxylate (0.428 g, 1.55 mmol), DCM (20 mL) and trifluoro acetic acid (5.0 mL) to afford 0.400 g of the desired product.

Step-3:—Preparation of 5-(5-(aminomethyl)-2-chlorophenyl)-2-(3-(trifluoromethyl)phenyl)-2H-1,2,4-triazol-3(4H)-one The title compound was prepared according to the procedure described in Intermediate-66 by using N-(4-chloro-3-(1-(3-(trifluoromethyl)phenyl)-4,5-dihydro-5-oxo-1H-1,2,4-triazol-3-yl)benzyl)-2,2,2-trifluoroacetamide (0.400 g), KOH (0.200 g), water (2 mL) and THF (5.0 mL) to afford 0.200 g of the desired product.

Intermediate-97 tert-Butyl 2-(2-chloro-5-{[(2-methylpropanoyl)amino]methyl}phenyl)hydrazinecarboxylate

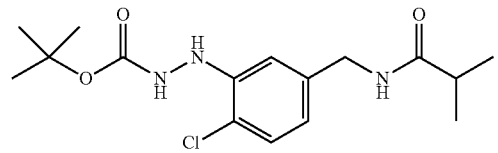 [SMILES: CC(C)C(=O)NCc1ccc(Cl)c(NNC(=O)OC(C)(C)C)c1]

The title compound was prepared according to the procedure described in step-3 of Intermediate-7 by using N-(4-chloro-3-hydrazinylbenzyl)-2-methylpropanamide (2.5 g, 0.010 mol), BOC anhydride (2.5 g, 0.011 mol), Na$_2$CO$_3$ (1.6 g, 0.015 mol), acetonitrile (20 mL) and water (5 mL) to afford 1.500 g of the desired product. $^1$H NMR (300 MHz, DMSO d$_6$): δ 1.03 (d, J=6.6 Hz, 6H), 1.41 (s, 9H), 2.36-2.40 (m, 1H), 4.09 (d, J=6.3 Hz, 1H), 4.15 (d, J=5.4 Hz, 2H), 7.18 (d, J=7.8 Hz, 2H), 7.32 (s, 1H), 8.24 (m, 2H); MS (m/z): 340.8 (M−H)$^−$.

Intermediate-98

N-(4-Chloro-3-(4,5-dihydro-3-(4-iodophenyl)-5-oxo-1,2,4-triazol-1-yl)benzyl)isobutyramide

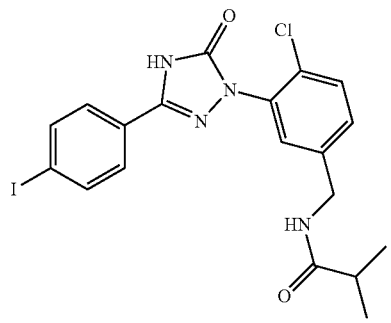 [SMILES: CC(C)C(=O)NCc1ccc(Cl)c(-n2nc(-c3ccc(I)cc3)[nH]c2=O)c1]

The title compound was prepared according to the procedure described in Example-83 by using 4-iodobenzoyl isocyanate (Intermediate-67, 1.500 g), tert-butyl 2-(2- chloro-5-{[(2-methylpropanoyl)amino]methyl}phenyl)hydrazinecarboxylate (Intermediate-97, 1.0 g), DCM (20 mL), and trifluoro acetic acid (5.0 mL) to afford 0.500 g of the desired product. $^1$H NMR (400 MHz, DMSO $d_6$): δ 1.02 (d, J=6.9 Hz, 6H), 2.44 (m, 1H), 4.28 (d, J=8.7 Hz, 2H), 7.28 (br s, 1H), 7.35 (d, J=7.8 Hz, 1H), 7.44 (s, 1H), 7.61 (d, J=8.7 Hz, 1H), 7.91 (d, J=8.1 Hz, 2H), 8.38 (m, 1H), 12.61 (m, 1H); MS (m/z): 495.7 (M–H)$^-$.

Intermediate-99

3-Fluoro-4-(trifluoromethyl)benzoyl isocyanate

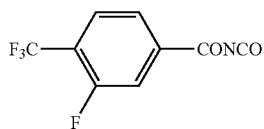

The title compound was prepared according to the procedure described in step-2 of Intermediate-8 by using 3-fluoro-4-(trifluoromethyl)benzamide (0.200 g), oxalyl chloride (0.025 mL) and EDC (15 mL) to afford 0.150 g of the desired product.

Intermediate-100

4-Chloro-3-(trifluoromethyl)benzoyl isocyanate

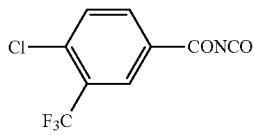

The title compound was prepared according to the procedure described in step-2 of Intermediate-8 by using 4-chloro-3-(trifluoromethyl)benzamide (0.200 g), oxalyl chloride (0.012 mL) and EDC (15 mL) to afford 0.150 g of the desired product.

Intermediate-101

4-Fluoro-3-(trifluoromethyl)benzoyl isocyanate

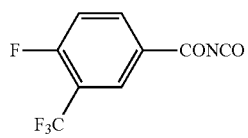

The title compound was prepared according to the procedure described in step-2 of Intermediate-8 by using 4-fluoro-3-(trifluoromethyl)benzamide (0.200 g), oxalyl chloride (0.012 mL) and EDC (15 mL) to afford 0.150 g of the desired product.

Intermediate-102

3-Fluoro-4-iodobenzoyl isocyanate

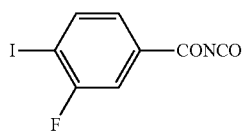

Step-1:—Preparation of 3-fluoro-4-iodobenzamide

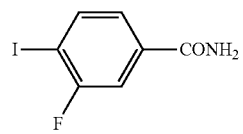 [SMILES: NC(=O)c1ccc(I)c(F)c1]

To a solution of 3-fluoro-4-iodobenzonitrile (2.7 g, 0.010 mmol) in DMSO (6.0 mL), $K_2CO_3$ (0.450 g, 0.003 mmol) and 30% $H_2O_2$ (2.4 mL) were added at 0-10° C. and the reaction mass was stirred at RT for 2 h. After completion of the reaction, the reaction mass was quenched in ice cold water. The obtained solid product was filtered off to afford 2.0 g of the desired title product. $^1$H NMR (400 MHz, DMSO $d_6$): δ 7.48-7.51 (m, 2H), 7.66 (br s, 1H), 7.69-7.70 (m, 1H), 8.09 (brs, 1H).

Step-2:—Preparation of 3-fluoro-4-iodobenzoyl isocyanate

The title compound was prepared according to the procedure described in step-2 of Intermediate-8 by using 3-fluoro-4-iodobenzamide (2.0 g), oxalyl chloride (0.120 mL) and EDC (25 mL) to afford 1.0 g of the desired product.

Intermediate-103

N-(3-(3-(4-(bromomethyl)phenyl)-4,5-dihydro-5-oxo-1,2,4-triazol-1-yl)-4-chlorobenzyl)pivalamide

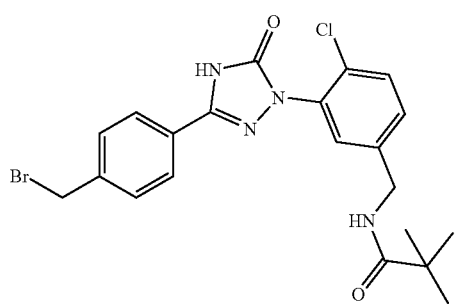 [SMILES: CC(C)(C)C(=O)NCc1ccc(Cl)c(-n2nc(-c3ccc(CBr)cc3)[nH]c2=O)c1]

Step-1:—Preparation of 4-(bromomethyl)benzamide

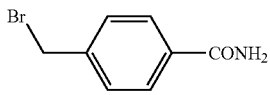

Stirred the solution of 4-(bromomethyl)benzonitrile (1.5 g) in conc. H$_2$SO$_4$ at 100° C. for 3-4 h. After completion of the reaction, the reaction mass was quenched in ice and filtered to afford 0.900 of desired product. 1H NMR (400 MHz, DMSO d$_6$): δ 4.71 (s, 2H), 7.26 (br s, 1H), 7.49 (d, J=7.8 Hz, 2H), 7.82 (d, J=7.8 Hz, 2H), 7.89 (br s, 1H); MS (m/z): 214.36 (M+H)$^+$.

Step-2:—Preparation of 4-(bromomethyl)benzoyl isocyanate

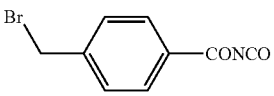

The title compound was prepared according to the procedure described in step-2 of Intermediate-8 by using 4-(bromomethyl)benzamide (0.200 g), oxalyl chloride (0.012 mL) and EDC (15 mL) to afford 0.150 g of the desired product.

Step-3:—Preparation of N-(3-(3-(4-(bromomethyl)phenyl)-4,5-dihydro-5-oxo-1,2,4-triazol-1-yl)-4-chlorobenzyl)pivalamide The title compound was prepared according to the procedure described in Example-83 by using 4-(bromomethyl)benzoyl isocyanate (0.150 g), tert-Butyl 2-(2-chloro-5-{[(2,2-dimethylpropanoyl)amino]methyl}phenyl)hydrazinecarboxylate (Intermediate-94, 0.150 g), DCM (20 mL), and trifluoro acetic acid (5.0 mL) to afford 0.100 g of the desired product. $^1$H NMR (400 MHz, DMSO d$_6$): δ 1.12 (s, 9H), 4.28 (br d, 2H), 4.75 (s, 2H), 7.34 (br d, 2H), 7.43 (br s, 1H), 7.60 (br d, 2H), 7.81 (br d, 2H), 8.17 (br s, 1H), 12.57 (s, 1H).

Intermediate-104

4-(5-isopropyl-1,3,4-oxadiazol-2-yl)benzoyl isocyanate

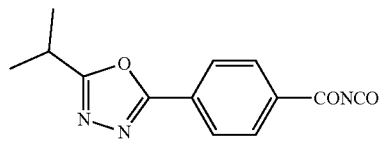

Step 1:—Preparation of 4-(5-isopropyl-1,3,4-oxadiazol-2-yl)benzamide

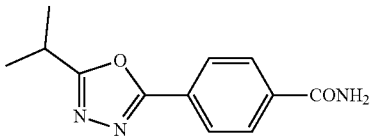 [SMILES: CC(C)c1nnc(-c2ccc(C(N)=O)cc2)o1]

The title compound was prepared according to the procedure described in step 1 of Intermediate-59 by using 4-(5-isopropyl-1,3,4-oxadiazol-2-yl)benzonitrile (0.500 g, 2.34 mmol), 50% H$_2$O$_2$ (5.0 mL), K$_2$CO$_3$ (0.097 g, 0.070 mmol) to afford 0.250 g of desired product. 1H NMR (400 MHz, DMSO d$_6$): δ 1.3 (s, 3H), 1.35 (s, 3H), 3.33 (m, 1H), 7.56 (br s, 1H), 8.06 (s, 4H), 8.16 (br s, 1H); MS (m/z): 232.30 (M+H)$^+$.

Step 2:—Preparation of 4-(5-isopropyl-1,3,4-oxadiazol-2-yl)benzoyl isocyanate The title compound was prepared according to the procedure described in step-2 of Intermediate-8 by using 4-(5-isopropyl-1,3,4-oxadiazol-2-yl)benzamide (0.200 g), oxalyl chloride (0.012 mL) and EDC (15 mL) to afford 0.150 g of the desired product.

Intermediate-105 tert-Butyl 2-(4-chloro-3-methylphenyl)hydrazinecarboxylate

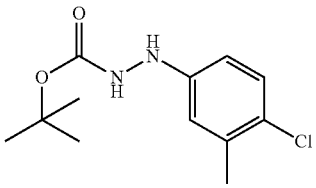 [SMILES: Cc1cc(NNC(=O)OC(C)(C)C)ccc1Cl]

Step-1:—Preparation of 1-(4-chloro-3-methylphenyl)hydrazine

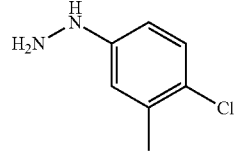

The title compound was prepared according to the procedure described in step-1 of Intermediate-61 by using N-4-chloro-3-methylbenzenamine (2.0 g, 0.014 mmol), NaNO$_2$ (01.16 g, 0.0169 mmol), SnCl$_2$.2H$_2$O (7.93 g, 0.0352 mmol) and conc. HCl (30 mL) to afford 1.5 g of the desired product.

Step-2:—Preparation of tert-butyl 2-(4-chloro-3-methylphenyl)hydrazinecarboxylate The title compound was prepared according to the procedure described in step-3 of Intermediate-7 by using 1-(4-chloro-3-methylphenyl)hydrazine (1.22 g, 0.011 mmol), BOC anhydride (2.0 g, 0.009 mmol), Na$_2$CO$_3$ (0.922 g, 0.008 mmol), acetonitrile (30 mL) and water (5 mL) to afford 1.0 g of the desired product. $^1$H NMR (300 MHz, DMSO d$_6$): δ 1.40 (s, 9H), 2.21 (s, 3H), 6.49 (d, J=8.4 Hz, 1H), 6.58 (s, 1H), 7.13 (d, J=8.7 Hz, 1H), 7.65 (s, 1H), 8.78 (s, 1H).

Intermediate-106

5-(5-(aminomethyl)-2-chlorophenyl)-2-(4-chloro-3-methylphenyl)-2H-1,2,4-triazol-3(4H)-one

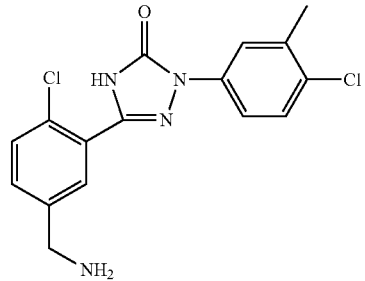 [SMILES: Cc1cc(-n2nc(-c3cc(CN)ccc3Cl)[nH]c2=O)ccc1Cl]

Step-1:—Preparation of N-(4-chloro-3-(1-(4-chloro-3-methylphenyl)-4,5-dihydro-5-oxo-1H-1,2,4-triazol-3-yl)benzyl)-2,2,2-trifluoroacetamide

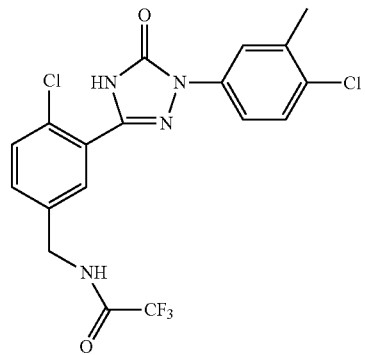 [SMILES: Cc1cc(-n2nc(-c3cc(CNC(=O)C(F)(F)F)ccc3Cl)[nH]c2=O)ccc1Cl]

The title compound was prepared according to the procedure described in Example-83 by using 2-chloro-5-((2,2,2-trifluoroacetamido)methyl)benzoyl isocyanate (step-3 of Intermediate-26, 1.0 g, 0.003 mmol), tert-butyl 2-(4-chloro-3-methylphenyl)hydrazinecarboxylate (Intermediate-105, 1.500 g), DCM (20 mL), and trifluoro acetic acid (5.0 mL) to afford 0.600 g of the desired product. $^1$H NMR (300 MHz, DMSO d$_6$): δ 2.38 (s, 3H), 4.45 (d, J=5.4 Hz, 2H), 7.53 (d, J=9.3 Hz, 2H), 7.67 (s, 2H), 7.82 (d, J=8.1 Hz, 1H), 7.92 (s, 1H), 10.08 (t, 1H), 12.61 (s, 1H); MS (m/z): 445.31 (M+H)$^+$.

Step-2:—Preparation of 3-(5-(aminomethyl)-2-chlorophenyl)-1-(3-methoxy-4-nitrophenyl)-1H-1,2,4-triazol-5(4H)-one The solution of N-(4-chloro-3-(1-(4-chloro-3-methylphenyl)-4,5-dihydro-5-oxo-1H-1,2,4-triazol-3-yl)benzyl)-2,2,2-trifluoroacetamide (0.550 g, 1.23 mmol) in 20% aq. KOH (20 mL) was stirred for 2-3 h at RT. Excess of solvent was removed under vacuum and filtered off remaining reaction mass to afford 0.400 g of desired product. MS (m/z): 349.34 (M)$^+$.

Intermediate-107 was prepared according to the procedure described for step-2 of Intermediate-26 by using 5-cyano-2-cyclopropylpyridine-3-carboxylic acid, oxalyl chloride, ammonia gas, DMF, THF and DCM.

| No. & Chemical Structure | Chemical name and Characterization data |
|---|---|
| Intermediate-107 | 5-cyano-2-cyclopropylpyridine-3-carboxamide. $^1$H NMR (300 MHz, DMSO d$_6$): δ 107 (m, 4H), 2.49 (s, 1H), 7.82 (s, 1H), 8.13 (s, 1H), 8.20 (s, 2H), 8.87 (s, 1H); MS (m/z): 188.04 (M + H)$^+$. |

The Intermediate-108 to Intermediate-115 were prepared by following the procedure described for step-1 of Intermediate-61 by using corresponding amine, NaNO$_2$, SnCl$_2$.H$_2$O, 4N HCl and followed by following the procedure described for step-3 of Intermediate-7 using BOC anhydride, Na$_2$CO$_3$ in acetonitrile and water.

| No. | Structure | Chemical name and Characterization data |
|---|---|---|
| Intermediate-108 | 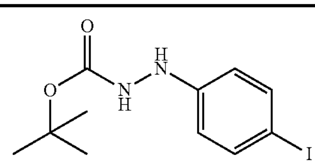 | tert-butyl 2-(4-iodophenyl)hydrazinecarboxylate. MS (m/z): 335.15 (M + H)$^+$. |
| Intermediate-109 | 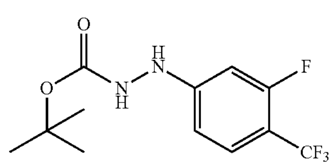 [SMILES: CC(C)(C)OC(=O)NNc1ccc(C(F)(F)F)c(F)c1] | tert-butyl 2-[3-fluoro-4-(trifluoromethyl)phenyl]hydrazinecarboxylate. MS (m/z): 295.21 (M + H)$^+$. |
| Intermediate-110 | 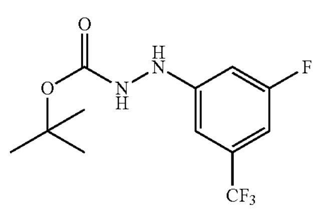 [SMILES: CC(C)(C)OC(=O)NNc1cc(F)cc(C(F)(F)F)c1] | tert-butyl 2-[3-fluoro-5-(trifluoromethyl)phenyl]hydrazinecarboxylate. MS (m/z): 295.24 (M + H)$^+$. |

-continued

| No. | Structure | Chemical name and Characterization data |
|---|---|---|
| Intermediate-111 | 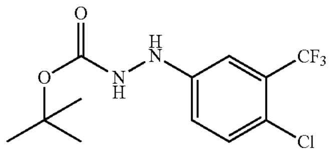 [SMILES: CC(C)(C)OC(=O)NNc1ccc(Cl)c(C(F)(F)F)c1] | tert-butyl 2-[4-chloro-3-(trifluoromethyl)phenyl] hydrazinecarboxylate. $^1$H NMR (300 MHz, DMSO $d_6$): δ 1.40 (s, 9H), 6.90 (d, J = 8.7 Hz, 1H), 7.01 (s, 1H), 7.45 (d, J = 9.0 Hz, 1H), 8.20 (s, 1H), 8.99 (br s, 1H. |
| Intermediate-112 | 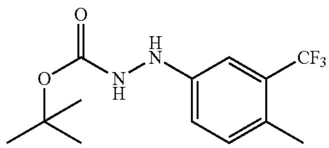 [SMILES: Cc1ccc(NNC(=O)OC(C)(C)C)cc1C(F)(F)F] | tert-butyl 2-[4-methyl-3-(trifluoromethyl)phenyl] hydrazinecarboxylate. $^1$H NMR (300 MHz, DMSO $d_6$): δ 1.40 (s, 9H), 2.28 (s, 3H), 6.80 (d, J = 8.4 Hz, 1H), 6.91 (s, 1H), 7.18 (d, J = 8.4 Hz, 1H), 7.84 (s, 1H), 8.88 (br s, 1H). |
| Intermediate-113 | 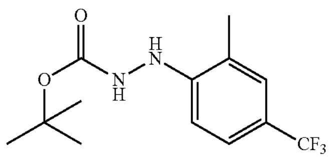 | tert-butyl 2-[2-methyl-4-(trifluoromethyl)phenyl] hydrazinecarboxylate. MS (m/z): 291.12 (M + H)$^+$. |
| Intermediate-114 | 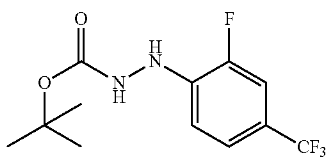 [SMILES: CC(C)(C)OC(=O)NNc1ccc(C(F)(F)F)cc1F] | tert-butyl 2-[2-fluoro-4-(trifluoromethyl)phenyl] hydrazinecarboxylate $^1$H NMR (300 MHz, DMSO $d_6$): δ 1.42 (s, 9H), 6.83 (t, 1H), 7.39 (d, J = 8.4 Hz, 1H), 7.44-7.48 (m, 1H), 8.28 (s, 1H), 9.03 (s, 1H). |
| Intermediate-115 | 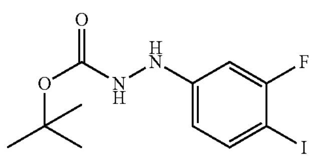 [SMILES: CC(C)(C)OC(=O)NNc1ccc(I)c(F)c1] | tert-butyl 2-(3-fluoro-4-iodophenyl) hydrazinecarboxylate. MS (m/z): 351.14 (M − H)$^−$. |

The Intermediate-116 to Intermediate-128 was prepared by following the procedure described for Example-83 by using corresponding starting material mentioned in the table below, DCM and TFA.

| Starting material used | Intermediate No. and Structure | Intermediate chemical name and characterization data |
|---|---|---|
| Intermediate-65 + Intermediate-67 | Intermediate-116 | N-(3-(4,5-dihydro-1-(4-iodophenyl)-5-oxo-1H-1,2,4-triazol-3-yl)-2,4-dimethylbenzyl)-2,2,2-trifluoroacetamide. $^1$H NMR (300 MHz, DMSO $d_6$): δ 2.19 (s, 3H), 2.21 (s, 3H), 4.41 (d, J = 4.8 Hz, 2H), 7.20 (d, J = 7.8 Hz, 1H), 7.29 (d, J = 7.8 Hz, 1H), 7.53-7.82 (m, 4H), 9.97 (s, 1H), 12.23 (s, 1H); MS (m/z): 517.301 (M + H)$^+$. |

| Starting material used | Intermediate No. and Structure | Intermediate chemical name and characterization data |
|---|---|---|
| Step 3 product of Intermediate-26 + Intermediate-110 | Intermediate-117 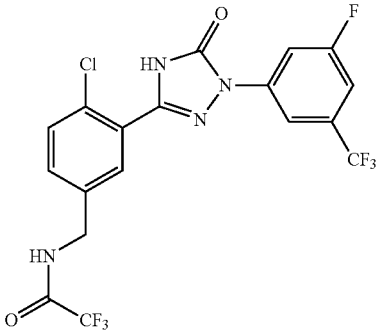 [SMILES: O=C(NCc1ccc(Cl)c(-c2nn(-c3cc(F)cc(C(F)(F)F)c3)c(=O)[nH]2)c1)C(F)(F)F] | N-(4-chloro-3-(1-(3-fluoro-5-(trifluoromethyl)phenyl)-4,5-dihydro-5-oxo-1H-1,2,4-triazol-3-yl)benzyl)-2,2,2-trifluoroacetamide. $^1$H NMR (300 MHz, DMSO d$_6$): δ 4.46 (d, 2H), 7.51 (m, 1H), 7.60 (d, J = 9.3 Hz, 1H), 7.66-7.69 (m, 2H), 8.08 (d, J = 13.8 Hz, 1H), 8.16 (s, 1H), 10.09 (m, 1H), 12.84 (m, 1H) |
| Step-3 product of Intermediate-26 + Intermediate-111 | Intermediate-118 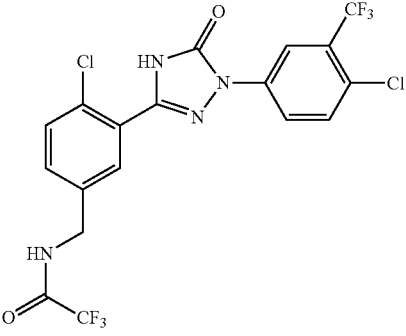 [SMILES: O=C(NCc1ccc(Cl)c(-c2nn(-c3ccc(Cl)c(C(F)(F)F)c3)c(=O)[nH]2)c1)C(F)(F)F] | N-(4-chloro-3-(1-(4-chloro-3-(trifluoromethyl)phenyl)-4,5-dihydro-5-oxo-1H-1,2,4-triazol-3-yl)benzyl)-2,2,2-trifluoroacetamide. $^1$H NMR (300 MHz, DMSO d$_6$): δ 4.46 (d, J = 6.0 Hz, 2H), 7.49 (d, J = 10.2 Hz, 1H), 7.67 (d, J = 8.4 Hz, 2H), 7.85 (d, J = 9.0 Hz, 1H), 8.24 (d; J = 8.7 Hz, 1H), 8.44 (s, 1H), 10.09 (t, 1H), 12.80 (s, 1H); MS (m/z): 499.31 (M + H)$^+$. |
| Intermediate-94 + Intermediate-102 | Intermediate-119 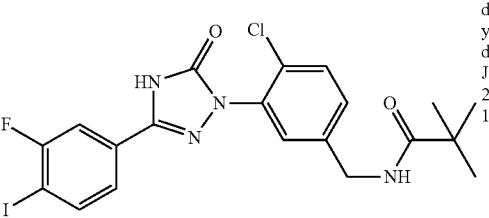 | N-(4-chloro-3-(3-(3-fluoro-4-iodophenyl)-4,5-dihydro-5-oxo-1,2,4-triazol-1-yl)benzyl)pivalamide. $^1$H NMR (300 MHz, DMSO d$_6$): δ 1.12 (s, 9H), 4.28 (d, J = 8.4 Hz, 2H), 7.34 (d, J = 7.8 Hz, 1H), 7.43-7.49 (m, 2H), 7.59-7.67 (m, 2H), 8.02 (t, J = 7.2 Hz, 1H), 8.19 (t, 1H), 12.67 (s, 1H); MS (m/z): 529.05 (M+ H)$^+$. |
| Step-3 product of Intermediate-26 + Intermediate-67 | Intermediate-120 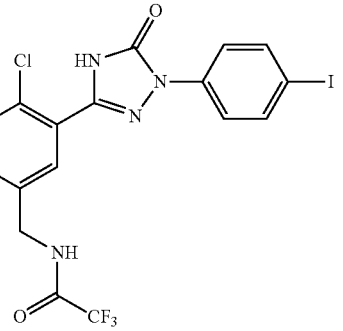 | N-(4-chloro-3-(4,5-dihydro-1-(4-iodophenyl)-5-oxo-1H-1,2,4-triazol-3-yl)benzyl)-2,2,2-trifluoroacetamide. $^1$H NMR (300 MHz, DMSO d$_6$): δ 4.44 (br s, 2H), 7.46-7.73 (m, 4H), 7.80 (s, 2H), 10.11 (s, 1H); MS (m/z): 523.09 (M + H)$^+$. |

-continued

| Starting material used | Intermediate No. and Structure | Intermediate chemical name and characterization data |
|---|---|---|
| Step-3 product of Intermediate-26 + Intermediate-112 | Intermediate-121 | N-(4-chloro-3-(1-(3-(trifluoromethyl)-4-methylphenyl)-4,5-dihydro-5-oxo-1H-1,2,4-triazol-3-yl)benzyl)-2,2,2-trifluoroacetamide. $^1$H NMR (300 MHz, DMSO d$_6$): δ 2.45 (s, 3H), 4.46 (d, J = 6.6 Hz, 2H), 7.49 (d, J = 7.8 Hz, 1H), 7.57 (d, J = 7.8 Hz, 1H); 7.68 (s, 2H), 8.10 (d, J = 8.7 Hz, 1H), 8.28 (s, 1H), 10.09 (br s, 1H), 12.69 (br s, 1H); MS (m/z): 476.91 (M − H)$^-$. |
| Intermediate-53 + [structure: 2-cyclopropyl-5-cyanopyridine-3-carbonyl chloride] | Intermediate-122 | 6-cyclopropyl-5-(1-(4-(trifluoromethyl)phenyl)-4,5-dihydro-5-oxo-1H-1,2,4-triazol-3-yl)pyridine-3-carbonitrile. $^1$H NMR (300 MHz, DMSO d$_6$): δ 1.18 (m, 2H), 1.39 (m, 2H), 3.01 (m, 1H), 7.85 (d, J = 9.0 Hz, 2H), 8.20 (d, J = 7.8 Hz, 2H), 8.45 (s, 1H), 8.99 (s, 1H), 12.82 (br s, 1H); MS (m/z): 372.24 (M + H)$^+$. |
| Step-3 product of Intermediate-26 + Intermediate-113 | Intermediate-123 | N-(4-chloro-3-(1-(4-(trifluoromethyl)-2-methylphenyl)-4,5-dihydro-5-oxo-1H-1,2,4-triazol-3-yl)benzyl)-2,2,2-trifluoroacetamide. $^1$H NMR (300 MHz, DMSO d$_6$): δ 2.39 (s, 3H), 4.44 (br d, 2H), 7.33-7.90 (m, 6H), 10.07 (br s, 1H), 12.51 (s, 1H); MS (m/z): 479.10 (M + H)$^+$. |
| Intermediate-47 + Intermediate-94 | Intermediate-124 | N-(4-chloro-3-(3-(2-fluoro-4-iodophenyl)-4,5-dihydro-5-oxo-1,2,4-triazol-1-yl)benzyl)pivalamide. $^1$H NMR (300 MHz, DMSO d$_6$): δ 1.11 (s, 9H), 4.28 (d, J = 5.7 Hz, 2H), 7.34 (d, J = 8.4 Hz, 1H), 7.42 (s, 1H), 7.53-7.61 (m, 2H), 7.75 (d, J = 7.2 Hz, 1H), 7.89 (d, J = 9.3 Hz, 1H), 8.18 (t, 1H), 12.43 (s, 1H); MS (m/z): 529.0110 (M + H)$^+$. |

-continued

| Starting material used | Intermediate No. and Structure | Intermediate chemical name and characterization data |
|---|---|---|
| Step-3 product of Intermediate-26 + Intermediate-109 | Intermediate-125 | N-(4-chloro-3-(1-(3-fluoro-4-(trifluoromethyl)phenyl)-4,5-dihydro-5-oxo-1H-1,2,4-triazol-3-yl)benzyl)-2,2,2-trifluoroacetamide. $^1$H NMR (300 MHz, DMSO d$_6$): δ 4.46 (d, J = 6.0 Hz, 2H), 7.50 (d, J = 8.7 Hz, 1H), 7.66 (s, 2H), 7.92-8.07 (m, 3H), 10.10 (t, 1H), 12.84 (m, 1H). |
| Step-3 product of Intermediate-26 + | Intermediate-126 | N-(4-chloro-3-(1-(2-fluoro-4-iodophenyl)-4,5-dihydro-5-oxo-1H-1,2,4-triazol-3-yl)benzyl)-2,2,2-trifluoroacetamide. $^1$H NMR (300 MHz, DMSO d$_6$): δ 4.44 (d, J = 5.1 Hz, 2H), 7.39-7.48 (m, 2H), 7.63 (br s, 2H), 7.74 (t, J = 8.4 Hz, 1H), 7.90 (d, J = 8.7 Hz, 1H), 10.08 (br s, 1H), 12.52 (s, 1H); MS (m/z): 540.98 (M + H)$^+$. |
| Step-3 product of Intermediate-26 + Intermediate-114 | Intermediate-127 | N-(4-chloro-3-(1-(2-fluoro-4-(trifluoromethyl)phenyl)-4,5-dihydro-5-oxo-1H-1,2,4-triazol-3-yl)benzyl)-2,2,2-trifluoroacetamide. $^1$H NMR (300 MHz, DMSO d$_6$): δ 4.44 (m, 2H), 7.34 (s, 1H), 7.49 (m, 2H), 7.75 (d, J = 7.8 Hz, 1H), 7.79-7.98 (m, 2H), 10.10 (br s, 1H), 12.64 (m, 1H); MS (m/z): 483.12 (M + H)$^+$ |
| Intermediate-65 + Intermediate-115 | Intermediate-128 | N-(3-(1-(3-fluoro-4-iodophenyl)-4,5-dihydro-5-oxo-1H-1,2,4-triazol-3-yl)-2,4-dimethylbenzyl)-2,2,2-trifluoroacetamide. MS (m/z): 535.01 (M + H)$^+$. |

The Intermediate-129 to Intermediate-137 were prepared by following the procedure described in step-2 of Intermediate-106 by using corresponding starting material mentioned in the table below, KOH and water.

| Starting material used | Intermediate No. and Structure | Intermediate chemical name and characterization data. |
|---|---|---|
| Intermediate-116 | Intermediate-129 | 5-(3-(aminomethyl)-2,6-dimethylphenyl)-2-(4-iodophenyl)-2H-1,2,4-triazol-3(4H)-one. $^1$H NMR (300 MHz, DMSO d$_6$): δ 2.10 (s, 3H), 2.12 (s, 3H), 3.13 (br s, 2H), 3.66 (s, 2H), 6.98 (d, J = 8.4 Hz, 1H), 7.21 (d, J = 8.1 Hz, 1H), 7.57 (d, J = 8.1 Hz, 2H), 7.90 (d, J = 8.7 Hz, 2H). |
| Intermediate-117 | Intermediate-130 | 5-(5-(aminomethyl)-2-chlorophenyl)-2-(3-fluoro-5-(trifluoromethyl)phenyl)-2H-1,2,4-triazol-3(4H)-one |
| Intermediate-118 | Intermediate-131 | 5-(5-(aminomethyl)-2-chlorophenyl)-2-(4-chloro-3-(trifluoromethyl)phenyl)-2H-1,2,4-triazol-3(4H)-one |
| Intermediate-120 | Intermediate-132 | 5-(5-(aminomethyl)-2-chlorophenyl)-2-(4-iodophenyl)-2H-1,2,4-triazol-3(4H)-one. $^1$H NMR (300 MHz, DMSO d$_6$): δ 3.36 (br s, 2H), 3.80 (br s, 2H), 7.41 (m, 1H), 7.47 (m, 1H), 7.6-7.72 (m, 2H); 7.77 (s, 1H), 7.87-7.90 (m, 2H). |

| Starting material used | Intermediate No. and Structure | Intermediate chemical name and characterization data. |
|---|---|---|
| Intermediate-121 | Intermediate-133 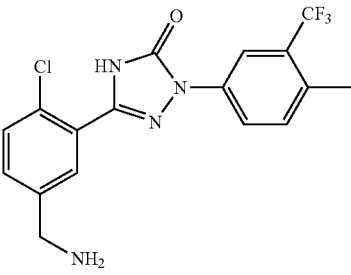 [SMILES: Cc1ccc(-n2nc(-c3cc(CN)ccc3Cl)[nH]c2=O)cc1C(F)(F)F] | 5-(5-(aminomethyl)-2-chlorophenyl)-2-(3-(trifluoromethyl)-4-methylphenyl)-2H-1,2,4-triazol-3(4H)-one. MS (m/z): 381.01 (M − H)⁻. |
| Intermediate-123 | Intermediate-134 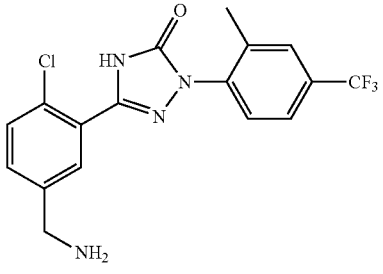 [SMILES: Cc1cc(C(F)(F)F)ccc1-n1nc(-c2cc(CN)ccc2Cl)[nH]c1=O] | 5-(5-(aminomethyl)-2-chlorophenyl)-2-(4-(trifluoromethyl)-2-methylphenyl)-2H-1,2,4-triazol-3(4H)-one. MS (m/z): 383.15 (M + H)⁺. |
| Intermediate-125 | Intermediate-135 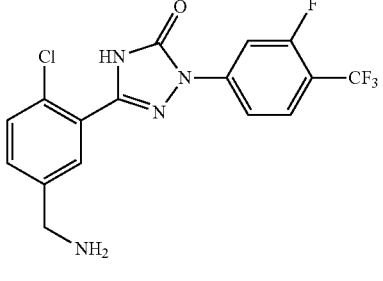 [SMILES: NCc1ccc(Cl)c(-c2nn(-c3ccc(C(F)(F)F)c(F)c3)c(=O)[nH]2)c1] | 5-(5-(aminomethyl)-2-chlorophenyl)-2-(3-fluoro-4-(trifluoromethyl)phenyl)-2H-1,2,4-triazol-3(4H)-one. MS (m/z): 387.21 (M + H)⁺. |
| Intermediate-127 | Intermediate-136 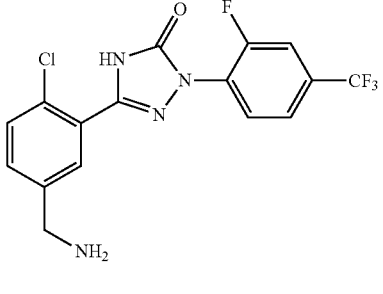 [SMILES: NCc1ccc(Cl)c(-c2nn(-c3ccc(C(F)(F)F)cc3F)c(=O)[nH]2)c1] | 5-(5-(aminomethyl)-2-chlorophenyl)-2-(2-fluoro-4-(trifluoromethyl)phenyl)-2H-1,2,4-triazol-3(4H)-one. MS (m/z): 387.06 (M + H)⁺. |

| Starting material used | Intermediate No. and Structure | Intermediate chemical name and characterization data. |
|---|---|---|
| Intermediate-128 | Intermediate-137 | 5-(3-(aminomethyl)-2,6-dimethylphenyl)-2-(3-fluoro-4-iodophenyl)-2H-1,2,4-triazol-3(4H)-one. MS (m/z): 439.24 (M + H)+. |

The Intermediate-138 to Intermediate-141 were prepared by following the procedure described in Example-108 by using corresponding starting material mentioned in the table below, TEA and THF.

| Starting material used | Intermediate No. and Structure | Intermediate chemical name and characterization data |
|---|---|---|
| Intermediate-129 + Pivaloyl chloride | Intermediate-138 | N-(3-(4,5-dihydro-1-(4-iodophenyl)-5-oxo-1H-1,2,4-triazol-3-yl)-2,4-dimethylbenzyl)pivalamide. $^1$H NMR (300 MHz, DMSO d$_6$): δ 1.19 (s, 9H), 2.15 (s, 3H), 2.19 (s, 3H), 4.22 (d, 2H), 7.17-7.21 (m, 2H), 7.79 (m, 4H), 8.00 (m, 1H), 12.00 (s, 1H). |
| Intermediate-132 + Pivaloyl chloride | Intermediate-139 | N-(4-chloro-3-(4,5-dihydro-1-(4-iodophenyl)-5-oxo-1H-1,2,4-triazol-3-yl)benzyl)pivalamide. $^1$H NMR (300 MHz, DMSO d$_6$): δ 1.13 (s, 9H), 4.29 (d, J = 5.4 Hz, 2H), 7.41 (d, J = 8.4 Hz, 1H), 7.59 (s, 2H), 7.80 (q, J = 6.3 Hz, 4H), 8.19 (m, 1H), 12.59 (s, 1H); MS (m/z): 511.16 (M + H)+. |

-continued

| Starting material used | Intermediate No. and Structure | Intermediate chemical name and characterization data |
|---|---|---|
| Intermediate-129 + Isopropyl chloride | Intermediate-140 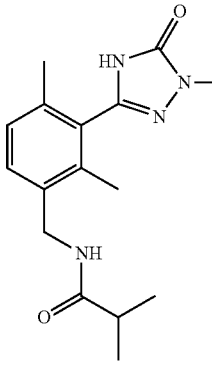 | N-(3-(4,5-dihydro-1-(4-iodophenyl)-5-oxo-1H-1,2,4-triazol-3-yl)-2,4-dimethylbenzyl)isobutyramide. $^1$H NMR (300 MHz, DMSO $d_6$): δ 1.23 (s, 3H), 1.35 (s, 3H), 2.06 (s, 3H), 2.20 (s, 3H), 4.23 (br s, 2H), 7.08 (d, J = 7.8 Hz, 1H), 7.20 (d, J = 7.5 Hz, 1H), 7.74 (d, J = 8.7 Hz, 2H), 7.85 (d, J = 8.1 Hz, 2H), 8.17 (t, 1H). |
| Intermediate-137 + Isopropyl chloride | Intermediate-141 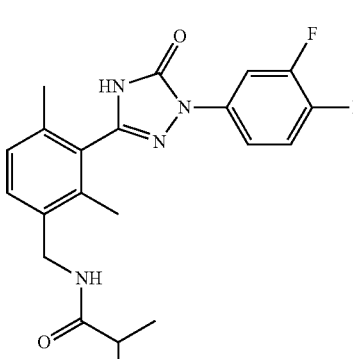 | N-(3-(1-(3-fluoro-4-iodophenyl)-4,5-dihydro-5-oxo-1H-1,2,4-triazol-3-yl)-2,4-dimethylbenzyl)isobutyramide. MS (m/z): 509.02 (M + H)$^+$. |

The Intermediate-142 was prepared by following the procedure described in Example-107 by using Intermediate-129, THF, DMF, 3-methoxy-2,2-dimethylpropanoic acid, TBTU and TEA.

| Starting material used | Intermediate No. and Structure | Intermediate chemical name and characterization data |
|---|---|---|
| Intermediate-129 | Intermediate-142 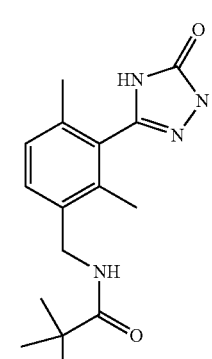 | N-(3-(4,5-dihydro-1-(4-iodophenyl)-5-oxo-1H-1,2,4-triazol-3-yl)-2,4-dimethylbenzyl)-3-hydroxy-2,2-dimethylpropanamide. $^1$H NMR (300 MHz, DMSO $d_6$): δ 1.08 (m, 6H), 2.15 (s, 3H), 2.19 (s, 3H), 3.41 (m, 2H), 4.25 (d, 2H), 4.92 (m, 1H), 6.93 (d, J = 6.9 Hz, 1H), 7.15 (d, J = 8.7 Hz, 1H), 7.28 (d, J = 8.1 Hz, 1H), 7.79 (s, 3H), 7.92 (t, 1H), 12.25 (s, 1H); MS (m/z): 521.18 (M + H)$^+$. |

The Intermediate-143 was prepared by following the procedure described in step-2 of Example-134 by using Intermediate-142, DAST and THF.

| Starting material used | Intermediate No and Structure | Intermediate chemical name and characterization data |
|---|---|---|
| Intermediate-142 | Intermediate-143 | N-(3-(4,5-dihydro-1-(4-iodophenyl)-5-oxo-1H-1,2,4-triazol-3-yl)-2,4-dimethylbenzyl)-3-fluoro-2,2-dimethylpropanamide. $^1$H NMR (300 MHz, DMSO d$_6$): δ 1.08 (m, 6H), 2.15 (s, 3H), 2.19 (s, 3H), 3.34 (m, 2H), 4.25 (d, 2H), 6.91 (m, 1H), 7.15 (m, 1H), 7.25-7.27 (m, 1H), 779 (s, 3H), 8.08 (s, 1H), 12.24 (s, 1H); MS (m/z): 521.03 (M + H)$^+$. |

Intermediate-144

N-(4-Chloro-3-(5-oxo-1-(4-(trifluoromethyl)phenyl)-4,5-dihydro-1H-1,2,4-triazol-3-yl)benzyl)-2-methyl-propane-2-sulfinamide

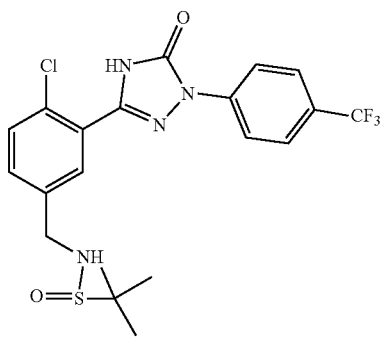 [SMILES: CC1(C)N(Cc2ccc(Cl)c(-c3nn(-c4ccc(C(F)(F)F)cc4)c(=O)[nH]3)c2)S1=O]

The title compound was prepared according to the procedure described in Example-108 by using 3-(5-(aminomethyl)-2-chlorophenyl)-1-(4-(trifluoromethyl)phenyl)-1H-1,2,4-triazol-5(4H)-one (Intermediate-63, 0.450 g, 1.22 mmol), 2-methylpropane-2-sulfinic chloride (0.205 g, 1.46 mmol), TEA (2.0 mL), DCM (10 mL) to afford 0.250 g of the desired product. $^1$H NMR (300 MHz, DMSO d$_6$): δ 1.23 (s, 9H), 4.24 (m, 2H), 7.63-7.87 (m, 4H), 7.86 (d, J=8.7 Hz, 2H), 8.19 (d, J=9.0 Hz, 2H); MS (m/z): 472.095 (M±H)$^+$.

Intermediate-145

5-Cyano-2-(difluoromethyl)nicotinoyl isocyanate

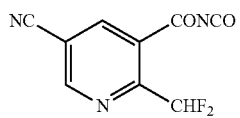

Step-1:—Preparation of ethyl 5-cyano-2-(difluoromethyl)nicotinate

The title compound was prepared according to the procedure described in step-2 of Example-134 by using ethyl 5-cyano-2-formylnicotinate (6.0 g, 0.029 mmol), DAST (11.8 mL, 0.088 mmol), DCM (200 mL) to afford 3.5 g of desired product. MS (m/z): 227.06 (M+H)$^+$.

Step-2:—Preparation of 5-cyano-2-(difluoromethyl)nicotinic acid

To a solution of ethyl 5-cyano-2-(difluoromethyl)nicotinate (1.2 g, 5.3 mmol) in THF:water (20 mL:5 mL) was added LiOH.H$_2$O (0.267 g, 6.3 mmol) at 0° C. and the reaction mass was stirred for 40-60 minutes. The reaction mass was acidified with dil. HCl and extracted with ethyl acetate. The organic layer was separated, dried over anhydrous sodium sulphate and concentrated to afford 0.700 g of the desired product. $^1$H NMR (300 MHz, DMSO d$_6$): δ 7.37-7.72 (t, J=53.7 Hz, 1H), 8.24 (s, 1H), 9.30 (s, 1H), 14.25 (br s, 1H); MS (m/z): 199.34 (M+H)$^+$.

Step-3:—Preparation of 5-cyano-2-(difluoromethyl)nicotinamide

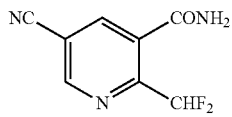

To a solution of 5-cyano-2-(difluoromethyl)nicotinic acid (0.600 g, 3.0 mmol) in dry DMF (20 mL), TBTU (10.0 g, 3.33 mmol) was added at 0° C. followed by slow addition of DIPEA (0.7 mL, 3.93 mmol). The reaction mass was stirred at 0° C. for 1 h and ammonium chloride (333 g, 60.7 mmol) was added. The reaction mass was stirred at RT for 30-48 h. After completion of reaction quenched the reaction mass with DCM, filtered off solid to afford 0.500 g of the desired product. $^1$H NMR (300 MHz, DMSO $d_6$): δ 8.16 (m, 1H), 8.63 (s, 1H), 9.22 (s, 1H).

Step-4:—Preparation of 5-cyano-2-(difluoromethyl)nicotinoyl isocyanate

The title compound was prepared according to the procedure described in step-2 of Intermediate-8 by using 5-cyano-2-(difluoromethyl)nicotinamide (1.0 g), oxalyl chloride (3.2 g, 25.3 mmol) and DCM (20 mL) to afford 1.0 g of the desired product.

Intermediate-146

N-(4-Chloro-3-(3-(4-iodophenyl)-5-oxo-4,5-dihydro-1H-1,2,4-triazol-1-yl)benzyl)-2,2,2-trifluoroacetamide

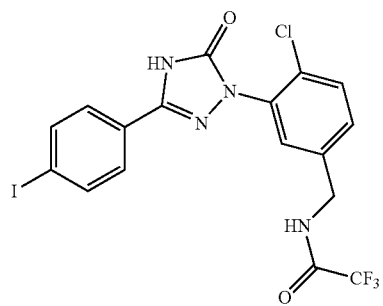 [SMILES: O=C(NCc1ccc(Cl)c(-n2nc(-c3ccc(I)cc3)[nH]c2=O)c1)C(F)(F)F]

Step-1:—Preparation N-(4-chloro-3-hydrazinylbenzyl)-2,2,2-trifluoroacetamide

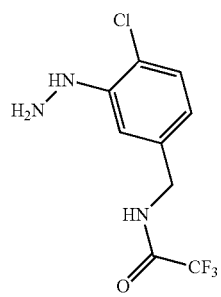 [SMILES: NNc1cc(CNC(=O)C(F)(F)F)ccc1Cl]

To a cold solution of N-(3-amino-4-chlorobenzyl)-2,2,2-trifluoroacetamide (0.500 g, 0.017 mmol) in 6N HCl (50.0 mL), aqueous solution of NaNO$_2$ (1.29 g, 0.018 mmol) was added at 0° C. and the reaction mass was stirred at 0-5° C. for 30 min. The reaction mass was added to a solution of SnCl$_2$.H$_2$O (22.18 g, 0.98 mmol) in 6N HCl at 0-5° C. and further continued stirring for 5-6 h at same temperature. The reaction mass was cooled, basified and extracted with DCM. The organic layer was separated, dried and concentrated to afford 0.700 g of the desired product. $^1$H NMR (300 MHz, DMSO $d_6$): δ 4.22 (br s, 2H), 4.29 (d, J=6.0 Hz, 2H), 6.42-6.67 (m, 2H), 7.14-7.16 (m, 2H), 9.98 (br s, 1H).

Step-2:—Preparation tert-butyl 2-(2-chloro-5-((2,2,2-trifluoroacetamido)methyl)phenyl) hydrazinecarboxylate

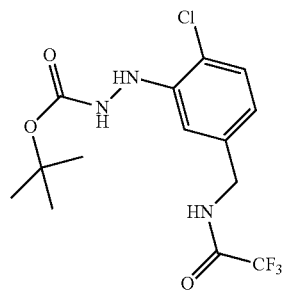 [SMILES: CC(C)(C)OC(=O)NNc1cc(CNC(=O)C(F)(F)F)ccc1Cl]

The title compound was prepared according to the procedure described in step-3 of Intermediate-7 by using N-(4-chloro-3-hydrazinylbenzyl)-2,2,2-trifluoroacetamide (0.350 g, 1.3 mmol), BOC anhydride (0.316 g, 1.4 mmol), Na$_2$CO$_3$ (1.19 g, 1.9 mmol), acetonitrile (20 mL) and water (10 mL) to afford 0.500 g of desired product. $^1$H NMR (300 MHz, DMSO $d_6$): δ 1.41 (s, 9H), 4.28 (d, J=5.7 Hz, 2H), 6.61-6.65 (m, 2H), 7.22 (d, J=8.1 Hz, 1H), 7.41 (s, 1H), 9.91 (s, 1H), 9.97 (s, 1H).

Step-3:—Preparation of N-(4-chloro-3-(4,5-dihydro-3-(4-iodophenyl)-5-oxo-1,2,4-triazol-1-yl)benzyl) isobutyramide The title compound was prepared according to the procedure described in Example-83 by using 4-iodobenzoyl isocyanate (Intermediate-67, 1.500 g), tert-butyl 2-(2-chloro-5-((2,2,2-trifluoroacetamido)methyl)phenyl) hydrazinecarboxylate (1:0 g), DCM (20 mL), and trifluoro acetic acid (5.0 mL) to afford 0.500 g of the desired product. $^1$H NMR (400 MHz, DMSO $d_6$): δ 4.44 (d, J=6.0 Hz, 2H), 7.41 (d, J=7.8 Hz, 1H), 7.52 (s, 1H), 7.60-7.67 (m, 2H), 7.81 (d, J=8.4 Hz, 1H), 7.90 (d, J=8.7 Hz, 2H), 10.09 (br s, 1H), 12.63 (s, 1H).

EXAMPLES

Example-1

2-(4-Bromophenyl)-4-(2-chloro-6-fluorophenyl)-2,5-dihydro-1,2,3,5-thiatriazole-1-oxide

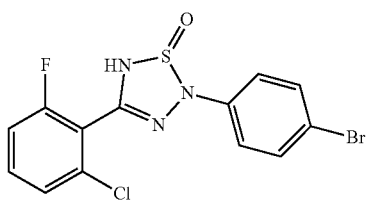 [SMILES: O=S1NC(c2c(F)cccc2Cl)=NN1c1ccc(Br)cc1]

The title compound was prepared according to the procedure described in step-4 of Intermediate-1 using N'-(4-bromophenyl)-2-chloro-6-fluorobenzenecarbohydrazonamide (step-3 of Intermediate-1, 0.100 g, 0.292 mmol), CHCl$_3$ (10 mL), pyridine (2.0 mL) and thionyl chloride (1.0 mL). The obtained product was purified with column chromatography on silica gel eluting with 0.5% MeOH: DCM to afford 0.050 g of the desired product. $^1$H NMR (300 MHz, DMSO d$_6$): δ 7.45 (t, J=6.9 Hz, 3H), 7.51-7.68 (m, 4H), 12.05 (br s, 1H); MS (m/z): 388.02 (M)$^-$.

Example-2

5-(2-Chloro-6-fluorophenyl)-2-{4-[6-(trifluoromethyl)pyridin-3-yl]phenyl}-2,4-dihydro-3H-1,2,4-triazol-3-one

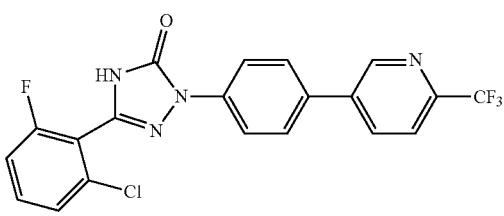 [SMILES: O=c1[nH]c(-c2c(F)cccc2Cl)nn1-c1ccc(-c2ccc(C(F)(F)F)nc2)cc1]

To a solution of 2-(4-bromophenyl)-5-(2-chloro-6-fluorophenyl)-2,4-dihydro-3H-1,2,4-triazol-3-one (Intermediate-1, 0.100 g, 0.271 mmol) in DMSO (3.0 mL) was added [6-(trifluoromethyl)pyridin-3-yl]boronic acid (0.078 g, 0.40 mmol), K$_2$CO$_3$ (0.112 g, 0.81 mmol) and tetrakistriphenyl phosphine palladium (0) (0.062 g, 0.054 mmol). The reaction mass was stirred at 110° C. for 24-48 h. The reaction mass was quenched in water and extracted with ethyl acetate. The organic layer was dried over anhydrous sodium sulphate and concentrated. The obtained product was purified with column chromatography on silica gel eluting with 4-5% EA: DCM to afford 0.030 g of the desired product. $^1$H NMR (300 MHz, DMSO d$_6$): δ 7.38-7.48 (m, 1H), 7.61-7.63 (m, 1H), 7.88-7.99 (m, 4H), 8.01-8.17 (m, 2H), 8.41 (d, J=7.8 Hz, 1H), 9.14 (s, 1H), 12.60 (br s, 1H). MS (m/z): 435.25 (M+H)$^+$.

Example-3

5-(2-Chloro-6-fluorophenyl)-2-(4-{[2-(trifluoromethyl)phenyl]ethynyl}phenyl)-2,4-dihydro-3H-1,2,4-triazol-3-one

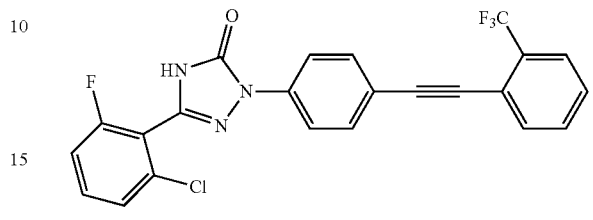

To a solution of 5-(2-chloro-6-fluorophenyl)-2-(4-ethynylphenyl)-2,4-dihydro-3H-1,2,4-triazol-3-one (Intermediate-2, 0.100 g, 0.319 mmol) in DMSO was added 1-iodo-2-(trifluoromethyl)benzene (0.13 g, 0.479 mmol), TBAF (0.301 g, 0.958 mmol) and bis(triphenylphosphine)palladium(II) chloride (0.050 g, 0.071 mmol). The reaction mass was stirred at 110° C. for 5-6 h. The reaction mass was quenched in water and extracted with DCM and concentrated. The obtained product was purified with column chromatography on silica gel eluting with 2.0% EA: DCM to afford 0.040 g of the desired product. $^1$H NMR (300 MHz, DMSO d$_6$): δ 7.50 (t, J=9.3 Hz, 1H), 7.57-7.73 (m, 6H), 7.82 (br s, 2H), 8.02 (d, J=8.7 Hz, 2H), 12.72 (br s, 1H). MS (m/z): 458.26 (M+H)$^+$.

Example-4

5-[2-Fluoro-6-(4-methylthiophen-2-yl)phenyl]-2-[4-(4-methylthiophen-2-yl)phenyl]-2,4-dihydro-3H-1,2,4-triazol-3-one

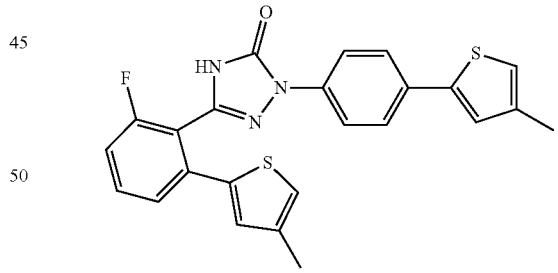

The title compound was prepared according to the procedure described in Example-2 using 2-(4-bromophenyl)-5-(2-chloro-6-fluorophenyl)-2,4-dihydro-3H-1,2,4-triazol-3-one (Intermediate-1, 0.100 g, 0.271 mmol), (4-methylthiophen-2-yl)boronic acid (0.059 g, 0.407 mmol), K$_2$CO$_3$ (0.112 g, 0.81 mmol), tetrakistriphenyl phosphine palladium (0) (0.062 g, 0.054 mmol) and DMSO (3.0 mL) to afford 0.020 g of desired product. $^1$H NMR (300 MHz, CDCl$_3$): δ 2.29 (s, 611), 6.86 (s, 1H), 6.91 (s, 2H), 7.13 (s, 1H), 7.21 (d, J=9.3 Hz, 1H), 7.39 (d, J=7.8 Hz, 1H), 7.48-7.55 (m, 1H), 7.61 (d, J=8.1 Hz, 2H), 7.92 (d, J=9.0 Hz, 2H), 9.27 (br s, 1H). MS (m/z): 384.88 (M–H)$^-$.

Example-5

5-(2-Chloro-6-fluorophenyl)-2-{4-[(6-fluoropyridin-3-yl)ethynyl]phenyl}-2,4-dihydro-3H-1,2,4-triazol-3-one

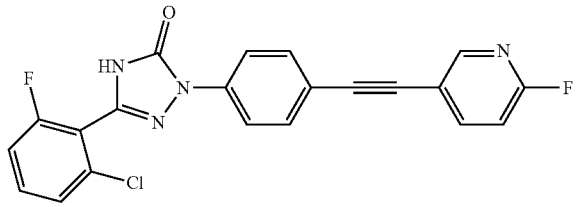 [SMILES: O=c1[nH]c(-c2c(F)cccc2Cl)nn1-c1ccc(C#Cc2ccc(F)nc2)cc1]

The title compound was prepared according to the procedure described in Example-3 using 5-(2-chloro-6-fluorophenyl)-2-(4-ethynylphenyl)-2,4-dihydro-3H-1,2,4-triazol-3-one (Intermediate-2, 0.100 g, 0.319 mmol), 2-fluoro-5-iodopyridine (0.106 g, 0.479 mmol), TBAF (0.201 g, 0.638 mmol), bis(triphenylphosphine)palladium(II) chloride (0.020 g, 0.028 mmol) and DMSO (3.0 mL). The obtained product was purified with column chromatography on silica gel eluting with 2.0% MeOH: DCM to afford 0.030 g of the desired product. $^1$H NMR (300 MHz, DMSO d$_6$): δ 7.30 (d, J=7.5 Hz, 1H), 7.51 (t, J=8.7 Hz, 1H), 7.58 (d, J=8.4 Hz, 1H), 7.70 (d, J=8.1 Hz, 3H), 8.03 (d, J=8.4 Hz, 2H), 8.20 (t, J=7.2 Hz, 1H), 8.49 (s, 1H), 12.73 (br s, 1H). MS (m/z): 407.33 (M−H)$^-$.

Example-6

5-(2-Chloro-6-fluorophenyl)-2-{4-[(4-chloro-2-fluorophenyl)ethynyl]phenyl}-2,4-dihydro-3H-1,2,4-triazol-3-one

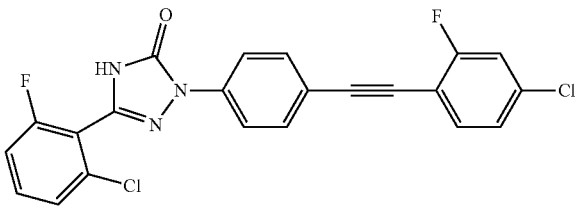 [SMILES: O=c1[nH]c(-c2c(F)cccc2Cl)nn1-c1ccc(C#Cc2ccc(Cl)cc2F)cc1]

The title compound was prepared according to the procedure described in Example-3 using 5-(2-chloro-6-fluorophenyl)-2-(4-ethynylphenyl)-2,4-dihydro-3H-1,2,4-triazol-3-one (Intermediate-2, 0.100 g, 0.319 mmol), 4-chloro-2-fluoro-1-iodobenzene (0.123 g, 0.479 mmol), TBAF (0.201 g, 0.638 mmol), bis(triphenylphosphine)palladium(II) chloride (0.020 g, 0.028 mmol) and DMSO (3.0 ml). The obtained crude product was purified with column chromatography on silica gel eluting with 1.0% MeOH: DCM to afford 0.045 g of the desired product. $^1$H NMR (300 MHz, DMSO d$_6$): δ 7.38 (d, J=8.4 Hz, 1H), 7.50 (t, J=8.7 Hz, 1H), 7.57-7.70 (m, 6H), 8.02 (d, J=8.7 Hz, 2H), 12.74 (br s, 1H). MS (m/z): 442.38 (M+).

Example-7

5-(2-Chloro-6-fluorophenyl)-2-(4-{[2-chloro-4-(trifluoromethyl)phenyl]ethynyl}phenyl)-2,4-dihydro-3H-1,2,4-triazol-3-one

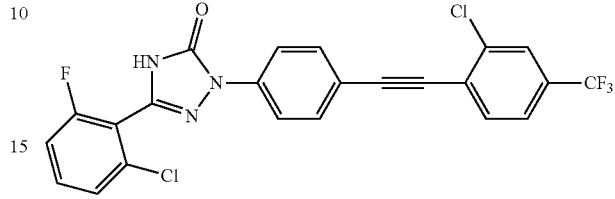

The title compound was prepared according to the procedure described in Example-3 using 5-(2-chloro-6-fluorophenyl)-2-(4-ethynylphenyl)-2,4-dihydro-3H-1,2,4-triazol-3-one (Intermediate-2, 0.100 g, 0.319 mmol), 2-chloro-1-iodo-4-(trifluoromethyl)benzene (0.147 g, 0.479 mmol), TBAF (0.201 g, 0.638 mmol), bis(triphenylphosphine)palladium(II) chloride (0.020 g, 0.028 mmol) and DMSO (3.0 mL). The obtained product was purified with column chromatography on silica gel eluting with 1.0% MeOH: DCM to afford 0.040 g of the desired product. $^1$H NMR (300 MHz, DMSO d$_6$): δ 7.51 (d, J=8.7 Hz, 1H), 7.59 (d, J=7.8 Hz, 1H), 7.67-7.87 (m, 3H), 7.84 (t, J=8.4 Hz, 2H), 8.05 (d, J=8.4 Hz, 2H), 8.11 (s, 1H), 12.75 (br s, 1H). MS (m/z): 492.22 (M+).

Example-8

5-(2-Chloro-6-fluorophenyl)-2-[3'-(trifluoromethoxy)biphenyl-4-yl]-2,4-dihydro-3H-1,2,4-triazol-3-one

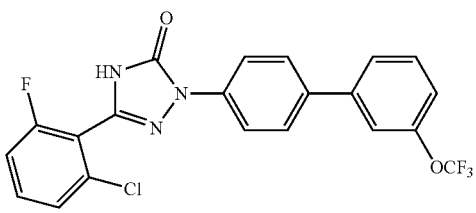 [SMILES: O=c1[nH]c(-c2c(F)cccc2Cl)nn1-c1ccc(-c2cccc(OC(F)(F)F)c2)cc1]

The title compound was prepared according to the procedure described in Example-2 using 5-(2-chloro-6-fluorophenyl)-2-(4-iodophenyl)-2,4-dihydro-3H-1,2,4-triazol-3-one (step-4 of Intermediate-2, 0.100 g, 0.242 mmol), [3-(trifluoromethoxy)phenyl]boronic acid (0.075 g, 0.363 mmol), K$_2$CO$_3$ (0.100 g, 0.726 mmol), tetrakistriphenyl phosphine palladium (0) (0.055 g, 0.048 mmol) and DMSO (3.0 mL) to afford 0.025 g of desired product. $^1$H NMR (300 MHz, CDCl$_3$): δ 7.19 (d, J=8.4 Hz, 1H), 7.35 (s, 1H), 7.39 (d, J=7.8 Hz, 1H), 7.46 (d, J=6.6 Hz, 1H), 7.53 (t, J=7.8 Hz, 2H), 7.65 (d, J=8.4 Hz, 2H), 8.12 (d, J=8.4 Hz, 214), 10.01 (br s, 1H).

Example-9

5-(2-Chloro-6-fluorophenyl)-2-(4-{[3-(trifluoromethyl)phenyl]amino}phenyl)-2,4-dihydro-3H-1,2,4-triazol-3-one

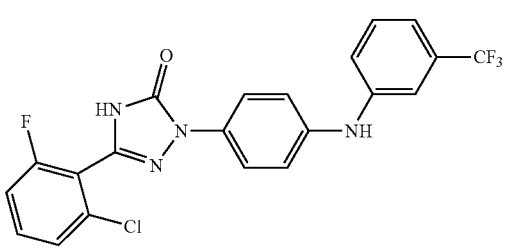 [SMILES: O=c1[nH]c(-c2c(F)cccc2Cl)nn1-c1ccc(Nc2cccc(C(F)(F)F)c2)cc1]

To a solution of 5-(2-chloro-6-fluorophenyl)-2-(4-iodophenyl)-2,4-dihydro-3H-1,2,4-triazol-3-one (step-4 of Intermediate-2, 0.100 g, 0.242 mmol) in toluene (5.0 mL) was added 3-(trifluoromethyl)aniline (0.076 g, 0.292 mmol), NaOtBu (0.035 g, 0.360 mmol), tris(dibenzylideneacetone)dipalladium(0) (0.022 g, 0.024 mmol) and 9,9-dimethyl-4,5-bis(diphenylphosphino)xanthene (0.021 g, 0.036 mmol). The reaction mixture was refluxed for 12 h. The reaction mass was quenched in water and extracted with ethyl acetate. The organic layer was dried over anhydrous sodium sulphate and concentrated. The obtained product was purified with column chromatography on silica gel eluting with 10% EA: DCM to afford 0.030 g of the desired product. $^1$H NMR (300 MHz, DMSO $d_6$): δ 7.09 (d, J=7.5 Hz, 1H), 7.20 (s, 1H), 7.24 (d, J=5.7 Hz, 2H), 7.31 (d, J=8.1 Hz, 1H), 7.41-7.59 (m, 3H), 7.69 (d, J=7.8 Hz, 1H), 7.81 (d, J=8.7 Hz, 2H), 8.64 (s, 1H), 12.51 (s, 1H). MS (m/z): 449.31 (M+H)$^+$.

Example-10

5-(2-Chloro-6-fluorophenyl)-2-{4-[(2,5-dichlorophenyl)ethynyl]phenyl}-2,4-dihydro-3H-1,2,4-triazol-3-one

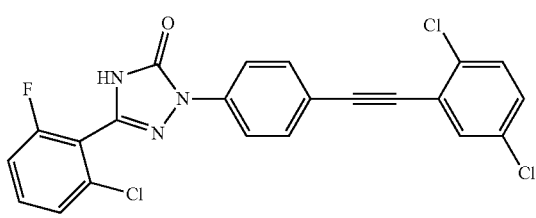 [SMILES: O=c1[nH]c(-c2c(F)cccc2Cl)nn1-c1ccc(C#Cc2cc(Cl)ccc2Cl)cc1]

The title compound was prepared according to the procedure described in Example-3 using 5-(2-chloro-6-fluorophenyl)-2-(4-ethynylphenyl)-2,4-dihydro-3H-1,2,4-triazol-3-one (Intermediate-2, 0.100 g, 0.319 mmol), 1,4-dichloro-2-iodobenzene (0.130 g, 0.470 mmol), TBAF (0.201 g, 0.638 mmol), bis(triphenylphosphine)palladium(II) chloride (0.020 g, 0.028 mmol) and DMSO (3.0 mL). The obtained product was purified with column chromatography on silica gel eluting with 1.0% MeOH: DCM to afford 0.040 g of the desired product. $^1$H NMR (300 MHz, DMSO $d_6$): δ 7.50-7.72 (m, 7H), 7.82 (s, 1H), 8.05 (d, J=8.7 Hz, 2H), 12.75 (br s, 1H). MS (m/z): 458.31 (M+).

Example-11

1-(4-Bromophenyl)-3-(2-chloro-6-fluorophenyl)-N-(3-methoxypropyl)-1H-1,2,4-triazol-5-amine

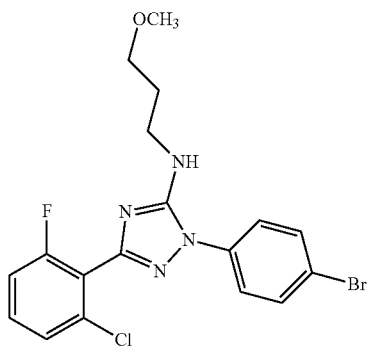 [SMILES: COCCCNc1nc(-c2c(F)cccc2Cl)nn1-c1ccc(Br)cc1]

To a solution of 1-(4-bromophenyl)-5-chloro-3-(2-chloro-6-fluorophenyl)-1H-1,2,4-triazole (Intermediate-3, 0.100 g, 0.257 mmol) in DMF (3.0 mL) was added 3-methoxypropan-1-amine (0.035 g, 0.386 mmol) and DIPEA (1.0 mL). The reaction mass was stirred at 80° C. for 5-6 h. The reaction mass was quenched in water and extracted with ethyl acetate. The organic layer was dried over anhydrous sodium sulphate and concentrated to afford 0.040 g of desired product. $^1$H NMR (300 MHz, DMSO $d_6$): δ 1.92 (d, J=5.4 Hz, 2H), 2.34 (t, J=7.5 Hz, 2H), 3.28 (s, 3H), 3.56-3.64 (m, 2H), 5.69 (m, 1H), 7.06-7.15 (m, 1H), 7.22-7.49 (m, 2H), 7.54 (d, J=10.2 Hz, 2H), 7.64 (d, J=8.4 Hz, 2H). MS (m/z): 441.19 (M+H)$^+$.

Example-12

1-(4-((3-Chloro-2-fluorophenyl)ethynyl)phenyl)-3-(2-chloro-6-fluorophenyl)-1H-1,2,4-triazol-5(4H)-one

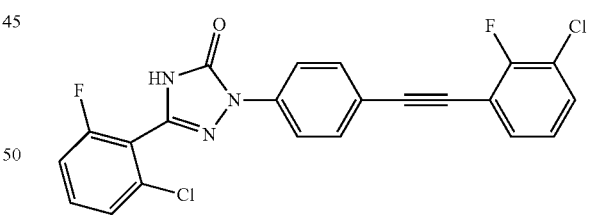

The title compound was prepared according to the procedure described in Example-3 using 5-(2-chloro-6-fluorophenyl)-2-(4-ethynylphenyl)-2,4-dihydro-3H-1,2,4-triazol-3-one (Intermediate-2, 0.100 g, 0.319 mmol), 1-chloro-2-fluoro-3-iodobenzene (0.123 g, 0.470 mmol), TBAF (0.201 g, 0.638 mmol), bis(triphenylphosphine)palladium(II) chloride (0.020 g, 0.028 mmol) and DMSO (3.0 mL). The obtained product was purified with column chromatography on silica gel eluting with 1.0% MeOH: DCM to afford 0.040 g of the desired product. $^1$H NMR (300 MHz, DMSO $d_6$): δ 7.29 (t, J=7.8 Hz, 1H), 7.50 (t, J=8.7 Hz, 1H), 7.57-7.72 (m, 6H), 8.04 (d, J=9.0 Hz, 2H), 12.74 (br s, 1H). MS (m/z): 442.35 (M+).

Example-13

5-(2-Chloro-6-fluorophenyl)-2-(4-{[5-(trifluoromethyl)pyridin-2-yl]ethynyl}phenyl)-2,4-dihydro-3H-1,2,4-triazol-3-one

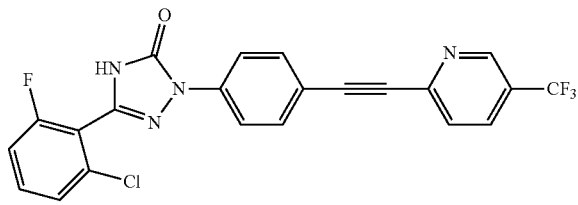 [SMILES: O=c1[nH]c(-c2c(F)cccc2Cl)nn1-c1ccc(C#Cc2ccc(C(F)(F)F)cn2)cc1]

The title compound was prepared according to the procedure described in Example-3 using 5-(2-chloro-6-fluorophenyl)-2-(4-ethynylphenyl)-2,4-dihydro-3H-1,2,4-triazol-3-one (Intermediate-2, 0.100 g, 0.319 mmol), 2-bromo-5-(trifluoromethyl)pyridine (0.108 g, 0.479 mmol), TBAF (0.201 g, 0.638 mmol), bis(triphenylphosphine)palladium (II) chloride (0.020 g, 0.028 mmol) and DMSO (3.0 mL). The obtained product was purified with column chromatography on silica gel eluting with 1.0% MeOH: DCM to afford 0.030 g of the desired product. $^1$H NMR (300 MHz, DMSO d$_6$): δ 7.51 (t, J=8.7 Hz, 1H), 7.59 (d, J=7.8 Hz, 1H), 7.70 (t, J=6.3 Hz, 1H), 7.79 (d, J=8.7 Hz, 2H), 7.89 (d, J=8.1 Hz, 1H), 8.06 (d, J=8.4 Hz, 2H), 8.29 (d, J=7.8 Hz, 1H), 9.00 (s, 1H), 12.75 (br s, 1H). MS (m/z): 459.37 (M+).

Example-14

5-(2-Chloro-6-fluorophenyl)-2-{4-[(3-chloropyridin-4-yl)ethynyl]phenyl}-2,4-dihydro-3H-1,2,4-triazol-3-one

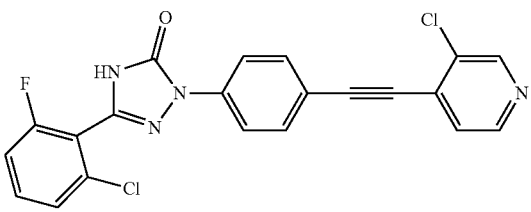 [SMILES: O=c1[nH]c(-c2c(F)cccc2Cl)nn1-c1ccc(C#Cc2ccncc2Cl)cc1]

The title compound was prepared according to the procedure described in Example-3 using 5-(2-chloro-6-fluorophenyl)-2-(4-ethynylphenyl)-2,4-dihydro-3H-1,2,4-triazol-3-one (Intermediate-2, 0.100 g, 0.319 mmol), 3-chloro-4-iodopyridine (Intermediate-4, 0.114 g, 0.429 mmol), TBAF (0.201 g, 0.638 mmol), bis(triphenylphosphine)palladium (II) chloride (0.020 g, 0.028 mmol) and DMSO (3.0 mL). The obtained product was purified with column chromatography on silica gel eluting with 1.0% MeOH: DCM to afford 0.035 g of the desired product. $^1$H NMR (300 MHz, DMSO d$_6$): δ 7.49 (1, J=8.7 Hz, 1H), 7.56 (d, J=11.7 Hz, 2H), 7.60-7.77 (m, 3H), 8.08 (d, J=8.4 Hz, 2H), 8.57 (d, J=5.1 Hz, 1H), 8.78 (s, 1H), 12.76 (br s, 1H). MS (m/z): 425.43 (M+).

Example-15

3-(2-Chloro-6-fluorophenyl)-1-(4-((2-morpholinopyrimidin-5-yl)ethynyl)phenyl)-1H-1,2,4-triazol-5(4H)-one

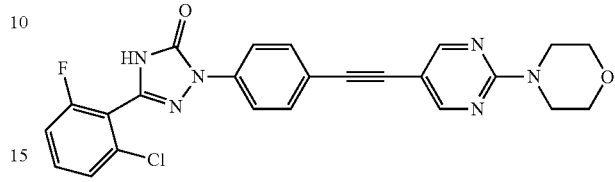

The title compound was prepared according to the procedure described in Example-3 using 5-(2-chloro-6-fluorophenyl)-2-(4-ethynylphenyl)-2,4-dihydro-3H-1,2,4-triazol-3-one (Intermediate-2, 0.100 g, 0.319 mmol), 4-(5-iodopyrimidin-2-yl)morpholine (Intermediate-5, 0.139 g, 0.470 mmol), TBAF (0.201 g, 0.638 mmol), bis(triphenylphosphine)palladium(II) chloride (0.020 g, 0.028 mmol) and DMSO (3.0 mL). The obtained product was purified with column chromatography on silica gel eluting with 2.0% MeOH: DCM to afford 0.035 g of the desired product. $^1$H NMR (300 MHz, DMSO d$_6$): δ 3.67 (br s, 4H), 3.76 (br s, 4H), 7.47-7.71 (m, 5H), 7.98 (d, J=9.0 Hz, 2H), 8.58 (s, 2H), 12.69 (s, 1H).

Example-16

5-(2-Chloro-6-fluorophenyl)-2-(4-{[6-(morpholin-4-yl)pyridin-3-yl]ethynyl}phenyl)-2,4-dihydro-3H-1,2,4-triazol-3-one

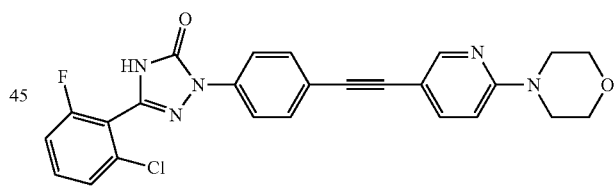

The title compound was prepared according to the procedure described in Example-3 using 5-(2-chloro-6-fluorophenyl)-2-(4-ethynylphenyl)-2,4-dihydro-3H-1,2,4-triazol-3-one (Intermediate-2, 0.100 g, 0.319 mmol), 4-(5-iodopyridin-2-yl)morpholine (Intermediate-6, 0.139 g, 0.470 mmol), TBAF (0.201 g, 0.638 mmol), bis(triphenylphosphine)palladium(II) chloride (0.020 g, 0.028 mmol) and DMSO (3.0 mL). The obtained product was purified with column chromatography on silica gel eluting with 2.0% MeOH: DCM to afford 0.020 g of the desired product. $^1$H NMR (300 MHz, DMSO d$_6$): δ 3.58-3.61 (m, 4H), 3.82-3.85 (br s, 4H), 6.64 (d, J=8.7 Hz, 1H), 7.19 (t, 0.1=8.7 Hz, 1H), 7.36-7.47 (m, 2H), 7.58 (d, J=8.4 Hz, 2H), 7.63-7.67 (m, 1H), 8.03 (d, J=9.0 Hz, 2H), 8.38 (s, 1H), 10.14 (br s, 1H); MS (m/z): 473.64 (M−H)⁻.

Example-17

4-[3-(2-Chloro-6-fluorophenyl)-5-oxo-4,5-dihydro-1H-1,2,4-triazol-1-yl]-N-(cyclopropylmethyl)benzamide

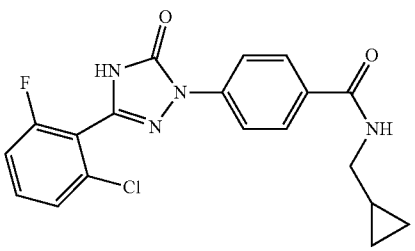 [SMILES: O=C(NCC1CC1)c1ccc(-n2nc(-c3c(F)cccc3Cl)[nH]c2=O)cc1]

To a solution of 4-[3-(2-chloro-6-fluorophenyl)-5-oxo-4,5-dihydro-1H-1,2,4-triazol-1-yl]benzoic acid (Intermediate-9, 0.100 g, 0.290 mmol) in THF was added di-isopropyl ethyl amine (1.0 mL) and TBTU (0.193 g, 0.590 mmol). The reaction mass was stirred at RT for 1 h. 1-cyclopropylmethanamine (0.048 g, 0.440 mmol) was added to the reaction mass and further stirred at RT for 15 h. The reaction mass was quenched in water and extracted with ethyl acetate. The organic layer was washed with NaHCO$_3$ solution and water, dried over anhydrous sodium sulphate and concentrated to afford 0.025 g of desired product. $^1$H NMR (300 MHz, DMSO d$_6$): δ 0.23 (br s, 1H), 0.44 (d, J=7.5 Hz, 1H), 0.83-0.85 (m, 1H), 1.06-1.024 (m, 1H), 1.31 (m, 1H), 3.14 (t, J=5.7 Hz, 2H), 7.50 (t, J=9.0 Hz, 1H), 7.58 (d, J=7.2 Hz, 1H), 7.67-7.72 (m, 1H), 7.95-8.00 (m, 4H), 8.59 (m, 1H), 12.70 (br s, 1H); MS (m/z): 387.35 (M+H)$^+$.

Example-18

4-[3-(2-Chloro-6-fluorophenyl)-5-oxo-4,5-dihydro-1H-1,2,4-triazol-1-yl]-N-[2-(trifluoromethyl)benzyl]benzamide

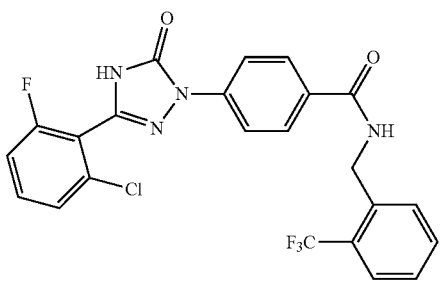 [SMILES: O=C(NCc1ccccc1C(F)(F)F)c1ccc(-n2nc(-c3c(F)cccc3Cl)[nH]c2=O)cc1]

The mixture of methyl 4-[3-(2-chloro-6-fluorophenyl)-5-oxo-4,5-dihydro-1H-1,2,4-triazol-1-yl]benzoate (step-2 of Intermediate-9, 0.100 g, 0.280 mmol), 1-[2-(trifluoromethyl)phenyl]methanamine (0.075 g, 0.430 mmol), 1,2,4-triazole (0.004 g, 0.05 mmol) and DBU (0.009 g, 0.005 mmol) was heated at 80-90° C. in seal tube for 15 h. The reaction mass was quenched in water and extracted with ethyl acetate. The organic layer was washed with dilute HCl and water, dried over anhydrous sodium sulphate and concentrated to afford 0.030 g of desired product. $^1$H NMR (300 MHz, DMSO d$_6$): δ 4.66-4.68 (d, J=4.2 Hz, 2H), 7.45-7.75 (m, 7H), 8.05 (s, 4H), 9.16 (br s, 1H), 12.73 (br s, 1H); MS (m/z): 489.42 (M–H)$^-$.

Example-19

5-[3-(2-Chloro-6-fluorophenyl)-5-oxo-4,5-dihydro-1H-1,2,4-triazol-1-yl]-N-(cyclopropylmethyl)-2-methoxybenzamide

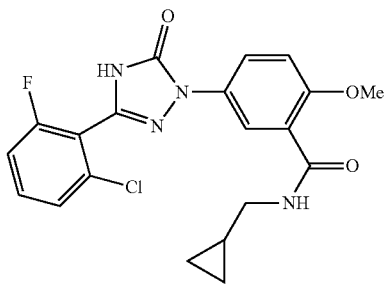 [SMILES: COc1ccc(-n2nc(-c3c(F)cccc3Cl)[nH]c2=O)cc1C(=O)NCC1CC1]

The title compound was prepared according to the procedure described in Example-17 by using 5-[3-(2-chloro-6-fluorophenyl)-5-oxo-4,5-dihydro-1H-1,2,4-triazol-1-yl]-2-methoxybenzoic acid (Intermediate-11, 0.100 g, 0.270 mmol), THF (5 mL), di-isopropyl ethyl amine (1.0 mL), TBTU (0.177 g, 0.540 mmol) and 1-cyclopropylmethanamine (0.045 g, 0.410 mmol) to afford 0.035 g of desired product. $^1$H NMR (300 MHz, DMSO d$_6$): δ 0.23-0.24 (m, 2H), 0.41-0.44 (m, 2H), 1.03 (m, 1H), 3.17 (t, J=7.2 Hz, 2H), 3.91 (s, 3H), 7.25 (d, =9.0 Hz, 1-1), 7.49 (t, J=8.7 Hz, 1H), 7.57 (d, 0.1=7.8 Hz, 1H), 7.65-7.70 (m, 1H), 7.98 (d, J=9.0 Hz, 1H), 8.23 (s, 1H), 8.32 (m, 1-1), 12.57 (s, 1H); MS (m/z): 415.23 (M–H)$^-$.

Example-20

5-[3-(2-Chloro-6-fluorophenyl)-5-oxo-4,5-dihydro-1H-1,2,4-triazol-1-yl]-2-methoxy-N-[2-(trifluoromethyl)benzyl]benzamide

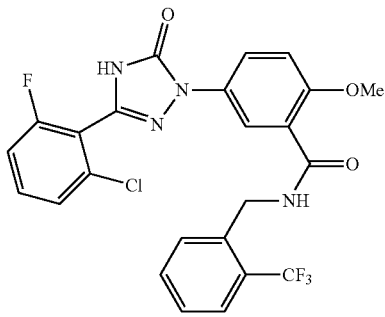 [SMILES: COc1ccc(-n2nc(-c3c(F)cccc3Cl)[nH]c2=O)cc1C(=O)NCc1ccccc1C(F)(F)F]

The title compound was prepared according to the procedure described in Example-17 by using 5-[3-(2-chloro-6-fluorophenyl)-5-oxo-4,5-dihydro-1H-1,2,4-triazol-1-yl]-2-methoxybenzoic acid (Intermediate-11, 0.100 g, 0.270 mmol), THF (5 mL), di-isopropyl ethyl amine (1.0 mL), TBTU (0.177 g, 0.540 mmol) and 1-[2-(trifluoromethyl)phenyl]methanamine (0.072 g, 0.410 mmol) to afford 0.035 g of desired product. $^1$H NMR (300 MHz, DMSO d$_6$): δ 3.95

(s, 3H), 4.62-4.71 (br s, 2H), 7.30 (d, J=8.7 Hz, 1H), 7.46-7.52 (m, 2H), 7.56-7.59 (m, 2H), 7.65-7.75 (m, 3H), 8.02 (dd, J=2.4 Hz, 1H), 8.28 (s, 1H), 8.90 (br s, 1H), 12.58 (s, 1H); MS (m/z): 519.30 (M–H)⁻.

Example-21

5-[3-(2-Chloro-6-fluorophenyl)-5-oxo-4,5-dihydro-1H-1,2,4-triazol-1-yl]-2-methoxy-N-{1-[2-(trifluoromethyl)phenyl]cyclopropyl}benzamide

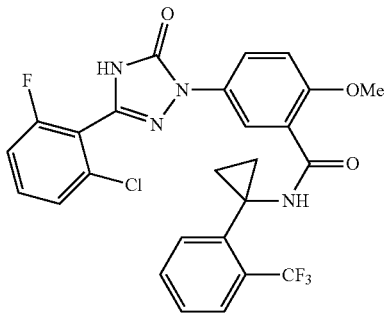 [SMILES: COc1ccc(-n2nc(-c3c(F)cccc3Cl)[nH]c2=O)cc1C(=O)NC1(c2ccccc2C(F)(F)F)CC1]

The title compound was prepared according to the procedure described in Example-17 by using 5-[3-(2-chloro-6-fluorophenyl)-5-oxo-4,5-dihydro-1H-1,2,4-triazol-1-yl]-2-methoxybenzoic acid (Intermediate-11, 0.100 g, 0.270 mmol), THF (5 mL), di-isopropyl ethyl amine (1.0 mL), TBTU (0.177 g, 0.540 mmol) and 1-[2-(trifluoromethyl)phenyl]cyclopropanamine (Intermediate-12, 0.066 g, 0.329 mmol) to afford 0.025 g of desired product. ¹H NMR (300 MHz, DMSO d₆): δ 1.26-1.28 (m, 4H), 3.91 (s, 3H), 7.24 (d, J=9.3 Hz, 1H), 7.11-7.48 (m, 6H), 7.98 (t, J=7.5 Hz, 2H), 8.27 (s, 1H), 8.74 (s, 1H), 12.56 (br s, 1H); MS (m/z): 545.31 (M–H)⁻.

Example-22

4-[3-(2-Chloro-6-fluorophenyl)-5-oxo-4,5-dihydro-1H-1,2,4-triazol-1-yl]-N-{1-[4-(trifluoromethyl)phenyl]cyclopropyl}benzamide

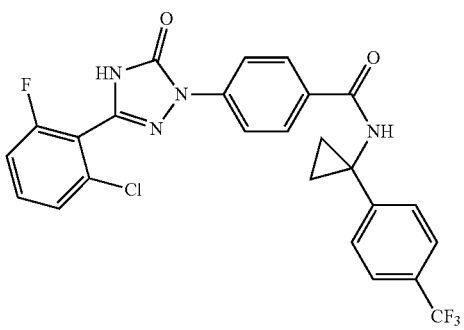 [SMILES: O=C(NC1(c2ccc(C(F)(F)F)cc2)CC1)c1ccc(-n2nc(-c3c(F)cccc3Cl)[nH]c2=O)cc1]

The title compound was prepared according to the procedure described in Example-17 by using 4-[3-(2-chloro-6-fluorophenyl)-5-oxo-4,5-dihydro-1H-1,2,4-triazol-1-yl] benzoic acid (Intermediate-9, 0.100 g, 0.290 mmol), THF (5 mL), di-isopropyl ethyl amine (2.0 mL), TBTU (0.193 g, 0.590 mmol) and 1-[4-(trifluoromethyl)phenyl]cyclopropanamine (Intermediate-13, 0.073 g, 0.350 mmol) to afford 0.030 g of desired product. ¹H NMR (300 MHz, DMSO d₆): δ 1.35 (s, 4H), 7.36 (d, J=7.8 Hz, 2H), 7.46-7.70 (m, 5H), 8.01 (s, 4H), 9.30 (s, 1H), 12-13 (br s, 1H); MS (m/z): 515.23 (M–H)⁻.

Example-23

5-[3-(2-Chloro-6-fluorophenyl)-5-oxo-4,5-dihydro-1H-1,2,4-triazol-1-yl]-2-methoxy-N-[1-[4-(trifluoromethyl)phenyl]cyclopropyl]benzamide

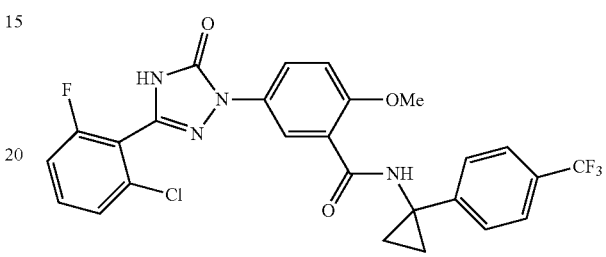

The title compound was prepared according to the procedure described in Example-17 by using 5-[3-(2-chloro-6-fluorophenyl)-5-oxo-4,5-dihydro-1H-1,2,4-triazol-1-yl]-2-methoxybenzoic acid (Intermediate-11, 0.100 g, 0.270 mmol), THF (10 mL), di-isopropyl ethyl amine (10.0 mL), TBTU (0.177 g, 0.540 mmol) and 1-[4-(trifluoromethyl)phenyl]cyclopropanamine (intermediate-13, 0.066 g, 0.320 mmol) to afford 0.025 g of desired product. ¹H NMR (300 MHz, DMSO d₆): δ 1.23 (s, 4H), 3.94 (s, 3H), 7.26 (d, J=9.0 Hz, 1H), 7.42 (d, J=8.4 Hz, 3H), 7.30-7.48 (m, 4H), 7.99 (d, J=9.3 Hz, 1H), 8.05 (s, 1H), 8.96 (s, 1H), 12.51 (br s, 1H); MS (m/z): 547.15 (M⁺).

Example-24

4-(3-(2-Chloro-6-fluorophenyl)-5-oxo-4,5-dihydro-1H-1,2,4-triazol-1-yl)-N-(1-(2-(trifluoromethyl)phenyl)cyclopropyl)benzamide

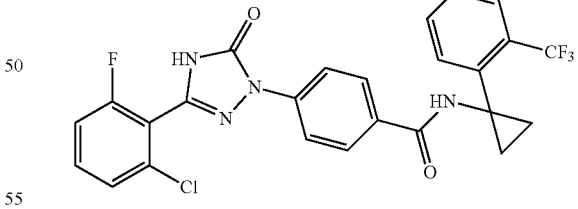

The title compound was prepared according to the procedure described in Example-17 by using 4-[3-(2-chloro-6-fluorophenyl)-5-oxo-4,5-dihydro-1H-1,2,4-triazol-1-yl] benzoic acid (Intermediate-9, 0.100 g, 0.290 mmol), THF (10 mL), di-isopropyl ethyl amine (10.0 mL), TBTU (0.177 g, 0.540 mmol) and 1-[2-(trifluoromethyl)phenyl]cyclopropanamine (Intermediate-12, 0.035 g, 0.350 mmol) to afford 0.020 g of desired product. ¹H NMR (300 MHz, DMSO d₆): δ 1.23 (s, 2H), 1.31 (s, 2H), 7.59 (d, J=7.2 Hz, 2H), 7.65-7.68 (m, 4H), 7.82 (d, J=12.0 Hz, 2H), 7.88-8.02 (m, 3H), 8.77 (s, 1H), 12.60 (br s, 1H); MS (m/z): 517.03 (M⁺).

Example-25

4-[3-(2-Chloro-6-fluorophenyl)-5-oxo-4,5-dihydro-1H-1,2,4-triazol-1-yl]-2-methoxy-N-[2-(trifluoromethyl)benzyl]benzamide

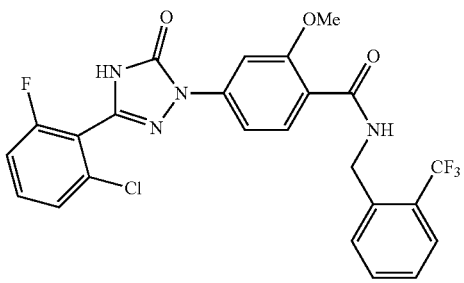 [SMILES: COc1cc(-n2nc(-c3c(F)cccc3Cl)[nH]c2=O)ccc1C(=O)NCc1ccccc1C(F)(F)F]

The title compound was prepared according to the procedure described in Example-17 by using 4-(3-(2-chloro-6-fluorophenyl)-5-oxo-4,5-dihydro-1H-1,2,4-triazol-1-yl)-2-methoxybenzoic acid (Intermediate-15, 0.100 g, 0.270 mmol), THF (5 mL), di-isopropyl ethyl amine (1.0 mL), TBTU (0.177 g, 0.540 mmol) and 1-[2-(trifluoromethyl)phenyl]methanamine (0.072 g, 0.410 mmol) to afford 0.025 g of desired product. $^1$H NMR (300 MHz, DMSO d$_6$): δ 3.96 (s, 3H), 4.70 (d, I=4.8 Hz, 2H), 7.45-7.50 (m, 3H), 7.57 (t, J=8.4 Hz, 2H), 7.67 (t, J=8.7 Hz, 2H), 7.71 (d, J=9.3 Hz, 2H), 7.92 (d, J=8.4 Hz, 1H), 8.80 (t, 1H), 12.77 (br s, 1H); MS (m/z): 519.43 (M−H)$^−$.

Example-26

4-(3-(2-Chloro-6-fluorophenyl)-5-oxo-4,5-dihydro-1H-1,2,4-triazol-1-yl)-2-methoxy-N-(1-(2-(trifluoromethyl)phenyl)cyclopropyl)benzamide

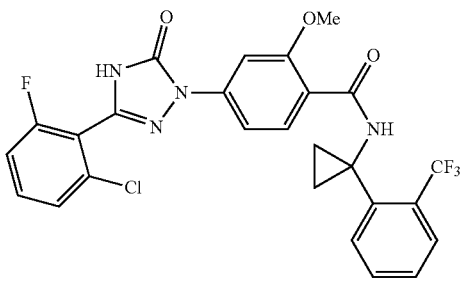 [SMILES: COc1cc(-n2nc(-c3c(F)cccc3Cl)[nH]c2=O)ccc1C(=O)NC1(c2ccccc2C(F)(F)F)CC1]

The title compound was prepared according to the procedure described in Example-17 by using 4-(3-(2-chloro-6-fluorophenyl)-5-oxo-4,5-dihydro-1H-1,2,4-triazol-1-yl)-2-methoxybenzoic acid (Intermediate-15, 0.100 g, 0.270 mmol), THF (5 mL), di-isopropyl ethyl amine (2.0 mL), TBTU (0.177 g, 0.540 mmol) and 1-[2-(trifluoromethyl)phenyl]cyclopropanamine (Intermediate-12, 0.082 g, 0.410 mmol) to afford 0.020 g of desired product. $^1$H NMR (300 MHz, DMSO d$_6$): δ 1.27-1.31 (m, 4H), 3.90 (s, 3H), 7.47 (t, J=8.1 Hz, 2H), 7.54-7.69 (m, 6H), 7.87 (t, J=8.4 Hz, 1H), 7.99 (d, J=7.8 Hz, 1H), 8.61 (s, 1H); MS (m/z): 547.15 (M$^+$).

Example-27

4-(3-(2-Chloro-6-fluorophenyl)-5-oxo-4,5-dihydro-1H-1,2,4-triazol-1-yl)-2-methoxy-N-(1-(4-(trifluoromethyl)phenyl)cyclopropyl)benzamide

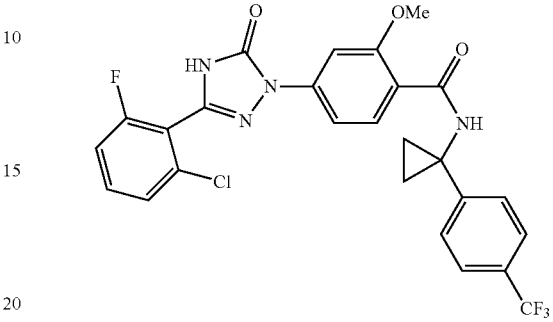

The title compound was prepared according to the procedure described in Example-17 by using 4-(3-(2-chloro-6-fluorophenyl)-5-oxo-4,5-dihydro-1H-1,2,4-triazol-1-yl)-2-methoxybenzoic acid (Intermediate-15, 0.100 g, 0.270 mmol), THF (5 mL), di-isopropyl ethyl amine (2.0 mL), TBTU (0.177 g, 0.540 mmol) and 1-[4-(trifluoromethyl)phenyl]cyclopropanamine (Intermediate-13, 0.066 g, 0.320 mmol) to afford 0.020 g of desired product. $^1$H NMR (300 MHz, DMSO d$_6$): δ 1.37 (s, 4H), 3.95 (s, 3H), 7.42 (d, J=7.8 Hz, 2H), 7.50 (t, J=8.7 Hz, 1H), 7.63 (t, J=7.8 Hz, 4H), 7.73 (t, J=12.3 Hz, 3H), 8.85 (s, 1H), 12.50 (br s, 1H); MS (m/z): 546.99 (M$^+$).

Example-28

4-(3-(2-Chloro-6-fluorophenyl)-5-oxo-4,5-dihydro-1H-1,2,4-triazol-1-yl)-N-(4-fluoro-2-(trifluoromethyl)benzyl)benzamide

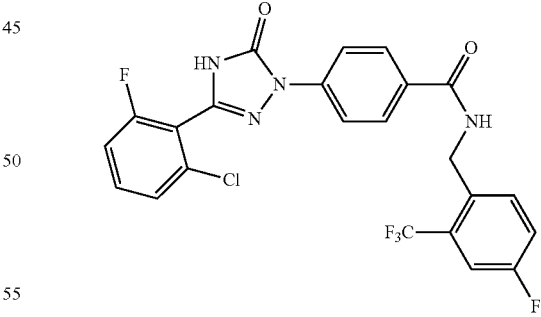

The title compound was prepared according to the procedure described in Example-17 by using 4-[3-(2-chloro-6-fluorophenyl)-5-oxo-4,5-dihydro-1H-1,2,4-triazol-1-yl] benzoic acid (Intermediate-9, 0.100 g, 0.30 mmol), THF (5 mL), di-isopropyl ethyl amine (2.0 mL), TBTU (0.177 g, 0.540 mmol) and 4-fluoro-2-trifluoromethyl benzylamine (0.089 g, 0.600 mmol) to afford 0.025 g of desired product. $^1$H NMR (300 MHz, DMSO d$_6$): δ 4.63 (d, J=4.5 Hz, 2H), 7.48-7.50 (m, 6H), 8.05 (s, 4H), 9.16 (t, 1H), 12.67 (br, 1H); MS (m/z): 509.05 (M+H)$^+$.

Example-29

4-(3-(2-Chloro-6-fluorophenyl)-5-oxo-4,5-dihydro-1H-1,2,4-triazol-1-yl)-N-(4-(trifluoromethyl)phenyl)benzamide

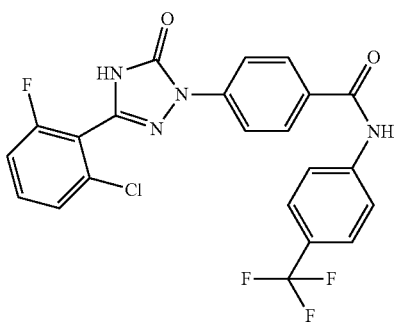 [SMILES: O=C(Nc1ccc(C(F)(F)F)cc1)c1ccc(-n2nc(-c3c(F)cccc3Cl)[nH]c2=O)cc1]

To a solution of 4-(3-(2-chloro-6-fluorophenyl)-5-oxo-4,5-dihydro-1H-1,2,4-triazol-1-yl)benzamide (Intermediate-17, 0.100 g, 0.301 mmol) in dry toluene (5 mL) was added 1-bromo-4-(trifluoromethyl)benzene (0.101 g, 0.451 mmol), sodium tert-butoxide (0.058 g, 0.602 mmol), tris(diphynylideneacetone)dipalladium(0) (0.005 g, 0.0006 mmol), 4,5 bis(diphenylphosphino) and 9,9-dimethylxanthene (0.005 g, 0.0009 mmol) under nitrogen atmosphere. The reaction mass was refluxed for 3-4 h. The reaction mass was quenched in water and extracted in ethyl acetate. The organic layer was concentrated to afford crude product which was purified by column chromatography to afford 0.015 g of desired product. $^1$H NMR (300 MHz, DMSO d$_6$): δ 7.40 (br s, 1H), 7.84 (t, J=9 Hz, 1H), 7.55 (d, 1H), 7.72-7.75 (m, 3H), 8.02 (d, J=8.1 Hz, 2H), 8.11 (br s, 3H) 10.61 (br s, 1H), 12.70 (br s, 1H). MS (m/z): 475.18 (M–H)$^−$.

Example-30

3-(2-Chloro-6-fluorophenyl)-1-(4-(3-(4-fluorophenyl)-1,2,4-oxadiazol-5-yl)phenyl)-1H-1,2,4-triazol-5(4H)-one

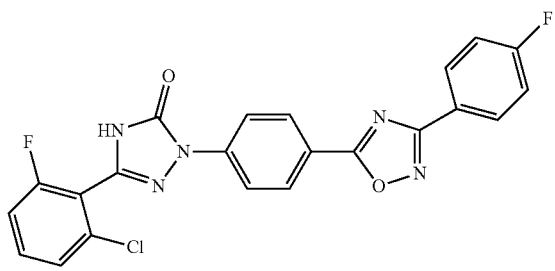 [SMILES: O=c1[nH]c(-c2c(F)cccc2Cl)nn1-c1ccc(-c2nc(-c3ccc(F)cc3)no2)cc1]

To a solution of 4-fluoro-N'-hydroxybenzimidamide (Intermediate-18, 0.073 g, 0.47 mmol) in dry DMF (3 mL) under nitrogen atmosphere was added 4-(3-(2-chloro-6-fluorophenyl)-5-oxo-4,5-dihydro-1H-1,2,4-triazol-1-yl)benzonitrile (step-4 of Intermediate-17, 0.100 g, 0.31 mmol) and ZnCl$_2$ (0.0087 g, 0.06 mmol). The reaction mass was heated at 100° C. for 8-10 h. The reaction mass was quenched with water, extracted in DCM and column purified to afford 0.025 g of desired product. $^1$HNMR (DMSO-d$_6$): δ 7.02 (br s, 1H), 7.33 (t, 1H), 7.45-7.54 (m, 2H), 7.61 (d, 1H), 7.70 (m, 1H), 7.83 (t, 1H), 8.09-8.17 (m, 2H), 8.26-8.30 (m, 2H), 12.81 (br s, 1H). MS (m/z): 452.05 [M+H]$^+$.

Example-31

4-(3-(2-Chloro-6-fluorophenyl)-5-oxo-4,5-dihydro-1H-1,2,4-triazol-1-yl)-N-(3-(trifluoromethyl)phenyl)benzamide

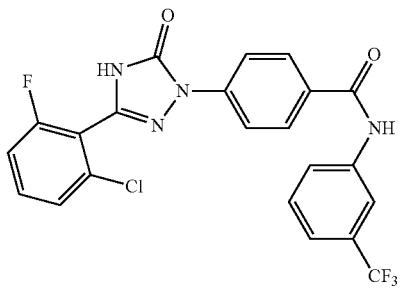 [SMILES: O=C(Nc1cccc(C(F)(F)F)c1)c1ccc(-n2nc(-c3c(F)cccc3Cl)[nH]c2=O)cc1]

To a solution of methyl 4-[3-(2-chloro-6-fluorophenyl)-5-oxo-4,5-dihydro-1H-1,2,4-triazol-1-yl]benzoate (step-2 of Intermediate-9, 0.100 g, 0.28 mmol) in dry toluene was added 3-trifluoromethyl aniline (0.070 g, 0.43 mmol) followed by addition of trimethyl aluminium (2M solution in toluene) (0.5 mL). The reaction mixture was refluxed for 1 h. The reaction mass was quenched in water and acidified with dilute HCl and extracted in DCM. The organic layer was dried over anhydrous sodium sulphate and concentrated to afford crude product, which was column purified to afford 0.040 g of desired product. $^1$HNMR (DMSO-d$_6$): δ 7.45-7.54 (m, 2H), 7.59 (m, 2H), 7.72 (q, J=6.3 Hz, 1H), 8.05-8.12 (m, 5H), 8.25 (s, 1H), 10.58 (br s, 1H), 12.77 (br s, 1H); MS (m/z): 477.08 [M+H]$^+$.

Example-32

4-(3-(2-Chloro-6-fluorophenyl)-5-oxo-4,5-dihydro-1H-1,2,4-triazol-1-yl)-N-(4-fluoro-3-(trifluoromethyl)phenyl)benzamide

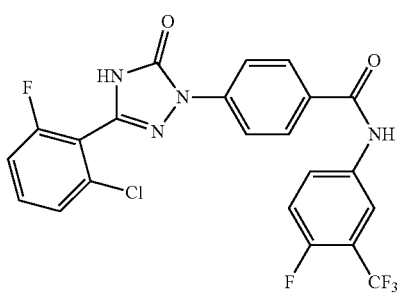 [SMILES: O=C(Nc1ccc(F)c(C(F)(F)F)c1)c1ccc(-n2nc(-c3c(F)cccc3Cl)[nH]c2=O)cc1]

The title compound was prepared according to the procedure described in Example-31, by using methyl 4-[3-(2-chloro-6-fluorophenyl)-5-oxo-4,5-dihydro-1H-1,2,4-triazol-1-yl]benzoate (step-2 of Intermediate-9, 0.100 g, 0.28 mmol), 4-fluoro-3-trifluoromethyl aniline (0.077 g, 0.43 mmol) and trimethyl aluminium (2M solution in toluene) (0.5 mL) to afford 0.043 g of desired product. $^1$HNMR (DMSO-d$_6$): δ 7.46-7.59 (m, 3H), 7.69 (t, J=6.3 Hz, 1H), 8.11 (br s, 5H), 8.26 (m, 1H), 10.59 (br s, 1H), 12.72 (br s, 1H); MS (m/z): 495.07 [M+H]$^+$.

Example-33

4-(3-(2-Chloro-6-fluorophenyl)-5-oxo-4,5-dihydro-1H-1,2,4-triazol-1-yl)-N-(4-fluoro-3-(trifluoromethyl)phenyl)-2-methoxybenzamide

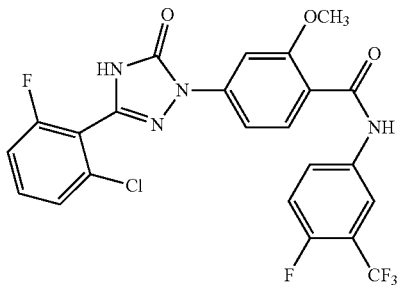 [SMILES: COc1cc(-n2nc(-c3c(F)cccc3Cl)[nH]c2=O)ccc1C(=O)Nc1ccc(F)c(C(F)(F)F)c1]

The title compound was prepared according to the procedure described in Example-31, by using methyl 4-(3-(2-chloro-6-fluorophenyl)-5-oxo-4,5-dihydro-1H-1,2,4-triazol-1-yl)-2-methoxybenzoate (step-2 of Intermediate-15, 0.100 g, 0.26 mmol), 4-fluoro-3-trifluoromethyl aniline (0.070 g, 1.5 mmol), trimethyl aluminium (2M solution in toluene) (0.5 mL) to afford 0.030 g of desired product. $^1$HNMR (DMSO-d$_6$): δ 194 (s, 3H), 7.50-7.60 (m, 3H), 7.67-7.72 (m, 2H), 7.77-7.82 (m, 2H), 8.01 (m, 1H), 8.26 (m, 1H), 10.38 (br s, 1H), 12.80 (br s, 1H); MS (m/z): 525.17 [M+H]$^+$.

Example-34

4-(3-(2-Chloro-6-fluorophenyl)-5-oxo-4,5-dihydro-1H-1,2,4-triazol-1-yl)-N-(2-fluoro-5-(trifluoromethyl)phenyl)benzamide

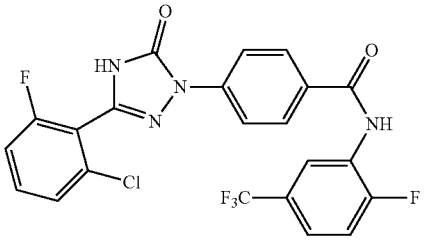 [SMILES: O=C(Nc1cc(C(F)(F)F)ccc1F)c1ccc(-n2nc(-c3c(F)cccc3Cl)[nH]c2=O)cc1]

The title compound was prepared according to the procedure described in Example-31, by using methyl 4-[3-(2-chloro-6-fluorophenyl)-5-oxo-4,5-dihydro-1H-1,2,4-triazol-1-yl]benzoate (step-2 of Intermediate-9, 0.100 g, 0.28 mmol), 2-fluoro-5-trifluoromethyl aniline (0.077 g, 0.43 mmol) and trimethyl aluminium (2M solution in toluene) (0.5 mL) to afford 0.050 g of desired product. $^1$HNMR (DMSO-d$_6$): δ 7.48-7.61 (m, 3H), 7.68-7.73 (m, 2H), 8.08-8.12 (m, 5H), 10.41 (br s, 1H), 12.78 (br s, 1H); MS (m/z): 493.09 [M–H]$^-$.

Example-35

4-(3-(2-Chloro-6-fluorophenyl)-5-oxo-4,5-dihydro-1H-1,2,4-triazol-1-yl)-N-(2-fluoro-4-methylphenyl)benzamide

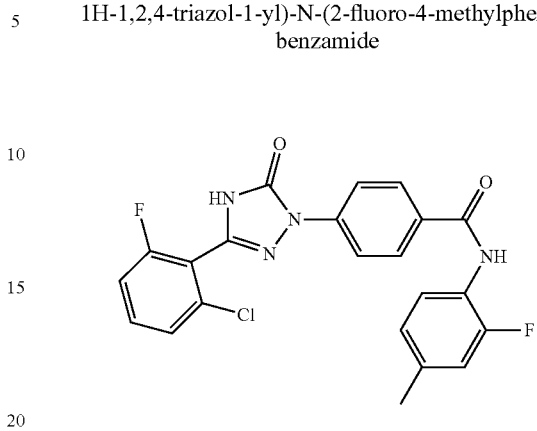

The title compound was prepared according to the procedure described in Example-31, by using methyl 4-[3-(2-chloro-6-fluorophenyl)-5-oxo-4,5-dihydro-1H-1,2,4-triazol-1-yl]benzoate (step-2 of Intermediate-9, 0.100 g, 0.28 mmol), 2-fluoro-4-methyl aniline (0.054 g, 0.43 mmol) and trimethyl aluminium (2M solution in toluene) (0.5 mL) to afford 0.055 g of desired product. $^1$HNMR (DMSO-d$_6$): δ 2.30 (s, 3H), 7.00 (d, J=7.8 Hz, 1H), 7.11 (d, J=11.7 Hz, 1H), 7.39-7.48 (m, 2H), 7.51-7.58 (d, 1H), 7.65-7.72 (m, 1H), 8.07 (br s, 4H), 10.04 (br s, 1H), 12.73 (br s, 1H); MS (m/z): 439.13 [M–H]$^-$.

Example-36

4-(3-(2-Chloro-6-fluorophenyl)-5-oxo-4,5-dihydro-1H-1,2,4-triazol-1-yl)-N-(2-fluoro-5-(trifluoromethyl)phenyl)-2-methoxybenzamide

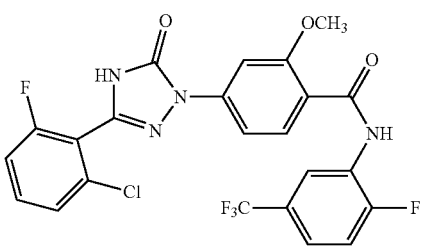 [SMILES: COc1cc(-n2nc(-c3c(F)cccc3Cl)[nH]c2=O)ccc1C(=O)Nc1cc(C(F)(F)F)ccc1F]

The title compound was prepared according to the procedure described in Example-31, by using methyl 4-(3-(2-chloro-6-fluorophenyl)-5-oxo-4,5-dihydro-1H-1,2,4-triazol-1-yl)-2-methoxybenzoate (step-2 of Intermediate-15, 0.100 g, 0.26 mmol), 2-fluoro-5-trifluoromethyl aniline (0.070 g, 0.39 mmol) and trimethyl aluminium (2M solution in toluene) (0.5 mL) to afford 0.049 g of desired product. $^1$HNMR (DMSO-d$_6$): δ 4.05 (s, 3H), 7.50 (t, J=8.4 Hz, 1H), 7.57-7.70 (m, 3H), 7.72-7.77 (m, 2H), 7.85 (s, 1H), 8.08 (d, J=8.4 Hz, 1H), 8.67 (d, J=6.3 Hz, 1H), 10.38 (br s, 1H), 12.82 (br s, 1H); MS (m/z): 525.15 [M+H]$^+$.

Example-37

N-(5-Chloro-2-methylphenyl)-4-(3-(2-chloro-6-fluorophenyl)-5-oxo-4,5-dihydro-1H-1,2,4-triazol-1-yl)benzamide

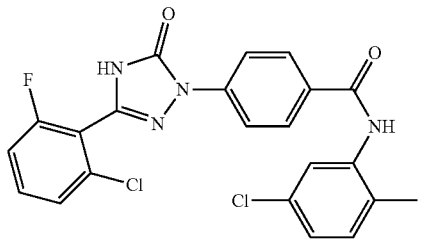 [SMILES: Cc1ccc(Cl)cc1NC(=O)c1ccc(-n2nc(-c3c(F)cccc3Cl)[nH]c2=O)cc1]

The title compound was prepared according to the procedure described in Example-31, by using methyl 4-[3-(2-chloro-6-fluorophenyl)-5-oxo-4,5-dihydro-1H-1,2,4-triazol-1-yl]benzoate (step-2 of Intermediate-9, 0.100 g, 0.28 mmol), 5-chloro-2-methyl aniline (0.062 g, 0.43 mmol) and trimethyl aluminium (2M solution in toluene) (0.5 mL) to afford 0.059 g of desired product. $^1$HNMR (DMSO-d$_6$): δ 2.23 (s, 3H), 7.23 (d, J=6.9 Hz, 1H), 7.30 (d, J=8.4 Hz, 1H), 7.53 (m, 2H), 7.59 (m, 1H), 7.71 (m, 1H), 8.10 (br s, 4H), 9.98 (br s, 1H), 12.76 (br s, 1H); MS (m/z): 457.18 [M]$^+$.

Example-38

N-(5-Chloro-2-methylphenyl)-4-(3-(2-chloro-6-fluorophenyl)-5-oxo-4,5-dihydro-1H-1,2,4-triazol-1-yl)-2-methoxybenzamide

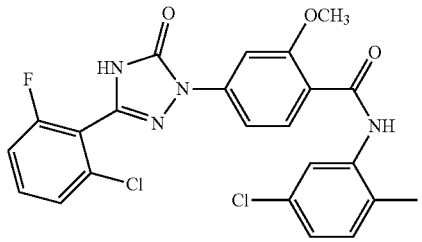 [SMILES: COc1cc(-n2nc(-c3c(F)cccc3Cl)[nH]c2=O)ccc1C(=O)Nc1cc(Cl)ccc1C]

The title compound was prepared according to the procedure described in Example-31, by using methyl 4-(3-(2-chloro-6-fluorophenyl)-5-oxo-4,5-dihydro-1H-1,2,4-triazol-1-yl)-2-methoxybenzoate (step-2 of Intermediate-15, 0.100 g, 0.26 mmol), 5-chloro-2-methyl aniline (0.057 g, 0.39 mmol) and trimethyl aluminium (2M solution in toluene) (0.5 mL) to afford 0.057 g of desired product. $^1$HNMR (DMSO-d$_6$): δ 2.32 (s, 3H), 4.05 (s, 3H), 7.13 (d, J=9.9 Hz, 1H), 7.30 (d, J=8.1 Hz, 1H), 7.49 (t, 1H), 7.59 (d, 1H), 7.61-7.75 (m, 2H), 7.84 (s, 1H), 8.08 (d, J=8.7 Hz, 1H), 8.19 (s, 1H), 9.94 (br s, 1H), 12.83 (br s, 1H); MS (m/z): 487.11 [M]$^+$.

Example-39

4-(3-(2-Chloro-6-fluorophenyl)-5-oxo-4,5-dihydro-1H-1,2,4-triazol-1-yl)-N-(2-fluoro-4-methylphenyl)-2-methoxybenzamide

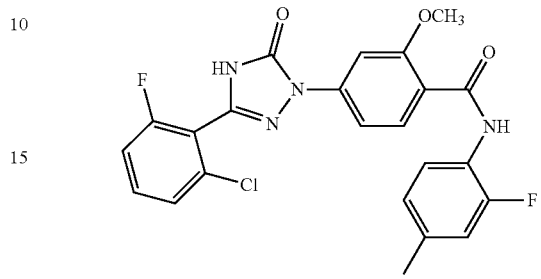

The title compound was prepared according to the procedure described in Example-31, by using methyl 4-(3-(2-chloro-6-fluorophenyl)-5-oxo-4,5-dihydro-1H-1,2,4-triazol-1-yl)-2-methoxybenzoate (step-2 of Intermediate-15, 0.100 g, 0.26 mmol), 2-fluoro-4-methyl aniline (0.050 g, 0.39 mmol) and trimethyl aluminium (2M solution in toluene) (0.5 mL) to afford 0.047 g of desired product. $^1$HNMR (DMSO-d$_6$): δ 2.30 (s, 3H), 4.03 (s, 3H), 7.02 (d, J=8.1 Hz, 1H), 7.14 (d, J=11.7 Hz, 1H), 7.51 (t, 1H), 7.58 (d, 1H), 7.65-7.75 (m, 2H), 7.85 (s, 1H), 8.04-8.10 (m, 2H), 10.07 (br s, 1H), 12.65 (br s, 1H); MS (m/z): 469.16 [M−H]$^-$.

Example-40

3-(2-Chloro-6-fluorophenyl)-1-(4-(3-(4-chlorophenyl)-1,2,4-oxadiazol-5-yl)-3-methoxyphenyl)-1H-1,2,4-triazol-5(4H)-one

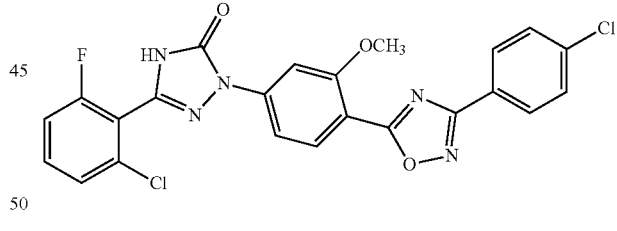

To a solution of 4-chloro-N-hydroxybenzimidamide (Intermediate-19, 0.069 g, 0.39 mmol) in dry toluene was added sodium hydride (0.016 g, 0.39 mmol). The reaction mixture was refluxed for 30 minutes followed by addition of methyl 4-(3-(2-chloro-6-fluorophenyl)-5-oxo-4,5-dihydro-1H-1,2,4-triazol-1-yl)-2-methoxybenzoate (step-2 of Intermediate-15, 0.100 g, 0.26 mmol). The reaction mixture was refluxed for 5-6 h. The reaction mixture was quenched in water and extracted with ethyl acetate. The organic layer was dried over anhydrous sodium sulphate and concentrated to afford crude product which was further purified by column chromatography to afford 0.015 g of desired product. $^1$HNMR (DMSO-d$_6$): δ 3.98 (s, 3H), 7.45-7.48 (m, 1H), 7.54 (d, J=8.1 Hz, 1H), 7.67 (d, J=8.4 Hz, 3H), 7.83 (d, J=8.1 Hz, 1H), 7.95 (s, 1H), 8.10 (d, J=8.4 Hz, 2H), 8.18 (d, J=8.7 Hz, 1H), 12.90 (br s, 1H). MS [M+H]$^+$:499.89.

Example-41

3-(2-Chloro-6-fluorophenyl)-1-(4-(3-(3,5-dimethoxyphenyl)-1,2,4-oxadiazol-5-yl)-3-methoxyphenyl)-1H-1,2,4-triazol-5(4H)-one

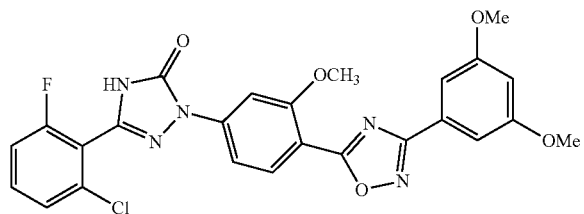 [SMILES: COc1cc(OC)cc(-c2noc(-c3ccc(-n4nc(-c5c(F)cccc5Cl)[nH]c4=O)cc3OC)n2)c1]

The title compound was prepared by following the procedure as described for Example-40 by using Methyl 4-(3-(2-chloro-6-fluorophenyl)-5-oxo-4,5-dihydro-1H-1,2,4-triazol-1-yl)-2-methoxybenzoate (step-2 of Intermediate-15, 0.100 g, 0.26 mmol), N'-hydroxy-3,5-dimethoxybenzimidamide (Intermediate-20, 0.077 g, 0.529 mmol), sodium hydride (0.006 g, 0.39 mmol) and dry THF (5.0 mL) at RT to afford 0.015 g of desired product. $^1$HNMR (DMSO-$d_6$): δ 3.84 (s, 6H), 3.99 (s, 3H), 6.73 (s, 1H), 7.19 (s, 2H), 7.47 (t, J=8.1 Hz, 1H), 7.56 (d, J=8.4 Hz, 1H), 7.67 (t, J=8.7 Hz, 1H), 7.81 (d, J=8.1 Hz, 1H), 7.93 (s, 1H), 8.19 (d, J=8.7 Hz, 1H), 12.61 (br s, 1H); MS (m/z): 523.89 [M+]$^+$.

Example-42

4-(3-(2,6-Dichlorophenyl)-5-oxo-4,5-dihydro-1H-1,2,4-triazol-1-yl)-2-methoxy-N-(3-(trifluoromethyl)phenyl)benzamide

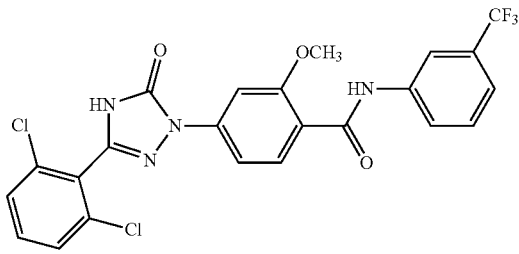 [SMILES: COc1cc(-n2nc(-c3c(Cl)cccc3Cl)[nH]c2=O)ccc1C(=O)Nc1cccc(C(F)(F)F)c1]

The title compound was prepared by following the procedure as described for Example-31 by using methyl 4-(3-(2,6-dichlorophenyl)-5-oxo-4,5-dihydro-1H-1,2,4-triazol-1-yl)-2-methoxybenzoate (Intermediate-21, 0.100 g, 0.25 mmol), 3-(trifluoromethyl)aniline (0.062 g, 0.38 mmol), trimethyl aluminium (2M solution in toluene) (0.5 mL) and dry toluene (5.0 mL) to afford 0.035 g of desired product. $^1$HNMR (DMSO-$d_6$): δ 3.95 (s, 3H), 7.45 (d, J=7.5 Hz, 1H), 7.59 (t, J=7.8 Hz, 1H), 7.76-7.68 (m, 5H), 7.82 (t, J=8.7 Hz, 1H), 7.98 (d, J=8.4 Hz, 1H), 8.25 (s, 1H), 10.37 (s, 1H), 12.75 (br s, 1H); MS (m/z): 524.96[M+H]$^+$.

Example-43

4-(3-(2,6-Dichlorophenyl)-5-oxo-4,5-dihydro-1H-1,2,4-triazol-1-yl)-N-(4-fluoro-3-(trifluoromethyl)phenyl)-2-methoxybenzamide

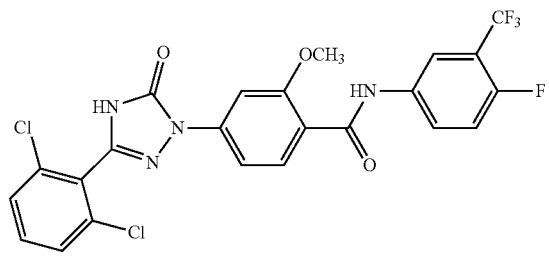 [SMILES: COc1cc(-n2nc(-c3c(Cl)cccc3Cl)[nH]c2=O)ccc1C(=O)Nc1ccc(F)c(C(F)(F)F)c1]

The title compound was prepared by following the procedure as described for Example-31 by using methyl 4-(3-(2,6-dichlorophenyl)-5-oxo-4,5-dihydro-1H-1,2,4-triazol-1-yl)-2-methoxybenzoate (Intermediate-21, 0.100 g, 0.25 mmol), 4-fluoro-3-(trifluoromethyl)aniline (0.069 g, 0.38 mmol), trimethyl aluminium (2M solution in toluene) (0.5 mL) and dry toluene (5.0 mL) to afford 0.050 g of desired product. $^1$HNMR (DMSO-$d_6$): δ 4.09 (s, 3H), 7.52 (t, J=9.6 Hz, 1H), 7.88-7.68 (m, 6H), 8.25 (s, 1H), 8.25 (d, J=6.9 Hz, 1H), 10.37 (s, 1H), 12.74 (s, 1H); MS (m/z): 540.91[M]$^+$.

Example-44

4-(3-(2,6-Dichlorophenyl)-5-oxo-4,5-dihydro-1H-1,2,4-triazol-1-yl)-N-(2-fluoro-5-(trifluoromethyl)phenyl)-2-methoxybenzamide

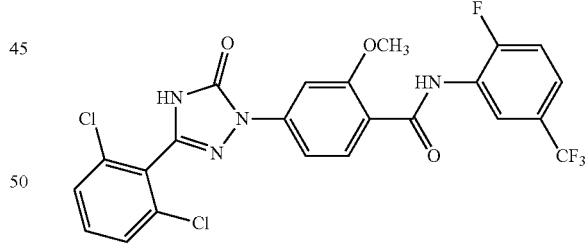

The title compound was prepared by following the procedure as described for Example-31 by using methyl 4-(3-(2,6-dichlorophenyl)-5-oxo-4,5-dihydro-1H-1,2,4-triazol-1-yl)-2-methoxybenzoate (Intermediate-21, 0.100 g, 0.25 mmol), 2-fluoro-5-(trifluoromethyl)aniline (0.069 g, 0.38 mmol), trimethyl aluminium (2M solution in toluene) (0.5 mL) and dry toluene (5.0 mL) to afford 0.035 g of desired product. $^1$HNMR (DMSO-$d_6$): δ 4.06 (s, 3H), 7.59 (d, J=7.8 Hz, 1H), 7.77-7.68 (m, 5H), 7.84 (s, 1H), 8.09 (d, J=8.7 Hz, 1H), 8.67 (d, J=6.9 Hz, 1H), 10.38 (s, 1H), 12.79 (br s, 1H); MS (m/z): 540.92 [M+H]$^+$.

Example-45

4-(3-(2-Chloro-6-fluorophenyl)-5-oxo-4,5-dihydro-1H-1,2,4-triazol-1-yl)-N-(6-fluorobenzo[d]thiazol-2-yl)-2-methoxybenzamide

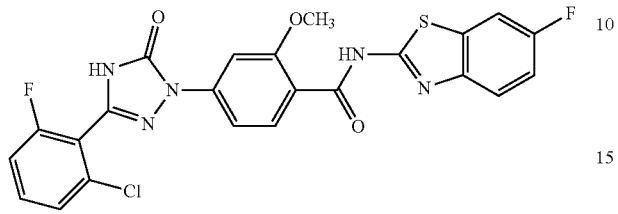

The title compound was prepared by following the procedure as described for Example-31 by using methyl 4-(3-(2-chloro-6-fluorophenyl)-5-oxo-4,5-dihydro-1H-1,2,4-triazol-1-yl)-2-methoxybenzoate (step-2 of Intermediate-15, 0.100 g, 0.26 mmol), 6-fluorobenzo[d]thiazol-2-amine (0.067 g, 0.397 mmol), trimethyl aluminium (2M solution in toluene) (0.5 mL) and dry toluene (5.0 mL) to afford 0.050 g of desired product. $^1$HNMR (DMSO-$d_6$): δ 3.99 (s, 3H), 7.32 (t, J=7.2 Hz, 1H), 7.51 (t, J=9.3 Hz, 1H), 7.59 (d, J=8.4 Hz, 1H), 7.68-7.80 (m, 4H), 7.94 (t, J=6.3 Hz, 2H), 11.98 (s, 1H), 12.83 (br s, 1H); MS (m/z): 512.97 [M−H]$^-$.

Example-46

N-(1H-Benzo[d]imidazol-2-yl)-4-(3-(2-chloro-6-fluorophenyl)-5-oxo-4,5-dihydro-1H-1,2,4-triazol-1-yl)-2-methoxybenzamide

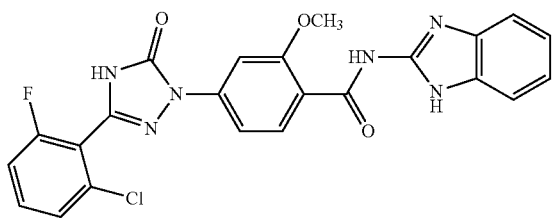 [SMILES: COc1cc(-n2nc(-c3c(F)cccc3Cl)[nH]c2=O)ccc1C(=O)Nc1nc2ccccc2[nH]1]

The title compound was prepared by following the procedure as described for Example-31 by using methyl 4-(3-(2-chloro-6-fluorophenyl)-5-oxo-4,5-dihydro-1H-1,2,4-triazol-1-yl)-2-methoxybenzoate (step-2 of Intermediate-15, 0.100 g, 0.26 mmol), benzo[d]imidazol-2-amine (0.046 g, 0.34 mmol), trimethyl aluminium (2M solution in toluene) (0.5 mL) and dry toluene (5.0 mL) to afford 0.040 g of desired product. $^1$HNMR (DMSO-$d_6$): δ 4.01 (s, 3H), 7.11 (m, 2H), 7.48-7.76 (m, 6H), 7.81 (s, 1H), 7.96 (d, J=9.0 Hz, 1H), 11.16 (br s, 1H), 12.28 (br s, 1H), 12.76 (br s, 1H); MS (m/z): 478.90 [M]$^+$

Example-47

3-(2-Chloro-6-fluorophenyl)-1-(4-(3-(3-fluoro-5-(trifluoromethyl)phenyl)-1,2,4-oxadiazol-5-yl)-3-methoxyphenyl)-1H-1,2,4-triazol-5(4H)-one

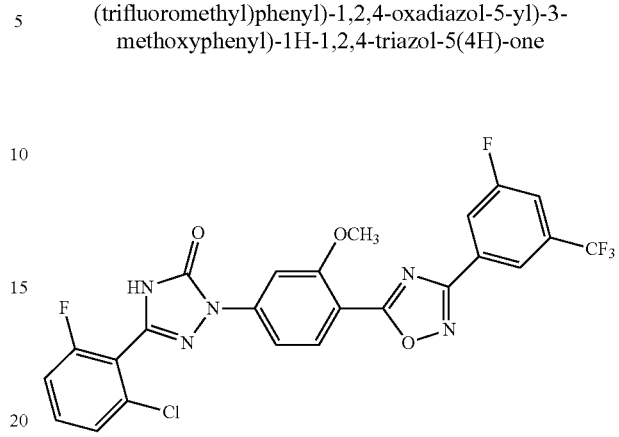

The title compound was prepared by following the procedure as described for Example-40 by using methyl 4-(3-(2-chloro-6-fluorophenyl)-5-oxo-4,5-dihydro-1H-1,2,4-triazol-1-yl)-2-methoxybenzoate (step-2 of Intermediate-15, 0.100 g, 0.26 mmol), 3-fluoro-N'-hydroxy-5-(trifluoromethyl)benzimidamide (Intermediate-22, 0.088 g, 0.39 mmol), sodium hydride (0.017 g, 0.42 mmol) and dry THF (5.0 mL) at RT to afford 0.010 g of desired product. $^1$HNMR (DMSO-$d_6$): δ 4.01 (s, 3H), 7.50 (m, 1H), 7.60 (m, 1H), 7.70 (m, 1H), 7.84 (m, 1H), 7.92 (br s, 1H), 8.02 (d, 1H), 8.18 (m, 2H), 8.25 (d, 1H), 12.95 (br s, 1H); MS (m/z): 550.07 [M]$^+$.

Example-48

4-(3-(2-Chloro-6-fluorophenyl)-5-oxo-4,5-dihydro-1H-1,2,4-triazol-1-yl)-2-methoxy-N-(5-(trifluoromethyl)-1,3,4-thiadiazol-2-yl)benzamide

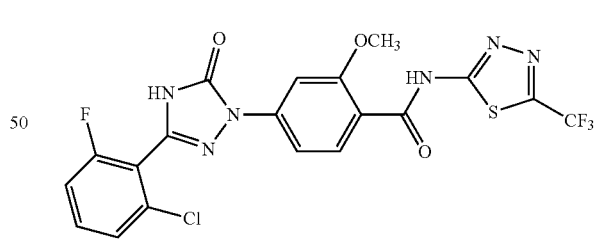

The title compound was prepared by following the procedure as described for Example-31 by using methyl 4-(3-(2-chloro-6-fluorophenyl)-5-oxo-4,5-dihydro-1H-1,2,4-triazol-1-yl)-2-methoxybenzoate (step-2 of Intermediate-15, 0.100 g, 0.26 mmol), 5-(trifluoromethyl)-1,3,4-thiadiazol-2-amine (0.059 g, 0.34 mmol), trimethyl aluminium (2M solution in toluene) (0.5 mL) and dry toluene (5.0 mL) to afford 0.025 g of desired product. $^1$HNMR (DMSO-$d_6$): δ 3.95 (s, 3H), 7.51 (t, J=9.0 Hz, 1H), 7.87-7.76 (m, 3H), 7.78 (s, 1H), 7.85 (d, J=8.7 Hz, 1H), 12.86 (br s, 2H); MS (m/z): 514.90 [M]$^+$.

Example-49

1-(4-(3-(4-Chlorophenyl)-1,2,4-oxadiazol-5-yl)-3-methoxyphenyl)-3-(2,6-dichlorophenyl)-1H-1,2,4-triazol-5(4H)-one

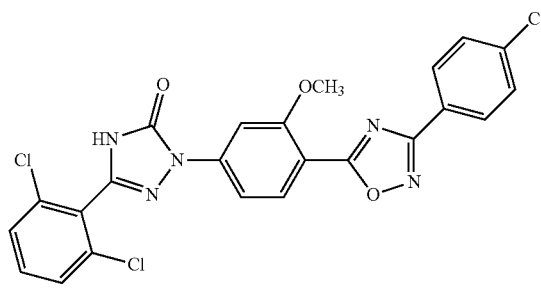 [SMILES: COc1cc(-n2nc(-c3c(Cl)cccc3Cl)[nH]c2=O)ccc1-c1nc(-c2ccc(Cl)cc2)no1]

The title compound was prepared by following the procedure as described for Example-40 by using methyl 4-(3-(2,6-dichlorophenyl)-5-oxo-4,5-dihydro-1H-1,2,4-triazol-1-yl)-2-methoxybenzoate (Intermediate-21, 0.100 g, 0.25 mmol), 4-chloro-N'-hydroxybenzimidamide (Intermediate-19, 0.064 g, 0.38 mmol), sodium hydride (0.020 g, 0.50 mmol) and dry THF (5.0 mL) at RT to afford 0.015 g of desired product. $^1$HNMR (DMSO-d$_6$): δ 4.00 (s, 3H), 7.66-7.72 (m, 5H), 7.81 (d, J=8.7 Hz, 1H), 7.89 (s, $^1$H), 8.10 (d, J=8.4 Hz, 2H), 8.22 (d, J=9.0 Hz, 1H), 12.82 (br s, 1H); MS (m/z): 515.84 [M+H]$^+$.

Example-50

3-(2,6-Dichlorophenyl)-1-(4-(3-isopropyl-1,2,4-oxadiazol-5-yl)-3-methoxyphenyl)-1H-1,2,4-triazol-5(4H)-one

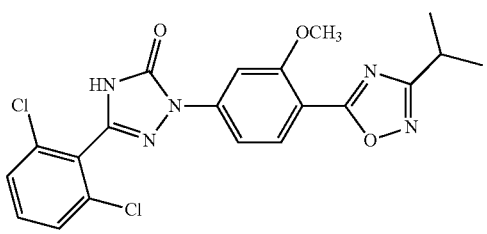 [SMILES: COc1cc(-n2nc(-c3c(Cl)cccc3Cl)[nH]c2=O)ccc1-c1nc(C(C)C)no1]

The title compound was prepared by following the procedure as described for Example-40 by using methyl 4-(3-(2,6-dichlorophenyl)-5-oxo-4,5-dihydro-1H-1,2,4-triazol-1-yl)-2-methoxybenzoate (Intermediate-21, 0.100 g, 0.25 mmol), N'-hydroxyisobutyrimidamide (0.077 g, 0.529 mmol), sodium hydride (0.020 g, 0.50 mmol) and dry THF (5.0 mL) at RT to afford 0.019 g of desired product. $^1$HNMR (DMSO-d$_6$): δ 1.31 (d, J=6.9 Hz, 6H), 3.12 (m, 1H), 3.95 (s, 3H), 7.65-7.78 (m, 4H), 7.56 (s, 1H), 8.09 (d, J=8.7 Hz, 1H), 12.83 (br s, 1H); MS (m/z): 447.96 [M+H]$^+$.

Example-51

3-(2-Chloro-6-fluorophenyl)-1-(4-(3-(4-chlorophenyl)-1,2,4-oxadiazol-5-yl)phenyl)-1H-1,2,4-triazol-5(4H)-one

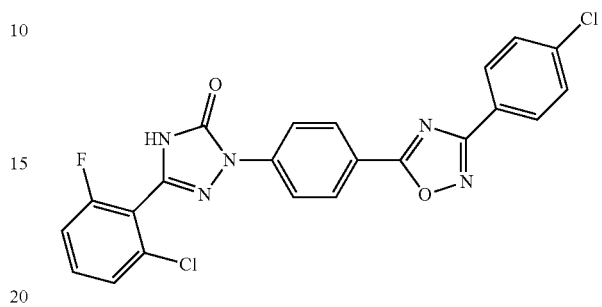

The title compound was prepared by following the procedure as described for Example-40 by using methyl 4-[3-(2-chloro-6-fluorophenyl)-5-oxo-4,5-dihydro-1H-1,2,4-triazol-1-yl]benzoate (step-2 of Intermediate-9, 0.100 g, 0.28 mmol), 4-chloro-N'-hydroxybenzimidamide (Intermediate-19, 0.073 g, 0.43 mmol), sodium hydride (0.018 g, 0.43 mmol) and dry THF (5.0 mL) to afford 0.025 g of desired product. $^1$HNMR (DMSO-d$_6$): δ 7.51 (t, J=8.7 Hz, 1H), 7.59 (d, J=8.4 Hz, 1H), 7.67-7.73 (m, 3H), 8.11 (d, J=8.1 Hz, 2H), 8.24-8.29 (m, 4H), 12.85 (br s, 1H); MS (m/z): 467.87 [M+H]$^+$.

Example-52

4-(3-(2-Chloro-5-(cyclopropanecarboxamidomethyl)phenyl)-5-oxo-4,5-dihydro-1H-1,2,4-triazol-1-yl)-2-methoxy-N-(3-(trifluoromethyl)phenyl)benzamide

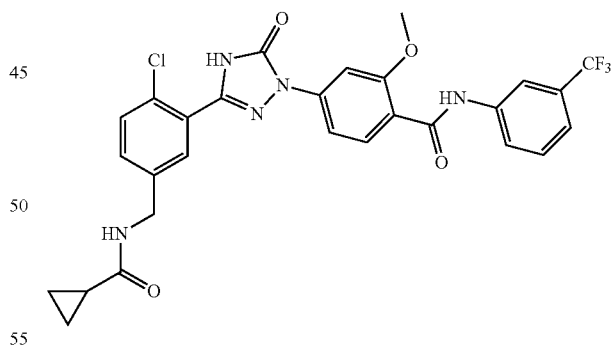

The title compound was prepared by following the procedure as described for step-2 of Intermediate-30 by using 4-(3-(5-(aminomethyl)-2-chlorophenyl)-5-oxo-4,5-dihydro-1H-1,2,4-triazol-1-yl)-2-methoxy-N-(3-(trifluoromethyl)phenyl)benzamide (Intermediate-26, 0.060 g, 0.11 mmol), cyclopropylcarbonyl chloride (0.019 g, 0.17 mmol), DIPEA (1 mL) and THF (5 mL) to afford 0.020 g of desired product. $^1$H NMR (300 MHz, DMSO d$_6$): 1.06 (m, 2H), 1.22 (m, 2H), 3.17 (m, 1H), 3.95 (s, 3H), 4.34 (d, J=6.0 Hz, 2H), 7.44-7.84 (m, 8H), 7.95 (d, J=9.0 Hz, 1H), 8.25 (s, 1H), 8.70 (m, 1H), 10.43 (m, 1H), 12.05 (m, 1H); MS (m/z): 584.35 (M+H$^+$).

Example-53

4-(3-(2-Chloro-6-methylphenyl)-5-oxo-4,5-dihydro-1H-1,2,4-triazol-1-yl)-N-(3-(difluoromethyl)-4-fluorophenyl)-2-methoxybenzamide

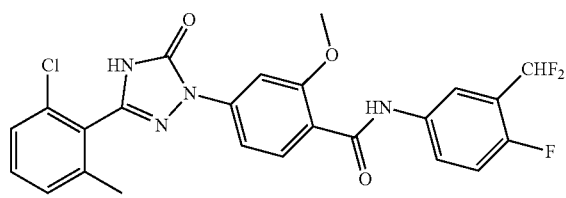 [SMILES: COc1cc(-n2nc(-c3c(C)cccc3Cl)[nH]c2=O)ccc1C(=O)Nc1ccc(F)c(C(F)F)c1]

The title compound was prepared by following the procedure as described for Example-31 by using methyl 4-(3-(2-chloro-6-methylphenyl)-5-oxo-4,5-dihydro-1H-1,2,4-triazol-1-yl)-2-methoxybenzoate (Intermediate-27, 0.100 g, 0.268 mmol), 3-(difluoromethyl)-4-fluoroaniline (Intermediate-28, 0.065 g, 0.403 mmol), trimethyl aluminium (2M solution in toluene) (0.5 mL) and dry toluene (5.0 mL) to afford 0.025 g of desired product. $^1$H NMR (300 MHz, DMSO d$_6$): δ 2.32 (s, 3H), 3.94 (s, 3H), 7.05-7.41 (m, 3H), 7.50 (s, 2H), 7.68-7.88 (m, 4H), 8.11 (m, 1H), 10.27 (s, 1H), 12.53 (s, 1H); MS (m/z): 503.10 (M+H$^+$).

Example-54

4-(3-(2-Chloro-6-methylphenyl)-5-oxo-4,5-dihydro-1H-1,2,4-triazol-1-yl)-N-(3-(difluoromethyl)phenyl)-2-methoxybenzamide

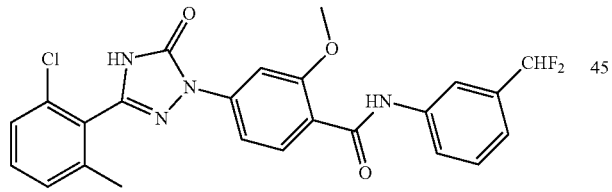

The title compound was prepared by following the procedure as described for Example-31 by using methyl 4-(3-(2-chloro-6-methylphenyl)-5-oxo-4,5-dihydro-1H-1,2,4-triazol-1-yl)-2-methoxybenzoate (Intermediate-27, 0.100 g, 0.268 mmol), 3-(difluoromethyl)aniline (Intermediate-29, 0.058 g, 0.40 mmol), trimethyl aluminium (2M solution in toluene) (0.5 mL) and dry toluene (5.0 mL) to afford 0.035 g of desired product. $^1$H NMR (300 MHz, DMSO d$_6$): δ 2.33 (s, 3H), 3.95 (s, 3H), 7.04 (m, 1H), 7.35 (d, 1H), 7.41 (m, 1H), 7.50 (m, 3H), 7.69 (d, J=8.7 Hz, 1H), 7.77-7.82 (m, 3H), 8.07 (s, 1H), 10.25 (s, 1H), 12.52 (br s, 1H); MS (m/z): 485.06 (M+H$^+$).

Example-55

3-(2-Chloro-6-methylphenyl)-1-(4-(3-(4-chlorophenyl)-1,2,4-oxadiazol-5-yl)-3-methoxy phenyl)-1H-1,2,4-triazol-5(4H)-one

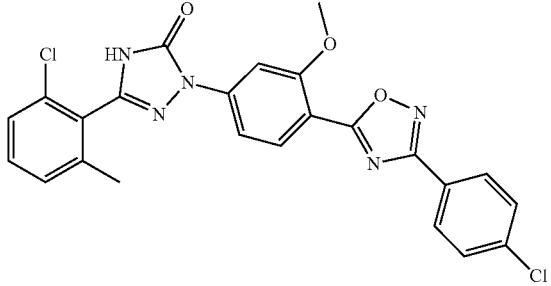 [SMILES: COc1cc(-n2nc(-c3c(C)cccc3Cl)[nH]c2=O)ccc1-c1nc(-c2ccc(Cl)cc2)no1]

The title compound was prepared by following the procedure as described for Example-40 by using methyl 4-(3-(2-chloro-6-methylphenyl)-5-oxo-4,5-dihydro-1H-1,2,4-triazol-1-yl)-2-methoxybenzoate (Intermediate-27, 0.100 g, 0.26 mmol), 4-chloro-N'-hydroxybenzimidamide (Intermediate-19, 0.069 g, 0.40 mmol), sodium hydride (0.022 g, 0.53 mmol) and dry THF (5.0 mL) to afford 0.020 g of desired product. $^1$H NMR (300 MHz, DMSO d$_6$): δ 2.33 (s, 3H), 4.00 (s, 3H), 7.41 (m, 1H), 7.51 (s, 2H), 7.67 (d, J=8.7 Hz, 2H), 7.83 (d, J=8.7 Hz, 1H), 7.90 (s, 1H), 8.10 (d, J=8.4 Hz, 2H), 8.22 (d, J=8.7 Hz, 1H), 12.63 (s, 1H); MS (m/z): 495.98 (M+H$^+$).

Example-56

4-(3-(2-Chloro-6-methylphenyl)-5-oxo-4,5-dihydro-1H-1,2,4-triazol-1-yl)-2-methoxy-N-(3-(trifluoromethyl)phenyl)benzamide

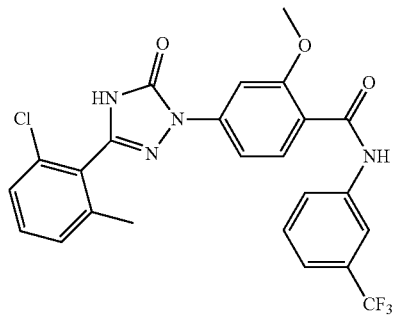 [SMILES: COc1cc(-n2nc(-c3c(C)cccc3Cl)[nH]c2=O)ccc1C(=O)Nc1cccc(C(F)(F)F)c1]

The title compound was prepared by following the procedure as described for Example-31 by using methyl 4-(3-(2-chloro-6-methylphenyl)-5-oxo-4,5-dihydro-1H-1,2,4-triazol-1-yl)-2-methoxybenzoate (Intermediate-27, 0.100 g, 0.268 mmol), 3-(trifluoromethyl)aniline (0.040 g, 0.403 mmol), trimethyl aluminium (2M solution in toluene) (0.5 mL) and dry toluene (5.0 mL) to afford 0.030 g of desired product. $^1$H NMR (300 MHz, DMSO d$_6$): δ 2.33 (s, 3H), 3.95 (s, 3H), 7.41-7.59 (m, 4H), 7.68 (t, J=6.9 Hz, 1H), 7.75 (d, 1H), 7.77-7.82 (m, 2H), 7.95 (d, J=8.4 Hz, 1H), 8.25 (s, 1H), 10.36 (s, 1H), 12.53 (br s, 1H); MS (m/z): 503.17 (M$^+$).

Example-57

N-(4-Chloro-3-(1-(4-(3-(4-chlorophenyl)-1,2,4-oxadiazol-5-yl)-3-methoxyphenyl)-5-oxo-4,5-dihydro-1H-1,2,4-triazol-3-yl)benzyl)cyclopropanecarboxamide

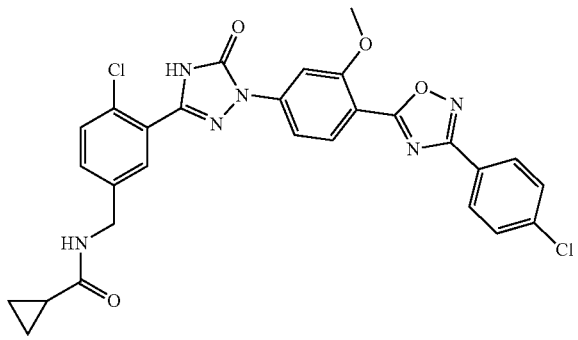 [SMILES: COc1cc(-n2nc(-c3cc(CNC(=O)C4CC4)ccc3Cl)[nH]c2=O)ccc1-c1nc(-c2ccc(Cl)cc2)no1]

The title compound was prepared by following the procedure as described for Example-40 by using methyl 4-(3-(2-chloro-6-(cyclopropanecarboxamidomethyl)phenyl)-5-oxo-4,5-dihydro-1H-1,2,4-triazol-1-yl)-2-methoxybenzoate (Intermediate-30, 0.100 g, 0.21 mmol), 4-chloro-N'-hydroxybenzimidamide (Intermediate-19, 0.056 g, 0.32 mmol), sodium hydride (0.018 g, 0.43 mmol) and dry THF (5.0 mL) to afford 0.020 g of desired product. $^1$H NMR (300 MHz, DMSO $d_6$): δ 1.21 (m, 2H), 1.59 (m, 2H), 3.04 (m, 1H), 3.98 (s, 3H), 4.31 (m, 2H), 7.53 (m, 2H), 7.64 (m, 3H), 7.82 (m, 1H), 7.92 (m, 1H), 8.08 (m, 2H), 8.20 (m, 1H), 8:67 (s, 1H), 12.77 (br s, 1H); MS (m/z): 577.07 (M+H$^+$).

Example-58

3-(2-Chloro-6-fluorophenyl)-1-(3-methoxy-4-(1,5,6-trimethyl-1H-benzo[d]imidazol-2-yl)phenyl)-1H-1,2,4-triazol-5(4H)-one

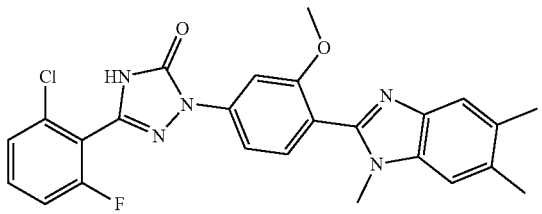 [SMILES: COc1cc(-n2nc(-c3c(F)cccc3Cl)[nH]c2=O)ccc1-c1nc2cc(C)c(C)cc2n1C]

The title compound was prepared by following the procedure as described for Example-31 by using methyl 4-(3-(2-chloro-6-fluorophenyl)-5-oxo-4,5-dihydro-1H-1,2,4-triazol-1-yl)-2-methoxybenzoate (step-2 of Intermediate-15, 0.100 g, 0.26 mmol), trimethylbenzene-1,2-diamine (Intermediate-31, 0.048 g, 0.32 mmol), trimethyl aluminium (2M solution in toluene) (0.5 mL), dry toluene (5.0 mL) to afford 0.030 g of desired product. $^1$H NMR (300 MHz, DMSO $d_6$): δ 2.33 (s, 3H), 2.36 (s, 3H), 3.56 (s, 3H), 3.85 (s, 3H), 7.33 (s, 1H), 7.41 (s, 1H), 7.47-7.59 (m, 3H), 7.66-7.78 (m, 3H), 12.5 (br s, 1H); MS (m/z): 478.29 (M+H$^+$).

Example-59

3-(2-Chloro-6-fluorophenyl)-1-(4-((2,5-dichlorophenyl)ethynyl)-3-methoxyphenyl)-1H-1,2,4-triazol-5(4H)-one

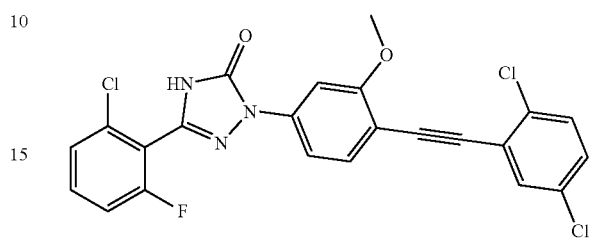

The title compound was prepared according to the procedure described in Example-3 using 3-(2-chloro-6-fluorophenyl)-1-(4-iodo-3-methoxyphenyl)-1H-1,2,4-triazol-5(4H)-one (Intermediate-32, 0.050 g, 0.11 mmol), 1,4-dichloro-2-ethynylbenzene (Intermediate-23, 0.029 g, 0.16 mmol), TBAF (0.101 g, 0.33 mmol), bis(triphenylphosphine)palladium(II) chloride (0.005 g, 0.04 mmol) and DMSO (3.0 mL) at 80° C. to afford 0.010 g of the desired product. $^1$H NMR (300 MHz, DMSO $d_6$): δ 3.89 (s, 3H), 7.49-7.56 (m, 3H), 7.59-7.73 (m, 6H), 12.90 (br s, 1H); MS (m/z): 487.95 (M+H$^+$).

Example-60

1-(4-((3-Chloro-2-fluorophenyl)ethynyl)-3-methoxyphenyl)-3-(2-chloro-6-fluorophenyl)-1H-1,2,4-triazol-5(4H)-one

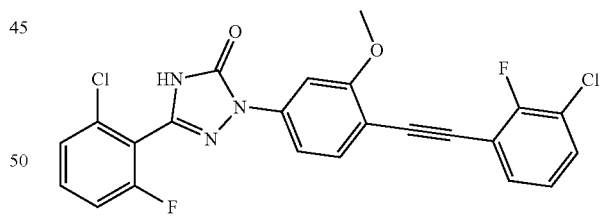

The title compound was prepared according to the procedure described in Example-3 using 3-(2-chloro-6-fluorophenyl)-1-(4-iodo-3-methoxyphenyl)-1H-1,2,4-triazol-5(4H)-one (Intermediate-32, 0.050 g, 0.11 mmol), 1-chloro-3-ethynyl-2-fluorobenzene (Intermediate-24, 0.033 g, 0.22 mmol), TBAF (0.080 g, 0.30 mmol), bis(triphenylphosphine)palladium(II) chloride (0.020 g, 0.022 mmol) and DMSO (3.0 ml) at 80° C. to afford 0.015 g of the desired product. $^1$H NMR (300 MHz, DMSO $d_6$): δ 3.89 (s, 3H), 7.28 (t, J=7.8 Hz, 1H), 7.48 (t, J=9.0 Hz, 1H), 7.56-7.70 (m, 7H), 12.79 (m, 1H); MS (m/z): 470.00 (M−H)$^−$.

Example-61

1-(4-((2-Chloro-4-(trifluoromethyl)phenyl)ethynyl)-3-methoxyphenyl)-3-(2-chloro-6-fluorophenyl)-1H-1,2,4-triazol-5(4H)-one

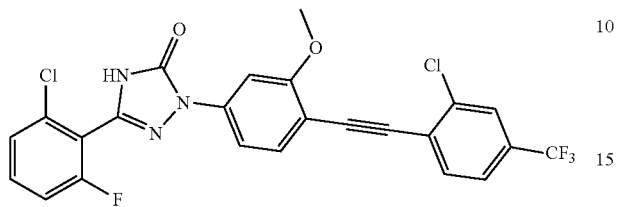

The title compound was prepared according to the procedure described in Example-3 using 3-(2-chloro-6-fluorophenyl)-1-(4-iodo-3-methoxyphenyl)-1H-1,2,4-triazol-5 (4H)-one (Intermediate-32, 0.050 g, 0.11 mmol), 2-chloro-1-ethynyl-4-(trifluoromethyl)benzene (Intermediate-25, 0.044 g, 0.22 mmol), TBAF (0.080 g, 0.30 mmol), bis (triphenylphosphine)palladium(II) chloride (0.020 g, 0.022 mmol) and DMSO (3.0 mL) at 80° C. to afford 0.012 g of desired product. $^1$H NMR (300 MHz, DMSO $d_6$): δ 3.89 (s, 3H), 7.52 (t, J=9.0 Hz, 1H), 7.56-7.75 (m, 6H), 7.83 (d, J=8.1 Hz, 1H), 8.02 (s, 1H), 12.78 (s, 1H); MS (m/z): 522.00 (M+H)$^+$.

Example-62

4-(3-(2-Chloro-6-cyanophenyl)-5-oxo-4,5-dihydro-1H-1,2,4-triazol-1-yl)-2-methoxy-N-(3-(trifluoromethyl)phenyl)benzamide

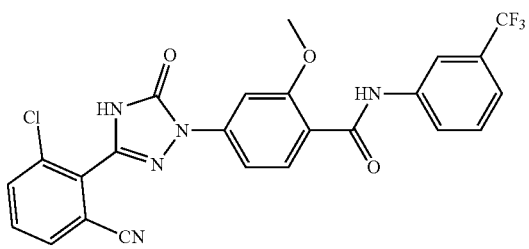 [SMILES: COc1cc(-n2nc(-c3c(Cl)cccc3C#N)[nH]c2=O)ccc1C(=O)Nc1cccc(C(F)(F)F)c1]

To a solution of 4-(3-(2-chloro-6-iodophenyl)-5-oxo-4,5-dihydro-1H-1,2,4-triazol-1-yl)-2-methoxy-N-(3-(trifluoromethyl)phenyl)benzamide (Intermediate-34, 0.130 g, 0.211 mmol) in DMF (5 mL) was added CuCN (0.020 g, 0.232 mmol) and reaction mixture was heated at 80° C. for 4-5 h. The reaction mass was quenched with aq. KMnO$_4$ solution and extracted with ethyl acetate. The organic layer was dried over anhydrous sodium sulphate and concentrated to afford 0.015 g of desired product. $^1$H NMR (300 MHz, DMSO $d_6$): δ 3.95 (s, 3H), 7.44 (d, J=7.8 Hz, 1H), 7.59 (t, J=8.4 Hz, 1H), 7.68 (d, J=8.1 Hz, 1H), 7.80-7.86 (m, 3H), 7.95 (d, J=8.7 Hz, 1H), 8.06-8.12 (m, 2H), 8.25 (s, 1H), 10.38 (s, 1H), 13.00 (br s, 1H); MS (m/z): 512.14 (M–H)$^-$.

Example-63

4-(3-(2-Chloro-5-(cyclopropanecarboxamidomethyl) phenyl)-5-oxo-4,5-dihydro-1H-1,2,4-triazol-1-yl)-N-(3-(difluoromethyl)-4-fluorophenyl)-2-methoxybenzamide

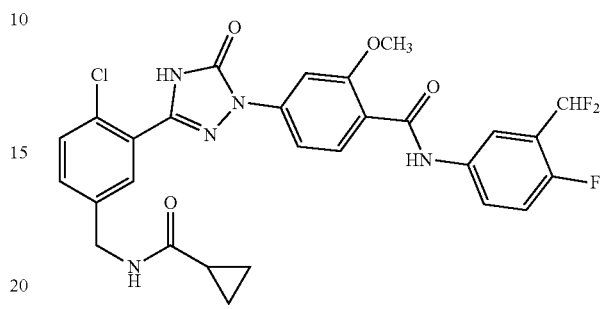

The title compound was prepared by following the procedure as described for step-2 of Intermediate-30, by using 4-(3-(5-(aminomethyl)-2-chlorophenyl)-5-oxo-4,5-dihydro-1H-1,2,4-triazol-1-yl)-N-(3-(difluoromethyl)-4-fluorophenyl)-2-methoxybenzamide (Intermediate-35, 0.050 g, 0.09 mmol), cyclopropylcarbonyl chloride (0.016 g, 0.14 mmol), DIPEA (2.0 mL) and THF (5 mL) to afford 0.015 g of desired product. $^1$H NMR (300 MHz, DMSO $d_6$): δ 0.67 (s, 4H), 1.59 (m, 1H), 3.92 (s, 3H), 3.32 (d, J=4.8 Hz, 2H), 7.03-7.33 (m, 1H), 7.35-7.47 (m, 3H), 7.62-7.68 (m, 2H), 7.76-7.84 (m, 2H), 8.09 (m, 2H), 8.70 (m, 1H), 10.28 (s, 1H), 12.69 (brs, 1H); MS (m/z): 586.12 (M+H)$^+$.

Example-64

N-(2-Chloro-5-(cyclopropanecarboxamidomethyl) phenyl)-4-(3-(2,6-dichlorophenyl)-5-oxo-4,5-dihydro-1H-1,2,4-triazol-1-yl)-2-methoxybenzamide

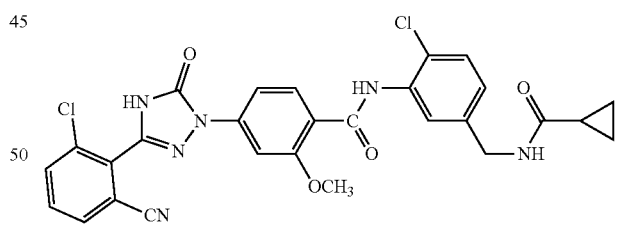

The title compound was prepared by following the procedure as described for Example-31 by using methyl 4-(3-(2,6-dichlorophenyl)-5-oxo-4,5-dihydro-1H-1,2,4-triazol-1-yl)-2-methoxybenzoate (Intermediate-21, 0.100 g, 0.25 mmol), N-(3-amino-4-chlorobenzyl)cyclopropanecarboxamide (Intermediate-36, 0.085 g, 038 mmol), trimethyl aluminium (2M solution in toluene) (1 ml) and dry toluene (5.0 mL) to afford 0.020 g of desired product. $^1$H NMR (300 MHz, DMSO $d_6$): δ 0.68 (d, J=8.1 Hz, 4H), 1.61 (m, 1H), 4.11 (s, 3H), 4.28 (d, J=5.4 Hz, 2H), 7.04 (d, J=6.9 Hz, 1H), 7.52 (d, J=8.7 Hz, 1H), 7.71-7.79 (m, 4H), 7.88 (s, 1H), 8.19 (d, J=9.0 Hz, 1H), 8.44 (s, 1H), 8.67 (m, 1H), 10.53 (s, 1H), 12.82 (br s, 1H); MS (m/z): 587.96 (M+H)$^+$.

Example-65

3-(2,6-Dichlorophenyl)-1-(3-methoxy-4-(5-(trifluoromethyl)-1H-benzo[d]imidazol-2-yl)phenyl)-1H-1,2,4-triazol-5(4H)-one

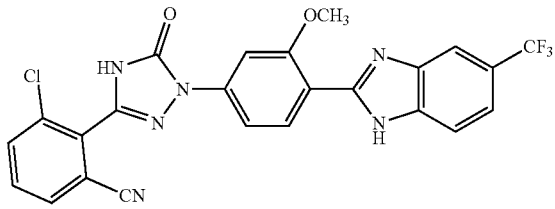 [SMILES: COc1cc(-n2nc(-c3c(Cl)cccc3C#N)[nH]c2=O)ccc1-c1nc2cc(C(F)(F)F)ccc2[nH]1]

The title compound was prepared by following the procedure as described for Example-31 by using methyl 4-(3-(2,6-dichlorophenyl)-5-oxo-4,5-dihydro-1H-1,2,4-triazol-1-yl)-2-methoxybenzoate (Intermediate-21, 0.150 g, 0.30 mmol), 4-(trifluoromethyl)benzene-1,2-diamine (0.081 g, 0.45 mmol), trimethyl aluminium (2M solution in toluene) (2 mL), dry toluene (5.0 mL) to afford 0.015 g of desired product. $^1$H NMR (300 MHz, DMSO d$_6$): δ 4.09 (s, 3H), 7.52 (s, 1H), 7.73-7.85 (m, 5H), 8.02-8.15 (m, 2H), 8.48 (m, 1H), 12.79 (br s, 1H), 13.33 (br s, 1H); MS (m/z): 520.14 (M+H)$^+$.

Example-66

N-(4-Chloro-3-(1-(4-(cyclopropanecarboxamido)-3-methoxyphenyl)-5-oxo-4,5-dihydro-1H-1,2,4-triazol-3-yl)benzyl)cyclopropanecarboxamide

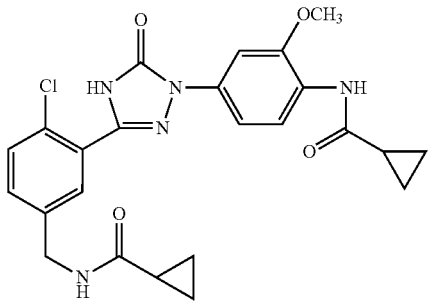 [SMILES: COc1cc(-n2nc(-c3cc(CNC(=O)C4CC4)ccc3Cl)[nH]c2=O)ccc1NC(=O)C1CC1]

The title compound was prepared by following the procedure as described for step-2 of Intermediate-30 by using N-(3-(1-(4-amino-3-methoxyphenyl)-5-oxo-4,5-dihydro-1H-1,2,4-triazol-3-yl)-4-chlorobenzyl)cyclopropanecarboxamide (Intermediate-37, 0.050 g, 0.120 mmol), cyclopropylcarbonyl chloride (0.018 g, 0.180 mmol), DIPEA (2.0 mL) and THF (5 mL) to afford 0.015 g of desired product. $^1$H NMR (300 MHz, DMSO d$_6$): δ 0.69 (s, 4H), 0.77 (s, 4H), 1.60 (m, 1H), 2.08 (m, 1H), 3.88 (s, 3H), 4.33 (d, J=5.4 Hz, 2H), 7.45 (m, 2H), 7.62 (s, 2H), 7.96 (d, J=8.4 Hz, 1H), 8.69 (m, 1H), 9.49 (s, 1H), 12.54 (s, 1H); MS (m/z): 482.10 (M+H)$^+$.

Example-67

4-(3-(2,6-Dichlorophenyl)-5-oxo-4,5-dihydro-1H-1,2,4-triazol-1-yl)-2-methoxy-N-(4-(methylsulfonyl)phenyl)benzamide

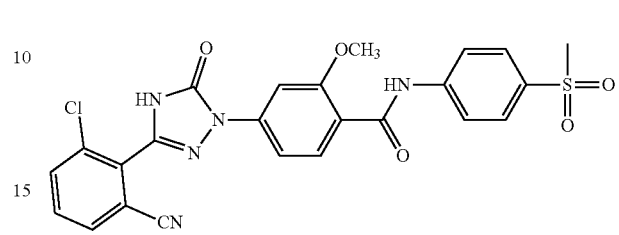

To a solution of 4-(3-(2,6-dichlorophenyl)-5-oxo-4,5-dihydro-1H-1,2,4-triazol-1-yl)-2-methoxy-N-(4-(methylthio)phenyl)benzamide (Intermediate-38, 0.070 g, 0.13 mmol) in mixture of acetonitrile:water (3 mL:3 mL) was added oxone (0.053 g, 0.34 mmol). The reaction mass was stirred at RT for 24 h. The reaction mass was diluted with water and extracted with DCM. The organic layer was dried over anhydrous sodium sulphate and concentrated to afford 0.020 g of desired product. $^1$H NMR (300 MHz, DMSO d$_6$): δ 3.18 (s, 3H), 3.94 (s, 3H), 7.68-7.76 (m, 7H), 7.80 (d, J=8.7 Hz, 1H), 7.90 (d, J=8.7 Hz, 1H), 7.99 (d, J=8.4 Hz, 1H), 10.48 (s, 1H), 12.76 (br s, 1H); MS (m/z): 531.14 (M+H)$^+$.

Example-68

4-(3-(2-Chloro-5-(cyclopropanecarboxamidomethyl)phenyl)-5-oxo-4,5-dihydro-1H-1,2,4-triazol-1-yl)-N-(3-(difluoromethyl)phenyl)-2-methoxybenzamide

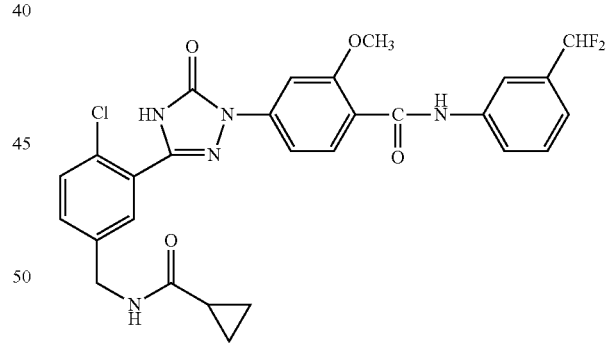

The title compound was prepared by following the procedure as described for step-2 of Intermediate-30 by using 4-(3-(5-(aminomethyl)-2-chlorophenyl)-5-oxo-4,5-dihydro-1H-1,2,4-triazol-1-yl)-N-(3-(difluoromethyl)phenyl)-2-methoxybenzamide (Intermediate-39, 0.050 g, 0.10 mmol), cyclopropane carbonyl chloride (0.016 g, 0.15 mmol), DIPEA (2.0 mL) and THF (2 mL) to afford 0.015 g of desired product. $^1$H NMR (300 MHz, DMSO d$_6$): δ 0.68 (d, J=8.7 Hz, 4H), 1.60 (m, 1H), 3.95 (s, 3H), 4.34 (d, J=5.4 Hz, 2H), 7.05 (m, 1H), 7.29 (d, J=7.9 Hz, 1H), 7.41-7.55 (m, 4H), 7.65 (d, J=9.0 Hz, 1H), 7.74 (s, 1H), 7.82 (d, J=8.7 Hz, 2H), 8.07 (s, 1H), 8.72 (m, 1H), 10.33 (s, 1H); MS (m/z): 566.29 (M−F)$^-$.

Example-69

4-(3-(2-Chloro-5-(N-cyclopropylsulfamoyl)phenyl)-5-oxo-4,5-dihydro-1H-1,2,4-triazol-1-yl)-2-methoxy-N-(3-(trifluoromethyl)phenyl)benzamide

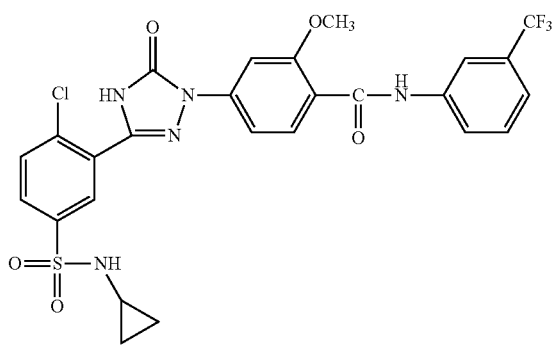 [SMILES: COc1cc(-n2nc(-c3cc(S(=O)(=O)NC4CC4)ccc3Cl)[nH]c2=O)ccc1C(=O)Nc1cccc(C(F)(F)F)c1]

The title compound was prepared by following the procedure as described for Example-31 by using methyl 4-(3-(2-chloro-5-(N-cyclopropylsulfamoyl) phenyl)-5-oxo-4,5-dihydro-1H-1,2,4-triazol-1-yl)-2-methoxybenzoate (Intermediate-40, 0.040 g, 0.08 mmol), 3-(trifluoromethyl)aniline (0.020 g, 0.12 mmol), trimethyl aluminium (2M solution in toluene) (1 ml) and dry toluene (5.0 mL) to afford 0.015 g of crude product, which was purified by washing with methanol:DCM:DEE to afford 0.015 g of pure product. $^1$H NMR (300 MHz, DMSO d$_6$): δ 0.42 (s, 2H), 0.54 (d, J=5.4 Hz, 2H), 2.20 (m, 1H), 3.96 (s, 3H), 7.45 (d, J=7.5 Hz, 1H), 7.61 (t, 1H), 7.70 (d, J=7.8 Hz, 1H), 7.80-7.84 (m, 2H), 7.96 (s, 3H), 8.18 (m, 2H), 8.26 (s, 1H), 10.40 (s, 1H), 12.88 (br s, 1H); MS (m/z): 606.13 (M−H)$^-$.

Example-70

4-(3-(2,6-Dichlorophenyl)-4-ethyl-5-oxo-4,5-dihydro-1H-1,2,4-triazol-1-yl)-2-methoxy-N-(3-(trifluoromethyl)phenyl)benzamide

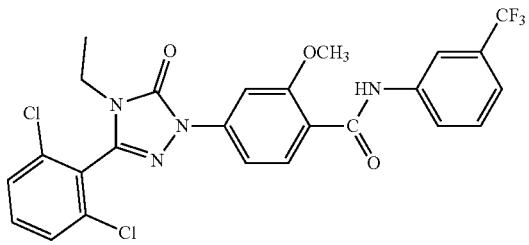 [SMILES: CCn1c(-c2c(Cl)cccc2Cl)nn(-c2ccc(C(=O)Nc3cccc(C(F)(F)F)c3)c(OC)c2)c1=O]

The title compound was prepared by following the procedure as described for Example-31 by using methyl 4-(3-(2,6-dichlorophenyl)-4-ethyl-5-oxo-4,5-dihydro-1H-1,2,4-triazol-1-yl)-2-methoxybenzoate (Intermediate-41, 0.040 g, 0.09 mmol), 3-(trifluoromethyl)aniline (0.010 g, 0.6 mmol), trimethyl aluminium (2M solution in toluene) (1 mL) and dry toluene (5.0 mL) to afford 0.015 g of crude product which was purified by column chromatography in basic alumina eluting with 0.2% methanol: DCM to afford 0.015 g of pure product. $^1$H NMR (300 MHz, DMSO d$_6$): δ 1.14 (t, 3H), 3.55-3.57 (m, 2H), 3.95 (s, 3H), 7.46 (m, 1H), 7.59 (t, 1H), 7.69-7.81 (m, 6H), 7.94 (m, 1H), 8.25 (s, 1H), 10.38 (s, 1H); MS (m/z): 551.11 (M+H)$^+$.

Example-71

1-(44(3-Chloro-2-fluorophenyl)ethynyl)phenyl)-3-(2-chloro-6-fluorophenyl)-4-ethyl-1H-1,2,4-triazol-5 (4H)-one

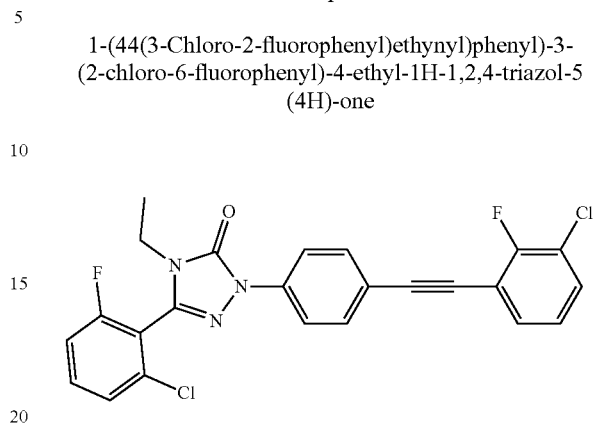

The title compound was prepared by following the procedure as described for Intermediate-41 by using 1-(44(3-chloro-2-fluorophenyl)ethynyl)phenyl)-3-(2-chloro-6-fluorophenyl)-1H-1,2,4-triazol-5(4H)-one (Example-12, 0.070 g, 0.15 mmol), dry DMF (3 mL), NaH (0.010 g, 0.23 mmol) and ethyl bromide (0.026 g, 0.23 mmol) to afford 0.030 g of the crude product which was purified by column chromatography in basic alumina eluting with 0.2% methanol: DCM to afford 0.030 g of pure product. $^1$H NMR (300 MHz, DMSO d$_6$): δ 1.09 (t, 3H), 3.56 (m, 2H), 7.29 (t, 1H), 7.52-7.84 (m, 7H), 8.04 (d, J=8.1 Hz, 2H); MS (m/z): 470.06 (M+H)$^+$.

Example-72

4-(3-(2-Chloro-5-(cyclopropanecarboxamidomethyl) phenyl)-5-oxo-4,5-dihydro-1H-1,2,4-triazol-1-yl)-N-(3-(trifluoromethyl)phenyl)benzamide

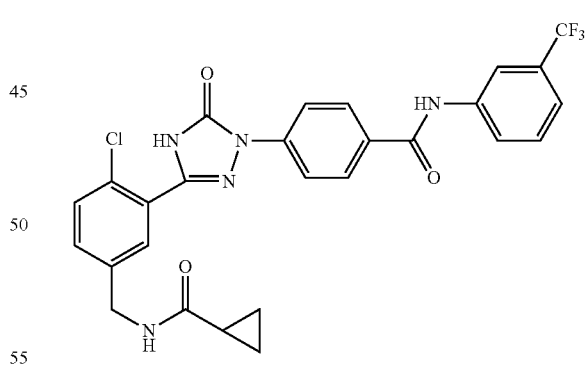

The title compound was prepared by following the procedure as described for Example-31 by using methyl 4-(3-(2-chloro-5-(cyclopropane carboxamidomethyl)phenyl)-5-oxo-4,5-dihydro-1H-1,2,4-triazol-1-yl)benzoate (Intermediate-42, 0.100 g, 0.24 mmol), 3-(trifluoromethyl) aniline (0.050 g, 0.36 mmol), trimethyl aluminium (2M solution in toluene) (1 mL) and dry toluene (8.0 mL). The reaction mass was quenched in water, extracted with DCM and the organic layer was concentrated to afford 0.010 g of desired product. $^1$H NMR (300 MHz, DMSO d$_6$): δ 0.70 (s, 4H), 1.62 (m, 1H), 4.33 (d, J=6.3 Hz, 2H), 7.44-7.67 (m, 4H), 8.10-8.26 (m, 6H), 8.68 (m, 1H), 10.53 (s, 1H), 12.68 (br s, 1H); MS (m/z): 554.30 (M−H)⁻.

Example-73

4-(3-(2-Chloro-6-cyanophenyl)-5-oxo-4,5-dihydro-1H-1,2,4-triazol-1-yl)-N-(4-fluoro-3-(trifluoromethyl)phenyl)-2-methoxybenzamide

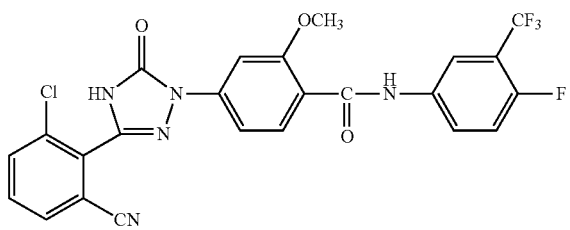 [SMILES: COc1cc(-n2nc(-c3c(Cl)cccc3C#N)[nH]c2=O)ccc1C(=O)Nc1ccc(F)c(C(F)(F)F)c1]

The title compound was prepared by following the procedure as described for Example-62 by using 4-(3-(2-chloro-6-iodophenyl)-5-oxo-4,5-dihydro-1H-1,2,4-triazol-1-yl)-N-(4-fluoro-3-(trifluoromethyl)phenyl)-2-methoxybenzamide (Intermediate-43, 0.130 g, 0.21 mmol), DMF (4 mL) and CuCN (0.020 g, 0.23 mmol) to afford 0.030 g of crude product which was further purified by column chromatography in basic alumina eluting with 50% methanol: DCM and few drops of 10% ammonia to afford 0.030 g of pure product. ¹H NMR (300 MHz, DMSO d₆): δ 3.94 (s, 3H), 7.52 (t, 1H), 7.68 (d, J=7.8 Hz, 1H), 7.81 (m, 3H), 8.05-8.12 (m, 3H), 8.26 (s, 1H), 10.40 (s, 1H), 13.01 (br s, 1H); MS (m/z): 532.12 (M+H)⁺.

Example-74

3-(4(3-Chloro-2-fluorophenyl)ethynyl)-3-methoxyphenyl)-1-(2,6-dichlorophenyl)-1H-1,2,4-triazol-5(4H)-one

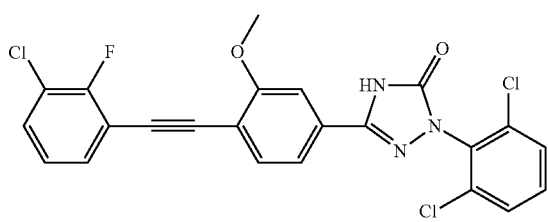 [SMILES: COc1cc(-c2nn(-c3c(Cl)cccc3Cl)c(=O)[nH]2)ccc1C#Cc1cccc(Cl)c1F]

To a solution of 1-(2,6-dichlorophenyl)-3-(4-iodo-3-methoxyphenyl)-1H-1,2,4-triazol-5(4H)-one (Intermediate-45, 0.070 g, 0.15 mmol) in DMSO (3.0 mL) was added 1-chloro-3-ethynyl-2-fluorobenzene (Intermediate-24, 0.035 g, 0.22 mmol), TBAF (0.080 g, 0.30 mmol) and bis(triphenylphosphine)palladium(II) chloride (0.020 g, 0.022 mmol). The reaction mass was stirred at 80° C. for 5-6 h. The reaction mass was quenched in water and extracted with DCM and concentrated. The obtained product was purified with column chromatography on silica gel eluting with 2.0% EA: DCM to afford 0.020 g of the desired product. ¹H NMR (300 MHz, DMSO d₆): δ 3.92 (s, 3H), 7.29 (t, J=8.4 Hz, 1H), 7.48-7.72 (m, 8H), 12-13 (br s, 1H); MS (adz): 488.00 (M⁺).

Example-75

3-(4-((2-Chloro-4-(trifluoromethyl)phenyl)ethynyl)-3-methoxyphenyl)-1-(2,6-dichlorophenyl)-1H-1,2,4-triazol-5(4H)-one

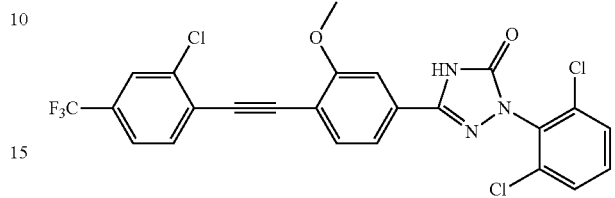

The title compound was prepared according to, the procedure described in Example-3 using 1-(2,6-dichlorophenyl)-3-(4-iodo-3-methoxyphenyl)-1H-1,2,4-triazol-5(4H)-one (Intermediate-45, 0.070 g, 0.15 mmol), 2-chloro-1-ethynyl-4-(trifluoromethyl)benzene (Intermediate-25, 0.046 g, 0.22 mmol), TBAF (0.080 g, 0.30 mmol), bis(triphenylphosphine)palladium(II) chloride (0.020 g, 0.022 mmol) and DMSO (3.0 mL) at 80° C. to afford. 0.020 g of the desired product. ¹H NMR (300 MHz, DMSO d₆): δ 3.95 (s, 3H), 7.50-7.53 (m, 2H), 7.56-7.79 (m, 5H), 7.88 (d, J=8.4 Hz, 1H), 8.05 (s, 1H), 12.04 (s, 1H); MS (adz): 538.07 (M⁺).

Example-76

4-(1-(2,6-Dichlorophenyl)-5-oxo-4,5-dihydro-1H-1,2,4-triazol-3-yl)-2-methoxy-N-(3-(trifluoromethyl)phenyl)benzamide

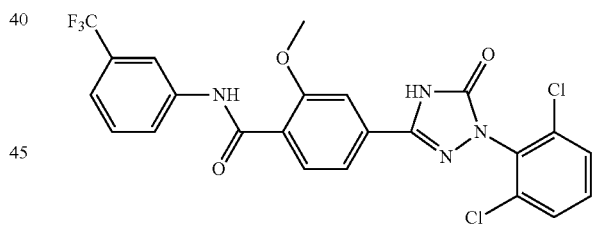

To a solution of methyl 4-(1-(2,6-dichlorophenyl)-5-oxo-4,5-dihydro-1H-1,2,4-triazol-3-yl)-2-methoxybenzoate (Intermediate-46, 0.070 g, 0.17 mmol) in dry toluene was added 3-(trifluoromethyl)aniline (0.043 g, 0.17 mmol) followed by addition of trimethyl aluminum (2M solution in toluene) (0.5 ML). The reaction mixture was refluxed for 1 hr under inert atmosphere. The reaction mixture was brought to RT and quenched with water. Few drops of dilute HCl were added and the reaction mixture was extracted with DCM and concentrated. The obtained product was purified with column chromatography to afford 0.050 g of desired product. ¹H NMR (300 MHz, DMSO d₆): δ 3.95 (s, 3H), 7.46 (d, J=6.9 Hz, 1H), 7.54-7.65 (m, 4H), 7.72-7.76 (m, 3H), 7.94 (d, J=8.4 Hz, 1H), 8.24 (s, 1H), 10.51 (s, 1H), 12.85 (s, 1H); MS (m/z): 523.04 (M⁺).

Example-77

4-(1-(2,6-Dichlorophenyl)-5-oxo-4,5-dihydro-1H-1,2,4-triazol-3-yl)-N-(4-fluoro-3-(trifluoromethyl)phenyl)-2-methoxybenzamide

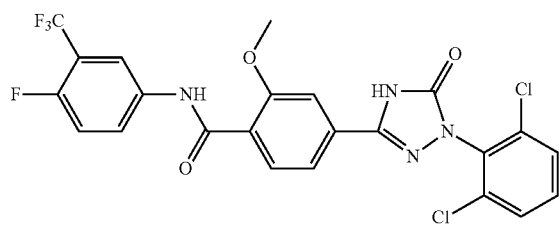 [SMILES: COc1cc(-c2nn(-c3c(Cl)cccc3Cl)c(=O)[nH]2)ccc1C(=O)Nc1ccc(F)c(C(F)(F)F)c1]

The title compound was prepared by following the procedure as described for step-6 of Intermediate-26 by using methyl 4-(1-(2,6-dichlorophenyl)-5-oxo-4,5-dihydro-1H-1,2,4-triazol-3-yl)-2-methoxybenzoate (Intermediate-46, 0.070 g, 0.17 mmol), 4-fluoro-3-(trifluoromethyl)aniline (0.048 g, 0.26 mmol), trimethyl aluminum (2M solution in toluene) (0.5 mL) and dry toluene (5.0 mL) to afford 0.040 g of desired product. $^1$H NMR (300 MHz, DMSO d$_6$): δ 3.95 (s, 3H), 7.49-7.64 (m, 4H), 7.72-7.76 (m, 3H), 7.99 (m, 1H), 8.25 (m, 1H), 10.52 (s, 1H), 12.86 (s, 1H); MS (m/z): 541.05 (M$^+$).

Example-78

N-(4-Chloro-3-(3-(4-(2,5-dichlorophenyl)ethynyl)-2-fluorophenyl)-5-oxo-4,5-dihydro-1H-1,2,4-triazol-1-yl)benzyl)cyclopropanecarboxamide

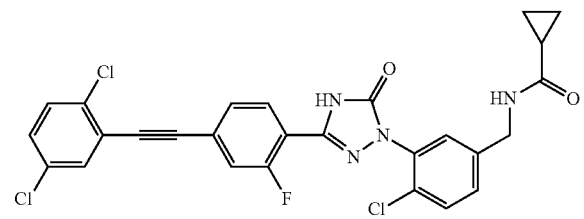 [SMILES: O=C(NCc1ccc(Cl)c(-n2nc(-c3ccc(C#Cc4cc(Cl)ccc4Cl)cc3F)[nH]c2=O)c1)C1CC1]

The title compound was prepared according to the procedure described in Example-3 by using N-(4-chloro-3-(3-(2-fluoro-4-iodophenyl)-5-oxo-4,5-dihydro-1H-1,2,4-triazol-1-yl)benzyl)cyclopropanecarboxamide (Intermediate-48, 0.060 g, 0.10 mmol), 1,4-dichloro-2-ethynylbenzene (Intermediate-23, 0.026 g, 0.15 mmol), TBAF (0.064 g, 0.20 mmol), bis(triphenylphosphine)palladium(II) chloride (0.064 g, 0.20 mmol) and DMSO (3.0 mL) at 80° C. to afford 0.020 g of the desired product. $^1$H NMR (300 MHz, DMSO d$_6$): δ 0.68 (m, 4H), 1.60 (m, 1H), 4.33 (d, J=5.7 Hz, 2H), 7.38 (d, J=7.8 Hz, 1H), 7.47 (s, 1H), 7.57-7.69 (m, 5H), 7.86-7.94 (m, 2H), 8.68 (m, 1H), 12.45 (br s, 1H); MS (m/z): 557.05 (M+H$^+$).

Example-79

N-(4-Chloro-3-(3-(4-((4-chloro-2-fluorophenyl)ethynyl)-2-fluorophenyl)-5-oxo-4,5-dihydro-1H-1,2,4-triazol-1-yl)benzyl)cyclopropanecarboxamide

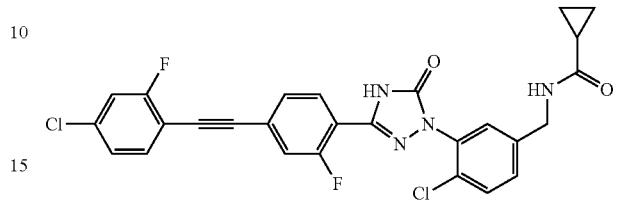

The title compound was prepared according to the procedure described in Example-3 using N-(4-chloro-3-(3-(2-fluoro-4-iodophenyl)-5-oxo-4,5-dihydro-1H-1,2,4-triazol-1-yl)benzyl) cyclopropanecarboxamide (Intermediate-48, 0.050 g, 0.097 mmol), 4-chloro-1-ethynyl-2-fluorobenzene (Intermediate-49, 0.022 g, 0.14 mmol), TBAF (0.061 g, 0.19 mmol), bis(triphenylphosphine)palladium(II) chloride (catalytic) and DMSO (1.0 mL) at 80° C. to afford 0.025 g of the desired product. $^1$H NMR (300 MHz, DMSO d$_6$): δ 0.65-0.68 (m, 4H), 1.60 (m, 1H), 4.32 (d, J=6.0 Hz, 2H), 7.33-7.52 (m, 3H), 7.55-7.74 (m, 5H), 7.90 (m, 1H), 8.68 (m, 1H), 12.0 (br s, 1H); MS (m/z): 539.0 (M$^+$).

Example-80

N-(4-Chloro-3-(3-(2-fluoro-4-((3-(trifluoromethyl)phenyl)ethynyl)phenyl)-5-oxo-4,5-dihydro-1H-1,2,4-triazol-1-yl)benzyl)cyclopropanecarboxamide

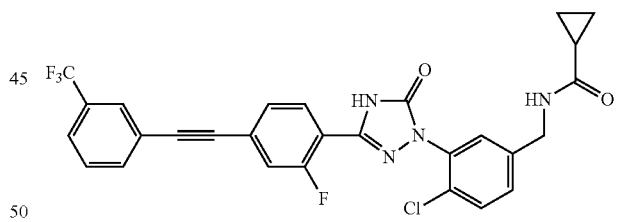

The title compound was prepared according to the procedure described in Example-3 by using N-(4-chloro-3-(3-(2-fluoro-4-iodophenyl)-5-oxo-4,5-dihydro-1H-1,2,4-triazol-1-yl)benzyl) cyclopropanecarboxamide (Intermediate-48, 0.050 g, 0.097 mmol), 1-ethynyl-3-(trifluoromethyl)benzene (Intermediate-50, 0.025 g, 0.14 mmol), TBAF (0.061 g, 0.19 mmol), bis(triphenylphosphine)palladium(II) chloride (catalytic) and DMSO (1.0 mL) at 80° C. to afford 0.020 g of the desired product. $^1$H NMR (300 MHz, DMSO d$_6$): δ 0.65-0.70 (m, 4H), 1.60 (m, 1H), 4.31 (d, J=6.0 Hz, 2H), 7.28-7.41 (m, 2H), 7.51-7.61 (m, 4H), 7.67-7.97 (m, 4H), 8.68 (m, 1H), 12.0 (br s, 1H); MS (m/z): 555.05 (M+H$^+$).

Example-81

N-(4-Chloro-3-(3-(4-((3-chloro-2-fluorophenyl)ethynyl)-2-fluorophenyl)-5-oxo-4,5-dihydro-1H-1,2,4-triazol-1-yl)benzyl)cyclopropanecarboxamide

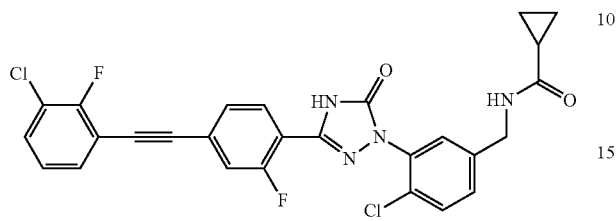

The title compound was prepared according to the procedure described in Example-3 using N-(4-chloro-3-(3-(2-fluoro-4-iodophenyl)-5-oxo-4,5-dihydro-1H-1,2,4-triazol-1-yl)benzyl) cyclopropanecarboxamide (intermediate-48, 0.050 g, 0.097 mmol), 1-chloro-3-ethynyl-2-fluorobenzene (Intermediate-24, 0.022 g, 0.14 mmol), TBAF (0.061 g, 0.19 mmol), bis(triphenylphosphine)palladium(II) chloride (catalytic) and DMSO (1.0 mL) at 80° C. to afford 0.030 g of the desired product. $^1$H NMR (300 MHz, DMSO d$_6$): δ 0.69 (m, 4H), 1.60 (m, 1H), 4.33 (d, J=5.7 Hz, 2H), 7.30-7.41 (m, 3H), 7.48-7.74 (m, 5H), 7.87-7.93 (m, 1H), 8.69 (m, 1H), 12.40-12.58 (br s, 1H); MS (m/z): 539.36 (M$^+$).

Example-82

N-(4-Chloro-3-(3-(4-((2-chloro-4-(trifluoromethyl)phenyl)ethynyl)-2-fluorophenyl)-5-oxo-4,5-dihydro-1H-1,2,4-triazol-1-yl)benzyl)cyclopropanecarboxamide

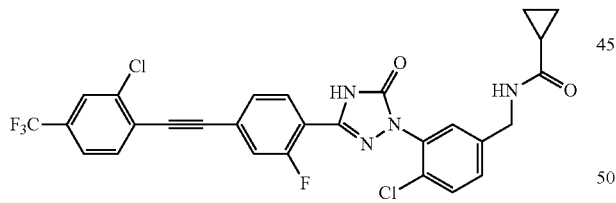

The title compound was prepared according to the procedure described in Example-3 by using N-(4-chloro-3-(3-(2-fluoro-4-iodophenyl)-5-oxo-4,5-dihydro-1H-1,2,4-triazol-1-yl)benzyl) cyclopropanecarboxamide (Intermediate-48, 0.060 g, 0.117 mmol), 2-chloro-1-ethynyl-4-(trifluoromethyl)benzene (Intermediate-25, 0.037 g, 0.175 mmol), TBAF (0.073 g, 0.234 mmol), bis(triphenylphosphine)palladium(II) chloride (catalytic) and DMSO (1.0 mL) at 80° C. to afford 0.030 g of the desired product. $^1$H NMR (300 MHz, DMSO d$_6$): δ 0.66-0.69 (m, 4H), 1.60 (m, 1H), 4.33 (d, J=6.0 Hz, 2H), 7.40 (d, J=8.4 Hz, 1H), 7.48 (s, 1H), 7.62-7.64 (m, 2H), 7.73 (d, J=11.4 Hz, 1H), 7.82 (d, J=7.8 Hz, 1H), 7.92-7.97 (m, 2H), 8.09 (s, 1H), 8.69 (m, 1H), 12.00 (br s, 1H); MS (m/z): 589.14 (M$^+$).

Example-83

N-(4-Chloro-3-(1-(3,4-dichlorophenyl)-5-oxo-4,5-dihydro-1H-1,2,4-triazol-3-yl)-2-fluorobenzyl)pivalamide

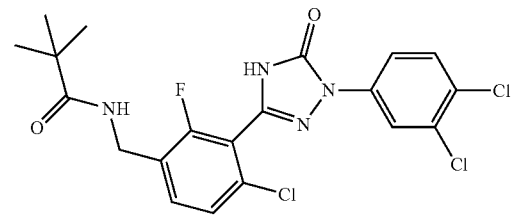 [SMILES: CC(C)(C)C(=O)NCc1ccc(Cl)c(-c2nn(-c3ccc(Cl)c(Cl)c3)c(=O)[nH]2)c1F]

To a solution of tert-butyl 2-(3,4-dichlorophenyl)hydrazinecarboxylate (Intermediate-52, 0.060 g, 0.21 mmol) in DCM (10 mL) was added solution of 6-chloro-2-fluoro-3-(pivalamidomethyl)benzoyl isocyanate (Intermediate-51, 0.101 g, 0.32 mmol) in DCM and the reaction mixture was stirred for 20 h at room temperature, followed by addition of TFA (3 mL) and further stirred for 20 h at room temperature. The reaction mass was quenched in water, extracted with DCM and concentrated to afford crude product which was purified by column chromatography eluting with MeOH:DCM to afford 0.007 g of pure product. $^1$H NMR (300 MHz, CDCl$_3$): δ 1.20 (s, 9H), 4.44 (d, J=5.4 Hz, 2H), 6.20 (m, 1H), 7.29 (m, 1H), 7.41-7.49 (m, 2H), 7.91 (d, J=8.1 Hz, 1H), 8.15 (s, 1H); MS (m/z): 471.26 (M$^+$).

Example-84

N-(4-Chloro-2-fluoro-3-(5-oxo-1-(4-(trifluoromethyl)phenyl)-4,5-dihydro-1H-1,2,4-triazol-3-yl)benzyl)pivalamide

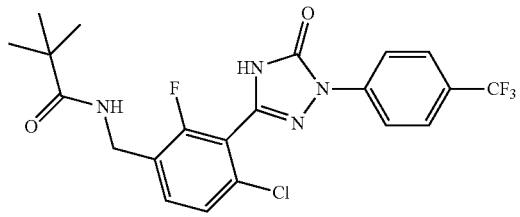 [SMILES: CC(C)(C)C(=O)NCc1ccc(Cl)c(-c2nn(-c3ccc(C(F)(F)F)cc3)c(=O)[nH]2)c1F]

The title compound was prepared by following the procedure as described for Example-83 by using tert-butyl 2-(4-(trifluoromethyl)phenyl) hydrazinecarboxylate (Intermediate-. 53, 0.060 g, 0.21 mmol), 6-chloro-2-fluoro-3-(pivalamidomethyl)benzoyl isocyanate (Intermediate-51, 0.101 g, 0.32 mmol), DCM (10 mL) and TFA (3 mL) to afford 0.025 g of pure product. $^1$H NMR (300 MHz, CDCl$_3$): δ 1.19 (s, 9H), 4.40 (m, 2H), 6.22 (m, 1H), 7.26 (m, 1H), 7.35 (m, 1H), 7.62 (d, J=8.1 Hz, 2H), 8.12 (d, J=7.8 Hz, 2H); MS (m/z): 471.18 (M+H$^+$).

Example-85

N-(4-Chloro-j-(1-(2,4-difluorophenyl)-5-oxo-4,5-dihydro-1H-1,2,4-triazol-3-yl)-2-fluorobenzyl)pivalamide

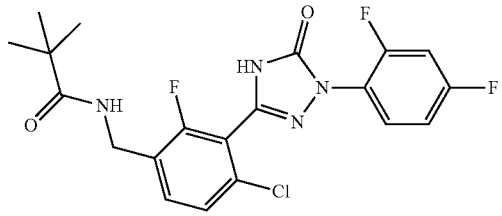 [SMILES: CC(C)(C)C(=O)NCc1ccc(Cl)c(-c2nn(-c3ccc(F)cc3F)c(=O)[nH]2)c1F]

The title compound was prepared by following the procedure as described for Example-83 by using tert-butyl 2-(2,4-difluorophenyl)hydrazinecarboxylate (Intermediate-54, 0.060 g, 0.21 mmol), 6-chloro-2-fluoro-3-(pivalamidomethyl)benzoyl isocyanate (Intermediate-51, 0.101 g, 0.32 mmol), DCM (10 mL) and TFA (3 mL) to afford 0.018 g of pure product. $^1$H NMR (300 MHz, CDCl$_3$): δ 1.16 (s, 9H), 4.38 (d, J=5.4 Hz, 2H), 6.25 (m, 1H), 6.79-6.82 (m, 1H), 6.90-6.96 (m, 2H), 7.20-7.32 (m, 2H), 7.50-7.53 (m, 1H); MS (m/z): 437.26 (M−H$^−$).

Example-86

N-(4-Chloro-2-fluoro-3-(1-(4-methoxyphenyl)-5-oxo-4,5-dihydro-1H-1,2,4-triazol-3-yl)benzyl)pivalamide

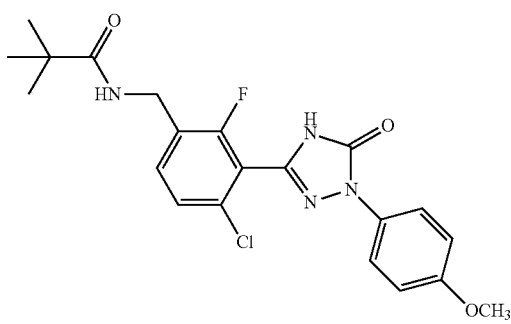 [SMILES: COc1ccc(-n2nc(-c3c(Cl)ccc(CNC(=O)C(C)(C)C)c3F)[nH]c2=O)cc1]

The title compound was prepared by following the procedure as described for Example-83 by using tert-butyl 2-(4-methoxyphenyl)hydrazinecarboxylate (Intermediate-55, 0.060 g, 0.21 mmol), 6-chloro-2-fluoro-3-(pivalamidomethyl)benzoyl isocyanate (Intermediate-51, 0.101 g, 0.32 mmol), DCM (10 mL) and TFA (3 mL) to afford 0.018 g of pure product. $^1$H NMR (400 MHz, CDCl$_3$): δ 1.20 (s, 9H), 3.82 (s, 3H), 4.46 (d, J=5.8 Hz, 2H), 6.12 (m, 1H), 6.95 (d, J=8.9 Hz, 2H), 7.26-7.30 (m, 1H), 7.43 (t, J=7.9 Hz, 1H), 7.82 (d, J=8.9 Hz, 2H), 11.01 (br s, 1H); MS (m/z): 433.20 (M+H$^+$).

Example-87

N-(4-Chloro-2-fluoro-3-(3-(2-fluoro-4-(trifluoromethyl)phenyl)-5-oxo-4,5-dihydro-1H-1,2,4-triazol-1-yl)benzyl)pivalamide

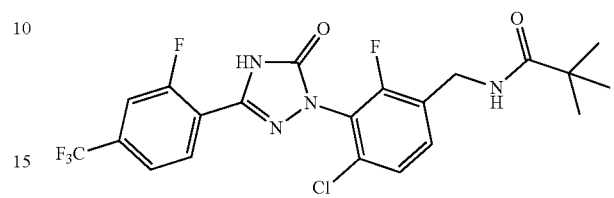

The title compound was prepared by following the procedure as described for Example-83 by using tert-butyl 2-(6-chloro-2-fluoro-3-(pivalamidomethyl)phenyl) hydrazinecarboxylate (Intermediate-57; 0.050 g, 0.13 mmol), 2-fluoro-4-(trifluoromethyl)benzoyl isocyanate (Intermediate-56, 0.10 g, 0.26 mmol), DCM (10 mL) and TFA (3 mL) to afford 0.030 g of pure product. $^1$H NMR (400 MHz, CDCl$_3$): δ 1.20 (s, 9H), 4.48 (d, J=5.7 Hz, 2H), 6.13 (m, 1H), 7.31 (d, J=8.5 Hz, 1H), 7.41-7.51 (m, 3H), 8.12 (t, J=7.9 Hz, 1H); MS (m/z): 489.20 (M+H$^+$).

Example-88

N-(4-Chloro-3-(3-(2-chloro-6-fluorophenyl)-5-oxo-4,5-dihydro-1H-1,2,4-triazol-1-yl)-2-fluorobenzyl)pivalamide

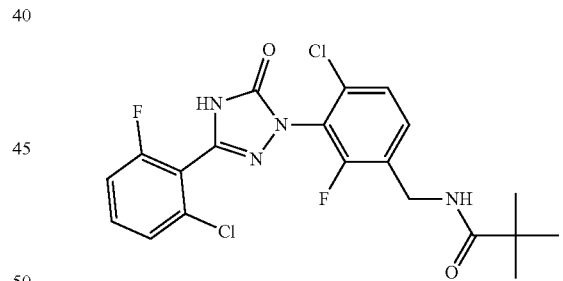

The title compound was prepared by following the procedure as described for Example-83 by using tert-butyl 2-(6-chloro-2-fluoro-3-(pivalamidomethyl)phenyl) hydrazinecarboxylate (Intermediate-57, 0.050 g, 0.13 mmol), 2-chloro-6-fluorobenzoyl isocyanate (Intermediate-8, 0.060 g, 0.26 mmol), DCM (10 mL) and TFA (3 mL) to afford 0.025 g of pure product. $^1$H NMR (400 MHz, CDCl$_3$): δ 1.19 (s, 9H), 4.48 (m, 2H), 6.09 (m, 1H), 7.15 (t, J=8.4 Hz, 1H), 7.32 (t, J=8.2 Hz, 21-1), 7.40-7.45 (m, 2H), 10.66 (br s, 1H); MS (m/z): 455.21 (M$^+$).

Example-89

N-(4-chloro-3-(1-(4-cyanophenyl)-5-oxo-4,5-dihydro-1H-1,2,4-triazol-3-yl)-2-fluorobenzyl)pivalamide

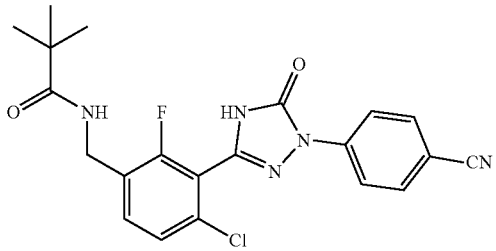 [SMILES: CC(C)(C)C(=O)NCc1ccc(Cl)c(-c2nn(-c3ccc(C#N)cc3)c(=O)[nH]2)c1F]

The title compound was prepared by following the procedure as described for Example-83 by using tert-butyl 2-(4-cyanophenyl)hydrazinecarboxylate (step-2 of Intermediate 17, 0.060 g, 0.25 mmol), 6-chloro-2-fluoro-3-(pivalamidomethyl)benzoyl isocyanate (Intermediate-51, 0.160 g, 0.51 mmol), DCM (10 mL) and TFA (3 mL) to afford 0.020 g of pure product. $^1$H NMR (400 MHz, CDCl$_3$): δ 1.20 (s, 9H), 4.45 (d, J=5.9 Hz, 2H), 6.19 (m, 1H), 7.32 (d, J=8.4 Hz, 1H), 7.43 (t, J=7.9 Hz, 1H), 7.73 (d, J=8.8 Hz, 2H), 8.19 (d, J=8.4 Hz, 2H), 10.72 (br s, 1H); MS (m/z): 426.27 (M–H$^-$).

Example-90

N-(4-Chloro-3-(3-(4-chloro-2-fluorophenyl)-5-oxo-4,5-dihydro-1H-1,2,4-triazol-1-yl)-2-fluorobenzyl)pivalamide

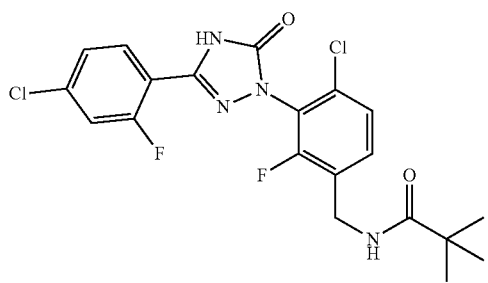 [SMILES: CC(C)(C)C(=O)NCc1ccc(Cl)c(-n2nc(-c3ccc(Cl)cc3F)[nH]c2=O)c1F]

The title compound was prepared by following the procedure as described for Example-83 by using tert-butyl 2-(6-chloro-2-fluoro-3-(pivalamidomethyl)phenyl) hydrazinecarboxylate (Intermediate-57, 0.050 g, 0.13 mmol), 4-chloro-2-fluorobenzoyl isocyanate (Intermediate-58, 0.060 g, 0.26 mmol), DCM (10 mL) and TFA (3 mL) to afford 0.025 g of desired product. $^1$H NMR (400 MHz, CDCl$_3$): δ 1.21 (s, 9H), 4.50 (t, J=7.2 Hz, 2H), 6.07 (m, 1H), 7.22-7.26 (m, 2H), 7.32 (d, J=8.4 Hz, 1H), 7.44 (t, J=8.1 Hz, 1H), 7.93 (t, J=8.6 Hz, 1H); MS (m/z): 455.08 (M$^+$).

Example-91

N-(4-Chloro-3-(3-(4-chloro-2-fluorophenyl)-5-oxo-4,5-dihydro-1H-1,2,4-triazol-1-yl)benzyl)cyclopropanecarboxamide

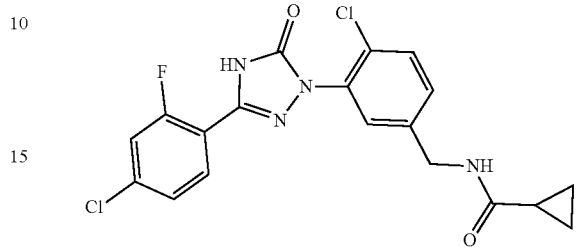

The title compound was prepared by following the procedure as described for Example-83 by using tert-butyl 2-(2-chloro-5-(cyclopropanecarboxamidomethyl) phenyl) hydrazinecarboxylate (step-7 of Intermediate-48, 0.060 g, 0.17 mmol), 4-chloro-2-fluorobenzoyl isocyanate (Intermediate-58, 0.035 g, 0.71 mmol), DCM (10 mL) and TFA (3 mL) to afford 0.040 g of desired product. $^1$H NMR (400 MHz, DMSO d$_6$): δ 0.67-0.69 (m, 4H), 1.59-1.60 (m, 1H), 4.31 (d, J=5.9 Hz, 2H), 7.36 (dd, J=6.24 Hz, 1H), 7.45 (dd, J=8.5 Hz, 2H), 7.59 (d, J=8.3 Hz, 1H), 7.65 (d, J=8.8 Hz, 1H), 7.83 (t, J=8.3 Hz, 1H), 7.64 (t, J=6 Hz, 1H), 12.51 (br s, 1H); MS (m/z): 421.08 (M$^+$).

Example-92

N-(4-Chloro-3-(3-(2-fluoro-4-(trifluoromethyl)phenyl)-5-oxo-4,5-dihydro-1H-1,2,4-triazol-1-yl)benzyl)cyclopropanecarboxamide

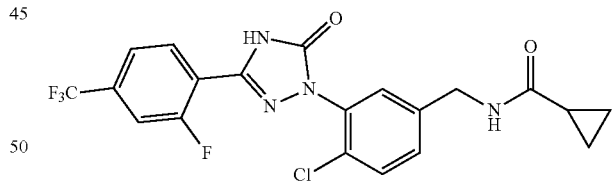

The title compound was prepared by following the procedure as described for Example-83 by using tert-butyl 2-(2-chloro-5-(cyclopropanecarboxamidomethyl) phenyl) hydrazinecarboxylate (step-7 of Intermediate-48, 0.060 g, 0.17 mmol), 2-fluoro-4-(trifluoromethyl)benzoyl isocyanate (Intermediate-56, 0.035 g, 0.82 mmol), DCM (10 mL) and TFA (3 mL) to afford 0.045 g of desired product. $^1$H NMR (400 MHz, DMSO d$_6$): δ 0.67 (m, 4H), 1.60 (m, 1H), 4.3 (d, J=5.9 Hz, 2H), 7.37 (d, J=6.4 Hz, 1H), 7.46 (s, 1H), 7.60 (d, J=8.3 Hz, 1H), 7.74 (d, J=8.2 Hz, 1H), 7.89 (d, J=10.56 Hz, 1H), 8.05 (t, J=7.7 Hz, 1H), 8.65 (t, J=5.8 Hz, 1H), 12.6 (br s, 1H); MS (m/z): 454.98 (M$^+$).

Example-93

N-(4-Chloro-2-fluoro-3-(5-oxo-3-(4-(trifluoromethyl)phenyl)-4,5-dihydro-1H-1,2,4-triazol-1-yl)benzyl)pivalamide

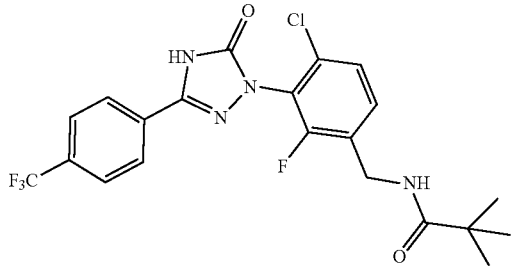 [SMILES: CC(C)(C)C(=O)NCc1ccc(Cl)c(-n2nc(-c3ccc(C(F)(F)F)cc3)[nH]c2=O)c1F]

The title compound was prepared by following the procedure as described for Example-83 by using tert-butyl 2-(6-chloro-2-fluoro-3-(pivalamidomethyl)phenyl) hydrazinecarboxylate (Intermediate-57, 0:050 g, 0.13 mmol), 4-(trifluoromethyl) benzoyl isocyanate (Intermediate-59, 0.060 g, 0.26 mmol), DCM (10 mL) and TFA (3 mL) to afford 0.045 g of desired product. $^1$H NMR (400 MHz, DMSO d$_6$): δ 1.12 (s, 9H), 4.30 (d, J=4.4 Hz, 2H), 7.41 (t, J=8 Hz, 1H), 7.53 (d, J=8.5 Hz, 1H), 7.91 (d, J=8.4 Hz, 2H), 8.0 (d, J=8.2 Hz, 2H), 8.17 (t, J=5.8 Hz, 1H), 12.9 (br s, 1H); MS (m/z): 471.10 (M+H$^+$).

Example-94

N-(4-Chloro-2-fluoro-3-(5-oxo-1-(5-(trifluoromethyl)pyridin-2-yl)-4,5-dihydro-1H-1,2,4-triazol-3-yl)benzyl)pivalamide

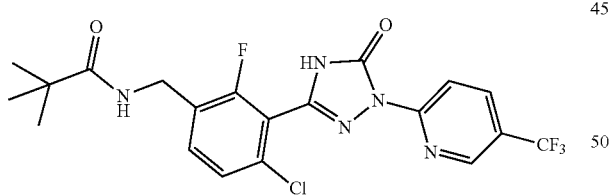

The title compound was prepared by following the procedure as described for Example-83 by using tert-butyl 2-(5-(trifluoromethyl)pyridin-2-yl)hydrazinecarboxylate (Intermediate-60, 0.050 g, 0.18 mmol), 6-chloro-2-fluoro-3-(pivalamidomethyl)benzoyl isocyanate (Intermediate-51, 0.120 g, 0.36 mmol), DCM (10 mL) and TFA (3 mL) to afford 0.012 g of desired product. $^1$H NMR (400 MHz, DMSO d$_6$): δ 1.13 (s, 9H), 4.30 (d, J=5.6 Hz, 2H), 7.11 (br s, 1H), 7.46 (1, J=8 Hz, 1H), 7.52 (d, J=8.8 Hz, 1H), 8.14 (m, 1H), 8.28 (d, J=8.8 Hz, 1H), 8.35 (dd, J=7.2 Hz, 1H), 8.87 (s, 1H); MS (m/z): 472.24 (M+H$^+$).

Example-95

N-(4-Chloro-2-fluoro-3-(5-oxo-1-(6-(trifluoromethyl)pyridin-3-yl)-4,5-dihydro-1H-1,2,4-triazol-3-yl)benzyl)pivalamide

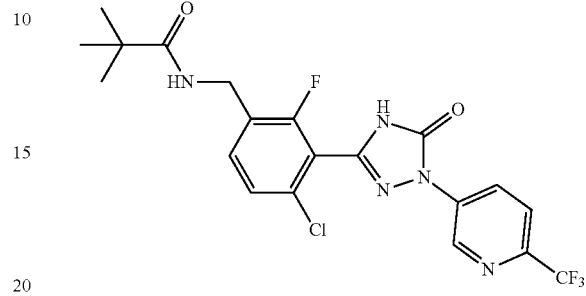

The title compound was prepared by following the procedure as described for Example-83 by using tert-butyl 2-(6-(trifluoromethyl)pyridin-3-yl) hydrazine carboxylate (Intermediate-61, 0.050 g, 0.18 mmol), 6-chloro-2-fluoro-3-(pivalamidomethyl)benzoyl isocyanate (Intermediate-51, 0.120 g, 0.36 mmol), DCM (10 mL) and TFA (3 mL) to afford 0.013 g of desired product. $^1$H NMR (400 MHz, DMSO d$_6$): δ 1.13 (s, 9H), 4.30 (d, J=5.6 Hz, 2H), 7.11 (br s, 1H), 7.46 (t, J=8 Hz, 1H), 7.53 (d, J=8.4 Hz, 1H), 8.02 (d, J=8.4 Hz, 1H), 8.16 (m, 1H), 8.56 (dd, J=6.4 Hz, 1H), 9.30 (m, 1H); MS (m/z): 472.26 (M+H$^+$).

Example-96

4-Chloro-N-cyclopropyl-3-(5-oxo-1-(4-(trifluoromethyl)phenyl)-4,5-dihydro-1H-1,2,4-triazol-3-yl)benzenesulfonamide

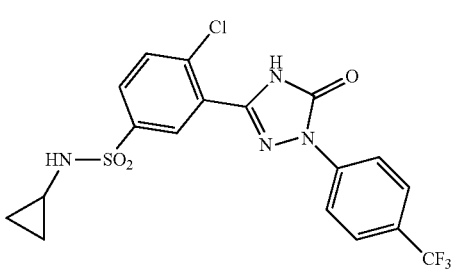 [SMILES: O=c1[nH]c(-c2cc(S(=O)(=O)NC3CC3)ccc2Cl)nn1-c1ccc(C(F)(F)F)cc1]

The title compound was prepared by following the procedure as described for Example-83 by using tert-butyl 2-(4-(trifluoromethyl)phenyl)hydrazinecarboxylate (Intermediate-53, 0.050 g, 0.18 mmol), 2-chloro-5-(N-cyclopropylsulfamoyl)benzoyl isocyanate (step-4 of Intermediate-40, 0.108 g, 0.36 mmol), DCM (10 mL) and TFA (3 mL) to afford 0.050 g of desired product. $^1$H NMR (400 MHz, DMSO d$_5$): δ 0.40-0.42 (m, 2H), 0.50-0.54 (m, 2H), 2.17-2.21 (m, 1H), 7.85 (d, J=8.8 Hz, 2H), 7.92-7.98 (m, 2H), 8.15-8.21 (m, 4H), 12.84 (s, 1H); MS (m/z): 457.15 (M+H$^+$).

Example-97

4-Chloro-3-(1-(4-chlorophenyl)-5-oxo-4,5-dihydro-1H-1,2,4-triazol-3-yl)-N-cyclopropylbenzenesulfonamide

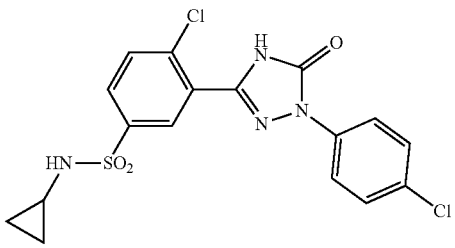 [SMILES: O=c1[nH]c(-c2cc(S(=O)(=O)NC3CC3)ccc2Cl)nn1-c1ccc(Cl)cc1]

The title compound was prepared by following the procedure as described for Example-83 by using tert-butyl 2-(4-chlorophenyl)hydrazinecarboxylate (Intermediate-62, 0.050 g, 0.20 mmol), 2-chloro-5-(N-cyclopropylsulfamoyl) benzoyl isocyanate (step-4 of Intermediate-40, 0.123 g, 0.41 mmol), DCM (10 mL) and TFA (3 mL) to afford 0.025 g of pure product. $^1$H NMR (400 MHz, DMSO d$_6$): δ 0.39-0.41 (m, 2H), 0.49-0.52 (m, 2H), 2.17-2.20 (m, 1H), 7.52-7.55 (d, J=8.0 Hz, 2H), 7.91-8.00 (m, 5H), 8.14 (m, 1H), 12.60 (br s, 1H); MS (m/z): 425.10 (M$^+$).

Example-98

N-(4-Chloro-3-(1-(4-chlorophenyl)-5-oxo-4,5-dihydro-1H-1,2,4-triazol-3-yl)-2-fluorobenzyl)pivalamide

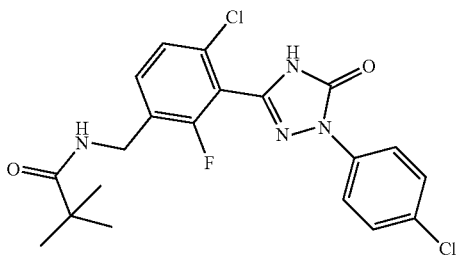 [SMILES: CC(C)(C)C(=O)NCc1ccc(Cl)c(-c2nn(-c3ccc(Cl)cc3)c(=O)[nH]2)c1F]

The title compound was prepared by following the procedure as described for Example-83 by using tert-butyl 2-(4-chlorophenyl)hydrazinecarboxylate (Intermediate-62, 0.050 g, 0.20 mmol), 6-chloro-2-fluoro-3-(pivalamidomethyl)benzoyl isocyanate (Intermediate-51, 0.130 g, 0.41 mmol), DCM (10 mL) and TFA (3 mL) to afford 0.040 g of pure product. $^1$H NMR (400 MHz, DMSO d$_6$): δ 1.12 (s, 9H), 4.30 (d, J=6.0 Hz, 2H), 7.24-7.47 (m, 2H), 7.52 (d, J=7.2 Hz, 2H), 7.94 (d, J=8.8 Hz, 2H), 8.16 (m, 1H), 12.10 (br s, 1H); MS (m/z): 437:16 (M$^+$).

Example-99

N-(4-Chloro-3-(5-oxo-1-(4-(trifluoromethyl)phenyl)-4,5-dihydro-1H-1,2,4-triazol-3-yl)benzyl)-2,2,2-trifluoroacetamide

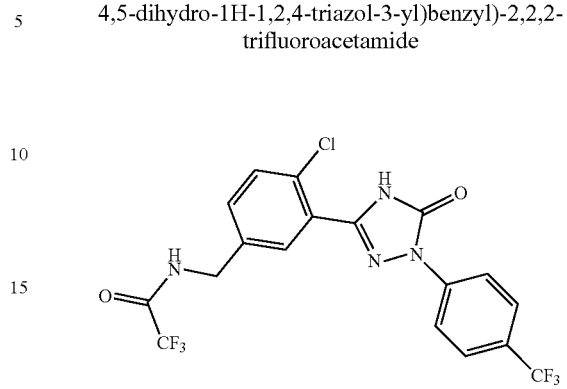

The title compound was prepared according to the procedure described for Example-83 by using tert-butyl 2-(4-(trifluoromethyl)phenyl)hydrazinecarboxylate (Intermediate-53, 1.00 g, 3.63 mmol), 2-chloro-5-((2,2,2-trifluoroacetamido)methyl) benzoyl isocyanate (step-3 of Intermediate-26, 1.30 g, 4.03 mmol), DCM (20 mL) and TFA (5.0 mL) to afford 0.700 g of the desired product. $^1$H NMR (400 MHz, DMSO d$_6$): δ 4.44-4.46 (d, J=6 Hz, 2H), 7.48-7.50 (d, J=8.4 Hz, 1H), 7.65-7.68 (m, 2H), 7.84-7.86 (d, J=8.8 Hz, 2H), 8.17-8.19 (d, J=8.4 Hz, 2H), 10.05 (br s, 1H), 12.69 (br s, 1H); MS (m/z): 463.17 (M−H$^−$).

Example-100

N-(4-Chloro-3-(5-oxo-1-(4-(trifluoromethyl)phenyl)-4,5-dihydro-1H-1,2,4-triazol-3-yl)benzyl)pivalamide

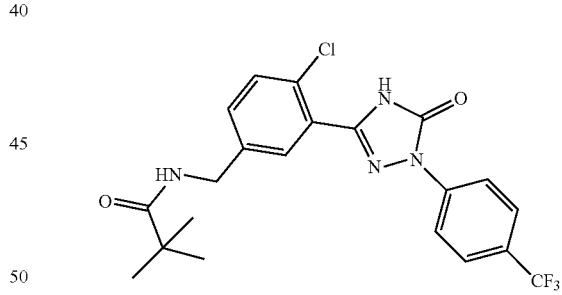

To a solution of 3-(5-(aminomethyl)-2-chlorophenyl)-1-(4-(trifluoromethyl)phenyl)-1H-1,2,4-triazol-5(4H)-one (Intermediate-63, 0.070 g, 0.189 mmol) in dry THF (5 mL) was added DIPEA (3 mL) and stirred for 20 minutes. The reaction mixture was cooled to 0° C. and pivaloyl chloride (0.025 g, 0.283 mmol) was added and stirred for 3 h at RT. The reaction mass was quenched in water, extracted with DCM: MeOH and concentrated to afford of the crude product which was purified by column chromatography eluting with MeOH:DCM to afford 0.030 g of the desired title product. $^1$H NMR (400 MHz, DMSO d$_6$): δ 1.12 (s, 9H), 4.28-4.30 (d, J=6 Hz, 2H), 7.39-7.42 (d, J=8. Hz, 1H), 7.59-7.61 (d, J=6.4 Hz, 2H), 7.84-7.86 (d, J=8.8 Hz, 2H), 8.14-8.19 (m, 3H), 12.59 (br s, 1H); MS (m/z): 451.29 (M−H$^−$).

Example-101

(R)—N-(4-Chloro-3-(5-oxo-1-(4-(trifluoromethyl)phenyl)-4,5-dihydro-1H-1,2,4-triazol-3-yl)benzyl)tetrahydrofuran-2-carboxamide

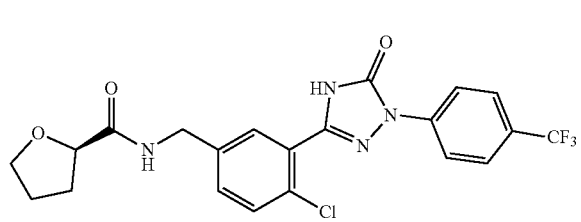 [SMILES: O=C(NCc1ccc(Cl)c(-c2nn(-c3ccc(C(F)(F)F)cc3)c(=O)[nH]2)c1)[C@H]1CCCO1]

To a solution of 3-(5-(aminomethyl)-2-chlorophenyl)-1-(4-(trifluoromethyl)phenyl)-1H-1,2,4-triazol-5(4H)-one (Intermediate-63, 0.070 g, 0.189 mmol) in dry THF:DMF (4:1 mL) was added TBTU (0.182 g, 0.567 mmol) and TEA (3 mL) and stirred for 1 h under nitrogen atmosphere. To the reaction mixture (R)-(±)tetrahydro-2-furoic acid (0.032 g, 0.283 mmol) was added and stirred for 18 h at room temperature. The reaction mass was quenched in water, extracted with ethyl acetate and concentrated to afford crude product which was purified by column chromatography eluting with MeOH: DCM to afford 0.025 g of the desired title product. $^1$H NMR (400 MHz, DMSO $d_6$): δ 1.23 (s, 2H), 1.74-1.92 (m, 3H), 2.09-2.24, (m, 1H), 3.75-3.80 (m, 1H), 3.89-3.94 (m, 1H), 4.26-4.37 (m, 3H), 7.43-7.45 (d, J=8.4 Hz, 1H), 7.61-7.63 (d, J=8.4 Hz, 2H), 7.85-7.87 (d, J=8.8 Hz, 2H), 8.19-8.21 (d, J=8.8 Hz, 2H), 8.50-8.53 (m, 1H), 12.71 (br s, 1H); MS (m/z): 465.55 (M−H$^-$).

Example-102

N-(4-Chloro-3-(5-oxo-1-(4-(trifluoromethyl)phenyl)-4,5-dihydro-1H-1,2,4-triazol-3-yl)benzyl)cyclopropanesulfonamide

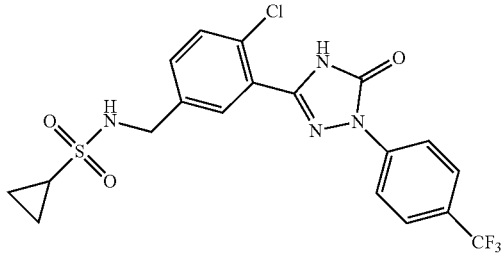 [SMILES: O=c1[nH]c(-c2cc(CNS(=O)(=O)C3CC3)ccc2Cl)nn1-c1ccc(C(F)(F)F)cc1]

The title compound was prepared according to the procedure described in Example-100 by using 3-(5-(aminomethyl)-2-chlorophenyl)-1-(4-(trifluoromethyl)phenyl)-1H-1,2,4-triazol-5(4H)-one (Intermediate-63, 0.070 g, 0.189 mmol), cyclopropanesulfonyl chloride (0.2 mL), DIPEA (3 mL), and dry THF (5 mL) to afford 0.029 g of pure product. $^1$H NMR (400 MHz, DMSO $d_6$): δ 0.86-0.92 (m, 4H), 1.14-1.24 (m, 1H), 4.26-4.28 (d, J=6.4 Hz, 2H), 7.57-7.60 (d, J=8.4 Hz, 1H), 7.63-7.68 (d, J=8.4 Hz, 1H), 7.58-7.81 (m, 1H), 7.86-7.88 (d, J=8.8 Hz, 2H), 8.19-8.21 (d, J=8.4 Hz, 2H), 12.89 (br s, 1H); MS (m/z): 471.30 (M−H$^-$).

Example-103

N-(4-Chloro-3-(1-cyclohexyl-5-oxo-4,5-dihydro-1H-1,2,4-triazol-3-yl)-2-fluorobenzyl)pivalamide

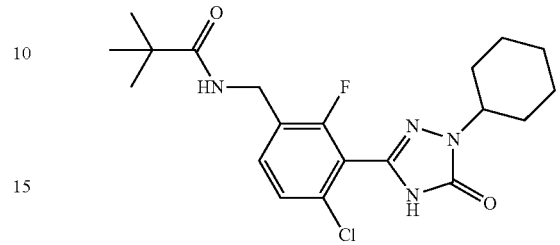

The title compound was prepared by following the procedure as described for Example-83 by using tert-butyl 2-(cyclohexyl)hydrazinecarboxylate (Intermediate-64, 0.050 g, 0.23 mmol), 6-chloro-2-fluoro-3-(pivalamidomethyl)benzoyl isocyanate (Intermediate-51, 0.225 g, 0.70 mmol), DCM (10 mL) and TFA (3 mL) to afford 0.015 g of pure product. $^1$H NMR (400 MHz, DMSO $d_6$): δ 1.13 (s, 9H), 1.22-1.23 (m, 2H), 1.30-1.37 (m, 2H), 1.62-1.64 (m, 2H), 1.78-1.81 (m, 4H), 3.90-3.92 (m, 1H), 4.27-4.28 (d, J=4.8 Hz, 2H), 7.37-7.41 (t, 1H), 7.46-7.48 (d, 1H), 8.17 (br s, 1H); MS (m/z): 409.36 (M+H$^+$).

Example-104

N-(4-Chloro-3-(5-oxo-1-(4-(trifluoromethyl)phenyl)-4,5-dihydro-1H-1,2,4-triazol-3-yl)benzyl)-2-fluorobenzamide

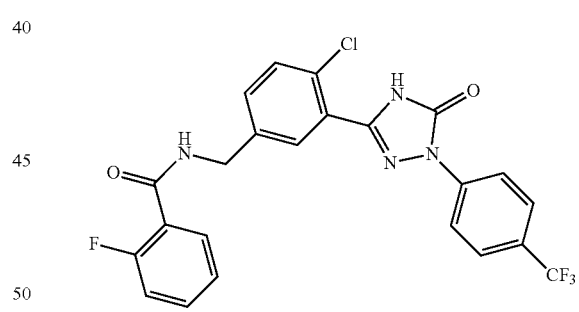

To a solution of 3-(5-(aminomethyl)-2-chlorophenyl)-1-(4-(trifluoromethyl)phenyl)-1H-1,2,4-triazol-5(4H)-one (Intermediate-63, 0.060 g, 0.162 mmol) in dry THF (5 mL) was added DIPEA (3 mL) and stirred for 20 minutes. The reaction mixture was cooled to 0° C. and 2-fluorobenzoyl chloride (0.038 g, 0.243 mmol) was added and stirred for 3 h at room temperature. The reaction mass was quenched in water, extracted with DCM:MeOH and concentrated to afford crude product which was purified by column chromatography eluting with MeOH:DCM to afford 0.030 g of pure product. $^1$H NMR (400 MHz, DMSO $d_6$): δ 4.50-4.52 (d, J=8 Hz, 2H), 7.25-7.33 (m, 2H), 7.52-7.55 (m, 2H), 7.63-7.65 (m, 2H), 7.72-7.86 (d, J=2.4 Hz, 1H), 7.83-7.86 (d, J=11.6 Hz, 21-1), 8.17-8.20 (d, J=11.6 Hz, 2H), 8.95-8.99 (t, 1H), 12.69 (br s, 1H); MS (m/z): 491.17 (M+H+).

Example-105

N-(4-Chloro-3-(5-oxo-1-(4-(trifluoromethyl)phenyl)-4,5-dihydro-H-1,2,4-triazol-3-yl)benzyl)isoxazole-5-carboxamide

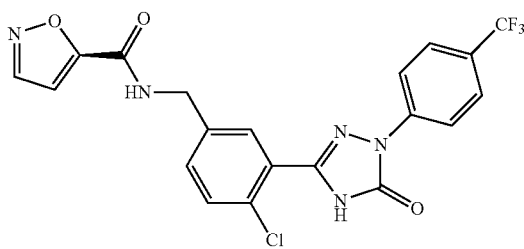

To a solution of 3-(5-(aminomethyl)-2-chlorophenyl)-1-(4-(trifluoromethyl)phenyl)-1H-1,2,4-triazol-5(4H)-one (Intermediate-63, 0.060 g, 0.162 mmol) in dry THF (5 mL) was added DIPEA (3 mL) and stirred for 20 minutes. The reaction mixture was cooled to 0° C. and isoxazole-5-carbonyl chloride (0.032 g, 0.243 mmol) was added and stirred for 3 h at room temperature. The reaction mass was quenched in water, extracted with DCM:MeOH and concentrated to afford crude product which was purified by column chromatography eluting with MeOH:DCM to afford 0.030 g of pure product. $^1$H NMR (400 MHz, DMSO d$_6$): δ 4.50-4.52 (d, J=8 Hz, 2H), 7.09-7.10 (d, J=2 Hz, 1H), 7.43-7.45 (d, J=8.4 Hz, 1H), 7.50-7.53 (d, J=10.4 Hz, 1H), 7.59-7.64 (d, J=18 Hz, 1H), 7.82-7.85 (d, J=8.8 Hz, 2H), 8.17-8.19 (d, J=8.4 Hz, 2H), 8.74-8.75 (d, J=2 Hz, 1H), 9.58-9.61 (t, 1H), 12.61-12.74 (br s, 1H); MS (m/z): 464.11 (M+H+).

Example-106

N-(3-(1-(4-(Trifluoromethyl)phenyl)-4,5-dihydro-5-oxo-1H-1,2,4-triazol-3-yl)-2,4-dimethylbenzyl)-2,2,2-trifluoroacetamide

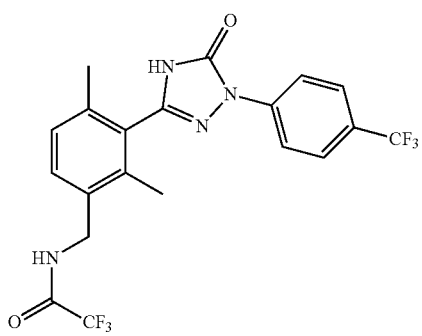 [SMILES: Cc1ccc(CNC(=O)C(F)(F)F)c(C)c1-c1nn(-c2ccc(C(F)(F)F)cc2)c(=O)[nH]1]

The title compound was prepared according to the procedure described in Example-83 by using tert-butyl 2-(4-(trifluoromethyl)phenyl)hydrazinecarboxylate (Intermediate-53, 1.00 g, 3.63 mmol), 3-((2,2,2-trifluoroacetamido)methyl)-2,6-dimethylbenzoyl isocyanate (Intermediate-65, 1.00 g, 3.33 mmol), DCM (20 mL), trifluoro acetic acid (5.0 mL) to afford 0.700 g of the desired product. $^1$H NMR (400 MHz, DMSO d$_6$): δ 2.20 (s, 3H), 2.22 (s, 3H), 4.40 (d, J=4.2 Hz, 2H), 7.21 (d, J=6.0 Hz, 1H), 7.29 (d, J=6.0 Hz, 1H), 7.82 (d, J=6.6 Hz, 1H), 8.17 (d, J=6.6 Hz, 1H), 9.95 (t, J=6.9 Hz, 1H), 12.32 (br s, 1H); MS (m/z): 457.26 (M−H)−.

Example-107

(R)—N-(2,4-Dimethyl-3-(5-oxo-1-(4-(trifluoromethyl)phenyl)-4,5-dihydro-1H-1,2,4-triazol-3-yl)benzyl)tetrahydrofuran-2-carboxamide

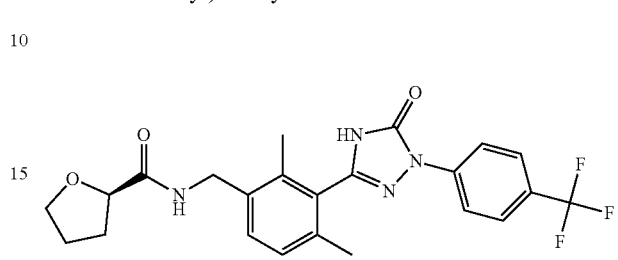

To a solution of 5-(3-(aminomethyl)-2,6-dimethylphenyl)-2-(4-(trifluoromethyl)phenyl)-2H-1,2,4-triazol-3(4H)-one (Intermediate-66, 0.050 g, 0.138 mmol) in dry THF:DMF (4 mL:1 mL), TBTU (0.132 g, 0.414 mmol) and TEA (1.0 mL) were added and the reaction mass was stirred for 1 h under nitrogen atmosphere. To the reaction mass, (R)-(−)-tetrahydrofuran-2-carboxylic acid (0.024 g, 0.207 mmol) was added and stirred for 18 h at room temperature. After completion of the reaction, the reaction mass was quenched in water, extracted with ethyl acetate and concentrated to afford crude product which was purified by column chromatography by eluting with solution of 2% ammonia in 10% MeOH:DCM to afford 0.017 g of the title product. $^1$H NMR (400 MHz, DMSO d$_6$): δ 1.79 (m, 3H), 1.87 (m, 3H), 2.20 (s, 611), 3.74-3.79 (m, 1H), 3.88-3.92 (m, 1H), 4.25 (d, J=4.5 Hz, 2H), 7.16 (d, J=6.0 Hz, 1H), 7.25 (d, J=6.0 Hz, 1H), 7.82 (d, J=6.6 Hz, 1H), 8.17 (d, J=6.3 Hz, 2H), 8.24 (t, J=4.8 Hz, 2H), 12.30 (br s, 1H); MS (m/z): 461.14 (M+H)+.

Example-108

N-(3-(1-(4-(Trifluoromethyl)phenyl)-4,5-dihydro-5-oxo-1H-1,2,4-triazol-3-yl)-2,4-dimethylbenzyl)pivalamide

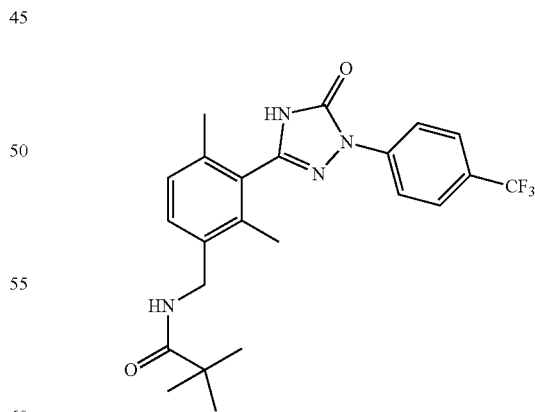

To a solution of 5-(3-(aminomethyl)-2,6-dimethylphenyl)-2-(4-(trifluoromethyl)phenyl)-2H-1,2,4-triazol-3(4H)-one (Intermediate-66, 0.050 g) in dry THF (5 mL), TEA (3 mL) was added and stirred the reaction mixture for 20 minutes. The reaction mixture was cooled to 0° C. and pivaloyl chloride (0.05 g, 0.563 mmol) was added and stirred for 3 h at RT. After completion of the reaction, the reaction mass was quenched with water, extracted with DCM:MeOH. The organic layer was separated, concentrated, and purified by column chromatography to afford 0.012 g of the desired title product. ¹H NMR (400 MHz, DMSO d₆): δ 1.15 (s, 9H), 2.18 (s, 3H), 2.22 (s, 3H), 4.24 (d, J=12.6 Hz, 2H), 7.19 (d, 1H), 7.25 (d, 1H), 7.84 (d, J=5.7 Hz, 2H), 8.0 (t, 1H), 8.20 (d, J=6.4 Hz, 2H), 12.30 (br s, 1H); MS (m/z): 447.20 (M+H)⁺.

Example-109

(S)—N-(4-Chloro-3-(1-(4-(trifluoromethyl)phenyl)-4,5-dihydro-5-oxo-1H-1,2,4-triazol-3-yl)benzyl)-tetrahydro furan-2-carboxamide

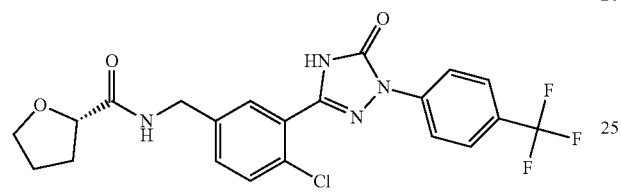

The title compound was prepared according to the procedure described in Example-107 by using 3-(5-(aminomethyl)-2-chlorophenyl)-1-(4-(trifluoromethyl)phenyl)-1H-1,2,4-triazol-5(4H)-one (Intermediate-63, 0.070 g, 0.189 mmol), THF:DMF (5 mL:1 mL), (S)-(−) tetrahydrofuran-2-carboxylic acid (0.032 g, 0.283 mmol), TBTU (0.182 g, 0.567 mmol), and TEA (3.0 mL). The obtained crude was purified by column chromatography on basic alumina by eluting solution of 2% ammonia in 10.0% MeOH:DCM to afford 0.010 g of the desired product. ¹H NMR (300 MHz, DMSO d₆): δ 1.80 (m, 3H), 2.15 (m, 1H), 3.75 (m, 1H), 3.94 (m, 1H), 4.27-4.32 (m, 3H), 7.42 (d, 1H), 7.60 (d, 2H), 7.85 (d, J=5.4 Hz, 2H), 8.20 (d, J=4.5 Hz, 2H), 8.52 (s, 1H), 12.50 (s, 1H); MS (m/z): 467.08 (M+H)⁺.

Example-110

N-(4-Chloro-3-(1-(4-(trifluoromethyl)phenyl)-4,5-dihydro-5-oxo-1H-1,2,4-triazol-3-yl)benzyl)-1-methyl-1H-imidazole-2-carboxamide

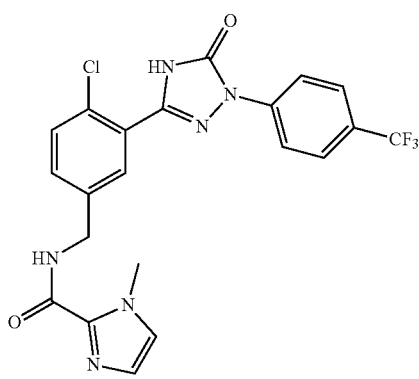 [SMILES: Cn1ccnc1C(=O)NCc1ccc(Cl)c(-c2nn(-c3ccc(C(F)(F)F)cc3)c(=O)[nH]2)c1]

The title compound was prepared according to the procedure described in Example-108 by using 3-(5-(aminomethyl)-2-chlorophenyl)-1-(4-(trifluoromethyl)phenyl)-1H-1,2,4-triazol-5(4H)-one (Intermediate-63, 0.070 g, 0.189 mmol), 1-methyl-1H-imidazole-2-carbonyl chloride (0.026 g, 0.283 mmol), dry THF (5 mL), DIPEA (2 mL). The obtained crude was purified by column chromatography using 2% ammonia in 20% MeOH:DCM as mobile phase to afford 0.020 g of the desired title product. ¹H NMR (300 MHz, DMSO d₆): δ 3.50 (s, 3H), 4.41 (d, J=18.0 Hz, 1H), 6.99 (s, 1H), 7.43 (br, 2H), 7.67 (d, 1H), 7.78 (s, 1H), 8.28 (d, J=4.5 Hz, 2H), 8.30 (s, 1H), 9.08 (t, 1H); MS (m/z): 477.10 (M+H)⁺.

Example-111

N-(4-Chloro-2-fluoro-3-(4,5-dihydro-3-(4-(3,3-dimethylbut-1-ynyl)phenyl)-5-oxo-1,2,4-triazol-1-yl)benzyl)pivalamide

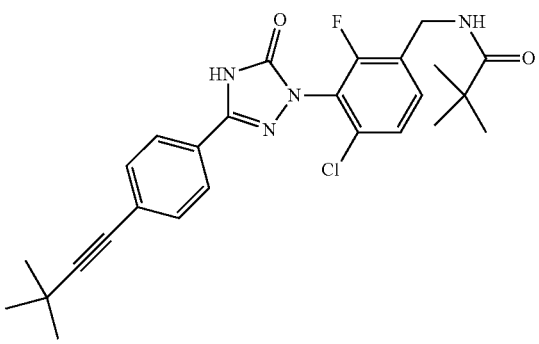 [SMILES: CC(C)(C)C#Cc1ccc(-c2nn(-c3c(Cl)ccc(CNC(=O)C(C)(C)C)c3F)c(=O)[nH]2)cc1]

To a solution of N-(4-chloro-2-fluoro-3-(4,5-dihydro-3-(4-iodophenyl)-5-oxo-1,2,4-triazol-1-yl)benzyl)pivalamide (Intermediate-68, 0.050 g, 0.094 mmol) in DMSO (3.0 mL), 3,3-dimethylbut-1-yne (0.011 g, 0.142 mmol), TBAF (0.074 g, 0.283 mmol) and bis(triphenylphosphine)palladium(II) chloride (0.020 g, 0.022 mmol) were added and the reaction mass was stirred at 80° C. for 5-6 h. After completion of the reaction, the reaction mass was quenched with water and extracted with DCM and concentrated. The obtained crude product was purified with column chromatography on silica gel column and 2.0% EA: DCM as mobile phase to afford 0.022 g of the desired title product. ¹H NMR (400 MHz, DMSO d₆): δ 1.09 (s, 9H), 1.25 (s, 9H), 4.31 (br s, 2H), 7.35-7.51 (m, 4H), 7.80 (d, J=8.3 Hz, 2H), 8.18-8.20 (m, 1H); MS (m/z): 481.14 (M−H)⁻.

Example-112

N-(4-Chloro-3-(3-(4-(2-cyclopropylethynyl)phenyl)-4,5-dihydro-5-oxo-1,2,4-triazol-1-yl)-2-fluorobenzyl)pivalamide

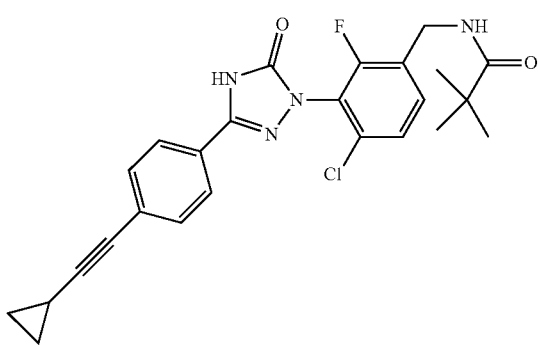 [SMILES: CC(C)(C)C(=O)NCc1ccc(Cl)c(-n2nc(-c3ccc(C#CC4CC4)cc3)[nH]c2=O)c1F]

The title compound was prepared according to the procedure described in Example-111 by using N-(4-chloro-2-fluoro-3-(4,5-dihydro-3-(4-iodophenyl)-5-oxo-1,2,4-triazol-1-yl)benzyl)pivalamide (Intermediate-68, 0.050 g, 0.094 mmol), ethynylcyclopropane (0.009 g, 0.142 mmol), TBAF (0.074 g, 0.283 mmol), bis(triphenylphosphine)palladium(11) chloride (0.003 g, 0.003 mmol) and DMSO (3.0 mL) to afford 0.018 g of the desired title product. $^1$H NMR (400 MHz, DMSO $d_6$): δ 0.75 (m, 2H), 0.77-0.91 (m, 2H), 1.36 (s, 9H), 1.53-1.59 (m, 2H), 7.38 (t, J=5.9 Hz, 1H), 7.46-7.52 (m, 3H), 8.79 (d, J=4.4 Hz, 2H), 8.19 (t, J=4.3 Hz, 1H); MS (m/z): 467.15 (M+H)$^+$.

Example-113

N-(4-Chloro-2-fluoro-5-(1-(4-(trifluoromethyl)phenyl)-4,5-dihydro-5-oxo-1H-1,2,4-triazol-3-yl)benzyl)-2,2,2-trifluoroacetamide

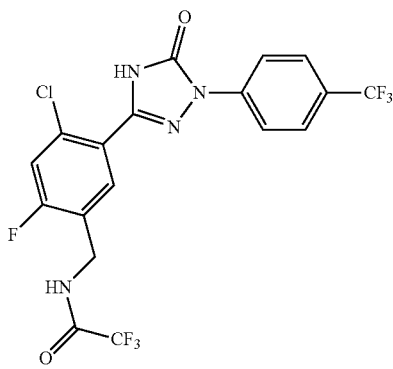 [SMILES: O=C(NCc1cc(-c2nn(-c3ccc(C(F)(F)F)cc3)c(=O)[nH]2)c(Cl)cc1F)C(F)(F)F]

The title compound was prepared according to the procedure described in Example-83 by using tert-butyl 2-(4-(trifluoromethyl)phenyl)hydrazinecarboxylate (Intermediate-53, 0.300 g), 5-((2,2,2-trifluoroacetamido)methyl)-2-chloro-4-fluorobenzoyl isocyanate (Intermediate-69, 0.300 g), DCM (20 mL), trifluoro acetic acid (5.0 mL) to afford 0.030 g of the desired product. $^1$H NMR (400 MHz, DMSO $d_6$): δ 4.49 (m, 2H), 7.74-7.77 (m, 1H), 7.78-7.80 (m, 1H), 7.87 (d, J=5.1 Hz, 2H), 8.19 (d, J=4.2 Hz, 2H), 10.06 (m, 1H), 12.76 (s, 1H); MS (m/z): 467.15 (M+H)$^+$.

Example-114

N-(4-Chloro-2-fluoro-5-(1-(4-(trifluoromethyl)phenyl)-4,5-dihydro-S-oxo-1H-1,2,4-triazol-3-yl)benzyl)pivalamide

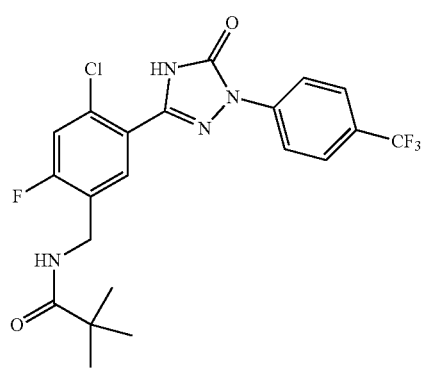 [SMILES: CC(C)(C)C(=O)NCc1cc(-c2nn(-c3ccc(C(F)(F)F)cc3)c(=O)[nH]2)c(Cl)cc1F]

The title compound was prepared according to the procedure described in Example-108 by using 5-(5-(aminomethyl)-2-chloro-4-fluorophenyl)-2-(4-(trifluoromethyl)phenyl)-2H-1,2,4-triazol-3(4H)-one (Intermediate-70, 0.080 g, 0.206 mmol), pivaloyl chloride (0.027 g, 0.227 mmol), THF (5.0 mL) and TEA (0.2 mL) to afford 0.043 g of the desired product. $^1$H NMR (400 MHz, DMSO $d_6$): δ 1.13 (s, 9H), 4.31-4.32 (m, 2H), 7.86 (d, J=6.5 Hz, 2H), 8.13-8.18 (m, 3H), 12.70 (s, 1H); MS (m/z): 471.14 (M+H)$^+$.

Example-115

N-(4-Chloro-3-(1-(4-(trifluoromethyl)phenyl)-4,5-dihydro-5-oxo-1H-1,2,4-triazol-3-yl)benzyl)-3-hydroxy-2,2-dimethylpropanamide

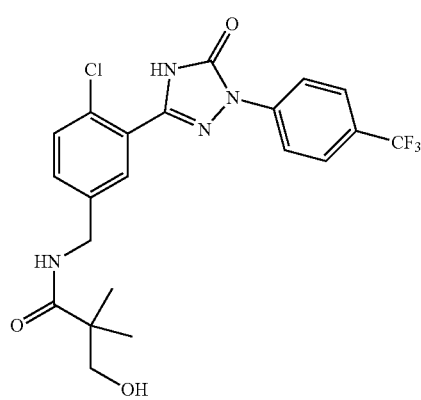 [SMILES: CC(C)(CO)C(=O)NCc1ccc(Cl)c(-c2nn(-c3ccc(C(F)(F)F)cc3)c(=O)[nH]2)c1]

The title compound was prepared according to the procedure described in Example-107 by using 3-(5-(aminomethyl)-2-chlorophenyl)-1-(4-(trifluoromethyl)phenyl)-1H-1,2,4-triazol-5(4H)-one (Intermediate-63, 0.100 g, 0.271 mmol), THF:DMF (5 mL:1 mL), 3-methoxy-2,2-dimethylpropanoic acid (0.053 g, 0.407 mmol), TBTU (0.261 g, 0.813 mmol), TEA (2.0 mL). The obtained crude was purified by column chromatography using basic alumina as stationary phase and eluting with the solution of 2% ammonia in 10.0% MeOH:DCM to afford 0.012 g of the desired product. $^1$H NMR (300 MHz, DMSO d$_6$): δ 1.05 (s, 6H), 3.30 (s, 2H), 4.30 (d, J=4.5 Hz, 1H), 4.36 (s, 1H), 7.53 (d, J=6.3 Hz, 1H), 7.75 (s, 1H), 8.08 (t, J=4.5 Hz, 1H), 8.21 (d, J=6.3 Hz, 2H); MS (m/z): 469.04 (M+H)$^+$.

Example-116

N-(4-Chloro-3-(1-(4-chloro-3-fluorophenyl)-4,5-dihydro-5-oxo-1H-1,2,4-triazol-3-yl)benzyl)-2,2,2-trifluoroacetamide

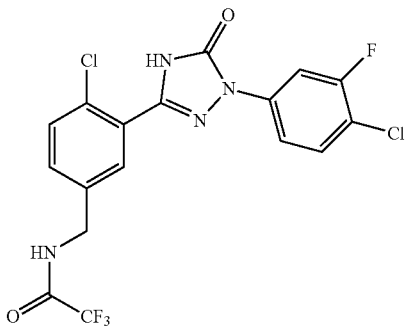 [SMILES: O=C(NCc1ccc(Cl)c(-c2nn(-c3ccc(Cl)c(F)c3)c(=O)[nH]2)c1)C(F)(F)F]

The title compound was prepared according to the procedure described in Example-83 by using tert-butyl 2-(4-chloro-3-fluorophenyl)hydrazinecarboxylate (Intermediate-71, 0.828 g, 0.003 mmol), 2-chloro-5-((2,2,2-trifluoroacetamido)methyl)benzoyl isocyanate (step-3 of Intermediate-26, 1.3 g, 0.043 mmol), DCM (20 mL), trifluoro acetic acid (5.0 mL) to afford 0.500 g of the desired product. $^1$H NMR (300 MHz, DMSO d$_6$): δ 4.45 (d, 2H), 7.48 (d, J=15.0 Hz, 1H), 7.68-7.83 (m, 3H), 7.85 (d, 1H), 7.99 (d, J=17.1 Hz, 1H), 10.08 (d, J=12.0 Hz, 1H), 12.73 (s, 1H).

Example-117

N-(4-Chloro-3-(4,5-dihydro-1-(4,4-dimethylcyclohexyl)-5-oxo-1H-1,2,4-triazol-3-yl)benzyl)-2,2,2-trifluoroacetamide

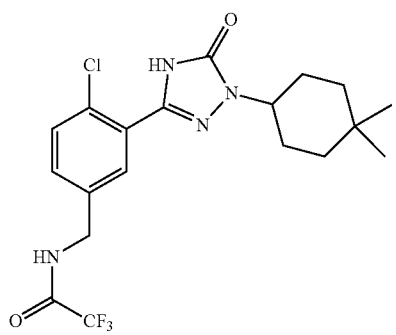 [SMILES: CC1(C)CCC(n2nc(-c3cc(CNC(=O)C(F)(F)F)ccc3Cl)[nH]c2=O)CC1]

The title compound was prepared according to the procedure described in Example-83 by using 4,4-dimethyl tert-butyl 2-cyclohexyl hydrazinecarboxylate (Intermediate-72, 0.269 g, 1.1 mmol), 2-chloro-5-((2,2,2-trifluoroacetamido)methyl)benzoyl isocyanate (step-2 of Intermediate-26, 0.400 g, 1.2 mmol), DCM (20 mL), trifluoro acetic acid (5.0 mL) to afford 0.200 g of the desired product. $^1$H NMR (300 MHz, DMSO d$_6$): δ 1.33 (s, 6H), 1.43-1.91 (m, 8H), 3.86-3.94 (m, 1H), 4.41 (d, J=4.5 Hz, 2H), 7.38 (d, J=7.5 Hz, 1H), 7.53 (s, 1H), 7.58 (d, J=6.3 Hz, 1H), 10.02-10.04 (m, 1H), 11.95 (s, 1H); MS (m/z): 431.17 (M+H)$^+$.

Example-118

N-(4-Chloro-3-(4,5-dihydro-1-(4,4-dimethylcyclohexyl)-5-oxo-1H-1,2,4-triazol-3-yl)benzyl)pivalamide

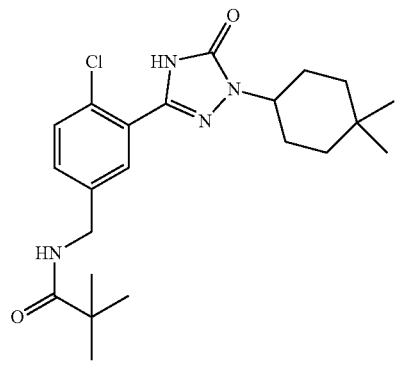 [SMILES: CC1(C)CCC(n2nc(-c3cc(CNC(=O)C(C)(C)C)ccc3Cl)[nH]c2=O)CC1]

To a solution of 5-(5-(aminomethyl)-2-chlorophenyl)-2-(4,4-dimethylcyclohexyl)-2H-1,2,4-triazol-3(4H)-one (Intermediate-73, 0.070 g, 0.202 mmol) in dry THF (5.0 mL), DIPEA (2.0 mL) and pivaloyl chloride (0.30 g, 0.242 mmol) were added and the reaction mass was stirred at RT for 16 h. After completion of the reaction, the reaction mass was quenched with water and extracted with 10% MeOH:DCM. The organic layer was washed with dilute HCl and concentrated. The obtained crude was purified with column chromatography on basic alumina by eluting with 2.0% MeOH:DCM to afford 0.040 g of the desired product. $^1$H NMR (300 MHz, DMSO d$_6$): δ 1.44 (s, 6H), 1.47 (s, 9H), 1.81-1.94 (m, 8H), 3.86-190 (m, 1H), 4.40 (s, 214), 7.33 (d, J=1.5 Hz, 1H), 7.45 (s, 114), 7.50 (d, J=2.1 Hz, 1H), 8.16 (t, 1H), 11.93 (s, 1H); MS (m/z): 419.21 (M+H)$^+$.

Example-119

(R)—N-(4-chloro-2-fluoro-5-(5-oxo-1-(4-(trifluoromethyl)phenyl)-4,5-dihydro-1H-1,2,4-triazol-3-yl)benzyl)tetrahydrofuran-2-carboxamide

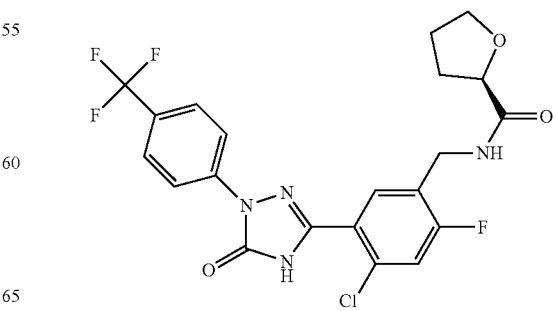

The title compound was prepared according to the procedure described in Example-107 by using 5-(5-(aminomethyl)-2-chloro-4-fluorophenyl)-2-(4-(trifluoromethyl)phenyl)-2H-1,2,4-triazol-3(4H)-one (Intermediate-70, 0.090 g, 0.233 mmol), THF:DMF (5 mL:1 mL), (R)-(−)-tetrahydrofuran-2-carboxylic acid (0.040 g, 0.349 mmol), TBTU (0.224 g, 0.699 mmol), and TEA (0.5 mL). The obtained crude was purified with column chromatography using basic alumina as stationary phase and 2% ammonia in 10.0% MeOH:DCM solution as mobile phase to afford 0.015 g of the desired product. $^1$H NMR (400 MHz, DMSO d$_6$): δ 1.78-1.91 (m, 2H), 2.09-2.15 (m, 1H), 3.74 (m, 1H), 3.88-3.94 (m, 1H), 4.28 (m, 1H), 4.43 (m, 2H), 7.65 (m, 2H), 7.86 (d, J=8.72 Hz, 2H), 8.18 (d, J=8.52 Hz, 2H), 8.45 (d, J=16.0 Hz, 1H), 12.71 (s, 1H).

Example-120

N-(3-(1-tert-Butyl-4,5-dihydro-5-oxo-1H-1,2,4-triazol-3-yl)-4-chlorobenzyl)-2,2,2-trifluoroacetamide

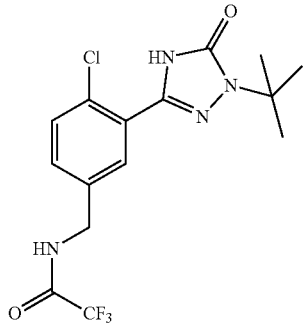 [SMILES: CC(C)(C)n1nc(-c2cc(CNC(=O)C(F)(F)F)ccc2Cl)[nH]c1=O]

The title compound was prepared according to the procedure described in Example-83 by using tert-butyl 2-tert-butylhydrazinecarboxylate (Intermediate-74, 0.233 g, 1.2 mmol), 2-chloro-5-((2,2,2-trifluoroacetamido)methyl)benzoyl isocyanate (step-3 of Intermediate-26, 0.400 g, 1.2 mmol), DCM (10 mL), trifluoro acetic acid (5.0 mL) to afford 0.100 g of the desired product. $^1$H NMR (400 MHz; DMSO d$_6$): δ 1.52 (s, 9H), 4.42 (s, 2H), 7.39 (d, 1H), 7.41 (s, 1H), 7.58 (d, J=2.1 Hz, 2H), 10.0 (br s, 1H), 12.0 (br s, 1H); MS (m/z): 377.20 (M+H)$^+$.

Example-121

N-(3-(1-tert-Butyl-4,5-dihydro-5-oxo-1H-1,2,4-triazol-3-yl)-4-chlorobenzyl)pivalamide

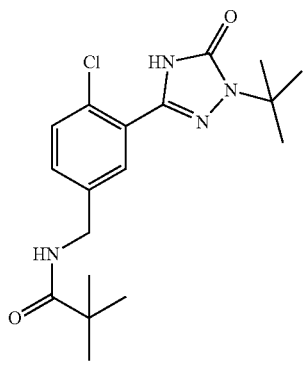 [SMILES: CC(C)(C)C(=O)NCc1ccc(Cl)c(-c2nn(C(C)(C)C)c(=O)[nH]2)c1]

The title compound was prepared according to the procedure described in Example-108 by using 2-tert-butyl-5-(5-(aminomethyl)-2-chlorophenyl)-2H-1,2,4-triazol-3(4H)-one (intermediate-75, 0.250 g), pivaloyl chloride (1.0 mL), DIPEA (2.0 mL), and dry THF (5 mL) to afford 0.180 g of desired product. $^1$H NMR (400 MHz, DMSO d$_6$): δ 1.08 (s, 9H), 1.49 (s, 9H), 4.24 (d, J=4.5 Hz, 2H), 7.32 (dd, J=4.5 Hz, 3.6 Hz, 2H), 7.43 (s, 1H), 7.50 (s, 1H), 8.14 (d, J=4.5 Hz, 1H); MS (m/z): 365.20 (M+H)$^+$.

Example-122

N-(4-Chloro-3-(1-(4-(trifluoromethyl)phenyl)-4,5-dihydro-5-oxo-1H-1,2,4-triazol-3-yl)benzyl)-3-methoxy-2,2-dimethylpropanamide

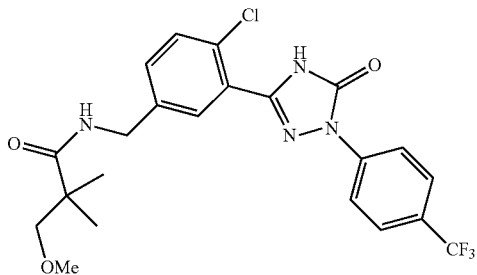 [SMILES: COCC(C)(C)C(=O)NCc1ccc(Cl)c(-c2nn(-c3ccc(C(F)(F)F)cc3)c(=O)[nH]2)c1]

To a solution of 3-(5-(aminomethyl)-2-chlorophenyl)-1-(4-(trifluoromethyl)phenyl)-1H-1,2,4-triazol-5(4H)-one (Intermediate-63, 0.250 g, 0.678 mmol) in THF:DMF (5 mL:1 mL), TBTU (0.653 g, 2.3 mmol), TEA (4.0 mL) were added and the reaction mass was stirred at RT for 1 h. To the reaction mixture, 3-methoxy-2,2-dimethylpropanoic acid (0.134 g, 1.01 mmol) was added and stirring was continued at RT for 2 days. After completion of the reaction, the reaction mass was quenched with water and extracted with ethyl acetate. The organic layer was separated, dried and concentrated to obtain crude product. The obtained crude was purified with column chromatography on basic alumina by eluting with 5.0% MeOH:DCM to afford 0.110 g of the desired product. $^1$H NMR (400 MHz, DMSO d$_6$): δ 1.15 (s, 6H), 1.18 (s, 3H), 3.09 (t, 2H), 4.32 (d, J=11.4 Hz, 2H), 7.43 (dd, J=4.5 Hz, 3.6 Hz, 1H), 7.45 (d, 1H), 7.86 (d, J=5.4 Hz, 2H), 8.15 (t, 1H), 8.20 (d, 2H), 12.50 (br s, 1H); MS (m/z): 483.20 (M+H)$^+$.

Example-123

N-(4-Chloro-3-(1-(4-chloro-3-fluorophenyl)-4,5-dihydro-5-oxo-1H-1,2,4-triazol-3-yl)benzyl)pivalamide

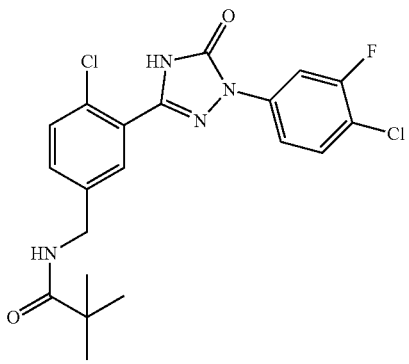 [SMILES: CC(C)(C)C(=O)NCc1ccc(Cl)c(-c2nn(-c3ccc(Cl)c(F)c3)c(=O)[nH]2)c1]

The title compound was prepared according to the procedure described in Example-108 by using 5-(5-(aminomethyl)-2-chlorophenyl)-2-(4-chloro-3-fluorophenyl)-2H-1,2,4-triazol-3(4H)-one (Intermediate-76, 0.250 g), pivaloyl chloride (1.0 mL), DIPEA (2.0 mL), dry THF (5 mL) to afford 0.110 g of the desired product. $^1$H NMR (400 MHz, DMSO d$_6$): δ 1.24 (s, 9H), 4.30 (d, J=14.7 Hz, 2H), 7.40 (dd, J=4.5 Hz, 3.6 Hz, 1H), 7.43 (d, 1H), 7.60 (d, J=5.4 Hz, 1H), 7.74 (d, 1H), 7.98 (d, 1H), 8.18 (t, J=15.0 Hz, 1 1H), 12.70 (s, 1H); MS (m/z): 437.59 (M+H)$^+$.

Example-124

N-(4-Chloro-2-fluoro-5-(4,5-dihydro-1-(4,4-dimethylcyclohex yl)-5-oxo-1H-1,2,4-triazol-3-yl)benzyl)-2,2,2-trifluoroacetamide

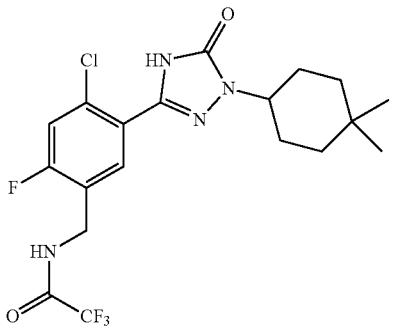 [SMILES: CC1(C)CCC(n2nc(-c3cc(CNC(=O)C(F)(F)F)c(F)cc3Cl)[nH]c2=O)CC1]

The title compound was prepared according to the procedure described in Example-83 by using 4,4-dimethyl tert-butyl 2-cyclohexyl hydrazinecarboxylate (Intermediate-72, 0.400 g), 5-((2,2,2-trifluoroacetamido)methyl)-2-chloro-4-fluorobenzoyl isocyanate (Intermediate-69, 0.400 g), DCM (10 mL), trifluoro acetic acid (5.0 mL) to afford 0.150 g of the desired product. $^1$H NMR (400 MHz, DMSO d$_6$): δ 0.93 (s, 6H), 1.32-1.35 (m, 2H), 1.36-1.46 (m, 2H), 1.59-1.62 (m, 2H), 1.83-1.87 (m, 2H), 3.89 (m, 1H), 4.42 (m, 2H), 7.72 (m, 2H), 10.0 (s, 1H), 12.01 (s, 1H); MS (m/z): 449.48 (M+H)$^+$.

Example-125

N-(4-Chloro-2-fluoro-5-(4,5-dihydro-1-(4,4-dimethylcyclohexyl)-5-oxo-1H-1,2,4-triazol-3-yl)benzyl)pivalamide

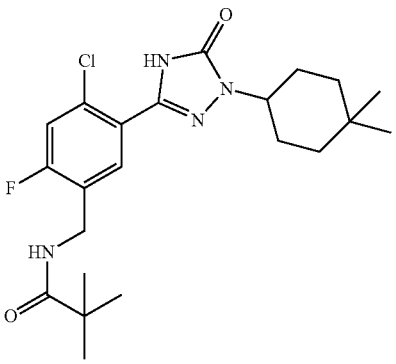 [SMILES: CC1(C)CCC(n2nc(-c3cc(CNC(=O)C(C)(C)C)c(F)cc3Cl)[nH]c2=O)CC1]

The title compound was prepared according to the procedure described in Example-108 by using 5-(5-(aminomethyl)-2-chloro-4-fluorophenyl)-2-(4,4-dimethylcyclohexyl)-2H-1,2,4-triazol-3(4H)-one (Intermediate-77, 0.200 g), pivaloyl chloride (0.5 mL), TEA (2.0 mL), dry THF (5 mL) to afford 0.033 g of the desired product. $^1$H NMR (300 MHz, CDCl$_3$): δ 1.36 (s, 6H), 1.37 (s, 9H), 1.62 (m, 2H), 1.79 (m, 1H), 1.82 (m, 2H), 1.89 (m, 2H), 3.46-3.94 (m, 1H), 4.28 (s, 2H), 7.47 (d, J=7.9 Hz, 1110, 7.59 (d, J=9.72 Hz, 1H), 8.15 (m, 1H), 11.95 (s, 1H); MS (m/z): 436.55 (M+H)$^+$.

Example-126

N-(4-Chloro-5-(1-(4-chlorophenyl)-4,5-dihydro-5-oxo-1H-1,2,4-triazol-3-yl)-2-fluorobenzyl)pivalamide

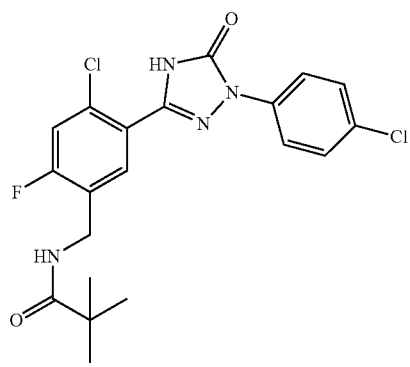 [SMILES: CC(C)(C)C(=O)NCc1cc(-c2nn(-c3ccc(Cl)cc3)c(=O)[nH]2)c(Cl)cc1F]

The title compound was prepared according to the procedure described in Example-108 by using 5-(5-(aminomethyl)-2-chloro-4-fluorophenyl)-2-(4-chlorophenyl)-2H-1,2,4-triazol-3(4H)-one (Intermediate-78, 0.120 g), pivaloyl chloride (0.5 mL), TEA (2.0 mL), dry THF (5 mL) to afford 0.033 g of the desired product. $^1$H NMR (300 MHz, DMSO): δ 1.12 (s, 9H), 4.30 (br s, 2H), 7.53-7.63 (m, 4H), 7.95 (d, 0.1=12.8 Hz, 2H), 8.14 (s, 1H), 12.61 (s, 1H); MS (m/z): 437.47 (M+H)$^+$.

Example-127

N-(4-Chloro-5-(1-(4-(trifluoromethyl)phenyl)-4,5-dihydro-5-oxo-1H-1,2,4-triazol-3-yl)-2-methoxybenzyl)pivalamide

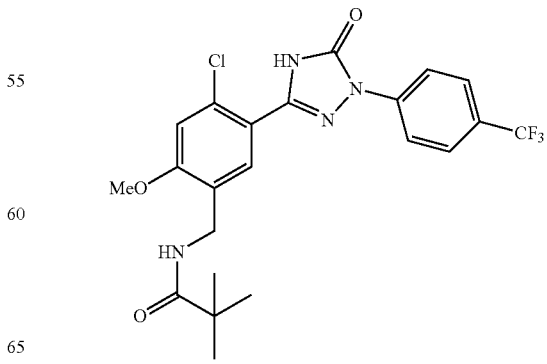

The title compound was prepared according to the procedure described in Example-108 by using 5-(5-(aminomethyl)-2-chloro-4-methoxyphenyl)-2-(4-(trifluoro methyl)phenyl)-2H-1,2,4-triazol-3(4H)-one (Intermediate-79, 0.200 g), pivaloyl chloride (0.2 mL), TEA (2.0 mL), dry THF (5 mL) to afford 0.015 g of the desired product. ¹H NMR (300 MHz, CDCl₃): δ 1.15 (s, 9H), 3.91 (s, 3H), 4.22 (m, 2H), 7.26 (s, 1H), 7.42 (s, 1H), 7.87 (m, 2H), 7.99 (m, 1H), 8.15 (m, 2H), 12.57 (s, 1H); MS (m/z): 483.38 (M+H)⁺.

Example-128

N-(4-Chloro-2-fluoro-5-(1-(4-fluoro-3-(trifluoromethyl)phenyl)-4,5-dihydro-5-oxo-1H-1,2,4-triazol-3-yl)benzyl)pivalamide

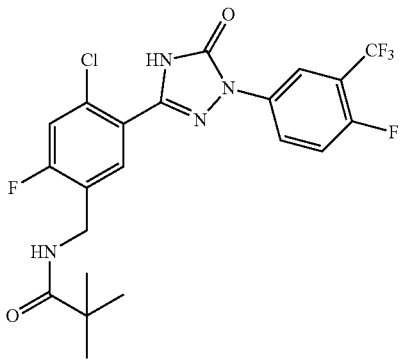

The title compound was prepared according to the procedure described in Example-108 by using 5-(5-(aminomethyl)-2-chloro-4-fluorophenyl)-2-(4-fluoro-3-(trifluoromethyl) phenyl)-2H-1,2,4-triazol-3(4H)-one (Intermediate-81, 0.300 g), pivaloyl chloride (0.3 mL), TEA (2.0 mL), dry THF (5 mL) to afford 0.065 g of the desired product. ¹H NMR (300 MHz, CDCl₃): δ 1.12 (s, 9H), 4.30 (m, 2H), 7.61-7.69 (m, 3H), 8.16 (br s, 1H), 8.25 (br s, 2H), 12.73 (s, 1H); MS (m/z): 489.47 (M+H)⁺.

Example-129

N-(4-Chloro-2-fluoro-5-(1-(6-(trifluoromethyl)pyridin-3-yl)-4,5-dihydro-5-oxo-1H-1,2,4-triazol-3-yl)benzyl)pivalamide

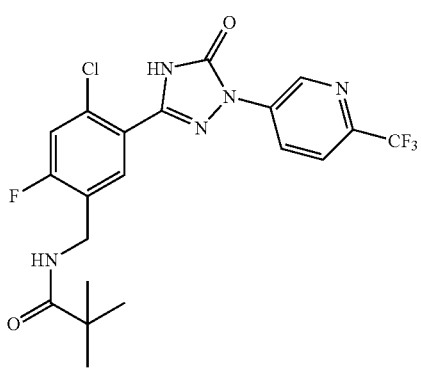 [SMILES: CC(C)(C)C(=O)NCc1cc(-c2nn(-c3ccc(C(F)(F)F)nc3)c(=O)[nH]2)c(Cl)cc1F]

The title compound was prepared according to the procedure described in Example-108 by using 5-(5-(aminomethyl)-2-chloro-4-fluorophenyl)-2-(6-(trifluoromethyl)pyridin-3-yl)-2H-1,2,4-triazol-3(4H)-one (Intermediate-82, 0.300 g), pivaloyl chloride (0.3 mL), TEA (2.0 mL), dry THF (10 mL) to afford 0.050 g of the desired product. ¹H NMR (300 MHz, CDCl₃): δ 1.12 (s, 9H), 4.31 (d, J=6.8 Hz, 2H), 7.63-7.71 (m, 2H), 8.05-8.07 (m, 1H), 8.16 (m, 1H), 8.55 (d, J=13.2 Hz, 1H), 9.29 (s, 1H), 12.85 (s, 1H); MS (m/z): 472.41 (M+H)⁺.

Example-130

N-(2,4-Dichloro-5-(3-(4-(2-cyclopropylethynyl)phenyl)-4,5-dihydro-5-oxo-1,2,4-triazol-1-yl)benzyl)pivalamide

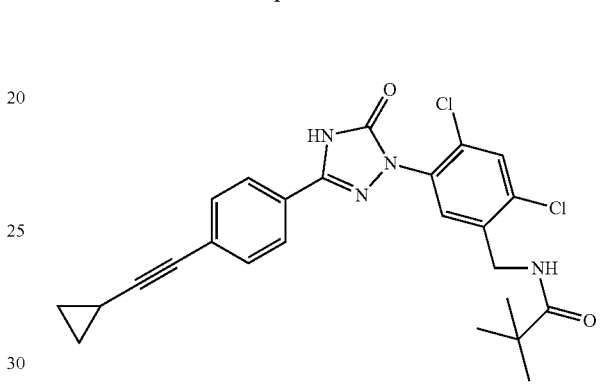

The title compound was prepared according to the procedure described in Example-111 using N-(2,4-dichloro-5-(4,5-dihydro-3-(4-iodophenyl)-5-oxo-1,2,4-triazol-1-yl)benzyl) pivalamide (Intermediate-84, 0.150 g, 0.028 mmol), ethynylcyclopropane (0.038 g, 0.56 mmol), TBAF (0.268 g, 0.85 mmol), bis(triphenylphosphine)palladium(II) chloride (catalytic) and DMSO (3.0 mL) to afford 0.050 g of the desired product. ¹H NMR (300 MHz, DMSO d₆): δ 0.77 (m, 2H), 0.93 (m, 2H), 1.21 (s, 9H), 1.58 (m, 1H), 4.32 (d, J=6.3 Hz, 2H), 7.50-7.53 (m, 3H), 7.82-7.91 (m, 2H), 7.95 (s, 1H), 8.21 (m, 1H)

Example-131

N-(4-Chloro-5-(1-(3-chloro-4-fluorophenyl)-4,5-dihydro-5-oxo-1H-1,2,4-triazol-3-yl)-2-fluorobenzyl)pivalamide

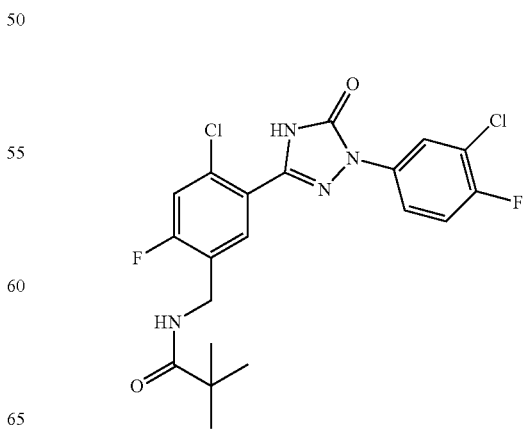

The title compound was prepared according to the procedure described in Example-108 by using 5-(5-(aminomethyl)-2-chloro-4-fluorophenyl)-2-(3-chloro-4-fluorophenyl)-2H-1,2,4-triazol-3(4H)-one (Intermediate-86, 0.300 g), pivaloyl chloride (0.3 mL), TEA (2.0 mL), dry THF (10 mL) to afford 0.083 g of the desired product. $^1$H NMR (300 MHz, DMSO): δ 1.13 (s, 9H), 4.30 (d, J=6.4 Hz, 2H), 7.53-7.66 (s, 3H), 7.91-8.15 (s, 3H), 12.67 (s, 1H); MS (adz): 455.19 (M+H)$^+$.

Example-132

N-(4-Chloro-5-(1-(4-chlorophenyl)-4,5-dihydro-5-oxo-1H-1,2,4-triazol-3-yl)-2-fluorobenz yl)-2-fluorobenzamide

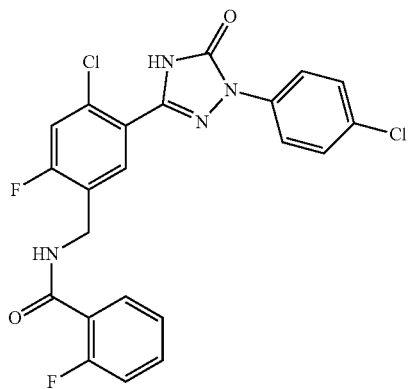 [SMILES: O=C(NCc1cc(-c2nn(-c3ccc(Cl)cc3)c(=O)[nH]2)c(Cl)cc1F)c1ccccc1F]

A mixture of 2-fluoro benzoic acid (0.400 g), thionyl chloride (20 mL) and DMF (cat. amt.) was refluxed for 5 h and excess of solvent was removed under reduced pressure to obtain crude product. The obtained crude product was added to the solution of 5-(5-(aminomethyl)-2-chloro-4-fluorophenyl)-2-(4-chlorophenyl)-2H-1,2,4-triazol-3 (4H)-one (Intermediate-78, 0.250 g) and DIPEA (1.0 mL) in THF (20 mL) and the reaction mass was stirred for 3 h. After completion of reaction, reaction mass was quenched with water and extracted with ethyl acetate. The organic layer was separated, concentrated to afford 0.032 g of the desired product. $^1$H NMR (300 MHz, DMSO): δ 4.53 (br s, 2H), 7.29 (m, 2H), 7.70 (m, 3H), 7.78 (m, 3H), 7.95 (br s, 2H), 8.94 (br s, 1H), 12.63 (br s, 1H); MS (m/z): 475.39 (M+H)$^+$.

Example-133

N-(4-Chloro-2-fluoro-5-(1-(4-(trifluoromethyl)phenyl)-4,5-dihydro-5-oxo-1H-1,2,4-triazol-3-yl)benzyl)isobutyramide

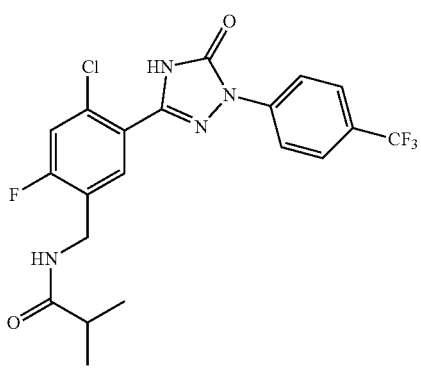 [SMILES: CC(C)C(=O)NCc1cc(-c2nn(-c3ccc(C(F)(F)F)cc3)c(=O)[nH]2)c(Cl)cc1F]

The title compound was prepared according to the procedure described in Example-108 by using 5-(5-(aminomethyl)-2-chloro-4-fluorophenyl)-2-(4-(trifluoromethyl)phenyl)-2H-1,2,4-triazol-3(4H)-one (Intermediate-70, 0.100 g), 2-methylpropanoyl chloride (0.1 mL), TEA (0.1 mL), dry THF (5 mL) to afford 0.028 g of the desired product. $^1$H NMR (300 MHz, DMSO): δ 1.01 (s, 6H), 4.32 (d, J=7.6 Hz, 2H), 7.67-7.71 (m, 2H), 7.85 (d, J=11.2 Hz, 2H), 8.17 (d, J=11.6 Hz, 2H), 8.36 (m, 1H), 12.73 (s, 1H); MS (m/z): 457.37 (M+H)$^+$.

Example-134

N-(4-Chloro-5-(1-(4-chlorophenyl)-4,5-dihydro-5-oxo-1H-1,2,4-triazol-3-yl)-2-fluorobenzyl)-3-fluoro-2,2-dimethylpropanamide

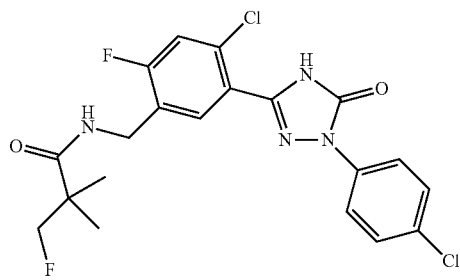 [SMILES: CC(C)(CF)C(=O)NCc1cc(-c2nn(-c3ccc(Cl)cc3)c(=O)[nH]2)c(Cl)cc1F]

Step-1:—Preparation of N-(4-chloro-5-(1-(4-chlorophenyl)-4,5-dihydro-5-oxo-1H-1,2,4-triazol-3-yl)-2-fluorobenzyl)-3-hydroxy-2,2-dimethylpropanamide

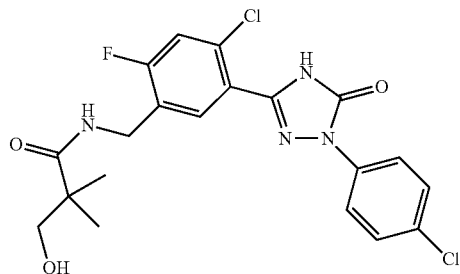 [SMILES: CC(C)(CO)C(=O)NCc1cc(-c2nn(-c3ccc(Cl)cc3)c(=O)[nH]2)c(Cl)cc1F]

The title compound was prepared according to the procedure described in Example-107 by using 5-(5-(aminomethyl)-2-chloro-4-fluorophenyl)-2-(4-chlorophenyl)-2H-1,2,4-triazol-3(4H)-one (Intermediate-78, 0.250 g, 0.708 mmol), THF:DMF (5 mL: 1 mL), 3-hydroxy-2,2-dimethylpropanoic acid (0.091 g, 0.407 mmol), TBTU (0.340 g, 1.062 mmol), TEA (2.0 mL) to afford 0.150 g of the desired product. $^1$H NMR (300 MHz, CDCl$_3$): δ 1.05 (s, 6H), 2.68 (s, 2H), 4.32 (d, J=8.0 Hz, 2H), 7.53 (d, J=12.0 Hz, 2H), 7.64-7.67 (m, 2H), 7.95-7.98 (m, 2H), 8.08 (br s, 1H); MS (m/z): 453.27 (M$^+$H)$^+$.

Step-2:—Preparation N-(4-chloro-5-(1-(4-chlorophenyl)-4,5-dihydro-5-oxo-1H-1,2,4-triazol-3-yl)-2-fluorobenz yl)-3-fluoro-2,2-dimethylpropanamide To a solution of N-(4-chloro-5-(1-(4-chlorophenyl)-4,5-dihydro-5-oxo-1H-1,2,4-triazol-3-yl)-2-fluorobenzyl)-3-hydroxy-2,2-dimethylpropanamide (0.150 g, 0.330 mmol) in THF (5.0 mL), DAST (0.079 g, 0.495 mmol) was added at 0-5° C. and stirred at RT for 5-6 h. After completion of the reaction, the reaction mass was quenched with water and extracted with ethyl acetate. The organic layer was separated, concentrated and the obtained crude was purified with column chromatography using basic alumina by eluting with solution of 2% ammonia in 10.0% MeOH: DCM to afford 0.013 g of the desired product. $^1$H NMR (300 MHz, CDCl$_3$): δ 1.13 (s, 6H), 4.32 (m, 3H), 4.46 (s, 1H), 7.55 (m, 2H), 7.69 (m, 2H), 7.94-7.97 (m, 2H), 8.31 (s, 1H), 12.61 (s, 1H); MS (m/z): 454.25 (M+H)$^+$.

Example-135

N-(4-Chloro-5-(1-(3-chloro-4-methylphenyl)-4,5-dihydro-5-oxo-1H-1,2,4-triazol-3-yl)-2-fluorobenzyl)pivalamide

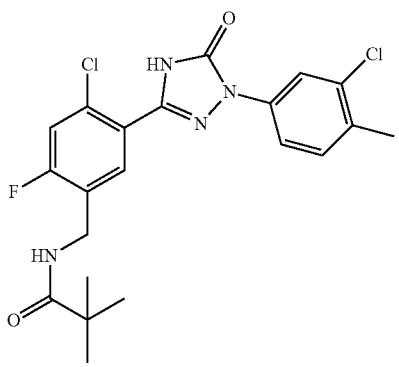 [SMILES: Cc1ccc(-n2nc(-c3cc(CNC(=O)C(C)(C)C)c(F)cc3Cl)[nH]c2=O)cc1Cl]

The title compound was prepared according to the procedure described in Example-108 by using 5-(5-(aminomethyl)-2-chloro-4-fluorophenyl)-2-(3-chloro-4-methylphenyl)-2H-1,2,4-triazol-3(4H)-one (Intermediate-88, 0.200 g), pivaloyl chloride (0.5 mL), TEA (2.0 mL), dry THF (5 mL) to afford 0.074 g of the desired product. $^1$H NMR (300 MHz, DMSO d$_6$): δ 1.11 (s, 9H), 2.32 (s, 3H), 4.29 (d, J=8.8 Hz, 2H), 7.43 (d, J=11.6 Hz, 1H), 7.60-7.67 (m, 1H), 7.79 (d, J=10.4 Hz, 1H), 7.96 (s, 1H), 8.15 (m, 1H), 12.60 (s, 1H); MS (m/z): 451.52 (M+H)$^+$.

Example-136

N-(4-Chloro-5-(3-(4-(2-cyclopropylethynyl)phenyl)-4,5-dihydro-5-oxo-1,2,4-triazol-1-yl)-2-fluorobenzyl)pivalamide

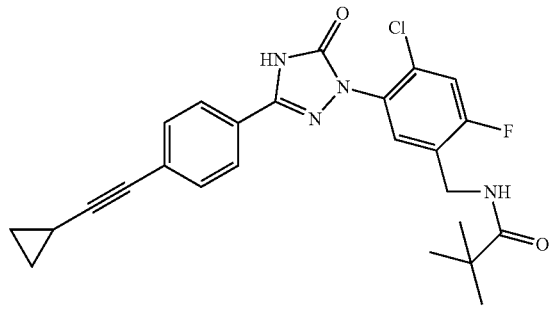 [SMILES: CC(C)(C)C(=O)NCc1cc(-n2nc(-c3ccc(C#CC4CC4)cc3)[nH]c2=O)c(Cl)cc1F]

The title compound was prepared according to the procedure described in Example-111 using N-(4-chloro-2-fluoro-5-(4,5-dihydro-3-(4-iodophenyl)-5-oxo-1,2,4-triazol-1-yl)benzyl)pivalamide (Intermediate-90, 0.200 g, 0.370 mmol), ethynylcyclopropane (0.050 g, 0.75 mmol), TBAF (0.360 g, 1.13 mmol), bis(triphenylphosphine)palladium(II) chloride (catalytic) and DMSO (3.0 mL) at 80° C. to afford 0.080 g of the desired product. $^1$H NMR (300 MHz, DMSO d$_6$): δ 0.77 (br s, 9H), 0.92 (br s, 2H), 1.10 (s, 3H), 1.57 (m, 1H), 4.30 (d, J=5.4 Hz, 2H), 7.43-7.50 (m, 3H), 7.65 (d, J=5.4 Hz, 2H), 7.77 (d, J=5.1 Hz, 2H), 12.57 br s, 1H); MS (m/z): 467.36 (M+H)$^+$.

Example-137

N-(4-Chloro-2-fluoro-5-(4,5-dihydro-3-(4-(3,3-dimethylbut-1-ynyl)phenyl)-5-oxo-1,2,4-triazol-1-yl)benzyl)pivalamide

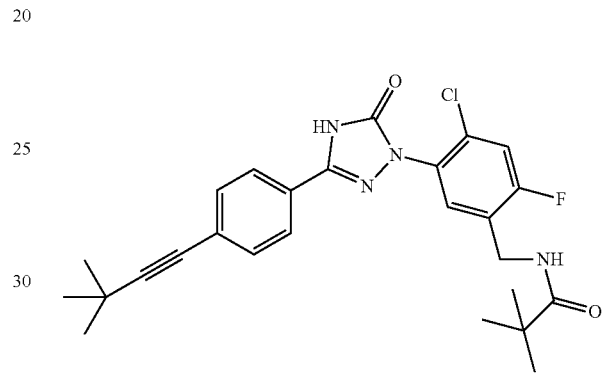

The title compound was prepared according to the procedure described in Example-111 using N-(4-chloro-2-fluoro-5-(4,5-dihydro-3-(4-iodophenyl)-5-oxo-1,2,4-triazol-1-yl)benzyl)pivalamide (Intermediate-90, 0.100 g, 0.189 mmol), 3,3-dimethylbut-1-yne (0.031 g, 0.378 mmol), TBAF (0.178 g, 0.567 mmol), bis(triphenylphosphine)palladium(II) chloride (catalytic) and DMSO (3.0 mL) to afford 0.050 g of the desired product. $^1$H NMR (300 MHz, DMSO d$_6$): δ 1.10 (s, 9H), 1.30 (s, 9H), 4.30 (d, J=9.0 Hz, 2H), 7.43-7.50 (m, 3H), 7.65 (d, J=9.3 Hz, 1H), 7.78 (d, J=8.1 Hz, 2H), 8.14 (br s, 1H), 12.60 (br s, 1H); MS (m/z): 483.29 (M+H)$^+$.

Example-138

N-(4-Chloro-3-(1-(6-(trifluoromethyl)pyridin-3-yl)-4,5-dihydro-5-oxo-1H-1,2,4-triazol-3-yl)benzyl)pivalamide

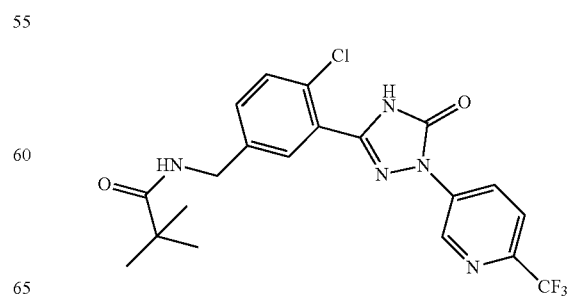

The title compound was prepared according to the procedure described in Example-108 by using 5-(5-(aminomethyl)-2-chlorophenyl)-2-(6-(trifluoromethyl)pyridin-3-yl)-2H-1,2,4-triazol-3(4H)-one (Intermediate-91, 0.350 g, 0.945 mmol), pivaloyl chloride (0120 g, 0.945 mmol), DIPEA (2.0 mL), dry THF (10 mL) to afford 0.080 g of the desired product. $^1$H NMR (300 MHz, DMSO d$_6$): δ 1.11 (s, 9H), 4.30 (d, J=6.3 Hz, 2H), 7.43 (d, 0.1=8.4 Hz, 1H), 7.61-7.64 (m, 2H), 8.06 (d, 0.1=9.0 Hz, 1H), 8.19 (m, 1H), 8.58 (d, J=8.4 Hz, 1H), 9.32 (s, 1H), 12.82 (s, 1H); MS (m/z): 454.50 (M+H)$^+$.

Example-139

N-(4-Chloro-3-(1-(3-chloro-4-fluorophenyl)-4,5-dihydro-5-oxo-1H-1,2,4-triazol-3-yl)benzyl)pivalamide

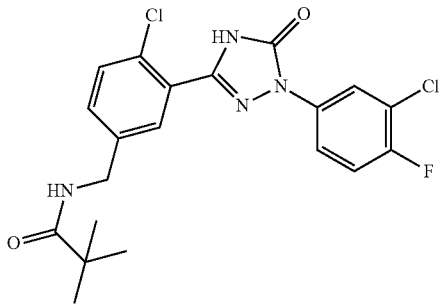 [SMILES: CC(C)(C)C(=O)NCc1ccc(Cl)c(-c2nn(-c3ccc(F)c(Cl)c3)c(=O)[nH]2)c1]

The title compound was prepared according to the procedure described in Example-108 by using 5-(5-(aminomethyl)-2-chlorophenyl)-2-(3-chloro-4-fluorophenyl)-2H-1,2,4-triazol-3(4H)-one (Intermediate-92, 0.300 g, 0.852 mmol), pivaloyl chloride (0.108 g, 0.852 mmol), DIPEA (2.0 mL), dry THF (10 mL) to afford 0.050 g of the desired product. $^1$H NMR (300 MHz, DMSO d$_6$): δ 1.13 (s, 9H), 4.29 (d, J=5.4 Hz, 2H), 7.40 (d, J=7.8 Hz, 1H), 7.52-7.59 (m, 3H), 7.91-8.18 (m, 3H), 12.65 (s, 114); MS (m/z): 437.23 (M+H)$^+$.

Example-140

N-(4-Chloro-3-(1-(3-chloro-4-methylphenyl)-4,5-dihydro-5-oxo-1H-1,2,4-triazol-3-yl)benzyl)pivalamide

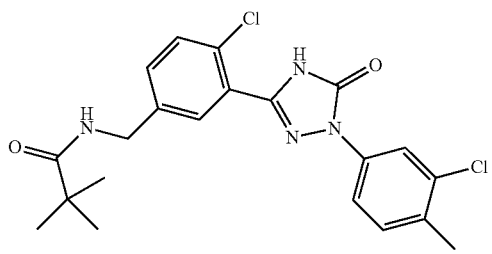 [SMILES: Cc1ccc(-n2nc(-c3cc(CNC(=O)C(C)(C)C)ccc3Cl)[nH]c2=O)cc1Cl]

The title compound was prepared according to the procedure described in Example-108 by using 5-(5-(aminomethyl)-2-chlorophenyl)-2-(3-chloro-4-methylphenyl)-2H-1,2,4-triazol-3(4H)-one (Intermediate-93, 0.350 g, 1.00 mmol), pivaloyl chloride (0.128 g, 1.0 mmol), DIPEA (2.0 mL), dry THF (10 mL) to afford 0.200 g of the desired product. $^1$H NMR (300 MHz, DMSO d$_6$): δ 1.13 (s, 9H), 2.34 (s, 3H), 4.29 (d, J=6.3 Hz, 2H), 7.39-7.47 (m, 2H), 7.58-7.61 (m, 2H), 7.82 (d, J=8.7 Hz, 1H), 8.01 (s, 1H), 8.18 (t, 1H), 12.58 (s, 1H); MS (m/z): 433.19 (M+H)$^+$.

Example-141

N-(4-Chloro-3-(3-(4-(2-cyclopropyl ethynyl)phenyl)-4,5-dihydro-5-oxo-1,2,4-triazol-1-yl)benzyl)pivalamide

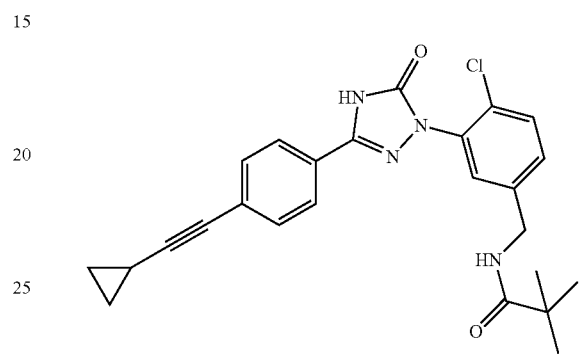

To a solution of N-(4-chloro-3-(4,5-dihydro-3-(4-iodophenyl)-5-oxo-1,2,4-triazol-1-yl)benzyl)pivalamide (Intermediate-95, 0.100 g, 0.196 mmol) in DMSO (3.0 mL), ethynylcyclopropane (0.035 g, 0.530 mmol), TBAF (0.150 g, 0.574) and bis(triphenylphosphine)palladium(II) chloride_(catalytic) were added and the reaction mass was stirred at 80° C. for 5-6 h. After completion of the reaction, the reaction mass was quenched with water and extracted with DCM and concentrated to afford 0.050 g of the desired title product. $^1$H NMR (300 MHz, DMSO d$_6$): δ 0.76-0.91 (m, 2H), 0.91-0.92 (m, 2H), 1.11 (s, 9H), 1.57 (m, 1H), 4.28 (br d, 2H), 7.31-7.34 (br d, 1H), 7.42 (br s, 1H), 7.47-7.50 (br m, 2H), 7.60 (d, J=8.4 Hz, 1H), 7.78 (d, J=8.4 Hz, 2H), 8.18 (s, 1H), 12.58 (s, 1H); MS (m/z): 449.52 (M+H)$^+$.

Example-142

N-(4-Chloro-3-(1-(3-(trifluoromethyl)phenyl)-4,5-dihydro-5-oxo-1H-1,2,4-triazol-3-yl)benzyl)pivalamide

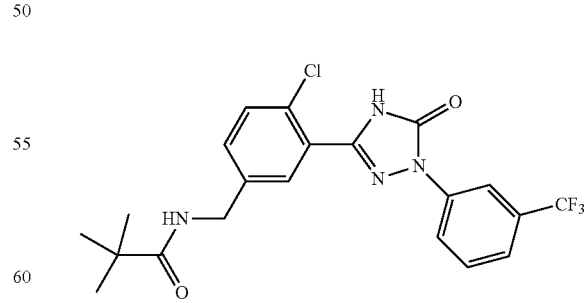

The title compound was prepared according to the procedure described in Example-108 by using 5-(5-(aminomethyl)-2-chlorophenyl)-2-(3-(trifluoromethyl)phenyl)-2H-1,2,4-triazol-3(4H)-one (Intermediate-96, 0.250 g, 0.678 mmol), pivaloyl chloride (0.3 mL), TEA (2.0 mL), and dry THF (5 mL) to afford 0.150 g of the desired product. ¹H NMR (300 MHz, DMSO d₆): δ 1.13 (s, 9H), 4.30 (d, J=6.0 Hz, 2H), 7.41-7.43 (m, 1H), 7.59-7.62 (m, 3H), 7.71-7.76 (m, 1H), 8.19-8.29 (m, 3H), 12.68 (s, 1H); MS (m/z): 453.38 (M+H)⁺.

Example-143

N-(4-Chloro-3-(4,5-dihydro-3-(4-(3,3-dimethylbut-1-ynyl)phenyl)-5-oxo-1,2,4-triazol-1-yl)benzyl)isobutyramide

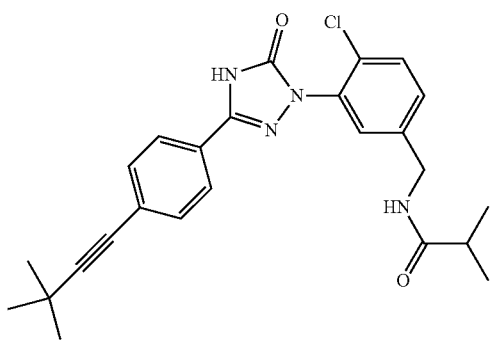 [SMILES: CC(C)C(=O)NCc1ccc(Cl)c(-n2nc(-c3ccc(C#CC(C)(C)C)cc3)[nH]c2=O)c1]

The title compound was prepared according to the procedure described in Example-111 by using N-(4-chloro-3-(4,5-dihydro-3-(4-iodophenyl)-5-oxo-1,2,4-triazol-1-yl)benzyl)isobutyramide (Intermediate-98, 0.060 g, 0.120 mmol), 3,3-dimethylbut-1-yne (0.014 g, 0.181 mmol), TBAF (0.094 g, 0.362 mmol), bis(triphenylphosphine)palladium (II)chloride (0.003 g, 0.003 mmol) and DMSO (3.0 mL) to afford 0.015 g of the desired product. ¹H NMR (400 MHz, DMSO d₆): δ 1.03 (s, 6H), 1.30 (s, 9H), 2.50 (m, 1H), 4.27 (d, J=5.4 Hz, 2H), 7.35 (d, J=8.7 Hz, 1H), 7.44-7.50 (m, 3H), 7.61 (d, J=8.1 Hz, 1H), 7.80 (d, =8.1 Hz, 2H), 8.38 (m, 1H); MS (m/z): 449.9 (M–H)⁻.

Example-144

N-(4-Chloro-3-(1-(4-(trifluoromethyl)phenyl)-4,5-dihydro-5-oxo-1H-1,2,4-triazol-3-yl)benzyl)isobutyramide

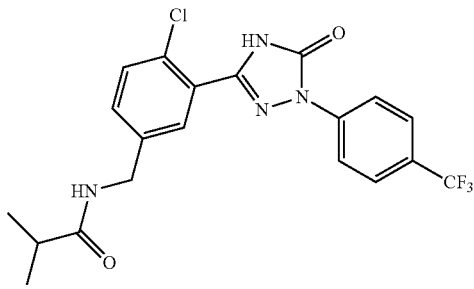 [SMILES: CC(C)C(=O)NCc1ccc(Cl)c(-c2nn(-c3ccc(C(F)(F)F)cc3)c(=O)[nH]2)c1]

The title compound was prepared according to the procedure described in Example-108 by using 3-(5-(aminomethyl)-2-chlorophenyl)-1-(4-(trifluoromethyl)phenyl)-1H-1,2,4-triazol-5(4H)-one (Intermediate-63, 0.250 g, 0.678 mmol), isobutyryl chloride (0.108 g, 1.01 mmol), TEA (2.0 mL), and dry THF (5 mL) to afford 0.350 g of the desired product. ¹H NMR (300 MHz, DMSO d₆): δ 1.14 (d, J=6.6 Hz, 6H), 2.41-2.43 (m, 1H), 4.30 (d, J=6.3 Hz, 2H), 7.43 (d, J=8.1 Hz, 1H), 7.61-7.64 (m, 2H), 7.86 (d, J=9.3 Hz, 2H), 8.20 (d, J=8.4 Hz, 2H), 8.38 (m, 1H), 12.69 (s, 1H); MS (m/z): 43924 (M+H)⁺.

Example-145

N-(4-Chloro-3-(3-(4-(trifluoromethyl)phenyl)-4,5-dihydro-5-oxo-1,2,4-triazol-1-yl)benzyl)pivalamide

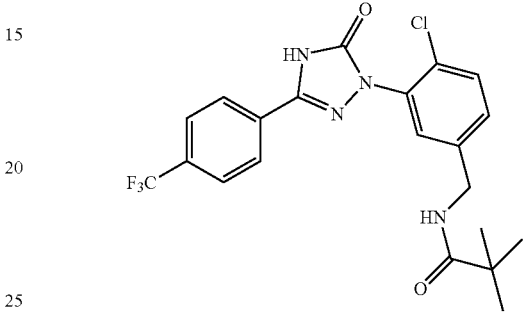

The title compound was prepared according to the procedure described in Example-83 by using tert-butyl 2-(2-chloro-5-{[(2,2-dimethylpropanoyl)amino]methyl}phenyl)hydrazinecarboxylate (Intermediate-94, 0.150 g, 0.420 mmol), 4-(trifluoromethyl)benzoyl isocyanate (Intermediate-59, 0.181 g, 0.84 mmol), DCM (15 mL), and trifluoro acetic acid (3.0 mL) to afford 0.070 g of the desired product. ¹H NMR (300 MHz, DMSO d₆): δ 1.13 (s; 9H), 4.29 (d, J=5.4 Hz, 2H), 7.36 (d, J=8.7 Hz, 1H), 7.45 (s, 1H), 7.62 (d, J=8.4 Hz, 1H), 7.92 (d, J=8.4 Hz, 2H), 8.06 (d, J=8.4 Hz, 2H), 8.19 (m, 1H), 12.79 (s, 1H); MS (m/z): 456.59 (M+H)⁺.

Example-146

N-(4-Chloro-3-(3-(3-fluoro-4-(trifluoromethyl)phenyl)-4,5-dihydro-5-oxo-1,2,4-triazol-1-yl)benzyl)pivalamide

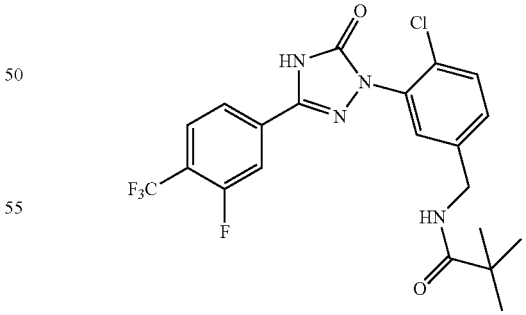

The title compound was prepared according to the procedure described in Example-83 by using 3-fluoro-4-(trifluoromethyl)benzoyl isocyanate (Intermediate-99, 2.0 g), tert-butyl 2-(2-chloro-5-{[(2,2-dimethylpropanoyl)amino]methyl}phenyl)hydrazinecarboxylate (Intermediate-94, 1.0 g), DCM (15 mL), and trifluoro acetic acid (3.0 mL) to afford 0.900 g of the desired product. ¹H NMR (300 MHz, DMSO d$_6$): δ 1.12 (s, 9H), 4.29 (d, J=5.4 Hz, 2H), 7.35 (d, J=8.4 Hz, 1H), 7.44 (s, 1H), 7.62 (d, J=8.7 Hz, 1H), 7.86-8.10 (m, 3H), 8.19 (m, 1H), 12.86 (s, 1H); MS (m/z): 471.35 (M+H)$^+$.

Example-147

N-(4-Chloro-3-(3-(4-chloro-3-(trifluoromethyl)phenyl)-4,5-dihydro-5-oxo-1,2,4-triazol-1-yl)benzyl)pivalamide

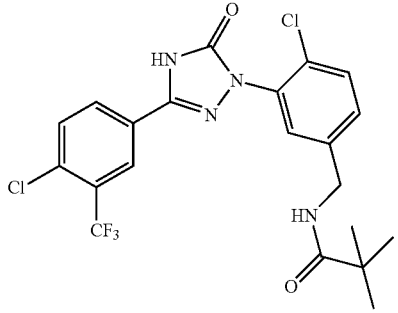 [SMILES: CC(C)(C)C(=O)NCc1ccc(Cl)c(-n2nc(-c3ccc(Cl)c(C(F)(F)F)c3)[nH]c2=O)c1]

The title compound was prepared according to the procedure described in Example-83 by using 4-chloro-3-(trifluoromethyl)benzoyl isocyanate (Intermediate-100, 2.0 g), tert-butyl 2-(2-chloro-5-{[(2,2-dimethylpropanoyl)amino]methyl}phenyl)hydrazinecarboxylate (Intermediate-94, 1.0 g), DCM (15 mL), and trifluoro acetic acid (3.0 mL) to afford 0.900 g of the desired product. $^1$H NMR (300 MHz, DMSO d$_6$): δ 1.12 (s, 9H), 4.29 (d, J=5.1 Hz, 2H), 7.36 (d, J=9.3 Hz, 1H), 7.43 (s, 1H), 7.61 (d, J=8.4 Hz, 1H), 7.93 (d, J=9.0 Hz, 1H), 8.10-8.18 (m, 2H), 8.27 (s, 1H), 12.82 (s, 1H); MS (m/z): 487.29 (M+H)$^+$.

Example-148

N-(4-Chloro-3-(3-(4-fluoro-3-(trifluoromethyl)phenyl)-4,5-dihydro-5-oxo-1,2,4-triazol-1-yl)benzyl)pivalamide

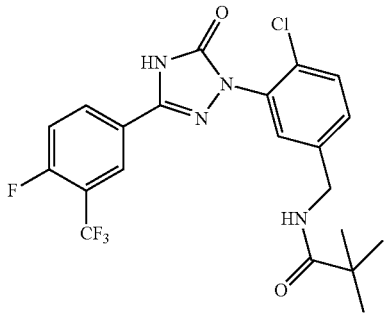

The title compound was prepared according to the procedure described in Example-83 by using 4-fluoro-3-(trifluoromethyl)benzoyl isocyanate (Intermediate-101, 0.196 g, 0.84 mmol), tert-butyl 2-(2-chloro-5-([[(2,2-dimethylpropanoyl)amino]methyl)phenyl)hydrazinecarboxylate (Intermediate-94, 0.150 g, 0.420 mmol), DCM (15 mL), and trifluoro acetic acid (3.0 mL) to afford 0.090 g of the desired product. $^1$H NMR (300 MHz, DMSO d$_6$): δ 1.12 (s, 9H), 4.29 (d, J=5.7 Hz, 2H), 7.35 (d, J=8.4 Hz, 1H), 7.43 (s, 1H), 7.60 (d, J=8.7 Hz, 1H), 7.70-7.76 (m, 1H), 8.19-8.23 (m, 3H), 12.76 (s, 1H); MS (m/z): 471.32 (M+H)$^+$.

Example-149

N-(4-Chloro-3-(3-(3-fluoro-4-(3,3-dimethylbut-1-ynyl)phenyl)-4,5-dihydro-5-oxo-1,2,4-triazol-1-yl)benz yl)isobutyramide

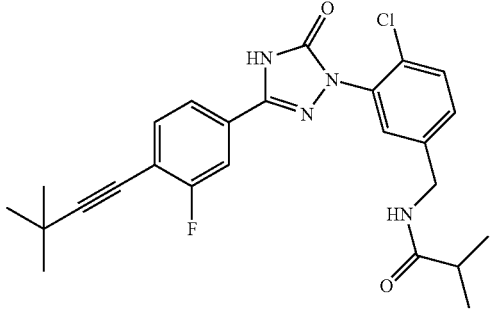 [SMILES: CC(C)C(=O)NCc1ccc(Cl)c(-n2nc(-c3ccc(C#CC(C)(C)C)c(F)c3)[nH]c2=O)c1]

Step 1:—Preparation of N-(4-chloro-3-(3-(3-fluoro-4-iodophenyl)-4,5-dihydro-5-oxo-1,2,4-triazol-1-yl)benzyl)isobutyramide

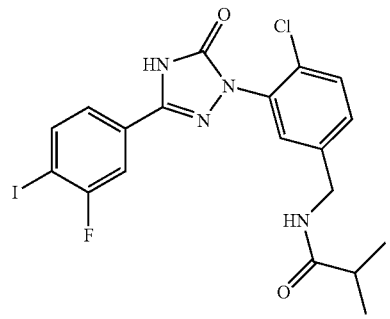 [SMILES: CC(C)C(=O)NCc1ccc(Cl)c(-n2nc(-c3ccc(I)c(F)c3)[nH]c2=O)c1]

The title compound was prepared according to the procedure described in Example-83 by using 3-fluoro-4-iodobenzoyl isocyanate (Intermediate-102, 1.0 g), tert-butyl 2-(2-chloro-5-{[(2-methylpropanoyl)amino]methyl}phenyl)hydrazinecarboxylate (Intermediate-97, 0.800 g), DCM (15 mL), and trifluoro acetic acid (3.0 mL) to afford 0.900 g of the desired product. $^1$H NMR (300 MHz, DMSO d$_6$): δ 1.30 (s, 6H), 2.43-2.45 (m, 1H), 4.26 (m, 2H), 7.01 (m, 1H), 7.46-7.49 (m, 1H), 7.63-7.66 (m, 1H), 7.84-7.91 (m, 1H), 8.01-8.06 (m, 1H), 8.22 (s, 1H), 8.36 (br s, 1H), 12.66 (m, 1H); MS (m/z): 515.21 (M+H)$^+$.

Step-2:—Preparation of N-(4-chloro-3-(3-(3-fluoro-4-(3,3-dimethylbut-1-ynyl)phenyl)-4,5-dihydro-5-oxo-1,2,4-triazol-1-yl)benzyl)isobutyramide The title compound was prepared according to the procedure described in Example-111 by using N-(4-chloro-3-(3-(3-fluoro-4-iodophenyl)-4,5-dihydro-5-oxo-1,2,4-triazol-1-yl)benzyl)isobutyramide (0.080 g, 0.155 mmol), 3,3-dimethylbut-1-yne (0.019 g, 0.233 mmol), TBAF (0.121 g, 0.466 mmol), bis(triphenylphosphine)palladium(II)chloride (0.004 g, 0.006 mmol) and DMSO (3.0 mL) to afford 0.009 g of the desired product. $^1$H NMR (300 MHz, DMSO d$_6$): δ 1.02 (d, J=6.9 Hz, 6H), 1.31 (s, 9H), 2.39-2.42 (m, 1H), 4.29 (d, J=5.7 Hz, 2H), 7.35 (d, J=7.5 Hz, 1H), 7.43 (s, 1H), 7.57-7.67 (m, 4H), 8.37 (m, 1H), 13.0 (br s, 1H); MS (m/z): 469.31 (M+H)$^+$.

Example-150

N-(4-Chloro-3-(3-(4-(2-cyclopropylethynyl)-3-fluorophenyl)-4,5-dihydro-5-oxo-1,2,4-triazol-1-yl)benzyl)isobutyramide

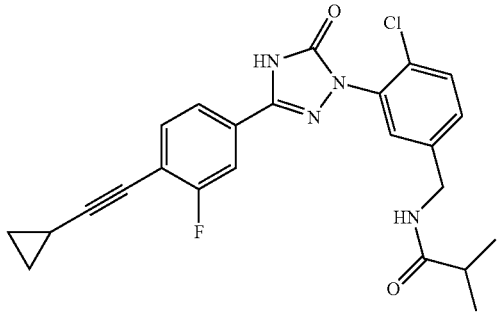 [SMILES: CC(C)C(=O)NCc1ccc(Cl)c(-n2nc(-c3ccc(C#CC4CC4)c(F)c3)[nH]c2=O)c1]

The title compound was prepared according to the procedure, described in Example-111 by using N-(4-chloro-3-(3-(3-fluoro-4-iodophenyl)-4,5-dihydro-5-oxo-1,2,4-triazol-1-yl)benzyl)isobutyramide (step 1 of Example-149, 0.080 g, 0.155 mmol), ethynylcyclopropane (0.019 g, 0.233 mmol), TBAF (0.121 g, 0.466 mmol), bis(triphenylphosphine)palladium(II) chloride (0.004 g, 0.006 mmol) and DMSO (3.0 mL) to afford 0.009 g of the desired product. $^1$H NMR (300 MHz, DMSO $d_6$): δ 0.79-0.92 (m, 2H), 1.011 (m, 2H), 1.30 (s, 6H), 1.63 (m, 1H), 2.39 (m, 1H), 4.28 (d, J=5.7 Hz, 2H), 7.35 (m, 1H), 7.43 (s, 1H), 7.57-7.67 (m, 4H), 8.37 (m, 1H); MS (m/z): 453.24 (M+H)$^+$.

Example-151

N-(4-Chloro-3-(4,5-dihydro-5-oxo-3-(4-((pyrrolidin-1-yl)methyl)phenyl)-1,2,4-triazol-1-yl)benzyl)pivalamide

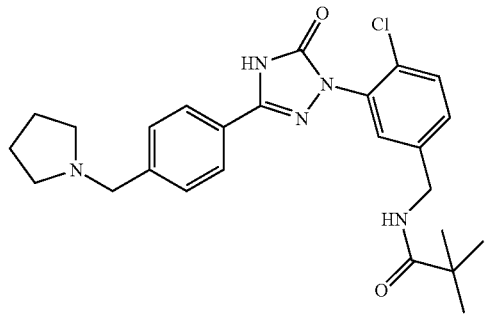 [SMILES: CC(C)(C)C(=O)NCc1ccc(Cl)c(-n2nc(-c3ccc(CN4CCCC4)cc3)[nH]c2=O)c1]

To a cold solution of pyrolidine (0.060 g, 0.830 mmol) in DMF was added NaH (0.034 g, 0.830 mmol) at 0° C. and stirred the reaction mass for 1 h. Then solution of N-(3-(3-(4-(bromomethyl)phenyl)-4,5-dihydro-5-oxo-1,2,4-triazol-1-yl)-4-chlorobenzyl)pivalamide (Intermediate-103, 0.200 g, 0.419) in DMF was added at 0° C. and continued stirring at 5-10° C. for 2-3 h. The reaction mass was quenched in ice and pH adjusted to 6-7 and extracted with DCM. The organic layer was dried over anhydrous sodium sulphate and concentrated. The obtained crude product was purified by column chromatography on basic alumina, eluting with 5% MeOH:DCM to afford 0.020 g of the desired product. $^1$H NMR (300 MHz, DMSO $d_6$): δ 1.23 (s, 9H), 1.79 (br s, 4H), 2.53 (br s, 4H), 3.66 (s, 2H), 4.48 (d, J=5.7 Hz, 2H), 6.08 (m, 1H), 7.26-7.54 (m, 5H), 7.79 (d, J=7.8 Hz, 2H); MS (m/z): 468.51 (M+H)$^+$.

Example-152

N-(3-(3-(4-((2,2,2-Trifluoroethoxy)methyl)phenyl)-4,5-dihydro-5-oxo-1,2,4-triazol-1-yl)-4-chlorobenzyl)pivalamide

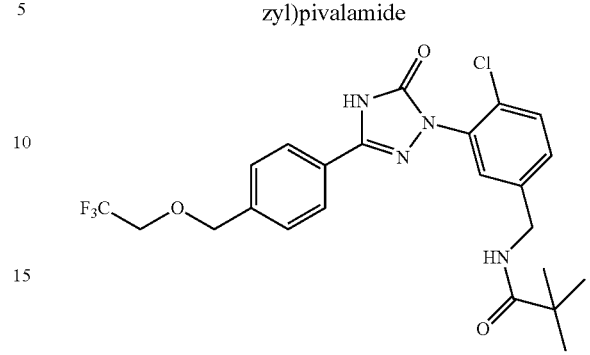

To a solution of 2,2,2-trifluoro ethanol (0.042 g, 0.410 mmol) in THF was added NaH (0.017 g, 0.041 mmol) at 10° C. and continued stirring at RT for 1 h. Then solution of N-(3-(3-(4-(bromomethyl)phenyl)-4,5-dihydro-5-oxo-1,2,4-triazol-1-yl)-4-chlorobenzyl)pivalamide (Intermediate-103, 0.100 g, 0.041 mmol) in THF and TBAI (0.004 g, 0.0012 mmol) were added to the reaction mixture. The reaction mass was refluxed for 2-3 h. The reaction mass was quenched in ice and pH adjusted to 6-7 and extracted with DCM. The organic layer was dried over anhydrous sodium sulphate and concentrated to afford 0.060 g of desired product. $^1$H NMR (300 MHz, DMSO $d_6$): δ 1.12 (s, 9H), 4.11-4.17 (m, 2H), 4.28 (d, J=5.4 Hz, 2H), 4.71 (s, 2H), 7.28 (d, J=9.0 Hz, 1H), 7.41 (s, 1H), 7.46 (d, J=7.8 Hz, 2H), 7.57 (d, J=8.1 Hz, 1H), 7.85 (d, J=8.1 Hz, 2H), 8.18 (t, 1H); MS (m/z): 497.31 (M+H)$^+$.

Example-153

N-(4-Chloro-3-(4,5-dihydro-3-(4-(5-isopropyl-1,3,4-oxadiazol-2-yl)phenyl)-5-oxo-1,2,4-triazol-1-yl)benzyl)pivalamide

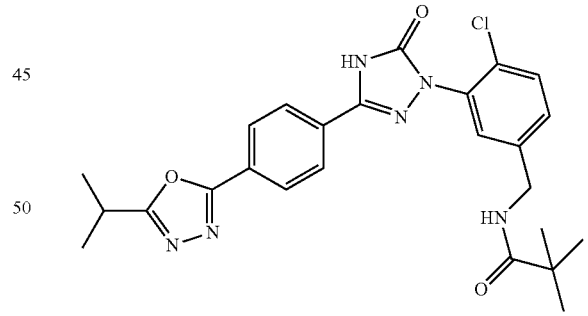

The title compound was prepared according to the procedure described in Example-83 by using 4-(5-isopropyl-1,3,4-oxadiazol-2-yl)benzoyl isocyanate (Intermediate-104, 0.196 g, 0.84 mmol), tert-butyl 2-(2-chloro-5-{[(2,2-dimethylpropanoyl)amino]methyl}phenyl)hydrazinecarboxylate (Intermediate-94, 0.150 g, 0.420 mmol), DCM (15 mL), and trifluoro acetic acid (3.0 mL) to afford 0.090 g of the desired product. $^1$H NMR (300 MHz, DMSO $d_6$): δ 1.06 (s, 9H), 1.35 (s, 6H), 3.25 (m, 1H), 4.27 (d, J=5.4 Hz, 2H), 7.34 (d, J=8.1 Hz, 1H), 7.44 (s, 1H), 7.59 (d, J=8.4 Hz, 1H), 8.01-8.04 (m, 2H), 8.10-8.17 (m, 3H), 12.73 (s, 1H); MS (m/z): 495.39 (M+H)$^+$.

Example-154

N-(4-Chloro-3-(1-(4-chloro-3-methylphenyl)-4,5-dihydro-5-oxo-1H-1,2,4-triazol-3-yl)benzyl)pivalamide

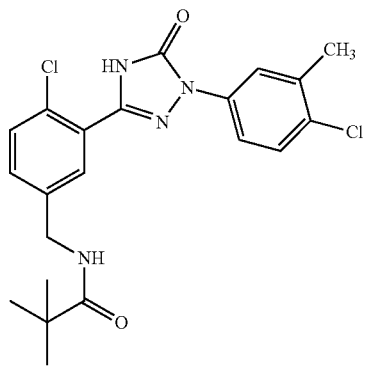 [SMILES: Cc1cc(-n2nc(-c3cc(CNC(=O)C(C)(C)C)ccc3Cl)[nH]c2=O)ccc1Cl]

The title compound was prepared according to the procedure described in Example-108 by using 5-(5-(aminomethyl)-2-chlorophenyl)-2-(4-chloro-3-methylphenyl)-2H-1,2,4-triazol-3(4H)-one (Intermediate-106, 0.300 g, 0.859 mmol), pivaloyl chloride (0.130 g, 1.03 mmol), TEA (2.0 mL), dry THF (5 mL) to afford 0.140 g of the desired product. $^1$H NMR (300 MHz, DMSO $d_6$): δ 1.13 (s, 9H), 2.37 (s, 3H), 4.29 (d, J=5.7 Hz, 2H), 7.41 (d, J=8.7 Hz, 1H), 7.51 (d, J=8.7 Hz, 1H), 7.58 (s, 2H), 7.70 (br d, 1H), 7.91 (s, 1H), 8.20 (d, J=6.0 Hz, 1H), 12.56 (s, 1H); MS (m/z): 433.38 (M+H)$^+$.

Example-155 to Example-163 were prepared by following the procedure described in Example-108 by using corresponding intermediates mentioned in table below, TEA and THF.

| Intermediates used | Example No. and Structure | Example chemical name and characterization data |
|---|---|---|
| Intermediate-106 + Isobutyryl chloride | Example-155 | N-(4-Chloro-3-(1-(4-chloro-3-methylphenyl)-4,5-dihydro-5-oxo-1H-1,2,4-triazol-3-yl)benzyl)isobutyramide. $^1$H NMR (300 MHz, DMSO $d_6$): δ 1.02 (s, 3H), 1.05 (s, 3H), 2.38 (s, 3H), 4.29 (d, J = 6.0Hz, 2H), 7.42 (d, J = 9.0 Hz, 1H), 7.52 (d, J = 8.7 Hz, 1H), 7.60 (s, 2H), 7.82 (br d, 1H), 7.91 (s, 1H), 8.38 (t, 1H), 12.57 (s, 1H); MS (m/z): 433.30 (M + H)$^+$. |
| Intermediate-130 + Pivaloyl chloride | Example-156 | N-(4-Chloro-3-(1-(3-fluoro-5-(trifluoromethyl)phenyl)-4,5-dihydro-5-oxo-1H-1,2,4-triazol-3-yl)benzyl)pivalamide. $^1$H NMR (300 MHz, DMSO $d_6$): δ 1.13 (s, 9H), 4.30 (d, J = 6.3 Hz, 2H), 7.42 (d, J = 8.40 Hz, 1H), 7.61 (m, 3H), 8.09 (d, 1H), 8.14 (s, 1H), 8.20 (t, 1H), 12.80 (s, 1H); MS (m/z): 471.39 (M + H)$^+$. |

| Intermediates used | Example No. and Structure | Example chemical name and characterization data |
|---|---|---|
| Intermediate-131 + Pivaloyl chloride | Example-157 | N-(4-Chloro-3-(1-(4-chloro-3-(trifluoromethyl)phenyl)-4,5-dihydro-5-oxo-1H-1,2,4-triazol-3-yl)benzyl)pivalamide. $^1$H NMR (300 MHz, DMSO d$_6$): δ 1.13 (s, 9H), 4.30 (d, J = 6.0 Hz, 2H), 7.42 (d, J = 7.20 Hz, 1H), 7.62 (d, J = 8.10 Hz, 2H), 7.86 (d, J = 8.7 Hz, 1H), 8.19-8.26 (m, 2H), 8.42 (s, 1H), 12.76 (s, 1H); MS (m/z): 487.43 (M + H)$^+$. |
| Intermediate-133 + Pivaloyl chloride | Example-158 | N-(4-Chloro-3-(1-(3-(trifluoromethyl)-4-methylphenyl)-4,5-dihydro-5-oxo-1H-1,2,4-triazol-3-yl)benzyl)pivalamide. $^1$H NMR (300 MHz, DMSO d$_6$): δ 1.13 (s, 9H), 2.46 (s, 3H), 4.31 (d, J = 5.7 Hz, 2H), 7.39 (d, J = 7.8 Hz, 2H), 7.57 (d, 2H), 7.68 (d, 2H), 7.80 (s, 1H), 12.47 (s, 1H); MS (m/z): 467.22 (M + H)$^+$. |
| Intermediate-134 + Pivaloyl chloride | Example-159 | N-(4-Chloro-3-(1-(4-(trifluoromethyl)-2-methylphenyl)-4,5-dihydro-5-oxo-1H-1,2,4-triazol-3-yl)benzyl)pivalamide. $^1$H NMR (300 MHz, DMSO d$_6$): δ 1.12 (s, 9H), 2.39 (s, 3H), 4.28 (d, 2H), 7.43 (d, 1H), 7.55-7.60 (m, 3H), 8.12 (d, 1H), 8.20 (m, 1H), 8.29 (s, 1H), 12.65 (s, 1H); MS (m/z): 467.15 (M + H)$^+$. |

| Intermediates used | Example No. and Structure | Example chemical name and characterization data |
|---|---|---|
| Intermediate-135 + Pivaloyl chloride | Example-160 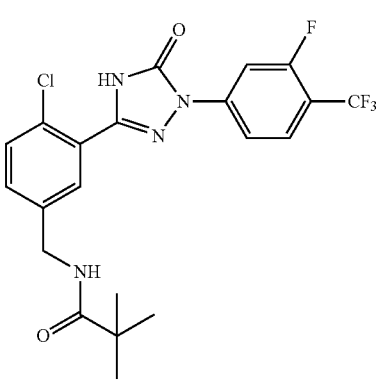 [SMILES: CC(C)(C)C(=O)NCc1ccc(Cl)c(-c2nn(-c3ccc(C(F)(F)F)c(F)c3)c(=O)[nH]2)c1] | N-(4-Chloro-3-(1-(3-fluoro-4-(trifluoromethyl)phenyl)-4,5-dihydro-5-oxo-1H-1,2,4-triazol-3-yl)benzyl)pivalamide. $^1$H NMR (300 MHz, DMSO d$_6$): δ 1.13 (s, 9H), 4.29 (d, J = 4.8 Hz, 2H), 7.43 (m, 1H), 7.60-7.61 (m, 2H), 7.91-7.94 (m, 1H), 7.98-8.06 (m, 2H), 8.19 (t, 1H); MS (m/z): 471.18 (M + H)$^+$. |
| Intermediate-135 + Isobutyryl chloride | Example-161 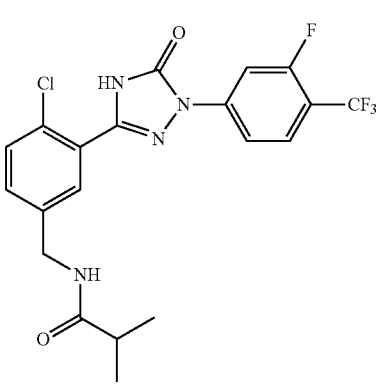 [SMILES: CC(C)C(=O)NCc1ccc(Cl)c(-c2nn(-c3ccc(C(F)(F)F)c(F)c3)c(=O)[nH]2)c1] | N-(4-Chloro-3-(1-(3-fluoro-4-(trifluoromethyl)phenyl)-4,5-dihydro-5-oxo-1H-1,2,4-triazol-3-yl)benzyl)isobutyramide. $^1$H NMR (300 MHz, DMSO d$_6$): δ 1.02 (s, 3H), 1.05 (s, 3H), 2.43 (m, 1H), 4.29 (d, J = 6.6 Hz, 2H), 7.42 (d, J = 7.5 Hz, 1H), 7.60 (s, 1H), 7.63 (br s, 1H), 7.91 (t, J = 6.9 Hz, 1H), 7.99-8.08 (m, 2H), 8.40 (t, 1H); MS (m/z): 455.01 (M + H)$^+$. |
| Intermediate-63 + Isopropyl sulfonyl chloride | Example-162 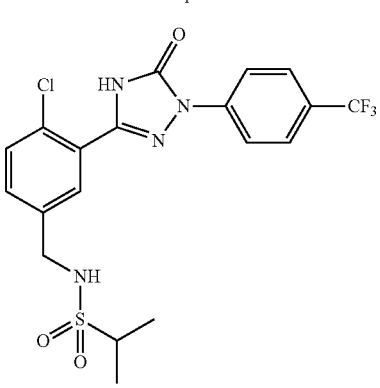 | N-(4-Chloro-3-{5-oxo-1-[4-(trifluoromethyl)phenyl]-4,5-dihydro-1H-1,2,4-triazol-3-yl}benzyl)propane-2-sulfonamide. $^1$H NMR (300 MHz, DMSO d$_6$): δ 1.22 (s, 3H), 1.24 (s, 3H), 3.17 (m, 1H), 4.23 (d, J = 6.0 Hz, 2H), 7.56 (d, J = 7.8 Hz, 1H), 7.65-7.72 (m, 3H), 7.87 (d, J = 8.4 Hz, 2H), 8.19 (d, J = 8.7 Hz 2H), 12.72 (s, 1H); MS (m/z): 475.15 (M + H)$^+$. |

-continued

| Intermediates used | Example No. and Structure | Example chemical name and characterization data |
|---|---|---|
| Intermediate-136 + Pivaloyl chloride | Example-163 | N-(4-Chloro-3-(1-(2-fluoro-4-(trifluoromethyl)phenyl)-4,5-dihydro-5-oxo-1H-1,2,4-triazol-3-yl)benzyl)pivalamide. $^1$H NMR (300 MHz, DMSO $d_6$): δ 1.12 (s, 9H), 7.28 (d, J = 5.7 Hz, 2H), 7.40 (d, J = 7.8 Hz, 1H), 7.57-7.62 (m, 2H), 7.75 (d, J = 7.8 Hz, 1H), 7.90-7.98 (m, 2H), 8.18 (t, 1H), 12.59 (s, 1H); MS (m/z): 471.17 (M + H)$^+$. |

Example-164 to Example-171 were prepared by following the procedure described in Example-111 by using corresponding intermediates mentioned in table below, bis(triphenylphosphine)palladium(II) chloride, TBAF and DMSO.

| Intermediates used | Example No. and Structure | Example chemical name and Characterization data |
|---|---|---|
| Intermediate-140 + 3,3-dimethylbut-1-yne | Example-164 | N-(3-(4,5-Dihydro-1-(4-(3,3-dimethylbut-1-ynyl)phenyl)-5-oxo-1H-1,2,4-triazol-3-yl)-2,4-dimethylbenzyl)isobutyramide. $^1$H NMR (300 MHz, DMSO $d_6$): δ 1.01 (s, 3H), 1.04 (s, 3H), 1.26 (s, 9H), 2.16 (s, 3H), 2.20 (s, 3H), 2.42 (m, 1H), 4.24 (d, J = 6.3 Hz, 2H), 7.17 (d, J = 7.8 Hz, 1H), 7.27 (d, J = 8.4 Hz, 1H), 7.43 (d, J = 8.7 Hz, 2H), 7.92 (d, J = 9.0 Hz, 2H), 8.19 (t, 1H), 12.23 (s, 1H); MS (m/z): 445.26 (M + H)$^+$. |
| Intermediate-138 + Ethynylcyclopropane | Example-165 | N-(3-(1-(4-(2-Cyclopropylethynyl)phenyl)-4,5-dihydro-5-oxo-1H-1,2,4-triazol-3-yl)-2,4-dimethylbenzyl)pivalamide. $^1$H NMR (300 MHz, DMSO $d_6$): δ 0.73 (m, 2H), 0.88 (m, 2H), 1.14 (s, 9H), 1.54 (s, 3H), 2.16 (s, 3H), 2.19 (s, 3H), 4.23 (d, J = 6.0 Hz, 2H), 7.16 (d, J = 8.4 Hz, 1H), 7.23 (d, J = 7.8 Hz, 1H), 7.43 (d, J = 8.4 Hz, 2H), 7.91 (d, J = 9.0 Hz, 2H), 8.00 (t, 1H), 12.22 (s, 1H); MS (m/z): 443.51 (M + H)$^+$. |

| Intermediates used | Example No. and Structure | Example chemical name and Characterization data |
|---|---|---|
| Intermediate-119 + Ethynylcyclopropane | Example-166 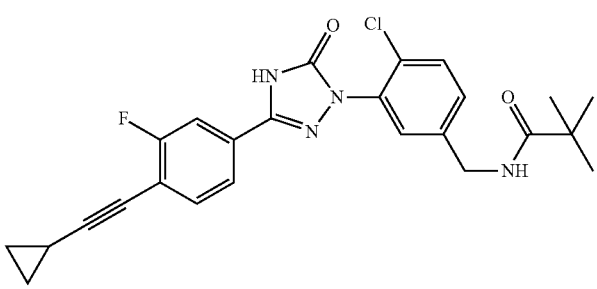 [SMILES: CC(C)(C)C(=O)NCc1ccc(Cl)c(-n2nc(-c3ccc(C#CC4CC4)c(F)c3)[nH]c2=O)c1] | N-(4-Chloro-3-(3-(4-(2-cyclopropylethynyl)-3-fluorophenyl)-4,5-dihydro-5-oxo-1,2,4-triazol-1-yl)benzyl)pivalamide. $^1$H NMR (300 MHz, DMSO d$_6$): δ 0.80 (m, 2H), 0.93-0.95 (m, 2H), 1.12 (s, 9H), 1.63 (m, 1H), 4.28 (d, J = 6.3 Hz, 2H), 7.35 (d, J = 9.0 Hz, 1H), 7.43 (s, 1H), 7.59-7.67 (m, 4H), 8.19 (t, 1H), 12.66 (s, 1H); MS (m/z): 467.24 (M + H)$^+$. |
| Intermediate-139 + Ethynylcyclopropane | Example-167 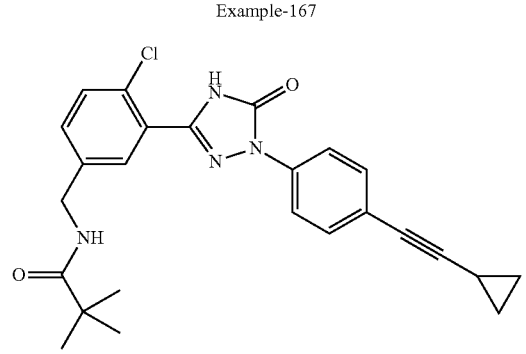 | N-(4-Chloro-3-(1-(4-(2-cyclopropylethynyl)phenyl)-4,5-dihydro-5-oxo-1H-1,2,4-triazol-3-yl)benzyl)pivalamide. $^1$H NMR (300 MHz, DMSO d$_6$): δ 0.73 (m, 2H), 0.89 (m, 2H), 1.13 (s, 9H), 1.54 (m, 1H), 4.30 (d, 2H), 7.41-7.47 (m, 2H), 7.58 (s, 2H), 7.81 (m, 1H), 7.91 (d, J = 6.3 Hz, 2H), 8.18 (br s, 1H), 12.56 (s, 1H); MS (m/z): 449.30 (M + H)$^+$. |
| Intermediate-124 + Ethynylcyclopropane | Example-168 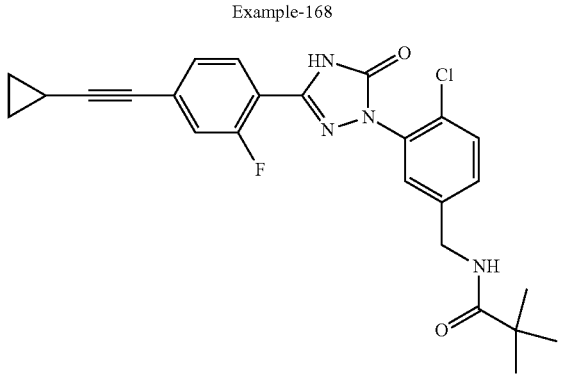 | N-(4-Chloro-3-(3-(4-(2-cyclopropylethynyl)-2-fluorophenyl)-4,5-dihydro-5-oxo-1,2,4-triazol-1-yl)benzyl)pivalamide. $^1$H NMR (300 MHz, DMSO d$_6$): δ 0.78 (m, 2H), 0.93 (m, 2H), 1.12 (s, 9H), 1.59 (m, 1H), 4.28 (d, J = 6.6 Hz, 2H), 7.34 (d, J = 8.4 Hz, 2H), 7.41 (m, 2H), 7.62 (d, J = 7.8 Hz, 1H), 7.75 (d, J = 7.8 Hz, 1H), 8.19 (t, 1H), 12.40 (s, 1H); MS (m/z): 467.20 (M)$^+$. |
| Intermediate-143 + Ethynylcyclopropane | Example-169 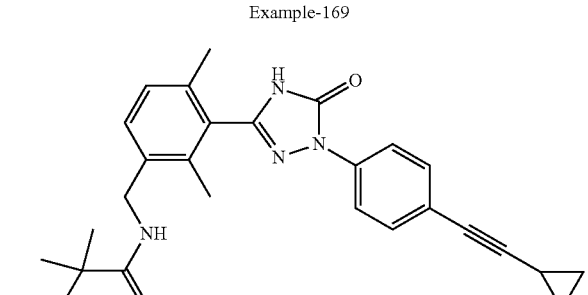 | N-(3-(1-(4-(2-Cyclopropylethynyl)phenyl)-4,5-dihydro-5-oxo-1H-1,2,4-triazol-3-yl)-2,4-dimethylbenzyl)-3-fluoro-2,2-dimethylpropanamide. $^1$H NMR (300 MHz, DMSO d$_6$): δ 0.74 (m, 2H), 0.85 (m, 2H), 1.15 (s, 6H), 1.54 (m, 1H), 2.15 (s, 3H), 2.19 (s, 3H), 4.27 (d, 2H), 4.43 (s, 1H), 4.49 (s, 1H), 7.17-7.24 (m, 2H), 7.43 (d, J = 8.4 Hz, 2H), 7.90 (d, J = 8.7 Hz, 2H), 8.16 (s, 1H), 12.22 (s, 1H); MS (m/z): 461.21 (M + H)$^+$. |

-continued

| Intermediates used | Example No. and Structure | Example chemical name and Characterization data |
|---|---|---|
| Intermediate-141 + 3,3-dimethylbut-1-yne | Example-170 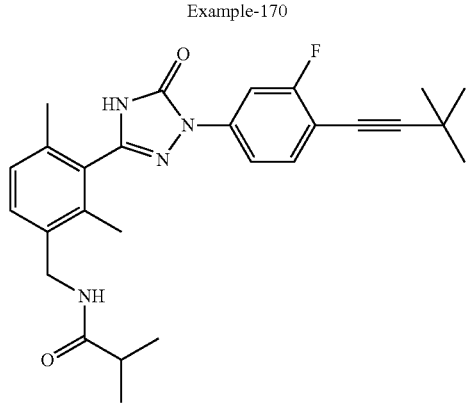 | N-(3-(1-(3-Fluoro-4-(3,3-dimethylbut-1-ynyl)phenyl)-4,5-dihydro-5-oxo-1H-1,2,4-triazol-3-yl)-2,4-dimethylbenzyl)isobutyramide. $^1$H NMR (300 MHz, DMSO d$_6$): δ 1.01 (s, 3H), 1.04 (s, 3H), 1.23 (s, 9H), 2.15 (s, 3H), 2.20 (s, 3H), 4.25 (d, 2H), 7.18 (m, 1H), 7.26 (m, 1H), 7.51 (m, 1H), 7.84 (m, 2H), 8.19 (t, 1H), 12.35 (s, 1H); MS (m/z): 463.151 (M + H)$^+$. |
| Intermediate-45 + 1,4-dichloro-2-ethynylbenzene | Example-171 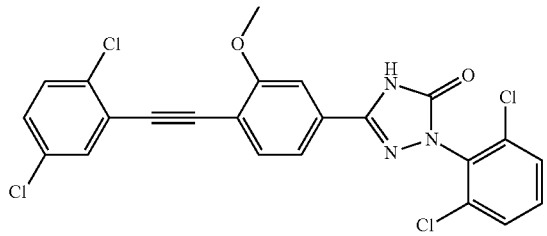 [SMILES: COc1cc(-c2nn(-c3c(Cl)cccc3Cl)c(=O)[nH]2)ccc1C#Cc1cc(Cl)ccc1Cl] | 2-(2,6-Dichlorophenyl)-5-(4-(2-(2,5-dichlorophenyl)ethynyl)-3-methoxyphenyl)-2H-1,2,4-triazol-3 (4H)-one. $^1$H NMR (300 MHz, DMSO d$_6$): δ 3.92 (s, 3H), 7.54 (m, 4H), 7.58-7.69 (m, 4H), 7.75 (s, 1H), 12-13 (br s, 1H); MS (m/z): 506.01 (M + H)$^+$. |

Example-172 was prepared by following the procedure described in Intermediate-41 by using corresponding intermediates mentioned in table below, NaH and DMF.

| Intermediate used | Example No. and Structure | Example chemical name and characterization data |
|---|---|---|
| Intermediate-103 + 3,5-dimethyl-1H-pyrazole | Example-172 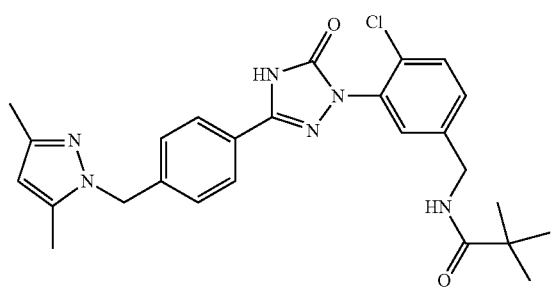 [SMILES: Cc1cc(C)n(Cc2ccc(-c3nn(-c4cc(CNC(=O)C(C)(C)C)ccc4Cl)c(=O)[nH]3)cc2)n1] | N-(4-Chloro-3-(4,5-dihydro-3-(4-((3,5-dimethyl-1H-pyrazol-1-yl)methyl)phenyl)-5-oxo-1,2,4-triazol-1-yl)benzyl)pivalamide. $^1$H NMR (300 MHz, DMSO d$_6$): δ 1.11 (s, 9H), 2.10 (s, 3H), 2.15 (s, 3H), 4.28 (d, J = 5.1 Hz, 2H), 5.24 (s, 2H), 5.87 (s, 1H), 7.19 (d, J = 7.8 Hz, 2H), 7.32 (d, J = 8.7 Hz, 1H), 7.22 (s, 1H), 7.59 (d, J = 8.1 Hz, 1H), 7.79 (d, J = 7.5 Hz, 1H), 8.18 (t, 1H); MS (m/z): 493.36 (M)$^+$. |

Example-173 and Example-174 were prepared by following the procedure as described in Example-83 by using corresponding intermediates mentioned in table below, TFA and DCM.

| Intermediates used | Example No. and Structure | Example chemical name and characterization data |
|---|---|---|
| Intermediate-109 + Intermediate-51 | Example-173 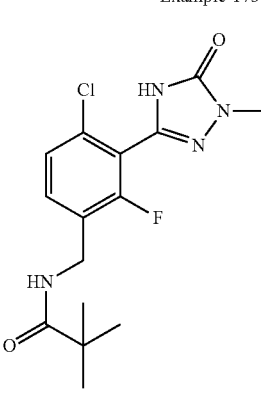 | N-(4-Chloro-2-fluoro-3-(1-(3-fluoro-4-(trifluoromethyl)phenyl)-4,5-dihydro-5-oxo-1H-1,2,4-triazol-3-yl)benzyl)pivalamide. $^1$H NMR (300 MHz, CDCl$_3$): δ 1.21 (s, 9H), 4.46 (d, J = 5.7 Hz, 2H), 6.21 (t, 1H), 6.42 (d, 1H), 7.32 (s, 1H), 7.42 (t, 1H), 7.65 (t, 1H), 7.96 (m, 2H); MS (m/z): 489.56 (M)$^+$. |
| Intermediate-111 + Intermediate-51 | Example-174 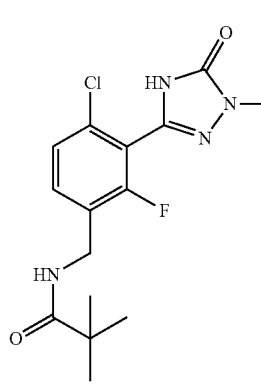 | N-(4-Chloro-3-(1-(4-chloro-3-(trifluoromethyl)phenyl)-4,5-dihydro-5-oxo-1H-1,2,4-triazol-3-yl)-2-fluorobenzyl)pivalamide. $^1$H NMR (300 MHz, DMSO d$_6$): δ 1.13 (s, 9H), 4.30 (d, J = 6.0 Hz, 2H), 7.46 (d, J = 7.8 Hz, 1H), 7.55 (d, J = 8.1 Hz, 1H), 7.85 (d, J = 8.1 Hz, 1H), 8.20 (t, 2H), 8.41 (s, 1H), 12.90 (m, 1H); MS (m/z): 505.27 (M + H)$^+$. |

Example-175 was prepared by following the procedure as described in described for step-2 of Example-134 by using Example-115, DAST and THF.

| Intermediates used | Example No. and Structure | Example chemical name and characterization data |
|---|---|---|
| Example-115 | Example-175 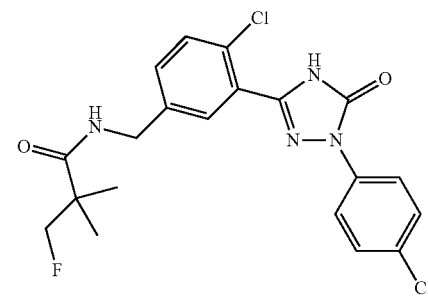 | N-(4-Chloro-3-(1-(4-(trifluoromethyl)phenyl)-4,5-dihydro-5-oxo-1H-1,2,4-triazol-3-yl)benzyl)-3-fluoro-2,2-dimethylpropanamide. $^1$H NMR (300 MHz, DMSO d$_6$): δ 1.15 (s, 6H), 4.33 (m, 4H), 7.41 (d, J = 7.2 Hz, 1H), 7.61 (d, J = 7.8 Hz, 2H), 7.85 (d, J = 9.3 Hz, 2H), 8.20 (d, J = 8.4 Hz, 2H), 8.35 (t, 1H), 12.71 (m, 1H); MS (m/z): 471.28 (M + H)$^+$. |

Example-176 to Example-179 were prepared by following the procedure as described for step-6 of Intermediate-26 by using corresponding intermediates used mentioned in table below, trimethyl aluminium (2M solution in toluene) and dry toluene.

| Intermediates used | Example No. and Structures | Example chemical name and characterization data |
|---|---|---|
| Step-5 of Intermediate-45 + methyl 4-(trifluoromethyl) benzoate | Example-176 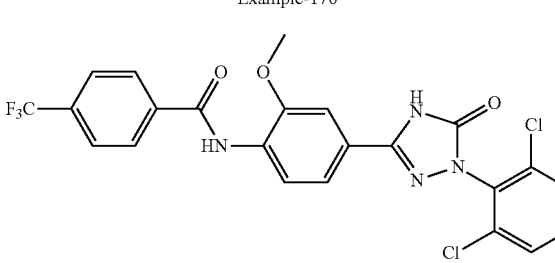 | N-(4-(1-(2,6-Dichlorophenyl)-4,5-dihydro-5-oxo-1H-1,2,4-triazol-3-yl)-2-methoxyphenyl)-4-(trifluoromethyl)benzamide. $^1$H NMR (300 MHz, DMSO $d_6$): δ 3.91 (s, 3H), 7.49-7.64 (m, 3H), 7.72.-7.74 (m, 2H), 7.91 (d, J = 8.4 Hz, 2H), 7.98 (d, J = 8.4 Hz, 1H), 8.15 (d, J = 8.1 Hz, 2H), 9.90 (s, 1H), 12.70 (s, 1H); MS (m/z): 523.10 (M + H)$^+$. |
| Step-5 of Intermediate-45 + methyl 3,5-difluorobenzoate | Example-177 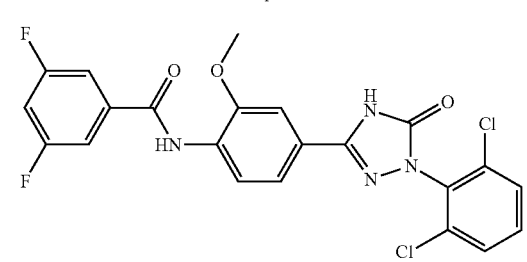 | N-(4-(1-(2,6-Dichlorophenyl)-4,5-dihydro-5-oxo-1H-1,2,4-triazol-3-yl)-2-methoxyphenyl)-3,5-difluorobenzamide. $^1$H NMR (300 MHz, DMSO $d_6$): δ 3.90 (s, 3H), 7.47-7.61 (m, 4H), 7.64.-7.72 (m, 4H), 7.88 (d, J = 7.8 Hz, 1H), 9.86 (s, 1H), 12.69 (s, 1H); MS (m/z): 491.03 (M + H)$^+$. |
| Intermediate-46 + 2-fluoro-5-(trifluoromethyl) aniline | Example-178 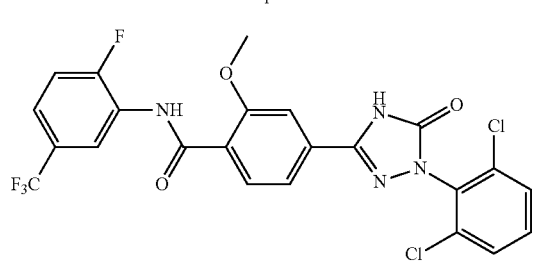 | 4-(1-(2,6-Dichlorophenyl)-4,5-dihydro-5-oxo-1H-1,2,4-triazol-3-yl)-N-(2-fluoro-5-(trifluoromethyl)phenyl)-2-methoxybenzamide. $^1$H NMR (300 MHz, DMSO $d_6$): δ 4.06 (s, 3H), 7.60-7.65 (m, 5H), 7.55.-7.67 (m, 2H), 8.03 (d, J = 7.8 Hz, 1H), 8.60 (s, 1H), 10.44 (s, 1H), 12.90 (s, 1H); MS (m/z): 541.05 (M + H)$^+$. |
| Intermediate-46 + 2-chloro-4-methyl aniline | Example-179 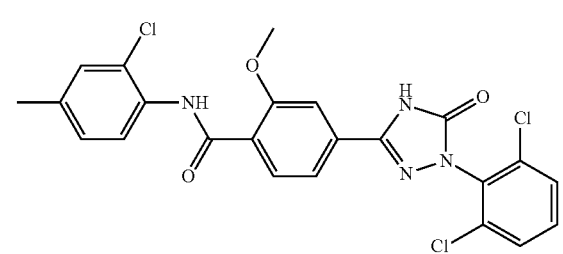 [SMILES: COc1cc(-c2nn(-c3c(Cl)cccc3Cl)c(=O)[nH]2)ccc1C(=O)Nc1ccc(C)cc1Cl] | N-(2-Chloro-4-methylphenyl)-4-(1-(2,6-dichlorophenyl)-4,5-dihydro-5-oxo-1H-1,2,4-triazol-3-yl)-2-methoxybenzamide. $^1$H NMR (300 MHz, DMSO $d_6$): δ 2.30 (s, 3H), 4.13 (s, 3H), 7.20 (d, J = 8.7 Hz, 1H), 7.41 (s, 1H), 7.41-7.75 (m, 5H), 8.15 (d, J = 7.8 Hz, 1H), 8.30 (d, J = 8.4 Hz, 1H), 10.47 (s, 1H), 12.91 (s, 1H); MS (m/z): 503.00 (M + H)$^+$. |

Example-180

N-((6-Cyclopropyl-5-(1-(4-(trifluoromethyl)phenyl)-4,5-dihydro-5-oxo-1H-1,2,4-triazol-3-yl)pyridin-3-yl)methyl)pivalamide

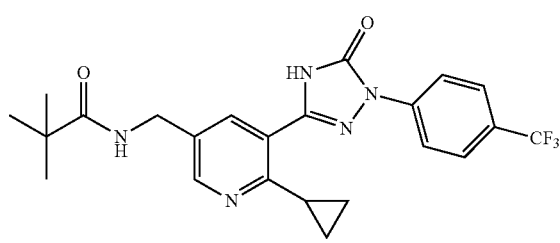 [SMILES: CC(C)(C)C(=O)NCc1cnc(C2CC2)c(-c2nn(-c3ccc(C(F)(F)F)cc3)c(=O)[nH]2)c1]

Step-1:—Preparation of tert-butyl (6-cyclopropyl-5-(1-(4-(trifluoromethyl)phenyl)-4,5-dihydro-5-oxo-1H-1,2,4-triazol-3-yl)pyridin-3-yl)methylcarbamate

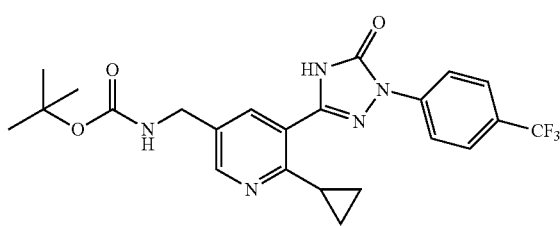 [SMILES: CC(C)(C)OC(=O)NCc1cnc(C2CC2)c(-c2nn(-c3ccc(C(F)(F)F)cc3)c(=O)[nH]2)c1]

A solution of 6-cyclopropyl-5-(1-(4-(trifluoromethyl)phenyl)-4,5-dihydro-5-oxo-1H-1,2,4-triazol-3-yl)pyridine-3-carbonitrile (0.110 g) in ethanol (10 mL) and BOC anhydride (0.150 g), TEA (1.0 mL), Pd/C (catalytic amount) was stirred under hydrogen atmosphere under 35-40 psi pressure in Parr apparatus for 4-5 h. The reaction mass was filtered and the obtained filtrate was concentrated to afford 0.100 g of desired product. $^1$H NMR (300 MHz, DMSO $d_6$): δ 0.93-0.98 (m, 4H), 1.36 (s, 9H), 2.09 (m, 1H), 4.12 (d, J=5.7 Hz, 2H), 7.51 (m, 1H), 7.69 (s, 1H), 7.88 (d, J=8.4 Hz, 2H), 8.43 (d, J=7.8 Hz, 2H); MS (m/z): 476.13 (M+H)$^+$.

Step-2:—Preparation N-((6-cyclopropyl-5-(1-(4-(trifluoromethyl)phenyl)-4,5-dihydro-5-oxo-1H-1,2,4-triazol-3-yl)pyridin-3-yl)methyl)pivalamide Stirred a solution of tert-butyl (6-cyclopropyl-5-(1-(4-(trifluoromethyl)phenyl)-4,5-dihydro-5-oxo-1H-1,2,4-triazol-3-yl)pyridin-3-yl)methylcarbamate (0.100 g) in EtOC:HCl (5.0 mL) for 6 h at RT. Excess of solvent was removed and added DCM (5.0 mL), TEA (0.5 mL) and pivaloyl chloride (0.045 g) under nitrogen atmosphere o the reaction mixture. The reaction mass was stirred at RT for 4 h. Excess of solvent was removed under vacuum and the residue was diluted with water, extracted with EtOAC and concentrated to afford 0.020 g of the product. $^1$H NMR (300 MHz, DMSO $d_6$): δ 0.98 (m, 4H), 1.12 (s, 9H), 2.73 (m, 1H), 4.27 (d, J=6.0 Hz, 2H), 7.78 (s, 1H), 7.85 (d, J=8.7 Hz, 2H), 8.13 (t, 1H), 8.19 (d, J=9.3 Hz, 2H), 8.40 (s, 1H), 12.75 (s, 1H); MS (m/z): 460.30 (M+H)$^+$

Example-181

N-(4-Chloro-3-(1-(4-(2-cyclopropylethynyl)-2-fluorophenyl)-4,5-dihydro-5-oxo-1H-1,2,4-triazol-3-yl)benzyl)pivalamide

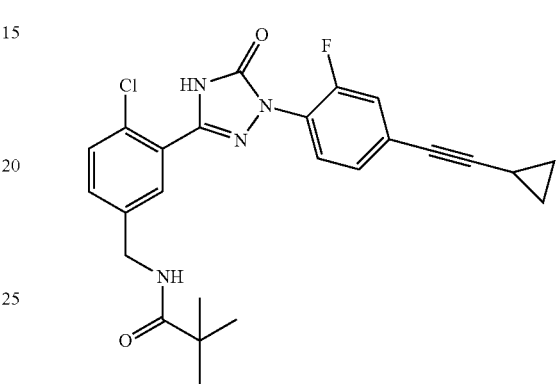

Step 1:—Preparation of N-(4-chloro-3-(1-(4-(2-cyclopropylethynyl)-2-fluorophenyl)-4,5-dihydro-5-oxo-1H-1,2,4-triazol-3-yl)benzyl)-2,2,2-trifluoroacetamide

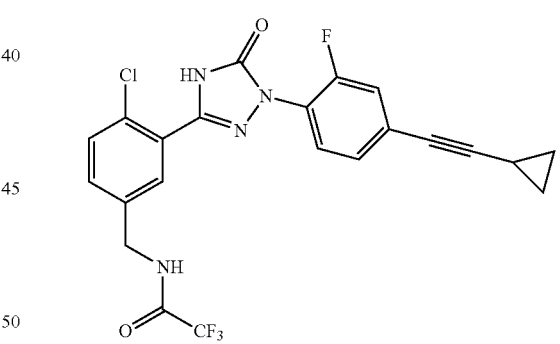

The title compound was prepared according to the procedure described in Example-111 by using N-(4-chloro-3-(1-(2-fluoro-4-iodophenyl)-4,5-dihydro-5-oxo-1H-1,2,4-triazol-3-yl)benzyl)-2,2,2-trifluoroacetamide (Intermediate-126, 1.100 g, 3.88 mmol), ethynylcyclopropane (0.127 g, 1.93 mmol), TBAF (1.10 g, 3.88 mmol), bis(triphenylphosphine)palladium(II) chloride (0.036 g, 0.051 mmol) and DMSO (3.0 mL) to afford 0.400 g of the desired title product. $^1$H NMR (400 MHz, DMSO $d_6$): δ 0.95 (m, 4H), 1.56 (m, 1H), 4.44 (br s, 2H), 7.32 (d, J=7.8 Hz, 1H), 7.42-7.46 (m, 2H), 7.58 (t, J=7.8 Hz, 1H), 7.65 (m, 3H), 10.12 (br s, 1H); MS (m/z): 479.11 (M+H)$^+$.

Step 2:—Preparation of 5-(5-(aminomethyl)-2-chlorophenyl)-2-(4-(2-cyclopropylethynyl)-2-fluorophenyl)-2H-1,2,4-triazol-3(4H)-one

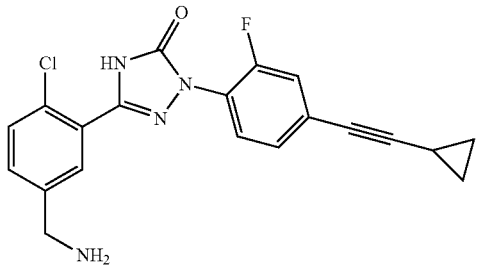 [SMILES: NCc1ccc(Cl)c(-c2nn(-c3ccc(C#CC4CC4)cc3F)c(=O)[nH]2)c1]

The title compound was prepared by following the procedure as described in step-2 of Intermediate-106 by using N-(4-chloro-3-(1-(4-(2-cyclopropylethynyl)-2-fluorophenyl)-4,5-dihydro-5-oxo-1H-1,2,4-triazol-3-yl)benzyl)-2,2,2-trifluoroacetamide (0.300 g), KOH (0.300 g), water (2.0 mL), THF (10.0 mL) to afford 0.200 g of desired product. MS (m/z): 383.16 (M+H)$^+$.

Step-3:—Preparation of N-(4-chloro-3-(1-(4-(2-cyclopropylethynyl)-2-fluorophenyl)-4,5-dihydro-5-oxo-1H-1,2,4-triazol-3-yl)benzyl)pivalamide The title compound was prepared according to the procedure described in Example-108 by using 5-(5-(aminomethyl)-2-chlorophenyl)-2-(4-(2-cyclopropylethynyl)-2-fluorophenyl)-2H-1,2,4-triazol-3(4H)-one (0.100 g, 0.266 mmol), pivaloyl chloride (0.040 g, 0.319 mmol), THF (10.0 mL) and TEA (2 mL) to afford 0.040 g of the desired product. $^1$H NMR (400 MHz, DMSO d$_6$): δ 038 (m, 2H), 0.919 (m, 2H), 1.11 (br s, 9H), 1.56 (m, 1H), 4.28 (br d, 2H), 7.32-7.41 (m, 3H), 7.56 (br s, 3H), 8.16 (s, 1H), 12.46 (s, 1H); MS (m/z): 467.22 (M+H)$^+$.

Example-182

N-(4-Chloro-3-(5-oxo-1-(4-(trifluoromethyl)phenyl)-4,5-dihydro-1H-1,2,4-triazol-3-yl)benzyl)-2-methylpropane-2-sulfonamide

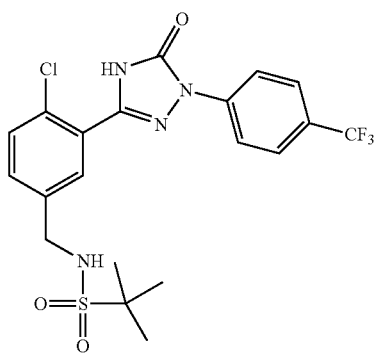 [SMILES: CC(C)(C)S(=O)(=O)NCc1ccc(Cl)c(-c2nn(-c3ccc(C(F)(F)F)cc3)c(=O)[nH]2)c1]

To a solution of N-(4-chloro-3-(5-oxo-1-(4-(trifluoromethyl)phenyl)-4,5-dihydro-1H-1,2,4-triazol-3-yl)benzyl)-2-methylpropane-2-sulfinamide (Intermediate-144, 0.075 g, 0.158 mmol) in mixture of DCM:acetonitrile:water (0.2 ml:0.2 mL:0.3 mL), sodium periodate (0.050 g, 0.238 mmol) and ruthenium chloride (0.001 g, 0.003 mmol) were added and the reaction mass was stirred at RT for 4 h. After completion of the reaction the reaction mass was filtered through celite bed and extracted with DCM. The organic layer was separated, dried over anhydrous sodium sulphate and concentrated. The obtained product was purified with column chromatography on neutral alumina eluting with 10% MeOH: DCM to afford 0.020 g of the desired product. $^1$H NMR (300 MHz, DMSO d$_6$): δ 1.30 (s, 9H), 4.31 (d, J=6.0 Hz, 2H), 7.55-7.71 (m, 4H), 7.86 (d, J=8.7 Hz, 2H), 8.19 (d, J=9.0 Hz, 2H), 12.71 (s, 1H). MS (m/z): 489.04 (M+H)$^+$.

Example-183

6-(Difluoromethyl)-5-(5-oxo-1-(4-(trifluoromethyl)phenyl)-4,5-dihydro-1H-1,2,4-triazol-3-yl)nicotinonitrile

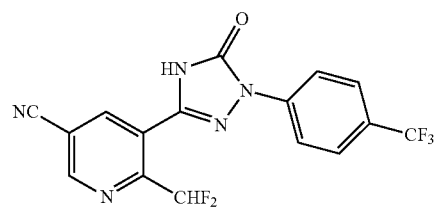 [SMILES: N#Cc1cnc(C(F)F)c(-c2nn(-c3ccc(C(F)(F)F)cc3)c(=O)[nH]2)c1]

The title compound was prepared by following the procedure as described in Example-83 by using 5-cyano-2-(difluoromethyl)nicotinoyl isocyanate (Intermediate-145, 0.900 g, 4.03 mmol), tert-butyl 2-(4-(trifluoromethyl)phenyl)hydrazinecarboxylate (Intermediate-53, 1.0 g, 163 mmol), TFA (10 mL), DCM (40 mL) to afford 0.350 g of the desired product. $^1$H NMR (300 MHz, DMSO d$_6$): δ 7.45-7.56 (t, J=53.4 Hz, 1H), 7.90 (d, J=9.3 Hz, 2H), 8.20 (d, J=8.7 Hz, 2H), 8.77 (s, 1H), 9.32 (s, 1H), 13.01 (s, 1H); MS (m/z): 382.15 (M+H)$^+$.

Example-184

N-(4-Chloro-3-(5-oxo-1-(4-(trifluoromethyl)phenyl)-4,5-dihydro-1H-1,2,4-triazol-3-yl)benzyl)cyclobutanecarboxamide

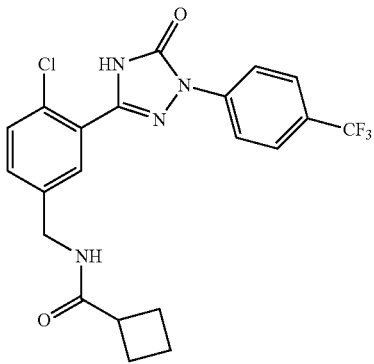 [SMILES: O=C(NCc1ccc(Cl)c(-c2nn(-c3ccc(C(F)(F)F)cc3)c(=O)[nH]2)c1)C1CCC1]

The title compound was prepared according to the procedure described in Example-108 by using 3-(5-(aminomethyl)-2-chlorophenyl)-1-(4-(trifluoromethyl)phenyl)-1H-1,2,4-triazol-5(4H)-one (Intermediate-63, 0.100 g, 0.271 mmol), TEA (1.0 mL), DCM (10 mL), cyclobutanecarbonyl chloride (0.041 g, 0.352 mmol) to afford 0.020 g of the desired product. $^1$H NMR (300 MHz, DMSO d$_6$): δ 2.05 (m, 6H), 3.08 (m, 1H), 4.29 (m, 2H), 7.44 (m, 1H), 7.60 (m, 2H), 7.86 (m, 2H), 8.17 (m, 3H), 12.69 (s, 1H); MS (m/z): 451.07 (M+H)$^+$.

Example-185

N-(4-Chloro-3-(5-oxo-1-(4-(trifluoromethyl)phenyl)-4,5-dihydro-1H-1,2,4-triazol-3-yl)benzyl)cyclopentanecarboxamide

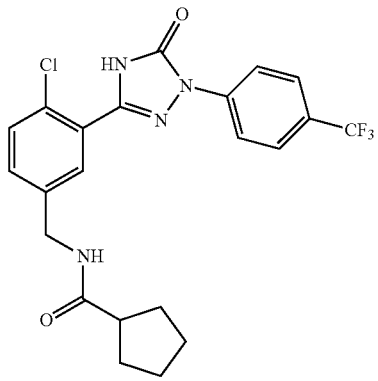 [SMILES: O=C(NCc1ccc(Cl)c(-c2nn(-c3ccc(C(F)(F)F)cc3)c(=O)[nH]2)c1)C1CCCC1]

The title compound was prepared according to the procedure described in Example-17 by using 3-(5-(aminomethyl)-2-chlorophenyl)-1-(4-(trifluoromethyl)phenyl)-1H-1,2,4-triazol-5(4H)-one (Intermediate-63, 0.100 g, 0.271 mmol), TEA (1.0 mL), TBTU (0.261 g, 0.813 mmol), THF:DMF (10 mL), cyclopentanecarboxylic acid (0.061 g, 0.542 mmol) to afford 0.025 g of the desired product. $^1$H NMR (300 MHz, DMSO d$_6$): δ 1.50-1.76 (m, 8H), 2.62 (s, 1H), 4.30 (d, 2H), 7.45 (m, 1H), 7.61 (m, 2H), 7.85 (d, J=9.6 Hz, 2H), 8.19 (d, J=8.1 Hz, 2H), 8.40 (m, 1H), 12.69 (s, 1H); MS (m/z): 465.08 (M+H)$^+$.

Example-186

N-(((6-(Difluoromethyl)-5-(5-oxo-1-(4-(trifluoromethyl)phenyl)-4,5-dihydro-1H-1,2,4-triazol-3-yl)pyridin-3-yl)methyl)pivalamide

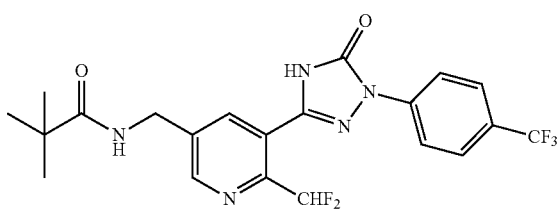 [SMILES: CC(C)(C)C(=O)NCc1cnc(C(F)F)c(-c2nn(-c3ccc(C(F)(F)F)cc3)c(=O)[nH]2)c1]

Step-1:—Preparation of 3-(5-(aminomethyl)-2-(difluoromethyl)pyridin-3-yl)-1-(4-(trifluoromethyl)phenyl)-1H-1,2,4-triazol-5(4H)-one

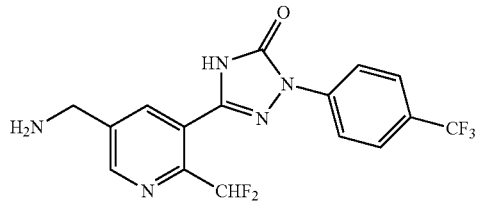 [SMILES: NCc1cnc(C(F)F)c(-c2nn(-c3ccc(C(F)(F)F)cc3)c(=O)[nH]2)c1]

The title compound was prepared according to the procedure described in Intermediate-16 by using 6-(difluoromethyl)-5-(5-oxo-1-(4-(trifluoromethyl)phenyl)-4,5-dihydro-1H-1,2,4-triazol-3-yl)nicotinonitrile (Example-183, 0.050 g, 0.13 mmol), Raney Ni (catalytic amount), TEA (0.040 g, 0.39 mmol) in ethanol (20 mL) to afford 0.50 g of the desired product.

Step-2:—Preparation of N-((6-(difluoromethyl)-5-(5-oxo-1-(4-(trifluoromethyl)phenyl)-4,5-dihydro-1H-1,2,4-triazol-3-yl)pyridin-3-yl)methyl)pivalamide The title compound was prepared by following the procedure as described in Example-108 by using 3-(5-(aminomethyl)-2-(difluoromethyl)pyridin-3-yl)-1-(4-(trifluoromethyl)phenyl)-1H-1,2,4-triazol-5(4H)-one (0.50 g, 0.12 mmol), pivaloyl chloride (0.018 g, 0.14 mmol), TEA (0.038 g, 0.37 mmol) in DCM (10 mL) to afford 0.010 g of the desired product. $^1$H NMR (300 MHz, DMSO d$_6$): δ 1.18 (s, 9H), 4.38 (s, 2H), 7.24-7.63 (m, 1H), 7.64 (d, J=8.4 Hz, 2H), 7.99 (s, 1H), 8.10 (d, J=8.4 Hz, 2H), 8.61 (s, 1H); MS (m/z): 470.25 (M+H)$^+$.

Example-187

N-((6-(Difluoromethyl)-5-(5-oxo-1-(4-(trifluoromethyl)phenyl)-4,5-dihydro-1H-1,2,4-triazol-3-yl)pyridin-3-yl)methyl)isobutyramide

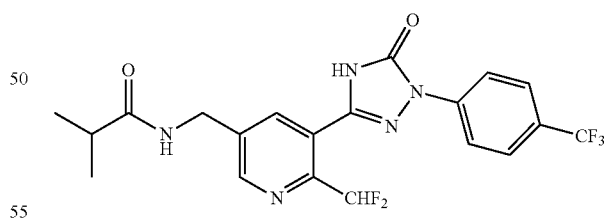

The title compound was prepared by following the procedure as described in Example-108 by using 3-(5-(aminomethyl)-2-(difluoromethyl)pyridin-3-yl)-1-(4-(trifluoromethyl)phenyl)-1H-1,2,4-triazol-5(4H)-one (step-1 of Example-186, 0.50 g, 0.12 mmol), isobutyryl chloride (0.017 g, 0.15 mmol), TEA (0.042 g, 0.41 mmol) and DCM (10 mL) to afford 0.015 g of the desired product. $^1$H NMR (300 MHz, DMSO d$_6$): δ 1.14-1.21 (m, 6H), 2.47 (m, 1H), 4.47 (s, 2H), 7.32-7.54 (m, 1H), 7.72 (d, J=8.7 Hz, 2H), 8.09 (br s, 1H), 8.18 (d, J=7.8 Hz, 2H), 8.70 (s, 1H); MS (m/z): 456.14 (M+H)$^+$.

Example-188

N-((6-(Difluoromethyl)-5-(5-oxo-1-(4-(trifluoromethyl)phenyl)-4,5-dihydro-1H-1,2,4-triazol-3-yl)pyridin-3-yl)methyl)propane-2-sulfonamide

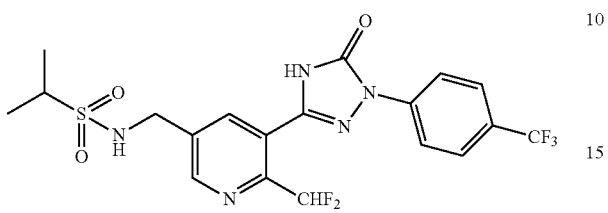

The title compound was prepared by following the procedure as described in Example-108 by using 3-(5-(aminomethyl)-2-(difluoromethyl)pyridin-3-yl)-1-(4-(trifluoromethyl)phenyl)-1H-1,2,4-triazol-5(4H)-one (step-1 of Example-186, 0.75 g, 0.19 mmol), isopropyl sulphonyl chloride (0.042 g, 0.29 mmol), TEA (0.059 g, 0.58 mmol), and DCM (10 mL) to afford 0.012 g of desired product. $^1$H NMR (300 MHz, DMSO d$_6$): δ 1.32 (s, 3H), 1.35 (s, 3H), 3.15 (m, 1H), 4.36 (s, 2H), 7.26-7.66 (m, 3H), 8.08-8.11 (m, 3H), 8.65 (s, 1H); MS (m/z): 492.08 (M+H)$^+$.

Example-189

N-((6-(Difluoromethyl)-5-(5-oxo-1-(4-(trifluoromethyl)phenyl)-4,5-dihydro-1H-1,2,4-triazol-3-yl)pyridin-3-yl)methyl)cyclobutanecarboxamide

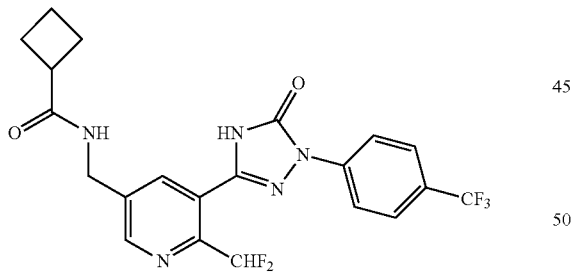

The title compound was prepared by following the procedure as described in Example-108 by using 3-(5-(aminomethyl)-2-(difluoromethyl)pyridin-3-yl)-1-(4-(trifluoromethyl)phenyl)-1H-1,2,4-triazol-5(4H)-one (step-1 of Example-186, 0.75 g, 0.19 mmol), cyclobutane carbonyl chloride (0.035 g, 0.29 mmol), TEA (0.059 g, 0.58 mmol) and DCM (10 mL) to afford 0.020 g of the desired product. $^1$H NMR (300 MHz, DMSO d$_6$): δ 1.89-2.29 (m, 7H), 4.45 (s, 2H), 7.31-7.52 (m, 1H), 7.72 (d, J=8.4 Hz, 2H), 8.05 (s, 1H), 8.18 (d, J=8.4 Hz, 2H), 8.66 (s, 1H); MS (m/z): 468.26 (M+H)$^+$.

Example-190

N-(4-Chloro-3-(3-(4-(cyclopropylethynyl)phenyl)-5-oxo-4,5-dihydro-1H-1,2,4-triazol-1-yl)benzyl)-2,2,2-trifluoroacetamide

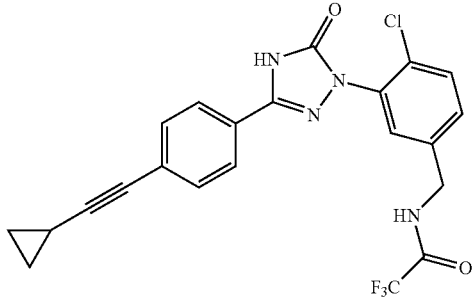 [SMILES: O=C(NCc1ccc(Cl)c(-n2nc(-c3ccc(C#CC4CC4)cc3)[nH]c2=O)c1)C(F)(F)F]

The title compound was prepared according to the procedure described in Example 111 using N-(4-chloro-3-(3-(4-iodophenyl)-5-oxo-4,5-dihydro-1H-1,2,4-triazol-1-yl)benzyl)-2,2,2-trifluoroacetamide (Intermediate-146, 0.300 g, 0.568 mmol), ethynylcyclopropane (0.056 g, 0.852 mmol), TBAF (0.444 g, 1.72 mmol), bis(triphenylphosphine)palladium(II) chloride (0.016 g, 0.022 mmol) and DMSO (3.0 mL) to afford 0.020 g of the desired product. $^1$H NMR (300 MHz, DMSO d$_6$): δ 0.75 (m, 2H), 0.90 (m, 2H), 1.55 (m, 1H), 4.43 (d, J=6.0 Hz, 2H), 7.38 (d, J=6.6 Hz, 1H), 7.46-7.51 (m, 3H), 7.64 (d, J=8.1 Hz, 1H), 7.76 (d, J=8.4 Hz, 2H), 10.06 (m, 1H), 12-13 (br s, 1H). MS (m/z): 461.12 (M+H)$^+$.

Example-191

N-(4-Chloro-3-(3-(4-(cyclopropylethynyl)phenyl)-5-oxo-4,5-dihydro-1H-1,2,4-triazol-1-yl)benzyl)-3-hydroxy-2,2-dimethylpropanamide

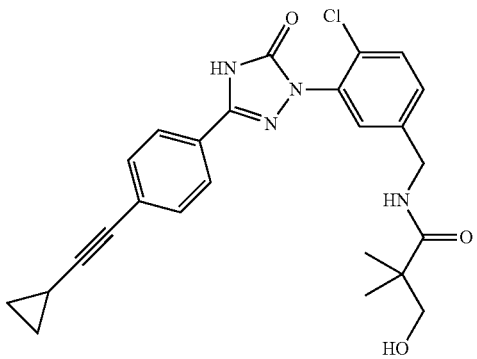 [SMILES: CC(C)(CO)C(=O)NCc1ccc(Cl)c(-n2nc(-c3ccc(C#CC4CC4)cc3)[nH]c2=O)c1]

Step-1:—Preparation of 1-(5-(aminomethyl)-2-chlorophenyl)-3-(4-(cyclopropylethynyl)phenyl)-1H-1,2,4-triazol-5(4H)-one

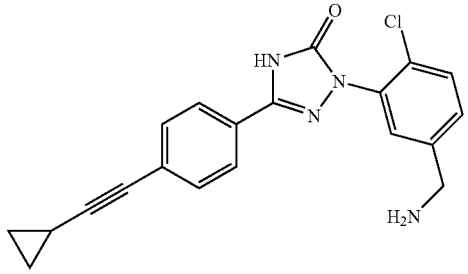 [SMILES: NCc1ccc(Cl)c(-n2nc(-c3ccc(C#CC4CC4)cc3)[nH]c2=O)c1]

The title compound was prepared by following the procedure as described in step-2 of Intermediate-106 by using N-(4-chloro-3-(3-(4-(cyclopropylethynyl)phenyl)-5-oxo-4,5-dihydro-1H-1,2,4-triazol-1-yl)benzyl)-2,2,2-trifluoroacetamide (Example-190, 0.100 g), LiOH (0.100 g), water (2.0 mL), THF (10.0 mL) to afford 0.050 g of the desired product. MS (m/z): 365.83 (M+H)$^+$.

Step-2:—Preparation of N-(4-chloro-3-(3-(4-(cyclopropylethynyl)phenyl)-5-oxo-4,5-dihydro-1H-1,2,4-triazol-1-yl)benzyl)-3-hydroxy-2,2-dimethylpropanamide The title compound was prepared according to the procedure described in Example-107 by using 1-(5-(aminomethyl)-2-chlorophenyl)-3-(4-(cyclopropylethynyl)phenyl)-1H-1,2,4-triazol-5(4H)-one (0.080 g, 0.228 mmol), DMF (5 mL), 3-methoxy-2,2-dimethylpropanoic acid (0.040 g, 0.342 mmol), BOP (0.151 g, 0.342 mmol), TEA (2.0 mL) to afford 0.010 g of the desired product. $^1$H NMR (300 MHz, DMSO d$_6$): δ 0.75 (m, 2H), 0.83 (m, 1H), 1.10 (s, 6H), 1.51 (m, 1H), 3.34 (m 2H), 4.31 (br s, 2H), 4.85 (m, 1H), 7.37-7.50 (m, 3H), 7.58 (d, J=7.8 Hz, 1H), 7.77-7.83 (m, 3H), 8.11 (br s, 1H), 12.56 (s, 1H); MS (m/z): 465.07 (M+H)$^+$.

Example-192

3-Fluoro-N-((6-(difluoromethyl)-5-(1-(4-(trifluoromethyl)phenyl)-4,5-dihydro-5-oxo-1H-1,2,4-triazol-3-yl)pyridin-3-yl)methyl)-2,2-dimethylpropanamide

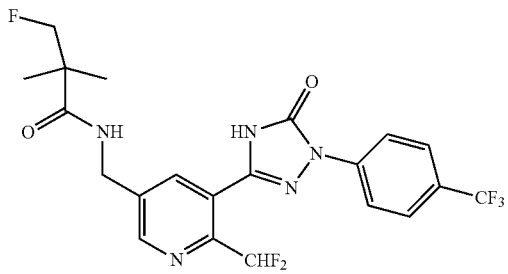 [SMILES: CC(C)(CF)C(=O)NCc1cnc(C(F)F)c(-c2nn(-c3ccc(C(F)(F)F)cc3)c(=O)[nH]2)c1]

Step-1:—Preparation of N-((6-(difluoromethyl)-5-(1-(4-(trifluoromethyl)phenyl)-4,5-dihydro-5-oxo-1H-1,2,4-triazol-3-yl)pyridin-3-yl)methyl)-3-hydroxy-2,2-dimethylpropanamide

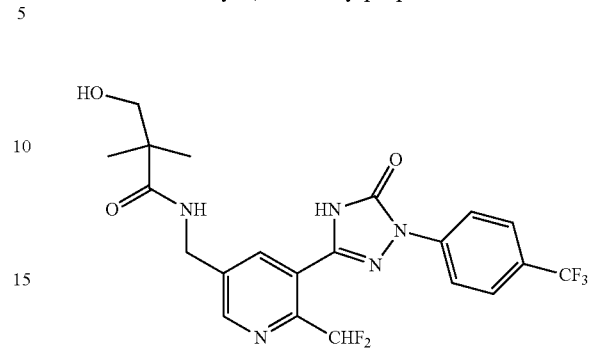

The title compound was prepared by following the procedure as described in Example-107 by using 3-(5-(aminomethyl)-2-(difluoromethyl)pyridin-3-yl)-1-(4-(trifluoromethyl)phenyl)-1H-1,2,4-triazol-5(4H)-one (step-1 of Example-186, 0.130 g, 0.33 mmol), DMF (5 mL), 3-methoxy-2,2-dimethylpropanoic acid (0.060 g, 0.50 mmol), BOP (0.224 g, 0.50 mmol), TEA (2.0 mL) to afford 0.070 g of the desired product. MS (m/z): 486.22 (M+H)$^+$.

Step-2:—Preparation of 3-fluoro-N-((6-(difluoromethyl)-5-(1-(4-(trifluoromethyl)phenyl)-4,5-dihydro-5-oxo-1H-1,2,4-triazol-3-yl)pyridin-3-yl)methyl)-2,2-dimethylpropanamide The title compound was prepared by following the procedure as described in step-2 of Example-134 by using N-((6-(difluoromethyl)-5-(1-(4-(trifluoromethyl)phenyl)-4,5-dihydro-5-oxo-1H-1,2,4-triazol-3-yl)pyridin-3-yl)methyl)-3-hydroxy-2,2-dimethylpropanamide (0.060 g, 0.12 mmol), DAST (0.060 g, 0.37 mmol), DCM (10 mL) to afford 0.005 g the desired product. $^1$H NMR (300 MHz, DMSO d$_6$): δ 0.80 (br s, 6H), 4.22 (br s, 1H), 4.38-4.42 (m, 3H), 7.41-7.66 (m, 3H), 7.95 (br s, 1H), 8.08-8.11 (m, 2H), 8.61 (s, 1H); MS (m/z): 488.23 (M+H)$^+$.

Pharmacological Activity

In-Vitro Protocol for Screening of mPGES-1 Inhibitors:

mPGES-1 (Microsomal prostaglandin E synthase-1) is a microsomal enzyme that converts endoperoxide substrate PGH$_2$ (prostaglandin H$_2$) to product PGE$_2$ (prostaglandin E$_2$) by isomerization in the presence of reduced glutathione (GSH). mPGES-1 inhibitors were screened by assessing their ability to inhibit formation of PGE$_2$ from PGH$_2$ in the presence of mPGES-1 using an anti-PGE$_2$ antibody based detection method. Recombinant human mPGES-1 was generated in-house by expression in CHO cells (Ouellet M et al. (2002), Protein Expression and Purification 26: 489-495). The assay was set up using crude microsomal fractions at a protein concentration of 40-60 µg/mL. Test compounds were prepared in 100% dimethyl sulfoxide (DMSO) to obtain 20 mM stock solution and then diluted using assay buffer comprising 0.1 M Potassium phosphate buffer with 2 mM EDTA. The final concentration of DMSO in the reaction was 0.5% (v/v). Negative controls were comprised of all assay reagents except the enzyme. Positive controls were comprised of the enzyme reaction in the absence of any inhibitor. Test compounds were incubated for 10 minutes in assay buffer containing 2.5 mM GSH and mPGES-1 enzyme followed by addition of $PGH_2$ at a concentration of 15 μM for 1 minute. The reaction was stopped by addition of Stannous chloride (11 mg/ml) and $PGE_2$ levels were measured (Masse F et al. (2005), Journal of Biomolecular Screening 10(6) 599-605; Goedken R E et al. (2008), Journal of Biomolecular Screening 13 (7): 619-625) by HTRF kit (CisBio)).

Inhibition of mPGES-1 enzyme activity was measured using the percent of reaction occurring in the positive control. Concentration response curves were plotted using percent inhibition of maximum enzyme reaction. The $IC_{50}$ value was calculated from the concentration response curve by nonlinear regression analysis using GraphPad PRISM software.

The compounds prepared were tested using the above assay procedure and the results obtained are given in Table 1. Percentage inhibition at concentrations of 1.0 μM, 3.0 μM or 10.0 μM are given in the table along with $IC_{50}$ (nM) details for selected examples. The compounds prepared were tested using the above assay procedure and were found to have $IC_{50}$ less than 200 nM, preferably less than 100 nM, more preferably less than 50 nM or most preferably less than 20 nM.

The $IC_{50}$ (nM) values of some of the compounds are set forth in Table 1 wherein "A" refers to an $IC_{50}$ value of less than 50 nM, "B" refers to $IC_{50}$ value in range of 50.01 to 100.0 nM and "C" refers to $IC_{50}$ values more than 100 nM.

TABLE 1

| Sr. No. | Example No. | Percentage inhibition at 1 μM | 3 μM | 10 μM | $IC_{50}$ (nM) |
|---|---|---|---|---|---|
| 1. | Example-1 | 9.32 | — | 68.18 | — |
| 2. | Example-2 | 17.97 | — | 18.97 | — |
| 3. | Example-3 | 88.90 | 96.79 | — | A |
| 4. | Example-4 | 46.43 | — | 69.70 | — |
| 5. | Example-5 | 91.83 | — | 86.21 | A |
| 6. | Example-6 | 83.89 | — | 87.67 | A |
| 7. | Example-7 | 89.12 | — | 95.25 | A |
| 8. | Example-8 | 84.86 | — | 87.24 | B |
| 9. | Example-9 | 1.53 | — | 23.19 | — |
| 10. | Example-10 | 84.88 | — | 91.21 | A |
| 11. | Example-11 | 2.34 | — | 71.72 | — |
| 12. | Example-12 | 84.76 | — | 87.54 | A |
| 13. | Example-13 | 86.27 | — | 90.42 | C |
| 14. | Example-14 | 95.99 | — | 95.82 | B |
| 15. | Example-15 | 64.15 | — | 83.79 | — |
| 16. | Example-16 | 40.88 | — | 92.28 | — |
| 17. | Example-17 | 2.52 | — | 44.08 | — |
| 18. | Example-18 | 56.23 | — | 98.10 | — |
| 19. | Example-19 | 5.11 | — | 29.66 | — |
| 20. | Example-20 | 22.37 | — | 87.36 | — |
| 21. | Example-21 | 76.06 | — | 91.78 | — |
| 22. | Example-22 | 39.26 | — | 99.73 | — |
| 23. | Example-23 | 13.25 | — | 52.94 | — |
| 24. | Example-24 | 70.96 | — | 83.09 | — |
| 25. | Example-25 | 74.44 | — | 88.92 | C |
| 26. | Example-26 | 80.56 | — | 88.14 | C |
| 27. | Example-27 | 72.84 | — | 97.54 | — |
| 28. | Example-28 | 72.22 | — | 95.51 | — |
| 29. | Example-29 | 79.21 | — | 85.78 | C |
| 30. | Example-30 | 89.60 | — | 94.52 | A |
| 31. | Example-31 | 96.88 | — | 98.63 | B |
| 32. | Example-32 | 88.85 | — | 93.97 | B |
| 33. | Example-33 | 89.42 | — | 96.78 | A |
| 34. | Example-34 | 70.73 | — | 92.28 | — |
| 35. | Example-35 | 37.43 | — | 59.15 | — |
| 36. | Example-36 | 97.34 | — | 98.90 | A |
| 37. | Example-37 | 50.96 | — | 94.31 | — |
| 38. | Example-38 | 87.36 | — | 84.91 | B |
| 39. | Example-39 | 90.06 | — | 96.37 | B |
| 40. | Example-40 | 89.05 | — | 90.68 | A |
| 41. | Example-41 | 58.81 | — | 87.08 | — |
| 42. | Example-42 | 96.55 | — | 99.65 | A |
| 43. | Example-43 | 98.58 | — | 99.05 | A |
| 44. | Example-44 | 97.37 | — | 99.03 | A |
| 45. | Example-45 | 81.65 | — | 90.11 | A |
| 46. | Example-46 | 59.77 | — | 72.09 | — |
| 47. | Example-47 | 89.46 | — | 96.51 | A |
| 48. | Example-48 | 98.33 | — | 100.00 | A |
| 49. | Example-49 | 89.15 | — | 96.34 | A |
| 50. | Example-50 | 95.32 | — | 99.85 | B |
| 51. | Example-51 | 88.29 | — | 85.96 | A |
| 52. | Example-52 | 96.44 | — | 98.34 | A |
| 53. | Example-53 | 82.70 | — | 97.89 | A |
| 54. | Example-54 | 89.36 | — | 97.50 | B |
| 55. | Example-55 | 80.95 | 91.85 | — | A |
| 56. | Example-56 | 98.08 | — | 98.54 | A |
| 57. | Example-57 | 98.73 | 98.55 | — | A |
| 58. | Example-58 | 95.20 | — | 97.32 | B |
| 59. | Example-59 | 93.91 | — | 96.80 | A |
| 60. | Example-60 | 95.39 | — | 93.07 | A |
| 61. | Example-61 | 92.44 | — | 96.85 | A |
| 62. | Example-62 | 97.77 | — | 98.29 | A |
| 63. | Example-63 | 92.41 | — | 94.79 | A |
| 64. | Example-64 | 28.94 | — | 63.78 | — |
| 65. | Example-65 | 75.45 | — | 94.48 | — |
| 66. | Example-66 | 87.85 | — | 98.83 | C |
| 67. | Example-67 | 72.71 | — | 96.32 | — |
| 68. | Example-68 | 97.39 | — | 96.41 | A |
| 69. | Example-69 | 86.44 | — | 89.11 | C |
| 70. | Example-70 | 0.55 | — | 6.63 | — |
| 71. | Example-71 | 12.95 | — | 17.88 | — |
| 72. | Example-72 | 99.24 | 99.05 | — | A |
| 73. | Example-73 | 92.38 | — | 92.43 | A |
| 74. | Example-74 | 93.25 | — | 98.71 | B |
| 75. | Example-75 | 99.07 | — | 98.31 | A |
| 76. | Example-76 | 95.62 | — | 95.38 | A |
| 77. | Example-77 | 93.21 | — | 98.06 | B |
| 78. | Example-78 | 99.94 | — | 99.88 | A |
| 79. | Example-79 | 99.14 | — | 97.14 | A |
| 80. | Example-80 | 96.99 | — | 97.10 | A |
| 81. | Example-81 | 99.76 | — | 98.05 | A |
| 82. | Example-82 | 98.26 | — | 98.96 | A |
| 83. | Example-83 | 97.49 | — | 99.86 | A |
| 84. | Example-84 | 98.81 | — | 99.51 | A |
| 85. | Example-85 | 22.58 | — | 69.28 | — |
| 86. | Example-86 | 79.87 | — | 96.68 | C |
| 87. | Example-87 | 93.36 | — | 99.19 | B |
| 88. | Example-88 | 3.34 | — | 39.18 | — |
| 89. | Example-89 | 95.30 | — | 99.06 | A |
| 90. | Example-90 | 81.74 | — | 97.20 | C |
| 91. | Example-91 | 66.15 | — | 94.31 | — |
| 92. | Example-92 | 76.02 | — | 99.37 | C |
| 93. | Example-93 | 96.83 | — | 99.60 | A |
| 94. | Example-94 | 87.02 | — | 100.00 | C |
| 95. | Example-95 | 98.71 | — | 99.04 | A |
| 96. | Example-96 | 52.25 | — | 68.70 | — |
| 97. | Example-97 | 20.19 | — | 6.88 | — |
| 98. | Example-98 | 97.52 | — | 99.45 | A |
| 99. | Example-99 | 95.30 | — | 98.55 | A |
| 100. | Example-100 | 99.97 | — | 98.56 | A |

TABLE 1-continued

| Sr. No. | Example No. | Percentage inhibition at 1 μM | 3 μM | 10 μM | IC$_{50}$ (nM) |
|---|---|---|---|---|---|
| 101. | Example-101 | 94.97 | — | 98.18 | A |
| 102. | Example-102 | 96.52 | — | 98.03 | A |
| 103. | Example-103 | 19.92 | — | 51.12 | — |
| 104. | Example-104 | 96.91 | — | 99.50 | A |
| 105. | Example-105 | 73.88 | — | 95.96 | C |
| 106. | Example-106 | 92.03 | — | 96.77 | C |
| 107. | Example-107 | 56.07 | — | 90.50 | — |
| 108. | Example-108 | 89.82 | — | 99.72 | C |
| 109. | Example-109 | 97.10 | — | 97.15 | B |
| 110. | Example-110 | 47.19 | — | 95.07 | — |
| 111. | Example-111 | 87.20 | — | 96.15 | A |
| 112. | Example-112 | 99.53 | — | 99.83 | A |
| 113. | Example-113 | 99.30 | — | 99.06 | A |
| 114. | Example-114 | 99.06 | — | 98.39 | A |
| 115. | Example-115 | 96.49 | — | 98.22 | A |
| 116. | Example-116 | 97.97 | — | 95.50 | A |
| 117. | Example-117 | 67.93 | — | 95.02 | — |
| 118. | Example-118 | 76.25 | — | 87.82 | C |
| 119. | Example-119 | 88.70 | — | 94.30 | A |
| 120. | Example-120 | 11.45 | — | 46.01 | — |
| 121. | Example-121 | 16.28 | — | 72.53 | — |
| 122. | Example-122 | 92.22 | — | 93.49 | A |
| 123. | Example-123 | 93.78 | — | 100.00 | A |
| 124. | Example-124 | 27.96 | — | 88.96 | — |
| 125. | Example-125 | 79.87 | — | 94.99 | — |
| 126. | Example-126 | 100.00 | — | 99.29 | A |
| 127. | Example-127 | 32.43 | — | 58.48 | — |
| 128. | Example-128 | 91.83 | — | 89.35 | A |
| 129. | Example-129 | 93.50 | — | 92.14 | A |
| 130. | Example-130 | 96.56 | — | 97.79 | B |
| 131. | Example-131 | 100.00 | — | 99.23 | A |
| 132. | Example-132 | 91.76 | — | 89.83 | A |
| 133. | Example-133 | 98.00 | — | 97.89 | A |
| 134. | Example-134 | 91.45 | — | 93.88 | A |
| 135. | Example-135 | 92.26 | — | 98.89 | A |
| 136. | Example-136 | 95.06 | — | 94.79 | A |
| 137. | Example-137 | 93.36 | — | 93.06 | A |
| 138. | Example-138 | 93.30 | — | 92.91 | A |
| 139. | Example-139 | 93.94 | — | 99.06 | A |
| 140. | Example-140 | 97.36 | — | 98.11 | A |
| 141. | Example-141 | 97.57 | — | 97.48 | A |
| 142. | Example-142 | 97.25 | — | 93.98 | A |
| 143. | Example-143 | 99.21 | — | 90.70 | A |
| 144. | Example-144 | 97.49 | — | 92.73 | A |
| 145. | Example-145 | 94.24 | — | 98.86 | A |
| 146. | Example-146 | 100.00 | — | 99.73 | A |
| 147. | Example-147 | 98.64 | — | 97.61 | A |
| 148. | Example-148 | 98.91 | — | 97.78 | A |
| 149. | Example-149 | 98.34 | — | 94.61 | A |
| 150. | Example-150 | 98.38 | — | 99.52 | A |
| 151. | Example-151 | 64.96 | — | 95.89 | — |
| 152. | Example-152 | 96.01 | — | 100.00 | A |
| 153. | Example-153 | 93.94 | — | 99.65 | B |
| 154. | Example-154 | 95.18 | — | 100.00 | A |
| 155. | Example-155 | 99.74 | — | 97.08 | A |
| 156. | Example-156 | 98.50 | — | 99.25 | A |
| 157. | Example-157 | 98.54 | — | 96.46 | A |
| 158. | Example-158 | 99.05 | — | 99.70 | A |
| 159. | Example-159 | 75.40 | — | 96.76 | C |
| 160. | Example-160 | 96.62 | — | 97.33 | A |
| 161. | Example-161 | 98.04 | — | 99.36 | A |
| 162. | Example-162 | 99.35 | — | 99.33 | A |
| 163. | Example-163 | 91.82 | — | 98.66 | A |
| 164. | Example-164 | 98.30 | — | 97.19 | A |
| 165. | Example-165 | 97.91 | — | 99.51 | A |
| 166. | Example-166 | 99.68 | — | 100.00 | A |
| 167. | Example-167 | 99.03 | — | 98.43 | A |
| 168. | Example-168 | 100.00 | — | 98.89 | A |
| 169. | Example-169 | 95.54 | — | 99.17 | C |
| 170. | Example-170 | 99.83 | — | 98.87 | A |
| 171. | Example-171 | 95.22 | — | 99.60 | A |
| 172. | Example-172 | 91.86 | — | 99.04 | C |
| 173. | Example-173 | 96.77 | — | 98.95 | A |
| 174. | Example-174 | 99.90 | — | 100.00 | A |
| 175. | Example-175 | 99.44 | — | 99.44 | A |
| 176. | Example-176 | 45.84 | — | 89.54 | — |
| 177. | Example-177 | 29.89 | — | 71.07 | — |
| 178. | Example-178 | 42.72 | — | 91.55 | — |
| 179. | Example-179 | 50.59 | — | 95.17 | — |
| 180. | Example-180 | 72.34 | — | 92.51 | C |
| 181. | Example-181 | 88.24 | — | 94.28 | A |
| 182. | Example-182 | 92.94 | — | 94.05 | A |
| 183. | Example-183 | 41.55 | — | 85.5 | — |
| 184. | Example-184 | 98.59 | — | 94.26 | A |
| 185. | Example-185 | 96.06 | — | 98.3 | A |
| 186. | Example-186 | 96.84 | — | 98.02 | A |
| 187. | Example-187 | 98.63 | — | 97.51 | A |
| 188. | Example-188 | 89.49 | — | 99.32 | B |
| 189. | Example-189 | 96.17 | — | 98.48 | A |
| 190. | Example-190 | 100 | — | 100 | A |
| 191. | Example-191 | 93.5 | — | 100 | C |
| 192. | Example-192 | 99.3 | — | 99.31 | A |

Screening for mPGES-1 Inhibitors Using the A549 Cell Based Assay

The inhibition of mPGES-1 enzyme in the A549 cell line was monitored as inhibition of IL-1β induced PGE$_2$ release. A549 cells were maintained in DMEM medium with 10% FBS and 1% Penicillin-Streptomycin Solution in 5% CO$_2$ at 37° C. Cells were seeded 24 h prior to the assay in 96 well plates in DMEM containing 1% Penicillin-Streptomycin and 2% FBS so as to get ~40,000 cells per well on the day of experiment. The assay was carried out in a total volume of 200 μL. Test compounds were dissolved in dimethyl sulfoxide (DMSO) to prepare 2 mM stock solution and then diluted using plain DMEM. The final concentration of DMSO in the reaction was 0.55% (v/v). Cells were treated with test compounds for 30 minutes followed by addition of IL-1β at a final concentration of 10 ng/mL for 16-20 h. Plates were then centrifuged at 1000 rpm for 10 min at 4° C. Supernatants were collected and analyzed by the addition of PGE$_2$-D2 and anti-PGE$_2$ cryptate conjugate supplied by the CisBio HTRF kit in a 96 well half area Blackwell EIA/RIA plate. The assay plate was incubated overnight at 4-5° C. before being read in an Artemis (K-101) (Japan) HTRF plate reader and levels of PGE$_2$ calculated by extrapolation from the standard curve.

The concentration response curves were plotted as a percentage of maximal response obtained in the absence of test antagonist. The IC$_{50}$ value was calculated from the concentration response curve by nonlinear regression analysis using GraphPad PRISM software.

What is claimed is:

1. A method of relieving a mPGES-1 mediated disease, disorder, syndrome or condition in a subject comprising administering an effective amount of a compound of formula

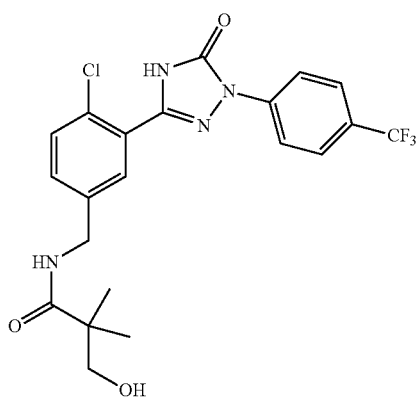 [SMILES: CC(C)(CO)C(=O)NCc1ccc(Cl)c(-c2nn(-c3ccc(C(F)(F)F)cc3)c(=O)[nH]2)c1]

or a pharmaceutically acceptable salt thereof, wherein the mPGES-1 mediated disease, disorder, syndrome or condition is selected from the group consisting of inflammation, pain, inflammatory pain, chronic pain, acute pain, arthritis, osteoarthritis and cancer.

2. The method according to claim 1, wherein the disease, disorder, syndrome or condition is pain.

3. The method according to claim 1, wherein the disease, disorder, syndrome or condition is inflammation.

4. The method according to claim 1, wherein the disease, disorder, syndrome or condition is rheumatoid arthritic pain, osteoarthritic pain, or neuropathic pain.

5. The method according to claim 1, wherein the disease, disorder, syndrome or condition is rheumatoid arthritic pain.

6. The method according to claim 1, wherein the disease, disorder, syndrome or condition is osteoarthritic pain.

7. The method according to claim 1, wherein the disease, disorder, syndrome or condition is cancer.

8. A method of relieving a mPGES-1 mediated disease, disorder, syndrome or condition in a subject comprising administering an effective amount of a compound of formula

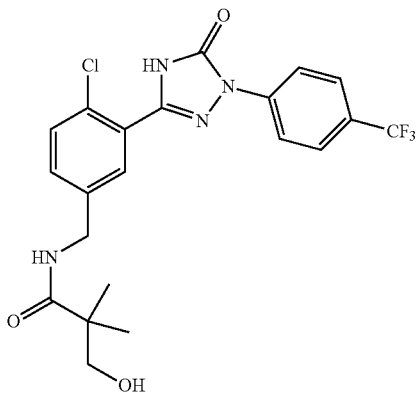 [SMILES: CC(C)(CO)C(=O)NCc1ccc(Cl)c(-c2nn(-c3ccc(C(F)(F)F)cc3)c(=O)[nH]2)c1]

or a pharmaceutically acceptable salt thereof,
wherein the mPGES-1 mediated disease, disorder, syndrome or condition is selected from the group consisting of inflammation, a brain tumor, breast cancer, a gastrointestinal carcinoid tumor, kidney cancer, thyroid cancer, colon cancer, adrenocortical carcinoma, basal cell carcinoma, carcinoma of unknown primary, cardiac (heart) tumors, ductal carcinoma in situ, lobular carcinoma in situ, merkel cell carcinoma, midline tract carcinoma involving NUT gene, squamous cell carcinoma, thymoma and thymic carcinoma, and carcinoma of ureter and renal pelvis.

\* \* \* \* \*